US011674149B2

(12) United States Patent
Zhou et al.

(10) Patent No.: US 11,674,149 B2
(45) Date of Patent: Jun. 13, 2023

(54) NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

(71) Applicant: Ceres, Inc., Thousand Oaks, CA (US)

(72) Inventors: Fasong Zhou, Oxnard, CA (US); Kenneth A. Feldmann, Tucson, AZ (US); Julissa Sosa, Northridge, CA (US)

(*) Notice: Subject to any disclaimer, the term of this patent is extended or adjusted under 35 U.S.C. 154(b) by 43 days.

(21) Appl. No.: 17/221,604

(22) Filed: Apr. 2, 2021

(65) Prior Publication Data

US 2021/0317469 A1   Oct. 14, 2021

Related U.S. Application Data

(60) Division of application No. 16/750,667, filed on Jan. 23, 2020, now Pat. No. 11,028,405, which is a division of application No. 16/265,525, filed on Feb. 1, 2019, now Pat. No. 10,619,166, which is a division of application No. 15/962,986, filed on Apr. 25, 2018, now Pat. No. 10,233,461, which is a division of application No. 15/679,052, filed on Aug. 16, 2017, now Pat. No. 10,006,043, which is a division of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007.

(60) Provisional application No. 60/782,735, filed on Mar. 14, 2006.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8271* (2013.01)

(58) Field of Classification Search
None
See application file for complete search history.

(56) References Cited

U.S. PATENT DOCUMENTS

| 6,281,411 B1 | 8/2001 | Adams et al. |
| 6,867,351 B2 | 3/2005 | da Costa e Silva et al. |
| 9,765,355 B2 | 9/2017 | Zhou et al. |
| 10,006,043 B2 | 6/2018 | Zhou et al. |
| 10,233,461 B2 | 3/2019 | Zhou et al. |
| 10,619,166 B2 | 4/2020 | Zhou et al. |
| 11,028,405 B2 | 6/2021 | Zhou et al. |
| 11,034,972 B2 | 6/2021 | Zhou et al. |
| 11,142,772 B2 | 10/2021 | Zhou et al. |
| 11,447,792 B2 | 9/2022 | Zhou et al. |
| 11,459,581 B2 | 10/2022 | Zhou et al. |
| 2004/0034888 A1 | 2/2004 | Liu et al. |
| 2006/0107345 A1* | 5/2006 | Alexandrov ......... C07K 14/415 536/23.6 |
| 2006/0150283 A1 | 7/2006 | Alexandrov et al. |
| 2007/0214517 A1 | 9/2007 | Alexandrov et al. |
| 2013/0042367 A1 | 2/2013 | Nadzan et al. |
| 2015/0259699 A1* | 9/2015 | Nadzan ............. C12N 15/8261 800/267 |
| 2017/0037426 A1 | 2/2017 | Alexandrov et al. |
| 2018/0223303 A1* | 8/2018 | Alexandrov ....... C12N 15/8273 |
| 2020/0115719 A1 | 4/2020 | Zhou et al. |
| 2020/0181636 A1 | 6/2020 | Zhou et al. |
| 2021/0095304 A1 | 4/2021 | Zhou et al. |
| 2021/0130841 A1 | 5/2021 | Zhou et al. |
| 2021/0348184 A1 | 11/2021 | Zhou et al. |

FOREIGN PATENT DOCUMENTS

| EP | 1033405 | 6/2000 |
| WO | WO 1999/061616 A2 | 12/1999 |
| WO | WO 2001/055433 | 8/2001 |
| WO | WO 2004/092326 A2 | 10/2004 |
| WO | WO 20041092326 A3 | 10/2004 |
| WO | WO 2006/026756 A2 | 3/2006 |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Kang et al. (Cell death and differentiation, 13:84-95, 2006).*
Wells (Biochemistry 29:8509-8517, 1990).*
Guo et al. (PNAS, 101: 9205-9210, 2004).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
U.S. Appl. No. 17/064,117, filed Oct. 6, 2020, Zhou et al.
Rhoads et al., *The FASEB Journal*, 11:331-340, 1997.
Aroca et al., "The role of aquaporins and membrane damage in chilling and hydrogen peroxide induced changes in the hydraulic conductance of maize roots", *Plant Physiol.*, 137(1):341-53, 2005, Epub. Dec. 10, 2004.

(Continued)

*Primary Examiner* — Vinod Kumar
(74) *Attorney, Agent, or Firm* — Dentons US LLP

(57) ABSTRACT

The present invention relates to isolated nucleic acid molecules and their corresponding encoded polypeptides able confer the trait of improved plant size, vegetative growth, growth rate, seedling vigor and/or biomass in plants challenged with saline and/or oxidative stress conditions. The present invention further relates to the use of these nucleic acid molecules and polypeptides in making transgenic plants, plant cells, plant materials or seeds of a plant having plant size, vegetative growth, growth rate, seedling vigor and/or biomass that are improved in saline and/or oxidative stress conditions with respect to wild-type plants grown under similar conditions.

8 Claims, 18 Drawing Sheets

Specification includes a Sequence Listing.

(56) References Cited

OTHER PUBLICATIONS

Aviv et al., "Runaway cell death, but not basal disease resistance, in Isd1 is SA and NIM1/NPR1-dependent", *Plant J.*, 29(3):381-91, 2002.
Borsani et al., "Evidence for the role of salicylic acid in the oxidative damage generated by NaCl and osmotic stress in *Arabidopsis* seedlings," *Plant Physiol.*, 126:1024-1030, 2001.
Brisson et al., "Function of Oxidative CROSS-Linking of Cell Wall Structural Proteins in Plant Disease Resistance," *Plant Cell*, 6(12):1703-1712, 1994.
Cao et al., "Characterization of an *Arabidopsis* mutant that is nonresponsive to inducers of systemic acquired-resistance," *Plant Cell*, 6:1583-1592, 1994.
Dat et al., "Changes in salicylic acid and antioxidants during induced thermotolerance in mustard seedlings," *Plant Physiol.*, 118:1455-1461, 1998.
Delaney et al., "A central role of salicylic acid in plant-disease resistance," *Science*, 266:1247-1250, 1994.
Kim et al.,, "Effects of salicylic acid on paraquat tolerance in *Arabidopsis thaliana* plants," *J. Plant Biol.*, 46:31-37, 2003.
Lamb et al., "The oxidative burst in plant disease resistance," *Annu. Rev. Plant Physiol. Plant Mol. Biol.*, 48:251-275, Jun. 1997.
Larkindale et al., "Protection against heat stress-induced oxidative damage in *Arabidopsis* involves calcium, abscisic acid, ethylene, and salicylic acid," *Plant Physiol.*, 128:682-695, 2002.
Lee et al., "Rapid accumulation of hydrogen peroxide in cucumber roots due to exposure to low temperature appears to mediate decreases in water transport," *J. Exp. Bot.*, 55(403):1733-41, Epub. Jun. 18, 2004.
Levine et al., "H2O2 from the oxidative burst orchestrates the plant hypersensitive disease resistance response," *Cell*, 18,79(4):583-93, 1994.
Luna et al., "Drought controls on H2O2 accumulation, catalase (CAT) activity and CAT gene expression in wheat," *J Exp Bot.*, 56(411):417-23, 2005, Epub. Nov. 29, 2004. 2004.
Martinez et al., "Salicylic acid regulates flowering time and links defence responses and reproductive development," *Plant J*, 37:209-217, 2004.
Noctor et al., "Drought and oxidative load in the leaves of C3 plants: a predominant role for photorespiration?" *Ann Bot* (*Lond*), 89:841-50, 2002.
Rusterucci et al., "The disease resistance signaling components EDS1 and PAD4 are essential regulators of the cell death pathway controlled by LSD1 in Arabidopsis," *Plant Cell*, 2001.
Scott et al., "Salicylate accumulation inhibits growth at chilling temperature in *Arabidopsis*," *Plant Physiol.*, 135:1040-1049, 2004.
Senaratna et al., "Acetyl salicylic acid (Aspirin) and salicylic acid induce multiple stress tolerance in bean and tomato plants," *Plant Growth Regul.*, 30:157-161, 2000.
Surplus et al., "Ultraviolet-B-induced responses in *Arabidopsis thaliana*: role of salicylic acid and reactive oxygen species in the regulation of transcripts encoding photosynthetic and acidic pathogenesis-related proteins," *Plant Cell Environ.*, 21:685-694, 1998.
Zhou et al., "High humidity suppresses ssi4-mediated cell death and disease resistance upstream of MAP kinase activation, H2O2 production and defense gene expression," *Plant J*, 39(6):920-32, 2004.
Zhou et al., "Proton extrusion is an essential signaling component in the HR of epidermal single cells in the barley-powdery mildew interaction," *Plant J.*, 23(2):245-54, 2000.
Ngo et al., *The Protein Folder Problem and Tertiary Structure Prediction*, K. Merz., and S. Le Grand (eds.), 492-495, 1994.
NCBI GenBank Accession No. NP 179785 (Aug. 21, 2001).
NCBI GenBank Accession No. NP 665906 (Jan. 29, 2002).
NCBI GenBank Accession No. NP665305 (Jan. 29, 2002).
NCBI GenBank Accession No. NP567957 (Jan. 30, 2002).
NCBI GenBank Accession No. NP 566785 (Jan. 29, 2002).
NCBI GenBank Accession No. NP_567754 (Jan. 29, 2002).
NCBI GenBank Accession No. NM 129505 (Aug. 21, 2001).
NCBI GenBank Accession No. NM '119581 (Jan. 30, 2002).
NCBI GenBank Accession No. BT018295 (Oct. 27, 2004).
NCBI GenBank Accession No. NM_127763 (Nov. 4, 2005).
NCBI GenBank Accession No. BT003928 (Feb. 14, 2003).
NCBI GenBank Accession No. AY086786 (Jan. 27, 2006).
NCBI GenBank Accession No. AY092961 (Apr. 21, 2002).
NCBI GenBank Accession No. AF410323 (Aug. 27, 2001).
USPTO: Office Action regarding U.S. Appl. No. 16/265,525, dated Sep. 20, 2019.
Response to Office Action regarding U.S. Appl. No. 16/265,525, filed Nov. 19, 2019.
Supplemental Response to Office Action regarding U.S. Appl. No. 16/265,525, filed Nov. 27, 2019.
USPTO: Notice of Allowance regarding U.S. Appl. No. 16/265,525, dated Dec. 4, 2019.
U.S. Appl. No. 17/220,681, filed Apr. 1, 2021, Zhou et al.
U.S. Appl. No. 17/813,816, filed Jul. 20, 2022, Zhou et al.
U.S. Appl. No. 17/813,842, filed Jul. 20, 2022, Zhou et al.

* cited by examiner

| | | | | | | |
|---|---|---|---|---|---|---|
| SEQ ID NO: 85 | K H E A V M K R E R | A L A Y A F N Y Q Q | - - - - - - - - | - - - - - - - - | - - - - - - - | 253 |
| SEQ ID NO: 98 | L H S R R H A G G - | Y S P D F N G G D D | - - - - - - - - | - - - - - - - - | - - - - - - - | 309 |
| SEQ ID NO: 100 | L Q E T X X V S G - | T T A S G V - - - - | W R L P P L D G H G | - - W R N D F G | - - - - V S | 310 |
| SEQ ID NO: 88 | L E R Q S N Y S S - | C C T E S L G G E - | - - - M S P S S T S D | - - L R R W L R | | 355 |
| SEQ ID NO: 96 | S E Q R S T V S S - | S C A E S L G G E P | - - - A S P S S T T D | - - L R R W L R | | 361 |
| SEQ ID NO: 93 | S E Q R S T V S S L | S C A E S V G G E P | - - - V S P S S T T D | - - L R R W L R | | 373 |
| SEQ ID NO: 107 | S E Q R S N V S S - | S C A E S L G G D V | - - - V S P S S T T D | - - L R R W L R | | 291 |

| | | | | |
|---|---|---|---|---|
| SEQ ID NO:42 | F N R F A – – – – – | – – – – – – – – – – | – – – – – – – – – – | 517 |
| SEQ ID NO:47 | F G S E A A L H Q M | – – – – – – – – – – | – – – – – – – – – – | 476 |
| SEQ ID NO:44 | C S L P N W D R Q A | Q M E H Y T P I R – | – – – – – – – – – – | 450 |
| SEQ ID NO:54 | – – – – – – – – – – | F F K – – – – – – – | – – – – – – – – – – | 384 |
| SEQ ID NO:43 | – – – – – – – – – – | – – – – – – – – – – | – – – – – – – – – – | 383 |
| SEQ ID NO:41 | Y T S F F S S N P L | F F Q – – – – – – – | – – – – – – – – – – | 252 |
| SEQ ID NO:45 | H S S F L V – – – – | – – – – – – – – – – | – – – – – – – – – – | 403 |
| SEQ ID NO:60 | Y – – – – – – – – – | – – – – – – – – – – | – – – – – – – – – – | 477 |
| SEQ ID NO:69 | – – – – – – – – – – | – – – – – – – – – – | – – – – – – – – – – | 464 |
| SEQ ID NO:66 | – – – – – – – – – – | – – – – – – – – – – | – – – – – – – – – – | 457 |
| SEQ ID NO:68 | – – – – – – – – – – | – – – – – – – – – – | – – – – – – – – – – | 455 |

| | | | | | | | |
|---|---|---|---|---|---|---|---|
| SEQ·ID·NO·24 | PSYMAPTASA | KARIRGQGSP | RIAQEKP-EK | NGTTRRHSLP | PAANGKLSTM | | 558 |
| SEQ·ID·NO·33 | PSYMAATQSA | KAKLRGNSSP | KLSSDSA-EK | NGFTRRHSLP | SSNNGKMVSH | | 539 |
| SEQ·ID·NO·2 | PSYMAATESL | KAKLRAQNSP | RVDDSDSAEK | NGFTRRHSLP | SGTNS--- | | 561 |
| SEQ·ID·NO·19 | PSYMAAPTESA | KAKLRI--GPP | RLDDSDLPVDK | NGFTRRQSLP | SAANN--- | | 539 |
| SEQ·ID·NO·13 | PSYMAAPTESA | KAKLRGAQNSP | RLDSDSPADM | NGLNRRYSLP | TSTNN-I- | | 564 |
| SEQ·ID·NO·29 | PSYMAATESA | KAKLRGAQGSP | RFIPEAV-EK | NNHTRRHSLP | SSTNNTGSQ | | 513 |
| SEQ·ID·NO·8 | PSYMAAPTESA | KAKLRAQGGSP | RFGQDGS-ER | NNITRRHSLP | SSTNSKINSP | | 547 |
| SEQ·ID·NO·27 | PSYMAATESA | KAKLRMQGSP | RFSEDRV-EK | | SSTNSKI-SSE | | 570 |
| SEQ·ID·NO·24 | SPRAHRLLIA | SAKGSMNSDR | SFSSSKDIGG | KRFKPITIHK | PFCQFLLHYL | | 608 |
| SEQ·ID·NO·33 | SPRTQRPANA | GCKDGAKGDK | AMLSSRDASE | RPLKA--- | --- | | 574 |
| SEQ·ID·NO·2 | ---------- | ---------- | ---------- | RAI-KA--- | --- | | 566 |
| SEQ·ID·NO·19 | ---------- | ---------- | ---------- | RAI-KT--- | --- | | 544 |
| SEQ·ID·NO·13 | SPHTQRQVRV | AGKGAI-SDK | SQSSKDAND | RAI-RA--- | --- | | 569 |
| SEQ·ID·NO·29 | SPRTQRPVQS | GGGKGGHRSDR | TVSSSRDGNG | KVVRA--- | --- | | 548 |
| SEQ·ID·NO·8 | SPRTQRAVHG | SGGKGGNKSDK | SLLSSRDGNA | KVL-QA--- | --- | | 582 |
| SEQ·ID·NO·27 | ---------- | ---------- | ---------- | KGAQP--- | --- | | 605 |
| SEQ·ID·NO·24 | HPFNKFSSCL | YQTSRRKLSG | NGESTKAE-- | --- | --- | | 636 |
| SEQ·ID·NO·33 | ---------- | --EWRR---- | --- | --- | --- | | 578 |
| SEQ·ID·NO·2 | ---------- | --EWKR---- | --- | --- | --- | | 570 |
| SEQ·ID·NO·19 | ---------- | --EWRRW--- | --- | --- | --- | | 548 |
| SEQ·ID·NO·13 | ---------- | --EWRR---- | --- | --- | --- | | 574 |
| SEQ·ID·NO·29 | ---------- | --EWRR---- | --- | --- | --- | | 552 |
| SEQ·ID·NO·8 | ---------- | --EWRR---- | --- | --- | --- | | 586 |
| SEQ·ID·NO·27 | ---------- | --EWKRSWCS | SETWSIAGRE | YVD | | | 626 |

FIG. 5 (continued)

| SEQ·ID·NO·35 | MRGFPVPVTS | WSSAALLGRS | ISSARDAAEA | SSPITAAEMV | RVAKEVANAA | 50 |
| SEQ·ID·NO·36 | ———MESRL | LRSAALLARA | ARLARAAATS | TGRAVTAE—— | HLAEVVASAA | 43 |

| SEQ·ID·NO·35 | DACGVSGKKL | LEAAEALSRS | DTDAEPRRRA | AERIFDAASM | VAKEADASGA | 100 |
| SEQ·ID·NO·36 | GDRGFPSGAL | RQAALALARS | —SAPEARPRA | TAEVVRAAAM | VFRAAQEAGS | 92 |

| SEQ·ID·NO·35 | SGLSDAAQNL | TCATYAFSVA | ASGWGSLPES | STSGRDAGDL | LTEPLLGSCQ | 150 |
| SEQ·ID·NO·36 | PGVAEVAGDL | AHAAHDCVRA | ————LVES | GPAAERPRCL | LR——LWRRKN | 134 |

| SEQ·ID·NO·35 | DKNEKMTGEG | KDFSEM——— | RNSAADSSPL | QQSEIKESSL | FGKCKELLNY | 196 |
| SEQ·ID·NO·36 | RHNKNAAGEA | DLEAPLLHPH | ERPSSSSSPI | GASLSEIIEL | SESERDFINY | 184 |

| SEQ·ID·NO·35 | GFLGGPALLP | YL——GSGLRK | TVSPCSPSVF | HYIFSSWWIC | ————— | 235 |
| SEQ·ID·NO·36 | GMFGALAIFP | YLTRTGGLKS | AYSPLSPSTF | HIIFCTWWIC | VGLDVLCGNR | 234 |

| SEQ·ID·NO·35 | ————— | ————— | ————— | ————— | ————— | 235 |
| SEQ·ID·NO·36 | GRAMMKNILA | FILAFYARAS | ARLAILGVSL | LVILYSHLEL | APNEIYTLYI | 284 |

| SEQ·ID·NO·35 | VVGSHEQGDL | KILHIDRITS | HPND——K | 260 |
| SEQ·ID·NO·36 | LLGAATCMHL | LVWAMDYMSR | APGDAAD | 311 |

FIG. 6

SEQUENCE LISTING

```
<160> NUMBER OF SEQ ID NOS: 168

<210> SEQ ID NO 1
<211> LENGTH: 2343
<212> TYPE: DNA
<213> ORGANISM: Panicum virgatum
<220> FEATURE:
<221> NAME/KEY: misc_feature
<223> OTHER INFORMATION: Ceres CLONE ID no.1792354
<220> FEATURE:
<221> NAME/KEY: misc_feature
<223> OTHER INFORMATION: Encodes the peptide sequence at SEQ ID NO. 2

<400> SEQUENCE: 1
agtgactagt gagctcactc cctcctcctt cccacttgac tctgcccgcc agctactgaa      60
ccaaccaaca aatacctccg ggctccctcc ggctttgcca ctcccatgga ttggaggttg     120
gaggcctgaa gggggaggtg ggtcgccgga cagggacggg gagacggcga gagggcgttc     180
cgcaggagcc gttcccgtgc ttcctccacc gaccgggccg acgcgccgcg ccgctgtttc     240
aggttccaga atttcaagta ttggccgctt taggatacta tgggaaagtc cccggggaag     300
tggatcaagt ctgtgctctt ggggaagaaa tcgactaaat ccggttctac caaggcaaat     360
gagtcgaagg ctacaaataa caatggacac tcagctgggg aggagcgtgc attttctgaa     420
aattctccag tgatctctga gccggtgctt gttgaagccc acaaaaatgg agctgtttca     480
gttaatggga aggctgaaga tgtcaatttg ccaagtgaca gggctggcca acaagatctg     540
cagaaccaaa gtattgttga gtccgaaaca tcagttcctg ggcaattggg agaagaccaa     600
gctgcagtga aggcacaggc agcatttcgc ggttacctag cacgaaggtc attccgtgca     660
ttgaaaggta tcataagact ccaggtactg attcgagggc atcttgtaag gagacaggct     720
gtttcaaccc ttcgaactac ttggttgatt gtgaagtttc aatctctagt tcgtggaaga     780
aatgtcagac tctctggtgc tgacattcaa ctcaatgtga agcttggcca acataacctt     840
ggtggcacta gatcatctga tgcatggaaa gagaagttat cttcaaatgc ctatgttcgg     900
aagcttctgt cttcaccaat agtgctagaa cctcttcact tccagtatga caagagggat     960
cccaattcaa cctataactg gctagagaga tggaccatag gctgcatctg gaagcctgtt    1020
tttcaaccaa aaagagttcc tgatgggaaa ctgctggtaa ggaaggctag ttatgcaatg    1080
gaaactgaat cagccaagtt aaagcgcaac attaggaagg gctctgctgc tacagttgag    1140
agtttccata caagagtgac tggtgaatct gagaaactta aacgtaatcc aaagaaattc    1200
tcaaacttcc ctgctgactc agtaccagat agccagttat ctgaacttga gaaggttaaa    1260
aggaacctga ggaaggtaac tgattccatg gctgaagcct caaagatctc tagttccagg    1320
gttgattcct caaaggtatc tgattctaca cctgatgctc caaaagtatc taatcctgtg    1380
gccgaaatct caaagacatc tagtctcctg aacgggatct ctgaccatca agacagccaa    1440
tgtgaaaaag cactacagaa tacacgtgag gcttcatttc ctcttgaaac tcaagattac    1500
```

-continued

```
tctggcaatg gtcagctatt ggaatattca gatatggata acttcgactt ggtacctggt    1560
ttgaaaagtg atctggaaac tcagcttgat tcagtttcta taggagaaaa tgttgatgag    1620
cccactgttg gtgcttcagc agctgaaggt atgccactgc agaacattga tgagcccatt    1680
agtttaggga agaaagagga agcaaggtcc aaggaagagc atctgtctaa tggaagcctt    1740
agaactggca agagaaagtc ttcatcccca tacaaatcag aatatgtgga aaacgggact    1800
cacactactc ctgctcagcc aaggaagcca agctatatgg ctgcaacgga gtctgcgaag    1860
gcgaaattac gagcacagaa ttcacccagg gtggattctg attcatcagc agaaaagaat    1920
ggcttcactc gacgccactc tcttccttcc ggtacaaaca gtagggcgat caaagctgaa    1980
tggaagcgct gaggaggcat tgacttgaat tgaatagtgc gattgtctga atctctgctg    2040
ggtgaactct gccgctgctt gctccttttt atttatcctg cgatgtaaag agaagacatt    2100
gtccctgtat tgaacaatct ttgtgatgag tgcgtctggt tcagtctgtg gtaggttcac    2160
gtgccaggcc tagtgccccg ttcattgtat agtcacagtt ctctcgggat tgaaatcgat    2220
tcctcgtgta agctgatgtt aggactgcag tctgatcgaa taacatcatc cgcttgcaca    2280
ctgccttaag cccttaattg atatgatacc gggcaatttc gtgaaaaaaa aaaaaaaaa    2340
aaa                                                                  2343
```

<210> SEQ ID NO 2
<211> LENGTH: 570
<212> TYPE: PRT
<213> ORGANISM: Panicum virgatum
<220> FEATURE:
<221> NAME/KEY: misc_feature
<223> OTHER INFORMATION: Ceres CLONE ID no.1792354
<220> FEATURE:
<221> NAME/KEY: misc_feature
<223> OTHER INFORMATION: Score of 822.8 for HMM of FIGURE 5.
<220> FEATURE:
<221> NAME/KEY: misc_feature
<222> LOCATION: (106)..(126)
<223> OTHER INFORMATION: Pfam Name: IQ Pfam Description: IQ calmodulin-
      binding motif

<400> SEQUENCE: 2

```
Met Gly Lys Ser Pro Gly Lys Trp Ile Lys Ser Val Leu Leu Gly Lys
1               5                   10                  15

Lys Ser Thr Lys Ser Gly Ser Thr Lys Ala Asn Glu Ser Lys Ala Thr
            20                  25                  30

Asn Asn Asn Gly His Ser Ala Gly Glu Glu Arg Ala Phe Ser Glu Asn
        35                  40                  45

Ser Pro Val Ile Ser Glu Pro Val Leu Val Glu Ala His Lys Asn Gly
    50                  55                  60

Ala Val Ser Val Asn Gly Lys Ala Glu Asp Val Asn Leu Pro Ser Asp
65                  70                  75                  80

Arg Ala Gly Gln Gln Asp Leu Gln Asn Gln Ser Ile Val Glu Ser Glu
                85                  90                  95

Thr Ser Val Pro Gly Gln Leu Gly Glu Asp Gln Ala Ala Val Lys Ala
            100                 105                 110

Gln Ala Ala Phe Arg Gly Tyr Leu Ala Arg Arg Ser Phe Arg Ala Leu
        115                 120                 125

Lys Gly Ile Ile Arg Leu Gln Val Leu Ile Arg Gly His Leu Val Arg
    130                 135                 140

Arg Gln Ala Val Ser Thr Leu Arg Thr Thr Trp Leu Ile Val Lys Phe
145                 150                 155                 160
```

-continued

Gln Ser Leu Val Arg Gly Arg Asn Val Arg Leu Ser Gly Ala Asp Ile
            165                 170                 175

Gln Leu Asn Val Lys Leu Gly Gln His Asn Leu Gly Gly Thr Arg Ser
            180                 185                 190

Ser Asp Ala Trp Lys Glu Lys Leu Ser Ser Asn Ala Tyr Val Arg Lys
            195                 200                 205

Leu Leu Ser Ser Pro Ile Val Leu Glu Pro Leu His Phe Gln Tyr Asp
210                 215                 220

Lys Arg Asp Pro Asn Ser Thr Tyr Asn Trp Leu Glu Arg Trp Thr Ile
225                 230                 235                 240

Gly Cys Ile Trp Lys Pro Val Phe Gln Pro Lys Arg Val Pro Asp Gly
            245                 250                 255

Lys Leu Leu Val Arg Lys Ala Ser Tyr Ala Met Glu Thr Glu Ser Ala
            260                 265                 270

Lys Leu Lys Arg Asn Ile Arg Lys Gly Ser Ala Ala Thr Val Glu Ser
            275                 280                 285

Phe His Thr Arg Val Thr Gly Glu Ser Glu Lys Leu Lys Arg Asn Pro
            290                 295                 300

Lys Lys Phe Ser Asn Phe Pro Ala Asp Ser Val Pro Asp Ser Gln Leu
305                 310                 315                 320

Ser Glu Leu Glu Lys Val Lys Arg Asn Leu Arg Lys Val Thr Asp Ser
            325                 330                 335

Met Ala Glu Ala Ser Lys Ile Ser Ser Ser Arg Val Asp Ser Ser Lys
            340                 345                 350

Val Ser Asp Ser Thr Pro Asp Ala Pro Lys Val Ser Asn Pro Val Ala
            355                 360                 365

Glu Ile Ser Lys Thr Ser Ser Leu Leu Asn Gly Ile Ser Asp His Gln
            370                 375                 380

Asp Ser Gln Cys Glu Lys Ala Leu Gln Asn Thr Arg Glu Ala Ser Phe
385                 390                 395                 400

Pro Leu Glu Thr Gln Asp Tyr Ser Gly Asn Gly Gln Leu Leu Glu Tyr
            405                 410                 415

Ser Asp Met Asp Asn Phe Asp Leu Val Pro Gly Leu Lys Ser Asp Leu
            420                 425                 430

Glu Thr Gln Leu Asp Ser Val Ser Ile Gly Glu Asn Val Asp Glu Pro
            435                 440                 445

Thr Val Gly Ala Ser Ala Ala Glu Gly Met Pro Leu Gln Asn Ile Asp
450                 455                 460

Glu Pro Ile Ser Leu Gly Lys Lys Glu Glu Ala Arg Ser Lys Glu Glu
465                 470                 475                 480

His Leu Ser Asn Gly Ser Leu Arg Thr Gly Lys Arg Lys Ser Ser Ser
            485                 490                 495

Pro Tyr Lys Ser Glu Tyr Val Glu Asn Gly Thr His Thr Thr Pro Ala
            500                 505                 510

Gln Pro Arg Lys Pro Ser Tyr Met Ala Ala Thr Glu Ser Ala Lys Ala
            515                 520                 525

Lys Leu Arg Ala Gln Asn Ser Pro Arg Val Asp Ser Asp Ser Ser Ala
530                 535                 540

Glu Lys Asn Gly Phe Thr Arg Arg His Ser Leu Pro Ser Gly Thr Asn
545                 550                 555                 560

Ser Arg Ala Ile Lys Ala Glu Trp Lys Arg
            565                 570

-continued

```
<210> SEQ ID NO 3
<211> LENGTH: 2278
<212> TYPE: DNA
<213> ORGANISM: Gossypium hirsutum
<220> FEATURE:
<221> NAME/KEY: misc_feature
<223> OTHER INFORMATION: Ceres CLONE ID no.1925477
<220> FEATURE:
<221> NAME/KEY: misc_feature
<223> OTHER INFORMATION: Encodes the peptide sequence at SEQ ID NO 4

<400> SEQUENCE: 3
cccgctccat tgatgtcact aaccctaatt atacttacac acctacttct cttgtgattc      60
atttacaca tttaatttct gaaggccgtt ttcatctctt tcttagcttt tatttagttt     120
taaattcact ccaaaaaaaa aaaaaaaaac actgcacggg aatctcttgt tcgaggaatc     180
cttcacggta cgaaattcgt tcttcagatc tctgaatgct cactgtttaa ctgttccttg     240
gttttttctt ctggtaatgg cagcttagta gcgaacaagg acttcaaatt tgctgcattt     300
ttcagatttc cagatttaga aacttggaat tttaattatt tttgggtcta acggagatgg     360
gaaaatctcc agcaaaatgg atcaagacct tacttcttgg gaagaaatct tcaaagtcca     420
gtttctcaaa aggaaaagag aagctgaaat ctgcaaataa aggtgaggtt ttggtttctt     480
ccaaggtgac tgtgtctgac ctatcagtgg atcctccatc aatttcagca cctattctag     540
tgaatagcgc taggaatgtg gtggactctg agaagggtat acctgcccaa ttgccaaatg     600
atggggcaaa tattccatct ccaaaagtgg atggaaatga tgccacaact ggtaattttg     660
gtaacccaga aaatcctgat aggattgggc ttgacccagc tgctgtgacg gtacaggctg     720
ctttcagagg ttatctggct cgcagggcat ttcgaaccct caagggcatt ataaggctgc     780
aagcagttat tcgtggtcac ttggttagaa gacaagctgt tgctacttta tgctgtacat     840
ggggaattgt taagttgcaa gcactagctc gtggtcaaaa ggtcagatgt tcagatattg     900
ccatggaaat acaagaaaaa catctaagac tgcttcaggg ttctaaaagc tcggattcta     960
ttggagtgag cacatcttct aaggtgaaga atttatcaaa taatgtgttt gttcagaagc    1020
ttttggcctc atcaccttct gtattacctc tacaacttca atatgttcca gaggagccta    1080
actcatcctg gcagtggctt ctacgatgga caatgtcaca ttttttgggta tccccttta    1140
aaccagttag gagtggaaag acaaaacgaa gtattcagaa actgtccaat gcaaaagttg    1200
ttaatggatc tagtcattct accttggagc atgaaaaaaa caaacgaggt gtgaggagag    1260
tttctggcaa ctcagcagca gattcagttc ggaagcatcc acaaaatgag cttgagaggg    1320
ttaagcgcag tttacgaaag ctttctgact cttcaaagga ggtttctgat aagtctgaag    1380
tttttaatga gaaaacaaag aagactccga aaaaaacttc taattctaat gaccctgatt    1440
tttcagaaca ggaatccgct gagaagataa gagatgtgac tgcaacacta tcagaactgt    1500
caattcttga ggcagatctg aaaatttccc tagaagatcc ttctcttggt gagcctaatc    1560
tctgtcctgc agttgatttg tcacctgctg aaaacaatcg taaacttgag gtaatagagg    1620
agttaatctc taaagacaag caggttggtg atgagagctc aaacacaagc caaagaagag    1680
cttctttccc tgcaaaaatt gataatcagg cgaatgggtt aaatctcatg ccaaaagtgc    1740
ccagttatat ggcagcaact gaatctgcaa aagctagact taggggtcaa ggctccccaa    1800
tgtttacccc ggaggctgtt gagaaaaatg ggttaaacag gcgatattct ctgccatctt    1860
caacctatag taatacaagt tcacagtccc cacatggtca aagacgggtt cgagtagctg    1920
gcaaaggtgc taacatcagt gacaaatctc aatcatcctc taaagatgct aatgataagg    1980
```

-continued

```
ttgtcagagc tgagtggagg aggtaattct tgcatgggga attgtttcga tgaagtttcc      2040
atggagtttg tgcacggatg ctacttaaca aaacttccct tatgtgttgt aaacttctga      2100
tgtttggttg tagaagcagg agagtgaatc atctaatctt tgttgcttg gtgtatcttt       2160 ttaagtttcc ttggcacttt caggtttgta gatgggtaaa tatttgtaga tgttacagtt     2220
ggttatttgg tttatttggt tcgtttgtgt ttgtacgcaa aaaaaaaaaa aaaaaaa         2278
```

<210> SEQ ID NO 4
<211> LENGTH: 549
<212> TYPE: PRT
<213> ORGANISM: Gossypium hirsutum
<220> FEATURE:
<221> NAME/KEY: misc_feature
<223> OTHER INFORMATION: Ceres CLONE ID no.1925477
<220> FEATURE:
<221> NAME/KEY: misc_feature
<223> OTHER INFORMATION: Score of 1112.9 for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (113)..(133)
<223> OTHER INFORMATION: Pfam Name: IQ Pfam Description: IQ calmodulin-
    binding motif

<400> SEQUENCE: 4

```
Met Gly Lys Ser Pro Ala Lys Trp Ile Lys Thr Leu Leu Gly Lys
1               5                   10                  15

Lys Ser Ser Lys Ser Ser Phe Ser Lys Gly Lys Glu Lys Leu Lys Ser
            20                  25                  30

Ala Asn Lys Gly Glu Val Leu Val Ser Ser Lys Val Thr Val Ser Asp
        35                  40                  45

Leu Ser Val Asp Pro Pro Ser Ile Ser Ala Pro Ile Leu Val Asn Ser
    50                  55                  60

Ala Arg Asn Val Val Asp Ser Glu Lys Gly Ile Pro Ala Gln Leu Pro
65                  70                  75                  80

Asn Asp Gly Ala Asn Ile Pro Ser Pro Lys Val Asp Gly Asn Asp Ala
                85                  90                  95

Thr Thr Gly Asn Phe Gly Asn Pro Glu Asn Pro Asp Arg Ile Gly Leu
            100                 105                 110

Asp Pro Ala Ala Val Thr Val Gln Ala Ala Phe Arg Gly Tyr Leu Ala
        115                 120                 125

Arg Arg Ala Phe Arg Thr Leu Lys Gly Ile Ile Arg Leu Gln Ala Val
    130                 135                 140

Ile Arg Gly His Leu Val Arg Arg Gln Ala Val Ala Thr Leu Cys Cys
145                 150                 155                 160

Thr Trp Gly Ile Val Lys Leu Gln Ala Leu Ala Arg Gly Gln Lys Val
                165                 170                 175

Arg Cys Ser Asp Ile Ala Met Glu Ile Gln Glu Lys His Leu Arg Leu
            180                 185                 190

Leu Gln Gly Ser Lys Ser Ser Asp Ser Ile Gly Val Ser Thr Ser Ser
        195                 200                 205

Lys Val Lys Asn Leu Ser Asn Asn Val Phe Val Gln Lys Leu Leu Ala
    210                 215                 220

Ser Ser Pro Ser Val Leu Pro Leu Gln Leu Gln Tyr Val Pro Glu Glu
225                 230                 235                 240

Pro Asn Ser Ser Trp Gln Trp Leu Leu Arg Trp Thr Met Ser His Phe
```

```
                    245                 250                 255
Trp Val Ser Pro Leu Lys Pro Val Arg Ser Gly Lys Thr Lys Arg Ser
                260                 265                 270

Ile Gln Lys Leu Ser Asn Ala Lys Val Val Asn Gly Ser Ser His Ser
            275                 280                 285

Thr Leu Glu His Glu Lys Asn Lys Arg Gly Val Arg Val Ser Gly
    290                 295                 300

Asn Ser Ala Ala Asp Ser Val Arg Lys His Pro Gln Asn Glu Leu Glu
305                 310                 315                 320

Arg Val Lys Arg Ser Leu Arg Lys Leu Ser Asp Ser Ser Lys Glu Val
                325                 330                 335

Ser Asp Lys Ser Glu Val Phe Asn Glu Lys Thr Lys Thr Pro Lys
            340                 345                 350

Lys Thr Ser Asn Ser Asn Asp Pro Asp Phe Ser Glu Gln Glu Ser Ala
                355                 360                 365

Glu Lys Ile Arg Asp Val Thr Ala Thr Leu Ser Glu Leu Ser Ile Leu
    370                 375                 380

Glu Ala Asp Leu Lys Ile Ser Leu Glu Asp Pro Ser Leu Gly Glu Pro
385                 390                 395                 400

Asn Leu Cys Pro Ala Val Asp Leu Ser Pro Ala Glu Asn Asn Arg Lys
                405                 410                 415

Leu Glu Val Ile Glu Glu Leu Ile Ser Lys Asp Lys Gln Val Gly Asp
            420                 425                 430

Glu Ser Ser Asn Thr Ser Gln Arg Arg Ala Ser Phe Pro Ala Lys Ile
                435                 440                 445

Asp Asn Gln Ala Asn Gly Leu Asn Leu Met Pro Lys Val Pro Ser Tyr
450                 455                 460

Met Ala Thr Glu Ser Ala Lys Ala Arg Leu Arg Gly Gln Gly Ser
465                 470                 475                 480

Pro Met Phe Thr Pro Glu Ala Val Glu Lys Asn Gly Leu Asn Arg Arg
                485                 490                 495

Tyr Ser Leu Pro Ser Ser Thr Tyr Ser Asn Thr Ser Ser Gln Ser Pro
            500                 505                 510

His Gly Gln Arg Arg Val Arg Val Ala Gly Lys Gly Ala Asn Ile Ser
    515                 520                 525

Asp Lys Ser Gln Ser Ser Ser Lys Asp Ala Asn Asp Lys Val Val Arg
530                 535                 540

Ala Glu Trp Arg Arg
545

<210> SEQ ID NO 5
<211> LENGTH: 1908
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1521592
<220> FEATURE:
<221> NAME/KEY: misc_feature
<223> OTHER INFORMATION: Encodes the peptide sequence at SEQ ID NO 6

<400> SEQUENCE: 5
atggggagaa aatcacctgc gaaatggata aagactgttt tgtttggaaa gaagtcttcc      60
aaatctctta ttgtcaaagg aagggagaga actgtgaatg acaaagagac attggttgct     120
gtcagagccg tggaagctga gtgtgacctca gttcctccgg tggtcaagcc gacagccccc     180
```

-continued

| | |
|---|---|
| actaccacta atatcactga aaggatgtta gagctagaga gcagggaaac tacagaatca | 240 |
| tcacgtgatg gaggtatatt gtcaactgga aatcaagatg caaatcattc tcaattatac | 300 |
| actcctgatg ctcctccatc tgatgctgac aaaataaggc ttgatgaagc tgcgacaatg | 360 |
| gcacaagccg catttagggg ttacttggct cgccgagcat ttcgagctct taaaggcata | 420 |
| ataaggcttc aggctcttat ccgtggacac ttggttagaa ggcaagctgt tgctactctc | 480 |
| tgctgtgtgc tcggagttgt caagttacag gctcttgctc gaggaagaat ggttaggaat | 540 |
| tcagagattg gctatgaggt tcataaatta tgcagccaag taaaactgcc ggagggcaag | 600 |
| cttgcagatt ctagtggagt tggtatacaa atggccaagc tgtcatcaaa tgcttttgtt | 660 |
| cgcaagcttc ttgctccatc acctgctgta atgcctttgc aactcccta tgattccatg | 720 |
| gaaccaaact cagttgcaaa ctggttagag tgctggtcag cgtcctcttt ctggaaacca | 780 |
| gttccccaac caaaaaaaat tacttgctca aaaactcaga gaaagcagag taatggtcaa | 840 |
| atagtggaag ctgaaactgg taggccaaag cgcactgttc ggagggtccc tgctgcaaat | 900 |
| gttgacagta cctcagtaca agcagcctct gaatttgaga acccaagcg caatttgagg | 960 |
| aaagtttcaa gccatccagc tgattcagca gaaaattcac agattgagct tgaaaaggta | 1020 |
| aagcgcagct aagaaaggt taataacccc gttatagaaa actctgctca ttcagaggtt | 1080 |
| gaaaatgaaa agccaaagca aggtctagaa aaggtatctg gcacttcagg tgataatgtt | 1140 |
| ttgggatgga gcgtaagtaa ttcagctgag aagatgaaga agaagctac cttgacaaca | 1200 |
| tccaatgtac ctgatgtggt gaagaatgat ccaaacttga tgtccaagtt gcctgatgca | 1260 |
| gagacagctg atgaacctgt agaaatgatc aaggcattgg aatcatcaca tgacgatcaa | 1320 |
| gctgtggtag aatctaaagc ttcagtagat actggtggta tagttgagaa tatgcaaata | 1380 |
| aatgggaagt ccatacacca ggatgatcca acaagcaatg aaaatcacaa aactgccaag | 1440 |
| aaaccttcat tcacaatgaa accagaacgt gccgagaatg ggctacagag cagtcccacc | 1500 |
| ctccctagct acatggcagc aactgaatct gcaaaggcaa agctgagaat gcaaggctcc | 1560 |
| ccaagattta gtgaagatcg agttgagaaa ataacatca cccgtcgtca ttctctgccc | 1620 |
| tcttcaacta atagcaaaat cagctccgag tccccgagga cacaaagagc agttcatggt | 1680 |
| agtggcaaag gggggaataa gagtgacaag tctttattgt cttcaagaga tggaaatgct | 1740 |
| aagggagccc aaccagagtg gaagagatca tggtgtagca gtgaaacatg gtctatagcc | 1800 |
| ggaaggggg gaataaagag aaaagaagga aaaaaaaata aaagtccacc aatgacaaac | 1860 |
| caacccccta acattgacac gcgtcgcccc aaaataaaga ggacatga | 1908 |

<210> SEQ ID NO 6
<211> LENGTH: 589
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1521592
<220> FEATURE:
<221> NAME/KEY: misc_feature
<223> OTHER INFORMATION: Score of 1414.1 for HMM of FIGURE 5.
<220> FEATURE:
<221> NAME/KEY: misc_feature
<223> OTHER INFORMATION: Functional Homolog Of Ceres CLONE ID no.
       1792354 at SEQ ID NO. 2
<220> FEATURE:
<221> NAME/KEY: misc_feature
<222> LOCATION: (115)..(135)
<223> OTHER INFORMATION: Pfam Name: IQ Pfam Description: IQ calmodulin-
       binding motif

```
<400> SEQUENCE: 6

Met Gly Arg Lys Ser Pro Ala Lys Trp Ile Lys Thr Val Leu Phe Gly
1               5                   10                  15

Lys Lys Ser Ser Lys Ser Leu Ile Val Lys Gly Arg Glu Arg Thr Val
            20                  25                  30

Asn Asp Lys Glu Thr Leu Val Ala Val Arg Ala Val Glu Ala Asp Val
        35                  40                  45

Thr Ser Val Pro Pro Val Val Lys Pro Thr Ala Pro Thr Thr Thr Asn
50                  55                  60

Ile Thr Glu Arg Met Leu Glu Leu Glu Ser Arg Glu Thr Thr Glu Ser
65                  70                  75                  80

Ser Arg Asp Gly Gly Ile Leu Ser Thr Gly Asn Gln Asp Ala Asn His
                85                  90                  95

Ser Gln Leu Tyr Thr Pro Asp Ala Pro Ser Asp Ala Asp Lys Ile
            100                 105                 110

Arg Leu Asp Glu Ala Ala Thr Met Ala Gln Ala Ala Phe Arg Gly Tyr
        115                 120                 125

Leu Ala Arg Arg Ala Phe Arg Ala Leu Lys Gly Ile Ile Arg Leu Gln
    130                 135                 140

Ala Leu Ile Arg Gly His Leu Val Arg Arg Gln Ala Val Ala Thr Leu
145                 150                 155                 160

Cys Cys Val Leu Gly Val Val Lys Leu Gln Ala Leu Ala Arg Gly Arg
                165                 170                 175

Met Val Arg Asn Ser Glu Ile Gly Tyr Glu Val His Lys Leu Cys Ser
            180                 185                 190

Gln Val Lys Leu Pro Glu Gly Lys Leu Ala Asp Ser Ser Gly Val Gly
        195                 200                 205

Ile Gln Met Ala Lys Leu Ser Ser Asn Ala Phe Val Arg Lys Leu Leu
    210                 215                 220

Ala Pro Ser Pro Ala Val Met Pro Leu Gln Leu Pro Tyr Asp Ser Met
225                 230                 235                 240

Glu Pro Asn Ser Val Ala Asn Trp Leu Glu Cys Trp Ser Ala Ser Ser
                245                 250                 255

Phe Trp Lys Pro Val Pro Gln Pro Lys Lys Ile Thr Cys Ser Lys Thr
            260                 265                 270

Gln Arg Lys Gln Ser Asn Gly Gln Ile Val Glu Ala Glu Thr Gly Arg
        275                 280                 285

Pro Lys Arg Thr Val Arg Arg Val Pro Ala Ala Asn Val Asp Ser Thr
    290                 295                 300

Ser Val Gln Ala Ala Ser Glu Phe Glu Lys Pro Lys Arg Asn Leu Arg
305                 310                 315                 320

Lys Val Ser Ser His Pro Ala Asp Ser Ala Glu Asn Ser Gln Ile Glu
                325                 330                 335

Leu Glu Lys Val Lys Arg Ser Leu Arg Lys Val Asn Asn Pro Val Ile
            340                 345                 350

Glu Asn Ser Ala His Ser Glu Val Asn Glu Lys Pro Lys Gln Gly
        355                 360                 365

Leu Glu Lys Val Ser Gly Thr Ser Gly Asp Asn Val Leu Gly Trp Ser
    370                 375                 380

Val Ser Asn Ser Ala Glu Lys Met Lys Lys Glu Ala Thr Leu Thr Thr
385                 390                 395                 400

Ser Asn Val Pro Asp Val Val Lys Asn Asp Pro Asn Leu Met Ser Lys
                405                 410                 415

Leu Pro Asp Ala Glu Thr Ala Asp Glu Pro Val Glu Met Ile Lys Ala
            420                 425                 430
```

Leu Glu Ser Ser His Asp Asp Gln Ala Val Val Glu Ser Lys Ala Ser
        435                 440                 445

Val Asp Thr Gly Gly Ile Val Glu Asn Met Gln Ile Asn Gly Lys Ser
    450                 455                 460

Ile His Gln Asp Asp Pro Thr Ser Asn Glu Asn His Lys Thr Ala Lys
465                 470                 475                 480

Lys Pro Ser Phe Thr Met Lys Pro Glu Arg Ala Glu Asn Gly Leu Gln
                485                 490                 495

Ser Ser Pro Thr Leu Pro Ser Tyr Met Ala Ala Thr Glu Ser Ala Lys
            500                 505                 510

Ala Lys Leu Arg Met Gln Gly Ser Pro Arg Phe Ser Glu Asp Arg Val
        515                 520                 525

Glu Lys Asn Asn Ile Thr Arg Arg His Ser Leu Pro Ser Ser Thr Asn
    530                 535                 540

Ser Lys Ile Ser Ser Glu Ser Pro Arg Thr Gln Arg Ala Val His Gly
545                 550                 555                 560

Ser Gly Lys Gly Gly Asn Lys Ser Asp Lys Ser Leu Leu Ser Ser Arg
                565                 570                 575

Asp Gly Asn Ala Lys Gly Ala Gln Pro Glu Trp Lys Arg
            580                 585

<210> SEQ ID NO 7
<211> LENGTH: 2059
<212> TYPE: DNA
<213> ORGANISM: Glycine max
<220> FEATURE:
<221> NAME/KEY: misc_feature
<223> OTHER INFORMATION: Ceres CLONE ID no.463594
<220> FEATURE:
<221> NAME/KEY: misc_feature
<223> OTHER INFORMATION: Encodes the peptide sequence at SEQ ID NO 8

<400> SEQUENCE: 7
attgtttggt tctggttctc aggaatggta gatttgaggt gaagacgttc cacattggtc    60
aggtcccgat ctcacgatgg ggaagtcacc aggaaaatgg atcaaaactg tactgttcgg   120
gaaaaagtca tctaaatcaa atatttcaaa aggcagagag aagcttgtta atcaaaaagg   180
agtagtagtt acctccaagg tgccagaaac tggtttggct ttagaaccaa cctccgatac   240
tattgccaga catgaggaag atccagagct ggaaaataaa gaagcagaaa atgttttacc   300
cgggaatcaa gaaatagaca cagtgggatc aattaatgaa gatgctgcac tagatccaga   360
gaaaatgagc tggaggaag cagctacaaa ggcacaagct gctttcaggg gttatttggc   420
tcggagagca tttagggctc taaaaggaat aataaggttg caagcactca tccgtgggca   480
cttggttagg agacaagctg ttgttacatt atgctcaatg tatggtattg tcaagtttca   540
agcacttgtt cgtggaggaa tagttagaca gtctaatgtt ggatctgaaa tccatgagaa   600
gtccaatata ttgaaccctc tggatggcaa gcttgtcaag ccaaatgcta tgttcacgaa   660
aattaccaag ctgtctgcaa atgctttcat tcggaagctt cttacttcgt caactacaat   720
aatggcgctg cggttgcaat atgttcccgg cgatccaaat tcagtcctaa gttggttgga   780
gcgctggtca gcatctcact tttgaaacc agttccccaa cccaagaaaa ttcgagatac   840
taagtctcag agaaagcatg caatatttc agttggagat actcatgtga gcaagtcaaa   900
acgaatcaac aggaagcttc ctactgcaag ttttgactcg gtcccagtgc aagcaaatcc   960
tgaatttgaa aaaccaaaac gaaacacaag gaaaatttca aaccaatcct cagatcctca  1020

-continued

```
tgtgcaggaa aacccacaaa gtgagcttga aaagattaaa cgtaacttga gaaaggttta    1080
taacccagtt gttgagaatg ctgttccgtc agaagttgaa tccgaaatgc caaaggatca    1140
tttggaaaag gtaacagtta cctcatgcct tgctgtttca gagcaagagg tcattagttc    1200
taatgagaag atcaagaagg aagcaatatt aactgtttcc agtgtgccag atatagaaac    1260
tactccaaga ctttcagtta gtaaggaggt gtctgacaca ccaagcagtt atcaagtgac    1320
tgtggaatca aaaccattga ctgagattac aactaaagat aaaaacattt ctgtttctga    1380
cgaagtaaaa aatgagccca tagatttacc agagcctatt tgtaaagatg aaaattctca    1440
cttaacaaat ggagatttga gtcacaagga agatcaaata ggcagtgaaa accagaaacc    1500
aaaccaaaaa gcctcaattg tagcaaagca ggaacgtgca gagaatggta tacagaatag    1560
tccaacatta ccgagttaca tggcagcaac tgaatctgca aaggcaaagt tgagggcaca    1620
aggatcccca agatttggac aggatggaag tgaaagaaac aaccatactc ggcgacattc    1680
tctgccatcc tcaactaaca gcaaaattaa ttcaccttca cctaggcaca agagaccagt    1740
tcaatcaggt ggcaaaggtg gccacagaag tgacagaact gtatcatctt ctagagatgg    1800
gaatggaaag gtaattcaag cagagtggag gcggtaattt gaggaaggcc gatgttctgg    1860
aggaacatga ggagggcgaa accgtgtgtg gtttatatgt atctttgatg agaattgttg    1920
aatggatagg actataggtg tgcttgaatt caggttattt cttcatttgc tgcattttgg    1980
gctttgaggg tgatttgtac attataggtt tctagttttg catgatgcaa ctataactaa    2040
atttaattat gttttaagc                                                 2059
```

<210> SEQ ID NO 8
<211> LENGTH: 586
<212> TYPE: PRT
<213> ORGANISM: Glycine max
<220> FEATURE:
<221> NAME/KEY: misc_feature
<223> OTHER INFORMATION: Ceres CLONE ID no.463594
<220> FEATURE:
<221> NAME/KEY: misc_feature
<223> OTHER INFORMATION: Score of 730.7 for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (100)..(120)
<223> OTHER INFORMATION: Pfam Name: IQ Pfam Description: IQ calmodulin-
    binding motif

<400> SEQUENCE: 8

```
Met Gly Lys Ser Pro Gly Lys Trp Ile Lys Thr Val Leu Phe Gly Lys
1               5                   10                  15

Lys Ser Ser Lys Ser Asn Ile Ser Lys Gly Arg Glu Lys Leu Val Asn
            20                  25                  30

Gln Lys Gly Val Val Val Thr Ser Lys Val Pro Glu Thr Gly Leu Ala
        35                  40                  45

Leu Glu Pro Thr Ser Asp Thr Ile Ala Arg His Glu Glu Asp Pro Glu
    50                  55                  60

Leu Glu Asn Lys Glu Ala Glu Asn Val Leu Pro Gly Asn Gln Glu Ile
65                  70                  75                  80

Asp Thr Val Gly Ser Ile Asn Glu Asp Ala Ala Leu Asp Pro Glu Lys
                85                  90                  95

Met Arg Leu Glu Glu Ala Ala Thr Lys Ala Gln Ala Ala Phe Arg Gly
            100                 105                 110
```

Tyr Leu Ala Arg Arg Ala Phe Arg Ala Leu Lys Gly Ile Ile Arg Leu
            115                 120                 125

Gln Ala Leu Ile Arg Gly His Leu Val Arg Gln Ala Val Val Thr
        130                 135                 140

Leu Cys Ser Met Tyr Gly Ile Val Lys Phe Gln Ala Leu Val Arg Gly
145                 150                 155                 160

Gly Ile Val Arg Gln Ser Asn Val Gly Ser Glu Ile His Glu Lys Ser
                165                 170                 175

Asn Ile Leu Asn Pro Leu Asp Gly Lys Leu Val Lys Pro Asn Ala Met
            180                 185                 190

Phe Thr Lys Ile Thr Lys Leu Ser Ala Asn Ala Phe Ile Arg Lys Leu
        195                 200                 205

Leu Thr Ser Ser Thr Thr Ile Met Ala Leu Arg Leu Gln Tyr Val Pro
    210                 215                 220

Gly Asp Pro Asn Ser Val Leu Ser Trp Leu Glu Arg Trp Ser Ala Ser
225                 230                 235                 240

His Phe Trp Lys Pro Val Pro Gln Pro Lys Lys Ile Arg Asp Thr Lys
                245                 250                 255

Ser Gln Arg Lys His Gly Asn Ile Ser Val Gly Asp Thr His Val Ser
            260                 265                 270

Lys Ser Lys Arg Ile Asn Arg Lys Leu Pro Thr Ala Ser Phe Asp Ser
        275                 280                 285

Val Pro Val Gln Ala Asn Pro Glu Phe Glu Lys Pro Lys Arg Asn Thr
    290                 295                 300

Arg Lys Ile Ser Asn Gln Ser Ser Asp Pro His Val Gln Glu Asn Pro
305                 310                 315                 320

Gln Ser Glu Leu Glu Lys Ile Lys Arg Asn Leu Arg Lys Val Tyr Asn
                325                 330                 335

Pro Val Val Glu Asn Ala Val Pro Ser Glu Val Glu Ser Glu Met Pro
            340                 345                 350

Lys Asp His Leu Glu Lys Val Thr Val Thr Ser Cys Leu Ala Val Ser
        355                 360                 365

Glu Gln Glu Val Ile Ser Ser Asn Glu Lys Ile Lys Lys Glu Ala Ile
    370                 375                 380

Leu Thr Val Ser Ser Val Pro Asp Ile Glu Thr Thr Pro Arg Leu Ser
385                 390                 395                 400

Val Ser Lys Glu Val Ser Asp Thr Pro Ser Ser Tyr Gln Val Thr Val
                405                 410                 415

Glu Ser Lys Pro Leu Thr Glu Ile Thr Thr Lys Asp Lys Asn Ile Ser
            420                 425                 430

Val Ser Asp Glu Val Lys Asn Glu Pro Ile Asp Leu Pro Glu Pro Ile
        435                 440                 445

Cys Lys Asp Glu Asn Ser His Leu Thr Asn Gly Asp Leu Ser His Lys
    450                 455                 460

Glu Asp Gln Ile Gly Ser Glu Asn Gln Lys Pro Asn Gln Lys Ala Ser
465                 470                 475                 480

Ile Val Ala Lys Gln Glu Arg Ala Glu Asn Gly Ile Gln Asn Ser Pro
                485                 490                 495

Thr Leu Pro Ser Tyr Met Ala Ala Thr Glu Ser Ala Lys Ala Lys Leu
            500                 505                 510

Arg Ala Gln Gly Ser Pro Arg Phe Gly Gln Asp Gly Ser Glu Arg Asn
        515                 520                 525

```
Asn His Thr Arg Arg His Ser Leu Pro Ser Ser Thr Asn Ser Lys Ile
    530                 535                 540

Asn Ser Pro Ser Pro Arg Thr Gln Arg Pro Val Gln Ser Gly Gly Lys
545                 550                 555                 560

Gly Gly His Arg Ser Asp Arg Thr Val Ser Ser Ser Arg Asp Gly Asn
                565                 570                 575

Gly Lys Val Ile Gln Ala Glu Trp Arg Arg
                580                 585

<210> SEQ ID NO 9
<211> LENGTH: 587
<212> TYPE: PRT
<213> ORGANISM: Arabidopsis thaliana
<220> FEATURE:
<221> NAME/KEY: misc_feature
<223> OTHER INFORMATION: Public GI ID no.22330633
<220> FEATURE:
<221> NAME/KEY: misc_feature
<223> OTHER INFORMATION: Score of 545.5 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (113)..(132)
<223> OTHER INFORMATION: Pfam Name: IQ Pfam Description: IQ calmodulin-
      binding motif

<400> SEQUENCE: 9

Met Gly Lys Ser Thr Lys Trp Leu Lys Asn Val Leu Gly Lys Lys
1               5                   10                  15

Thr Ser Lys Ser Ser Gly Ser Lys Asp Lys Glu Arg Val Val Ser Gly
                20                  25                  30

Lys Glu Val Leu Val Thr Ser Lys Val Glu Glu Ser Asp Val Val Ser
                35                  40                  45

Asp Leu Pro Ser Phe Glu Val Ala Glu Thr Asn Thr Val Asp Arg Ser
    50                  55                  60

Gly Gly Met Leu Glu Thr Gln Asn Val Gly Pro Glu Glu Ile Ser Asp
65                  70                  75                  80

Asp Glu Ile Glu Leu Pro Gly Lys Ser Thr Asp Ser Gln Asn Val
                85                  90                  95

Ala Pro Val Gln Asp His Ser Leu Ser Asp Ala Glu Arg Ile Gln Arg
                100                 105                 110

Glu Ile Ala Ala Thr Ser Val Gln Ala Ala Phe Arg Gly Tyr Leu Ala
                115                 120                 125

Arg Arg Ala Phe Trp Ala Leu Lys Gly Ile Ile Arg Leu Gln Ala Leu
    130                 135                 140

Ile Arg Gly His Leu Val Arg Arg Gln Ala Ala Thr Leu Phe Ser
145                 150                 155                 160

Val Met Gly Ile Val Arg Leu Gln Ala Phe Ala Arg Gly Arg Glu Ile
                165                 170                 175

Arg Lys Ser Asp Ile Gly Val Gln Val Tyr Arg Lys Cys Arg Leu Gln
                180                 185                 190

Leu Leu Gln Gly Asn Lys Leu Ala Asn Pro Thr Asp Ala Tyr Leu Gly
                195                 200                 205

Ile Lys Lys Leu Thr Ala Asn Ala Phe Ala Gln Lys Leu Leu Ala Ser
    210                 215                 220

Ser Pro Lys Val Leu Pro Val His Ala Tyr Asp Thr Ser Asn Pro Asn
225                 230                 235                 240
```

```
Ser Asn Leu Ile Trp Leu Glu Asn Trp Ser Ala Ser Cys Phe Trp Lys
            245                 250                 255

Pro Val Pro Gln Pro Lys Lys Thr Ile Ser Arg Lys Pro Gln Asn Arg
        260                 265                 270

Leu Leu Val Glu Ala Glu Ser Ala Lys Pro Lys Lys Ser Val Arg Lys
    275                 280                 285

Val Pro Ala Ser Asn Phe Glu Ser Ser Val Gln Thr Ser Phe Glu
290                 295                 300

Phe Glu Lys Pro Lys Arg Ser Phe Arg Lys Val Ser Ser Gln Ser Ile
305                 310                 315                 320

Glu Pro Pro Ala Val Glu Asp Pro Gln Ile Glu Leu Glu Lys Val Lys
                325                 330                 335

Arg Ser Leu Arg Lys Val His Asn Pro Val Val Glu Ser Ser Ile Gln
            340                 345                 350

Pro Gln Arg Ser Pro Arg Lys Glu Val Glu Lys Pro Lys Leu Gly Val
        355                 360                 365

Glu Lys Thr Arg Glu Ser Ser Tyr Pro Leu Val His Glu Thr Ala Glu
    370                 375                 380

Glu Pro Val Asn Val Cys Asp Glu Lys Lys Gln Glu Ile Ser Glu
385                 390                 395                 400

Gln Pro Glu Glu Val His Ala Leu Glu Met Glu Val His Thr Pro
                405                 410                 415

Gly Pro Leu Glu Thr Asn Glu Ala Leu Asp Ser Ser Leu Val Asn Gln
            420                 425                 430

Ile Asp Ser Asn Glu Lys Ala Met Val Glu Glu Lys Pro Ser Met Glu
        435                 440                 445

Lys Asp Thr Lys Glu Glu Lys Thr Pro Lys Pro Asn Asn Lys Glu Asn
    450                 455                 460

Ser Ala Gly Lys Glu Asn Gln Lys Ser Arg Lys Lys Gly Ser Ala Thr
465                 470                 475                 480

Ser Lys Thr Glu Arg Glu Glu Ser Asn Gly His His Glu Thr Ser Pro
                485                 490                 495

Ser Ile Pro Ser Tyr Met Gln Ala Thr Lys Ser Ala Lys Ala Lys Leu
            500                 505                 510

Arg Leu Gln Gly Ser Pro Lys Ser Ala Glu Gln Asp Gly Thr Glu Lys
        515                 520                 525

Ala Thr Val Pro Arg Arg His Ser Leu Pro Ser Pro Gly Asn Gly Arg
    530                 535                 540

Ile Thr Ser His Ser Pro Arg Thr Thr Arg Leu Ala Asn Ser Gly Asp
545                 550                 555                 560

Lys Thr Gly Asn Lys Lys Glu Lys Pro Leu Leu Ser Ser Arg Glu Gly
                565                 570                 575

Asn Ala Lys Thr Thr Pro Ala Glu Arg Lys Arg
            580                 585

<210> SEQ ID NO 10
<211> LENGTH: 2049
<212> TYPE: DNA
<213> ORGANISM: Zea mays
<220> FEATURE:
<221> NAME/KEY: misc_feature
<223> OTHER INFORMATION: Ceres CLONE ID no.345954
<220> FEATURE:
<221> NAME/KEY: misc_feature
<223> OTHER INFORMATION: Encodes the peptide sequence at SEQ ID NO 11
```

<400> SEQUENCE: 10

```
gttttcgcc gagcagttcg cgtgctcccc tccacaggcc gacgcggcga cgccgctgtt      60
tcaggttctg gaatttccag tgcgggtgca ttaggctgct atgggcaagt cgccggggaa    120
gtggatcaaa tcggtgcttt tggggaagaa atctaccaag tcaggtccta ccaagtcgaa    180
tgaatctaag gctgacaaca acagatactc gaccggggag gaccgcacat tgtctgagag    240
ttctcctgtg atttctgagc cggtactagt taacatccac aagaacgtag ctatcaatgg    300
gaaggctgca gatgccagtg atagggcacg gcaacaagat ccgcagagcc aaagcgttgt    360
tgagtccaga tcatcggctc cagctgctca gctgggagaa gatcaagctg cagcgaaggc    420
acaggcagcc tttcgtggtt acctggcacg aaggtcattc cgtgcattaa aaggtatcgt    480
aagactccag gcgctgattc gagggtatct tgtaaggagg caggctgtat caacccttcg    540
cgcaacatgg ttgattgtga agtttcaggc tctagttcgt ggaagaaatg ttagactctc    600
tggcagtcgc atgcagctca atgtgaagtt tggtcagagt aactttgggg gtgttagatc    660
gtctgatgca tggaaagaga agctatcttc aaatgcttat gttcggaagc ttctgtcttc    720
accaattgtt ttagaacctc ttcacttcca gtatgacaag agggatccca attcaaccta    780
taactggttt gagagatgga ccataggttg catctggaag cctgcttttc aacccaaaag    840
agttgctgat gggaaaccac tggtaaagaa ggctagttat gcaatggaaa ctcaatcagc    900
caagttaaaa cgcaacattc ggaagggttc tgctgctatc gctgggagtt tccatacatc    960
tggtgaatct gataaagtaa aaaggaatcc aaagaatttc tctagcttcc ctgctgattc   1020
agtaccagat agccagttat ctgaacttga aaaggttaaa aggaacctca ggaaggtaac   1080
tgattcgatg gctgaagcct caaagatatc tagttccagg gttgattcct cgaaggtatg   1140
taattctaca gctgaggttc caaaggaatc taatcctgtg gcagaaatct caaagatacg   1200
tagtctcctg aatgggatct ctgaccatca ggatattcaa tgtgagaata cacgtgaatc   1260
ttcatttcct cttggaactc aagaagactc tgacaatgat catctattgc gatattcaaa   1320
tatggatagc ttggacttgg tacctggttt gaaaagtgat caggaaattc agctggattc   1380
ggtttctata ggagaaaatg ttgatgatcc cactgttgtt gctccagcag ttgaagaaat   1440
gtcaccgcaa acattgata cggaagacaa tgttttatgc aagaaagagg aagcaaggtc   1500
caaggaagag cacttgtcta atggaagcct tagaactagc aagaggaagt cttcattccc   1560
caacaaatca gaatatgtag aaaatgggac tcacgctact cctgttcagc aacgcagcc    1620
aagctatatg gctgcaacgg agtccgcaaa ggcgaaattg cgagcccaga attcacccag   1680
tctggattct gattcagcgg cagaaaagaa tggtttcacc cgacgccact ctcttccttc   1740
cagtacaaag agtagagcac ttaaagctga atggaagcgc tgaagaggca acccatcgtc   1800
cacttgaatt gaattgtgca ctgctctgaa acttcgctgg atgaactcga ccggtcttgt   1860
cccatgttct tgctgtattg aacaaccccct tgtgaagttg cgattctggt tcagtttgtc   1920
gtaggttcat gtgcaaccac tagtgccttg tgtcgtatat tgcatggttc ttgtcgaagg   1980
aacaatgcct gcgaaagctg atgttaggac tgcattaact gaataacatc acccagttgc   2040
ccaggtctt                                                            2049
```

<210> SEQ ID NO 11
<211> LENGTH: 560
<212> TYPE: PRT
<213> ORGANISM: Zea mays
<220> FEATURE:
<221> NAME/KEY: misc_feature -continued

```
<223> OTHER INFORMATION: Ceres CLONE ID no.345954
<220> FEATURE:
<221> NAME/KEY: misc_feature
<223> OTHER INFORMATION: Score of 757.6 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (101)..(121)
<223> OTHER INFORMATION: Pfam Name: IQ Pfam Description: IQ calmodulin-
      binding motif

<400> SEQUENCE: 11
```

Met Gly Lys Ser Pro Gly Lys Trp Ile Lys Ser Val Leu Leu Gly Lys
1               5                   10                  15

Lys Ser Thr Lys Ser Gly Pro Thr Lys Ser Asn Glu Ser Lys Ala Asp
            20                  25                  30

Asn Asn Arg Tyr Ser Thr Gly Glu Asp Arg Thr Leu Ser Glu Ser Ser
        35                  40                  45

Pro Val Ile Ser Glu Pro Val Leu Val Asn Ile His Lys Asn Val Ala
    50                  55                  60

Ile Asn Gly Lys Ala Ala Asp Ala Ser Asp Arg Ala Arg Gln Gln Asp
65                  70                  75                  80

Pro Gln Ser Gln Ser Val Val Glu Ser Arg Ser Ser Ala Pro Ala Ala
                85                  90                  95

Gln Leu Gly Glu Asp Gln Ala Ala Lys Ala Gln Ala Ala Phe Arg
            100                 105                 110

Gly Tyr Leu Ala Arg Arg Ser Phe Arg Ala Leu Lys Gly Ile Val Arg
        115                 120                 125

Leu Gln Ala Leu Ile Arg Gly Tyr Leu Val Arg Gln Ala Val Ser
    130                 135                 140

Thr Leu Arg Ala Thr Trp Leu Ile Val Lys Phe Gln Ala Leu Val Arg
145                 150                 155                 160

Gly Arg Asn Val Arg Leu Ser Gly Ser Arg Met Gln Leu Asn Val Lys
                165                 170                 175

Phe Gly Gln Ser Asn Phe Gly Val Arg Ser Ser Asp Ala Trp Lys
            180                 185                 190

Glu Lys Leu Ser Ser Asn Ala Tyr Val Arg Lys Leu Leu Ser Ser Pro
        195                 200                 205

Ile Val Leu Glu Pro Leu His Phe Gln Tyr Asp Lys Arg Asp Pro Asn
    210                 215                 220

Ser Thr Tyr Asn Trp Phe Glu Arg Trp Thr Ile Gly Cys Ile Trp Lys
225                 230                 235                 240

Pro Ala Phe Gln Pro Lys Arg Val Ala Asp Gly Lys Pro Leu Val Lys
                245                 250                 255

Lys Ala Ser Tyr Ala Met Glu Thr Gln Ser Ala Lys Leu Lys Arg Asn
            260                 265                 270

Ile Arg Lys Gly Ser Ala Ala Ile Ala Gly Ser Phe His Thr Ser Gly
        275                 280                 285

Glu Ser Asp Lys Val Lys Arg Asn Pro Lys Asn Phe Ser Ser Phe Pro
    290                 295                 300

Ala Asp Ser Val Pro Asp Ser Gln Leu Ser Glu Leu Glu Lys Val Lys
305                 310                 315                 320

Arg Asn Leu Arg Lys Val Thr Asp Ser Met Ala Glu Ala Ser Lys Ile
                325                 330                 335

Ser Ser Ser Arg Val Asp Ser Ser Lys Val Cys Asn Ser Thr Ala Glu
            340                 345                 350

Val Pro Lys Glu Ser Asn Pro Val Ala Glu Ile Ser Lys Ile Arg Ser
355                 360                 365

Leu Leu Asn Gly Ile Ser Asp His Gln Asp Ile Gln Cys Glu Asn Thr
        370                 375                 380

Arg Glu Ser Ser Phe Pro Leu Gly Thr Gln Glu Asp Ser Asp Asn Asp
385                 390                 395                 400

His Leu Leu Arg Tyr Ser Asn Met Asp Ser Leu Asp Leu Val Pro Gly
                405                 410                 415

Leu Lys Ser Asp Gln Glu Ile Gln Leu Asp Ser Val Ser Ile Gly Glu
            420                 425                 430

Asn Val Asp Asp Pro Thr Val Val Ala Pro Val Glu Glu Met Ser
                435                 440                 445

Pro Gln Asn Ile Asp Thr Glu Asp Asn Val Leu Cys Lys Lys Glu Glu
        450                 455                 460

Ala Arg Ser Lys Glu Glu His Leu Ser Asn Gly Ser Leu Arg Thr Ser
465                 470                 475                 480

Lys Arg Lys Ser Ser Phe Pro Asn Lys Ser Glu Tyr Val Glu Asn Gly
                485                 490                 495

Thr His Ala Thr Pro Val Gln Pro Thr Gln Pro Ser Tyr Met Ala Ala
            500                 505                 510

Thr Glu Ser Ala Lys Ala Lys Leu Arg Ala Gln Asn Ser Pro Ser Leu
        515                 520                 525

Asp Ser Asp Ser Ala Ala Glu Lys Asn Gly Phe Thr Arg Arg His Ser
    530                 535                 540

Leu Pro Ser Ser Thr Lys Ser Arg Ala Leu Lys Ala Glu Trp Lys Arg
545                 550                 555                 560

<210> SEQ ID NO 12
<211> LENGTH: 2049
<212> TYPE: DNA
<213> ORGANISM: Zea mays
<220> FEATURE:
<221> NAME/KEY: misc_feature
<223> OTHER INFORMATION: Ceres CLONE ID no.345954
<220> FEATURE:
<221> NAME/KEY: misc_feature
<223> OTHER INFORMATION: Encodes the peptide sequence at SEQ ID NO 11

<400> SEQUENCE: 12
gtttttcgcc gagcagttcg cgtgctcccc tccacaggcc gacgcggcga cgccgctgtt      60
tcaggttctg gaatttccag tgcgggtgca ttaggctgct atgggcaagt cgccggggaa     120
gtggatcaaa tcggtgcttt tggggaagaa atctaccaag tcaggtccta ccaagtcgaa     180
tgaatctaag gctgacaaca acagatactc gaccggggag gaccgcacat tgtctgagag     240
ttctcctgtg atttctgagc cggtactagt taacatccac aagaacgtag ctatcaatgg     300
gaaggctgca gatgccagtg ataggcacg gcaacaagat ccgcagagcc aaagcgttgt     360
tgagtccaga tcatcggctc cagctgctca gctgggagaa gatcaagctg cagcgaaggc     420
acaggcagcc tttcgtggtt acctggcacg aaggtcattc cgtgcattaa aggtatcgt      480 aagactccag gcgctgattc gagggtatct tgtaaggagg caggctgtat caacccttcg     540
cgcaacatgg ttgattgtga agtttcaggc tctagttcgt ggaagaaatg ttagactctc     600
tggcagtcgc atgcagctca atgtgaagtt tggtcagagt aactttgggg gtgttagatc     660
gtctgatgca tggaaagaga agctatcttc aaatgcttat gttcggaagc ttctgtcttc     720

```
accaattgtt ttagaacctc ttcacttcca gtatgacaag agggatccca attcaaccta      780
taactggttt gagagatgga ccataggttg catctggaag cctgcttttc aacccaaaag      840
agttgctgat gggaaaccac tggtaaagaa ggctagttat gcaatggaaa ctcaatcagc      900
caagttaaaa cgcaacattc ggaagggttc tgctgctatc gctgggagtt ccatacatc       960 tggtgaatct gataaagtaa aaaggaatcc aaagaatttc tctagcttcc ctgctgattc     1020
agtaccagat agccagttat ctgaacttga aaaggttaaa aggaacctca ggaaggtaac     1080
tgattcgatg gctgaagcct caaagatatc tagttccagg gttgattcct cgaaggtatg     1140
taattctaca gctgaggttc caaggaatc taatcctgtg gcagaaatct caaagatacg      1200
tagtctcctg aatgggatct ctgaccatca ggatattcaa tgtgagaata cacgtgaatc     1260
ttcatttcct cttggaactc aagaagactc tgacaatgat catctattgc gatattcaaa     1320
tatggatagc ttggacttgg tacctggttt gaaaagtgat caggaaattc agctggattc     1380
ggtttctata ggagaaaatg ttgatgatcc cactgttgtt gctccagcag ttgaagaaat     1440
gtcaccgcaa acattgata cggaagacaa tgttttatgc aagaaagagg aagcaaggtc      1500
caaggaagag cacttgtcta atggaagcct tagaactagc aagaggaagt cttcattccc     1560
caacaaatca gaatatgtag aaaatgggac tcacgctact cctgttcagc aacgcagcc      1620 aagctatatg gctgcaacgg agtccgcaaa ggcgaaattg cgagcccaga attcacccag     1680
tctggattct gattcagcgg cagaaaagaa tggtttcacc cgacgccact ctcttccttc     1740
cagtacaaag agtagagcac ttaaagctga atggaagcgc tgaagaggca acccatcgtc     1800
cacttgaatt gaattgtgca ctgctctgaa acttcgctgg atgaactcga ccggtcttgt     1860
cccatgttct tgctgtattg aacaacccct tgtgaagttg cgattctggt tcagtttgtc     1920
gtaggttcat gtgcaaccac tagtgccttg tgtcgtatat tgcatggttc ttgtcgaagg     1980
aacaatgcct gcgaaagctg atgttaggac tgcattaact gaataacatc acccagttgc     2040
ccaggtctt                                                            2049
```

<210> SEQ ID NO 13
<211> LENGTH: 574
<212> TYPE: PRT
<213> ORGANISM: Zea mays
<220> FEATURE:
<221> NAME/KEY: misc_feature
<223> OTHER INFORMATION: Ceres LOCUS ID no. Os01m05025_AP003288
<220> FEATURE:
<221> NAME/KEY: misc_feature
<223> OTHER INFORMATION: Score of 858.7for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (98)..(118)
<223> OTHER INFORMATION: Pfam Name: IQ Pfam Description: IQ calmodulin-
    binding motif

<400> SEQUENCE: 13

Met Gly Lys Ser Pro Ala Lys Trp Ile Lys Ser Val Leu Leu Gly Lys
1               5                   10                  15

Lys Ser Ala Lys Ser Asn Ser Thr Lys Ala Lys Asp Leu Ala Lys Ala
            20                  25                  30

Ala Asn Asn Lys Pro Val Leu Ser Glu Asp Pro Val Ile Ser Glu
        35                  40                  45

```
Pro Ala Leu Val Asn Ser His Asn Asp Gly Asn Ala Glu Asn Cys Lys
 50                  55                  60

Leu Pro Asn Gly Val Ala Val Glu Ala Met Gly Gln Gly Val Glu Asn
 65                  70                  75                  80

Gln Asn Ile Val Gly Ser Lys Ala Pro Thr Ser Pro Glu Lys Leu Ser
                 85                  90                  95

Glu Glu Leu Ala Ala Val Lys Ala Gln Ala Ala Phe Arg Gly Tyr Leu
            100                 105                 110

Ala Arg Arg Ala Phe Arg Ala Leu Lys Gly Ile Ile Arg Leu Gln Ala
        115                 120                 125

Leu Ile Arg Gly His Leu Val Arg Arg Gln Ala Ala Ser Thr Leu Arg
130                 135                 140

Val Thr Trp Leu Ile Val Lys Leu Gln Ala Leu Val Arg Gly Arg Asn
145                 150                 155                 160

Val Arg Leu Ser Gly Ala Ser Ile Gln Phe Val Lys Ser Gly Gln
                165                 170                 175

His Lys Phe Leu Ser Asp Lys Pro Ser Asp Ala Trp Lys Glu Lys Val
            180                 185                 190

Ser Ser Asn Ala Tyr Val Arg Lys Leu Leu Ser Ser Ile Gly Leu
        195                 200                 205

Glu Ala Leu His Leu Gln Tyr Asp Lys Arg Asp Pro Asn Ser Leu Tyr
            210                 215                 220

Asn Trp Leu Glu Arg Trp Thr Ile Ser Gln Ile Trp Lys Ser Ser Ser
225                 230                 235                 240

Gln Pro Lys Lys Val Ala Asp Gly Lys Pro Gln Val Arg Lys Ala Ser
                245                 250                 255

Tyr Ala Met Glu Thr Glu Ser Ala Lys Leu Lys Arg Asn Val Arg Lys
            260                 265                 270

Ser Ser Ala Val Thr Val Asp Ser Phe Gln Thr Asn Met Thr Val Glu
        275                 280                 285

Pro Glu Lys Ile Lys Arg Asn Ser Arg Lys Phe Ser Ser Ser Ala Ala
    290                 295                 300

Asp Ser Val Pro Asp Ser Gln Leu Ser Glu Leu Glu Lys Val Lys Arg
305                 310                 315                 320

Asn Leu Arg Lys Val Thr Asn Ser Met Ala Glu Ala Ser Lys Ile Ser
                325                 330                 335

Ser Ser Arg Ala Asp Ala Ser Lys Val Ser Ser Met Ala Asp Ala
            340                 345                 350

Ser Lys Val Ser Ser Ser Thr Ala Asp Ala Ser Lys Val Ser Asp Ser
        355                 360                 365

Val Ala Gln Ile Pro Pro Ser Leu Val Asn Gly Ile Ser Asp His Gln
370                 375                 380

Asp Asn Gln Cys Glu Glu Ala Gln Gln Asn Ala Cys Val Ser Phe Pro
385                 390                 395                 400

Pro Glu Thr Gln Glu Leu His Ser Gly Ile Leu Leu Glu Asp Asn Ser
                405                 410                 415

His Met Asn Leu Leu Glu Pro Asp Leu Ile Ser Asn Pro Glu Thr Pro
            420                 425                 430

Phe Thr Ser Ile Leu Thr Trp Glu Lys Phe Asn Asp Ser Thr Ala Asp
        435                 440                 445

Ala Gln Glu Val Glu Val Leu Pro Leu Gln Asn Ile Asp Asn Glu Asp
    450                 455                 460

Asn Phe Pro Glu Asn Gly Val Leu Gly Lys Lys Glu Lys Pro Arg Ser
465                 470                 475                 480

Lys Glu Glu Pro Leu Ser Asn Gly Asn Leu Lys Thr Ser Lys Arg Arg
                485                 490                 495
```

```
Ser Ser Phe Ser Thr Lys Ser Asp Tyr Pro Glu Asn Gly Ala Gln Asn
            500                 505                 510

Thr Pro Val Pro Arg Arg Lys Pro Ser Tyr Met Ala Ala Thr Glu Ser
            515                 520                 525

Ala Lys Ala Lys Leu Arg Gly Gln Asn Ser Pro Arg Leu Asp Ser Asp
530                 535                 540

Ser Pro Ala Asp Met Asn Gly Phe Thr Arg Arg Gln Ser Leu Pro Ser
545                 550                 555                 560

Ser Thr Asn Asn Arg Ala Ile Arg Ala Glu Trp Arg Arg Trp
                565                 570

<210> SEQ ID NO 14
<211> LENGTH: 582
<212> TYPE: PRT
<213> ORGANISM: Oryza sativa subsp. indica
<220> FEATURE:
<221> NAME/KEY: misc_feature
<223> OTHER INFORMATION: Public GI ID no.125527495
<220> FEATURE:
<221> NAME/KEY: misc_feature
<223> OTHER INFORMATION: Score of 851.5 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (98)..(118)
<223> OTHER INFORMATION: Pfam Name: IQ Pfam Description: IQ calmodulin-
      binding motif

<400> SEQUENCE: 14

Met Gly Lys Ser Pro Ala Lys Trp Ile Lys Ser Val Leu Leu Gly Lys
1               5                   10                  15

Lys Ser Ala Lys Ser Asn Ser Thr Lys Ala Lys Asp Leu Ala Lys Ala
            20                  25                  30

Ala Asn Asn Lys Pro Val Leu Ser Glu Asp Pro Val Ile Ser Glu
        35                  40                  45

Pro Ala Leu Val Asn Ser His Asn Asp Gly Asn Ala Glu Asn Cys Lys
50                  55                  60

Leu Pro Asn Gly Val Ala Val Glu Ala Met Gly Gln Gly Val Glu Asn
65                  70                  75                  80

Gln Asn Ile Val Gly Ser Lys Ala Pro Thr Ser Pro Glu Lys Leu Ser
                85                  90                  95

Glu Glu Leu Ala Ala Val Lys Ala Gln Ala Ala Phe Arg Gly Tyr Leu
            100                 105                 110

Ala Arg Arg Ala Phe Arg Ala Leu Lys Gly Ile Ile Arg Leu Gln Ala
        115                 120                 125

Leu Ile Arg Gly His Leu Val Arg Arg Gln Ala Ala Ser Thr Leu Arg
130                 135                 140

Val Thr Trp Leu Ile Val Lys Leu Gln Ala Leu Val Arg Gly Arg Asn
145                 150                 155                 160

Val Arg Leu Ser Gly Ala Ser Ile Gln Phe Val Val Lys Ser Gly Gln
                165                 170                 175

His Lys Phe Leu Ser Asp Lys Pro Ser Asp Ala Trp Lys Glu Lys Val
            180                 185                 190

Ser Ser Asn Ala Tyr Val Arg Lys Leu Leu Ser Ser Ser Ile Gly Leu
        195                 200                 205

Glu Ala Leu His Leu Gln Tyr Asp Lys Arg Asp Pro Asn Ser Leu Tyr
```

```
            210                 215                 220
Asn Trp Leu Glu Arg Trp Thr Ile Ser Gln Ile Trp Lys Ser Ser Ser
225                 230                 235                 240

Gln Pro Lys Lys Val Ala Asp Gly Lys Pro Gln Val Arg Lys Ala Ser
                245                 250                 255

Tyr Ala Met Glu Thr Glu Ser Ala Lys Leu Lys Arg Asn Val Arg Lys
            260                 265                 270

Ser Ser Ala Val Thr Val Asp Ser Phe Gln Thr Asn Met Thr Val Glu
        275                 280                 285

Pro Glu Lys Ile Lys Arg Asn Ser Arg Lys Phe Ser Ser Ser Ala Ala
    290                 295                 300

Asp Ser Val Pro Asp Ser Gln Leu Ser Glu Leu Glu Lys Val Lys Arg
305                 310                 315                 320

Asn Leu Arg Lys Val Thr Asn Ser Met Ala Glu Ala Ser Lys Ile Ser
                325                 330                 335

Ser Ser Arg Ala Asp Ala Ser Lys Val Ser Ser Ser Met Ala Asp Ala
            340                 345                 350

Ser Lys Val Ser Ser Ser Thr Ala Asp Ala Ser Lys Val Ser Asp Ser
        355                 360                 365

Val Ala Gln Ile Pro Pro Ser Leu Val Asn Gly Ile Ser Asp His Gln
    370                 375                 380

Asp Asn Gln Cys Glu Glu Ala Gln Gln Asn Ala Cys Val Ser Phe Pro
385                 390                 395                 400

Pro Glu Thr Gln Glu Leu His Ser Gly Ile Leu Leu Glu Asp Asn Ser
                405                 410                 415

His Met Asn Leu Leu Glu Pro Asp Leu Ile Ser Asn Pro Glu Thr Pro
            420                 425                 430

Phe Thr Ser Ile Leu Thr Trp Glu Lys Phe Asn Asp Ser Thr Ala Asp
        435                 440                 445

Ala Gln Glu Val Glu Val Leu Pro Leu Gln Asn Ile Asp Asn Glu Asp
    450                 455                 460

Asn Phe Pro Glu Asn Gly Val Leu Gly Lys Lys Glu Lys Pro Arg Ser
465                 470                 475                 480

Lys Glu Glu Pro Leu Ser Asn Gly Asn Leu Lys Thr Ser Lys Arg Arg
                485                 490                 495

Ser Ser Phe Ser Thr Lys Ser Asp Tyr Pro Glu Asn Gly Ala Gln Asn
            500                 505                 510

Thr Pro Val Pro Arg Arg Lys Pro Ser Tyr Met Ala Ala Thr Glu Ser
        515                 520                 525

Ala Lys Ala Lys Leu Arg Gly Gln Asn Ser Pro Arg Leu Asp Ser Asp
    530                 535                 540

Ser Pro Ala Asp Met Asn Gly Phe Thr Arg Arg Gln Ser Leu Pro Ser
545                 550                 555                 560

Ser Thr Asn Ser Lys Leu Asn Pro His Ser Pro His Thr Gln Gly Pro
                565                 570                 575

Ile Tyr Phe Lys Phe Asp
            580

<210> SEQ ID NO 15
<211> LENGTH: 580
<212> TYPE: PRT
<213> ORGANISM: Oryza sativa subsp. indica
<220> FEATURE:
<221> NAME/KEY: misc_feature
<223> OTHER INFORMATION: Public GI ID no.125553119
```

```
<220> FEATURE:
<221> NAME/KEY: misc_feature
<223> OTHER INFORMATION: Score of 656.4 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2

<400> SEQUENCE: 15
```

| | | | | | | | | | | | | | | |
|---|---|---|---|---|---|---|---|---|---|---|---|---|---|---|
| Met | Gly | Lys | Ser | Pro | Ala | Lys | Trp | Ile | Lys | Ser | Val | Leu | Phe | Gly | Lys |
| 1 | | | | 5 | | | | | 10 | | | | | 15 | |

Lys Ser Ser Arg Ser Gly Ser Thr Lys Ala Lys Asp Leu Ser Lys Gly
                20                  25                  30

Ser Asn Asn Lys Gly Tyr Ala Ala Gly Lys Asp Ala Gly Phe Glu
        35                  40                  45

Ser Ser Pro Val Ile Ser Glu Pro Val Leu Val Thr Pro His Asn Asn
        50                  55                  60

Glu Ala Val Gln Glu Val Gly Arg Gly Glu Asn Ser Ser Leu Gln Gly
65                  70                  75                  80

Glu Val Val Arg Asp Val Ser Gln Asp Leu Glu Lys Gln Asn Thr
                85                  90                  95

Val Val Ser Asp Ala Ser Asn Asp Pro Glu Arg Leu Arg Glu Glu Gln
                100                 105                 110

Ala Ala Val Lys Ala Gln Ala Ala Phe Arg Gly Tyr Leu His Gly Ile
                115                 120                 125

Gly Pro Gly Thr Ser Gly Ile Pro Cys Val Glu Arg Asn His Lys Thr
130                 135                 140

Pro Ser Pro Asp Ser Trp Ala Ser Arg Lys Glu Ala Ser Arg Cys Asn
145                 150                 155                 160

Ser Ser Cys Asn Met Val Asp Cys Glu Val Ser Ser Ser Pro Trp
                165                 170                 175

Leu Thr Arg Pro His Thr Arg Asn Met Cys Pro Asn Leu Leu Ala Leu
                180                 185                 190

Lys Pro His Lys Gln Pro Ile Met Leu Tyr Lys Ser Tyr Lys Ser Gly
                195                 200                 205

Lys Arg Asp Ala Trp Lys Glu Lys Leu Ser Ser Asn Ala Phe Ala Arg
210                 215                 220

Lys Leu Leu Ala Ser Pro Ile Leu Val Glu Ala Leu His Phe Gln Tyr
225                 230                 235                 240

Asp Glu Arg Asp Pro Asn Ser Ala Phe Asn Trp Leu Glu Arg Trp Thr
                245                 250                 255

Ile Gly Arg Val Trp Arg Pro Ile Ser His Pro Lys Arg Ala Ala Val
                260                 265                 270

Thr Asp Ala Lys Pro His Thr Arg Lys Ala Ser Tyr Ala Met Glu Thr
                275                 280                 285

Glu Ser Gly Lys Leu Lys Arg Asn Ser Arg Arg Ser Ser Ala Ala Pro
                290                 295                 300

Val Glu Ser Ser Gln Thr Asn Met Ala Met Glu Thr Glu Lys Ser Arg
305                 310                 315                 320

Arg Asn Pro Arg Lys Phe Thr Ser Ser Thr Ala Asp Ser Val Pro Glu
                325                 330                 335

Ser Gln Leu Thr Glu Leu Glu Lys Val Lys Arg Asn Leu Arg Lys Val
                340                 345                 350

Thr Asn Ser Met Ala Glu Ala Ser Lys Val Ser Thr Pro Ala Thr Glu
                355                 360                 365

Ile Pro Glu Arg Gln Glu Val Gln Cys Glu Lys Pro Gln Arg Thr Ala
    370                 375                 380

Glu Glu Val Pro Asn Tyr Pro Glu Ile Gln Glu Pro Gln Asn Gly Asn
385                 390                 395                 400

Leu Leu Glu Asn Ala Lys Thr Asp Ile Leu Val Pro Asp Leu Gln Pro
                405                 410                 415

Glu Pro Glu Val Pro Ser Tyr Gln Val Glu Thr Glu Lys Val Ala
                420                 425                 430

Glu Leu Thr Val Ala Asp Pro Ala Val Glu Thr Met Pro Leu Gln Asp
                435                 440                 445

Ile His Asn Glu Glu Asn Ala Leu Val Asn Asp Met Glu Gln Arg Ser
    450                 455                 460

Lys Glu Glu Pro Leu Ser Thr Glu Ser Leu Lys Ser Lys Arg Arg
465                 470                 475                 480

Ser Ser Phe Ser Thr Lys Thr Glu Tyr Pro Glu Asn Gly Ser Lys Asn
                485                 490                 495

Ser Pro Ala Val Pro Ser Tyr Met Ala Ala Thr Gln Ser Ala Lys Ala
                500                 505                 510

Lys Leu Arg Gly Gln Asn Leu Pro Arg Leu Ser Ser Asp Ser Ala Glu
                515                 520                 525

Lys Asn Gly Phe Thr Arg Arg His Ser Leu Pro Ser Ser Asn Gly Lys
                530                 535                 540

Leu Asn Ser His Ser Pro Arg Thr Gln Arg Pro Thr His Ala Gly Gly
545                 550                 555                 560

Lys Glu Gly Val Lys Ala Asp Lys Ser Met Leu Ser Ser Arg Asp Ala
                565                 570                 575

Ser Gly Lys Leu
            580

<210> SEQ ID NO 16
<211> LENGTH: 2368
<212> TYPE: DNA
<213> ORGANISM: Zea mays
<220> FEATURE:
<221> NAME/KEY: misc_feature
<223> OTHER INFORMATION: Ceres CLONE ID no.236431
<220> FEATURE:
<221> NAME/KEY: misc_feature
<223> OTHER INFORMATION: Encodes the peptide sequence at SEQ ID NO 17

<400> SEQUENCE: 16
agctgattta ttttctctcg ctctcgcctt cgcggcgctg cctgcgcagt actacgagct    60
agcaggctag cagcaccagg accaggagcc tcttcccaca cttccgctct tcctctctct   120
ctttcctctc gagaatggtt gtgtaggcgg gcgcaggagg gaggagagag aggggagcta   180
gctagggttt tgcgtcgccg ccttctgtta cccttaggct ctgaacccct ccggtccagt   240
gcggcggcgg attaggctcc gatggggaag tctccggcga agtggatcaa gtccgtgctc   300
ttcggtaaaa agtcgtcgtc gaggtccggc tccaccaagg ccaaggattt atcgaagggt   360
accactaaca aagcggcggc tgctgctgct gccgggaagg agcctgcgtt ctctgagagc   420
tctccggtca tctcggagcc tgtgcttgtt agcgcccaca caatgagac cgcgcgggag   480 gccgctaagg gtgagaattc cagcgtgcaa gaagtgccag tgactgatgt tagtcaagac   540
ttggagaagc agggcactgt tgggtctgat acgtctaatg atgctgagag gttgagggaa   600
gagcaagcgg ccgtgaaggc acaagctgcc ttcgtggtt atctggcacg ccagcattc    660 cgtgccctga aagggatcat aagactacag gcactgattc ggggacatct tgtaaggagg   720

-continued

```
caagctgttt caactctccg tgctacatgg ttgattgtga agtttcaagc ccttgtccgt    780
ggaaggaacg ttagactttc taaagtttcc attcaaccaa ctacggaact ttcccaacag    840
aacttcgggg gttctaaacc tggttcctgg aaggagaagt tgtcttcaaa tgcatttgct    900
cggaagcttc tctcttcacc aattgtggtt gaggctcttc atgtccagta tgatgagatg    960
gaccctaatt cggccttcaa ttggttagag aggtggacag taagtcatgt ctggaagcct   1020
atttcccaac caaagagagt tggtgctgat actaagcctc atacaaggaa ggccagttat   1080
gcaatggaaa cagagtcagc gaaattaaag cgtaatgcac ggaagagccc tgcagtgcca   1140
tttgagcctt ctcaaacaaa caccaccatt gaaaatgaga agacaagacg gaatccaagg   1200
aaattaagta gcactcctgc tgagtcagtt cccgatggcc agttaacaga acttgagaag   1260
gttaaacgta gccttaggaa ggttactagt tccatggttg aaacctcaaa ggtgcctagc   1320
ccaacaactg agattcctga ccgtcaagag gtacaatgtg agagaccact aagaagtgca   1380
aagcaagctc caattcatgt tgagaatcaa gaacctcaga atgttaatct atcggacaat   1440
gcaaagatgg atattctggt accagatatc cagcctgacg tggaagttgc ttcagatcta   1500
gtcacaatca caaatgaaga aaagttgat gagacaccgt ctgttgttgc tccagcgact   1560
gaaattatgc cactgcaaga catcaacagc gaagaaaatg ctttggtgaa tgatgtggaa   1620
gagagatcca agaagaaca tccatctact gataacctga aaggcagcaa gaggaggtct   1680
tcattctcag ttaagcctga atatccagaa aatggctcca aaaattctcc agctctgcca   1740
agctacatgg ctgctacaca atctgcaaag gcgaaactgc ggggggaattg ttcaccaaga   1800
cttagctctg attcagcaga gaaaaacggg ttcactcgtc gtcactccct tccgtcccct   1860
aacaatggta agataattc acattctcca cgtacgcaaa ggccaaccca tgctggtggc   1920
aaggacggag caaaaggcga caaggctatg ctgtcatcaa gagatgcgag cgagagacca   1980
ctgaaagctg agtggagacg ctgaggtggc gaatcaaaac cccaaaccct ccatttggtt   2040
agtgcaacta tttggggttgg tggatggcgt ctgcagtttg ctccgattgt tttgcttgtg   2100
atgtaaaaaa gacgttatca tcatcatccg aggcgatgaa cgggttcagc tttgttgtga   2160
tgaatctgct gggagtcaac ttatttacag ggttttgggt catgcctttt gtgatgtata   2220
gctgaagtat tttcccggtt tgtttttgtt tcccagaccc ccagactccc ccctcccct   2280
cctgcttgct gagagggctg ctgatgttag agagaacgag aacctgtatg gattgagttg   2340
aacagaacaa tcttagtccc gtttggtc                                      2368
```

<210> SEQ ID NO 17
<211> LENGTH: 580
<212> TYPE: PRT
<213> ORGANISM: Zea mays
<220> FEATURE:
<221> NAME/KEY: misc_feature
<223> OTHER INFORMATION: Ceres CLONE ID no.236431
<220> FEATURE:
<221> NAME/KEY: misc_feature
<223> OTHER INFORMATION: Score of 1099.7 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (114)..(134)
<223> OTHER INFORMATION: Pfam Name: IQ Pfam Description: IQ calmodulin-
      binding motif

<400> SEQUENCE: 17

```
Met Gly Lys Ser Pro Ala Lys Trp Ile Lys Ser Val Leu Phe Gly Lys
1               5                   10                  15

Lys Ser Ser Arg Ser Gly Ser Thr Lys Ala Lys Asp Leu Ser Lys
            20                  25                  30

Gly Thr Thr Asn Lys Ala Ala Ala Ala Ala Ala Gly Lys Glu Pro
        35                  40                  45

Ala Phe Ser Glu Ser Ser Pro Val Ile Ser Glu Pro Val Leu Val Ser
    50                  55                  60

Ala His Asn Asn Glu Thr Ala Arg Glu Ala Ala Lys Gly Glu Asn Ser
65                  70                  75                  80

Ser Val Gln Glu Val Pro Val Thr Asp Val Ser Gln Asp Leu Glu Lys
                85                  90                  95

Gln Gly Thr Val Gly Ser Asp Thr Ser Asn Asp Ala Glu Arg Leu Arg
                100                 105                 110

Glu Glu Gln Ala Ala Val Lys Ala Gln Ala Ala Phe Arg Gly Tyr Leu
                115                 120                 125

Ala Arg Arg Ala Phe Arg Ala Leu Lys Gly Ile Ile Arg Leu Gln Ala
        130                 135                 140

Leu Ile Arg Gly His Leu Val Arg Arg Gln Ala Val Ser Thr Leu Arg
145                 150                 155                 160

Ala Thr Trp Leu Ile Val Lys Phe Gln Ala Leu Val Arg Gly Arg Asn
                165                 170                 175

Val Arg Leu Ser Lys Val Ser Ile Gln Pro Thr Thr Glu Leu Ser Gln
                180                 185                 190

Gln Asn Phe Gly Gly Ser Lys Pro Gly Ser Trp Lys Glu Lys Leu Ser
        195                 200                 205

Ser Asn Ala Phe Ala Arg Lys Leu Leu Ser Ser Pro Ile Val Val Glu
    210                 215                 220

Ala Leu His Val Gln Tyr Asp Glu Met Asp Pro Asn Ser Ala Phe Asn
225                 230                 235                 240

Trp Leu Glu Arg Trp Thr Val Ser His Val Trp Lys Pro Ile Ser Gln
                245                 250                 255

Pro Lys Arg Val Gly Ala Asp Thr Lys Pro His Thr Arg Lys Ala Ser
                260                 265                 270

Tyr Ala Met Glu Thr Glu Ser Ala Lys Leu Lys Arg Asn Ala Arg Lys
                275                 280                 285

Ser Pro Ala Val Pro Phe Glu Pro Ser Gln Thr Asn Thr Thr Ile Glu
        290                 295                 300

Asn Glu Lys Thr Arg Arg Asn Pro Arg Lys Leu Ser Ser Thr Pro Ala
305                 310                 315                 320

Glu Ser Val Pro Asp Gly Gln Leu Thr Glu Leu Glu Lys Val Lys Arg
                325                 330                 335

Ser Leu Arg Lys Val Thr Ser Ser Met Val Glu Thr Ser Lys Val Pro
            340                 345                 350

Ser Pro Thr Thr Glu Ile Pro Asp Arg Gln Glu Val Gln Cys Glu Arg
        355                 360                 365

Pro Leu Arg Ser Ala Lys Gln Ala Pro Ile His Val Glu Asn Gln Glu
    370                 375                 380

Pro Gln Asn Val Asn Leu Ser Asp Asn Ala Lys Met Asp Ile Leu Val
385                 390                 395                 400

Pro Asp Ile Gln Pro Asp Val Glu Val Ala Ser Asp Leu Val Thr Ile
                405                 410                 415
```

```
Thr Asn Glu Glu Lys Val Asp Glu Thr Pro Ser Val Val Ala Pro Ala
            420                 425                 430

Thr Glu Ile Met Pro Leu Gln Asp Ile Asn Ser Glu Glu Asn Ala Leu
                435                 440                 445

Val Asn Asp Val Glu Glu Arg Ser Lys Glu Glu His Pro Ser Thr Asp
        450                 455                 460

Asn Leu Lys Gly Ser Lys Arg Ser Ser Phe Ser Val Lys Pro Glu
465                 470                 475                 480

Tyr Pro Glu Asn Gly Ser Lys Asn Ser Pro Ala Leu Pro Ser Tyr Met
                485                 490                 495

Ala Ala Thr Gln Ser Ala Lys Ala Lys Leu Arg Gly Asn Cys Ser Pro
            500                 505                 510

Arg Leu Ser Ser Asp Ser Ala Glu Lys Asn Gly Phe Thr Arg Arg His
            515                 520                 525

Ser Leu Pro Ser Pro Asn Asn Gly Lys Ile Ile Ser His Ser Pro Arg
            530                 535                 540

Thr Gln Arg Pro Thr His Ala Gly Gly Lys Asp Gly Ala Lys Gly Asp
545                 550                 555                 560

Lys Ala Met Leu Ser Ser Arg Asp Ala Ser Glu Arg Pro Leu Lys Ala
                565                 570                 575

Glu Trp Arg Arg
            580

<210> SEQ ID NO 18
<211> LENGTH: 2129
<212> TYPE: DNA
<213> ORGANISM: Triticum aestivum
<220> FEATURE:
<221> NAME/KEY: misc_feature
<223> OTHER INFORMATION: Ceres CLONE ID no.908518
<220> FEATURE:
<221> NAME/KEY: misc_feature
<223> OTHER INFORMATION: Encodes the peptide sequence at SEQ ID NO 19

<400> SEQUENCE: 18
agaacctctc tctctcctct gctccacgcc acagaagaga acaaacagta ggaggagcgc      60
tctccttcgg ccgcgagcgt ctgcgtcccg caatggaggc gtgatggttg gcgcggatag     120
aggggtagcg ggacagggaa ggtgagcaat ctgccgggag agcgccgacg ccccgcccag     180
tccagcccag gtccagaatt ccggtgtttt gagcagtttt agtaggctgc tatggggaag     240
tccccggcca gtggataaag tccgtgctc ctcgggaaga atcaacaaa atccaattct      300 accaaggcaa aggatcttcc agcaaaggct gcaaacagca acggatgcac tgctgggaag     360
gagcctgaat cctctgataa ttctcccctc atctcggagc cggtacttgt tagctcccac     420
aatgtgtctg aaatttccaa cttgcccaat gggagggcaa tcgaaaacat ggttagagtt     480
gggtccgaca cgcaaattag tccagagaaa ctgagagaag aactagcagc agtgaaggcg     540
caagccgctt ttcgaggtta cctggcacgc agggccttcc gcgcattaaa aggtatcatc     600
agacttcagg cactgattcg agggcatctt gtaaggaggc aggccgtttc aacccttcgt     660
ggaacatggt tgattgtgaa gtttcaagct ctagttcgtg aagaaatgt tagatttct       720 agtgctgcca cgcaattagc tgtgaagttt ggtcaacata gtatggggg tgacaagtcg     780 tcggatgcat ggaaggagaa gctatcttca catccatatg ttcgaaagct tctgtcttca     840 ccaatttttgg tacaagctct tcacgttcag tatgatgaga caaacccca ttcagccctc      900 aactggctgg agagatggac aataagctgc atctggaagc ctgtttccaa accaaaaata     960
```

-continued

```
gttactgacg ggaaaccaca agtaaggagg gccagttatg ccatggaaac tcactcagca    1020
aagttaaagc gcaatgttcg gaagtcttct actgccactg ttgagactca ggcaaatacc    1080
gttgaatctg aaaaatggaa agaaaccca cggaaattga atggctcacc tgctgattca    1140
gtaccagaca gccagttatc tgaacttgag aaggttaaaa ggaaccttaa gaaggcagct    1200
aactccatgg ctgaagcctc taagatatct accaaggctg atgtgttgaa ggtacctaat    1260
tccatagctg atgagctgaa gatacttggt tccatggctg aactatcaaa aaaatccagc    1320
ataccaaacg gtatctctga ccatcaagac agcgaatgcg agaaagcact agagagtaca    1380
cgtgaggctg tgtttcctct tggaactcaa gattctcaca gtggcaatct tttggaaaat    1440
tcaaatataa gtaagttggt acctgacata aaatatgatc tagaagcatc attcttaggg    1500
gacaaagtta atgaacccac tactgtcgct caagcagatg aagtcataca actgcagaac    1560
cttgataacg gatatgatat tatagaaagg aaagaagaga ctaggtccaa ggaagaacct    1620
ctgcctaatg gaagccttaa aaccaagaga aggtcttcgt tctctaattc agaatacccct   1680 gagagtggaa ccaagaacac tccagttcca tcaaggaagc aagctatat ggctccaaca    1740 gaatcgttaa aggcgaaatt gcgaggacca cccagattag actctgatct accagtggac    1800
aagaatgcct tcactcgccg tcagtctctt ccttctgctg caaacaatag agcaatcaaa    1860
acagaatgga ggcggtgaag aggctatcaa gcttccaaca aagggtgca ttattgtgga    1920 agaaatttca agctgtataa attattgatt agtttatgaa gtttgctgat gtctacctgt    1980
ctctgtcctt gttgttctgt ctacgttata acatatgtt cttacgccct tttcgaacta    2040
gcttgtggtg atatgtttgg tgctattttt tcctcgagtt atcttatagt tccttggtcc    2100
gtgtattaaa tgtaaaaaaa aaaaaaaaa                                      2129
```

<210> SEQ ID NO 19
<211> LENGTH: 548
<212> TYPE: PRT
<213> ORGANISM: Triticum aestivum
<220> FEATURE:
<221> NAME/KEY: misc_feature
<223> OTHER INFORMATION: Ceres CLONE ID no.908518
<220> FEATURE:
<221> NAME/KEY: misc_feature
<223> OTHER INFORMATION: Score of 1274.3 for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (97)..(117)
<223> OTHER INFORMATION: Pfam Name: IQ Pfam Description: IQ calmodulin-
    binding motif

<400> SEQUENCE: 19

Met Gly Lys Ser Pro Ala Lys Trp Ile Lys Ser Val Leu Leu Gly Lys
1               5                   10                  15

Lys Ser Thr Lys Ser Asn Ser Thr Lys Ala Lys Asp Leu Pro Ala Lys
            20                  25                  30

Ala Ala Asn Ser Asn Gly Cys Thr Ala Gly Lys Glu Pro Glu Ser Ser
        35                  40                  45

Asp Asn Ser Pro Leu Ile Ser Glu Pro Val Leu Ser Ser His Asn
    50                  55                  60

Val Ser Glu Ile Ser Asn Leu Pro Asn Gly Arg Ala Ile Glu Asn Met
65                  70                  75                  80

Val Arg Val Gly Ser Asp Thr Gln Ile Ser Pro Glu Lys Leu Arg Glu

-continued

```
                    85                  90                  95
Glu Leu Ala Ala Val Lys Ala Gln Ala Ala Phe Arg Gly Tyr Leu Ala
                100                 105                 110
Arg Arg Ala Phe Arg Ala Leu Lys Gly Ile Ile Arg Leu Gln Ala Leu
                115                 120                 125
Ile Arg Gly His Leu Val Arg Arg Gln Ala Val Ser Thr Leu Arg Gly
                130                 135                 140
Thr Trp Leu Ile Val Lys Phe Gln Ala Leu Val Arg Gly Arg Asn Val
145                 150                 155                 160
Arg Phe Ser Ser Ala Ala Thr Gln Leu Ala Val Lys Phe Gly Gln His
                165                 170                 175
Lys Tyr Gly Gly Asp Lys Ser Ser Asp Ala Trp Lys Glu Lys Leu Ser
                180                 185                 190
Ser His Pro Tyr Val Arg Lys Leu Leu Ser Ser Pro Ile Leu Val Gln
                195                 200                 205
Ala Leu His Val Gln Tyr Asp Glu Thr Asn Pro Asn Ser Ala Leu Asn
                210                 215                 220
Trp Leu Glu Arg Trp Thr Ile Ser Cys Ile Trp Lys Pro Val Ser Lys
225                 230                 235                 240
Pro Lys Ile Val Thr Asp Gly Lys Pro Gln Val Arg Arg Ala Ser Tyr
                245                 250                 255
Ala Met Glu Thr His Ser Ala Lys Leu Lys Arg Asn Val Arg Lys Ser
                260                 265                 270
Ser Thr Ala Thr Val Glu Thr Gln Ala Asn Thr Val Glu Ser Glu Lys
                275                 280                 285
Trp Lys Arg Asn Pro Arg Lys Leu Asn Gly Ser Pro Ala Asp Ser Val
                290                 295                 300
Pro Asp Ser Gln Leu Ser Glu Leu Glu Lys Val Lys Arg Asn Leu Lys
305                 310                 315                 320
Lys Ala Ala Asn Ser Met Ala Glu Ala Ser Lys Ile Ser Thr Lys Ala
                325                 330                 335
Asp Val Leu Lys Val Pro Asn Ser Ile Ala Asp Glu Leu Lys Ile Leu
                340                 345                 350
Gly Ser Met Ala Glu Leu Ser Lys Lys Ser Ile Pro Asn Gly Ile
                355                 360                 365
Ser Asp His Gln Asp Ser Glu Cys Glu Lys Ala Leu Glu Ser Thr Arg
                370                 375                 380
Glu Ala Val Phe Pro Leu Gly Thr Gln Asp Ser His Ser Gly Asn Leu
385                 390                 395                 400
Leu Glu Asn Ser Asn Ile Ser Lys Leu Val Pro Asp Ile Lys Tyr Asp
                405                 410                 415
Leu Glu Ala Ser Phe Leu Gly Asp Lys Val Asn Glu Pro Thr Thr Val
                420                 425                 430
Ala Gln Ala Asp Glu Val Ile Gln Leu Gln Asn Leu Asp Asn Gly Tyr
                435                 440                 445
Asp Ile Ile Glu Arg Lys Glu Thr Arg Ser Lys Glu Glu Pro Leu
                450                 455                 460
Pro Asn Gly Ser Leu Lys Thr Lys Arg Ser Ser Phe Ser Asn Ser
465                 470                 475                 480
Glu Tyr Pro Glu Ser Gly Thr Lys Asn Thr Pro Val Pro Ser Arg Lys
                485                 490                 495
Pro Ser Tyr Met Ala Pro Thr Glu Ser Leu Lys Ala Lys Leu Arg Gly
                500                 505                 510
```

-continued

```
Pro Pro Arg Leu Asp Ser Asp Leu Pro Val Asp Lys Asn Ala Phe Thr
        515                 520                 525

Arg Arg Gln Ser Leu Pro Ser Ala Ala Asn Asn Arg Ala Ile Lys Thr
    530                 535                 540

Glu Trp Arg Arg
545

<210> SEQ ID NO 20
<211> LENGTH: 574
<212> TYPE: PRT
<213> ORGANISM: Oryza sativa subsp. japonica
<220> FEATURE:
<221> NAME/KEY: misc_feature
<223> OTHER INFORMATION: Public GI ID no.115465121
<220> FEATURE:
<221> NAME/KEY: misc_feature
<223> OTHER INFORMATION: Score of 966.7 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (111)..(131)
<223> OTHER INFORMATION: Pfam Name: IQ Pfam Description: IQ calmodulin-
      binding motif

<400> SEQUENCE: 20

Met Gly Lys Ser Pro Ala Lys Trp Ile Lys Ser Val Leu Phe Gly Lys
1               5                   10                  15

Lys Ser Ser Arg Ser Gly Ser Thr Lys Ala Lys Asp Leu Ser Lys Gly
            20                  25                  30

Ser Asn Asn Lys Gly Tyr Ala Ala Ala Gly Lys Asp Ala Gly Phe Glu
        35                  40                  45

Ser Ser Pro Val Ile Ser Glu Pro Val Leu Val Thr Pro His Asn Asn
    50                  55                  60

Glu Ala Val Gln Glu Val Gly Arg Gly Glu Asn Ser Ser Leu Gln Gly
65                  70                  75                  80

Glu Val Val Val Arg Asp Val Ser Gln Asp Leu Glu Lys Gln Asn Thr
                85                  90                  95

Val Val Ser Asp Ala Ser Asn Asp Pro Glu Arg Leu Arg Glu Glu Gln
            100                 105                 110

Ala Ala Val Lys Ala Gln Ala Ala Phe Arg Gly Tyr Leu Ala Arg Arg
        115                 120                 125

Ala Phe Arg Ala Leu Lys Gly Ile Ile Arg Leu Gln Ala Leu Ile Arg
    130                 135                 140

Gly His Leu Val Arg Arg Gln Ala Val Ala Thr Leu Arg Ala Thr Trp
145                 150                 155                 160

Leu Ile Val Lys Phe Gln Ala Leu Val Arg Gly Arg Asn Val Arg Leu
                165                 170                 175

Ser Thr Asn Thr Ile Gln Val Asn Trp Lys Leu Val Gln Gln Gln Ser
            180                 185                 190

Gly Ser Gly Lys Arg Asp Ala Trp Lys Glu Lys Leu Ser Ser Asn Ala
        195                 200                 205

Phe Ala Arg Lys Leu Leu Ala Ser Pro Ile Leu Val Glu Ala Leu His
    210                 215                 220

Phe Gln Tyr Asp Glu Arg Asp Pro Asn Ser Ala Phe Asn Trp Leu Glu
225                 230                 235                 240

Arg Trp Thr Ile Gly Arg Val Trp Arg Pro Ile Ser His Pro Lys Arg
```

```
                    245                 250                 255
Ala Ala Val Thr Asp Ala Lys Pro His Thr Arg Lys Ala Ser Tyr Ala
                260                 265                 270

Met Glu Thr Glu Ser Gly Lys Leu Lys Arg Asn Ser Arg Arg Ser Ser
            275                 280                 285

Ala Ala Pro Val Glu Ser Ser Gln Thr Asn Ile Ala Met Glu Thr Glu
        290                 295                 300

Lys Ser Arg Arg Asn Pro Arg Lys Phe Thr Ser Ser Thr Ala Asp Ser
305                 310                 315                 320

Val Pro Glu Ser Gln Leu Thr Glu Leu Glu Lys Val Lys Arg Asn Leu
                325                 330                 335

Arg Lys Val Thr Asn Ser Met Ala Glu Ala Ser Lys Val Ser Thr Pro
                340                 345                 350

Ala Thr Glu Ile Pro Glu Arg Gln Glu Val Gln Cys Glu Lys Pro Gln
                355                 360                 365

Arg Thr Ala Glu Glu Val Pro Asn Tyr Pro Glu Ile Gln Glu Pro Gln
            370                 375                 380

Asn Gly Asn Leu Leu Glu Asn Ala Lys Thr Asp Ile Leu Val Pro Asp
385                 390                 395                 400

Leu Gln Pro Glu Pro Glu Val Pro Ser Tyr Gln Val Glu Thr Glu Glu
                405                 410                 415

Lys Val Ala Glu Leu Thr Val Ala Asp Pro Thr Val Glu Thr Met Pro
                420                 425                 430

Leu Gln Asp Ile His Asn Glu Glu Asn Ala Leu Val Asn Asp Met Glu
            435                 440                 445

Gln Arg Ser Lys Glu Glu Pro Leu Ser Thr Glu Ser Leu Lys Ser Ser
        450                 455                 460

Lys Arg Arg Ser Ser Phe Ser Thr Lys Thr Glu Tyr Pro Glu Asn Gly
465                 470                 475                 480

Ser Lys Asn Ser Pro Ala Val Pro Ser Tyr Met Ala Ala Thr Gln Ser
                485                 490                 495

Ala Lys Ala Lys Leu Arg Gly Gln Asn Ser Pro Arg Leu Ser Ser Asp
                500                 505                 510

Ser Ala Glu Lys Asn Gly Phe Thr Arg Arg His Ser Leu Pro Ser Ser
            515                 520                 525

Asn Gly Lys Leu Asn Ser His Ser Pro Arg Thr Gln Arg Pro Thr His
        530                 535                 540

Ala Gly Gly Lys Glu Gly Val Lys Ala Asp Lys Ser Met Leu Ser Ser
545                 550                 555                 560

Arg Asp Ala Ser Glu Arg Pro Ala Lys Ala Glu Trp Lys Arg
                565                 570

<210> SEQ ID NO 21
<211> LENGTH: 2529
<212> TYPE: DNA
<213> ORGANISM: Panicum virgatum
<220> FEATURE:
<221> NAME/KEY: misc_feature
<223> OTHER INFORMATION: Ceres CLONE ID no.1791910
<220> FEATURE:
<221> NAME/KEY: misc_feature
<223> OTHER INFORMATION: Encodes the peptide sequence at SEQ ID NO 22

<400> SEQUENCE: 21
ggattggagg ttggaggcct gaaggggggag gtgggtcgcc ggacagggac ggggagacgg      60
cgagagggcg ttccgcagga gccgttcccg tgcttcctcc accgaccggg ccgacgcgcc     120
```

-continued

```
gcgccgctgt tcaggttcc cgccctgca tttttctgct tgtgcttgcg ctagttgcga       180
gggtaggttg cggcgttaga gattggttcg cggcttctgt gcggcgctgt gtttgtttgg     240
ccagatccgc gtgtgtgctg ctgactcttc gtgatttcct cttctgtttg agctttcctt    300
gctcggcttt gtgctgctgc ctgcctgctg cttcttttc tggccactgc atttgggttg      360
tgtgccgcgc tacttatcct gctctgcttg tgtttaagat tacagctcgt gtttctttca    420
acgatatttt caccttttgtt tcatcacttg ggaagctggg gccgtaaaag agtctgctaa   480
accatgctaa ctttagcgaa attactgtta ctccagctgt ccagcatgtt ccttccttca    540
tcttagtgaa aataaagtat gttgtggcat actggtatgg atctgtgcat tgctgagctc    600
ctctgtttac aggttccaga atttcaagta ttggccgctt taggatacta tgggaaagtc    660
cccggggaag tggatcaagt ctgtgctctt ggggaagaaa tcgactaaat ccggttctac    720
caaggcaaat gagtcggcta caaataacaa tggacactca gctggggagg agcgtgcatt   780
ttctgaaaat tctccagtga tctctgagcc ggtgcttgtt gaagcccaca aaaatggagc    840
tgtttcagtt aatgggaagg ctgaagatgt caatttgcca agtgacaggg ctggccaaca    900
agatctgcag aaccaaagta ttgttgagtc cgaaacatca gttcctgggc aattgggaga    960
agaccaagct gcagtgaagg cacaggcagc atttcgcggt tacctagcac gaaggtcatt    1020
ccgtgcattg aaaggtatca taagactcca ggcactgatt cgagggcatc ttgtaaggag    1080
acaggctgtt caacccttc aaactacttg gttgattgtg aagtttcaat ctctagttcg     1140
tggaagaaat gtcagactct ctggtgctga cattcaactc aatgtgaagc ttggccaaca    1200
taaccttggt ggcactagat catctgatgc atggaaagag aagttatctt caaatgccta    1260
tgttcggaag cttctgtctt caccaatagt gctagaacct cttcacttcc agtatgacaa    1320
gagggatccc aattcaacct ataactggct agagagatgc accataggct gcatctggaa    1380
gcctgttttt caaccaaaaa gagttcctga tgggaaactg ctggtaagga aggctagtta    1440
tgcaatggaa actgaatcag ccaagttaaa gcgcaacatt aggaagggct ctgctgctac    1500
agttgagagt ttccatacaa gagtgactgg tgaatctgag aaacttaaac gtaatccaaa    1560
gaaattctca aacttccctg ctgactcagt accagatagc cagttatctg aacttgagaa    1620
ggttaaaagg aacctgagga aggtaactga ttccatggct gaagcctcaa agatctctag    1680
ttccagggtt gattcctcaa aggtatctga ttctacacct gatgctccaa aagtatctaa    1740
tcctgtggcc gaaatctcaa agacatctag tctcctgaac gggatctctg accatcaaga    1800
cagccaatgt gaaaaagcac tacagaatac acgtgaggct tcatttcctc ttgaaactca   1860
agattactct ggcaatggtc agctattgga atattcagat atggataact tcgacttggt    1920
acctggtttg aaaagtgatc tggaaactca gcttgattca gtttctatag agaaaatgt     1980 tgatgagccc actgttggtg cttcagcagc tgaaggtatg ccactgcaga acattgataa    2040
gcccaatagt ttagggaaga aagaggaagc aaggtccaag gaagagcatc tgtctaatgg    2100
aagccttaga actggcaaga gaaagtcttc atccccatac aaatcagaat atgtggaaaa    2160
cgggactcac actactcctg ctcagccaag gaagccaagc tatatggctg caacggagtc    2220
tgcgaaggcg aaattacgag cacagaattc acccagggtg gattctgatt catcagcaga    2280
aaagaatggc ttcactcgac gccactctct tccttccggt acaaacagta gggcgatcaa    2340
agctgaatgg aagcgctgag gaggcattgg cttgaattga atagtgcgat tgtctgaatc    2400
tctgctgggt gaactctgcc gctgcttgct ccttttttatt tatcctgcga tgtaaagaga   2460
```

```
agacgttgtc cctgtattga acaatctttg tgatgagtgc gtctggttca aaaaaaaaaa    2520
aaaaaaaaa                                                            2529
```

<210> SEQ ID NO 22
<211> LENGTH: 569
<212> TYPE: PRT
<213> ORGANISM: Panicum virgatum
<220> FEATURE:
<221> NAME/KEY: misc_feature
<223> OTHER INFORMATION: Ceres CLONE ID no.1791910
<220> FEATURE:
<221> NAME/KEY: misc_feature
<223> OTHER INFORMATION: Score of 824.9 for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (105)..(125)
<223> OTHER INFORMATION: Pfam Name: IQ Pfam Description: IQ calmodulin-
    binding motif

<400> SEQUENCE: 22

```
Met Gly Lys Ser Pro Gly Lys Trp Ile Lys Ser Val Leu Leu Gly Lys
1               5                   10                  15

Lys Ser Thr Lys Ser Gly Ser Thr Lys Ala Asn Glu Ser Ala Thr Asn
            20                  25                  30

Asn Asn Gly His Ser Ala Gly Glu Glu Arg Ala Phe Ser Glu Asn Ser
        35                  40                  45

Pro Val Ile Ser Glu Pro Val Leu Val Glu Ala His Lys Asn Gly Ala
    50                  55                  60

Val Ser Val Asn Gly Lys Ala Glu Asp Val Asn Leu Pro Ser Asp Arg
65                  70                  75                  80

Ala Gly Gln Gln Asp Leu Gln Asn Gln Ser Ile Val Glu Ser Glu Thr
                85                  90                  95

Ser Val Pro Gly Gln Leu Gly Glu Asp Gln Ala Ala Val Lys Ala Gln
            100                 105                 110

Ala Ala Phe Arg Gly Tyr Leu Ala Arg Arg Ser Phe Arg Ala Leu Lys
        115                 120                 125

Gly Ile Ile Arg Leu Gln Ala Leu Ile Arg Gly His Leu Val Arg Arg
    130                 135                 140

Gln Ala Val Ser Thr Leu Gln Thr Thr Trp Leu Ile Val Lys Phe Gln
145                 150                 155                 160

Ser Leu Val Arg Gly Arg Asn Val Arg Leu Ser Gly Ala Asp Ile Gln
                165                 170                 175

Leu Asn Val Lys Leu Gly Gln His Asn Leu Gly Gly Thr Arg Ser Ser
            180                 185                 190

Asp Ala Trp Lys Glu Lys Leu Ser Ser Asn Ala Tyr Val Arg Lys Leu
        195                 200                 205

Leu Ser Ser Pro Ile Val Leu Glu Pro Leu His Phe Gln Tyr Asp Lys
    210                 215                 220

Arg Asp Pro Asn Ser Thr Tyr Asn Trp Leu Glu Arg Cys Thr Ile Gly
225                 230                 235                 240

Cys Ile Trp Lys Pro Val Phe Gln Pro Lys Arg Val Pro Asp Gly Lys
                245                 250                 255

Leu Leu Val Arg Lys Ala Ser Tyr Ala Met Glu Thr Glu Ser Ala Lys
            260                 265                 270

Leu Lys Arg Asn Ile Arg Lys Gly Ser Ala Ala Thr Val Glu Ser Phe
```

```
            275                 280                 285
His Thr Arg Val Thr Gly Glu Ser Glu Lys Leu Lys Arg Asn Pro Lys
290                 295                 300

Lys Phe Ser Asn Phe Pro Ala Asp Ser Val Pro Asp Ser Gln Leu Ser
305                 310                 315                 320

Glu Leu Glu Lys Val Lys Arg Asn Leu Arg Lys Val Thr Asp Ser Met
                325                 330                 335

Ala Glu Ala Ser Lys Ile Ser Ser Ser Arg Val Asp Ser Ser Lys Val
                340                 345                 350

Ser Asp Ser Thr Pro Asp Ala Pro Lys Val Ser Asn Pro Val Ala Glu
                355                 360                 365

Ile Ser Lys Thr Ser Ser Leu Leu Asn Gly Ile Ser Asp His Gln Asp
            370                 375                 380

Ser Gln Cys Glu Lys Ala Leu Gln Asn Thr Arg Glu Ala Ser Phe Pro
385                 390                 395                 400

Leu Glu Thr Gln Asp Tyr Ser Gly Asn Gly Gln Leu Glu Tyr Ser
                    405                 410                 415

Asp Met Asp Asn Phe Asp Leu Val Pro Gly Leu Lys Ser Asp Leu Glu
                420                 425                 430

Thr Gln Leu Asp Ser Val Ser Ile Gly Glu Asn Val Asp Glu Pro Thr
            435                 440                 445

Val Gly Ala Ser Ala Ala Glu Gly Met Pro Leu Gln Asn Ile Asp Lys
450                 455                 460

Pro Asn Ser Leu Gly Lys Lys Glu Ala Arg Ser Lys Glu His
465                 470                 475                 480

Leu Ser Asn Gly Ser Leu Arg Thr Gly Lys Arg Lys Ser Ser Pro
                485                 490                 495

Tyr Lys Ser Glu Tyr Val Glu Asn Gly Thr His Thr Thr Pro Ala Gln
                500                 505                 510

Pro Arg Lys Pro Ser Tyr Met Ala Ala Thr Glu Ser Ala Lys Ala Lys
            515                 520                 525

Leu Arg Ala Gln Asn Ser Pro Arg Val Asp Ser Asp Ser Ser Ala Glu
530                 535                 540

Lys Asn Gly Phe Thr Arg Arg His Ser Leu Pro Ser Gly Thr Asn Ser
545                 550                 555                 560

Arg Ala Ile Lys Ala Glu Trp Lys Arg
                565
```

<210> SEQ ID NO 23
<211> LENGTH: 567
<212> TYPE: PRT
<213> ORGANISM: Oryza sativa subsp. japonica
<220> FEATURE:
<221> NAME/KEY: misc_feature
<223> OTHER INFORMATION: Public GI ID no.125595019
<220> FEATURE:
<221> NAME/KEY: misc_feature
<223> OTHER INFORMATION: Score of 928.2 for HMM of FIGURE 5.
<220> FEATURE:
<221> NAME/KEY: misc_feature
<223> OTHER INFORMATION: Functional Homolog Of Ceres CLONE ID no.
    1792354 at SEQ ID NO. 2
<220> FEATURE:
<221> NAME/KEY: misc_feature
<222> LOCATION: (111)..(131)
<223> OTHER INFORMATION: Pfam Name: IQ Pfam Description: IQ calmodulin-
    binding motif

<400> SEQUENCE: 23

```
Met Gly Lys Ser Pro Ala Lys Trp Ile Lys Ser Val Leu Phe Gly Lys
1               5                   10                  15

Lys Ser Ser Arg Ser Gly Ser Thr Lys Ala Lys Asp Leu Ser Lys Gly
            20                  25                  30

Ser Asn Asn Lys Gly Tyr Ala Ala Gly Lys Asp Ala Gly Phe Glu
        35                  40                  45

Ser Ser Pro Val Ile Ser Glu Pro Val Leu Val Thr Pro His Asn Asn
50                  55                  60

Glu Ala Val Gln Glu Val Gly Arg Gly Glu Asn Ser Ser Leu Gln Gly
65                  70                  75                  80

Glu Val Val Val Arg Asp Val Ser Gln Asp Leu Glu Lys Gln Asn Thr
                85                  90                  95

Val Val Ser Asp Ala Ser Asn Asp Pro Glu Arg Leu Arg Glu Glu Gln
            100                 105                 110

Ala Ala Val Lys Ala Gln Ala Ala Phe Arg Gly Tyr Leu Ala Arg Arg
            115                 120                 125

Ala Phe Arg Ala Leu Lys Gly Ile Ile Arg Leu Gln Ala Leu Ile Arg
        130                 135                 140

Gly His Leu Val Arg Arg Gln Ala Val Ala Thr Leu Arg Ala Thr Trp
145                 150                 155                 160

Leu Ile Val Lys Phe Gln Ala Leu Val Arg Gly Arg Asn Val Arg Leu
                165                 170                 175

Ser Thr Asn Thr Ile Gln Val Asn Trp Lys Leu Val Gln Gln Gln Ser
            180                 185                 190

Gly Ser Gly Lys Arg Asp Ala Trp Lys Glu Lys Leu Ser Ser Asn Ala
        195                 200                 205

Phe Ala Arg Lys Leu Leu Ala Ser Pro Ile Leu Val Glu Ala Leu His
    210                 215                 220

Phe Gln Tyr Asp Glu Arg Asp Pro Asn Ser Ala Phe Asn Trp Leu Glu
225                 230                 235                 240

Arg Trp Thr Ile Gly Arg Val Trp Arg Pro Ile Ser His Pro Lys Arg
                245                 250                 255

Ala Ala Val Thr Asp Ala Lys Pro His Thr Arg Lys Ala Ser Tyr Ala
            260                 265                 270

Met Glu Thr Glu Ser Gly Lys Leu Lys Arg Asn Ser Arg Arg Ser Ser
        275                 280                 285

Ala Ala Pro Val Glu Ser Ser Gln Thr Asn Ile Ala Met Glu Thr Glu
        290                 295                 300

Lys Ser Arg Arg Asn Pro Arg Lys Phe Thr Ser Ser Thr Ala Asp Ser
305                 310                 315                 320

Val Pro Glu Ser Gln Leu Thr Glu Leu Glu Lys Val Lys Arg Asn Leu
                325                 330                 335

Arg Lys Val Thr Asn Ser Met Ala Glu Ala Ser Lys Val Ser Thr Pro
            340                 345                 350

Ala Thr Glu Ile Pro Glu Arg Gln Glu Val Gln Cys Glu Lys Pro Gln
        355                 360                 365

Arg Thr Ala Glu Glu Val Pro Asn Tyr Pro Glu Ile Gln Glu Pro Gln
    370                 375                 380

Asn Gly Asn Leu Leu Glu Asn Ala Lys Thr Asp Ile Leu Val Pro Asp
385                 390                 395                 400

Leu Gln Pro Glu Pro Glu Val Pro Ser Tyr Gln Val Glu Thr Glu Glu
                405                 410                 415

Lys Val Ala Glu Leu Thr Val Ala Asp Pro Thr Val Glu Thr Met Pro
```

-continued

```
                    420                 425                 430
Leu Gln Asp Ile His Asn Glu Glu Asn Ala Leu Val Asn Asp Met Glu
            435                 440                 445

Gln Arg Ser Lys Glu Glu Pro Leu Ser Thr Glu Ser Leu Lys Ser Ser
        450                 455                 460

Lys Arg Arg Ser Ser Phe Ser Thr Lys Thr Glu Tyr Pro Glu Asn Gly
465                 470                 475                 480

Ser Lys Asn Ser Pro Ala Val Pro Ser Tyr Met Ala Ala Thr Gln Ser
                485                 490                 495

Ala Lys Ala Lys Leu Arg Gly Gln Asn Ser Pro Arg Leu Ser Ser Asp
            500                 505                 510

Ser Ala Glu Lys Asn Gly Phe Thr Arg Arg His Ser Leu Pro Ser Ser
        515                 520                 525

Asn Gly Lys Leu Asn Ser His Ser Pro Arg Thr Gln Arg Pro Thr His
    530                 535                 540

Ala Gly Gly Lys Glu Gly Val Lys Ala Asp Lys Ser Met Leu Ser Ser
545                 550                 555                 560

Arg Asp Ala Ser Gly Lys Leu
                565

<210> SEQ ID NO 24
<211> LENGTH: 636
<212> TYPE: PRT
<213> ORGANISM: Arabidopsis thaliana
<220> FEATURE:
<221> NAME/KEY: misc_feature
<223> OTHER INFORMATION: Public GI ID no.42568886
<220> FEATURE:
<221> NAME/KEY: misc_feature
<223> OTHER INFORMATION: Score of 1517.7 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (129)..(149)
<223> OTHER INFORMATION: Pfam Name: IQ Pfam Description: IQ calmodulin-
      binding motif

<400> SEQUENCE: 24

Met Gly Lys Thr Pro Ser Pro Gly Lys Trp Ile Lys Ser Leu Leu Gly
1               5                   10                  15

Lys Lys Ser Ser Lys Ser Ser Leu Glu Lys Gly Gly Glu Lys Leu Arg
            20                  25                  30

Ser Ala Lys Lys Glu Glu Leu Val Lys Val Lys Asp Asn Asn Val
        35                  40                  45

Ser Lys Leu Pro Thr Glu Pro Pro Val Val Ser Ser Gln Glu Val Ala
    50                  55                  60

Ala Thr Gln Thr Val Val Val Pro Asp Val Val Ile Ala Glu Lys Gln
65                  70                  75                  80

Leu Ser Gly Asp Ile Glu Gly Asp Glu Ser Asn Val Asn Leu Glu
                85                  90                  95

Ser Gly Asn Asp Ser Glu Glu Val Lys Leu Glu Glu Ala Ala Thr Lys
            100                 105                 110

Val Gln Ala Ala Leu Arg Ala Gln Gln Ala Arg Glu Glu Ser Gln Asn
        115                 120                 125

Leu Lys Gly Ile Thr Arg Val Gln Ala Val Ile Arg Gly His Leu Val
    130                 135                 140
```

-continued

```
Arg Arg Gln Ala Val Ala Thr Tyr Ser Cys Ile Trp Gly Ile Val Lys
145                 150                 155                 160

Val Gln Ala Leu Val Arg Gly Lys Lys Ala Arg Ser Ser Glu Thr Val
            165                 170                 175

Ala Gln Leu Gln Lys Thr Asn Thr Glu Thr Glu Thr Ser Glu Thr Leu
        180                 185                 190

Gln Gly Ser Thr Tyr Ser Trp Met Glu Asn Pro Thr Lys Leu Ser Met
    195                 200                 205

Ile Asp Lys Leu Leu Val Ser Ser Pro Thr Thr Leu Pro Leu Lys Ile
210                 215                 220

Gln Tyr Ser Pro Glu Asp Pro Asn Ser Ala Lys Val Trp Leu Gly Arg
225                 230                 235                 240

Trp Thr Gln Leu Gln Val Trp Ala Pro Gly Pro Leu Val Val Lys Asn
            245                 250                 255

Leu Val Pro Lys Ser Gln Thr Lys Lys Arg Ser Phe Gln Ala Val Glu
        260                 265                 270

Ala Glu Lys Gly Lys Leu Lys Arg Gly Val Arg Lys Pro Thr Gly Val
    275                 280                 285

Ser Thr Thr Ala Asn Ser Ser Thr Ser Arg Ser Thr Ala Asp Asn Glu
290                 295                 300

Lys Pro Lys Arg Thr Val Arg Lys Ala Ser Thr Leu Gly Lys Glu Leu
305                 310                 315                 320

Ser Lys Ile Glu Asn Asp Lys Ser Lys Gln Ser Ser Arg Lys Ser Thr
            325                 330                 335

Ser Ala Ile Lys Glu Gly Ser Ser Val Glu Val Lys Asp Glu Lys Pro
        340                 345                 350

Arg Ile Ser His Lys Lys Ala Ser Leu Ser Asn Gly Ile Gly Lys Ala
    355                 360                 365

Thr Arg Lys Ser Ala Glu Lys Lys Glu Ile Ala Asp Ala Val Gln
370                 375                 380

Lys Glu Leu Pro Ile Glu Glu Val Ser Val Ser Leu Val Asp Ala Pro
385                 390                 395                 400

Glu Asp Glu Lys Met Asn Leu Ile Pro Val Thr Ile Ser Lys Glu Ser
            405                 410                 415

Asp Leu Asp Lys Asp Glu Lys Ser Leu Val Leu Asp Lys Pro Glu Gln
        420                 425                 430

Asp Glu Leu Arg Thr Ala Glu Arg Asp Asp Lys Ala Glu Glu Leu
    435                 440                 445

Lys Thr Ala Glu Arg Asp Asp Ser Ala Glu Lys Ile Gln Glu Pro
450                 455                 460

Asp Ala Gln Ile Ser Ser Glu Asn Gly Asn Val Ala Ser Glu Asn Thr
465                 470                 475                 480

Lys Pro Ser Asp Arg Arg Ala Ser Leu Pro Ala Lys Ile Glu Asn His
            485                 490                 495

His Gln Asp Asp Gly Leu Thr Gln Ser Gly Arg Lys Ile Pro Ser Tyr
        500                 505                 510

Met Ala Pro Thr Ala Ser Ala Lys Ala Arg Ile Arg Gly Gln Gly Ser
    515                 520                 525

Pro Arg Ile Ala Gln Glu Lys Pro Glu Lys Asn Gly Thr Thr Arg Arg
530                 535                 540

His Ser Leu Pro Pro Ala Ala Asn Gly Lys Leu Ser Thr Met Ser Pro
545                 550                 555                 560

Arg Ala His Arg Leu Leu Ile Ala Ser Ala Lys Gly Ser Met Asn Ser
```

-continued

```
                565                 570                 575

Asp Arg Ser Phe Ser Ser Ser Lys Asp Ile Gly Gly Lys Arg Phe Lys
            580                 585                 590

Pro Ile Thr Ile His Lys Pro Phe Cys Gln Phe Leu Leu His Tyr Leu
        595                 600                 605

His Pro Phe Asn Lys Phe Ser Ser Cys Leu Tyr Gln Thr Ser Arg Arg
    610                 615                 620

Lys Leu Ser Gly Asn Gly Glu Ser Thr Lys Ala Glu
625                 630                 635

<210> SEQ ID NO 25
<211> LENGTH: 650
<212> TYPE: PRT
<213> ORGANISM: Arabidopsis thaliana
<220> FEATURE:
<221> NAME/KEY: misc_feature
<223> OTHER INFORMATION: Public GI ID no.2947062
<220> FEATURE:
<221> NAME/KEY: misc_feature
<223> OTHER INFORMATION: Score of 1502.4 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (143)..(163)
<223> OTHER INFORMATION: Pfam Name: IQ Pfam Description: IQ calmodulin-
      binding motif

<400> SEQUENCE: 25

Met Gly Lys Thr Pro Ser Pro Gly Lys Trp Ile Lys Ser Leu Leu Gly
1               5                   10                  15

Lys Lys Ser Ser Lys Ser Ser Leu Glu Lys Gly Gly Glu Lys Leu Val
            20                  25                  30

Arg Arg Val Asn Arg Ser Ala Lys Lys Glu Glu Leu Val Val Lys Val
        35                  40                  45

Lys Asp Asn Asn Val Ser Lys Leu Pro Thr Glu Pro Pro Val Val Ser
    50                  55                  60

Ser Gln Glu Val Ala Ala Thr Gln Thr Val Val Pro Asp Val Val
65                  70                  75                  80

Ile Ala Glu Lys Gln Leu Ser Gly Asp Ile Glu Gly Asp Glu Ser Ser
                85                  90                  95

Asn Val Asn Leu Glu Ser Gly Asn Asp Ser Glu Glu Val Lys Leu Glu
            100                 105                 110

Glu Ala Ala Thr Lys Val Gln Ala Ala Leu Arg Ala Gln Gln Val Asn
        115                 120                 125

Val Tyr Ile Phe Asp Ile Leu Ala Arg Glu Glu Ser Gln Asn Leu Lys
    130                 135                 140

Gly Ile Thr Arg Val Gln Ala Val Ile Arg Gly His Leu Val Arg Arg
145                 150                 155                 160

Gln Ala Val Ala Thr Tyr Ser Cys Ile Trp Gly Ile Val Lys Val Gln
                165                 170                 175

Ala Leu Val Arg Gly Lys Lys Ala Arg Ser Ser Glu Thr Val Ala Gln
            180                 185                 190

Leu Gln Lys Thr Asn Thr Glu Thr Glu Thr Ser Glu Thr Leu Gln Gly
        195                 200                 205

Ser Thr Tyr Ser Trp Met Glu Asn Pro Thr Lys Leu Ser Met Ile Asp
    210                 215                 220
```

```
Lys Leu Leu Val Ser Ser Pro Thr Thr Leu Pro Leu Lys Ile Gln Tyr
225                 230                 235                 240

Ser Pro Glu Asp Pro Asn Ser Ala Lys Val Trp Leu Gly Arg Trp Thr
            245                 250                 255

Gln Leu Gln Val Trp Ala Pro Gly Pro Leu Val Val Lys Asn Leu Val
        260                 265                 270

Pro Lys Ser Gln Thr Lys Lys Arg Ser Phe Gln Ala Val Glu Ala Glu
    275                 280                 285

Lys Gly Lys Leu Lys Arg Gly Val Arg Lys Pro Thr Gly Val Ser Thr
290                 295                 300

Thr Ala Asn Ser Ser Thr Ser Arg Ser Thr Ala Asp Asn Glu Lys Pro
305                 310                 315                 320

Lys Arg Thr Val Arg Lys Ala Ser Thr Leu Gly Lys Glu Leu Ser Lys
            325                 330                 335

Ile Glu Asn Asp Lys Ser Lys Gln Ser Ser Arg Lys Ser Thr Ser Ala
        340                 345                 350

Ile Lys Glu Gly Ser Ser Val Glu Val Lys Asp Glu Lys Pro Arg Ile
    355                 360                 365

Ser His Lys Lys Ala Ser Leu Ser Asn Gly Ile Gly Lys Ala Thr Arg
370                 375                 380

Lys Ser Ala Glu Lys Lys Glu Ile Ala Asp Ala Val Gln Lys Glu
385                 390                 395                 400

Leu Pro Ile Glu Glu Val Ser Val Ser Leu Val Asp Ala Pro Glu Asp
            405                 410                 415

Glu Lys Met Asn Leu Ile Pro Val Thr Ile Ser Lys Glu Ser Asp Leu
        420                 425                 430

Asp Lys Asp Glu Lys Ser Leu Val Leu Asp Lys Pro Glu Gln Asp Glu
    435                 440                 445

Leu Arg Thr Ala Glu Arg Asp Asp Lys Ala Glu Glu Leu Lys Thr
    450                 455                 460

Ala Glu Arg Asp Asp Ser Ala Glu Glu Lys Ile Gln Glu Pro Asp Ala
465                 470                 475                 480

Gln Ile Ser Ser Glu Asn Gly Asn Val Ala Ser Glu Asn Thr Lys Pro
            485                 490                 495

Ser Asp Arg Arg Ala Ser Leu Pro Ala Lys Ile Glu Asn His His Gln
        500                 505                 510

Asp Asp Gly Leu Thr Gln Ser Gly Arg Lys Ile Pro Ser Tyr Met Ala
    515                 520                 525

Pro Thr Ala Ser Ala Lys Ala Arg Ile Arg Gly Gln Gly Ser Pro Arg
    530                 535                 540

Ile Ala Gln Glu Lys Pro Glu Lys Asn Gly Thr Thr Arg Arg His Ser
545                 550                 555                 560

Leu Pro Pro Ala Ala Asn Gly Lys Leu Ser Thr Met Ser Pro Arg Ala
            565                 570                 575

His Arg Leu Leu Ile Ala Ser Ala Lys Gly Ser Met Asn Ser Asp Arg
        580                 585                 590

Ser Phe Ser Ser Ser Lys Asp Ile Gly Gly Lys Arg Phe Lys Pro Ile
    595                 600                 605

Thr Ile His Lys Pro Phe Cys Gln Phe Leu His Tyr Leu His Pro
    610                 615                 620

Phe Asn Lys Phe Ser Ser Cys Leu Tyr Gln Thr Ser Arg Arg Lys Leu
625                 630                 635                 640

Ser Gly Asn Gly Glu Ser Thr Lys Ala Glu
```

<210> SEQ ID NO 26
<211> LENGTH: 1881
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1468228
<220> FEATURE:
<221> NAME/KEY: misc_feature
<223> OTHER INFORMATION: Encodes the peptide sequence at SEQ ID NO 27

<400> SEQUENCE: 26

```
atggggagaa aatcacctgc gaaatggata agactgtttt tgtttggaaa gaagtcttcc        60
aaatctctta ttgtcaaagg aagggagaga actgtgaatg acaaagagac attggttgct       120
gtcagagccg tggaagctga tgtgacctca gttcctccgg tggtcaagcc gacagccccc       180
actaccacta atatcactga aaggatgtta gagctagaga gcaggaaaac tacagaatca       240
tcacgtgatg gaggtatatt gtcaactgga aatcaagatc aaatcattc tcaattatac        300
actcctgatg ctcctccatc tgatgctgac aaaataaggc ttgatgaagc tgcgacaatg       360
gcacaagccg catttagggg ttacttgata ggtgcactac tggggctgtt ttcatggacc       420
ttgagggttc gactgacttg gtaccaggct cgccgagcat ttcgagctct taaaggcata       480
ataaggcttc aggctcttat ccgtggacac ttggttagaa ggcaagctgt tgctactctc       540
tgctgtgtgc tcggagttgt caagttacag gctcttgctc aggaagaat ggttaggaat         600
tcagagattg ctatgaggt tcataaatta tgcagccaag taaaactgcc ggagggcaag        660
cttgcagatt ctagtggagt tggtatacaa atggccaagc tgtcatcaaa tgcttttgtt       720
cgcaagcttc ttgctccatc acctgctgta atgccttttgc aactccccta tgattccatg      780
gaaccaaact cagttgcaaa ctggttagag tgctggtcag cgtcctcttt ctggaaacca       840
gttccccaac caaaaaaaat tacttgctca aaaactcaga gaaagcagag taatggtcaa       900
atagtggaag ctgaaactgg taggccaaag cgcactgttc ggagggtccc tgctgcaaat       960
gttgacagta cctcagtaca agcagcctct gaatttgaga acccaagcg caatttgagg      1020
aaagtttcaa gccatccagc tgattcagca gaaaattcac agattgagct tgaaaaggta      1080
aagcgcagct taagaaaggt taataacccc gttatagaaa actctgctca ttcagaggtt      1140
gaaaatgaaa agccaaagca aggtctagaa aaggtatctg gcacttcagg tgataatgtt      1200
ttgggatgga gcgtaagtaa ttcagctgag aagatgaaga agaagctac cttgacaaca      1260
tccaatgtac ctgatgtggt gaagaatgat ccaaacttga tgtccaagtt gcctgatgca      1320
gagacagctg atgaacctgt agaaatgatc aaggcattgg aatcatcaca tgacgatcaa      1380
gctgtggtag aatctaaagc ttcagtagat actggtggta tagttgagaa tatgcaaata      1440
aatgggaagt ccatacacca ggatgatcca acaagcaatg aaaatcacaa aactgccaag      1500
aaaccttcat tcacaatgaa accagaacgt gccgagaatg ggctacagag cagtcccacc      1560
ctccctagct acatggcagc aactgaatct gcaaaggcaa agctgagaat gcaaggctcc      1620
ccaagattta gtgaagatcg agttgagaaa ataacatca cccgtcgtca ttctctgccc       1680
tcttcaacta atagcaaaat cagctccgag tccccgagga cacaaagagc agttcatggt      1740
agtggcaaag gggggaataa gagtgacaag tctttattgt cttcaagaga tggaaatgct      1800
aagggagccc aaccagagtg gaagagatca tggtgtagca gtgaaacatg gtctatagcc      1860
ggaagggagt atgtggatta a                                               1881
```

```
<210> SEQ ID NO 27
<211> LENGTH: 626
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1468228
<220> FEATURE:
<221> NAME/KEY: misc_feature
<223> OTHER INFORMATION: Score of 1490.5 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (157)..(177)
<223> OTHER INFORMATION: Pfam Name: IQ Pfam Description: IQ calmodulin-
      binding motif

<400> SEQUENCE: 27

Met Gly Arg Lys Ser Pro Ala Lys Trp Ile Lys Thr Val Leu Phe Gly
1               5                   10                  15

Lys Lys Ser Ser Lys Ser Leu Ile Val Lys Gly Arg Glu Arg Thr Val
            20                  25                  30

Asn Asp Lys Glu Thr Leu Val Ala Val Arg Ala Val Glu Ala Asp Val
        35                  40                  45

Thr Ser Val Pro Pro Val Val Lys Pro Thr Ala Pro Thr Thr Thr Asn
    50                  55                  60

Ile Thr Glu Arg Met Leu Glu Leu Glu Ser Arg Glu Thr Thr Glu Ser
65                  70                  75                  80

Ser Arg Asp Gly Gly Ile Leu Ser Thr Gly Asn Gln Asp Ala Asn His
                85                  90                  95

Ser Gln Leu Tyr Thr Pro Asp Ala Pro Pro Ser Asp Ala Asp Lys Ile
            100                 105                 110

Arg Leu Asp Glu Ala Ala Thr Met Ala Gln Ala Ala Phe Arg Gly Tyr
        115                 120                 125

Leu Ile Gly Ala Leu Leu Gly Leu Phe Ser Trp Thr Leu Arg Val Arg
    130                 135                 140

Leu Thr Trp Tyr Gln Ala Arg Arg Ala Phe Arg Ala Leu Lys Gly Ile
145                 150                 155                 160

Ile Arg Leu Gln Ala Leu Ile Arg Gly His Leu Val Arg Arg Gln Ala
                165                 170                 175

Val Ala Thr Leu Cys Cys Val Leu Gly Val Val Lys Leu Gln Ala Leu
            180                 185                 190

Ala Arg Gly Arg Met Val Arg Asn Ser Glu Ile Gly Tyr Glu Val His
        195                 200                 205

Lys Leu Cys Ser Gln Val Lys Leu Pro Glu Gly Lys Leu Ala Asp Ser
    210                 215                 220

Ser Gly Val Gly Ile Gln Met Ala Lys Leu Ser Ser Asn Ala Phe Val
225                 230                 235                 240

Arg Lys Leu Leu Ala Pro Ser Pro Ala Val Met Pro Leu Gln Leu Pro
                245                 250                 255

Tyr Asp Ser Met Glu Pro Asn Ser Val Ala Asn Trp Leu Glu Cys Trp
            260                 265                 270

Ser Ala Ser Ser Phe Trp Lys Pro Val Pro Gln Pro Lys Lys Ile Thr
        275                 280                 285

Cys Ser Lys Thr Gln Arg Lys Gln Ser Asn Gly Gln Ile Val Glu Ala
```

```
                290                 295                 300
Glu Thr Gly Arg Pro Lys Arg Thr Val Arg Arg Val Pro Ala Ala Asn
305                 310                 315                 320

Val Asp Ser Thr Ser Val Gln Ala Ala Ser Glu Phe Glu Lys Pro Lys
            325                 330                 335

Arg Asn Leu Arg Lys Val Ser Ser His Pro Ala Asp Ser Ala Glu Asn
        340                 345                 350

Ser Gln Ile Glu Leu Glu Lys Val Lys Arg Ser Leu Arg Lys Val Asn
    355                 360                 365

Asn Pro Val Ile Glu Asn Ser Ala His Ser Glu Val Glu Asn Glu Lys
370                 375                 380

Pro Lys Gln Gly Leu Glu Lys Val Ser Gly Thr Ser Gly Asp Asn Val
385                 390                 395                 400

Leu Gly Trp Ser Val Ser Asn Ser Ala Glu Lys Met Lys Lys Glu Ala
            405                 410                 415

Thr Leu Thr Thr Ser Asn Val Pro Asp Val Val Lys Asn Asp Pro Asn
        420                 425                 430

Leu Met Ser Lys Leu Pro Asp Ala Glu Thr Ala Asp Glu Pro Val Glu
    435                 440                 445

Met Ile Lys Ala Leu Glu Ser Ser His Asp Asp Gln Ala Val Val Glu
    450                 455                 460

Ser Lys Ala Ser Val Asp Thr Gly Gly Ile Val Glu Asn Met Gln Ile
465                 470                 475                 480

Asn Gly Lys Ser Ile His Gln Asp Asp Pro Thr Ser Asn Glu Asn His
            485                 490                 495

Lys Thr Ala Lys Lys Pro Ser Phe Thr Met Lys Pro Glu Arg Ala Glu
        500                 505                 510

Asn Gly Leu Gln Ser Ser Pro Thr Leu Pro Ser Tyr Met Ala Ala Thr
    515                 520                 525

Glu Ser Ala Lys Ala Lys Leu Arg Met Gln Gly Ser Pro Arg Phe Ser
530                 535                 540

Glu Asp Arg Val Glu Lys Asn Asn Ile Thr Arg Arg His Ser Leu Pro
545                 550                 555                 560

Ser Ser Thr Asn Ser Lys Ile Ser Ser Glu Ser Pro Arg Thr Gln Arg
            565                 570                 575

Ala Val His Gly Ser Gly Lys Gly Gly Asn Lys Ser Asp Lys Ser Leu
        580                 585                 590

Leu Ser Ser Arg Asp Gly Asn Ala Lys Gly Ala Gln Pro Glu Trp Lys
    595                 600                 605

Arg Ser Trp Cys Ser Ser Glu Thr Trp Ser Ile Ala Gly Arg Glu Tyr
    610                 615                 620

Val Asp
625

<210> SEQ ID NO 28
<211> LENGTH: 2050
<212> TYPE: DNA
<213> ORGANISM: Gossypium hirsutum
<220> FEATURE:
<221> NAME/KEY: misc_feature
<223> OTHER INFORMATION: Ceres CLONE ID no.1942388
<220> FEATURE:
<221> NAME/KEY: misc_feature
<223> OTHER INFORMATION: Encodes the peptide sequence at SEQ ID NO 29

<400> SEQUENCE: 28
```

| | |
|---|---|
| atttagtttt aaattcacta aaaaaaagcc tgcacgagat tctcttgttc gaggaatcct | 60 |
| tcacgatctc tgaatgctca cagttccggt aatggcagct tagtaccgaa caaggacttc | 120 |
| atatttgata ctcttttcag atttccagat ttagaaactt gggatttaa ttattttgg | 180 |
| gtttaactga gatggggaaa tctccagcga aatggatcaa gaccttgctt cttgggaaga | 240 |
| aatcttcaaa gtccagtttc tcaaaggaa aagataagct gaattctgca aataaaggtg | 300 |
| aggttttggt ttcttccaag gtaactgtgt ctgacctatc agcggattct ccatcgattt | 360 |
| cagcacctat tctagtgagc cgtgctagga atgtgatgga ctctgagaag ggtatacctg | 420 |
| cccaattgcc gattgatggg gaaaatattc catctctaaa agtggatgga ataatgcca | 480 |
| caaccggtaa ttttggtaac ccagaaaatc ctgataggat taggcttgac ccagctgctg | 540 |
| tgacagtaca ggctgctttc agaggttatc tggctcgccg ggaatttcga atcctcaagg | 600 |
| gcattataag gctgcaggca gttattcgtg gtcacttggt tagaagacaa gctgttgcta | 660 |
| ctttatgctg tacatgggga attgttaagt tgcaagcact agctcgtggt caaaaggtca | 720 |
| gatgttcaga tattgccatg gaaatacagg aaaaacatct aagactgctt cagggtttga | 780 |
| aaagctcaaa ttctgtagga gcgagcatat cttctacagt gaagaattta tcaagtaatg | 840 |
| tgtttgttca gaagctttg gcctcgtcac cttctgtatt gcctctacaa cttcagtatg | 900 |
| ttccagagga gcctaactca tcctggcaat ggcttcaacg atggacaaga tcacaatttt | 960 |
| gggaataccc ctcaaaacca attaggagtg aaagacaaa gctaagtgtt cagaaactat | 1020 |
| cctttgcaaa agctgttaat ggatctagtc attctacatt ggagtatgaa aaaaataaac | 1080 |
| gaggtctgag gagaatttct gtcaactcag cagcagattc agttcgggag catccacaaa | 1140 |
| atgagctcga gagggttaag cgcaatttaa gaaagctttc caactcttca aaggaggtta | 1200 |
| ctgataagtc tgagtttgtt aatgagaaaa caaagaagac tctgaaaaaa tattctagtt | 1260 |
| ctaatggccc tgatgtttta gaacaggaat ctgctgagaa gataagagat gtgactgcaa | 1320 |
| cactatcaga actgtcaatt cttgaggcag atctgaaatt ttcctcagaa catgcttctc | 1380 |
| ttggtgagcc tattgtctgt cctgcagttg attttccacc ggccaaaaac aatggtaaaa | 1440 |
| ttgagcacat gccactaaca gaggagttaa actctaagga tgagcaggtc ggtgatgaga | 1500 |
| gctcaaacac aaaccaaaga agagcttctt tcccagcaaa tattgataat caggcaaatc | 1560 |
| ggttaaatca catgccaaaa gtgcccagtt atatggcacc aactgaatct gcgaaagcta | 1620 |
| gacttagggg tcaagggtcc ccaaggttta tccccgaggc tgttgagaaa atgggttaa | 1680 |
| acaggcggta ttctttgcca acttcaacca atagtaatac aggttcacaa tccccacata | 1740 |
| ctcaaagaca ggttcgagta gctggcaaag gtgctatcat cagtgacaaa tctcaatcat | 1800 |
| cctctaaaga tgctaatgat aaggtggtca gagccgagtg gaggaggtaa ttcttgcaca | 1860 |
| aggaattgtt tcgatgaagt ttccatgggt aaatatttgt agatgttaca gttgtttatt | 1920 |
| tggttcgttt ttgtttggac gtaaaattct ttggatcccc tgttcactct tttctaccat | 1980 |
| ttaatatcat aggaatagag tgtgcccatc tccatatctg gctttcgtag aaaaaaaaaa | 2040 |
| aaaaaaaaaa | 2050 |

<210> SEQ ID NO 29
<211> LENGTH: 552
<212> TYPE: PRT
<213> ORGANISM: Gossypium hirsutum
<220> FEATURE:
<221> NAME/KEY: misc_feature
<223> OTHER INFORMATION: Ceres CLONE ID no.1942388
<220> FEATURE:

```
<221> NAME/KEY: misc_feature
<223> OTHER INFORMATION: Score of 1315.8 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (113)..(133)
<223> OTHER INFORMATION: Pfam Name: IQ Pfam Description: IQ calmodulin-
      binding motif

<400> SEQUENCE: 29
```

| | | | | | | | | | | | | | | |
|---|---|---|---|---|---|---|---|---|---|---|---|---|---|---|
| Met | Gly | Lys | Ser | Pro | Ala | Lys | Trp | Ile | Lys | Thr | Leu | Leu | Gly | Lys |
| 1 | | | | 5 | | | | | 10 | | | | | 15 |
| Lys | Ser | Ser | Lys | Ser | Ser | Phe | Ser | Lys | Gly | Lys | Asp | Lys | Leu | Asn | Ser |
| | | | 20 | | | | | 25 | | | | | 30 | |
| Ala | Asn | Lys | Gly | Glu | Val | Leu | Val | Ser | Lys | Val | Thr | Val | Ser | Asp |
| | | 35 | | | | | 40 | | | | | 45 | | |
| Leu | Ser | Ala | Asp | Ser | Pro | Ser | Ile | Ser | Ala | Pro | Ile | Leu | Val | Ser | Arg |
| | 50 | | | | | 55 | | | | | 60 | | | | |
| Ala | Arg | Asn | Val | Met | Asp | Ser | Glu | Lys | Gly | Ile | Pro | Ala | Gln | Leu | Pro |
| 65 | | | | | 70 | | | | | 75 | | | | | 80 |
| Ile | Asp | Gly | Glu | Asn | Ile | Pro | Ser | Leu | Lys | Val | Asp | Gly | Asn | Asn | Ala |
| | | | | 85 | | | | | 90 | | | | | 95 | |
| Thr | Thr | Gly | Asn | Phe | Gly | Asn | Pro | Glu | Asn | Pro | Asp | Arg | Ile | Arg | Leu |
| | | | 100 | | | | | 105 | | | | | 110 | | |
| Asp | Pro | Ala | Ala | Val | Thr | Val | Gln | Ala | Ala | Phe | Arg | Gly | Tyr | Leu | Ala |
| | | 115 | | | | | 120 | | | | | 125 | | | |
| Arg | Arg | Glu | Phe | Arg | Ile | Leu | Lys | Gly | Ile | Ile | Arg | Leu | Gln | Ala | Val |
| | 130 | | | | | 135 | | | | | 140 | | | | |
| Ile | Arg | Gly | His | Leu | Val | Arg | Arg | Gln | Ala | Val | Ala | Thr | Leu | Cys | Cys |
| 145 | | | | | 150 | | | | | 155 | | | | | 160 |
| Thr | Trp | Gly | Ile | Val | Lys | Leu | Gln | Ala | Leu | Ala | Arg | Gly | Gln | Lys | Val |
| | | | | 165 | | | | | 170 | | | | | 175 | |
| Arg | Cys | Ser | Asp | Ile | Ala | Met | Glu | Ile | Gln | Glu | Lys | His | Leu | Arg | Leu |
| | | | 180 | | | | | 185 | | | | | 190 | | |
| Leu | Gln | Gly | Leu | Lys | Ser | Ser | Asn | Ser | Val | Gly | Ala | Ser | Ile | Ser | Ser |
| | | 195 | | | | | 200 | | | | | 205 | | | |
| Thr | Val | Lys | Asn | Leu | Ser | Ser | Asn | Val | Phe | Val | Gln | Lys | Leu | Leu | Ala |
| | 210 | | | | | 215 | | | | | 220 | | | | |
| Ser | Ser | Pro | Ser | Val | Leu | Pro | Leu | Gln | Leu | Gln | Tyr | Val | Pro | Glu | Glu |
| 225 | | | | | 230 | | | | | 235 | | | | | 240 |
| Pro | Asn | Ser | Ser | Trp | Gln | Trp | Leu | Gln | Arg | Trp | Thr | Arg | Ser | Gln | Phe |
| | | | | 245 | | | | | 250 | | | | | 255 | |
| Trp | Glu | Tyr | Pro | Ser | Lys | Pro | Ile | Arg | Ser | Gly | Lys | Thr | Lys | Leu | Ser |
| | | | 260 | | | | | 265 | | | | | 270 | | |
| Val | Gln | Lys | Leu | Ser | Phe | Ala | Lys | Ala | Val | Asn | Gly | Ser | Ser | His | Ser |
| | | 275 | | | | | 280 | | | | | 285 | | | |
| Thr | Leu | Glu | Tyr | Glu | Lys | Asn | Lys | Arg | Gly | Leu | Arg | Arg | Ile | Ser | Val |
| | 290 | | | | | 295 | | | | | 300 | | | | |
| Asn | Ser | Ala | Ala | Asp | Ser | Val | Arg | Glu | His | Pro | Gln | Asn | Glu | Leu | Glu |
| 305 | | | | | 310 | | | | | 315 | | | | | 320 |
| Arg | Val | Lys | Arg | Asn | Leu | Arg | Lys | Leu | Ser | Asn | Ser | Ser | Lys | Glu | Val |
| | | | | 325 | | | | | 330 | | | | | 335 | |
| Thr | Asp | Lys | Ser | Glu | Phe | Val | Asn | Glu | Lys | Thr | Lys | Lys | Thr | Leu | Lys |
| | | | 340 | | | | | 345 | | | | | 350 | | |

```
Lys Tyr Ser Ser Ser Asn Gly Pro Asp Val Leu Glu Gln Glu Ser Ala
            355                 360                 365

Glu Lys Ile Arg Asp Val Thr Ala Thr Leu Ser Glu Leu Ser Ile Leu
        370                 375                 380

Glu Ala Asp Leu Lys Phe Ser Ser Glu His Ala Ser Leu Gly Glu Pro
385                 390                 395                 400

Ile Val Cys Pro Ala Val Asp Phe Pro Pro Ala Lys Asn Asn Gly Lys
                405                 410                 415

Ile Glu His Met Pro Leu Thr Glu Glu Leu Asn Ser Lys Asp Glu Gln
                420                 425                 430

Val Gly Asp Glu Ser Ser Asn Thr Asn Gln Arg Arg Ala Ser Phe Pro
            435                 440                 445

Ala Asn Ile Asp Asn Gln Ala Asn Arg Leu Asn His Met Pro Lys Val
        450                 455                 460

Pro Ser Tyr Met Ala Pro Thr Glu Ser Ala Lys Ala Arg Leu Arg Gly
465                 470                 475                 480

Gln Gly Ser Pro Arg Phe Ile Pro Glu Ala Val Glu Lys Asn Gly Leu
                485                 490                 495

Asn Arg Arg Tyr Ser Leu Pro Thr Ser Thr Asn Ser Asn Thr Gly Ser
                500                 505                 510

Gln Ser Pro His Thr Gln Arg Gln Val Arg Val Ala Gly Lys Gly Ala
            515                 520                 525

Ile Ile Ser Asp Lys Ser Gln Ser Ser Lys Asp Ala Asn Asp Lys
        530                 535                 540

Val Val Arg Ala Glu Trp Arg Arg
545                 550

<210> SEQ ID NO 30
<211> LENGTH: 570
<212> TYPE: PRT
<213> ORGANISM: Arabidopsis thaliana
<220> FEATURE:
<221> NAME/KEY: misc_feature
<223> OTHER INFORMATION: Public GI ID no.12324824
<220> FEATURE:
<221> NAME/KEY: misc_feature
<223> OTHER INFORMATION: Score of 428.7 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (105)..(124)
<223> OTHER INFORMATION: Pfam Name: IQ Pfam Description: IQ calmodulin-
      binding motif

<400> SEQUENCE: 30

Met Ile Val Phe Phe Phe Phe Phe Cys Ser Asn Tyr Ser Tyr Asn
1               5                   10                  15

Asn Ala Gln Arg Val Val Ser Gly Lys Glu Val Leu Val Thr Ser Lys
            20                  25                  30

Val Glu Glu Ser Asp Val Val Ser Asp Leu Pro Ser Phe Glu Val Ala
        35                  40                  45

Glu Thr Asn Thr Val Asp Arg Ser Gly Gly Met Leu Glu Thr Gln Asn
    50                  55                  60

Val Gly Pro Glu Glu Ile Ser Asp Asp Glu Ile Glu Leu Pro Glu Gly
65                  70                  75                  80

Lys Ser Thr Asp Ser Gln Asn Val Ala Pro Val Gln Asp His Ser Leu
```

-continued

```
                85                  90                  95
Ser Asp Ala Glu Arg Ile Gln Arg Glu Ile Ala Ala Thr Ser Val Gln
                100                 105                 110
Ala Ala Phe Arg Gly Tyr Leu Ala Arg Arg Ala Phe Trp Ala Leu Lys
                115                 120                 125
Gly Ile Ile Arg Leu Gln Ala Leu Ile Arg Gly His Leu Val Arg Arg
            130                 135                 140
Gln Ala Val Ala Thr Leu Phe Ser Val Met Gly Ile Val Arg Leu Gln
145                 150                 155                 160
Ala Phe Ala Arg Gly Arg Glu Ile Arg Lys Ser Asp Ile Gly Val Gln
                165                 170                 175
Val Tyr Arg Lys Cys Arg Leu Gln Leu Leu Gln Gly Asn Lys Leu Ala
                180                 185                 190
Asn Pro Thr Asp Ala Tyr Leu Gly Ile Lys Lys Leu Thr Ala Asn Ala
                195                 200                 205
Phe Ala Gln Lys Leu Leu Ala Ser Ser Pro Lys Val Leu Pro Val His
                210                 215                 220
Ala Tyr Asp Thr Ser Asn Pro Asn Ser Asn Leu Ile Trp Leu Glu Asn
225                 230                 235                 240
Trp Ser Ala Ser Cys Phe Trp Lys Pro Val Pro Gln Pro Lys Lys Thr
                245                 250                 255
Ile Ser Arg Lys Pro Gln Asn Arg Leu Leu Val Glu Ala Glu Ser Ala
                260                 265                 270
Lys Pro Lys Lys Ser Val Arg Lys Val Pro Ala Ser Asn Phe Glu Ser
                275                 280                 285
Ser Ser Val Gln Thr Ser Phe Glu Phe Glu Lys Pro Lys Arg Ser Phe
            290                 295                 300
Arg Lys Val Ser Ser Gln Ser Ile Glu Pro Pro Ala Val Glu Asp Pro
305                 310                 315                 320
Gln Ile Glu Leu Glu Lys Val Lys Arg Ser Leu Arg Lys Val His Asn
                325                 330                 335
Pro Val Val Glu Ser Ser Ile Gln Pro Gln Arg Ser Pro Arg Lys Glu
                340                 345                 350
Val Glu Lys Pro Lys Leu Gly Val Glu Lys Thr Arg Glu Ser Ser Tyr
            355                 360                 365
Pro Leu Val His Glu Thr Ala Glu Glu Pro Val Asn Val Cys Asp Glu
            370                 375                 380
Lys Lys Lys Gln Glu Ile Ser Glu Gln Pro Glu Glu Val His Ala
385                 390                 395                 400
Leu Glu Met Glu Val His Thr Pro Gly Pro Leu Glu Thr Asn Glu Ala
                405                 410                 415
Leu Asp Ser Ser Leu Val Asn Gln Ile Asp Ser Asn Glu Lys Ala Met
            420                 425                 430
Val Glu Glu Lys Pro Ser Met Glu Lys Asp Thr Lys Glu Glu Lys Thr
            435                 440                 445
Pro Lys Pro Asn Asn Lys Glu Asn Ser Ala Gly Lys Glu Asn Gln Lys
        450                 455                 460
Ser Arg Lys Lys Gly Ser Ala Thr Ser Lys Thr Glu Arg Glu Glu Ser
465                 470                 475                 480
Asn Gly His His Glu Thr Ser Pro Ser Ile Pro Ser Tyr Met Gln Ala
                485                 490                 495
Thr Lys Ser Ala Lys Ala Lys Leu Arg Leu Gln Gly Ser Pro Lys Ser
            500                 505                 510
```

-continued

```
Ala Glu Gln Asp Gly Thr Glu Lys Ala Thr Val Pro Arg Arg His Ser
        515                 520                 525

Leu Pro Ser Pro Gly Asn Gly Arg Ile Thr Ser His Ser Pro Arg Thr
530                 535                 540

Thr Arg Leu Ala Asn Ser Gly Asp Lys Thr Gly Asn Lys Lys Glu Lys
545                 550                 555                 560

Pro Leu Leu Ser Ser Arg Glu Gly Asn Gly
                565                 570

<210> SEQ ID NO 31
<211> LENGTH: 570
<212> TYPE: PRT
<213> ORGANISM: Arabidopsis thaliana
<220> FEATURE:
<221> NAME/KEY: misc_feature
<223> OTHER INFORMATION: Public GI ID no.5882749
<220> FEATURE:
<221> NAME/KEY: misc_feature
<223> OTHER INFORMATION: Score of 428.1 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2
<220> FEATURE:
<221> NAME/KEY: misc_feature
<222> LOCATION: (105)..(124)
<223> OTHER INFORMATION: Pfam Name: IQ Pfam Description: IQ calmodulin-
      binding motif

<400> SEQUENCE: 31

Met Glu Met Leu Ala Tyr Phe Leu Ser Glu Phe Gln Ile Cys Tyr Asn
1               5                   10                  15

Asn Ala Gln Arg Val Val Ser Gly Lys Glu Val Leu Val Thr Ser Lys
            20                  25                  30

Val Glu Glu Ser Asp Val Val Ser Asp Leu Pro Ser Phe Glu Val Ala
        35                  40                  45

Glu Thr Asn Thr Val Asp Arg Ser Gly Gly Met Leu Glu Thr Gln Asn
    50                  55                  60

Val Gly Pro Glu Glu Ile Ser Asp Asp Glu Ile Glu Leu Pro Glu Gly
65                  70                  75                  80

Lys Ser Thr Asp Ser Gln Asn Val Ala Pro Val Gln Asp His Ser Leu
                85                  90                  95

Ser Asp Ala Glu Arg Ile Gln Arg Glu Ile Ala Thr Ser Val Gln
            100                 105                 110

Ala Ala Phe Arg Gly Tyr Leu Ala Arg Arg Ala Phe Trp Ala Leu Lys
        115                 120                 125

Gly Ile Ile Arg Leu Gln Ala Leu Ile Arg Gly His Leu Val Arg Arg
    130                 135                 140

Gln Ala Val Ala Thr Leu Phe Ser Val Met Gly Ile Val Arg Leu Gln
145                 150                 155                 160

Ala Phe Ala Arg Gly Arg Glu Ile Arg Lys Ser Asp Ile Gly Val Gln
                165                 170                 175

Val Tyr Arg Lys Cys Arg Leu Gln Leu Leu Gln Gly Asn Lys Leu Ala
            180                 185                 190

Asn Pro Thr Asp Ala Tyr Leu Gly Ile Lys Lys Leu Thr Ala Asn Ala
        195                 200                 205

Phe Ala Gln Lys Leu Leu Ala Ser Ser Pro Lys Val Leu Pro Val His
    210                 215                 220

Ala Tyr Asp Thr Ser Asn Pro Asn Ser Asn Leu Ile Trp Leu Glu Asn
```

225                 230                 235                 240

Trp Ser Ala Ser Cys Phe Trp Lys Pro Val Pro Gln Pro Lys Thr
                        245                 250                 255

Ile Ser Arg Lys Pro Gln Asn Arg Leu Leu Val Glu Ala Glu Ser Ala
                    260                 265                 270

Lys Pro Lys Ser Val Arg Lys Val Pro Ala Ser Asn Phe Glu Ser
                275                 280                 285

Ser Ser Val Gln Thr Ser Phe Glu Phe Glu Lys Pro Lys Arg Ser Phe
                290                 295                 300

Arg Lys Val Ser Ser Gln Ser Ile Glu Pro Ala Val Glu Asp Pro
    305                 310                 315                 320

Gln Ile Glu Leu Glu Lys Val Lys Arg Ser Leu Arg Lys Val His Asn
                    325                 330                 335

Pro Val Val Glu Ser Ser Ile Gln Pro Gln Arg Ser Pro Arg Lys Glu
                    340                 345                 350

Val Glu Lys Pro Lys Leu Gly Val Glu Lys Thr Arg Glu Ser Ser Tyr
                    355                 360                 365

Pro Leu Val His Glu Thr Ala Glu Glu Pro Val Asn Val Cys Asp Glu
                370                 375                 380

Lys Lys Lys Gln Glu Ile Ser Glu Gln Pro Glu Glu Val His Ala
    385                 390                 395                 400

Leu Glu Met Glu Val His Thr Pro Gly Pro Leu Glu Thr Asn Glu Ala
                    405                 410                 415

Leu Asp Ser Ser Leu Val Asn Gln Ile Asp Ser Asn Glu Lys Ala Met
                420                 425                 430

Val Glu Glu Lys Pro Ser Met Glu Lys Asp Thr Lys Glu Glu Lys Thr
                    435                 440                 445

Pro Lys Pro Asn Asn Lys Glu Asn Ser Ala Gly Lys Glu Asn Gln Lys
                450                 455                 460

Ser Arg Lys Lys Gly Ser Ala Thr Ser Lys Thr Glu Arg Glu Ser
    465                 470                 475                 480

Asn Gly His His Glu Thr Ser Pro Ser Ile Pro Ser Tyr Met Gln Ala
                    485                 490                 495

Thr Lys Ser Ala Lys Ala Lys Leu Arg Leu Gln Gly Ser Pro Lys Ser
                    500                 505                 510

Ala Glu Gln Asp Gly Thr Glu Lys Ala Thr Val Pro Arg Arg His Ser
                515                 520                 525

Leu Pro Ser Pro Gly Asn Gly Arg Ile Thr Ser His Ser Pro Arg Thr
                530                 535                 540

Thr Arg Leu Ala Asn Ser Gly Asp Lys Thr Gly Asn Lys Lys Glu Lys
    545                 550                 555                 560

Pro Leu Leu Ser Ser Arg Glu Gly Asn Gly
                    565                 570

<210> SEQ ID NO 32
<211> LENGTH: 1461
<212> TYPE: DNA
<213> ORGANISM: Zea mays
<220> FEATURE:
<221> NAME/KEY: misc_feature
<223> OTHER INFORMATION: Ceres CLONE ID no.325403
<220> FEATURE:
<221> NAME/KEY: misc_feature
<223> OTHER INFORMATION: Encodes the peptide sequence at SEQ ID NO 33

<400> SEQUENCE: 32

| | |
|---|---|
| aaatgcattt gctcgcaagc ttctatcttc atcaattgtg gttgaggctc ttcacttcca | 60 |
| gtatgatgag atggaccta attcagcctt caattggtta gagaggtgga cgataagtca | 120 |
| tgtctggaag cccacttccc agccaaggag agttagtgct gatgctaagc cacatacaag | 180 |
| gaaggccagc tatgcaatgg aaacagagtc agtgaaatta aagcgtaatg cacggaggag | 240 |
| ctctgcagtg ccatttgaac cttctcaaac aaacactgcc attgaaattg agaagacaag | 300 |
| acggaatcca aggaaattaa gtagcactcc tgctgagtca gttcctgatg ccagttaac | 360 |
| agaacttgag aaggttaaac gtagccttag gaaggttact aattctgtgg ctgaaacctc | 420 |
| gaaggcacct agtccaaaaa ctgagattcc taaccatcaa gaggtccaat gtgagagacc | 480 |
| actaagaaga gcaaaacagg ttccaattca tcttgagaat caagagcctg ataatgttaa | 540 |
| tctgttggac aatgcaaaga tggatattct ggtacctgat atccagcctg atgtggaagt | 600 |
| tgcttcagat ccagtcacca tcactaatga agaaaatgtt gatgaaccac catctgttgt | 660 |
| tgctccagtg gccgaaatta tgcccctgca agacatcaac aacgatgaaa atgctttggt | 720 |
| gaatgatgtg gaagagagat ccaaagaaga acatccttgt actgagagcc tgaaaggcag | 780 |
| caagaggagg tcttcattct cagctaagcc tgaatatcca gaaaatggct ccaaaaattc | 840 |
| tccagctctg ccaagctaca tggctgctac acaatcagca aaggcgaaac tgcggggaaa | 900 |
| tagctcacca aaacttagct ctgattcagc agagaaaaac ggcttcactc gtcgtcactc | 960 |
| ccttccatcc tctaacaacg gtaagatggt ttcacattct ccacgtacac aaaggccagc | 1020 |
| taatgctggt tgcaaggatg gagcgaaagg tgacaaggct atgctgtcat caagagatgc | 1080 |
| aagcgagaga ccactgaaag ctgagtggag acgttgaggc ggcgaatcaa atccaaatcc | 1140 |
| tccatttgat tagcgtgacc gtttgggtgg atggatcgcc cttgcagttt gctcggattt | 1200 |
| gttttgtttg tgatgtaaaa aaatgatgtc gtcatcgtcg gcgagatgaa tgaaccggct | 1260 |
| ttgttgtgat gaatccgctg ggagtcaact tatttattat agggttttcc gtcatgcctt | 1320 |
| ttgtgatgta tagctgaagt attttcccgg tttgttttgg ttcccagacc cccagacttc | 1380 |
| ctcccttctt gttgagagct gctgatgtta gagagaatga aacatgcat ggattgagtt | 1440 |
| gaacaatctt acccatttgg t | 1461 |

```
<210> SEQ ID NO 33
<211> LENGTH: 371
<212> TYPE: PRT
<213> ORGANISM: Zea mays
<220> FEATURE:
<221> NAME/KEY: misc_feature
<223> OTHER INFORMATION: Ceres CLONE ID no.325403
<220> FEATURE:
<221> NAME/KEY: misc_feature
<223> OTHER INFORMATION: Score of 576.4 for HMM of FIGURE 5.
<220> FEATURE:
<221> NAME/KEY: misc_feature
<223> OTHER INFORMATION: Functional Homolog Of Ceres CLONE ID no.
      1792354 at SEQ ID NO. 2

<400> SEQUENCE: 33
```

Asn Ala Phe Ala Arg Lys Leu Leu Ser Ser Ser Ile Val Val Glu Ala
 1               5                  10                  15

Leu His Phe Gln Tyr Asp Glu Met Asp Pro Asn Ser Ala Phe Asn Trp
            20                  25                  30

Leu Glu Arg Trp Thr Ile Ser His Val Trp Lys Pro Thr Ser Gln Pro
        35                  40                  45

Arg Arg Val Ser Ala Asp Ala Lys Pro His Thr Arg Lys Ala Ser Tyr
    50                  55                  60

Ala Met Glu Thr Glu Ser Val Lys Leu Lys Arg Asn Ala Arg Arg Ser
 65                  70                  75                  80

Ser Ala Val Pro Phe Glu Pro Ser Gln Thr Asn Ala Ile Glu Ile
                 85                  90                  95

Glu Lys Thr Arg Arg Asn Pro Arg Lys Leu Ser Ser Thr Pro Ala Glu
            100                 105                 110

Ser Val Pro Asp Gly Gln Leu Thr Glu Leu Glu Lys Val Lys Arg Ser
        115                 120                 125

Leu Arg Lys Val Thr Asn Ser Val Ala Glu Thr Ser Lys Ala Pro Ser
    130                 135                 140

Pro Lys Thr Glu Ile Pro Asn His Gln Glu Val Gln Cys Glu Arg Pro
145                 150                 155                 160

Leu Arg Arg Ala Lys Gln Val Pro Ile His Leu Glu Asn Gln Glu Pro
                165                 170                 175

Asp Asn Val Asn Leu Leu Asp Asn Ala Lys Met Asp Ile Leu Val Pro
            180                 185                 190

Asp Ile Gln Pro Asp Val Glu Val Ala Ser Asp Pro Val Thr Ile Thr
        195                 200                 205

Asn Glu Glu Asn Val Asp Glu Pro Pro Ser Val Ala Pro Val Ala
    210                 215                 220

Glu Ile Met Pro Leu Gln Asp Ile Asn Asn Asp Glu Asn Ala Leu Val
225                 230                 235                 240

Asn Asp Val Glu Glu Arg Ser Lys Glu Glu His Pro Cys Thr Glu Ser
                245                 250                 255

Leu Lys Gly Ser Lys Arg Arg Ser Phe Ser Ala Lys Pro Glu Tyr
            260                 265                 270

Pro Glu Asn Gly Ser Lys Asn Ser Pro Ala Leu Pro Ser Tyr Met Ala
        275                 280                 285

Ala Thr Gln Ser Ala Lys Ala Lys Leu Arg Gly Asn Ser Ser Pro Lys
    290                 295                 300

Leu Ser Ser Asp Ser Ala Glu Lys Asn Gly Phe Thr Arg Arg His Ser
305                 310                 315                 320

Leu Pro Ser Ser Asn Asn Gly Lys Met Val Ser His Ser Pro Arg Thr
                325                 330                 335

Gln Arg Pro Ala Asn Ala Gly Cys Lys Asp Gly Ala Lys Gly Asp Lys
            340                 345                 350

Ala Met Leu Ser Ser Arg Asp Ala Ser Glu Arg Pro Leu Lys Ala Glu
        355                 360                 365

Trp Arg Arg
    370

<210> SEQ ID NO 34
<211> LENGTH: 783
<212> TYPE: DNA
<213> ORGANISM: Oryza sativa subsp. Japonica
<220> FEATURE:
<221> NAME/KEY: misc_feature
<223> OTHER INFORMATION: Ceres GI ID no.56784328
<220> FEATURE:
<221> NAME/KEY: misc_feature
<223> OTHER INFORMATION: Encodes the peptide sequence at SEQ ID NO. 35

<400> SEQUENCE: 34
atgcggggtt tccccgttcc ggtgacgagt tggagctccg ccgcgctcct gggccgctcc     60
atctcctcgg ccagggacgc ggccgaggcc tcctccccca tcaccgccgc ggagatggtc    120

-continued

```
cgggtggcga aggaggtggc caacgccgcc gacgcctgcg gagtctccgg caagaagctg    180
ctggaggctg cggaagcgct gtccaggtcc gacaccgacg cggagccgag gcggcgcgcc    240
gccgagcgga ttttcgatgc ggcgtccatg gtggccaagg aggccgacgc gtcaggagcg    300
tcgggtctct cagatgcggc ccaaaatctg acctgcgcga cctacgcgtt ctcggtagcc    360
gcctcgggat gggggtcctt gccggagtcc agcacgagcg ggagggacgc cggcgacctc    420
ctaaccgagc cccttcttgg gtcatgtcag gacaagaacg agaagatgac cggcgagggc    480
aaggacttca gcgagatgag gaatagtgca gcggactctg atccacttca gcaatcggag    540
attaaggagt cgtcccttt tggaaaatgc aaagaactcc tcaattatgg ttttcttgga    600
ggtcctgccc tcctacccta tctaggctct ggactgagga aaacagtgtc accctgcagc    660
ccgtctgtct tccactacat cttctcgtcg tggtggattt gcattgttgt cggatcacat    720
gaacaaggag acttgaagat attacatatc gatagaatca cttctcatcc aaatgataag    780
tag                                                                  783
```

<210> SEQ ID NO 35
<211> LENGTH: 260
<212> TYPE: PRT
<213> ORGANISM: Oryza sativa subsp. Japonica
<220> FEATURE:
<221> NAME/KEY: misc_feature
<223> OTHER INFORMATION: Ceres GI ID no.56784328
<220> FEATURE:
<221> NAME/KEY: misc_feature
<223> OTHER INFORMATION: Score of 660.5 for HMM of FIGURE 6.

<400> SEQUENCE: 35

```
Met Arg Gly Phe Pro Val Pro Val Thr Ser Trp Ser Ser Ala Ala Leu
1               5                   10                  15

Leu Gly Arg Ser Ile Ser Ser Ala Arg Asp Ala Ala Glu Ala Ser Ser
            20                  25                  30

Pro Ile Thr Ala Ala Glu Met Val Arg Val Ala Lys Glu Val Ala Asn
        35                  40                  45

Ala Ala Asp Ala Cys Gly Val Ser Gly Lys Lys Leu Leu Glu Ala Ala
    50                  55                  60

Glu Ala Leu Ser Arg Ser Asp Thr Asp Ala Glu Pro Arg Arg Arg Ala
65                  70                  75                  80

Ala Glu Arg Ile Phe Asp Ala Ala Ser Met Val Ala Lys Glu Ala Asp
                85                  90                  95

Ala Ser Gly Ala Ser Gly Leu Ser Asp Ala Ala Gln Asn Leu Thr Cys
            100                 105                 110

Ala Thr Tyr Ala Phe Ser Val Ala Ala Ser Gly Trp Gly Ser Leu Pro
        115                 120                 125

Glu Ser Ser Thr Ser Gly Arg Asp Ala Gly Asp Leu Thr Glu Pro
    130                 135                 140

Leu Leu Gly Ser Cys Gln Asp Lys Asn Glu Lys Met Thr Gly Glu Gly
145                 150                 155                 160

Lys Asp Phe Ser Glu Met Arg Asn Ser Ala Ala Asp Ser Asp Pro Leu
                165                 170                 175

Gln Gln Ser Glu Ile Lys Glu Ser Leu Phe Gly Lys Cys Lys Glu
            180                 185                 190

Leu Leu Asn Tyr Gly Phe Leu Gly Gly Pro Ala Leu Leu Pro Tyr Leu
        195                 200                 205

Gly Ser Gly Leu Arg Lys Thr Val Ser Pro Cys Ser Pro Ser Val Phe
    210                 215                 220
```

```
His Tyr Ile Phe Ser Ser Trp Trp Ile Cys Ile Val Val Gly Ser His
225                 230                 235                 240

Glu Gln Gly Asp Leu Lys Ile Leu His Ile Asp Arg Ile Thr Ser His
                245                 250                 255

Pro Asn Asp Lys
            260

<210> SEQ ID NO 36
<211> LENGTH: 311
<212> TYPE: PRT
<213> ORGANISM: Oryza sativa subsp. Japonica
<220> FEATURE:
<221> NAME/KEY: misc_feature
<223> OTHER INFORMATION: Public GI ID no.56784330
<220> FEATURE:
<221> NAME/KEY: misc_feature
<223> OTHER INFORMATION: Score of 826.7 for HMM of FIGURE 6.
<220> FEATURE:
<221> NAME/KEY: misc_feature
<223> OTHER INFORMATION: Functional Homolog Of Ceres GI ID no. 56784328
      at SEQ ID NO. 35

<400> SEQUENCE: 36

Met Glu Ser Arg Leu Leu Arg Ser Ala Ala Leu Leu Ala Arg Ala Ala
1               5                   10                  15

Arg Leu Ala Arg Ala Ala Ala Thr Ser Thr Gly Arg Ala Val Thr Ala
            20                  25                  30

Glu His Leu Ala Glu Val Val Ala Ser Ala Ala Gly Asp Arg Gly Phe
        35                  40                  45

Pro Ser Gly Ala Leu Arg Gln Ala Ala Leu Ala Leu Ala Arg Ser Ser
    50                  55                  60

Ala Pro Glu Ala Arg Pro Arg Ala Thr Ala Glu Val Val Arg Ala Ala
65                  70                  75                  80

Ala Met Val Phe Arg Ala Ala Gln Glu Ala Gly Ser Pro Gly Val Ala
                85                  90                  95

Glu Val Ala Gly Asp Leu Ala His Ala Ala His Asp Cys Val Arg Ala
            100                 105                 110

Leu Val Glu Ser Gly Pro Ala Ala Glu Arg Pro Arg Cys Leu Leu Arg
        115                 120                 125

Leu Trp Arg Arg Lys Asn Arg His Asn Lys Asn Ala Ala Gly Glu Ala
    130                 135                 140

Asp Leu Glu Ala Pro Leu Leu His Pro His Glu Arg Pro Ser Ser Ser
145                 150                 155                 160

Ser Ser Pro Ile Gly Ala Ser Leu Ser Glu Ile Ile Glu Leu Ser Glu
                165                 170                 175

Ser Glu Arg Asp Phe Ile Asn Tyr Gly Met Phe Gly Ala Leu Ala Ile
            180                 185                 190

Phe Pro Tyr Leu Thr Arg Thr Gly Gly Leu Lys Ser Ala Tyr Ser Pro
        195                 200                 205

Leu Ser Pro Ser Thr Phe His Ile Ile Phe Cys Thr Trp Trp Ile Cys
    210                 215                 220

Val Gly Leu Asp Val Leu Cys Gly Asn Arg Gly Arg Ala Met Met Lys
225                 230                 235                 240

Asn Ile Leu Ala Phe Ile Leu Ala Phe Tyr Ala Arg Ala Ser Ala Arg
                245                 250                 255

Leu Ala Ile Leu Gly Val Ser Leu Leu Val Ile Leu Tyr Ser His Leu
            260                 265                 270
```

```
Glu Leu Ala Pro Asn Glu Ile Tyr Thr Leu Tyr Ile Leu Leu Gly Ala
            275                 280                 285

Ala Thr Cys Met His Leu Leu Val Trp Ala Met Asp Tyr Met Ser Arg
290                 295                 300

Ala Pro Gly Asp Ala Ala Asp
305                 310

<210> SEQ ID NO 37
<211> LENGTH: 311
<212> TYPE: PRT
<213> ORGANISM: Oryza sativa subsp. indica
<220> FEATURE:
<221> NAME/KEY: misc_feature
<223> OTHER INFORMATION: Public GI ID no.125528718
<220> FEATURE:
<221> NAME/KEY: misc_feature
<223> OTHER INFORMATION: Score of 812.3 for HMM of FIGURE 6.
<220> FEATURE:
<221> NAME/KEY: misc_feature
<223> OTHER INFORMATION: Functional Homolog Of Ceres GI ID no. 56784328
      at SEQ ID NO. 35

<400> SEQUENCE: 37

Met Glu Ser Arg Leu Leu Arg Ser Ala Ala Leu Leu Ala Arg Ala Ala
1               5                   10                  15

Arg Leu Ala Arg Ala Ala Ala Thr Ser Thr Gly Arg Ala Val Thr Ala
            20                  25                  30

Glu His Leu Ala Glu Val Val Ala Ser Ala Ala Gly Asp Arg Gly Phe
        35                  40                  45

Pro Ser Gly Ala Leu Arg Gln Ala Ala Leu Ala Leu Ala Arg Ser Ser
50                  55                  60

Ala Pro Glu Ala Ser Pro Arg Ala Ala Ala Glu Val Val His Ala Ala
65                  70                  75                  80

Ala Met Val Phe Arg Ala Ala Gln Glu Ala Gly Ser Pro Gly Val Ala
                85                  90                  95

Glu Val Ala Gly Asp Leu Ala His Ala Ala His Asp Cys Val Arg Ala
            100                 105                 110

Leu Val Glu Ser Gly Pro Ala Ala Glu Arg Pro Arg Cys Leu Leu Arg
        115                 120                 125

Leu Trp Arg Arg Lys Asn Arg His Asn Lys Asn Ala Ala Gly Glu Ala
130                 135                 140

Asp Leu Glu Ala Pro Leu Leu His Pro His Glu Arg Pro Ser Ser Ser
145                 150                 155                 160

Ser Ser Pro Ile Gly Ala Ser Leu Ser Asp Ile Ile Glu Leu Ser Gln
                165                 170                 175

Ser Glu Arg Asp Phe Ile Asn Tyr Gly Met Phe Gly Ala Leu Ala Ile
            180                 185                 190

Phe Pro Tyr Leu Thr Arg Thr Gly Gly Leu Lys Ser Ala Tyr Ser Pro
        195                 200                 205

Leu Ser Pro Ser Thr Phe His Ile Ile Phe Cys Thr Trp Trp Ile Cys
210                 215                 220

Val Gly Leu Asp Val Leu Cys Gly Asn Arg Gly Arg Ala Met Met Lys
225                 230                 235                 240

Asn Ile Leu Ala Phe Ile Leu Ala Phe Tyr Ala Arg Ala Ser Ala Arg
                245                 250                 255

Leu Ala Ile Leu Gly Val Ser Leu Leu Val Ile Leu Tyr Ser His Leu
            260                 265                 270

Glu Leu Ala Pro Asn Glu Ile Tyr Thr Leu Tyr Ile Leu Leu Gly Ala
```

```
                275                 280                 285
Ala Thr Cys Met His Leu Leu Val Trp Ala Met Asp Tyr Met Ser Arg
        290                 295                 300

Ala Pro Gly Asp Ala Ala Asp
305                 310

<210> SEQ ID NO 38
<211> LENGTH: 250
<212> TYPE: PRT
<213> ORGANISM: Oryza sativa subsp. japonica
<220> FEATURE:
<221> NAME/KEY: misc_feature
<223> OTHER INFORMATION: Public GI ID no.125572975
<220> FEATURE:
<221> NAME/KEY: misc_feature
<223> OTHER INFORMATION: Score of 571.2 for HMM of FIGURE 6.
<220> FEATURE:
<221> NAME/KEY: misc_feature
<223> OTHER INFORMATION: Functional Homolog Of Ceres GI ID no. 56784328
      at SEQ ID NO. 35

<400> SEQUENCE: 38

Met Arg Gly Phe Pro Val Pro Val Thr Ser Trp Ser Ala Ala Leu
1               5                   10                  15

Leu Gly Arg Ser Ile Ser Ser Ala Arg Asp Ala Ala Glu Ala Ser Ser
            20                  25                  30

Pro Ile Thr Ala Ala Glu Met Val Arg Val Ala Lys Glu Val Ala Asn
        35                  40                  45

Ala Ala Asp Ala Cys Gly Val Ser Gly Lys Lys Leu Leu Glu Ala Ala
    50                  55                  60

Glu Ala Leu Ser Arg Ser Asp Thr Asp Ala Glu Pro Arg Arg Arg Ala
65                  70                  75                  80

Ala Glu Arg Ile Phe Asp Ala Ala Ser Met Val Ala Lys Glu Ala Asp
                85                  90                  95

Ala Ser Gly Ala Ser Gly Leu Ser Asp Ala Ala Gln Asn Leu Thr Cys
            100                 105                 110

Ala Thr Tyr Ala Phe Ser Val Ala Ala Ser Gly Trp Gly Ser Leu Pro
        115                 120                 125

Glu Ser Ser Thr Ser Gly Arg Asp Ala Gly Asp Leu Leu Thr Glu Pro
    130                 135                 140

Leu Leu Gly Ser Cys Gln Asp Lys Asn Glu Lys Met Thr Gly Glu Gly
145                 150                 155                 160

Lys Asp Phe Ser Glu Met Arg Asn Ser Ala Ala Asp Ser Asp Pro Leu
                165                 170                 175

Gln Gln Ser Glu Ile Lys Glu Ser Ser Leu Phe Gly Lys Cys Lys Glu
            180                 185                 190

Leu Leu Asn Tyr Gly Phe Leu Gly Gly Pro Ala Leu Leu Pro Tyr Leu
        195                 200                 205

Gly Ser Gly Leu Arg Lys Thr Val Ser Pro Cys Ser Pro Ser Val Phe
    210                 215                 220

His Tyr Ile Phe Ser Ser Trp Trp Ile Cys Ile Val Val Asp Glu
225                 230                 235                 240

Leu Phe Val Arg Ile Ile Asp Cys Ser Gln
                245                 250

<210> SEQ ID NO 39
<211> LENGTH: 250
<212> TYPE: PRT
<213> ORGANISM: Oryza sativa subsp. indica
```

```
<220> FEATURE:
<221> NAME/KEY: misc_feature
<223> OTHER INFORMATION: Public GI ID no.125528716
<220> FEATURE:
<221> NAME/KEY: misc_feature
<223> OTHER INFORMATION: Score of 567.3 for HMM of FIGURE 6.
<220> FEATURE:
<221> NAME/KEY: misc_feature
<223> OTHER INFORMATION: Functional Homolog Of Ceres GI ID no. 56784328
      at SEQ ID NO. 35

<400> SEQUENCE: 39

Met Arg Gly Phe Pro Val Pro Val Thr Ser Trp Ser Ser Ala Ala Leu
1               5                   10                  15

Leu Gly Arg Ala Ile Ser Ser Ala Arg Asp Ala Glu Ala Ser Ser
            20                  25                  30

Pro Ile Thr Ala Ala Glu Met Val Arg Val Ala Lys Glu Val Ala Asn
        35                  40                  45

Ala Ala Asp Ala Cys Gly Val Ser Asp Lys Lys Leu Leu Glu Ala Ala
    50                  55                  60

Glu Ala Leu Ser Arg Ser Asp Thr Asp Ala Glu Pro Arg Arg Ala
65                  70                  75                  80

Ala Glu Arg Ile Phe Asp Ala Ala Ser Met Val Ala Lys Glu Ala Asp
                85                  90                  95

Ala Ser Gly Ala Ser Gly Leu Ser Asp Ala Ala Gln Asn Leu Thr Cys
            100                 105                 110

Ala Thr Tyr Ala Phe Ser Val Ala Ala Ser Gly Trp Gly Ser Leu Pro
        115                 120                 125

Glu Ser Ser Thr Ser Gly Arg Asp Ala Gly Asp Leu Leu Thr Glu Pro
130                 135                 140

Leu Leu Gly Ser Cys Gln Asp Lys Asn Glu Lys Met Thr Gly Glu Gly
145                 150                 155                 160

Lys Asp Phe Ser Glu Met Arg Asn Ser Ala Ala Asp Ser Asp Pro Leu
                165                 170                 175

Gln Gln Ser Glu Ile Lys Glu Ser Ser Leu Phe Gly Lys Cys Lys Glu
            180                 185                 190

Leu Leu Asn Tyr Gly Phe Leu Gly Gly Pro Ala Leu Leu Pro Tyr Leu
        195                 200                 205

Gly Ser Gly Leu Arg Lys Thr Val Ser Pro Cys Ser Pro Ser Val Phe
    210                 215                 220

His Tyr Ile Phe Ser Ser Trp Trp Ile Cys Ile Val Val Asp Glu
225                 230                 235                 240

Leu Phe Val Arg Ile Ile Asp Cys Ser Gln
                245                 250

<210> SEQ ID NO 40
<211> LENGTH: 1443
<212> TYPE: DNA
<213> ORGANISM: Arabidopsis thaliana
<220> FEATURE:
<221> NAME/KEY: misc_feature
<223> OTHER INFORMATION: Ceres SEEDLINE ID no.ME06748
<220> FEATURE:
<221> NAME/KEY: misc_feature
<223> OTHER INFORMATION: Encodes the peptide sequence at SEQ ID NO. 41

<400> SEQUENCE: 40
aattgtctct tctttctttt ttgtacttgt caaaaacaaa agaacaaca aaaaaatct    60 caaccgtaga aaattccgac aagagttcag ttcatacaat gaactaagta tgggtttctt   120
```

| | |
|---|---|
| tggaagactg ttcggaagta agaagcaaga aaaggcaaca ccgaacagac gaagatggag | 180 |
| cttcgctact agatcctcac atcccgagaa tgattcgtct tctcatccaa gcaagagacg | 240 |
| tggggatgaa gatgtcttaa acgccgacaa gcatgcgata gccgtcgcgg ctgctacagc | 300 |
| tgcagtggct gaagccgcac tcgctgctgc tcgtgcggcg gcggaagtcg tgagactcac | 360 |
| caatggtggt agaaactcgt cggtaaaaca aatcagtcgg agtaatcgtc ggtggtctca | 420 |
| agagtataaa gcagctatcc gcttttcgtg gctacttggc gaggagggcg ttgagagcac | 480 |
| tgaaggcatt agtgaagctt caagcgttgg tgaagggaca catagtaagg aaacaaacgg | 540 |
| ctgatatgct gcgtcgaatg caaacgctgg ttcggctcca gcacgagct agagcttcgc | 600 |
| gttcttctca cgtttctgac tcttcccatc cgccaacact aatgattcca tcttccccac | 660 |
| aatctttcca tgcacgatgc gtttcagagg ctgagtacag taaagtcatt gccatggatc | 720 |
| accaccacaa caaccaccgt tcaccgatgg gttcaagccg gttattagac caatggagga | 780 |
| cagaggaaag tctatggagc gcaccaaagt acaatgaaga tgatgacaaa atcctagaag | 840 |
| tcgacacttg gaagcctcac ttcagagagt caccaaggaa aagaggatct ctagtggttc | 900 |
| ctacaagtgt ggagaacagt ccacaattaa ggtctagaac aggaagcagc agtggtggtt | 960 |
| caaggagaaa aactcccttc acgcctgcga gaagcgagta cgagtactac tctgggtatc | 1020 |
| accctaacta catggctaac actgagtctt acaaagcaaa agtccgatca caaagcgcac | 1080 |
| caagacagag actacaagat ttaccttcag agagtggtta caagaggtct atacagggac | 1140 |
| agtattacta ctacacacct gctgcagagc gatcgtttga tcagcgttcg gataacggga | 1200 |
| tcgcgggtta cagaggagtt tctgatgggt tagatcgaaa ccaaagtgac aaatcgaaga | 1260 |
| tgtacacttc gttttcagt tctaatcctc ttttctttca atagtcgaga aaggatgaaa | 1320 |
| aaagtgagtg gaatgtgtaa aattagattt cgacacacga gtacagagac agccagtgat | 1380 |
| caatctgtgt tttgtactat tttctaattg actgtatcca acaagggtcc attcttgtct | 1440 |
| gac | 1443 |

<210> SEQ ID NO 41
<211> LENGTH: 252
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME06748
<220> FEATURE:
<221> NAME/KEY: misc_feature
<223> OTHER INFORMATION: Score of 176.1 for HMM of FIGURE 2.

<400> SEQUENCE: 41

```
Met Leu Arg Arg Met Gln Thr Leu Val Arg Leu Gln Ala Arg Ala Arg
1               5                   10                  15

Ala Ser Arg Ser Ser His Val Ser Asp Ser Ser His Pro Pro Thr Leu
                20                  25                  30

Met Ile Pro Ser Ser Pro Gln Ser Phe His Ala Arg Cys Val Ser Glu
            35                  40                  45

Ala Glu Tyr Ser Lys Val Ile Ala Met Asp His His Asn Asn His
        50                  55                  60

Arg Ser Pro Met Gly Ser Ser Arg Leu Leu Asp Gln Trp Arg Thr Glu
65                  70                  75                  80

Glu Ser Leu Trp Ser Ala Pro Lys Tyr Asn Glu Asp Asp Asp Lys Ile
                85                  90                  95

Leu Glu Val Asp Thr Trp Lys Pro His Phe Arg Glu Ser Pro Arg Lys
```

```
                    100                 105                 110
Arg Gly Ser Leu Val Pro Thr Ser Val Glu Asn Ser Pro Gln Leu
            115                 120                 125

Arg Ser Arg Thr Gly Ser Ser Gly Gly Ser Arg Arg Lys Thr Pro
        130                 135                 140

Phe Thr Pro Ala Arg Ser Glu Tyr Glu Tyr Tyr Ser Gly Tyr His Pro
145                 150                 155                 160

Asn Tyr Met Ala Asn Thr Glu Ser Tyr Lys Ala Lys Val Arg Ser Gln
                165                 170                 175

Ser Ala Pro Arg Gln Arg Leu Gln Asp Leu Pro Ser Glu Ser Gly Tyr
            180                 185                 190

Lys Arg Ser Ile Gln Gly Gln Tyr Tyr Tyr Thr Pro Ala Ala Glu
        195                 200                 205

Arg Ser Phe Asp Gln Arg Ser Asp Asn Gly Ile Ala Gly Tyr Arg Gly
        210                 215                 220

Val Ser Asp Gly Leu Asp Arg Asn Gln Ser Asp Lys Ser Lys Met Tyr
225                 230                 235                 240

Thr Ser Phe Phe Ser Ser Asn Pro Leu Phe Phe Gln
                245                 250

<210> SEQ ID NO 42
<211> LENGTH: 517
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME20711
<220> FEATURE:
<221> NAME/KEY: misc_feature
<223> OTHER INFORMATION: Score of 943.4 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (169)..(189)
<223> OTHER INFORMATION: Pfam Name: IQ Pfam Description: IQ calmodulin-
      binding motif

<400> SEQUENCE: 42

Met Gly Lys Lys Gly Ser Trp Phe Ser Ala Ile Lys Arg Val Phe Thr
1               5                   10                  15

Pro His Ser Lys Glu Lys Gln Leu Ser Asn Asn Asn Gln Glu Pro Glu
            20                  25                  30

Ile Lys Ser Glu Asn Lys Glu Lys Lys Lys Gly Phe Gly Lys Lys
        35                  40                  45

Leu Arg Asn Gly Glu Thr Asn Ser Phe Leu Pro Ile Phe Arg Gln Pro
50                  55                  60

Ser Ser Ile Glu Lys Ile Leu Ser Glu Ala Glu Arg Glu His Asn Leu
65                  70                  75                  80

Val Phe Arg Pro Pro Thr Pro Thr Asp Arg Ala Asn Ser Ser Ser Thr
                85                  90                  95

Ser Val Ala Ser Pro Leu Val Arg Pro Ala Ser Pro Lys Val Pro Ser
            100                 105                 110

Gln Arg Tyr Val Ser Ser Pro Lys Pro Ile Ser Pro Arg Val Ala Tyr
        115                 120                 125

Pro Gln Val His Tyr Pro Lys Pro Pro Ser Pro Lys Pro Pro Ser Pro
        130                 135                 140
```

```
Arg Ala Val Ser Pro Arg Ile Val Gln Arg Glu Phe Val His Arg
145                 150                 155                 160

Pro Glu Pro Ser Leu Leu Val Lys Asn Ala Tyr Ala Ile Lys Ile Gln
            165                 170                 175

Ala Ala Phe Arg Gly Tyr Met Ala Arg Arg Ser Phe Arg Ala Leu Lys
            180                 185                 190

Gly Leu Val Arg Leu Gln Gly Val Val Arg Gly His Ser Val Lys Arg
195                 200                 205

Gln Thr Met Asn Ala Met Lys Tyr Met Gln Leu Leu Val Arg Val Gln
210                 215                 220

Thr Gln Val Gln Ser Arg Arg Ile Gln Met Leu Glu Asn Arg Ala Arg
225                 230                 235                 240

Asn Asp Lys Asp Thr Lys Leu Val Ser Ser Arg Met Ser Asp
                245                 250                 255

Trp Asp Ser Val Leu Thr Lys Glu Glu Lys Asp Val Arg Leu His
            260                 265                 270

Arg Lys Ile Asp Ala Met Ile Lys Arg Glu Arg Ser Met Ala Tyr Ala
            275                 280                 285

Tyr Ser His Gln Leu Trp Lys Asn Ser Pro Lys Ser Ala Gln Asp Ile
290                 295                 300

Arg Thr Ser Gly Phe Pro Leu Trp Trp Asn Trp Val Asp Arg Gln Lys
305                 310                 315                 320

Asn Gln Asn Gln Pro Phe Arg Leu Thr Pro Thr Arg Pro Ser Leu Ser
                325                 330                 335

Pro Gln Pro Gln Ser Ser Asn Gln Asn His Phe Arg Leu Asn Asn Ser
            340                 345                 350

Phe Asp Thr Ser Thr Pro Asn Ser Ser Lys Ser Thr Phe Val Thr Pro
                355                 360                 365

Ser Arg Pro Ile His Thr Pro Gln Pro Tyr Ser Ser Val Ser Arg
        370                 375                 380

Tyr Ser Arg Gly Gly Gly Arg Ala Thr Gln Asp Ser Pro Phe Lys Asp
385                 390                 395                 400

Asp Asp Ser Leu Thr Ser Cys Pro Pro Phe Ser Ala Pro Ser Tyr Met
                405                 410                 415

Ala Pro Thr Val Ser Ala Lys Ala Lys Leu Arg Ala Asn Ser Asn Pro
            420                 425                 430

Lys Glu Arg Met Asp Arg Thr Pro Val Ser Thr Asn Glu Lys Arg Arg
                435                 440                 445

Ser Ser Phe Pro Leu Gly Ser Phe Lys Trp Asn Lys Gly Ser Leu Phe
            450                 455                 460

Met Ser Asn Asn Ser Asn Asn Lys Gly Pro Gly Ser Ser Ser Ser Gly
465                 470                 475                 480

Ala Val Val Leu Glu Lys His Lys Thr Leu Lys Ser Val Gly Asn Leu
            485                 490                 495

Ser Ile Asp Ser Thr Val Ser Met Pro Ala Thr Ile Gly Arg Arg Ala
            500                 505                 510

Phe Asn Arg Phe Ala
        515

<210> SEQ ID NO 43
<211> LENGTH: 383
<212> TYPE: PRT
<213> ORGANISM: Arabidopsis thaliana
<220> FEATURE:
<221> NAME/KEY: misc_feature
```

<223> OTHER INFORMATION: Ceres SEEDLINE ID no.ME18973
<220> FEATURE:
<221> NAME/KEY: misc_feature
<223> OTHER INFORMATION: Score of 543.8 for HMM of FIGURE 2.
<220> FEATURE:
<221> NAME/KEY: misc_feature
<223> OTHER INFORMATION: Functional Homolog Of Ceres SEEDLINE ID no.
ME06748 at SEQ ID NO. 41
<220> FEATURE:
<221> NAME/KEY: misc_feature
<222> LOCATION: (115)..(135)
<223> OTHER INFORMATION: Pfam Name: IQ Pfam Description: IQ calmodulin-
binding motif

<400> SEQUENCE: 43

```
Met Gly Arg Ala Thr Arg Trp Phe Lys Gly Leu Phe Gly Ile Lys Pro
1               5                   10                  15

Ser Ser Cys Ser Gly Thr Asp Ser Gly Thr Ile Ser Asn Arg Leu Asp
            20                  25                  30

Arg Ser Leu Cys Asp Ser Tyr Glu Thr Ile Pro Pro Asn Ile Ser Glu
        35                  40                  45

Lys Glu Ala Ala Trp Leu Arg Ser Phe Tyr Ala Ala Gly Glu Glu Glu
    50                  55                  60

Lys Glu Arg Arg Thr His Ala Ile Ala Val Ala Ala Thr Ala Ala
65                  70                  75                  80

Ala Ala Asp Ala Ala Val Ala Ala Ala Lys Ala Ala Ala Ala Val Val
                85                  90                  95

Arg Leu Gln Gly Gln Gly Lys Ser Gly Pro Leu Gly Gly Gly Lys Ser
            100                 105                 110

Arg Glu His Arg Ala Ala Met Gln Ile Gln Cys Ala Phe Arg Gly Tyr
        115                 120                 125

Leu Ala Arg Lys Ala Leu Arg Ala Leu Arg Gly Val Val Lys Ile Gln
    130                 135                 140

Ala Leu Val Arg Gly Phe Leu Val Arg Asn Gln Ala Ala Ala Thr Leu
145                 150                 155                 160

Arg Ser Met Glu Ala Leu Val Arg Ala Gln Lys Thr Val Lys Ile Gln
                165                 170                 175

Arg Ala Leu Arg Arg Asn Gly Asn Ala Ala Pro Ala Arg Lys Ser Thr
            180                 185                 190

Glu Arg Phe Ser Gly Ser Leu Glu Asn Arg Asn Asn Gly Glu Glu Thr
        195                 200                 205

Ala Lys Ile Val Glu Val Asp Thr Gly Thr Arg Pro Gly Thr Tyr Arg
    210                 215                 220

Ile Arg Ala Pro Val Leu Ser Gly Ser Asp Phe Leu Asp Asn Pro Phe
225                 230                 235                 240

Arg Arg Thr Leu Ser Ser Pro Leu Ser Gly Arg Val Pro Pro Arg Leu
                245                 250                 255

Ser Met Pro Lys Pro Glu Trp Glu Glu Cys Ser Ser Lys Phe Pro Thr
            260                 265                 270

Ala Gln Ser Thr Pro Arg Phe Ser Gly Ser Pro Ala Arg Ser Val
        275                 280                 285

Cys Cys Ser Gly Gly Gly Val Glu Ala Glu Val Asp Thr Glu Ala Asp
    290                 295                 300

Ala Asn Arg Phe Cys Phe Leu Ser Gly Glu Phe Asn Ser Gly Tyr Met
305                 310                 315                 320

Ala Asp Thr Thr Ser Phe Arg Ala Lys Leu Arg Ser His Ser Ala Pro
                325                 330                 335
```

-continued

```
Arg Gln Arg Pro Glu Ser Asn Ala Ser Ala Gly Gly Trp Arg Arg Ser
                340                 345                 350

Ile Gly Gly Gly Val Arg Met Gln Arg Gln Ser Cys Ser Gly Val
        355                 360                 365

Arg Glu Ala Val Val Gly Asn Ile Glu Arg Arg Arg Met Arg Trp
    370                 375                 380

<210> SEQ ID NO 44
<211> LENGTH: 460
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME08732
<220> FEATURE:
<221> NAME/KEY: misc_feature
<223> OTHER INFORMATION: Score of 822.2 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (128)..(148)
<223> OTHER INFORMATION: Pfam Name: IQ Pfam Description: IQ calmodulin-
      binding motif

<400> SEQUENCE: 44

Met Ala Lys Lys Lys Ser Trp Phe Ser Leu Val Lys Arg Leu Phe Ile
1               5                   10                  15

Trp Asp Thr His Ser Thr Gln Asp Lys Lys Glu Lys Arg Arg Lys Trp
            20                  25                  30

Ile Phe Gly Arg Leu Lys Ser Lys Arg Leu Pro Ser Ile Lys Ala Pro
        35                  40                  45

Leu Pro Ser Lys Gly Thr Thr Leu Ser Glu Ala Glu Gln Glu Gln Ser
    50                  55                  60

Lys His Ala Leu Thr Val Ala Ile Ala Ser Ala Ala Ala Glu Ala
65                  70                  75                  80

Ala Val Thr Ala Ala His Ala Ala Glu Val Val Arg Leu Thr Gly
                85                  90                  95

Gln Arg Asn Glu Asn Ser Glu Ser Gln Pro Val Lys Thr Arg Asn
            100                 105                 110

Gly Ala Pro Gln Ser Thr Tyr Gln Cys Gln Arg Glu Ile Lys Glu Ser
        115                 120                 125

Ala Ala Ala Ile Lys Ile Gln Thr Ala Phe Arg Gly Tyr Leu Ala Arg
130                 135                 140

Lys Ala Leu Arg Ala Leu Lys Gly Ile Val Lys Leu Gln Ala Ile Ile
145                 150                 155                 160

Arg Gly Arg Ala Val Arg Arg Gln Ala Met Ser Ser Leu Lys Cys Leu
                165                 170                 175

Gln Ser Ile Val Ser Ile Gln Ser Gln Val Cys Ala Arg Arg Leu Gln
            180                 185                 190

Met Val Glu Gly Arg Cys Asp Tyr Ser Glu Asn Glu Met Gln Asp
        195                 200                 205

Phe Lys Asp Lys Ile Ile Arg Met Asp Ser Asn Ser Glu Arg Lys Trp
    210                 215                 220

Asp Glu Ser Thr Val Leu Lys Glu Glu Val Asp Thr Ser Cys Thr Ser
225                 230                 235                 240

Lys Arg Glu Arg Thr Lys Glu Tyr Ser Phe Asn His Arg Ser Ala
                245                 250                 255
```

-continued

```
Glu Ser Glu Arg Ser Lys Val Asn Gly Arg Trp Arg Tyr Trp Leu Glu
            260                 265                 270

Gln Trp Val Asp Thr Gln Leu Ser Lys Ser Lys Glu Leu Glu Asp Leu
            275                 280                 285

Asp Ser Val Phe Ser Ser His Ser Arg Ala Gly Glu Glu Tyr Gly Gly
            290                 295                 300

Arg Gln Leu Lys Leu Arg Ser Asn Ile Gln Arg Gln Asn Pro Val Glu
305                 310                 315                 320

Gly Leu Asp Ser Pro Ile Leu Gly Ser Arg Arg Ser Phe Pro His Arg
                325                 330                 335

Arg Gln Cys Ser Val Gly Glu Asp His Ser Phe Leu Ser Ser Pro Ala
            340                 345                 350

Thr Pro Ala Tyr Met Ala Ala Thr Glu Ser Ala Lys Ala Lys Ala Arg
            355                 360                 365

Ser Thr Ser Ser Pro Lys Ile Arg Thr Gly Gly Asn Val Asp Met Asn
            370                 375                 380

Ser Asp Ser Tyr Ser Pro Cys Lys Lys Lys Leu Ser Ile Ala Ser Ser
385                 390                 395                 400

Ile Asn Ser Glu Met Leu Ser Asn Gly Arg Val Gly Lys Leu Ser Val
            405                 410                 415

Asn Gln Gln Gln Arg Ser Pro Ser Phe Lys Gly Leu Ser Val Pro Ile
            420                 425                 430

Lys Ser Ser Arg Thr Thr Ile Lys Asp Leu Ser Ile Asn Ser Asp Cys
            435                 440                 445

Ser Leu Pro Asn Trp Asp Arg Gln Ala Phe Phe Lys
            450                 455                 460

<210> SEQ ID NO 45
<211> LENGTH: 403
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME19657
<220> FEATURE:
<221> NAME/KEY: misc_feature
<223> OTHER INFORMATION: Score of 695.5 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (117)..(137)
<223> OTHER INFORMATION: Pfam Name: IQ Pfam Description: IQ calmodulin-
      binding motif

<400> SEQUENCE: 45

Met Gly Phe Phe Gly Arg Leu Phe Gly Ser Lys Lys Ser Asp Lys
1               5                   10                  15

Ala Ala Ser Ser Arg Asp Lys Arg Trp Ser Phe Thr Thr Arg Ser
            20                  25                  30

Ser Asn Ser Ser Lys Arg Ala Pro Ala Val Thr Ser Ala Ser Val Val
            35                  40                  45

Glu Gln Asn Gly Leu Asp Ala Asp Lys His Ala Ile Ala Val Ala Ala
            50                  55                  60

Ala Thr Ala Ala Val Ala Glu Ala Ala Leu Thr Ala Ala His Ala Ala
65                  70                  75                  80

Ala Glu Val Val Arg Leu Thr Ser Gly Asn Gly Gly Arg Asn Val Gly
```

```
                    85                  90                  95
Gly Gly Gly Asn Ser Ser Val Phe Gln Ile Gly Arg Ser Asn Arg Arg
                100                 105                 110
Trp Ala Gln Glu Asn Ile Ala Ala Met Lys Ile Gln Ser Ala Phe Arg
                115                 120                 125
Gly Tyr Leu Ala Arg Arg Ala Leu Arg Ala Leu Lys Ala Leu Val Lys
            130                 135                 140
Leu Gln Ala Leu Val Arg Gly His Ile Val Arg Lys Gln Thr Ala Asp
145                 150                 155                 160
Met Leu Arg Arg Met Gln Thr Leu Val Arg Leu Gln Ser Gln Ala Arg
                165                 170                 175
Ala Arg Ala Ser Arg Ser Ser His Ser Ser Ala Ser Phe His Ser Ser
                180                 185                 190
Thr Ala Leu Leu Phe Pro Ser Ser Ser Ser Pro Arg Ser Leu His
                195                 200                 205
Thr Arg Cys Val Ser Asn Ala Glu Val Ser Ser Leu Asp His Arg Gly
            210                 215                 220
Gly Ser Lys Arg Leu Asp Trp Gln Ala Glu Glu Ser Glu Asn Gly Asp
225                 230                 235                 240
Lys Ile Leu Glu Val Asp Thr Trp Lys Pro His Tyr His Pro Lys Pro
                245                 250                 255
Leu Arg Ser Glu Arg Asn Asn Glu Ser Pro Arg Lys Arg Gln Gln Ser
                260                 265                 270
Leu Leu Gly Pro Arg Ser Thr Glu Asn Ser Pro Gln Val Gly Ser Ser
            275                 280                 285
Gly Ser Arg Arg Thr Pro Phe Thr Pro Thr Ser Arg Ser Glu Tyr
                290                 295                 300
Ser Trp Gly Cys Asn Asn Tyr Tyr Tyr Ser Gly Tyr His Pro Asn Tyr
305                 310                 315                 320
Met Ala Asn Thr Glu Ser Tyr Lys Ala Lys Val Arg Ser Gln Ser Ala
                325                 330                 335
Pro Lys Gln Arg Val Glu Val Ser Asn Glu Thr Ser Gly Tyr Lys Arg
                340                 345                 350
Ser Val Gln Gly Gln Tyr Tyr Tyr Tyr Thr Ala Val Glu Glu Ser
            355                 360                 365
Leu Asp Val Gly Ser Ala Gly Tyr Tyr Gly Gly Gly Gly Asp Ser
            370                 375                 380
Asp Arg Leu Asn Arg Asn Gln Ser Ala Lys Ser Arg Met His Ser Ser
385                 390                 395                 400
Phe Leu Val

<210> SEQ ID NO 46
<211> LENGTH: 1711
<212> TYPE: DNA
<213> ORGANISM: Triticum aestivum
<220> FEATURE:
<221> NAME/KEY: misc_feature
<223> OTHER INFORMATION: Ceres CLONE ID no.835818
<220> FEATURE:
<221> NAME/KEY: misc_feature
<223> OTHER INFORMATION: Encodes the peptide sequence at SEQ ID NO 47

<400> SEQUENCE: 46
ccaaatccaa tgctctacat ttcttccttc tcgtgcccct tcttgatttg cgcatggaca     60
gtgacttgcg ttgccagcaa agagccatcc tgctaggccc tttgccaaca tctccgtaga    120
```

| | | | | |
|---|---|---|---|---|
| tcacattcca | gagcagatag | acagaagaat | ggagaggaag | aagaaggggt ggttcgagcg | 180 |
| catcaagagg | ctcttcatct | ccgaacccaa | gcagaaaccc | aaaccagaca agaaggtgaa | 240 |
| gagcaagaga | tggctggtag | ggaagctcaa | gacccagcac | tcgtttgccc tgccagctcc | 300 |
| ggagccggag | ccggcgacgg | gtcagattca | gataaggcag | gcggaggagg agcagagcaa | 360 |
| gcacgcagtg | gcggtcgcgc | tcgcctccgc | agcggccgca | gaggcagccg tcgcggccgc | 420 |
| ccacgcggcc | gcggaggtgg | tccgcctcac | aggaccgccc | tcgccggcgc cggcgccggc | 480 |
| gcgtgaggac | gccgcgtctt | ccggccacga | actgttcgcc | gccgtcgcga tccagtcagc | 540 |
| ctaccgcgga | tacctcgcgc | ggagggcact | gcgcgcgctc | aagggcctgg tgaggctgca | 600 |
| ggcggtgatc | cgcgggcagg | cggtgcggcg | gaagacggcg | gcgacgctgc ggggcctcga | 660 |
| gtcgctggtc | aagatccagg | cccggcagcg | cgccagggcc | gacgtcgacc acgagcacga | 720 |
| cggcgacgg | atggacgccc | tgctgaggag | aggccggag | ctgtacgccg ccgcgctgca | 780 |
| agagcagcag | cagagcagcc | gggggtggg | acggcagcac | cctctccaag gaagagatgg | 840 |
| gcgccgtgat | gaggagcagg | gaggaagccg | ccatcaagcg | cgtgcgcgcg ctgcagtacg | 900 |
| cctccatcca | gaacgagaag | atcggcatca | ggaggcagcc | catgtccagg gacgagatgg | 960 |
| agacgctcaa | ccagcgctgg | agctggctgg | aggagtgggt | cggctcgcag cccttcgaca | 1020 |
| aggacgtggc | cgtcgacgtg | gtcacccacc | cccaccgcc | gccgcctcgc tccagggact | 1080 |
| ccctcgcctg | cctcgaggac | gacgacgacc | atgatgacga | cggctatggc aggcggctcg | 1140 |
| gctactcgtc | caggcggtcc | ttcggccgcg | ccaggcgcac | gccagggagg gggagcgtcg | 1200 |
| acgacgggct | gcaggcctgc | tcgccggcgg | tggctttccc | ggggtacatg gcgtccacgg | 1260 |
| cgtccgccaa | ggccaagttc | cggtccatga | gcacgcccaa | ggagcgcttc gccgtgccat | 1320 |
| ccgacgcata | ctcggagcag | tgcttcgccg | accgcctcat | gtcacccatc ccgtccatgt | 1380 |
| cgccgatgcc | gtccatcgcc | agcgacatgg | gttttgctcg | ctccagcagg ccgccggttg | 1440 |
| cgcagcggtc | gccgcgtgtc | aagggggggc | cgatgacgcc | gtcgaggatc cgctccagga | 1500 |
| ggtcccccag | ccgccacagc | ttcggctctg | aagccgcgct | gcaccagatg cagatggagc | 1560 |
| actacacccc | tattcgctag | acacaaacaa | acttctttgt | aatgtgacca atgctgcctt | 1620 |
| gtttggcggg | cttgctctct | ctgggtctga | ccatggaaac | cttctcaaac tgaccgtgct | 1680 |
| gtgcgaatgc | aatatggatc | tgcaaacttt | c | | 1711 |

<210> SEQ ID NO 47
<211> LENGTH: 476
<212> TYPE: PRT
<213> ORGANISM: Triticum aestivum
<220> FEATURE:
<221> NAME/KEY: misc_feature
<223> OTHER INFORMATION: Ceres CLONE ID no.835818
<220> FEATURE:
<221> NAME/KEY: misc_feature
<223> OTHER INFORMATION: Score of 855.1 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41
<220> FEATURE:
<221> NAME/KEY: misc_feature
<222> LOCATION: (122)..(142)
<223> OTHER INFORMATION: Pfam Name: IQ Pfam Description: IQ calmodulin-
    binding motif

<400> SEQUENCE: 47

Met Glu Arg Lys Lys Lys Gly Trp Phe Glu Arg Ile Lys Arg Leu Phe
1               5                   10                  15

```
Ile Ser Glu Pro Lys Gln Lys Pro Lys Pro Asp Lys Lys Val Lys Ser
            20                  25                  30

Lys Arg Trp Leu Val Gly Lys Leu Lys Thr Gln His Ser Phe Ala Leu
        35                  40                  45

Pro Ala Pro Glu Pro Glu Pro Ala Thr Gly Gln Ile Gln Ile Arg Gln
    50                  55                  60

Ala Glu Glu Glu Gln Ser Lys His Ala Val Ala Val Ala Leu Ala Ser
65                  70                  75                  80

Ala Ala Ala Ala Glu Ala Ala Val Ala Ala Ala His Ala Ala Ala Glu
                85                  90                  95

Val Val Arg Leu Thr Gly Pro Pro Ser Pro Ala Pro Ala Pro Ala Arg
            100                 105                 110

Glu Asp Ala Ala Ser Ser Gly His Glu Leu Phe Ala Ala Val Ala Ile
            115                 120                 125

Gln Ser Ala Tyr Arg Gly Tyr Leu Ala Arg Arg Ala Leu Arg Ala Leu
    130                 135                 140

Lys Gly Leu Val Arg Leu Gln Ala Val Ile Arg Gly Gln Ala Val Arg
145                 150                 155                 160

Arg Lys Thr Ala Ala Thr Leu Arg Gly Leu Glu Ser Leu Val Lys Ile
            165                 170                 175

Gln Ala Arg Gln Arg Ala Arg Ala Asp Val Asp His Glu His Asp Gly
            180                 185                 190

Asp Gly Met Asp Ala Leu Leu Arg Arg Gly Arg Glu Leu Tyr Ala Ala
            195                 200                 205

Ala Leu Gln Glu Gln Gln Gln Ser Ser Arg Gly Trp Asp Gly Ser Thr
    210                 215                 220

Leu Ser Lys Glu Glu Met Gly Ala Val Met Arg Ser Arg Glu Glu Ala
225                 230                 235                 240

Ala Ile Lys Arg Val Arg Ala Leu Gln Tyr Ala Ser Ile Gln Asn Glu
            245                 250                 255

Lys Ile Gly Ile Arg Arg Gln Pro Met Ser Arg Asp Glu Met Glu Thr
            260                 265                 270

Leu Asn Gln Arg Trp Ser Trp Leu Glu Glu Trp Val Gly Ser Gln Pro
    275                 280                 285

Phe Asp Lys Asp Val Ala Val Asp Val Val Thr His Pro His Pro Pro
    290                 295                 300

Pro Pro Arg Ser Arg Asp Ser Leu Ala Cys Leu Glu Asp Asp Asp Asp
305                 310                 315                 320

His Asp Asp Asp Gly Tyr Gly Arg Arg Leu Gly Tyr Ser Ser Arg Arg
            325                 330                 335

Ser Phe Gly Arg Ala Arg Arg Thr Pro Gly Arg Gly Ser Val Asp Asp
            340                 345                 350

Gly Leu Gln Ala Cys Ser Pro Ala Val Ala Phe Pro Gly Tyr Met Ala
            355                 360                 365

Ser Thr Ala Ser Ala Lys Ala Lys Phe Arg Ser Met Ser Thr Pro Lys
            370                 375                 380

Glu Arg Phe Ala Val Pro Ser Asp Ala Tyr Ser Glu Gln Cys Phe Ala
385                 390                 395                 400

Asp Arg Leu Met Ser Pro Ile Pro Ser Met Ser Pro Met Pro Ser Ile
            405                 410                 415

Ala Ser Asp Met Gly Phe Ala Arg Ser Ser Arg Pro Pro Val Ala Gln
            420                 425                 430
```

```
                Arg Ser Pro Arg Val Lys Gly Gly Pro Met Thr Pro Ser Arg Ile Arg
                                435                 440                 445

Ser Arg Arg Ser Pro Ser Arg His Ser Phe Gly Ser Glu Ala Ala Leu
                    450                 455                 460

His Gln Met Gln Met Glu His Tyr Thr Pro Ile Arg
                465                 470                 475

<210> SEQ ID NO 48
<211> LENGTH: 1651
<212> TYPE: DNA
<213> ORGANISM: Panicum virgatum
<220> FEATURE:
<221> NAME/KEY: misc_feature
<223> OTHER INFORMATION: Ceres CLONE ID no.1796745
<220> FEATURE:
<221> NAME/KEY: misc_feature
<223> OTHER INFORMATION: Encodes the peptide sequence at SEQ ID NO 49

<400> SEQUENCE: 48
gtagcactag ccactctcac tcccccggc ggcatggaga aggagaagag gcggaggagc        60
tggttcgagc gcatcaggcg gctcttcacc tcctccgagc ccaaggagaa acccaaacct      120
gacaagaagg cgaagagcaa gcggtggcta ccggggaagc tgaggacgca gcagtcgttc      180
gctctgccgg cgccggcatc cgcggccgcg gacctgcaga tcaggcaggc ggaggacgag      240
cagagcaagc acgccgtgac cgtcgctctc gccaccgcgg cggccgccga ggccgcggtc      300
gccgccgcgc acgccgccgc cgaggtcgtc cgcctcaccg gccagcaggc cgcggcccg      360 ccggccgggc gggagcggga gctggaggag gaggagcatg ccgccgtctt gatccaatcg      420
gcgtaccgcg ggtacctggc tcggcgggcg ctgcgcgcgc tcaagggtct ggtgcggctg      480
caggcgctga tccggggca ggcggtgcgg caccagacgg cggccacgct gcgcggcctc      540
gagtccctga tgaggatcca ggcccagcac cgctcccggg ccggcggccc cgaccacccg      600
gcggcgctcg acggcaacga cgacgccttc ctgctccggc gcggccggga gctctacgcc      660
gccgcggtcc accagcagca gcaggcgggc agcaaagggt gggacagcag catcctcgcc      720
aaggaggaga tgcgcgccgt gatgcggagc cgggaggagg ccgccctcaa gcgcgtgcgc      780
gcgctgcagt acgcgtccct gcagagcgag cggctgggcg tccggcggcc gccgctgccc      840
agggacgagg aggcggacgc gctccaccgc cgctggagct ggctcgagga gtgggtcggc      900
gcgcagccgc ccttcgacaa ggacgtcccc gtggcgcacc agtcgcccta cagcagggac      960
gacgccgccg ccgccagggg ccgccagacg ccgggccggg ccgtcgaccc gctcgccggc     1020
ctcggcggcg cgacgccga ccggctcggt tgctcggcgc ggcggtcctt cgtgcggccg     1080
aggcgcgcgc cggcgcgggc gggcgactac ttctacgagg acgccgcgcc gtgctcgccg     1140
gcgacgttcc cggggtacat ggcgtccacg gcctccgcca aggccaagtt ccggtccatg     1200
agcacgccca aggagcgctt cgccggagcc gacgccttct ccgagcactg cttcccgttc     1260
gccgaccgca tgctctcgcc gatcccgtcc atgtcgccca tcccctccat cgccagcgac     1320
atgggcttcg ccaggtccac caggccgccc gccgcgcaga atcgccgcg ggtggcggcc     1380 aagggcccca tgacgccggc gcggtcgcgc tcacggaggt cgccgagcca ccacagcttc     1440
ggctccgagg ccgcgctgca ccaactgcag atggagcact acaccccagt ccggtgaaca     1500
agactacaga gagtgccttg cttcgttaca ctcttttgtg aagatacaat tccctgctcc     1560
cattcttttg tttgttcacc tttcttgaca gaagggttca actgttcaag tattcagtaa     1620
tggaatgcaa caacgtaaaa aaaaaaaaa a                                      1651
```

-continued

```
<210> SEQ ID NO 49
<211> LENGTH: 487
<212> TYPE: PRT
<213> ORGANISM: Panicum virgatum
<220> FEATURE:
<221> NAME/KEY: misc_feature
<223> OTHER INFORMATION: Ceres CLONE ID no.1796745
<220> FEATURE:
<221> NAME/KEY: misc_feature
<223> OTHER INFORMATION: Score of 472.4 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (121)..(141)
<223> OTHER INFORMATION: Pfam Name: IQ Pfam Description: IQ calmodulin-
      binding motif

<400> SEQUENCE: 49

Met Glu Lys Glu Lys Arg Arg Arg Ser Trp Phe Glu Arg Ile Arg Arg
 1               5                   10                  15

Leu Phe Thr Ser Ser Glu Pro Lys Glu Lys Pro Lys Pro Asp Lys Lys
                20                  25                  30

Ala Lys Ser Lys Arg Trp Leu Pro Gly Lys Leu Arg Thr Gln Gln Ser
            35                  40                  45

Phe Ala Leu Pro Ala Pro Ala Ser Ala Ala Ala Asp Leu Gln Ile Arg
    50                  55                  60

Gln Ala Glu Asp Glu Gln Ser Lys His Ala Val Thr Val Ala Leu Ala
65                  70                  75                  80

Thr Ala Ala Ala Glu Ala Ala Val Ala Ala Ala His Ala Ala Ala
                85                  90                  95

Glu Val Val Arg Leu Thr Gly Gln Gln Ala Ala Ala Pro Pro Ala Gly
            100                 105                 110

Arg Glu Arg Glu Leu Glu Glu Glu His Ala Ala Val Leu Ile Gln
            115                 120                 125

Ser Ala Tyr Arg Gly Tyr Leu Ala Arg Arg Ala Leu Arg Ala Leu Lys
    130                 135                 140

Gly Leu Val Arg Leu Gln Ala Leu Ile Arg Gly Gln Ala Val Arg His
145                 150                 155                 160

Gln Thr Ala Ala Thr Leu Arg Gly Leu Glu Ser Leu Met Arg Ile Gln
                165                 170                 175

Ala Gln His Arg Ser Arg Ala Gly Gly Pro Asp His Pro Ala Ala Leu
            180                 185                 190

Asp Gly Asn Asp Asp Ala Phe Leu Leu Arg Arg Gly Arg Glu Leu Tyr
    195                 200                 205

Ala Ala Ala Val His Gln Gln Gln Ala Gly Ser Lys Gly Trp Asp
    210                 215                 220

Ser Ser Ile Leu Ala Lys Glu Glu Met Arg Ala Val Met Arg Ser Arg
225                 230                 235                 240

Glu Glu Ala Ala Leu Lys Arg Val Arg Ala Leu Gln Tyr Ala Ser Leu
                245                 250                 255

Gln Ser Glu Arg Leu Gly Val Arg Arg Pro Leu Pro Arg Asp Glu
            260                 265                 270

Glu Ala Asp Ala Leu His Arg Arg Trp Ser Trp Leu Glu Glu Trp Val
    275                 280                 285

Gly Ala Gln Pro Pro Phe Asp Lys Asp Val Pro Val Ala His Gln Ser
    290                 295                 300
```

-continued

```
Pro Tyr Ser Arg Asp Asp Ala Ala Ala Arg Gly Arg Gln Thr Pro
305                 310                 315                 320

Gly Arg Ala Val Asp Pro Leu Ala Gly Leu Gly Gly Asp Ala Asp
                325                 330                 335

Arg Leu Gly Cys Ser Ala Arg Arg Ser Phe Val Arg Pro Arg Ala
            340                 345                 350

Pro Ala Arg Ala Gly Asp Tyr Phe Tyr Glu Asp Ala Ala Pro Cys Ser
            355                 360                 365

Pro Ala Thr Phe Pro Gly Tyr Met Ala Ser Thr Ala Ser Ala Lys Ala
            370                 375                 380

Lys Phe Arg Ser Met Ser Thr Pro Lys Glu Arg Phe Ala Gly Ala Asp
385                 390                 395                 400

Ala Phe Ser Glu His Cys Phe Pro Phe Ala Asp Arg Met Leu Ser Pro
                405                 410                 415

Ile Pro Ser Met Ser Pro Ile Pro Ser Ile Ala Ser Asp Met Gly Phe
                420                 425                 430

Ala Arg Ser Thr Arg Pro Pro Ala Ala Gln Arg Ser Pro Arg Val Ala
            435                 440                 445

Ala Lys Gly Pro Met Thr Pro Ala Arg Ser Arg Ser Arg Arg Ser Pro
    450                 455                 460

Ser His His Ser Phe Gly Ser Glu Ala Ala Leu His Gln Leu Gln Met
465                 470                 475                 480

Glu His Tyr Thr Pro Val Arg
                485

<210> SEQ ID NO 50
<211> LENGTH: 501
<212> TYPE: PRT
<213> ORGANISM: Oryza sativa subsp. indica
<220> FEATURE:
<221> NAME/KEY: misc_feature
<223> OTHER INFORMATION: Public GI ID no.125543896
<220> FEATURE:
<221> NAME/KEY: misc_feature
<223> OTHER INFORMATION: Score of 538.7 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41
<220> FEATURE:
<221> NAME/KEY: misc_feature
<222> LOCATION: (122)..(142)
<223> OTHER INFORMATION: Pfam Name: IQ Pfam Description: IQ calmodulin-
    binding motif

<400> SEQUENCE: 50

Met Glu Arg Lys Arg Arg Gly Trp Leu Glu Arg Ile Lys Arg Leu Phe
1               5                   10                  15

Val Ser Glu Pro Lys Gln Lys Pro Lys Pro Asp Lys Lys Val Lys Ser
                20                  25                  30

Lys Arg Trp Met Phe Ala Gly Lys Leu Lys Thr Gln His Ser Phe Ala
            35                  40                  45

Leu Pro Ala Pro Ala Pro Ala Val Glu Glu Glu Gln Ile Arg Gln Ala
        50                  55                  60

Glu Asp Glu Gln Ser Lys His Ala Met Ala Val Ala Leu Ala Thr Ala
65                  70                  75                  80

Ala Ala Ala Glu Ala Ala Val Ala Ala Ala His Ala Ala Ala Glu Val
                85                  90                  95

Val Arg Leu Thr Gly Lys Thr Ala Ala Leu Ala Pro Ala Pro Ala Thr
```

```
                100               105               110
Thr Thr Thr Pro Thr Pro Tyr Gly His Glu His Ala Ala Leu Met Ile
            115               120               125

Gln Ser Val Tyr Arg Gly Tyr Leu Ala Arg Arg Ala Leu Arg Ala Leu
            130               135           140

Lys Gly Leu Val Arg Leu Gln Ala Leu Ile Arg Gly Gln Ala Val Arg
145             150               155               160

Arg Gln Thr Ala Ala Thr Leu Arg Gly Leu Glu Ser Leu Met Lys Ile
                165               170               175

Gln Ala Arg Gln Arg Ala Arg Ala Ser Ser Ala Ala Ala Gly Gly
            180               185               190

Asp His Asn Ala Ala Asn Ser Pro Ala Pro Asp Gly Met Asp Ala Leu
            195               200           205

Leu Arg Arg Gly Arg Glu Leu Tyr Tyr Ala Ala Ala Ala Val His
            210               215               220

Glu Gln Gln Leu Ser Lys Gly Trp Asp Ser Ser Thr Leu Ser Lys Glu
225             230               235               240

Glu Met Ser Ala Met Ser Arg Ser Arg Glu Glu Ala Ala Leu Lys Arg
                245               250               255

Val Arg Ala Leu Gln Tyr Ala Ser Leu His Gln Ser Glu Lys Val Arg
                260               265               270

Val Arg Arg Gln Pro Met Ser Arg Glu Glu Met Glu Thr Leu Asn Gln
                275               280               285

Arg Trp Ser Trp Leu Glu Glu Trp Val Gly Ser Gln Pro Pro Phe Asp
            290               295               300

Lys Asp Ile Pro Val Ala His Gln Ser Pro Ser Arg Asp Ala Ala Gly
305             310               315               320

Ala Ala Met Asn Asp Asp Glu Arg Pro Pro Pro Pro Val Leu Arg
                325               330               335

Ser Arg Ser Arg Ala Asp Arg Leu Ala Cys Val Gly Gly Asp Asp Asp
            340               345               350

Asp Ala Asp Arg Gln Leu Gly Tyr Ser Ala Arg Arg Ser Phe Thr Arg
            355               360               365

Ala Gly Arg Arg Thr Pro Ala Arg Asp Asp Asp Gly Gly Ala Ala
            370               375               380

Ala Phe Pro Gly Tyr Met Ala Ser Thr Ala Ser Ala Lys Ala Lys Phe
385             390               395               400

Arg Ser Met Ser Thr Pro Lys Glu Arg Ser Gly Ala Gly Ala Ala Asp
                405               410               415

Ala Tyr Ser Glu Gln Cys Phe Pro Phe Ala Asp Arg Leu Leu Ser Pro
                420               425           430

Ile Pro Ser Met Ser Pro Ile Pro Ser Ile Ala Ser Asp Ile Val Phe
            435               440               445

Ala Arg Ser Ser Arg Pro Ala Ala Ala Gln Arg Ser Pro Arg Val Lys
450             455               460

Gly Pro Met Thr Pro Thr Arg Ser Arg Ser Arg Arg Ser Pro Gly Arg
465             470               475               480

His Ser Phe Ser Ser Glu Ala Ala Leu His Gln Leu Gln Met Glu Gln
            485               490               495

Tyr Thr Pro Ile Arg
            500

<210> SEQ ID NO 51
```

```
<211> LENGTH: 1494
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1483984
<220> FEATURE:
<221> NAME/KEY: misc_feature
<223> OTHER INFORMATION: Encodes the peptide sequence at SEQ ID NO 52

<400> SEQUENCE: 51
atgtcaggtc tatcagagtt gagaaatatg aaagttggaa aaaagatggg aggtcccatg     60
agtcttgaga aggatgttta tatgagttgt ggtgcttcaa tggctaagaa gagaagctgg    120
ttctatcgag tgagaaggtt atttacttct gacacacagt caagacaaga aaaggaaagg    180
agaagaaaat ggatgttttt tggaaagttt aaggtcaaga atagattggc ctccattgca    240
gctccatcat caccactaag agaagaagca gagaaggagc agagcaagca tgctctaagt    300
gttgctcttg ccactgctgc tgctgctgag gcagctgttg tagctgctca ggctgcggcc    360
gaggtggttt tgctcactgg tgttcctcat tctatcaatg aatatgagaa agaaaccgac    420
catttagcct tcgaagttca aggtgatgcc cctcattcca ctcatcaaca tgcgagggqg    480
atcaaagaac tggctgccat caaaattcaa gctacctttta ggggttacct tgcaaggaaa    540
gctttgcggg cgctgaaggg gatagtgaag cttcaagcaa ttatccgagg gcggaacgtg    600
agacgccaag ccatgactac tctaaaatgc ttgcaatcca ttgtaaatat ccagtcacaa    660
gtctgtgcaa aaaggatcca atggtggaa ggtgcttgga cctgtagtga aaataaacag    720
ttagaaaatt tgagtgacaa gataataaag atggatatga atagtgaaag aagatgggat    780
agcagccttc tgacaaagga gaggcagtt gcctcgtttc taagcaagaa agaggccgcg    840
attaagagaa acggataag agaatactgg ttcaaccgcc ggaattcagc tgaatcggag    900
cgaagcaagc caagtggaag gtggaggtac tggttagatc aatgggtgga tactcaactt    960
gttaagagta aagagcttga agatttggac tcagttttaa cctcaaatcc aaagcctgga   1020
gtggaatata gaggaaagca gattaaactg agaggtttgc agagactgta tcaccttgac   1080
agtgtagatt ctcccatttc agctccaaga aaatccttcc atagaaagca atgctcgttg   1140
ggagaagaca attcctttc tagatctcct gtggttccaa cttacatggc aacaactgaa   1200
tctgccaagg caaaaacaag atcaatgagc tcaccaaagc taaggccagg agtttttgat   1260
gcttactctg acagctattc tccatgtaag aataagcttt ctctgatatc atctacaact   1320
actgaagtgc cgagcagtgc taggtacgga aggcctagtg cttatcagca aaggtctcca   1380
agcttgaagg gccttccggg tccgataaaa tgtaaccggc caacgtcgaa agttcttagc   1440
tttgattcag attgctcatt aaagacttgg gataaacaaa gttcctttag atga         1494
```

<210> SEQ ID NO 52
<211> LENGTH: 464
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1483984
<220> FEATURE:
<221> NAME/KEY: misc_feature
<223> OTHER INFORMATION: Score of 498.0 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (130)..(150)
<223> OTHER INFORMATION: Pfam Name: IQ Pfam Description: IQ calmodulin-
      binding motif

<400> SEQUENCE: 52

| | | | | | | | | | | | | | | |
|---|---|---|---|---|---|---|---|---|---|---|---|---|---|---|
| Met | Ala | Lys | Lys | Arg | Ser | Trp | Phe | Tyr | Arg | Val | Arg | Arg | Leu | Phe | Thr |
| 1 | | | | 5 | | | | | 10 | | | | | 15 | |
| Ser | Asp | Thr | Gln | Ser | Arg | Gln | Glu | Lys | Glu | Arg | Arg | Lys | Trp | Met | |
| | | | 20 | | | | | 25 | | | | | 30 | | |
| Phe | Phe | Gly | Lys | Phe | Lys | Val | Lys | Asn | Arg | Leu | Ala | Ser | Ile | Ala | Ala |
| | | 35 | | | | | 40 | | | | | 45 | | | |
| Pro | Ser | Ser | Pro | Leu | Arg | Glu | Glu | Ala | Glu | Lys | Glu | Gln | Ser | Lys | His |
| 50 | | | | | 55 | | | | | 60 | | | | | |
| Ala | Leu | Ser | Val | Ala | Leu | Ala | Thr | Ala | Ala | Ala | Glu | Ala | Ala | Val | |
| 65 | | | | | 70 | | | | | 75 | | | | | 80 |
| Val | Ala | Ala | Gln | Ala | Ala | Glu | Val | Val | Leu | Leu | Thr | Gly | Val | Pro | |
| | | | | 85 | | | | | 90 | | | | | 95 | |
| His | Ser | Ile | Asn | Glu | Tyr | Glu | Lys | Glu | Thr | Asp | His | Leu | Ala | Phe | Glu |
| | | | | 100 | | | | | 105 | | | | | 110 | |
| Val | Gln | Gly | Asp | Ala | Pro | His | Ser | Thr | His | Gln | His | Ala | Arg | Gly | Ile |
| | | | 115 | | | | | 120 | | | | | 125 | | |
| Lys | Glu | Leu | Ala | Ala | Ile | Lys | Ile | Gln | Ala | Thr | Phe | Arg | Gly | Tyr | Leu |
| | 130 | | | | | 135 | | | | | 140 | | | | |
| Ala | Arg | Lys | Ala | Leu | Arg | Ala | Leu | Lys | Gly | Ile | Val | Lys | Leu | Gln | Ala |
| 145 | | | | | 150 | | | | | 155 | | | | | 160 |
| Ile | Ile | Arg | Gly | Arg | Asn | Val | Arg | Arg | Gln | Ala | Met | Thr | Thr | Leu | Lys |
| | | | | 165 | | | | | 170 | | | | | 175 | |
| Cys | Leu | Gln | Ser | Ile | Val | Asn | Ile | Gln | Ser | Gln | Val | Cys | Ala | Lys | Arg |
| | | | 180 | | | | | 185 | | | | | 190 | | |
| Ile | Gln | Met | Val | Glu | Gly | Ala | Trp | Thr | Cys | Ser | Glu | Asn | Lys | Gln | Leu |
| | | 195 | | | | | 200 | | | | | 205 | | | |
| Glu | Asn | Leu | Ser | Asp | Lys | Ile | Ile | Lys | Met | Asp | Met | Asn | Ser | Glu | Arg |
| | 210 | | | | | 215 | | | | | 220 | | | | |
| Arg | Trp | Asp | Ser | Ser | Leu | Leu | Thr | Lys | Glu | Glu | Ala | Val | Ala | Ser | Phe |
| 225 | | | | | 230 | | | | | 235 | | | | | 240 |
| Leu | Ser | Lys | Lys | Glu | Ala | Ala | Ile | Lys | Arg | Glu | Arg | Ile | Arg | Glu | Tyr |
| | | | | 245 | | | | | 250 | | | | | 255 | |
| Trp | Phe | Asn | Arg | Arg | Asn | Ser | Ala | Glu | Ser | Glu | Arg | Ser | Lys | Pro | Ser |
| | | | 260 | | | | | 265 | | | | | 270 | | |
| Gly | Arg | Trp | Arg | Tyr | Trp | Leu | Asp | Gln | Trp | Val | Asp | Thr | Gln | Leu | Val |
| | | 275 | | | | | 280 | | | | | 285 | | | |
| Lys | Ser | Lys | Glu | Leu | Glu | Asp | Leu | Asp | Ser | Val | Leu | Thr | Ser | Asn | Pro |
| | 290 | | | | | 295 | | | | | 300 | | | | |
| Lys | Pro | Gly | Val | Glu | Tyr | Arg | Gly | Lys | Gln | Ile | Lys | Leu | Arg | Gly | Leu |
| 305 | | | | | 310 | | | | | 315 | | | | | 320 |
| Gln | Arg | Leu | Tyr | His | Leu | Asp | Ser | Val | Asp | Ser | Pro | Ile | Ser | Ala | Pro |
| | | | | 325 | | | | | 330 | | | | | 335 | |
| Arg | Lys | Ser | Phe | His | Arg | Lys | Gln | Cys | Ser | Leu | Gly | Glu | Asp | Asn | Ser |
| | | | 340 | | | | | 345 | | | | | 350 | | |
| Phe | Ser | Arg | Ser | Pro | Val | Val | Pro | Thr | Tyr | Met | Ala | Thr | Thr | Glu | Ser |
| | | 355 | | | | | 360 | | | | | 365 | | | |
| Ala | Lys | Ala | Lys | Thr | Arg | Ser | Met | Ser | Ser | Pro | Lys | Leu | Arg | Pro | Gly |
| | 370 | | | | | 375 | | | | | 380 | | | | |
| Ser | Phe | Asp | Ala | Tyr | Ser | Asp | Ser | Tyr | Ser | Pro | Cys | Lys | Asn | Lys | Leu |

```
                385             390             395             400
Ser Leu Ile Ser Ser Thr Thr Thr Glu Val Pro Ser Ser Ala Arg Tyr
                    405                 410                 415

Gly Arg Pro Ser Ala Tyr Gln Gln Arg Ser Pro Ser Leu Lys Gly Leu
            420                 425                 430

Pro Gly Pro Ile Lys Cys Asn Arg Pro Thr Ser Lys Val Leu Ser Phe
        435                 440                 445

Asp Ser Asp Cys Ser Leu Lys Thr Trp Asp Lys Gln Ser Ser Phe Arg
    450                 455                 460

<210> SEQ ID NO 53
<211> LENGTH: 1579
<212> TYPE: DNA
<213> ORGANISM: Gossypium hirsutum
<220> FEATURE:
<221> NAME/KEY: misc_feature
<223> OTHER INFORMATION: Ceres CLONE ID no.1924654
<220> FEATURE:
<221> NAME/KEY: misc_feature
<223> OTHER INFORMATION: Encodes the peptide sequence at SEQ ID NO 54

<400> SEQUENCE: 53
aaggaaaaaa aactatagct ttcttcgttt atgtaatgga attcctcgcc aattctctct    60
caatctaagc tatccaagtt ccaaagacta agcttttttt gaagcggtga ttcctgtttg   120
attctcccaa atatttaag tattcagtgc accttttata cacaatccat atggaattta   180
ccactatact atattatata agatgatgtt aggatgcaga aatgtaaaaa ttcagaatag   240
tagtacctga agaagtgaga gttctttaat ggcgaagaag aagagctggt tcaatctagt   300
gaagaggttc tttctctttg agacacttat aaatgcacaa aaggataaca gaaggaaatg   360
gatgtttgga aggtttagga ccaaaaggtt agcatccatt aaagctccat caccaccaag   420
agacagcata aaatatgaaa cagaggagga ccagaagaaa catgccttaa cagtggcaat   480
tgccgcagtg gctgctgctg aagcagctgt tgcagctgct caggttgcag ccgaggttgt   540
tcgcctcaca ggcaatgacg cccctaaagc taaagaagaa caaaccaatg atgttaaacc   600
tgactgttct tcatctagtg agcttggcaa caagttccaa caacttgctg ctataaaaat   660
ccaggcttct tttcggggtt accttgcaag gaaagctttg agagcattga agggatagt   720 gaagcttcaa gcaattattc gaggccgagt tgtgagacga caagcattga ctgctttaaa   780
atgcttgcaa tcgattgtaa acattcagtc tcaagtttgt gcaaggagat tccaaattgt   840
agaaggcact tggcaacaac atgatgagaa caaagagttg ataactttga agataagat    900 tcttaaggtg gataccaaca gtcaaacaag atgggacaat tgtaatggag gattgaagta   960
ctggttagac caatgggtgg atactaaaag taaagatgtt gaagtcgaag acatagactc  1020
ggtttggact tcgaaccgca agcctacgag gctcaagact ttttcgagac agtatcattg  1080
tgatgcagaa ggggtagatt ctccggtacg ggttcaagga cgacgatcat ttcatggaaa  1140
gcagagttct ttaggagaag atagttcttt tattacatct cctgtagttc caacttacat  1200
ggcagcaaca caatctacta aagcaaaggt aaggtcaatg agttcaccaa agctaaggcc  1260
aggaacttgt gatactcaat ccgaaagcta ttcaccatat aagaacaagt cgtgtctcct  1320
atcttcagtt acaagcaagc ctaacgctta tgagcagaga tccccaacac taaagggtgt  1380
aaagtcaaag aaaaccttga aggatcttag ctttaactct taatgttcat tgcctaattg  1440
ggtgcaaaaa agcaccttca aatgactcga ccattgtgat gttttaggtc ccttggaagc  1500
aagtctttgt tattgtgttt gtgtgagatt gctgatgctg ttttgtgctt aaacaattga  1560
```
atgaatcaag ttttgtgtg                                              1579

<210> SEQ ID NO 54
<211> LENGTH: 384
<212> TYPE: PRT
<213> ORGANISM: Gossypium hirsutum
<220> FEATURE:
<221> NAME/KEY: misc_feature
<223> OTHER INFORMATION: Ceres CLONE ID no.1924654
<220> FEATURE:
<221> NAME/KEY: misc_feature
<223> OTHER INFORMATION: Score of 679.6 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41
<220> FEATURE:
<221> NAME/KEY: misc_feature
<222> LOCATION: (125)..(145)
<223> OTHER INFORMATION: Pfam Name: IQ Pfam Description: IQ calmodulin-
    binding motif

<400> SEQUENCE: 54

Met Ala Lys Lys Ser Trp Phe Asn Leu Val Lys Arg Phe Phe Leu
1               5                   10                  15

Phe Glu Thr Leu Ile Asn Ala Gln Lys Asp Asn Arg Arg Lys Trp Met
                20                  25                  30

Phe Gly Arg Phe Arg Thr Lys Arg Leu Ala Ser Ile Lys Ala Pro Ser
            35                  40                  45

Pro Pro Arg Asp Ser Ile Lys Tyr Glu Thr Glu Glu Asp Gln Lys Lys
        50                  55                  60

His Ala Leu Thr Val Ala Ile Ala Val Ala Ala Glu Ala Ala
65                  70                  75                  80

Val Ala Ala Ala Gln Val Ala Ala Glu Val Val Arg Leu Thr Gly Asn
                85                  90                  95

Asp Ala Pro Lys Ala Lys Glu Glu Gln Thr Asn Asp Val Lys Pro Asp
            100                 105                 110

Cys Ser Ser Ser Glu Leu Gly Asn Lys Phe Gln Gln Leu Ala Ala
        115                 120                 125

Ile Lys Ile Gln Ala Ser Phe Arg Gly Tyr Leu Ala Arg Lys Ala Leu
    130                 135                 140

Arg Ala Leu Lys Gly Ile Val Lys Leu Gln Ala Ile Ile Arg Gly Arg
145                 150                 155                 160

Val Val Arg Arg Gln Ala Leu Thr Ala Leu Lys Cys Leu Gln Ser Ile
                165                 170                 175

Val Asn Ile Gln Ser Gln Val Cys Ala Arg Arg Phe Gln Ile Val Glu
            180                 185                 190

Gly Thr Trp Gln Gln His Asp Glu Asn Lys Glu Leu Ile Thr Leu Lys
        195                 200                 205

Asp Lys Ile Leu Lys Val Asp Thr Asn Ser Gln Thr Arg Trp Asp Asn
    210                 215                 220

Cys Asn Gly Gly Leu Lys Tyr Trp Leu Asp Gln Trp Val Asp Thr Lys
225                 230                 235                 240

Ser Lys Asp Val Glu Val Glu Asp Ile Asp Ser Val Trp Thr Ser Asn
                245                 250                 255

Arg Lys Pro Thr Arg Leu Lys Thr Phe Ser Arg Gln Tyr His Cys Asp
            260                 265                 270

Ala Glu Gly Val Asp Ser Pro Val Arg Val Gln Gly Arg Arg Ser Phe
        275                 280                 285

His Gly Lys Gln Ser Ser Leu Gly Glu Asp Ser Ser Phe Ile Thr Ser
            290                 295                 300

Pro Val Val Pro Thr Tyr Met Ala Ala Thr Gln Ser Thr Lys Ala Lys
305                 310                 315                 320

Val Arg Ser Met Ser Ser Pro Lys Leu Arg Pro Gly Thr Cys Asp Thr
                325                 330                 335

Gln Ser Glu Ser Tyr Ser Pro Tyr Lys Asn Lys Ser Cys Leu Leu Ser
            340                 345                 350

Ser Val Thr Ser Lys Pro Asn Ala Tyr Glu Gln Arg Ser Pro Thr Leu
        355                 360                 365

Lys Gly Val Lys Ser Lys Lys Thr Leu Lys Asp Leu Ser Phe Asn Ser
    370                 375                 380

<210> SEQ ID NO 55
<211> LENGTH: 1032
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1468861
<220> FEATURE:
<221> NAME/KEY: misc_feature
<223> OTHER INFORMATION: Encodes the peptide sequence at SEQ ID NO 56

<400> SEQUENCE: 55
atgaaggcaa ggagagcact aagggcacta aaagctttgg tgaagcttca agccttagtg      60
agaggccaca ttgtgagaaa gcaaacagca gacatgctta ggcgtatgca gacattagtg     120
agactgcagg ctcgagcccg tgctagtcgc agttatgtgt cggactcatc gcacactact     180
ggcaagtcct ctcattctcg ttatgctgtc cctgcaagtc cttcaaagga tcacctgttt     240
cgtgtttcta gtaccaaatt tgatgggccc tcgattctca gagatgtgg ttcaaatgca      300 aactttaggg agagcattga ctttgacaaa gtaaaatggg gttcgaactg gctagaccgt     360
tggatggaag aaagtttttt gaatgaccat ggcagcaatc caccgagaag tcgaaatgct     420
gatgatgaga agagtgacaa gattcttgaa gtggacactt ggaagcccca tgtgaaatcc     480
caacaaagta atagaacatt tcagacttca gcagcatgctt ggcttcaga tcataacaat     540 cagagcttta tgactttga ctctatgtca aaactatcaa aaaagaacc gaatccaatg      600 ccgagcatct cttcaggaga aattttgcag tctcttaaat tacctctagg aaatgatgaa     660
gcagtttata ggaccgctga aatagcccct cgaatgttct ctgcaacatc tagacctgga     720
agtagtggtc ggagaggagg ccctttacac ccaacaagga gtgagtgctc gtggggcttc     780
tttaatggat actcgggtta ccccaactac atggctaaca ctgaatcatc tcgagccaag     840
gtcaggtcac aaagtgcccc aaggcagagg ctagagtttg agaaatatgg ttcaagcaga     900
agatctgttc aggggtattc tgattcagaa actcgttcag aaaggggttt tgctcaaaat     960
actgaacttc aaaacaaagc ttacgtagca tctggctact gaatagact agggacttcc    1020 gacttgaggt ga                                                        1032

<210> SEQ ID NO 56
<211> LENGTH: 343
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1468861
<220> FEATURE:
<221> NAME/KEY: misc_feature
<223> OTHER INFORMATION: Score of 100.0 for HMM of FIGURE 2.
<220> FEATURE:
<221> NAME/KEY: misc_feature
<223> OTHER INFORMATION: Functional Homolog Of Ceres SEEDLINE ID no. ME06748 at SEQ ID NO. 41
<220> FEATURE:
<221> NAME/KEY: misc_feature
<222> LOCATION: (10)..(30)
<223> OTHER INFORMATION: Pfam Name: IQ Pfam Description: IQ calmodulin-binding motif

<400> SEQUENCE: 56

```
Met Lys Ala Arg Arg Ala Leu Arg Ala Leu Lys Ala Leu Val Lys Leu
1               5                   10                  15

Gln Ala Leu Val Arg Gly His Ile Val Arg Lys Gln Thr Ala Asp Met
            20                  25                  30

Leu Arg Arg Met Gln Thr Leu Val Arg Leu Gln Ala Arg Ala Arg Ala
        35                  40                  45

Ser Arg Ser Tyr Val Ser Asp Ser Ser His Thr Thr Gly Lys Ser Ser
    50                  55                  60

His Ser Arg Tyr Ala Val Pro Ala Ser Pro Ser Lys Asp His Leu Phe
65                  70                  75                  80

Arg Val Ser Ser Thr Lys Phe Asp Gly Pro Ser Ile Leu Lys Arg Cys
                85                  90                  95

Gly Ser Asn Ala Asn Phe Arg Glu Ser Ile Asp Phe Asp Lys Val Lys
            100                 105                 110

Trp Gly Ser Asn Trp Leu Asp Arg Trp Met Glu Glu Ser Phe Leu Asn
        115                 120                 125

Asp His Gly Ser Asn Pro Pro Arg Ser Arg Asn Ala Asp Glu Lys
    130                 135                 140

Ser Asp Lys Ile Leu Glu Val Asp Thr Trp Lys Pro His Val Lys Ser
145                 150                 155                 160

Gln Gln Ser Asn Arg Thr Phe Gln Thr Ser Gln His Ala Leu Ala Ser
                165                 170                 175

Asp His Asn Asn Gln Ser Phe Met Thr Phe Asp Ser Met Ser Lys Leu
            180                 185                 190

Ser Lys Lys Glu Pro Asn Pro Met Pro Ser Ile Ser Ser Gly Glu Ile
        195                 200                 205

Leu Gln Ser Leu Lys Leu Pro Leu Gly Asn Asp Glu Ala Val Tyr Arg
    210                 215                 220

Thr Ala Glu Asn Ser Pro Arg Met Phe Ser Ala Thr Ser Arg Pro Gly
225                 230                 235                 240

Ser Ser Gly Arg Arg Gly Gly Pro Phe Thr Pro Thr Arg Ser Glu Cys
                245                 250                 255

Ser Trp Gly Phe Phe Asn Gly Tyr Ser Gly Tyr Pro Asn Tyr Met Ala
            260                 265                 270

Asn Thr Glu Ser Ser Arg Ala Lys Val Arg Ser Gln Ser Ala Pro Arg
        275                 280                 285

Gln Arg Leu Glu Phe Glu Lys Tyr Gly Ser Ser Arg Ser Val Gln
    290                 295                 300

Gly Tyr Ser Asp Ser Glu Thr Arg Ser Glu Arg Gly Phe Ala Gln Asn
305                 310                 315                 320

Thr Glu Leu Gln Asn Lys Ala Tyr Val Ala Ser Gly Tyr Leu Asn Arg
                325                 330                 335

Leu Gly Thr Ser Asp Leu Arg
            340
```

<210> SEQ ID NO 57
<211> LENGTH: 1646
<212> TYPE: DNA
<213> ORGANISM: Glycine max
<220> FEATURE:
<221> NAME/KEY: misc_feature
<223> OTHER INFORMATION: Ceres CLONE ID no.1641776
<220> FEATURE:
<221> NAME/KEY: misc_feature
<223> OTHER INFORMATION: Encodes the peptide sequence at SEQ ID NO 58

<400> SEQUENCE: 57

```
ctctctctca aaacccaaaa ctattcccctt gtgagaactg aggagacata ataatgggta      60
aggcgtcgaa gtggtttcgc gggcttcttg gtctcaaaaa acagagtat gccacctcac      120 ccgccaagcc tcccaaagag aaacgccggt ggagcttcgt taaatcatca tacacagaaa      180
aagacaacac cactgccgcc acgtgtccac cactaagaaa caacaacaac cacgcaatgg      240
cagtagcagc agccaccgct gcggtggccg aagcggcggt ggctgccgcc gaagcagccg      300
ccgtcgtggt gagactaact agtaacagcg gcaggtgcgc cgacggcgga cccacccgga      360
ttcgccaaca ttgggctgct gttaagattc aagccgcttt tcgtggctgt ttggcaagga      420
gagcactgcg agcattaaag ggattggtga agttgcaagc attggtgaga ggccacattg      480
agagaaaacg gacggcagag tggctgaaaa gattgcaagc actcttacat gcacagaccc      540
aagtttctgc agggttgacc ctgcatgcct caccttcgag ttcaaagtta tcaagccacc      600
tccaaggtcc agaaacaccc gaaaaatttg aaagccccat tagatctaag agcatgaaac      660
atgagcactc acctatactc aagagaaatg gctccaaatc ctgtgccctg atcaatggct      720
atcaagagat atgtgggagt agatcagaga gtcaagggaa tgaacaatta tggaactcag      780
gaagatcaat gaatagagca cacggctcca atgatgaaaa aaatggcaag gttcttgaag      840
ttgattctgg aaaaccgcac ttcacactaa agcgtcgaaa cctctcttac tccacaggct      900
ctgatcttta tagtaagagt ttgaacagca caaaggaatc aacatctctt caatctgctc      960
aaagtccatg ttgtgaggtt cagtctcaca gttacagctc gcaaaaagtg aacaatgagg     1020
ttgaggagag tccattctgc actgctgaca atagtccaca atacttatct gcctcttcta     1080
aagatgatgg cttcaaaaga agccctttta ctcctactag aagtgatggc tctagaagct     1140
acattcgcgg ttaccctgat tatcctagtt acatggcatg cactgaatct tcaaaggcaa     1200
aggccagatc tctgagtgca ccaaaacaaa ggcctcaaag tgagaggtct ggttcatcgg     1260
atagatactc actcaatgga tttgatatgt caagattggc cactcaaagg gcaatgcaag     1320
caagcttcac caacaaagca tatccaggtt ctggtcgttt ggacaagctt ggtatgcctg     1380
tggggtacag attctgattg agttatgttt atggtaagag ggttattttg tatctttat      1440 ttttcatagt cttaaagtct taatatctga tcttgctaac caaccggctg tactttgagc     1500
ttccattgcg attttgtgtc agcattagaa atctacaacc aaattaagtg catactgcta     1560
agtctcaact ttcaagtcat tttattactt ggataaactg tgtaaaagaa ttattatctt     1620
tgcctttcaa aaaaaaaaaa aaaaaa                                          1646
```

<210> SEQ ID NO 58
<211> LENGTH: 447
<212> TYPE: PRT
<213> ORGANISM: Glycine max
<220> FEATURE:
<221> NAME/KEY: misc_feature
<223> OTHER INFORMATION: Ceres CLONE ID no.1641776
<220> FEATURE:

<221> NAME/KEY: misc_feature
<223> OTHER INFORMATION: Score of 433.6 for HMM of FIGURE 2.
<220> FEATURE:
<221> NAME/KEY: misc_feature
<223> OTHER INFORMATION: Functional Homolog Of Ceres SEEDLINE ID no. ME06748 at SEQ ID NO. 41
<220> FEATURE:
<221> NAME/KEY: misc_feature
<222> LOCATION: (106)..(126)
<223> OTHER INFORMATION: Pfam Name: IQ Pfam Description: IQ calmodulin-binding motif

<400> SEQUENCE: 58

Met Gly Lys Ala Ser Lys Trp Phe Arg Gly Leu Leu Gly Leu Lys Lys
1 5 10 15

Thr Glu Tyr Ala Thr Ser Pro Ala Lys Pro Pro Lys Glu Lys Arg Arg
20 25 30

Trp Ser Phe Val Lys Ser Ser Tyr Thr Glu Lys Asp Asn Thr Thr Ala
35 40 45

Ala Thr Cys Pro Pro Leu Arg Asn Asn Asn Asn His Ala Met Ala Val
50 55 60

Ala Ala Ala Thr Ala Ala Val Ala Glu Ala Ala Val Ala Ala Ala Glu
65 70 75 80

Ala Ala Ala Val Val Val Arg Leu Thr Ser Asn Ser Gly Arg Cys Ala
85 90 95

Asp Gly Gly Pro Thr Arg Ile Arg Gln His Trp Ala Ala Val Lys Ile
100 105 110

Gln Ala Ala Phe Arg Gly Cys Leu Ala Arg Arg Ala Leu Arg Ala Leu
115 120 125

Lys Gly Leu Val Lys Leu Gln Ala Leu Val Arg Gly His Ile Glu Arg
130 135 140

Lys Arg Thr Ala Glu Trp Leu Lys Arg Leu Gln Ala Leu Leu His Ala
145 150 155 160

Gln Thr Gln Val Ser Ala Gly Leu Thr Leu His Ala Ser Pro Ser Ser
165 170 175

Ser Lys Leu Ser Ser His Leu Gln Gly Pro Glu Thr Pro Glu Lys Phe
180 185 190

Glu Ser Pro Ile Arg Ser Lys Ser Met Lys His Glu His Ser Pro Ile
195 200 205

Leu Lys Arg Asn Gly Ser Lys Ser Cys Ala Leu Ile Asn Gly Tyr Gln
210 215 220

Glu Ile Cys Gly Ser Arg Ser Glu Ser Gln Gly Asn Glu Gln Leu Trp
225 230 235 240

Asn Ser Gly Arg Ser Met Asn Arg Ala His Gly Ser Asn Asp Glu Arg
245 250 255

Asn Gly Lys Val Leu Glu Val Asp Ser Gly Lys Pro His Phe Thr Leu
260 265 270

Lys Arg Arg Asn Leu Ser Tyr Ser Thr Gly Ser Asp Leu Tyr Ser Lys
275 280 285

Ser Leu Asn Ser Thr Lys Glu Ser Thr Ser Leu Gln Ser Ala Gln Ser
290 295 300

Pro Cys Cys Glu Val Gln Ser His Ser Tyr Ser Ser Gln Lys Val Asn
305 310 315 320

Asn Glu Val Glu Glu Ser Pro Phe Cys Thr Ala Asp Asn Ser Pro Gln
325 330 335

Tyr Leu Ser Ala Ser Ser Lys Asp Asp Gly Phe Lys Arg Ser Pro Phe
340 345 350

-continued

```
Thr Pro Thr Arg Ser Asp Gly Ser Arg Ser Tyr Ile Arg Gly Tyr Pro
        355                 360                 365

Asp Tyr Pro Ser Tyr Met Ala Cys Thr Glu Ser Ser Lys Ala Lys Ala
    370                 375                 380

Arg Ser Leu Ser Ala Pro Lys Gln Arg Pro Gln Ser Glu Arg Ser Gly
385                 390                 395                 400

Ser Ser Asp Arg Tyr Ser Leu Asn Gly Phe Asp Met Ser Arg Leu Ala
                405                 410                 415

Thr Gln Arg Ala Met Gln Ala Ser Phe Thr Asn Lys Ala Tyr Pro Gly
            420                 425                 430

Ser Gly Arg Leu Asp Lys Leu Gly Met Pro Val Gly Tyr Arg Phe
        435                 440                 445
```

<210> SEQ ID NO 59
<211> LENGTH: 1434
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1438750
<220> FEATURE:
<221> NAME/KEY: misc_feature
<223> OTHER INFORMATION: Encodes the peptide sequence at SEQ ID NO 60

<400> SEQUENCE: 59

```
atgggcaaag cttccaaatg gttccgtgcc gttctcggat taaaaaaacc cgacccacca      60
ctagaccacc cccaaaccac tcgttctaaa gacaaacgga gatggagttt tgttaagtcc     120
cgccgtgaaa aagaccacga ccaccaacag cgacaacaag atattgaagc cagtaaaact     180
ggtgttctgt acgggcagga gtttgaggag gaccccaaca agcatgcggt cgctgtggct     240
gctgctaccg ctgcagtcgc ggaggctgct gttgcagcgg ctcaggcagc tgccgaggtt     300
gtgagactta cgagtagtgg gaggtgtgtt aataacagtg tcgcgaacgt tagcgggagt     360
cttggattac gtgaagacct cgctgctgtt aagattcaag ctgctttccg tggctacctg     420
gctaggagag cattacgggc gttaaaggca ttggtgagac ttcaagctct ggtaagaggt     480
cacattgaga ggaagcgaac tgcagagtgg cttcatcgaa tgcaagcttt gctgcgagcg     540
cagtctcgag cacgttctgg acgtgcccaa atttctgaat cttctcattc aagtagcaag     600
tcctctcgct ttcaacaccc tggtccgcca acccctgaaa aattcgagca tgccattcgt     660
gccaggagtg gaaaatatga acaatcatca atacttaaga gaactgggtc aaaatgtaaa     720
ggcagagcaa ttggtgatct agacgttgca cacttatcct taaattggtc agagcgtcgg     780
atggatgatc aaacatggga tcaccaagtc cctttggcag gaactggcac tattgatgat     840
gataagagtg acaagatcct tgagattgat actggaaaac ccacattacc cccaagcgt      900 agaaatctct tcactcttc tcacctttcc ctgtcagatc agtatagcca gtttcaca        960 actacaaaag actcgacagc ccatcaaact gttccaagtc cctcatcttg tgaagttcaa    1020
tctttaagtc cattgaagtt ttctcatgtt gtcgaagaag cattatgcac tgctgaaaat    1080
agcccacagt tctactctgc atcatcaagg ggtggtagta gtaagagaag tcccttcact    1140
cccagtagga gtgatggctc aagaaacttc ctaatcggtt attatggcta cccaaattat    1200
atgtgtaaca ctgaatcttc gagggctaag gcgagatctc ttagcgctcc aaaacaaaga    1260
ccccaatatg agagatccag ttcaaccagg agatactcgg ttctcgggtg tggtgagcca    1320
agatcgagta gtgcacagca tgcttctgcc ttgcgtgcaa gttttttcaag caaagcttac    1380
```
cctggatctg gtcgcttgga caagctggga atgcctattg ggcagggata ctaa    1434

<210> SEQ ID NO 60
<211> LENGTH: 477
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1438750
<220> FEATURE:
<221> NAME/KEY: misc_feature
<223> OTHER INFORMATION: Score of 852.9 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (126)..(146)
<223> OTHER INFORMATION: Pfam Name: IQ Pfam Description: IQ calmodulin-
      binding motif

<400> SEQUENCE: 60

Met Gly Lys Ala Ser Lys Trp Phe Arg Ala Val Leu Gly Leu Lys Lys
1               5                   10                  15

Pro Asp Pro Leu Asp His Pro Gln Thr Thr Arg Ser Lys Asp Lys
            20                  25                  30

Arg Arg Trp Ser Phe Val Lys Ser Arg Glu Lys Asp His Asp His
        35                  40                  45

Gln Gln Arg Gln Gln Asp Ile Glu Ala Ser Lys Thr Gly Val Leu Tyr
    50                  55                  60

Gly Gln Glu Phe Glu Glu Asp Pro Asn Lys His Ala Val Ala Val Ala
65                  70                  75                  80

Ala Ala Thr Ala Ala Val Ala Glu Ala Ala Val Ala Ala Ala Gln Ala
                85                  90                  95

Ala Ala Glu Val Val Arg Leu Thr Ser Ser Gly Arg Cys Val Asn Asn
            100                 105                 110

Ser Val Ala Asn Val Ser Gly Ser Leu Gly Leu Arg Glu Asp Leu Ala
        115                 120                 125

Ala Val Lys Ile Gln Ala Ala Phe Arg Gly Tyr Leu Ala Arg Arg Ala
    130                 135                 140

Leu Arg Ala Leu Lys Ala Leu Val Arg Leu Gln Ala Leu Val Arg Gly
145                 150                 155                 160

His Ile Glu Arg Lys Arg Thr Ala Glu Trp Leu His Arg Met Gln Ala
                165                 170                 175

Leu Leu Arg Ala Gln Ser Arg Ala Arg Ser Gly Arg Ala Gln Ile Ser
            180                 185                 190

Glu Ser Ser His Ser Ser Ser Lys Ser Ser Arg Phe Gln His Pro Gly
        195                 200                 205

Pro Pro Thr Pro Glu Lys Phe Glu His Ala Ile Arg Ala Arg Ser Gly
    210                 215                 220

Lys Tyr Glu Gln Ser Ser Ile Leu Lys Arg Thr Gly Ser Lys Cys Lys
225                 230                 235                 240

Gly Arg Ala Ile Gly Asp Leu Asp Val Ala His Leu Ser Leu Asn Trp
                245                 250                 255

Ser Glu Arg Arg Met Asp Asp Gln Thr Trp Asp His Gln Val Pro Leu
            260                 265                 270

Ala Gly Thr Gly Thr Ile Asp Asp Asp Lys Ser Asp Lys Ile Leu Glu
        275                 280                 285

```
Ile Asp Thr Gly Lys Pro His Ile Thr Pro Lys Arg Arg Asn Leu Phe
290                 295                 300
His Ser Ser His Leu Ser Leu Ser Asp Gln Tyr Ser His Ser Phe Thr
305                 310                 315                 320
Thr Thr Lys Asp Ser Thr Ala His Gln Thr Val Pro Ser Pro Ser Ser
                325                 330                 335
Cys Glu Val Gln Ser Leu Ser Pro Leu Lys Phe Ser His Val Val Glu
                340                 345                 350
Glu Ala Leu Cys Thr Ala Glu Asn Ser Pro Gln Phe Tyr Ser Ala Ser
                355                 360                 365
Ser Arg Gly Gly Ser Ser Lys Arg Ser Pro Phe Thr Pro Ser Arg Ser
370                 375                 380
Asp Gly Ser Arg Asn Phe Leu Ile Gly Tyr Tyr Gly Tyr Pro Asn Tyr
385                 390                 395                 400
Met Cys Asn Thr Glu Ser Ser Arg Ala Lys Ala Arg Ser Leu Ser Ala
                405                 410                 415
Pro Lys Gln Arg Pro Gln Tyr Glu Arg Ser Ser Ser Thr Arg Arg Tyr
                420                 425                 430
Ser Val Leu Gly Cys Gly Glu Pro Arg Ser Ser Ala Gln His Ala
                435                 440                 445
Ser Ala Leu Arg Ala Ser Phe Ser Ser Lys Ala Tyr Pro Gly Ser Gly
450                 455                 460
Arg Leu Asp Lys Leu Gly Met Pro Ile Gly Gln Gly Tyr
465                 470                 475

<210> SEQ ID NO 61
<211> LENGTH: 1431
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1447395
<220> FEATURE:
<221> NAME/KEY: misc_feature
<223> OTHER INFORMATION: Encodes the peptide sequence at SEQ ID NO 62

<400> SEQUENCE: 61
atgggtaaag cttccaaatg gttccgtgcc gttctcggcc tcaaaaaacc cgacccacca      60
ccagaccgcc ccgttacaac tcgttctaaa gaaaaaagga gatggagttt tgtcaagtcc     120
caccgtgaaa aagaccaaca ccatcaccaa cagcaacaac aagagacgga agccgttaaa     180
gcaggcgttt tgtacgggca ggagtttgag gaggacccaa acaagcatgc gatcgctgtg     240
gctgctgcta ctgctgcagt tgcggaggct gcagttgctg ccgcgcaggc agctgcagag     300
gtggtgcggt taacaagcag tgggaggtgt gttgataaca gtgttgcgta cgttagcggg     360
agtcctggct tacgtgaaga cttcgctgct gttaagatcg aagctgcttt tcgtggctac     420
ctggcaagga gagcgttaag agcattaaaa gcgttggtga ggcttcaggc actggtaaga     480
ggtcaccttg agaggaagcg aacagcagag tggcttcatc gaatgcaagc attgctgaga     540
gcgcaggctc gagcacgtgc aggacgtgcc caaatttctg aatcctccca ctcaagcagc     600
aagtcttctc gctatcacct ccctggtctg ccaacccatg aaaaatccga gcatgccatt     660
cgtgctacga gtggaaaata tgaacaatca tcaatgctta agagaactgg gtcaaaaact     720
aaaggcagag aaattgccga tcaagatgtt gcacacttat ccttcaattg gtcagaacat     780
ggaatggata gtagaaacatg ggatcatcaa gccccttcgc caggaactgg ccccattgat     840
gatgacaaga tccttgagat tgattctgga aaaccacata ttactcctaa acgcagaaat     900
```

```
ctctttcacc cttctcacct ttccttgtct gcggatcagt atagccatag tttcacaaca    960
tcaaaaggct ccacagtccg tcaagcagtt ccaagcccct catctggcga agttcaatct   1020
ttcagtccat tgaaattctc tcatgaggtt gaggaagcat tttgcaccgc tgataatagc   1080
ccgcaattct gctctgcatc atcaaggggg ggcagtggta agagaagtcc cttcactccc   1140
agtaggagtg gtggctctag aagcttcatg agtggatact ctgactaccc aaattatatg   1200
tgtaacactg aatcttcaag ggctaaggtg agatctctaa gcgctccaaa acaaagaccc   1260
cagtatgaga gatccagctc aaccaagaga tactcggttc tcggctttgg tgaacaaaga   1320
tcgagtagtg cacagagtgc ttctgccttg cgtgcaagtt ttacaagtaa agcttaccct   1380
ggatctggtc gtttggacag gctgggaatg cctgttgggc agaaatacta a            1431
```

<210> SEQ ID NO 62
<211> LENGTH: 476
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1447395
<220> FEATURE:
<221> NAME/KEY: misc_feature
<223> OTHER INFORMATION: Score of 696.6 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (149)..(169)
<223> OTHER INFORMATION: Pfam Name: IQ Pfam Description: IQ calmodulin-
      binding motif

<400> SEQUENCE: 62

Met Gly Lys Ala Ser Lys Trp Phe Arg Ala Val Leu Gly Leu Lys Lys
1               5                   10                  15

Pro Asp Pro Pro Asp Arg Pro Val Thr Thr Arg Ser Lys Glu Lys
            20                  25                  30

Arg Arg Trp Ser Phe Val Lys Ser His Arg Glu Lys Asp Gln His His
        35                  40                  45

His Gln Gln Gln Gln Glu Thr Glu Ala Val Lys Ala Gly Val Leu
    50                  55                  60

Tyr Gly Gln Glu Phe Glu Asp Pro Asn Lys His Ala Ile Ala Val
65                  70                  75                  80

Ala Ala Ala Thr Ala Ala Val Ala Glu Ala Val Ala Ala Ala Gln
                85                  90                  95

Ala Ala Ala Glu Val Val Arg Leu Thr Ser Ser Gly Arg Cys Val Asp
            100                 105                 110

Asn Ser Val Ala Tyr Val Ser Gly Ser Pro Gly Leu Arg Glu Asp Phe
        115                 120                 125

Ala Ala Val Lys Ile Glu Ala Ala Phe Arg Gly Tyr Leu Ala Arg Arg
    130                 135                 140

Ala Leu Arg Ala Leu Lys Ala Leu Val Arg Leu Gln Ala Leu Val Arg
145                 150                 155                 160

Gly His Leu Glu Arg Lys Arg Thr Ala Glu Trp Leu His Arg Met Gln
                165                 170                 175

Ala Leu Leu Arg Ala Gln Ala Arg Ala Arg Gly Arg Ala Gln Ile
            180                 185                 190

Ser Glu Ser Ser His Ser Ser Ser Lys Ser Ser Arg Tyr His Leu Pro

```
                195                 200                 205
Gly Leu Pro Thr His Glu Lys Ser Glu His Ala Ile Arg Ala Thr Ser
        210                 215                 220

Gly Lys Tyr Glu Gln Ser Ser Met Leu Lys Arg Thr Gly Ser Lys Thr
225                 230                 235                 240

Lys Gly Arg Glu Ile Ala Asp Gln Asp Val Ala His Leu Ser Phe Asn
                245                 250                 255

Trp Ser Glu His Gly Met Asp Ser Arg Thr Trp Asp His Gln Ala Pro
            260                 265                 270

Ser Pro Gly Thr Gly Pro Ile Asp Asp Lys Ile Leu Glu Ile Asp
        275                 280                 285

Ser Gly Lys Pro His Ile Thr Pro Lys Arg Arg Asn Leu Phe His Pro
    290                 295                 300

Ser His Leu Ser Leu Ser Ala Asp Gln Tyr Ser His Ser Phe Thr Thr
305                 310                 315                 320

Ser Lys Gly Ser Thr Val Arg Gln Ala Val Pro Ser Pro Ser Ser Gly
                325                 330                 335

Glu Val Gln Ser Phe Ser Pro Leu Lys Phe Ser His Glu Val Glu Glu
            340                 345                 350

Ala Phe Cys Thr Ala Asp Asn Ser Pro Gln Phe Cys Ser Ala Ser Ser
        355                 360                 365

Arg Gly Gly Ser Gly Lys Arg Ser Pro Phe Thr Pro Ser Arg Ser Gly
    370                 375                 380

Gly Ser Arg Ser Phe Met Ser Gly Tyr Ser Asp Tyr Pro Asn Tyr Met
385                 390                 395                 400

Cys Asn Thr Glu Ser Ser Arg Ala Lys Val Arg Ser Leu Ser Ala Pro
                405                 410                 415

Lys Gln Arg Pro Gln Tyr Glu Arg Ser Ser Thr Lys Arg Tyr Ser
            420                 425                 430

Val Leu Gly Phe Gly Glu Gln Arg Ser Ser Ala Gln Ser Ala Ser
        435                 440                 445

Ala Leu Arg Ala Ser Phe Thr Ser Lys Ala Tyr Pro Gly Ser Gly Arg
    450                 455                 460

Leu Asp Arg Leu Gly Met Pro Val Gly Gln Lys Tyr
465                 470                 475

<210> SEQ ID NO 63
<211> LENGTH: 484
<212> TYPE: PRT
<213> ORGANISM: Arabidopsis thaliana
<220> FEATURE:
<221> NAME/KEY: misc_feature
<223> OTHER INFORMATION: Public GI ID no.79482785
<220> FEATURE:
<221> NAME/KEY: misc_feature
<223> OTHER INFORMATION: Score of 311.2 for HMM of FIGURE 2.
<220> FEATURE:
<221> NAME/KEY: misc_feature
<223> OTHER INFORMATION: Functional Homolog Of Ceres SEEDLINE ID no.
     ME06748 at SEQ ID NO. 41
<220> FEATURE:
<221> NAME/KEY: misc_feature
<222> LOCATION: (167)..(187)
<223> OTHER INFORMATION: Pfam Name: IQ Pfam Description: IQ calmodulin-
     binding motif

<400> SEQUENCE: 63

Met Gly Lys Ala Ser Arg Trp Phe Arg Ser Leu Phe Gly Val Lys Lys
1               5                   10                  15
```

```
Pro Asp Pro Gly Tyr Pro Asp Leu Ser Val Glu Thr Pro Ser Arg Ser
            20                  25                  30

Thr Ser Ser Asn Leu Lys Arg Arg Trp Ser Phe Val Lys Ser Lys Arg
        35                  40                  45

Glu Lys Glu Ser Thr Pro Ile Asn Gln Val Pro His Thr Pro Ser Leu
    50                  55                  60

Pro Asn Ser Thr Pro Pro Pro Ser His His Gln Ser Ser Pro Arg
65              70                  75                  80

Arg Arg Arg Lys Gln Lys Pro Met Trp Glu Asp Glu Gly Ser Glu Asp
                85                  90                  95

Ser Asp Lys His Ala Ile Ala Val Ala Ala Thr Ala Ala Val Ala
            100                 105                 110

Glu Ala Ala Val Ala Ala Ala Asn Ala Ala Ala Ala Val Val Arg Leu
        115                 120                 125

Thr Ser Thr Ser Gly Arg Ser Thr Arg Ser Pro Val Lys Ala Arg Phe
    130                 135                 140

Ser Asp Gly Phe Asp Asp Val Val Ala His Gly Ser Lys Phe Tyr Gly
145                 150                 155                 160

His Gly Arg Asp Ser Cys Glu Leu Ala Val Ile Lys Ile Gln Ser Ile
                165                 170                 175

Phe Arg Gly Tyr Leu Ala Lys Arg Ala Leu Arg Ala Leu Lys Gly Leu
            180                 185                 190

Val Arg Leu Gln Ala Ile Val Arg Gly His Ile Glu Arg Lys Arg Met
        195                 200                 205

Ser Val His Leu Arg Arg Met His Ala Leu Val Arg Ala Gln Ala Arg
    210                 215                 220

Val Arg Ala Thr Arg Val Ile Val Thr Pro Glu Ser Ser Ser Ser Gln
225                 230                 235                 240

Ser Asn Asn Thr Lys Ser Ser His Phe Gln Asn Pro Gly Pro Pro Thr
                245                 250                 255

Pro Glu Lys Leu Glu His Ser Ile Ser Ser Arg Ser Ser Lys Leu Ala
            260                 265                 270

His Ser His Leu Phe Lys Arg Asn Gly Ser Lys Ala Ser Asp Asn Asn
        275                 280                 285

Arg Leu Tyr Pro Ala His Arg Glu Thr Phe Ser Ala Thr Asp Glu Glu
    290                 295                 300

Glu Lys Ile Leu Gln Ile Asp Arg Lys His Ile Ser Ser Tyr Thr Arg
305                 310                 315                 320

Arg Asn Arg Pro Asp Met Phe Tyr Ser Ser His Leu Ile Leu Asp Asn
                325                 330                 335

Ala Gly Leu Ser Glu Pro Val Phe Ala Thr Pro Phe Ser Pro Ser Ser
            340                 345                 350

Ser His Glu Glu Ile Thr Ser Gln Phe Cys Thr Ala Glu Asn Ser Pro
        355                 360                 365

Gln Leu Tyr Ser Ala Thr Ser Arg Ser Lys Arg Ser Ala Phe Thr Ala
    370                 375                 380

Ser Ser Ile Ala Pro Ser Asp Cys Thr Lys Ser Cys Cys Asp Gly Asp
385                 390                 395                 400

His Pro Ser Tyr Met Ala Cys Thr Glu Ser Ser Arg Ala Lys Ala Arg
                405                 410                 415

Ser Ala Ser Ala Pro Lys Ser Arg Pro Gln Leu Phe Tyr Glu Arg Pro
            420                 425                 430

Ser Ser Lys Arg Phe Gly Phe Val Asp Leu Pro Tyr Cys Gly Asp Thr
```

```
                       435                 440                 445

Lys Ser Gly Pro Gln Lys Gly Ser Ala Leu His Thr Ser Phe Met Asn
            450                 455                 460

Lys Ala Tyr Pro Gly Ser Gly Arg Leu Asp Arg Leu Gly Met Pro Ile
465                 470                 475                 480

Gly Tyr Arg Tyr

<210> SEQ ID NO 64
<211> LENGTH: 543
<212> TYPE: PRT
<213> ORGANISM: Arabidopsis thaliana
<220> FEATURE:
<221> NAME/KEY: misc_feature
<223> OTHER INFORMATION: Public GI ID no.3292832
<220> FEATURE:
<221> NAME/KEY: misc_feature
<223> OTHER INFORMATION: Score of 277.0 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (167)..(187)
<223> OTHER INFORMATION: Pfam Name: IQ Pfam Description: IQ calmodulin-
      binding motif

<400> SEQUENCE: 64

Met Gly Lys Ala Ser Arg Trp Phe Arg Ser Leu Phe Gly Val Lys Lys
1               5                   10                  15

Pro Asp Pro Gly Tyr Pro Asp Leu Ser Val Glu Thr Pro Ser Arg Ser
            20                  25                  30

Thr Ser Ser Asn Leu Lys Arg Arg Trp Ser Phe Val Lys Ser Lys Arg
        35                  40                  45

Glu Lys Glu Ser Thr Pro Ile Asn Gln Val Pro His Thr Pro Ser Leu
    50                  55                  60

Pro Asn Ser Thr Pro Pro Pro Ser His His Gln Ser Ser Pro Arg
65                  70                  75                  80

Arg Arg Arg Lys Gln Lys Pro Met Trp Glu Asp Glu Gly Ser Glu Asp
                85                  90                  95

Ser Asp Lys His Ala Ile Ala Val Ala Ala Thr Ala Ala Val Ala
            100                 105                 110

Glu Ala Ala Val Ala Ala Ala Asn Ala Ala Ala Val Val Arg Leu
        115                 120                 125

Thr Ser Thr Ser Gly Arg Ser Thr Arg Ser Pro Val Lys Ala Arg Phe
    130                 135                 140

Ser Asp Gly Phe Asp Asp Val Val Ala His Gly Ser Lys Phe Tyr Gly
145                 150                 155                 160

His Gly Arg Asp Ser Cys Glu Leu Ala Val Ile Lys Ile Gln Ser Ile
                165                 170                 175

Phe Arg Gly Tyr Leu Ala Lys Arg Ala Leu Arg Ala Leu Lys Gly Leu
            180                 185                 190

Val Arg Leu Gln Ala Ile Val Arg Gly His Ile Glu Arg Lys Arg Met
        195                 200                 205

Ser Val His Leu Arg Arg Met His Ala Leu Val Arg Ala Gln Ala Arg
    210                 215                 220

Val Arg Ala Thr Arg Val Ile Val Thr Pro Glu Ser Ser Ser Ser Gln
225                 230                 235                 240

Ser Asn Asn Thr Lys Ser Ser His Phe Gln Asn Pro Val Ser Leu Val
```

```
            245                 250                 255
Lys Phe Pro Met Ile Val Pro Phe Asn Leu Lys His Gly Pro Pro Thr
            260                 265                 270

Pro Glu Lys Leu Glu His Ser Ile Ser Ser Arg Ser Ser Lys Leu Ala
        275                 280                 285

His Ser His Leu Phe Lys Val Leu His Phe Gln Leu Leu Phe Val Ser
    290                 295                 300

Ser Val Phe Val Ala Cys Gly Pro Ile Ser Ser Lys Phe Gln Arg Leu
305                 310                 315                 320

Tyr Lys Leu Leu Thr Leu Leu Tyr Val Gln Asn Lys Ser Asn Leu Lys
                325                 330                 335

Asn Trp Asn Gly Ser Lys Ala Ser Asp Asn Asn Arg Leu Tyr Pro Ala
            340                 345                 350

His Arg Glu Thr Phe Ser Ala Thr Asp Glu Glu Lys Ile Leu Gln
        355                 360                 365

Ile Asp Arg Lys His Ile Ser Ser Tyr Thr Arg Arg Asn Arg Pro Asp
    370                 375                 380

Met Phe Tyr Ser Ser His Leu Ile Leu Asp Asn Ala Gly Leu Ser Glu
385                 390                 395                 400

Pro Val Phe Ala Thr Pro Phe Ser Pro Ser Ser His Glu Glu Ile
                405                 410                 415

Thr Ser Gln Phe Cys Thr Ala Glu Asn Ser Pro Gln Leu Tyr Ser Ala
            420                 425                 430

Thr Ser Arg Ser Lys Arg Ser Ala Phe Thr Ala Ser Ile Ala Pro
        435                 440                 445

Ser Asp Cys Thr Lys Ser Cys Cys Asp Gly Asp His Pro Ser Tyr Met
    450                 455                 460

Ala Cys Thr Glu Ser Ser Arg Ala Lys Ala Arg Ser Ala Ser Ala Pro
465                 470                 475                 480

Lys Ser Arg Pro Gln Leu Phe Tyr Glu Arg Pro Ser Ser Lys Arg Phe
                485                 490                 495

Gly Phe Val Asp Leu Pro Tyr Cys Gly Asp Thr Lys Ser Gly Pro Gln
            500                 505                 510

Lys Gly Ser Ala Leu His Thr Ser Phe Met Asn Lys Ala Tyr Pro Gly
        515                 520                 525

Ser Gly Arg Leu Asp Arg Leu Gly Met Pro Ile Gly Tyr Arg Tyr
    530                 535                 540
```

<210> SEQ ID NO 65
<211> LENGTH: 1799
<212> TYPE: DNA
<213> ORGANISM: Zea mays
<220> FEATURE:
<221> NAME/KEY: misc_feature
<223> OTHER INFORMATION: Ceres CLONE ID no.1559074
<220> FEATURE:
<221> NAME/KEY: misc_feature
<223> OTHER INFORMATION: Encodes the peptide sequence at SEQ ID NO 66

<400> SEQUENCE: 65

```
aagactctcc cagtcccttc ctctcctgct gcctttctct cttctcggtg aagcgtgtgt    60
tcatttcact gttttggttt catctcccgc tctttcttta ccccgtgctc cggccaagtg   120
ctggaaccaa gaaagcctca tggggcggcc ggccgacggg cggtagagag gcggagatgg   180
gctgggcgcc taggtggctg cgcgggctgc tcggcggcgg caggaaggcc gccgtgacga   240
agccggcgaa ggagaagaag ctctggggat tcgggaagtc cttccgggaa aaggaccccg   300
```

```
cgccagcgcc ggaacggcct cggacgcctt cggtgcagcc cacgcgacg cctcgccggg      360 ggtttgcggc ggcgccggat gaggcggacg acgagcagag caagcgtgct atcgctgtgg      420
ccgcggcgac ggcggcggtg cagaggccg ccgtcgctgc tgcccaggcg ccgccgccg       480 tggtgcggtt gacgagctcc ggccggtgcc caccgccggc cgccgcgaag cgggaggagt      540
gggcggctgt tcggatccag gccgctttcc gtggctacct ggcgaggcgg cgctgaagg       600 cgttgagggg gctggtgaag ctgcaggcgc tggtccgggg caacattgtg cggcggcagg      660
cggcggagac gctgcgatgc atgcacgcgc tcgtccgcgt ccaggcgcgc gcgcgcgcgt      720
gtcgcgcaat tcgctcgcag catgtcgcgg ctcatccgga tccgccaacg ccggagaagt      780
acgatcaggc gggtgccccc aggcacgccc gttccggctc tctgaaggca aactcttcca      840
agacgccggg cggcgagagg ctgggtaggg agaggtcgga tcttgcggg aggaactggc       900 tggaccgctg ggtggaggag aggtacacgg acgacgagaa gaacgccaag attctcgaag      960
tggacaacgg caagccaggg cggcacggtt ccaagcggcg cggcggcaac catcaccagt     1020
cgccgtgctc gacgatgacc tccgagcaga acagccggag ctacgcgacc atgccggagt     1080
cgccgtccaa ggactcgacg accgcgcagc agtccgtgcc gagcccgtcg tccgtgggca     1140
tggctgccga ggccctgagc ccgctgcgcg tgccagcgga catcgccgag ctctgcgaca     1200
gcccccagtt cttctcggcg acgtcgcggc ccggagctc caggagggg ggcgcgttca      1260 cgccggcggc caagagcgag tgctcgcgca gcctcttcgg cggctactcc gactgcccca     1320
actacatggc gaacacggag tcgttccgcg ccaaggcgcg ttcccagagc gcgcccaagc     1380
agaggccgca gcagcagtac gagaagtcgg gctccctccg cagggcgtcg cgcacgccc      1440 tcgcggcggg gccggcagcg gcacagaggt cggtggcctc gttgcacgcc atgaaggcgt     1500
atccgggctc cggcagattg gaccgacttg gcatgccggt caggtactga tccggatcct     1560
acctagctcg cttcaggata atgtggtgct gcgcctgaac tgattgatac ccagtgtctc     1620
aactcaagcg atgaggatga agtgaattct actagtggtc gttattagat cttgttcctt     1680
cggtggtgcc tattaccgtc aacagttttc tgtttgttgc tttgtgtagc gaagtgtaag     1740
ttgctggtac gtagctggta atactatgcg tgcttaaccg cgaaaaaaaa aaaaaaaa       1799
```

<210> SEQ ID NO 66
<211> LENGTH: 457
<212> TYPE: PRT
<213> ORGANISM: Zea mays
<220> FEATURE:
<221> NAME/KEY: misc_feature
<223> OTHER INFORMATION: Ceres CLONE ID no.1559074
<220> FEATURE:
<221> NAME/KEY: misc_feature
<223> OTHER INFORMATION: Score of 855.0 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41
<220> FEATURE:
<221> NAME/KEY: misc_feature
<222> LOCATION: (121)..(141)
<223> OTHER INFORMATION: Pfam Name: IQ Pfam Description: IQ calmodulin-
    binding motif

<400> SEQUENCE: 66

Met Gly Trp Ala Pro Arg Trp Leu Arg Gly Leu Leu Gly Gly Gly Arg
1               5                   10                  15

Lys Ala Ala Val Thr Lys Pro Ala Lys Glu Lys Lys Leu Trp Gly Phe
            20                  25                  30

-continued

Gly Lys Ser Phe Arg Glu Lys Asp Pro Ala Pro Ala Pro Glu Arg Pro
    35                  40                  45

Arg Thr Pro Ser Val Gln Pro Thr Ala Thr Pro Arg Arg Gly Phe Ala
    50                  55                  60

Ala Ala Pro Asp Glu Ala Asp Asp Glu Gln Ser Lys Arg Ala Ile Ala
65                  70                  75                  80

Val Ala Ala Ala Thr Ala Ala Val Ala Glu Ala Ala Val Ala Ala Ala
            85                  90                  95

Gln Ala Ala Ala Val Val Arg Leu Thr Ser Ser Gly Arg Cys Pro
            100                 105                 110

Pro Pro Ala Ala Ala Lys Arg Glu Glu Trp Ala Ala Val Arg Ile Gln
            115                 120                 125

Ala Ala Phe Arg Gly Tyr Leu Ala Arg Arg Ala Leu Lys Ala Leu Arg
            130                 135                 140

Gly Leu Val Lys Leu Gln Ala Leu Val Arg Gly Asn Ile Val Arg Arg
145                 150                 155                 160

Gln Ala Ala Glu Thr Leu Arg Cys Met His Ala Leu Val Arg Val Gln
                165                 170                 175

Ala Arg Ala Arg Ala Cys Arg Ala Ile Arg Ser Gln His Val Ala Ala
            180                 185                 190

His Pro Asp Pro Pro Thr Pro Glu Lys Tyr Asp Gln Ala Gly Ala Pro
            195                 200                 205

Arg His Ala Arg Ser Gly Ser Leu Lys Ala Asn Ser Ser Lys Thr Pro
    210                 215                 220

Gly Gly Glu Arg Leu Gly Arg Glu Arg Ser Glu Ser Cys Gly Arg Asn
225                 230                 235                 240

Trp Leu Asp Arg Trp Val Glu Glu Arg Tyr Thr Asp Asp Glu Lys Asn
                245                 250                 255

Ala Lys Ile Leu Glu Val Asp Asn Gly Lys Pro Gly Arg His Gly Ser
            260                 265                 270

Lys Arg Arg Gly Gly Asn His His Gln Ser Pro Cys Ser Thr Met Thr
    275                 280                 285

Ser Glu Gln Asn Ser Arg Ser Tyr Ala Thr Met Pro Glu Ser Pro Ser
    290                 295                 300

Lys Asp Ser Thr Thr Ala Gln Gln Ser Val Pro Ser Pro Ser Ser Val
305                 310                 315                 320

Gly Met Ala Ala Glu Ala Leu Ser Pro Leu Arg Val Pro Ala Asp Ile
            325                 330                 335

Ala Glu Leu Cys Asp Ser Pro Gln Phe Phe Ser Ala Thr Ser Arg Pro
            340                 345                 350

Gly Ser Ser Arg Arg Gly Gly Ala Phe Thr Pro Ala Ala Lys Ser Glu
            355                 360                 365

Cys Ser Arg Ser Leu Phe Gly Gly Tyr Ser Asp Cys Pro Asn Tyr Met
370                 375                 380

Ala Asn Thr Glu Ser Phe Arg Ala Lys Ala Arg Ser Gln Ser Ala Pro
385                 390                 395                 400

Lys Gln Arg Pro Gln Gln Gln Tyr Glu Lys Ser Gly Ser Leu Arg Arg
            405                 410                 415

Ala Ser Ala His Ala Leu Ala Ala Gly Pro Ala Ala Gln Arg Ser
            420                 425                 430

Val Ala Ser Leu His Ala Met Lys Ala Tyr Pro Gly Ser Gly Arg Leu
            435                 440                 445

Asp Arg Leu Gly Met Pro Val Arg Tyr
    450                 455

<210> SEQ ID NO 67
<211> LENGTH: 1821
<212> TYPE: DNA
<213> ORGANISM: Panicum virgatum
<220> FEATURE:
<221> NAME/KEY: misc_feature
<223> OTHER INFORMATION: Ceres CLONE ID no.1726548
<220> FEATURE:
<221> NAME/KEY: misc_feature
<223> OTHER INFORMATION: Encodes the peptide sequence at SEQ ID NO 68

<400> SEQUENCE: 67

| | | | | | |
|---|---|---|---|---|---|
| gtctagaccc | ttcctttctc | tcctgctgtc | ccttttgctc | ttctcggtgt | aagcgtgtgc | 60 |
| gcgtttcact | gctttggttt | catctcccgc | tctttctttc | ctccccactg | ctcctccggc | 120 |
| caagtgctgg | aacgaggaag | cctcatgcgg | ccgccggccg | gggagcggta | gagcgccgga | 180 |
| gatgggctgg | gcgcccaggt | ggctgcgcgg | gctgctcggc | ggcggcaaca | aggccgccga | 240 |
| gacgaagccc | gtgaaggaaa | agaggcgctg | ggggttcggg | aagtccttca | gggagaaggc | 300 |
| gccggcgccg | gtggcggcgc | ggcctccgac | gccgccggtg | cagcccacgg | cgacgcctcg | 360 |
| ccggggctac | gcgccggcgc | cggacgaggc | ggacgacgag | cagagcaagc | gcgccatcgc | 420 |
| ggtggccgcg | gccactgcgg | cggttgcgga | ggccgccgta | gccgcggcgc | aggcggccgc | 480 |
| cgccgtggtg | cggctgacga | gcagcgggcg | gtgcgcgccg | gccgccgcca | agcgggagga | 540 |
| gtgggcggct | gttcggatcc | aggccgcttt | ccgtggatac | ctggcgaggc | gggcgctcaa | 600 |
| ggcgctgcgg | gggctggtga | agctgcaggc | gctggttcgg | ggcaacatcg | tgcggcggca | 660 |
| ggcggcggag | acgctgcggt | gcatgcacgc | gctcgtccgc | gtccaggcgc | gcgcccgcgc | 720 |
| ctgccgcgca | attcgctcgc | agcaggtccc | ggctcaccca | gatccgccga | cgccggagaa | 780 |
| gtacgatcag | gcgggtgccc | ccaggcacgg | gcgttccggc | tctctaaagg | ggagctcgtc | 840 |
| gaagacaccg | ggcagcgaga | ggctgggcag | ggagaggtcg | gaatcttgcg | ggaggaactg | 900 |
| gctggaccgg | tgggtggagg | agaggtacat | ggacgacgag | aagaacgcca | agatcctgga | 960 |
| ggtggacaac | ggcaagccag | gcggtatgc | ttccaagagg | cgcggcggcg | gcggcaacca | 1020 |
| gcaccagtcg | ccgtgctcga | cgatgacgtc | cgaccagaac | agccggagct | acgcgaccat | 1080 |
| gccggagtcg | acgaccgcgc | agcggtccgt | gccgagcccg | ccgtcggtgg | catgggcga | 1140 |
| ggccctgagc | ccgctccgcc | tgcccgtgga | cattgccgag | ctctgcgaca | gcccacagtt | 1200 |
| cttctcggcg | tcgtctcggc | cggggagctc | ccggcggggg | cccttcaccc | cgagcaagag | 1260 |
| cgagtgctcc | cgcagcctct | tcgggggcta | ctccgactac | cccaactaca | tggccaacac | 1320 |
| ggagtcgttc | cgcgccaagg | cgcgctccca | gagcgcgccc | aagcagaggc | cgcactacga | 1380 |
| caagtccagc | tccctccgca | aggcgtcggc | ggcgcaggcc | tacttgacgg | ggccgtgcgc | 1440 |
| gccgacggcg | cagcagaggt | cggcggcctc | gctgacgcc | aagttcacca | acaaggcgta | 1500 |
| cccgggctct | ggcaggctgg | atcgactcgg | catgcccgtc | aagtactgat | cctgttatgt | 1560 |
| tatcctacca | aagttgcttt | ctggagtggt | gttgcttctt | gagcgatcag | tgtctcagct | 1620 |
| ctcgagcaag | gtcgatgaag | taaaatctag | tagtggtcgt | taggcttttg | tgtgccttcc | 1680 |
| tggtgctgtt | accctcgaca | gttttctgtt | tcttgctttt | taatagcgaa | gtgtaagttg | 1740 |
| gtagtagctg | cactgtaata | ctatctgtgc | tttaacagtt | taactgctaa | gtgctaactc | 1800 |
| caaaaaaaaa | aaaaaaaaaa | a | | | | 1821 |

```
<210> SEQ ID NO 68
<211> LENGTH: 455
<212> TYPE: PRT
<213> ORGANISM: Panicum virgatum
<220> FEATURE:
<221> NAME/KEY: misc_feature
<223> OTHER INFORMATION: Ceres CLONE ID no.1726548
<220> FEATURE:
<221> NAME/KEY: misc_feature
<223> OTHER INFORMATION: Score of 892.2 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (120)..(140)
<223> OTHER INFORMATION: Pfam Name: IQ Pfam Description: IQ calmodulin-
      binding motif

<400> SEQUENCE: 68

Met Gly Trp Ala Pro Arg Trp Leu Arg Gly Leu Leu Gly Gly Gly Asn
1               5                   10                  15

Lys Ala Ala Glu Thr Lys Pro Val Lys Glu Lys Arg Arg Trp Gly Phe
            20                  25                  30

Gly Lys Ser Phe Arg Glu Lys Ala Pro Ala Pro Val Ala Ala Arg Pro
        35                  40                  45

Pro Thr Pro Pro Val Gln Pro Thr Ala Thr Pro Arg Arg Gly Tyr Ala
    50                  55                  60

Pro Ala Pro Asp Glu Ala Asp Asp Glu Gln Ser Lys Arg Ala Ile Ala
65                  70                  75                  80

Val Ala Ala Thr Ala Ala Val Ala Glu Ala Ala Val Ala Ala Ala
                85                  90                  95

Gln Ala Ala Ala Val Val Arg Leu Thr Ser Ser Gly Arg Cys Ala
            100                 105                 110

Pro Ala Ala Ala Lys Arg Glu Glu Trp Ala Ala Val Arg Ile Gln Ala
        115                 120                 125

Ala Phe Arg Gly Tyr Leu Ala Arg Arg Ala Leu Lys Ala Leu Arg Gly
    130                 135                 140

Leu Val Lys Leu Gln Ala Leu Val Arg Gly Asn Ile Val Arg Arg Gln
145                 150                 155                 160

Ala Ala Glu Thr Leu Arg Cys Met His Ala Leu Val Arg Val Gln Ala
                165                 170                 175

Arg Ala Arg Ala Cys Arg Ala Ile Arg Ser Gln Gln Val Pro Ala His
            180                 185                 190

Pro Asp Pro Pro Thr Pro Glu Lys Tyr Asp Gln Ala Gly Ala Pro Arg
        195                 200                 205

His Gly Arg Ser Gly Ser Leu Lys Gly Ser Ser Lys Thr Pro Gly
    210                 215                 220

Ser Glu Arg Leu Gly Arg Glu Arg Ser Glu Ser Cys Gly Arg Asn Trp
225                 230                 235                 240

Leu Asp Arg Trp Val Glu Glu Arg Tyr Met Asp Asp Glu Lys Asn Ala
                245                 250                 255

Lys Ile Leu Glu Val Asp Asn Gly Lys Pro Gly Arg Tyr Ala Ser Lys
            260                 265                 270

Arg Arg Gly Gly Gly Gly Asn Gln His Gln Ser Pro Cys Ser Thr Met
        275                 280                 285

Thr Ser Asp Gln Asn Ser Arg Ser Tyr Ala Thr Met Pro Glu Ser Thr
    290                 295                 300
```

Thr Ala Gln Arg Ser Val Pro Ser Pro Pro Ser Val Gly Met Gly Glu
305                 310                 315                 320

Ala Leu Ser Pro Leu Arg Leu Pro Val Asp Ile Ala Glu Leu Cys Asp
                325                 330                 335

Ser Pro Gln Phe Phe Ser Ala Ser Ser Arg Pro Gly Ser Ser Arg Arg
            340                 345                 350

Gly Pro Phe Thr Pro Ser Lys Ser Glu Cys Ser Arg Ser Leu Phe Gly
        355                 360                 365

Gly Tyr Ser Asp Tyr Pro Asn Tyr Met Ala Asn Thr Glu Ser Phe Arg
    370                 375                 380

Ala Lys Ala Arg Ser Gln Ser Ala Pro Lys Gln Arg Pro His Tyr Asp
385                 390                 395                 400

Lys Ser Ser Ser Leu Arg Lys Ala Ser Ala Gln Ala Tyr Leu Thr
                405                 410                 415

Gly Pro Cys Ala Pro Thr Ala Gln Gln Arg Ser Ala Ala Ser Leu His
                420                 425                 430

Ala Lys Phe Thr Asn Lys Ala Tyr Pro Gly Ser Gly Arg Leu Asp Arg
                435                 440                 445

Leu Gly Met Pro Val Lys Tyr
    450                 455

<210> SEQ ID NO 69
<211> LENGTH: 464
<212> TYPE: PRT
<213> ORGANISM: Oryza sativa subsp. japonica
<220> FEATURE:
<221> NAME/KEY: misc_feature
<223> OTHER INFORMATION: Public GI ID no.115459996
<220> FEATURE:
<221> NAME/KEY: misc_feature
<223> OTHER INFORMATION: Score of 886.1 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (124)..(144)
<223> OTHER INFORMATION: Pfam Name: IQ Pfam Description: IQ calmodulin-
      binding motif

<400> SEQUENCE: 69

Met Gly Trp Ala Ser Arg Trp Leu Arg Gly Leu Leu Gly Gly Gly Lys
1               5                   10                  15

Lys Pro Asn Ser Gly Ser Gly Asp Pro Lys Pro Ala Arg Glu Lys Lys
                20                  25                  30

Arg Trp Gly Phe Gly Lys Ser Phe Arg Glu Lys Ser Pro Ala His Pro
            35                  40                  45

Pro Pro Pro Pro Pro Ser Ala Ala Val Gln Arg Ala Val Thr Pro
        50                  55                  60

Arg Arg Ala Tyr Thr Ala Ser Asp Glu Gly Asp Asp Glu Gln Ser Lys
65                  70                  75                  80

Arg Ala Ile Ala Val Ala Ala Thr Ala Ala Val Ala Glu Ala Ala
                85                  90                  95

Val Ala Ala Ala Gln Ala Ala Ala Val Val Arg Leu Thr Ser Ser
                100                 105                 110

Gly Arg Cys Ala Pro Ala Ala Ala Lys Arg Glu Glu Tyr Ala Ala Val
            115                 120                 125

Arg Ile Gln Ala Ala Phe Arg Gly Tyr Leu Ala Arg Arg Ala Leu Lys

```
                    130                 135                 140
Ala Leu Arg Gly Leu Val Lys Leu Gln Ala Leu Val Arg Gly Asn Ile
145                 150                 155                 160

Val Arg Arg Gln Ala Ala Glu Thr Leu Arg Cys Met His Ala Leu Val
            165                 170                 175

Arg Val Gln Arg Arg Ala Arg Ala Cys Arg Ala Ile Arg Ser Gln His
        180                 185                 190

Val Ser Ala His Pro Gly Pro Thr Pro Glu Lys Tyr Asp Gln Ala
    195                 200                 205

Thr His Glu Gly Val Pro Lys His Gly Arg Ser Gly Ser Leu Lys Gly
210                 215                 220

Ser Ser Ser Lys Thr Pro Gly Ser Glu Arg Leu Thr Arg Glu Arg Ser
225                 230                 235                 240

Glu Ser Cys Gly Arg Asn Trp Leu Asp Lys Trp Val Glu Glu Arg Tyr
            245                 250                 255

Leu Asp Asp Glu Lys Asn Ala Lys Ile Leu Glu Val Asp Thr Gly Lys
        260                 265                 270

Pro Gly Arg His Ala Ser Arg Arg Ser Gly Ser His His His His
    275                 280                 285

Ser Ser Cys Ser Ser Met Thr Ser Glu Gln Lys Ser Arg Ser Tyr Ala
290                 295                 300

Thr Met Pro Glu Ser Pro Ser Lys Asp Ser Thr Thr Ala Gln Gln Ser
305                 310                 315                 320

Val Pro Ser Pro Pro Ser Val Gly Met Ala Glu Ala Leu Ser Pro Leu
            325                 330                 335

Leu Met Ala Val Asp Ile Ala Glu Leu Cys Asp Ser Pro Gln Phe Phe
        340                 345                 350

Ser Ala Thr Ser Arg Pro Gly Ser Ser Arg Ser Arg Ala Phe Thr Pro
    355                 360                 365

Thr Lys Ser Glu Cys Ser Arg Ser Leu Phe Gly Gly Tyr Ser Asp Tyr
370                 375                 380

Pro Asn Tyr Met Ala Asn Thr Glu Ser Phe Arg Ala Lys Ala Arg Ser
385                 390                 395                 400

Gln Ser Ala Pro Lys Gln Arg Pro Gln Tyr Glu Lys Ser Ser Ser Leu
            405                 410                 415

Arg Lys Ala Ser Ala His Ala Phe Gly Pro Gly Ser Cys Ala Pro Val
        420                 425                 430

Ala Gln Arg Thr Thr Ala Ser Leu His Ser Lys Phe Thr Asn Lys Ala
    435                 440                 445

Tyr Pro Gly Ser Gly Arg Leu Asp Arg Leu Gly Met Pro Val Lys Tyr
450                 455                 460

<210> SEQ ID NO 70
<211> LENGTH: 1736
<212> TYPE: DNA
<213> ORGANISM: Triticum aestivum
<220> FEATURE:
<221> NAME/KEY: misc_feature
<223> OTHER INFORMATION: Ceres CLONE ID no.697034
<220> FEATURE:
<221> NAME/KEY: misc_feature
<223> OTHER INFORMATION: Encodes the peptide sequence at SEQ ID NO 71

<400> SEQUENCE: 70
gcctagactc ttcgtctccg tcctgcacct ttttcttctc tggcaagcct gtgcctgtgc    60
gcgtcgcgcc gttttgggtt tcatctcccg ctctttcttc ctcctccctg ctccggccaa   120
```

```
gtgctggaac caagagaagg cgatgggggc ggcggcggag gagcagtagc cggagggagg    180 ggatgggtg  ggcttcaagg tggctccgcg ggctgcttgg cggcggcaag aaggccggtc    240
ccgcctccgg cgagcacaag ccggagaggg agaagaagcg ctgggcttc  ggcaagtcct    300 tccgggagaa ggacccggtg cgtccaccga cgcctcctgt gcagcgggcg cgacgcccc    360 gccgcaccta cgcgacgtcg gatgacggcg gcgacgagca gaacaaacgc gctatcgccg    420
tggcggcggc gacggcggct gtggccgagg ccgccgttgc cgcggcgcag gcggccgccg    480
ccgtggtgcg gctgacgagc agcgggcggt gcccgccggc cggggcgaag catgaggagt    540
gggcggccgt ccggatccag gccgcttttcc gtggctacct ggcgaggcgc gcactgaagg    600
cgctccgcgg gctggtgaag ctgcaggcgc tggtccgcgg caacatcgtc cggcggcagg    660
cggccgagac gctccggtgc atgcaggcgc tcgtcagcgt gcagtcccgc gcgcgcgcca    720
gccgcgcaac ccgatcccgc caggccgcgg cacacccggg cgcgacgacg ccggagaagt    780
acgagcaggc ggcatacgat ggcgcgctca ggcacgccgc ttcaggctca ctcaagggag    840
gctcgtcaaa gacaccgggc agcgagagga tgagcaggga gaggtcagaa tcttgcggga    900
ggaactggct ggatcggtgg gtggaggaga ggtacatgga tgacgagaag aacgccaaga    960
ttctcgaggt ggaccccggc aagcccggcc ggcacgcttc caagaggcga agcagcggcg   1020
gcggccacca ccagtcgtcg tgctcaacca ggacatcaga gcagaacagc cggagctacg   1080
cgacgatgcc ggactcgccg tccagggact cgacgacggc gcagcagtcc gtgcccagcc   1140
cgtcgtcggt gggcatgggc gcgggcgagg ccctcagccc gctgcacatg ccggcagacc   1200
tcgcggcgga gctgtacgag agcccgcagt tcttctcggc gacgtcgcgg ccggggagct   1260
cgaagcgggg cgccttcttc acgccgacca agagcgagtg cgcgcgcagc ctcttcggcg   1320
gctactccga ctaccccaac tacatgtcca acacggagtc gttccgggcc aaggcgcggt   1380
cgcagagcgc gcccaagcag cggccgctgt acgagaagtc cgggtccctc cggaaggcgt   1440
cggcacacgc cttcgcgccg gggcagaggt cgtcggcgtc ggcgtccctg cacgccaggt   1500
tcaccaataa ggcgtaccct ggctccggca ggctggaccg gctgggcatg cctgtcaagt   1560 actgaacccct gccgccatgt gaccagtgtt aggtttgagc ttttgtgatg ctattaccgt   1620
cagaaagtac tttcctgtta ttgactgtga cttgttaagt gtaagttgct actgtactgg   1680
tgttcccgca aaaaaagtg  taagttgcta gtaatcaccc aaaaaaaaaa aaaaaa       1736
```

<210> SEQ ID NO 71
<211> LENGTH: 460
<212> TYPE: PRT
<213> ORGANISM: Triticum aestivum
<220> FEATURE:
<221> NAME/KEY: misc_feature
<223> OTHER INFORMATION: Ceres CLONE ID no.697034
<220> FEATURE:
<221> NAME/KEY: misc_feature
<223> OTHER INFORMATION: Score of 750.1 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (119)..(139)
<223> OTHER INFORMATION: Pfam Name: IQ Pfam Description: IQ calmodulin-
      binding motif

<400> SEQUENCE: 71

Met Gly Trp Ala Ser Arg Trp Leu Arg Gly Leu Leu Gly Gly Gly Lys

-continued

```
1               5                    10                   15
Lys Ala Gly Pro Ala Ser Gly Glu His Lys Pro Glu Arg Glu Lys Lys
                20                  25                  30
Arg Trp Gly Phe Gly Lys Ser Phe Arg Glu Lys Asp Pro Val Arg Pro
                35                  40                  45
Pro Thr Pro Pro Val Gln Arg Ala Ala Thr Pro Arg Arg Thr Tyr Ala
 50                 55                  60
Thr Ser Asp Asp Gly Gly Asp Glu Gln Asn Lys Arg Ala Ile Ala Val
 65                 70                  75                  80
Ala Ala Ala Thr Ala Ala Val Ala Glu Ala Ala Val Ala Ala Ala Gln
                85                  90                  95
Ala Ala Ala Ala Val Val Arg Leu Thr Ser Gly Arg Cys Pro Pro
                100                 105                 110
Ala Gly Ala Lys His Glu Glu Trp Ala Ala Val Arg Ile Gln Ala Ala
                115                 120                 125
Phe Arg Gly Tyr Leu Ala Arg Arg Ala Leu Lys Ala Leu Arg Gly Leu
                130                 135                 140
Val Lys Leu Gln Ala Leu Val Arg Gly Asn Ile Val Arg Arg Gln Ala
 145                150                 155                 160
Ala Glu Thr Leu Arg Cys Met Gln Ala Leu Val Ser Val Gln Ser Arg
                165                 170                 175
Ala Arg Ala Ser Arg Ala Thr Arg Ser Arg Gln Ala Ala His Pro
                180                 185                 190
Gly Ala Thr Thr Pro Glu Lys Tyr Glu Gln Ala Ala Tyr Asp Gly Ala
                195                 200                 205
Leu Arg His Gly Arg Ser Gly Ser Leu Lys Gly Gly Ser Ser Lys Thr
 210                215                 220
Pro Gly Ser Glu Arg Met Ser Arg Glu Arg Ser Glu Ser Cys Gly Arg
 225                230                 235                 240
Asn Trp Leu Asp Arg Trp Val Glu Glu Arg Tyr Met Asp Asp Glu Lys
                245                 250                 255
Asn Ala Lys Ile Leu Glu Val Asp Pro Gly Lys Pro Gly Arg His Ala
                260                 265                 270
Ser Lys Arg Arg Ser Ser Gly Gly His His Gln Ser Ser Cys Ser
                275                 280                 285
Thr Arg Thr Ser Glu Gln Asn Ser Arg Ser Tyr Ala Thr Met Pro Asp
                290                 295                 300
Ser Pro Ser Arg Asp Ser Thr Thr Ala Gln Gln Ser Val Pro Ser Pro
 305                310                 315                 320
Ser Ser Val Gly Met Gly Ala Gly Glu Ala Leu Ser Pro Leu His Met
                325                 330                 335
Pro Ala Asp Leu Ala Ala Glu Leu Tyr Glu Ser Pro Gln Phe Phe Ser
                340                 345                 350
Ala Thr Ser Arg Pro Gly Ser Ser Lys Arg Gly Ala Phe Phe Thr Pro
                355                 360                 365
Thr Lys Ser Glu Cys Ala Arg Ser Leu Phe Gly Gly Tyr Ser Asp Tyr
                370                 375                 380
Pro Asn Tyr Met Ser Asn Thr Glu Ser Phe Arg Ala Lys Ala Arg Ser
 385                390                 395                 400
Gln Ser Ala Pro Lys Gln Arg Pro Leu Tyr Glu Lys Ser Gly Ser Leu
                405                 410                 415
Arg Lys Ala Ser Ala His Ala Phe Ala Pro Gly Gln Arg Ser Ser Ala
                420                 425                 430
```

Ser Ala Ser Leu His Ala Arg Phe Thr Asn Lys Ala Tyr Pro Gly Ser
        435                 440                 445

Gly Arg Leu Asp Arg Leu Gly Met Pro Val Lys Tyr
    450                 455                 460

<210> SEQ ID NO 72
<211> LENGTH: 1433
<212> TYPE: DNA
<213> ORGANISM: Zea mays
<220> FEATURE:
<221> NAME/KEY: misc_feature
<223> OTHER INFORMATION: Ceres CLONE ID no.353438
<220> FEATURE:
<221> NAME/KEY: misc_feature
<223> OTHER INFORMATION: Encodes the peptide sequence at SEQ ID NO 73

<400> SEQUENCE: 72
atgatgtgta acctacgagc tgctctggta accgcttccc ctccagcaag gagaacgcca      60
ccttgtggcg tcagctctgc cgtcgtcttt actgcctgcg ccttccaggc ttcttcgttt     120
caggaagcaa ggcgaggcgg gcgctgaagg cgttgcgggg gctggtgaag ctgcaggcgc     180
tggtccgggg caacatcgtg cggcggcagg cggcggagac gctgcgatgc atgcacgcgc     240
tcgtccgcgt ccaggcgcgc gcgcgcgcct gccgcgcaat tcgctcgcag catgtcacgg     300
cgcatccgga cccgccgacg ccggagaagt acgagcaggc gggtgcggcc aggcacggcc     360
gttccggctc tctgaaggcg aactcttcga ggacaccggg cggcgagagg ctgggcaggg     420
agaggtcgga atcctgcggg aggaactggc tggaccgctg ggtggaggag aggtacatgg     480
acgacgagaa gaacgccaag attctcgagg tggacaacgg caagccaggg cgccggtatg     540
cttccaagag gcgcggcggc ggcggcgtcg gcggaaacca ccaccaccag caccaccagt     600
cgccgtgctc gacgacgatg ggctccgagc agaacagccg gagctacgcg accatgccgg     660
agtcgccgtc caaggactcg acgaccgcgc agcagtcggt gccgagcccg ccgtcggtgg     720
gcatggccga ggaggaggcc ctgagcccgc tgcgcgtgcc cgtgcccgcg gacgtggccg     780
agctctgcga cagcccccag ttcttctcgg ccacgtcgtc gcggcccggg agctcgaggc     840
ggggcccgtt cacgccgacg gccaagagcg agtgctcgcg cagcctcttc ggcggctact     900
ccgactaccc gaactacatg gccaacacgg agtcgttccg cgccaaggcg cggtcgcaga     960
gcgcgccgaa gcagaggccg cagtacgagc ggtccagctc cctacgcagg gcgtcggcgg    1020
cgcagaggtc ggcggcggcg gcggcctcct ccctgcacgc caagttcacc aacaaggcgt    1080 accccgggctc tggcaggctg gatcggcttg gcttgccggc caggtactga tactgagcct    1140
gcctaattcg cgtcaggatg atgtgctgcc gctgtgtctc gagcgaggag gacgacgacg    1200
aagaagtgca atcgactagt ggtagttagg ttccgccgtg ccttggttgt gctattacca    1260
tcaacagttt tttctgtttc ttgctttgtg tagctagcca tgtctaaagt tgctggtagc    1320
tgtaatgatg ctataatgcg tgcttaactg ctgacgaacc ttttcctct acatttccgt    1380 ggtatatata tatgtgccgt caaatcatgc atgggaattg aatgtgttgt tgc           1433

<210> SEQ ID NO 73
<211> LENGTH: 299
<212> TYPE: PRT
<213> ORGANISM: Zea mays
<220> FEATURE:
<221> NAME/KEY: misc_feature
<223> OTHER INFORMATION: Ceres CLONE ID no.353438
<220> FEATURE:
<221> NAME/KEY: misc_feature
<223> OTHER INFORMATION: Score of 204.3 for HMM of FIGURE 2.
<220> FEATURE:
<221> NAME/KEY: misc_feature
<223> OTHER INFORMATION: Functional Homolog Of Ceres SEEDLINE ID no.
ME06748 at SEQ ID NO. 41

<400> SEQUENCE: 73

Met His Ala Leu Val Arg Val Gln Ala Arg Ala Arg Ala Cys Arg Ala
1               5                   10                  15

Ile Arg Ser Gln His Val Thr Ala His Pro Asp Pro Thr Pro Glu
            20                  25                  30

Lys Tyr Glu Gln Ala Gly Ala Ala Arg His Gly Arg Ser Gly Ser Leu
        35                  40                  45

Lys Ala Asn Ser Ser Arg Thr Pro Gly Gly Glu Arg Leu Gly Arg Glu
50                  55                  60

Arg Ser Glu Ser Cys Gly Arg Asn Trp Leu Asp Arg Trp Val Glu Glu
65                  70                  75                  80

Arg Tyr Met Asp Asp Glu Lys Asn Ala Lys Ile Leu Glu Val Asp Asn
                85                  90                  95

Gly Lys Pro Gly Arg Arg Tyr Ala Ser Lys Arg Gly Gly Gly Gly
            100                 105                 110

Val Gly Gly Asn His His Gln His His Gln Ser Pro Cys Ser Thr
        115                 120                 125

Thr Met Gly Ser Glu Gln Asn Ser Arg Ser Tyr Ala Thr Met Pro Glu
130                 135                 140

Ser Pro Ser Lys Asp Ser Thr Thr Ala Gln Gln Ser Val Pro Ser Pro
145                 150                 155                 160

Pro Ser Val Gly Met Ala Glu Glu Ala Leu Ser Pro Leu Arg Val
            165                 170                 175

Pro Val Pro Ala Asp Val Ala Glu Leu Cys Asp Ser Pro Gln Phe Phe
        180                 185                 190

Ser Ala Thr Ser Ser Arg Pro Gly Ser Ser Arg Arg Gly Pro Phe Thr
    195                 200                 205

Pro Thr Ala Lys Ser Glu Cys Ser Arg Ser Leu Phe Gly Gly Tyr Ser
210                 215                 220

Asp Tyr Pro Asn Tyr Met Ala Asn Thr Glu Ser Phe Arg Ala Lys Ala
225                 230                 235                 240

Arg Ser Gln Ser Ala Pro Lys Gln Arg Pro Gln Tyr Glu Arg Ser Ser
                245                 250                 255

Ser Leu Arg Arg Ala Ser Ala Ala Gln Arg Ser Ala Ala Ala Ala
            260                 265                 270

Ser Ser Leu His Ala Lys Phe Thr Asn Lys Ala Tyr Pro Gly Ser Gly
        275                 280                 285

Arg Leu Asp Arg Leu Gly Leu Pro Ala Arg Tyr
    290                 295

<210> SEQ ID NO 74
<211> LENGTH: 499
<212> TYPE: PRT
<213> ORGANISM: Oryza sativa subsp. japonica
<220> FEATURE:
<221> NAME/KEY: misc_feature
<223> OTHER INFORMATION: Public GI ID no.125593074
<220> FEATURE:
<221> NAME/KEY: misc_feature
<223> OTHER INFORMATION: Score of 112.2 for HMM of FIGURE 2.
<220> FEATURE:
<221> NAME/KEY: misc_feature
<223> OTHER INFORMATION: Functional Homolog Of Ceres SEEDLINE ID no.

-continued

```
        ME06748 at SEQ ID NO. 41
<220> FEATURE:
<221> NAME/KEY: misc_feature
<222> LOCATION: (134)..(154)
<223> OTHER INFORMATION: Pfam Name: IQ Pfam Description: IQ calmodulin-
      binding motif

<400> SEQUENCE: 74

Met Gly Lys Ala Ala Arg Trp Phe Arg Asn Met Trp Gly Gly Gly Arg
1               5                   10                  15

Lys Glu Gln Lys Gly Glu Ala Pro Ser Gly Gly Lys Arg Trp Ser
                20                  25                  30

Phe Gly Lys Ser Ser Arg Asp Ser Ala Glu Ala Ala Ala Ala Ala
            35                  40                  45

Ala Ala Ala Ala Glu Ala Ser Gly Gly Asn Ala Ile Ala Arg Ala
        50                  55                  60

Ala Glu Ala Ala Trp Leu Arg Ser Val Tyr Ala Asp Thr Glu Arg Glu
65                  70                  75                  80

Gln Ser Lys His Ala Ile Ala Val Ala Ala Thr Ala Ala Ala
                85                  90                  95

Asp Ala Ala Val Ala Ala Gln Ala Ala Val Ala Val Val Arg Leu
            100                 105                 110

Thr Ser Lys Gly Arg Ser Ala Pro Val Leu Ala Thr Val Ala Gly
            115                 120                 125

Asp Thr Arg Ser Leu Ala Ala Ala Val Arg Ile Gln Thr Ala Phe
            130                 135                 140

Arg Gly Phe Leu Ala Lys Lys Ala Leu Arg Ala Leu Lys Ala Leu Val
145                 150                 155                 160

Lys Leu Gln Ala Leu Val Arg Gly Tyr Leu Val Arg Arg Gln Ala Ala
                165                 170                 175

Ala Thr Leu Gln Ser Met Gln Ala Leu Val Arg Ala Gln Ala Thr Val
            180                 185                 190

Arg Ala His Arg Ser Gly Ala Gly Ala Ala Ala Asn Leu Pro His Leu
            195                 200                 205

His His Ala Pro Phe Trp Pro Arg Arg Ser Leu Val Arg Arg Trp Leu
        210                 215                 220

Asn Leu Ala Asp Asp Ile Ala Met Tyr Met Phe Asp Val Asp Val Val
225                 230                 235                 240

Cys Trp Arg Trp Met Gln Gln Glu Arg Cys Ala Gly Asp Asp Thr Arg
                245                 250                 255

Ser Glu His Gly Val Ala Ala Tyr Ser Arg Arg Leu Ser Ala Ser Ile
            260                 265                 270

Glu Ser Ser Ser Tyr Gly Tyr Asp Arg Arg Pro Gln Asp Arg Gly Gly
            275                 280                 285

Gly His Arg Gly Gly Pro Ser Arg Gly Arg Arg Arg Gly Gly Arg
290                 295                 300

Ala Pro Pro Leu Leu Leu Asp Ala Arg Trp Val Arg Glu Arg Arg
305                 310                 315                 320

Gly Leu Val Arg Gln Leu His Val Val Ala Pro Val Leu Pro Pro
                325                 330                 335

Arg Arg Arg Ala Ala Pro His Arg Arg Pro Asp Val Ala Pro Leu
            340                 345                 350

Pro Arg Leu Arg Leu Val Arg Ala Gly Glu Gly Pro Ala Gly Asp Gly
            355                 360                 365

Ala Glu His Ala Ala Val Arg Ala Arg Ala Ala Asp Ala Asp Gln Glu
```

```
                  370              375              380
Arg Val Arg Arg Arg Arg Arg Arg His Pro Leu Val Ala Ala Gln
385                 390              395                 400

Leu Pro Glu Leu His Val Gln His Ala Val Arg Gly Arg Cys
            405             410                 415

Arg Ser Gln Ser Ala Pro Lys Gln Arg Pro Glu Thr Gly Ala Gly
                420             425             430

Ala Gly Gly Arg Lys Arg Val Pro Leu Ser Glu Val Val Val
        435             440             445

Glu Ser Arg Ala Ser Leu Ser Gly Val Gly Met Gln Arg Ser Cys Asn
450                 455             460

Arg Val Gln Glu Ala Phe Asn Phe Lys Thr Ala Val Val Gly Arg Leu
465                 470             475                 480

Asp Arg Ser Ser Glu Ser Gly Glu Asn Asp Arg His Ala Phe Leu Gln
                485             490             495

Arg Arg Trp

<210> SEQ ID NO 75
<211> LENGTH: 1807
<212> TYPE: DNA
<213> ORGANISM: Gossypium hirsutum
<220> FEATURE:
<221> NAME/KEY: misc_feature
<223> OTHER INFORMATION: Ceres CLONE ID no.1920115
<220> FEATURE:
<221> NAME/KEY: misc_feature
<223> OTHER INFORMATION: Encodes the peptide sequence at SEQ ID NO 76

<400> SEQUENCE: 75
ctcctttcct cagtaagctt acgaaacttc ttcttcgctt cttctctgca aatgaatccc      60
gagaaacctc ccaaaccctt atcttattac ccttttttcac cttcttctcc atcaccaaac   120 taacgttttcc gtacacaacg aacaaaatca aagcaatggg taaagcttcc aagtggttcc   180
gcagcatcct cggcttcaaa aatccgaccc ccataaccaa ccttctcctt cttcttcaaa    240
accaacttcc cataaagaca aacggcgttg gagtttcgtc aaatcgtacc gtgaaaaaga    300
ctcctccacg aacaatagta atgcgaagtt gccgtcgtct tcgcagcaac agaaagactc    360
tgtttccttc gttgaaagga aaggtgacaa tgaagtaacg gatcctagca agcacgccat    420
cgctgttgct gccgctactg ccgccgttgc cgaagcagcc gttgcggctg ctcaagctgc    480
cgctgcggtg gttaggctca ctagtaacag tggtaggtgc gcgcgtgaat cggcagcggt    540
ttacgtttgc aacaacaata gctatatagc acacgatgag tcatccgcca ttaagataca    600
atctgcattt cgtggatacc tggcaagaag agcattgcga gcactaaaag gattagtgag    660
actccaagca ttggttagag gtcatataga aaggaagaga actgcagaat ggttaagaag    720
gatgcaagca ttattgagag cacaagcacg tgctcgtgct ggccgggccc aaatttccga    780
gtcttcccaa tcaagctgca aatcgtctca cttccatcat ccggatccag caacccctga    840
aaaatttgaa catgttattc gatccaaggg tacaaaatat gaacaatcat caatgttgaa    900
gagaaatgga tcaaagtcaa gtggaaggac tgttgataat caagagaaat tacactcagg    960
ttggtatcgc cgtgttgatg agcaaacatg ggagcattca acaagaattg gtcctaatga   1020
tgatgaaaag aatgacaaaa tccttgaagt tgacactggg aaaccaaatt tcatctctaa   1080
acggagaaac ctctttcatt caacacatct ttctctgaat tctgatttat atagctgtag   1140
tttcactaat tcgagagact cacaccaaac agctcctagt ccttcatctg gtgaagttca   1200
```

-continued

```
gtctttaact ccattgatgc tgtctcactc tgaagcaata caggaaagcc ctttctgcgg    1260
tgctgttgat gataatagtc cacaattcta ttctgcatca tcaaaaggag ctagttccaa    1320
gagaagcccc ttcactcctg ctaagagtga tggcactaga agctacctaa gtggttactc    1380
agaccatcca aattacatgt cttacactga atcgtcaaaa gctaaggtaa ggtctttcag    1440
tgctccaaaa caaaggcctc attatgaaag atctagttca acaagaggt actccattca     1500 tggttttggt gaattgaaat caactacaca aaggtctgcc atgcatgcaa acttcgccag    1560
caaagcttac cccggttcgg gtaggttgga caggctagga atgccccttg gtatagata    1620 ctaaataatg gttttaccat ttggctaagg aatgttatgt agtttatgtt tagatgttaa    1680
cgatgatgac tctcacctac cctaatgtat ccatcctta atgttttagt gcatgtgagt    1740
tcccaagtta aaagaatag tagctgcttt acaagaagtt aaattagaaa aaaaaaaaa    1800 aaaaaaa                                                              1807
```

<210> SEQ ID NO 76
<211> LENGTH: 300
<212> TYPE: PRT
<213> ORGANISM: Gossypium hirsutum
<220> FEATURE:
<221> NAME/KEY: misc_feature
<223> OTHER INFORMATION: Ceres CLONE ID no.1920115
<220> FEATURE:
<221> NAME/KEY: misc_feature
<223> OTHER INFORMATION: Score of 34.2 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41

<400> SEQUENCE: 76

```
Met Gln Ala Leu Leu Arg Ala Gln Ala Arg Ala Arg Ala Gly Arg Ala
1               5                   10                  15

Gln Ile Ser Glu Ser Ser Gln Ser Ser Cys Lys Ser Ser His Phe His
            20                  25                  30

His Pro Asp Pro Ala Thr Pro Glu Lys Phe Glu His Val Ile Arg Ser
        35                  40                  45

Lys Gly Thr Lys Tyr Glu Gln Ser Ser Met Leu Lys Arg Asn Gly Ser
    50                  55                  60

Lys Ser Ser Gly Arg Thr Val Asp Asn Gln Glu Lys Leu His Ser Gly
65                  70                  75                  80

Trp Tyr Arg Arg Val Asp Glu Gln Thr Trp Glu His Ser Thr Arg Ile
                85                  90                  95

Gly Pro Asn Asp Asp Glu Lys Asn Asp Lys Ile Leu Glu Val Asp Thr
            100                 105                 110

Gly Lys Pro Asn Phe Ile Ser Lys Arg Arg Asn Leu Phe His Ser Thr
        115                 120                 125

His Leu Ser Leu Asn Ser Asp Leu Tyr Ser Cys Ser Phe Thr Asn Ser
    130                 135                 140

Arg Asp Ser His Gln Thr Ala Pro Ser Pro Ser Ser Gly Glu Val Gln
145                 150                 155                 160

Ser Leu Thr Pro Leu Met Leu Ser His Ser Glu Ala Ile Gln Glu Ser
                165                 170                 175

Pro Phe Cys Gly Ala Val Asp Asp Asn Ser Pro Gln Phe Tyr Ser Ala
            180                 185                 190

Ser Ser Lys Gly Ala Ser Ser Lys Arg Ser Pro Phe Thr Pro Ala Lys
        195                 200                 205
```

```
Ser Asp Gly Thr Arg Ser Tyr Leu Ser Gly Tyr Ser Asp His Pro Asn
    210                 215                 220

Tyr Met Ser Tyr Thr Glu Ser Ser Lys Ala Lys Val Arg Ser Phe Ser
225                 230                 235                 240

Ala Pro Lys Gln Arg Pro His Tyr Glu Arg Ser Ser Thr Lys Arg
                245                 250                 255

Tyr Ser Ile His Gly Phe Gly Glu Leu Lys Ser Thr Thr Gln Arg Ser
                260                 265                 270

Ala Met His Ala Asn Phe Ala Ser Lys Ala Tyr Pro Gly Ser Gly Arg
                275                 280                 285

Leu Asp Arg Leu Gly Met Pro Leu Gly Tyr Arg Tyr
    290                 295                 300

<210> SEQ ID NO 77
<211> LENGTH: 1614
<212> TYPE: DNA
<213> ORGANISM: Arabidopsis thaliana
<220> FEATURE:
<221> NAME/KEY: misc_feature
<223> OTHER INFORMATION: Ceres CLONE ID no.21821
<220> FEATURE:
<221> NAME/KEY: misc_feature
<223> OTHER INFORMATION: Encodes the peptide sequence at SEQ ID NO 78

<400> SEQUENCE: 77
ataatttgat gaacagtctt cttctctgat gcagaaaccc tctccctgaa tcttgattct      60
ctcacaatca agatttgaag caaacgtttt gagaaaaatc ttttgacacc atcaaatttg     120
gttggcggat tgtgggagga attccagagc aatatagcag tgatggttg tacaacaatg     180 gctaagaaga agggcttgtt cactgtattg aaaaggattt ttatttcaga agttaattca     240
gaaaagaaag agaagagaag aaaatggaca ttttggaagc ttaggattaa gaaaagatta     300
ccttccatta cagcacctcc agagcacagg acaagtcatg aatcgcatga ggaacagaag     360
gaggaaattg tgtcagatgt gggtgagatc agccaagtgt cttgtagtcg acagttagat     420
tccatagaag agtcaaaagg ttcaacatca ccagaaactg ctgatctggt agtccagtat     480
caaatgtttc ttaatagaca ggaagaagtt cttgctgcta ctcgcattca gaccgccttt     540
cggggtcatc ttgcaaggaa agctctacgt gccttgaagg aatagtgaa gctccaagca     600 tatatcagag tcgtgctgt gagacgccaa gcaatgacta cactaaaatg cctgcaatct     660
gttgtgaaca ttcagtcaca agtctgtggt aagagaacac agattcccgg aggtgttcac     720
agagattatg aagagagcaa tatattcaat gataacattc tcaaggtgga cacaaacggt     780
caaaagagat gggacgatag tcttttaaca aaggaagaaa aggaagcagt ggtaatgagc     840
aagaaagaag cttcactaag aagagaaagg ataaaggaat atgcagtcac ccaccggaaa     900
tctgcggagt cataccagaa acgaagtaac actaaatgga agtactggtt agacgaatgg     960
gtagatacac aactaaccaa gagcaaggag ctcgaagatc tcgacttctc ttcgaaaaca    1020
aaaccgaaag acgaaacttt gaacgagaag cagcttaaaa ctccaaggaa ctcatcacca    1080
agaagattag tgaataatca tagaagacaa gtttcaatag gtgaagatga acaaagccct    1140
gccgcggtca ctatcactac accaacttat atggttgcaa cagagtcagc aaaggcaaag    1200
tcaagatcat taagctcccc aaggataaga ccgagaagtt ttgacacaca gtcagagagt    1260
tactcgccat ataagaacaa gctatgcctg acgacatcca tgatgagtga agcaccaagc    1320
aaagtaagga ttgccaacaa tggcagtaac actagaccaa gtgcatacca gcaacggtct    1380
ccagggttaa gggatttaa cataggcccc ttgaaatcat gcaataataa taatactcta    1440
```

-continued

```
ttgaacgatc tcagcattaa ttcagaaaga tctctaccta gctggaacaa gcagagcagc    1500
ttgagatgag tggatattga accctgtata tatacatact acatacgttc caatgtttct    1560
tttgactttt gagggtcaca ctcacatatg tgtatcatca aatattgttt cgtt          1614
```

<210> SEQ ID NO 78
<211> LENGTH: 443
<212> TYPE: PRT
<213> ORGANISM: Arabidopsis thaliana
<220> FEATURE:
<221> NAME/KEY: misc_feature
<223> OTHER INFORMATION: Ceres CLONE ID no.21821
<220> FEATURE:
<221> NAME/KEY: misc_feature
<223> OTHER INFORMATION: Score of 237.2 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (111)..(131)
<223> OTHER INFORMATION: Pfam Name: IQ Pfam Description: IQ calmodulin-
      binding motif

<400> SEQUENCE: 78

Met Ala Lys Lys Lys Gly Leu Phe Thr Val Leu Lys Arg Ile Phe Ile
1               5                   10                  15

Ser Glu Val Asn Ser Glu Lys Lys Glu Lys Arg Arg Lys Trp Thr Phe
            20                  25                  30

Trp Lys Leu Arg Ile Lys Lys Arg Leu Pro Ser Ile Thr Ala Pro Pro
        35                  40                  45

Glu His Arg Thr Ser His Glu Ser His Glu Glu Gln Lys Glu Glu Ile
    50                  55                  60

Val Ser Asp Val Gly Glu Ile Ser Gln Val Ser Cys Ser Arg Gln Leu
65                  70                  75                  80

Asp Ser Ile Glu Glu Ser Lys Gly Ser Thr Ser Pro Glu Thr Ala Asp
                85                  90                  95

Leu Val Val Gln Tyr Gln Met Phe Leu Asn Arg Gln Glu Glu Val Leu
            100                 105                 110

Ala Ala Thr Arg Ile Gln Thr Ala Phe Arg Gly His Leu Ala Arg Lys
        115                 120                 125

Ala Leu Arg Ala Leu Lys Gly Ile Val Lys Leu Gln Ala Tyr Ile Arg
    130                 135                 140

Gly Arg Ala Val Arg Gln Ala Met Thr Thr Leu Lys Cys Leu Gln
145                 150                 155                 160

Ser Val Val Asn Ile Gln Ser Gln Val Cys Gly Lys Arg Thr Gln Ile
                165                 170                 175

Pro Gly Gly Val His Arg Asp Tyr Glu Glu Ser Asn Ile Phe Asn Asp
            180                 185                 190

Asn Ile Leu Lys Val Asp Thr Asn Gly Gln Lys Arg Trp Asp Asp Ser
        195                 200                 205

Leu Leu Thr Lys Glu Glu Lys Glu Ala Val Val Met Ser Lys Lys Glu
    210                 215                 220

Ala Ser Leu Arg Arg Glu Arg Ile Lys Glu Tyr Ala Val Thr His Arg
225                 230                 235                 240

Lys Ser Ala Glu Ser Tyr Gln Lys Arg Ser Asn Thr Lys Trp Lys Tyr
                245                 250                 255

Trp Leu Asp Glu Trp Val Asp Thr Gln Leu Thr Lys Ser Lys Glu Leu

```
                260                 265                 270
Glu Asp Leu Asp Phe Ser Ser Lys Thr Lys Pro Lys Asp Glu Thr Leu
            275                 280                 285

Asn Glu Lys Gln Leu Lys Thr Pro Arg Asn Ser Ser Pro Arg Arg Leu
        290                 295                 300

Val Asn Asn His Arg Arg Gln Val Ser Ile Gly Glu Asp Glu Gln Ser
305                 310                 315                 320

Pro Ala Ala Val Thr Ile Thr Pro Thr Tyr Met Val Ala Thr Glu
                325                 330                 335

Ser Ala Lys Ala Lys Ser Arg Ser Leu Ser Ser Pro Arg Ile Arg Pro
            340                 345                 350

Arg Ser Phe Asp Thr Gln Ser Glu Ser Tyr Ser Pro Tyr Lys Asn Lys
        355                 360                 365

Leu Cys Leu Thr Thr Ser Met Met Ser Glu Ala Pro Ser Lys Val Arg
    370                 375                 380

Ile Ala Asn Asn Gly Ser Asn Thr Arg Pro Ser Ala Tyr Gln Gln Arg
385                 390                 395                 400

Ser Pro Gly Leu Arg Gly Phe Asn Ile Gly Pro Leu Lys Ser Cys Asn
                405                 410                 415

Asn Asn Asn Thr Leu Leu Asn Asp Leu Ser Ile Asn Ser Glu Arg Ser
            420                 425                 430

Leu Pro Ser Trp Asn Lys Gln Ser Ser Leu Arg
        435                 440
```

<210> SEQ ID NO 79
<211> LENGTH: 1689
<212> TYPE: DNA
<213> ORGANISM: Glycine max
<220> FEATURE:
<221> NAME/KEY: misc_feature
<223> OTHER INFORMATION: Ceres CLONE ID no.560066
<220> FEATURE:
<221> NAME/KEY: misc_feature
<223> OTHER INFORMATION: Encodes the peptide sequence at SEQ ID NO 80

<400> SEQUENCE: 79

```
tttttatgg gatttgaaaa aatggatcac agacattgaa gttgacctat gtgttgatat      60
tcttaaatgg ccaaaaagaa gagctggttt agtctggtga agaggctctt tatatgggac    120
acacattcca cacaagataa gaaggagaaa agaaggaaat ggatatttgg aaggctaaag    180
agcaagagat tgccttcaat taaagctcca ctaccctcaa aaggaacaac actaagtgag    240
gcagagcaag aacagagcaa gcatgcttta acagtggcca ttgcctcagc agcagctgct    300
gaagctgctg ttactgctgc tcatgctgct gctgaggttg ttcgcctcac tgggcaacgc    360
aacgaaaact cagaagaatc tcaacctgtt aaaactagga atggtgctcc acaatccaca    420
taccagtgcc agagggagat taagaatct gctgcagcca tcaaaattca aactgcattt    480
cggggttacc tggcaaggaa ggctttgagg gcgttgaagg gaatagtgaa gcttcaagct    540
atcattcgtg gcagagccgt aagacgccaa gctatgagta gtcttaagtg cttacagtcc    600
attgtgagca tccagtcaca ggtctgtgca aggaggctcc aaatggttga agggagatgt    660
gattactctg aaaatgaaga gatgcaagat tttaaagaca aaataattag gatggactca    720
aacagtgaaa gaaagtggga tgaaagcact gtattgaagg aagaggtaga cacctcttgc    780
acaagcaaga gagaaagaac aaaagaatac tcatttaacc acagaaggtc agcagagtca    840
gaaagaagta aagtaaatgg aagatggagg tactggctag agcagtgggt agatacacaa    900
```

```
ctttcaaaga gtaaagagct tgaagattta gactcagttt ttagctcaca ttctagagct    960
ggggaggaat atggaggaag gcaacttaag ctgagaagta atattcagag acaaaatcca   1020
gttgaaggat tggattctcc aatacttggt tcaagaagat cttttcctca taggaggcag   1080
tgttcagtgg gagaggacca ctcatttta agctctcctg caactccagc atacatggct    1140
gcaacagaat cagcaaaagc aaaagcaaga tcaacaagct ccccaaaaat aaggactggg   1200
gggaatgtgg acatgaactc tgatagctat tcaccatgca agaaaaagct atccattgca   1260
tcttctatta acagtgaaat gcttagtaat ggtagggtgg gcaagctcag tgttaaccag   1320
cagcaaagat caccaagctt taagggactt tcagtgccta taaatcaag ccgaacaact    1380 atcaaggatc tcagtattaa ttcagattgc tcactcccta attgggatcg acaggctttc   1440
ttcaaatgaa tctatgaatg ctgatgttac tctttcttgc attaacacaa ttccttgtat   1500
catgtgaagg cttggaaaca ataactgttt ataaatatgt atgatatact atatgctatt   1560
ggatgttatt ttggttggga attgaacatt aatgtgacag aaaatagtta ttctggagat   1620
ataagatgaa ttgtatgatt aagaaagaag agatataaga tggattgtat gattaagaaa   1680
gaaggaaag                                                           1689
```

<210> SEQ ID NO 80
<211> LENGTH: 460
<212> TYPE: PRT
<213> ORGANISM: Glycine max
<220> FEATURE:
<221> NAME/KEY: misc_feature
<223> OTHER INFORMATION: Ceres CLONE ID no.560066
<220> FEATURE:
<221> NAME/KEY: misc_feature
<223> OTHER INFORMATION: Score of 822.2 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (128)..(148)
<223> OTHER INFORMATION: Pfam Name: IQ Pfam Description: IQ calmodulin-
      binding motif

<400> SEQUENCE: 80

Met Ala Lys Lys Lys Ser Trp Phe Ser Leu Val Lys Arg Leu Phe Ile
1               5                   10                  15

Trp Asp Thr His Ser Thr Gln Asp Lys Lys Glu Lys Arg Arg Lys Trp
            20                  25                  30

Ile Phe Gly Arg Leu Lys Ser Lys Arg Leu Pro Ser Ile Lys Ala Pro
        35                  40                  45

Leu Pro Ser Lys Gly Thr Thr Leu Ser Glu Ala Glu Gln Glu Gln Ser
    50                  55                  60

Lys His Ala Leu Thr Val Ala Ile Ala Ser Ala Ala Ala Glu Ala
65                  70                  75                  80

Ala Val Thr Ala Ala His Ala Ala Ala Glu Val Val Arg Leu Thr Gly
                85                  90                  95

Gln Arg Asn Glu Asn Ser Glu Glu Ser Gln Pro Val Lys Thr Arg Asn
            100                 105                 110

Gly Ala Pro Gln Ser Thr Tyr Gln Cys Gln Arg Glu Ile Lys Glu Ser
        115                 120                 125

Ala Ala Ala Ile Lys Ile Gln Thr Ala Phe Arg Gly Tyr Leu Ala Arg
    130                 135                 140

Lys Ala Leu Arg Ala Leu Lys Gly Ile Val Lys Leu Gln Ala Ile Ile

```
                145                 150                 155                 160
Arg Gly Arg Ala Val Arg Arg Gln Ala Met Ser Ser Leu Lys Cys Leu
            165                 170                 175

Gln Ser Ile Val Ser Ile Gln Ser Gln Val Cys Ala Arg Arg Leu Gln
            180                 185                 190

Met Val Glu Gly Arg Cys Asp Tyr Ser Glu Asn Glu Met Gln Asp
            195                 200                 205

Phe Lys Asp Lys Ile Ile Arg Met Asp Ser Asn Ser Glu Arg Lys Trp
210                 215                 220

Asp Glu Ser Thr Val Leu Lys Glu Val Asp Thr Ser Cys Thr Ser
225                 230                 235                 240

Lys Arg Glu Arg Thr Lys Glu Tyr Ser Phe Asn His Arg Arg Ser Ala
                245                 250                 255

Glu Ser Glu Arg Ser Lys Val Asn Gly Arg Trp Arg Tyr Trp Leu Glu
            260                 265                 270

Gln Trp Val Asp Thr Gln Leu Ser Lys Ser Lys Glu Leu Glu Asp Leu
            275                 280                 285

Asp Ser Val Phe Ser Ser His Ser Arg Ala Gly Glu Tyr Gly Gly
    290                 295                 300

Arg Gln Leu Lys Leu Arg Ser Asn Ile Gln Arg Gln Asn Pro Val Glu
305                 310                 315                 320

Gly Leu Asp Ser Pro Ile Leu Gly Ser Arg Ser Phe Pro His Arg
                325                 330                 335

Arg Gln Cys Ser Val Gly Glu Asp His Ser Phe Leu Ser Ser Pro Ala
            340                 345                 350

Thr Pro Ala Tyr Met Ala Ala Thr Glu Ser Ala Lys Ala Lys Ala Arg
                355                 360                 365

Ser Thr Ser Ser Pro Lys Ile Arg Thr Gly Gly Asn Val Asp Met Asn
            370                 375                 380

Ser Asp Ser Tyr Ser Pro Cys Lys Lys Lys Leu Ser Ile Ala Ser Ser
385                 390                 395                 400

Ile Asn Ser Glu Met Leu Ser Asn Gly Arg Val Gly Lys Leu Ser Val
                405                 410                 415

Asn Gln Gln Gln Arg Ser Pro Ser Phe Lys Gly Leu Ser Val Pro Ile
            420                 425                 430

Lys Ser Ser Arg Thr Thr Ile Lys Asp Leu Ser Ile Asn Ser Asp Cys
            435                 440                 445

Ser Leu Pro Asn Trp Asp Arg Gln Ala Phe Phe Lys
    450                 455                 460

<210> SEQ ID NO 81
<211> LENGTH: 501
<212> TYPE: PRT
<213> ORGANISM: Oryza sativa subsp. japonica
<220> FEATURE:
<221> NAME/KEY: misc_feature
<223> OTHER INFORMATION: Public GI ID no.115453071
<220> FEATURE:
<221> NAME/KEY: misc_feature
<223> OTHER INFORMATION: Score of 546.0 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (122)..(142)
<223> OTHER INFORMATION: Pfam Name: IQ Pfam Description: IQ calmodulin-
      binding motif
```

<400> SEQUENCE: 81

```
Met Glu Arg Lys Arg Arg Gly Trp Leu Glu Arg Ile Lys Arg Leu Phe
1               5                   10                  15

Val Ser Glu Pro Lys Gln Lys Pro Lys Pro Asp Lys Lys Val Lys Ser
            20                  25                  30

Lys Arg Trp Met Phe Ala Gly Lys Leu Lys Thr Gln His Ser Phe Ala
        35                  40                  45

Leu Pro Ala Pro Ala Pro Ala Val Glu Glu Gln Ile Arg Gln Ala
    50                  55                  60

Glu Asp Glu Gln Ser Lys His Ala Met Ala Val Ala Leu Ala Thr Ala
65                  70                  75                  80

Ala Ala Ala Glu Ala Ala Val Ala Ala Ala His Ala Ala Ala Glu Val
                85                  90                  95

Val Arg Leu Thr Gly Lys Thr Ala Ala Leu Ala Pro Ala Pro Ala Thr
            100                 105                 110

Thr Thr Thr Pro Thr Pro Tyr Gly His Glu His Ala Ala Leu Met Ile
        115                 120                 125

Gln Ser Val Tyr Arg Gly Tyr Leu Ala Arg Arg Ala Leu Arg Ala Leu
    130                 135                 140

Lys Gly Leu Val Arg Leu Gln Ala Leu Ile Arg Gly Gln Ala Val Arg
145                 150                 155                 160

Arg Gln Thr Ala Ala Thr Leu Arg Gly Leu Glu Ser Leu Met Lys Ile
                165                 170                 175

Gln Ala Arg Gln Arg Ala Arg Ala Ser Ser Ala Ala Ala Gly Gly
            180                 185                 190

Asp His Asn Ala Ala Asn Ser Pro Ala Pro Asp Gly Met Asp Ala Leu
        195                 200                 205

Leu Arg Arg Gly Arg Glu Leu Tyr Tyr Ala Ala Ala Ala Val His
    210                 215                 220

Glu Gln Gln Leu Ser Lys Gly Trp Asp Ser Ser Thr Leu Ser Lys Glu
225                 230                 235                 240

Glu Met Ser Ala Met Ser Arg Ser Arg Glu Glu Ala Ala Leu Lys Arg
                245                 250                 255

Val Arg Ala Leu Gln Tyr Ala Ser Leu His Gln Ser Glu Lys Val Gly
            260                 265                 270

Val Arg Arg Gln Pro Met Ser Arg Glu Glu Met Glu Thr Leu Asn Gln
        275                 280                 285

Arg Trp Ser Trp Leu Glu Glu Trp Val Gly Ser Gln Pro Pro Phe Asp
    290                 295                 300

Lys Asp Ile Pro Val Ala His Gln Ser Pro Ser Arg Asp Ala Ala Gly
305                 310                 315                 320

Ala Ala Met Asn Asp Asp Glu Arg Pro Pro Pro Pro Val Leu Arg
                325                 330                 335

Ser Arg Ser Arg Ala Asp Arg Leu Ala Cys Val Gly Gly Asp Asp Asp
            340                 345                 350

Asp Ala Asp Arg Gln Leu Gly Tyr Ser Ala Arg Arg Ser Phe Thr Arg
        355                 360                 365

Ala Gly Arg Arg Thr Pro Ala Arg Asp Asp Gly Gly Ala Ala
    370                 375                 380

Ala Phe Pro Gly Tyr Met Ala Ser Thr Ala Ser Ala Lys Ala Lys Phe
385                 390                 395                 400

Arg Ser Met Ser Thr Pro Lys Glu Arg Ser Gly Ala Gly Ala Ala Asp
```

|     |     |     |     | 405 |     |     |     |     | 410 |     |     |     |     | 415 |
| --- | --- | --- | --- | --- | --- | --- | --- | --- | --- | --- | --- | --- | --- | --- |
| Ala | Tyr | Ser | Glu | Gln | Cys | Phe | Pro | Phe | Ala | Asp | Arg | Leu | Leu | Ser | Pro |
|     |     |     | 420 |     |     |     |     | 425 |     |     |     |     | 430 |     |

| Ile | Pro | Ser | Met | Ser | Pro | Ile | Pro | Ser | Ile | Ala | Ser | Asp | Ile | Val | Phe |
| --- | --- | --- | --- | --- | --- | --- | --- | --- | --- | --- | --- | --- | --- | --- | --- |
|     |     |     | 435 |     |     |     |     | 440 |     |     |     |     | 445 |     |     |

| Ala | Arg | Ser | Ser | Arg | Pro | Ala | Ala | Ala | Gln | Arg | Ser | Pro | Arg | Val | Lys |
| --- | --- | --- | --- | --- | --- | --- | --- | --- | --- | --- | --- | --- | --- | --- | --- |
|     | 450 |     |     |     |     | 455 |     |     |     |     | 460 |     |     |     |     |

| Gly | Pro | Met | Thr | Pro | Thr | Arg | Ser | Arg | Ser | Arg | Arg | Ser | Pro | Gly | Arg |
| --- | --- | --- | --- | --- | --- | --- | --- | --- | --- | --- | --- | --- | --- | --- | --- |
| 465 |     |     |     |     | 470 |     |     |     |     | 475 |     |     |     |     | 480 |

| His | Ser | Phe | Gly | Ser | Glu | Ala | Ala | Leu | His | Gln | Leu | Gln | Met | Glu | Gln |
| --- | --- | --- | --- | --- | --- | --- | --- | --- | --- | --- | --- | --- | --- | --- | --- |
|     |     |     |     | 485 |     |     |     |     | 490 |     |     |     |     | 495 |     |

| Tyr | Thr | Pro | Ile | Arg |
| --- | --- | --- | --- | --- |
|     |     |     |     | 500 |

<210> SEQ ID NO 82
<211> LENGTH: 1814
<212> TYPE: DNA
<213> ORGANISM: Gossypium hirsutum
<220> FEATURE:
<221> NAME/KEY: misc_feature
<223> OTHER INFORMATION: Ceres CLONE ID no.1968211
<220> FEATURE:
<221> NAME/KEY: misc_feature
<223> OTHER INFORMATION: Encodes the peptide sequence at SEQ ID NO 83

<400> SEQUENCE: 82

```
aatttccccc ttcctctctc cctcctttcc tcagtaagct tacgaaactt cttcttcgct        60
tcttctctgc aaatgaatcc cgagaaacct cccaaaccct tatcttttta cccttttttca      120
ccttcttctc catcaccaaa ctaacgtttc cgtacacaac gaacaaaatc aaagcaatgg      180
gtaaagcttc caagtggttc cgcagcatcc tcggcttcaa aaaatccgac ccccataacc      240
aaccttctcc ttcttcttca aaaccaactt cccataaaga caaacggcgt tggagtttcg      300
tcaaatcgta ccgtgaaaaa gactcctcca cgaacaatag taatgcgaag ttgccgtcgt      360
cttcgcagca acagaaagac tctgtttcct tcgttgaaag gaaaggtgac aatgaagtaa      420
cggatcctag caagcacgcc atcgctgttg ctgccgctac tgccgccgtt gccgaagcag      480
ccgttgcggc tgctcaagct gccgctgcgg tggttaggct cactagtaac agtggtaggt      540
gcgcgcgtga atcggcagcg gtttacgttt gcaacaacaa tagctatata gcacacgatg      600
agtcatccgc cattaagata caatctgcat tcgtggata cctggcaaga agagcattgc      660
gagcactaaa aggattagtg agactccaag cattggttag aggtcatata gaaaggaaga      720
gaactgcaga atggttaaga aggatgcaag cattattgag agcacaagca cgtgctcgtg      780
ctggccgggc ccaaatttcc gagtcttccc aatcaagctg caaatcgtct cacttccatc      840
atccggatcc agcaaccact gaaaaatttg aacatgttat tcgatccaag ggtacaaaat      900
atgaacaatc atcaatgttg aagagaaatg gatcaaagtc aagtggaagg actgttgata      960
atcaagagaa attacactca ggttggtatc gccgtgttga tgagcaaaca tgggagcatt     1020
caacaagaat tggtcctaat gatgatgaaa agaatgacaa atccttgaa gttgacactg     1080
ggaaaccaaa tttcatctct aaacggagaa acctctttca ttcaacacat ctttctctga     1140
attctgattt atatagctgt agtttcacta attcgagaga ctcacaccaa acagctccta     1200
gtccttcatc tggtgaagtt cagtctttaa ctccattgat gctgtctcac tctgaagcaa     1260
tacaggaaag ccctttctgc ggtgctgttg atgataatag tccacaattc tattctgcat     1320
catcaaaagg agctagttcc aagagaagcc ccttcactcc tgctaagagt gatggcacta     1380
```

-continued

```
gaagctacct aagtggttac tcagaccatc caaattacat gtcttacact gaatcgtcaa    1440
aagctaaggt aaggtctttc agtgctccaa aacaaaggcc tcattatgaa agatctagtt    1500
caacaaagag gtactccatt catggttttg gtgaattgaa atcaactaca caaaggtctg    1560
ccatgcatgc aaacttcgcc agcaaagctt accccggttc gggtaggttg acaggctag    1620 gaatgcccct tgggtataga tactaaataa tggttttacc atttggctaa ggaatgttat    1680
gtagtttatg tttagatgtt aacgatgatg actctcacct accctaatgt atccatcctt    1740
taatgtttta gtgcatgtga gttcccaagt taaaagaat agtagctgct ttacaaaaaa     1800
aaaaaaaaaa aaaa                                                      1814
```

<210> SEQ ID NO 83
<211> LENGTH: 489
<212> TYPE: PRT
<213> ORGANISM: Gossypium hirsutum
<220> FEATURE:
<221> NAME/KEY: misc_feature
<223> OTHER INFORMATION: Ceres CLONE ID no.1968211
<220> FEATURE:
<221> NAME/KEY: misc_feature
<223> OTHER INFORMATION: Score of 555.8 for HMM of FIGURE 2.
<220> FEATURE:
<221> NAME/KEY: misc_feature
<223> OTHER INFORMATION: Functional Homolog Of Ceres SEEDLINE ID no.
    ME06748 at SEQ ID NO. 41
<220> FEATURE:
<221> NAME/KEY: misc_feature
<222> LOCATION: (142)..(162)
<223> OTHER INFORMATION: Pfam Name: IQ Pfam Description: IQ calmodulin-
    binding motif

<400> SEQUENCE: 83

```
Met Gly Lys Ala Ser Lys Trp Phe Arg Ser Ile Leu Gly Phe Lys Lys
1               5                   10                  15

Ser Asp Pro His Asn Gln Pro Ser Pro Ser Ser Ser Lys Pro Thr Ser
            20                  25                  30

His Lys Asp Lys Arg Arg Trp Ser Phe Val Lys Ser Tyr Arg Glu Lys
        35                  40                  45

Asp Ser Ser Thr Asn Asn Ser Asn Ala Lys Leu Pro Ser Ser Ser Gln
    50                  55                  60

Gln Gln Lys Asp Ser Val Ser Phe Val Glu Arg Lys Gly Asp Asn Glu
65                  70                  75                  80

Val Thr Asp Pro Ser Lys His Ala Ile Ala Val Ala Ala Ala Thr Ala
                85                  90                  95

Ala Val Ala Glu Ala Ala Val Ala Ala Ala Gln Ala Ala Ala Ala Val
            100                 105                 110

Val Arg Leu Thr Ser Asn Ser Gly Arg Cys Ala Arg Glu Ser Ala Ala
        115                 120                 125

Val Tyr Val Cys Asn Asn Asn Ser Tyr Ile Ala His Asp Glu Ser Ser
    130                 135                 140

Ala Ile Lys Ile Gln Ser Ala Phe Arg Gly Tyr Leu Ala Arg Arg Ala
145                 150                 155                 160

Leu Arg Ala Leu Lys Gly Leu Val Arg Leu Gln Ala Leu Val Arg Gly
                165                 170                 175

His Ile Glu Arg Lys Arg Thr Ala Glu Trp Leu Arg Arg Met Gln Ala
            180                 185                 190

Leu Leu Arg Ala Gln Ala Arg Ala Arg Ala Gly Arg Ala Gln Ile Ser
        195                 200                 205
```

```
Glu Ser Ser Gln Ser Ser Cys Lys Ser Ser His Phe His His Pro Asp
    210                 215                 220

Pro Ala Thr Pro Glu Lys Phe Glu His Val Ile Arg Ser Lys Gly Thr
225                 230                 235                 240

Lys Tyr Glu Gln Ser Ser Met Leu Lys Arg Asn Gly Ser Lys Ser Ser
                245                 250                 255

Gly Arg Thr Val Asp Asn Gln Glu Lys Leu His Ser Gly Trp Tyr Arg
            260                 265                 270

Arg Val Asp Glu Gln Thr Trp Glu His Ser Thr Arg Ile Gly Pro Asn
        275                 280                 285

Asp Asp Glu Lys Asn Asp Lys Ile Leu Glu Val Asp Thr Gly Lys Pro
    290                 295                 300

Asn Phe Ile Ser Lys Arg Arg Asn Leu Phe His Ser Thr His Leu Ser
305                 310                 315                 320

Leu Asn Ser Asp Leu Tyr Ser Cys Ser Phe Thr Asn Ser Arg Asp Ser
                325                 330                 335

His Gln Thr Ala Pro Ser Pro Ser Gly Glu Val Gln Ser Leu Thr
            340                 345                 350

Pro Leu Met Leu Ser His Ser Glu Ala Ile Gln Glu Ser Pro Phe Cys
        355                 360                 365

Gly Ala Val Asp Asp Asn Ser Pro Gln Phe Tyr Ser Ala Ser Ser Lys
370                 375                 380

Gly Ala Ser Ser Lys Arg Ser Pro Phe Thr Pro Ala Lys Ser Asp Gly
385                 390                 395                 400

Thr Arg Ser Tyr Leu Ser Gly Tyr Ser Asp His Pro Asn Tyr Met Ser
                405                 410                 415

Tyr Thr Glu Ser Ser Lys Ala Lys Val Arg Ser Phe Ser Ala Pro Lys
            420                 425                 430

Gln Arg Pro His Tyr Glu Arg Ser Ser Thr Lys Arg Tyr Ser Ile
        435                 440                 445

His Gly Phe Gly Glu Leu Lys Ser Thr Thr Gln Arg Ser Ala Met His
    450                 455                 460

Ala Asn Phe Ala Ser Lys Ala Tyr Pro Gly Ser Gly Arg Leu Asp Arg
465                 470                 475                 480

Leu Gly Met Pro Leu Gly Tyr Arg Tyr
                485
```

```
<210> SEQ ID NO 84
<211> LENGTH: 464
<212> TYPE: PRT
<213> ORGANISM: Oryza sativa subsp. indica
<220> FEATURE:
<221> NAME/KEY: misc_feature
<223> OTHER INFORMATION: Public GI ID no.116310011
<220> FEATURE:
<221> NAME/KEY: misc_feature
<223> OTHER INFORMATION: Score of 886.7 for HMM of FIGURE 2.
<220> FEATURE:
<221> NAME/KEY: misc_feature
<223> OTHER INFORMATION: Functional Homolog Of Ceres SEEDLINE ID no.
      ME06748 at SEQ ID NO. 41
<220> FEATURE:
<221> NAME/KEY: misc_feature
<222> LOCATION: (124)..(144)
<223> OTHER INFORMATION: Pfam Name: IQ Pfam Description: IQ calmodulin-
      binding motif

<400> SEQUENCE: 84

Met Gly Trp Ala Ser Arg Trp Leu Arg Gly Leu Leu Gly Gly Gly Lys
1               5                   10                  15
```

-continued

```
Lys Pro Asn Ser Gly Ser Gly Asp Pro Lys Pro Ala Arg Glu Lys Lys
            20                  25                  30

Arg Trp Gly Phe Gly Lys Ser Phe Arg Glu Lys Ser Pro Ala His Pro
        35                  40                  45

Pro Pro Pro Pro Pro Ser Ala Ala Val Gln Arg Ala Val Thr Pro
50                  55                  60

Arg Arg Ala Tyr Thr Ala Ser Asp Glu Gly Asp Asp Glu Gln Ser Lys
65                  70                  75                  80

Arg Ala Ile Ala Val Ala Ala Thr Ala Ala Val Ala Glu Ala Ala
                85                  90                  95

Val Ala Ala Ala Gln Ala Ala Ala Val Val Arg Leu Thr Ser Ser
                100                 105                 110

Gly Arg Cys Ala Pro Ala Ala Lys Arg Glu Glu Tyr Ala Ala Val
                115                 120                 125

Arg Ile Gln Ala Ala Phe Arg Gly Tyr Leu Ala Arg Arg Ala Leu Lys
    130                 135                 140

Ala Leu Arg Gly Leu Val Lys Leu Gln Ala Leu Val Arg Gly Asn Ile
145                 150                 155                 160

Val Arg Arg Gln Ala Ala Glu Thr Leu Arg Cys Met His Ala Leu Val
                165                 170                 175

Arg Val Gln Arg Arg Ala Arg Ala Cys Arg Ala Ile Arg Ser Gln His
                180                 185                 190

Val Ser Ala His Pro Gly Pro Pro Thr Pro Glu Lys Tyr Asp Gln Ala
                195                 200                 205

Thr His Glu Gly Val Pro Lys His Gly Arg Ser Gly Ser Leu Lys Gly
                210                 215                 220

Ser Ser Ser Lys Thr Pro Gly Ser Glu Arg Leu Thr Arg Glu Arg Ser
225                 230                 235                 240

Glu Ser Cys Gly Arg Asn Trp Leu Asp Lys Trp Val Glu Glu Arg Tyr
                245                 250                 255

Leu Asp Asp Glu Lys Asn Ala Lys Ile Leu Glu Val Asp Thr Gly Lys
                260                 265                 270

Pro Gly Arg His Ala Ser Arg Arg Ser Gly Ser His His His His
                275                 280                 285

Ser Ser Cys Ser Ser Met Thr Ser Glu Gln Lys Ser Arg Ser Tyr Ala
290                 295                 300

Thr Met Pro Glu Ser Pro Ser Lys Asp Ser Thr Thr Ala Gln Gln Ser
305                 310                 315                 320

Val Pro Ser Pro Pro Ser Val Gly Met Ala Glu Ala Leu Ser Pro Leu
                325                 330                 335

Arg Met Ala Val Asp Ile Ala Glu Leu Cys Asp Ser Pro Gln Phe Phe
                340                 345                 350

Ser Ala Thr Ser Arg Pro Gly Ser Ser Arg Ser Arg Ala Phe Thr Pro
                355                 360                 365

Thr Lys Ser Glu Cys Ser Arg Ser Leu Phe Gly Gly Tyr Ser Asp Tyr
                370                 375                 380

Pro Asn Tyr Met Ala Asn Thr Glu Ser Phe Arg Ala Lys Ala Arg Ser
385                 390                 395                 400

Gln Ser Ala Pro Lys Gln Arg Pro Gln Tyr Glu Lys Ser Ser Ser Leu
                405                 410                 415

Arg Lys Ala Ser Ala His Ala Phe Gly Pro Gly Ser Cys Ala Pro Val
                420                 425                 430
```

Ala Gln Arg Thr Thr Ala Ser Leu His Ser Lys Phe Thr Asn Lys Ala
        435                 440                 445

Tyr Pro Gly Ser Gly Arg Leu Asp Arg Leu Gly Met Pro Val Lys Tyr
        450                 455                 460

<210> SEQ ID NO 85
<211> LENGTH: 1019
<212> TYPE: DNA
<213> ORGANISM: Arabidopsis thaliana
<220> FEATURE:
<221> NAME/KEY: misc_feature
<223> OTHER INFORMATION: Ceres SEEDLINE ID no.ME08768
<220> FEATURE:
<221> NAME/KEY: misc_feature
<223> OTHER INFORMATION: Encodes the peptide sequence at SEQ ID NO. 86

<400> SEQUENCE: 85
gttactaatc tcacgcacat tctttctctc tctaaattct gcaccacaat ccgcaaaatg     60
accaaatact tcttgctgtg aatgtcgaaa atgcctgcag gcacaacatg tgaagtgatg    120
caaaacggca acacttgttt caccagatcc tttcgtcatt gatggggaag aaaggaggca    180
gctggttctc atctgtgaag aaagtttttca agtcatcttc taaagattcg ccccagcctg    240
agaagaagaa ggacaacaca cagaaattac agcatgaagt ggcagaggtg gtgtcctttg    300
agcattttcc tgcagagagt tctccagata atgtgagcaa tgcagagatg agtacgacat    360
caacgccagt gaccaacgaa gatagaagcc atgcgattgc cgttgcagca gcaactgccg    420
cagctgcaga agctgctgtg gtggctgctc aagcagctgc aagagttgta agattggcag    480
gaagttacgg gcggcagtcc aaggaagaaa gagcagcaac actcattcaa tcatactata    540
gaggctacct ggctcgacgt gcactacgag cattgaaggg attagtgagg ctgcaagcac    600
tggtgagggg acacaatgtg cggaagcaag cgcagatgac gatgcggtgc atgcaagcac    660
tggtgagggt gcaggcacga gtacgggctc gccgattcca attgagtcac gcggatcagg    720
aaagagagaa gaaagaagag cccaagccca tacccgtgcc cgtgcccatg agccccctga    780
gaagaataga cgacattaat gactgggaca ataggcgtca agtagctac aaaattaagg    840 aaaacgattt gcggaaacat gaagctgtaa tgaagagaga gagagctctt gcatacgctt    900
tcaactatca acaggttagt taatttgtca tgattaaatg ggaatatagt ggataaaata    960
gcttagtcta atattctttc aaaacggtac gtgcaattta atttatctat atcttcttt    1019

<210> SEQ ID NO 86
<211> LENGTH: 253
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME08768
<220> FEATURE:
<221> NAME/KEY: misc_feature
<223> OTHER INFORMATION: Score of 467.7 for HMM of FIGURE 1.
<220> FEATURE:
<221> NAME/KEY: misc_feature
<222> LOCATION: (116)..(136)
<223> OTHER INFORMATION: Pfam Name: IQ Pfam Description: IQ calmodulin-
      binding motif

<400> SEQUENCE: 86

Met Gly Lys Lys Gly Gly Ser Trp Phe Ser Ser Val Lys Lys Val Phe
1               5                   10                  15

Lys Ser Ser Ser Lys Asp Ser Pro Gln Pro Glu Lys Lys Lys Asp Asn
            20                  25                  30

```
Thr Gln Lys Leu Gln His Glu Val Ala Glu Val Val Ser Phe Glu His
            35                  40                  45

Phe Pro Ala Glu Ser Ser Pro Asp Asn Val Ser Asn Ala Glu Met Ser
 50                  55                  60

Thr Thr Ser Thr Pro Val Thr Asn Glu Asp Arg Ser His Ala Ile Ala
 65                  70                  75                  80

Val Ala Ala Ala Thr Ala Ala Ala Glu Ala Val Val Ala Ala
                 85                  90                  95

Gln Ala Ala Ala Arg Val Val Arg Leu Ala Gly Ser Tyr Gly Arg Gln
             100                 105                 110

Ser Lys Glu Glu Arg Ala Ala Thr Leu Ile Gln Ser Tyr Tyr Arg Gly
         115                 120                 125

Tyr Leu Ala Arg Arg Ala Leu Arg Ala Leu Lys Gly Leu Val Arg Leu
     130                 135                 140

Gln Ala Leu Val Arg Gly His Asn Val Arg Lys Gln Ala Gln Met Thr
145                 150                 155                 160

Met Arg Cys Met Gln Ala Leu Val Arg Val Gln Ala Arg Val Arg Ala
                 165                 170                 175

Arg Arg Phe Gln Leu Ser His Ala Asp Gln Glu Arg Glu Lys Lys Glu
             180                 185                 190

Glu Pro Lys Pro Ile Pro Val Pro Val Pro Met Ser Pro Leu Arg Arg
         195                 200                 205

Ile Asp Asp Ile Asn Asp Trp Asp Asn Arg Gln Ser Ser Tyr Lys
     210                 215                 220

Ile Lys Glu Asn Asp Leu Arg Lys His Glu Ala Val Met Lys Arg Glu
225                 230                 235                 240

Arg Ala Leu Ala Tyr Ala Phe Asn Tyr Gln Gln Val Ser
                 245                 250

<210> SEQ ID NO 87
<211> LENGTH: 1906
<212> TYPE: DNA
<213> ORGANISM: Gossypium hirsutum
<220> FEATURE:
<221> NAME/KEY: misc_feature
<223> OTHER INFORMATION: Ceres CLONE ID no.1943807
<220> FEATURE:
<221> NAME/KEY: misc_feature
<223> OTHER INFORMATION: Encodes the peptide sequence at SEQ ID NO 88

<400> SEQUENCE: 87
atctttttta tcttcacagt gttggtgtct tggctccttc ttcaaagctt cttttagctg     60
taaatgtagc ttggtttaac cctatccttt tgaatgggga tgaaaggagg gacttcatgg    120
ttgactgctg tgaaaagggc ttttagatct cctactaaag ataccatga agatgaaaag    180 gtaagtgttt caatctattt taatggctgt ttatgaatct aaaaagaaaa ccctttgatt    240 ttttttttata tagaagagag ataaacggag gtggatcttt aggaaacaaa atacaagtcc    300
tgtgaagagt gtaggtaata atggtggtgg tggtgcaagt acggcagcag cggagcaaag    360
acatgctatt gctgtggcgg tggctaaagc agctgaagct gaagctgcgg tggcgacggc    420
acaagcagct ttacaagctg ctcggttgac taaacctagt tatggcagga acatcactt    480 tgctgctatt gttattcaga cagcttttag aggctacctg gccaggagag ctctacgtgc    540
gttaaaaggg ctagtgaagt tacaagcttt agtgagaggt cacaacgtga gaaagcaagc    600
caagatgacg cttcgttgca tgcaagcact ggttaaagtt cagtctcgtg ttttagacca    660
aagaatgagg ctctcgcacg atggttgcag ccggaaatca gcatttagcg acaccaacag    720
```

```
tgtatgggaa tcacggtatc ttcaagatat atcggataga agatcattat cgagagaagg    780
aagtagcata gcagatgatt gggacgaaag gccacacaca gttgaagaag tgaaagctat    840
gttacaacat aggaaagaag ctgctttgaa acgtgaaaag agcttgtcac aagcactgtc    900
acaacagatg aggagagctc gaaggagtcc atcaatgggg ggacaagatg agtggcttga    960
tcgttggatg cctgctaaac catgggataa cagaggaaga gcttcaatgg atcaaagaga   1020
taatgtcaaa actgttgaaa tggacacttc acagccttat tcatatttag caccaaatta   1080
tagaagaaca aattcaaacc attatcacca aaggcctagt tcacctctcc atagggctca   1140
acacaatgca caacctttcc acccttctcc aattacaccc tctccatcga aaacacgtcc   1200
ggttcaagta cggtccgcga gccctcgttg cgttagggaa gaccgaacat cgttttcatc   1260
atcacaaaca ccaagtttaa ggtccaatta ttattacaca ggaagggtta gtactcaagc   1320
tagtactagc ataaacaatg ctactacatt gcctaattac atggcagcaa cagagtctgc   1380
aaaggctagg attaggtctc aaagtgcacc aagacagagg ccatcgacac cagagaggga   1440
ccgaatcggt tcagcaagga aaaggctatc gtttcccgtc ccggaaccat atggtatcgg   1500
gatggggtac ggaggttatg gtcatagctt gaggagcccg agttttaaaa gtgtaagcgg   1560
gtcgcaattc ggattggaac gacagtctaa ctattcatct tgttgtactg agagccttgg   1620
tggtgaaatg tcaccatctt caactagtga tctaagaagg tggttgaggt gatcccatca   1680
atgtagctgt tggtttttac tagtttata gtgtgtttcc attgttgatt ttaccaattc   1740
ttggttgaaa ttcaagcttt ataagtgagg caactgcgat gaacccttcc ttactgggat   1800
ctttcatgag attcataacc aaattgagtg tgtaatacta taaagtaact ctgtaattct   1860
gttttgtcat aactttttaa tatattaaag cttatcatct tttccg                  1906
```

<210> SEQ ID NO 88
<211> LENGTH: 355
<212> TYPE: PRT
<213> ORGANISM: Gossypium hirsutum
<220> FEATURE:
<221> NAME/KEY: misc_feature
<223> OTHER INFORMATION: Ceres CLONE ID no.1943807
<220> FEATURE:
<221> NAME/KEY: misc_feature
<223> OTHER INFORMATION: Score of 667.2 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86

<400> SEQUENCE: 88

Met Thr Leu Arg Cys Met Gln Ala Leu Val Lys Val Gln Ser Arg Val
1               5                   10                  15

Leu Asp Gln Arg Met Arg Leu Ser His Asp Gly Cys Ser Arg Lys Ser
            20                  25                  30

Ala Phe Ser Asp Thr Asn Ser Val Trp Glu Ser Arg Tyr Leu Gln Asp
        35                  40                  45

Ile Ser Asp Arg Arg Ser Leu Ser Arg Glu Gly Ser Ser Ile Ala Asp
    50                  55                  60

Asp Trp Asp Glu Arg Pro His Thr Val Glu Val Lys Ala Met Leu
65                  70                  75                  80

Gln His Arg Lys Glu Ala Ala Leu Lys Arg Glu Lys Ser Leu Ser Gln
                85                  90                  95

Ala Leu Ser Gln Gln Met Arg Arg Ala Arg Arg Ser Pro Ser Met Gly
            100                 105                 110

```
Gly Gln Asp Glu Trp Leu Asp Arg Trp Met Pro Ala Lys Pro Trp Asp
            115                 120                 125
Asn Arg Gly Arg Ala Ser Met Asp Gln Arg Asp Asn Val Lys Thr Val
        130                 135                 140
Glu Met Asp Thr Ser Gln Pro Tyr Ser Tyr Leu Ala Pro Asn Tyr Arg
145                 150                 155                 160
Arg Thr Asn Ser Asn His Tyr His Gln Arg Pro Ser Ser Pro Leu His
                165                 170                 175
Arg Ala Gln His Asn Ala Gln Pro Phe His Pro Ser Pro Ile Thr Pro
            180                 185                 190
Ser Pro Ser Lys Thr Arg Pro Val Gln Val Arg Ser Ala Ser Pro Arg
        195                 200                 205
Cys Val Arg Glu Asp Arg Thr Ser Phe Ser Ser Gln Thr Pro Ser
210                 215                 220
Leu Arg Ser Asn Tyr Tyr Tyr Thr Gly Arg Val Ser Thr Gln Ala Ser
225                 230                 235                 240
Thr Ser Ile Asn Asn Ala Thr Thr Leu Pro Asn Tyr Met Ala Ala Thr
                245                 250                 255
Glu Ser Ala Lys Ala Arg Ile Arg Ser Gln Ser Ala Pro Arg Gln Arg
            260                 265                 270
Pro Ser Thr Pro Glu Arg Asp Arg Ile Gly Ser Ala Arg Lys Arg Leu
        275                 280                 285
Ser Phe Pro Val Pro Glu Pro Tyr Gly Ile Gly Met Gly Tyr Gly Gly
290                 295                 300
Tyr Gly His Ser Leu Arg Ser Pro Ser Phe Lys Ser Val Ser Gly Ser
305                 310                 315                 320
Gln Phe Gly Leu Glu Arg Gln Ser Asn Tyr Ser Ser Cys Cys Thr Glu
                325                 330                 335
Ser Leu Gly Gly Glu Met Ser Pro Ser Ser Thr Ser Asp Leu Arg Arg
            340                 345                 350
Trp Leu Arg
        355

<210> SEQ ID NO 89
<211> LENGTH: 1677
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1471392
<220> FEATURE:
<221> NAME/KEY: misc_feature
<223> OTHER INFORMATION: Encodes the peptide sequence at SEQ ID NO 90

<400> SEQUENCE: 89
atggggaaga agggaggtag ctcatggttg accgttgtga aagggctttt tagatctcct      60
aataaagaaa atgacaagag aactgctggg actacaggcc atgaccaaga agaagatgaa     120
gaaaagaaga gagagaagag gaggtggctg tttaggaaac ctacgaatca agaaacagtg     180
acacaacaga tcctatcaaa ggcaggaaat gtcaaggcct ccacgggtgg tggtggaggt     240
gcaccgacag accatgtgtc ggcagctgca gcagctgagc aaaggcatgc aattgctgta     300
gctgttgcca ctgcagctgc agctgaaact gcattagcca ctgcccaggc ggccgtggag     360
gtggctaggc tcactaggcc ttcttatcac cctagaaac gttccgctgc cattgtcatt      420
caaaccgctt ttagaggata cctggcaagg cgggctcttc gcgcgcttaa agggctagtg     480
```

```
aagttgcaag ctttagtgag gggacacaat gtgagaaagc aggccaagat gaccctgaga    540
tgcatgcaag ctctggttcg agtgcaggct cgagtacttg accaacgcat gaggctttca    600
catgaaggca gcagggaatc tgcattcagt gacaccaata gcgtgtttga atcgcgatat    660
cttcaagaaa tttcagaaag aaagtcgatg tcaagacg gcagcagcat tgcagatgat      720
tgggatgatc ggccacgcac aattgaggaa gtcaaggcca tgttgcaacg caggaaagaa    780
gttgcattca gcgtgagaa ggccttatct caaggtttct ctcaacagat atggagaaac     840
cgtaggagcc catcaatggg caatgaaggt gagctccaag aaagatcaca atggcttgat    900
cattggatgc ctgcaaagcc gtgggacaat agcagcagag cacgagcctc aactgatcaa    960
agaaacccca tcaaaactgt agaaattgaa acctcccaac cttgctcata tttagctcct   1020
aattttggaa gaacgaacca aaccaatat caccaacacc agagatccaa ttcaataaac    1080
aatggtgtta catgctcggc tcctcctcca ctccatagag ctcatcaaaa tgcttctctc   1140
cgcaactctc ctattacacc ctccccgtca gaactaggc ctcttcaggt tcgttcagcg    1200
agtccccgat gtgctagaga agatagaagc tgtaattcct ctcgaacacc gagtttaagg   1260
tccaattacc tctataatgg caatctgaaa caacatggaa tcaggggtgg tgctgctagt   1320
gttagtggaa atgctaatgc tacattgcca aattacatgg ctacaactga gtccgccaag   1380
gctagattga gatcacagag tgcgccaagg caaagaccat caacaccaga gcgagacagg   1440
gttgggtctg caagaaaacg ctttttgtat cctgtccccg acccttacgg tgtcgggatg   1500
ggttatggtg gtgttggtta cgggcatggt ttcaggagtc ccagctttaa aagtgtaagt   1560
ggttcacatt ttggtggatt agaacaacaa tctaactatt cttcttgctg cactgatacc   1620
ttcggtgctg agatttcccc ttcttcaacg agcgaccaga gaaggtggtt gagataa      1677
```

<210> SEQ ID NO 90
<211> LENGTH: 382
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1471392
<220> FEATURE:
<221> NAME/KEY: misc_feature
<223> OTHER INFORMATION: Score of 422.0 for HMM of FIGURE 1.
<220> FEATURE:
<221> NAME/KEY: misc_feature
<223> OTHER INFORMATION: Functional Homolog Of Ceres SEEDLINE ID no.
    ME08768 at SEQ ID NO. 86

<400> SEQUENCE: 90

```
Met Thr Leu Arg Cys Met Gln Ala Leu Val Arg Val Gln Ala Arg Val
1               5                   10                  15

Leu Asp Gln Arg Met Arg Leu Ser His Glu Gly Ser Arg Glu Ser Ala
            20                  25                  30

Phe Ser Asp Thr Asn Ser Val Phe Glu Ser Arg Tyr Leu Gln Glu Ile
        35                  40                  45

Ser Glu Arg Lys Ser Met Ser Arg Asp Gly Ser Ser Ile Ala Asp Asp
    50                  55                  60

Trp Asp Asp Arg Pro Arg Thr Ile Glu Glu Val Lys Ala Met Leu Gln
65                  70                  75                  80

Arg Arg Lys Glu Val Ala Phe Lys Arg Glu Lys Ala Leu Ser Gln Gly
                85                  90                  95

Phe Ser Gln Gln Ile Trp Arg Asn Arg Ser Pro Met Gly Asn
            100                 105                 110
```

```
Glu Gly Glu Leu Gln Glu Arg Ser Gln Trp Leu Asp His Trp Met Pro
            115                 120                 125

Ala Lys Pro Trp Asp Asn Ser Arg Ala Arg Ala Ser Thr Asp Gln
130                 135                 140

Arg Asn Pro Ile Lys Thr Val Glu Ile Glu Thr Ser Gln Pro Cys Ser
145                 150                 155                 160

Tyr Leu Ala Pro Asn Phe Gly Arg Thr Asn Gln Asn Gln Tyr His Gln
                165                 170                 175

His Gln Arg Ser Asn Ser Ile Asn Asn Gly Val Thr Cys Ser Ala Pro
            180                 185                 190

Pro Pro Leu His Arg Ala His Gln Asn Ala Ser Leu Arg Asn Ser Pro
            195                 200                 205

Ile Thr Pro Ser Pro Ser Arg Thr Arg Pro Leu Gln Val Arg Ser Ala
210                 215                 220

Ser Pro Arg Cys Ala Arg Glu Asp Arg Ser Cys Asn Ser Ser Arg Thr
225                 230                 235                 240

Pro Ser Leu Arg Ser Asn Tyr Leu Tyr Asn Gly Asn Leu Lys Gln His
                245                 250                 255

Gly Ile Arg Gly Gly Ala Ala Ser Val Ser Gly Asn Ala Asn Ala Thr
            260                 265                 270

Leu Pro Asn Tyr Met Ala Thr Thr Glu Ser Ala Lys Ala Arg Leu Arg
            275                 280                 285

Ser Gln Ser Ala Pro Arg Gln Arg Pro Ser Thr Pro Glu Arg Asp Arg
            290                 295                 300

Val Gly Ser Ala Arg Lys Arg Leu Leu Tyr Pro Val Pro Asp Pro Tyr
305                 310                 315                 320

Gly Val Gly Met Gly Tyr Gly Val Gly Tyr Gly His Gly Phe Arg
                325                 330                 335

Ser Pro Ser Phe Lys Ser Val Ser Gly Ser His Phe Gly Gly Leu Glu
                340                 345                 350

Gln Gln Ser Asn Tyr Ser Ser Cys Cys Thr Asp Thr Phe Gly Ala Glu
            355                 360                 365

Ile Ser Pro Ser Ser Thr Ser Asp Gln Arg Arg Trp Leu Arg
370                 375                 380
```

<210> SEQ ID NO 91
<211> LENGTH: 527
<212> TYPE: PRT
<213> ORGANISM: Arabidopsis thaliana
<220> FEATURE:
<221> NAME/KEY: misc_feature
<223> OTHER INFORMATION: Public GI ID no.6715635
<220> FEATURE:
<221> NAME/KEY: misc_feature
<223> OTHER INFORMATION: Score of 916.5 for HMM of FIGURE 1.
<220> FEATURE:
<221> NAME/KEY: misc_feature
<223> OTHER INFORMATION: Functional Homolog Of Ceres SEEDLINE ID no.
    ME08768 at SEQ ID NO. 86
<220> FEATURE:
<221> NAME/KEY: misc_feature
<222> LOCATION: (121)..(141)
<223> OTHER INFORMATION: Pfam Name: IQ Pfam Description: IQ calmodulin-
    binding motif

<400> SEQUENCE: 91

```
Met Gly Lys Lys Asn Gly Ser Ser Ser Trp Leu Thr Ala Val Lys Arg
1               5                   10                  15

Ala Phe Arg Ser Pro Thr Lys Lys Asp His Ser Asn Asp Val Glu Glu
                20                  25                  30
```

```
Asp Glu Glu Lys Lys Arg Glu Lys Arg Arg Trp Phe Arg Lys Pro Ala
            35                  40                  45

Thr Gln Glu Ser Pro Val Lys Ser Ser Gly Ile Ser Pro Pro Ala Pro
    50                  55                  60

Gln Glu Asp Ser Leu Asn Val Asn Ser Lys Pro Ser Pro Glu Thr Ala
65                  70                  75                  80

Pro Ser Tyr Ala Thr Thr Thr Pro Pro Ser Asn Ala Gly Lys Pro Pro
                    85                  90                  95

Ser Ala Val Val Pro Ile Ala Thr Ser Ala Ser Lys Thr Leu Ala Pro
                100                 105                 110

Arg Arg Ile Tyr Tyr Ala Arg Glu Asn Tyr Ala Ala Val Val Ile Gln
                115                 120                 125

Thr Ser Phe Arg Gly Tyr Leu Ala Arg Arg Ala Leu Arg Ala Leu Lys
    130                 135                 140

Gly Leu Val Lys Leu Gln Ala Leu Val Arg Gly His Asn Val Arg Lys
145                 150                 155                 160

Gln Ala Lys Met Thr Leu Arg Cys Met Gln Ala Leu Val Arg Val Gln
                165                 170                 175

Ser Arg Val Leu Asp Gln Arg Lys Arg Leu Ser His Asp Gly Ser Arg
                180                 185                 190

Lys Ser Ala Phe Ser Asp Ser His Ala Val Phe Glu Ser Arg Tyr Leu
                195                 200                 205

Gln Asp Leu Ser Asp Arg Gln Ser Met Ser Arg Glu Gly Ser Ser Ala
    210                 215                 220

Ala Glu Asp Trp Asp Asp Arg Pro His Thr Ile Asp Ala Val Lys Val
225                 230                 235                 240

Met Leu Gln Arg Arg Arg Asp Thr Ala Leu Arg His Asp Lys Thr Asn
                245                 250                 255

Leu Ser Gln Ala Phe Ser Gln Lys Met Trp Arg Thr Val Gly Asn Gln
                260                 265                 270

Ser Thr Glu Gly His His Glu Val Glu Leu Glu Glu Arg Pro Lys
    275                 280                 285

Trp Leu Asp Arg Trp Met Ala Thr Arg Pro Trp Asp Lys Arg Ala Ser
    290                 295                 300

Ser Arg Ala Ser Val Asp Gln Arg Val Ser Val Lys Thr Val Glu Ile
305                 310                 315                 320

Asp Thr Ser Gln Pro Tyr Ser Arg Thr Gly Ala Gly Ser Pro Ser Arg
                325                 330                 335

Gly Gln Arg Pro Ser Ser Pro Ser Arg Thr Ser His His Tyr Gln Ser
                340                 345                 350

Arg Asn Asn Phe Ser Ala Thr Pro Ser Pro Ala Lys Ser Arg Pro Ile
                355                 360                 365

Leu Ile Arg Ser Ala Ser Pro Arg Cys Gln Arg Asp Pro Arg Glu Asp
    370                 375                 380

Arg Asp Arg Ala Ala Tyr Ser Tyr Thr Ser Asn Thr Pro Ser Leu Arg
385                 390                 395                 400

Ser Asn Tyr Ser Phe Thr Ala Arg Ser Gly Cys Ser Ile Ser Thr Thr
                405                 410                 415

Met Val Asn Asn Ala Ser Leu Leu Pro Asn Tyr Met Ala Ser Thr Glu
                420                 425                 430

Ser Ala Lys Ala Arg Ile Arg Ser His Ser Ala Pro Arg Gln Arg Pro
                435                 440                 445
```

Ser Thr Pro Glu Arg Asp Arg Ala Gly Leu Val Lys Lys Arg Leu Ser
    450                 455                 460

Tyr Pro Val Pro Pro Ala Glu Tyr Glu Asp Asn Asn Ser Leu Arg
465             470                 475                 480

Ser Pro Ser Phe Lys Ser Val Ala Gly Ser His Phe Gly Met Leu
            485                 490                 495

Glu Gln Gln Ser Asn Tyr Ser Ser Cys Cys Thr Glu Ser Asn Gly Val
            500                 505                 510

Glu Ile Ser Pro Ala Ser Thr Ser Asp Phe Arg Asn Trp Leu Arg
        515                 520                 525

<210> SEQ ID NO 92
<211> LENGTH: 1946
<212> TYPE: DNA
<213> ORGANISM: Triticum aestivum
<220> FEATURE:
<221> NAME/KEY: misc_feature
<223> OTHER INFORMATION: Ceres CLONE ID no.910109
<220> FEATURE:
<221> NAME/KEY: misc_feature
<223> OTHER INFORMATION: Encodes the peptide sequence at SEQ ID NO 93

<400> SEQUENCE: 92
atcaaacccc ccactgcccg cgccagccag ccgcggcaat aataataact ccgccgcctc     60
ctgccatgcc gcacgctagt agtagcacgc taggatcgag tagctcgtag cgtagccgtg    120
cgagggaggg aggtgggtcg atgcccgcgg ccgtgcaacc acagcaaccg cgagccggtg    180
gtgttggcca tgggaataa gaagggcggg tcgtcgtggc tcaccgccgt caagcgggcc     240
ttccgctcgc cgtccaagga ggacagcccc aagaagtctg cacgcctccg cgaggaccct    300
gacgccgacg aggacaagac caagaggag aggaggagat ggctcttcag gagatcctcg    360
tccccgtctc cgtctccggc gtctgccccc gcgccgccgg agcagcagca gtcggcgtcg    420
aggtcggcac ctgcacccgc tgtgacggac gagcagcgtc acgccatcgc gctggccgtg    480
gcgaccgcgg cgacggccga ggctgccgtg gccacggcgc aggcggcggc cgaggtcgtc    540
cgcctgaccc gcccctcctc cagcttcgtg cgggagcact acgctgccat cgtcgtacag    600
accgccttcc gaggctacct ggcgaggcgt gctctgcgcg cgctcaaggg gctggtgaag    660
ctgcaagcgc tagtgcgcgg gcacaacgtg cggaagcagg ccaacatgac gctgcggtgc    720
atgcaggcgc tggtgcgcgt ccaggcgcgg gtgcgcgacc agcggctgcg actctcccag    780
gagtccttgt ccgccgccgg tgcggctgcg tgcggcagca gcaaatcctc gtacagcgtt    840
gacacctccg ctttctggga ctccaagtac acccaagaat acgccgaacg ccgctctgtg    900
gagcggtcgc gagacggcag cagcttcgcc gccgaagact gggacgaccg gccgcggacg    960
atagaggaga ttcaggcgat gctgcagacg aggaaagacg ctgctctcaa gcgtgagaga    1020
gcgctctcat acgccttttc tcaccaaatt tggaggaacg ccgctccgtc agtcgaggag    1080
gagatgaacg tcgacgggca gccgcgctgg cggagaagt ggatggcgtc gcgcgcgtcg     1140
tttgatacaa acaggagcag cgcccgaact gccgcggcgg cggctgctgc ggcaccaggg    1200
cgcgcgtcca cggaccaccg cgaccaggtc aagacgttgg agatcgacac cgcacggcca    1260
ttctcctact ccacgcctcg ccggcatgcc ccaccgtcgc agcacgggaa cggctcgccg    1320
atgcaccgtg cgcaccacca ggcttcggtc acgccgtcac cggggaaggc gaggccaccg    1380
attcaggtgc gctccgcgag cccgcgagtg gagcgcggca agtggtgg aggaggaagc      1440 tacacaccga gcttgcactc ccagcgccac gcgtcctccg gctcggcggt gccgaactac    1500

```
atggcggcca cggaatctgc aaaggcacgt atccgctccc agagcgcgcc acggcaacgc   1560
cctgcaaccc cggagcgcga ccggccacag accgcctata accccgccgg agggagcgcc   1620
aagaagcggc tgtcgttccc cgtcccgcag acccgtacg gcgttgggta cgcgcagagc    1680
ctgcggagcc cgagcttcaa gagcgcgacg gggcggttca cctccgagca gcgttcgacc   1740
gtctcgtctc tgtcgtgcgc agagagcgtc ggcggggaac cagtctcccc gtcgtccacc   1800
actgacctcc gccgctggct ccgttgagtt gagccccggg cgaggtgttc gttgtaatac   1860
ctgcgttgct aattttctcg taatctcctc ggagaaaaat gaccttctcg taatctattt   1920
ttttgctgct aaaaaaaaaa aaaaaa                                        1946
```

<210> SEQ ID NO 93
<211> LENGTH: 543
<212> TYPE: PRT
<213> ORGANISM: Triticum aestivum
<220> FEATURE:
<221> NAME/KEY: misc_feature
<223> OTHER INFORMATION: Ceres CLONE ID no.910109
<220> FEATURE:
<221> NAME/KEY: misc_feature
<223> OTHER INFORMATION: Score of 1259.0 for HMM of FIGURE 1.
<220> FEATURE:
<221> NAME/KEY: misc_feature
<223> OTHER INFORMATION: Functional Homolog Of Ceres SEEDLINE ID no.
    ME08768 at SEQ ID NO. 86
<220> FEATURE:
<221> NAME/KEY: misc_feature
<222> LOCATION: (130)..(150)
<223> OTHER INFORMATION: Pfam Name: IQ Pfam Description: IQ calmodulin-
    binding motif

<400> SEQUENCE: 93

Met Gly Lys Lys Ala Gly Thr Thr Ser Ser Trp Leu Thr Ala Val Lys
1               5                   10                  15

Arg Ala Phe Arg Ser Pro Ser Lys Asp Asp Ser Pro Asn Lys Ala Ala
                20                  25                  30

Arg Leu Arg Asp Asp Thr Asp Asp Lys Gly Lys Arg Glu Arg Arg
            35                  40                  45

Arg Trp Leu Phe Arg Lys Ser Ser Pro Ser Ala Pro Pro Thr
50                  55                  60

Pro Pro Pro Gln Gln Gln Gln Gln Ser Arg Ala Ala Ala Val
65                  70                  75                  80

Thr Glu Glu Gln Arg His Ala Ile Ala Leu Ala Val Ala Thr Ala Ala
                85                  90                  95

Thr Ala Glu Ala Ala Val Ala Thr Ala Gln Ala Ala Glu Val Val
            100                 105                 110

Arg Leu Thr Arg Pro Ser Ser Ser Phe Val Arg Glu His Tyr Ala Ala
            115                 120                 125

Ile Val Val Gln Thr Ala Phe Arg Gly Tyr Leu Ala Arg Arg Ala Leu
        130                 135                 140

Arg Ala Leu Lys Gly Leu Val Lys Leu Gln Ala Leu Val Arg Gly His
145                 150                 155                 160

Asn Val Arg Lys Gln Ala Asn Met Thr Leu Arg Cys Met Gln Ala Leu
                165                 170                 175

Val Arg Val Gln Ala Arg Val Arg Asp Gln Arg Met Arg Leu Ser Gln
            180                 185                 190

Asp Ser Ile Ser Leu Ser Ala Ala Ala Ser Ala Ala Pro Cys Gly
        195                 200                 205

Ser Ser Lys Ser Ser Tyr Ser Val Asp Thr Ser Thr Phe Trp Asp Ser

```
             210                 215                 220
Lys Tyr Thr His Asp Phe Ala Ala Asp Arg Arg Ser Ile Glu Arg
225                 230                 235                 240

Ser Arg Asp Gly Ser Ser Phe Ala Ala Gly Asp Asp Trp Asp Arg
                245                 250                 255

Pro Arg Thr Ile Glu Glu Ile Gln Ala Met Leu Gln Thr Arg Lys Asp
                260                 265                 270

Ala Ala Leu Lys Arg Glu Arg Ala Leu Ser Tyr Ala Phe Ser His Gln
            275                 280                 285

Ile Trp Arg Asn Pro Ala Pro Ser Val Glu Glu Met Asp Val Asp Gly
290                 295                 300

Gln Pro Arg Trp Ala Glu Arg Trp Met Ala Ser Arg Ala Ser Phe Asp
305                 310                 315                 320

Thr Ser Arg Ser Thr Val Arg Ala Ser Ala Ala Ala Pro Gly Arg
                325                 330                 335

Ala Ser Thr Asp His Arg Asp Gln Val Lys Thr Leu Glu Ile Asp Thr
            340                 345                 350

Ala Arg Pro Phe Ser Tyr Ser Thr Pro Arg Arg His Gly Asn Ala Ser
            355                 360                 365

Tyr His Ala Ser Ser Ser Pro Met His Arg Ala His His Ser Pro
370                 375                 380

Val Thr Pro Ser Pro Ser Lys Ala Arg Pro Pro Ile Gln Val Arg Ser
385                 390                 395                 400

Ala Ser Pro Arg Val Glu Arg Gly Gly Gly Gly Gly Ser Tyr Thr
                405                 410                 415

Pro Ser Leu His Ser His Arg His His Ala Ser Ser Gly Gly Ala Ala
            420                 425                 430

Ala Val Pro Asn Tyr Met Ala Ala Thr Glu Ser Ala Lys Ala Arg Val
            435                 440                 445

Arg Ser Gln Ser Ala Pro Arg Gln Arg Pro Ala Thr Pro Glu Arg Asp
450                 455                 460

Arg Met Ser Phe Gly Gly Gly Gly Gly Gly Gly Ala Lys Lys Arg
465                 470                 475                 480

Leu Ser Phe Pro Val Pro Ile Asp Pro Tyr Gly Ala Tyr Ala Gln Ser
                485                 490                 495

Leu Arg Ser Pro Ser Phe Lys Ser Ala Ala Gly Arg Phe Ser Ser Glu
            500                 505                 510

Gln Arg Ser Asn Val Ser Ser Ser Cys Ala Glu Ser Leu Gly Gly Asp
            515                 520                 525

Val Val Ser Pro Ser Ser Thr Thr Asp Leu Arg Arg Trp Leu Arg
530                 535                 540

<210> SEQ ID NO 94
<211> LENGTH: 543
<212> TYPE: PRT
<213> ORGANISM: Oryza sativa subsp. japonica
<220> FEATURE:
<221> NAME/KEY: misc_feature
<223> OTHER INFORMATION: Public GI ID no.115474509
<220> FEATURE:
<221> NAME/KEY: misc_feature
<223> OTHER INFORMATION: Score of 1167.6 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86
<220> FEATURE:
<221> NAME/KEY: misc_feature
```

<222> LOCATION: (125)..(145)
<223> OTHER INFORMATION: Pfam Name: IQ Pfam Description: IQ calmodulin-
      binding motif

<400> SEQUENCE: 94

```
Met Gly Lys Lys Ala Gly Thr Thr Ser Ser Trp Leu Thr Ala Val Lys
1               5                   10                  15

Arg Ala Phe Arg Ser Pro Ser Lys Asp Asp Ser Pro Asn Lys Ala Ala
            20                  25                  30

Arg Leu Arg Asp Asp Thr Asp Asp Lys Gly Lys Arg Glu Arg Arg
        35                  40                  45

Arg Trp Leu Phe Arg Lys Ser Ser Pro Ser Ala Pro Pro Thr
50                  55                  60

Pro Pro Pro Pro Gln Gln Gln Gln Gln Ser Arg Ala Ala Ala Val
65                  70                  75                  80

Thr Glu Glu Gln Arg His Ala Ile Ala Leu Ala Val Ala Thr Ala Ala
                85                  90                  95

Thr Ala Glu Ala Ala Val Ala Thr Ala Gln Ala Ala Glu Val Val
            100                 105                 110

Arg Leu Thr Arg Pro Ser Ser Ser Phe Val Arg Glu His Tyr Ala Ala
            115                 120                 125

Ile Val Val Gln Thr Ala Phe Arg Gly Tyr Leu Ala Arg Arg Ala Leu
130                 135                 140

Arg Ala Leu Lys Gly Leu Val Lys Leu Gln Ala Leu Val Arg Gly His
145                 150                 155                 160

Asn Val Arg Lys Gln Ala Asn Met Thr Leu Arg Cys Met Gln Ala Leu
                165                 170                 175

Val Arg Val Gln Ala Arg Val Arg Asp Gln Arg Met Arg Leu Ser Gln
            180                 185                 190

Asp Ser Ile Ser Leu Ser Ala Ala Ala Ser Ala Ala Pro Cys Gly
            195                 200                 205

Ser Ser Lys Ser Ser Tyr Ser Val Asp Thr Ser Thr Phe Trp Asp Ser
210                 215                 220

Lys Tyr Thr His Asp Phe Ala Ala Ala Asp Arg Arg Ser Ile Glu Arg
225                 230                 235                 240

Ser Arg Asp Gly Ser Ser Phe Ala Ala Gly Asp Asp Trp Asp Asp Arg
                245                 250                 255

Pro Arg Thr Ile Glu Glu Ile Gln Ala Met Leu Gln Thr Arg Lys Asp
            260                 265                 270

Ala Ala Leu Lys Arg Glu Arg Ala Leu Ser Tyr Ala Phe Ser His Gln
            275                 280                 285

Ile Trp Arg Asn Pro Ala Pro Ser Val Glu Glu Met Asp Val Asp Gly
290                 295                 300

Gln Pro Arg Trp Ala Glu Arg Trp Met Ala Ser Arg Ala Ser Phe Asp
305                 310                 315                 320

Thr Ser Arg Ser Thr Val Arg Ala Ser Ala Ala Ala Pro Gly Arg
            325                 330                 335

Ala Ser Thr Asp His Arg Asp Gln Val Lys Thr Leu Glu Ile Asp Thr
            340                 345                 350

Ala Arg Pro Phe Ser Tyr Ser Thr Pro Arg Arg His Gly Asn Ala Ser
            355                 360                 365

Tyr His Ala Ser Ser Ser Pro Met His Arg Ala His His His Ser Pro
370                 375                 380

Val Thr Pro Ser Pro Ser Lys Ala Arg Pro Pro Ile Gln Val Arg Ser
```

```
                385                 390                 395                 400
            Ala Ser Pro Arg Val Glu Arg Gly Gly Gly Gly Gly Ser Tyr Thr
                            405                 410                 415

Pro Ser Leu His Ser His Arg His His Ala Ser Ser Gly Gly Ala Ala
                        420                 425                 430

Ala Val Pro Asn Tyr Met Ala Ala Thr Glu Ser Ala Lys Ala Arg Val
                        435                 440                 445

Arg Ser Gln Ser Ala Pro Arg Gln Arg Pro Ala Thr Pro Glu Arg Asp
                    450                 455                 460

Arg Met Ser Phe Gly Gly Gly Gly Gly Gly Gly Ala Lys Lys Arg
            465                 470                 475                 480

Leu Ser Phe Pro Val Pro Ile Asp Pro Tyr Gly Ala Tyr Ala Gln Ser
                            485                 490                 495

Leu Arg Ser Pro Ser Phe Lys Ser Ala Ala Gly Arg Phe Ser Ser Glu
                        500                 505                 510

Gln Arg Ser Asn Val Ser Ser Ser Cys Ala Glu Ser Leu Gly Gly Asp
                    515                 520                 525

Val Val Ser Pro Ser Ser Thr Thr Asp Leu Arg Arg Trp Leu Arg
                530                 535                 540

<210> SEQ ID NO 95
<211> LENGTH: 1812
<212> TYPE: DNA
<213> ORGANISM: Panicum virgatum
<220> FEATURE:
<221> NAME/KEY: misc_feature
<223> OTHER INFORMATION: Ceres CLONE ID no.1780908
<220> FEATURE:
<221> NAME/KEY: misc_feature
<223> OTHER INFORMATION: Encodes the peptide sequence at SEQ ID NO 96

<400> SEQUENCE: 95
gtgaccagcc agccatggag cgcggccaac gcccccgcg ccagcaataa tacaaccccc      60
ccaccacccg ggccgcgcct gcccgtcgcc ggacatgggc aagaagggcg gcgccacgtc     120
ctgactcacc gccgtcaagc gggccttccg ctcgccctcc aaggacgacg ccgcctcgcc     180
cgcaaggaag gcctcgcgcc tccgcgaccg cgacgacgcc cccgccgacg ccgaccaaga     240
caagcagggg aagcgggagc agcgccggcg atggctgttc cggaggtcct cctccccgtc     300 cccgtccct gccccgccg cgccgagca cccggccgtc acgaggagc agcgccacgc         360 catcgcgctg cgctggcga ccgccgccac ggccgaggcc gcgtggcca cggcgcaggc       420 ggcggcggag gtggtccgcc tcaccctccc cggcggcctc gccgcccgcg agcactacgc     480
cgccgtcctc atccagaccg ccttccgggg ctacctggcg cgccgcgcgc tgcgggcgct     540
caggggcctc gtcaagctgc aaacgctcgt gcgcggccac aacgtccgca agcaggccaa     600
catgacgctc cgctgcatgc aggcgctggt gcgcgtccag gcgcgcgtcc gggaccagcg     660
gatgcgcctc tcccaggact ccatgtccct gtcgtccgcc ccggcgccgc                720
cgcggcgccg tgcggcagca gcaagtcgtc gtacagcgtc gacacatcca cgttctggga    780
ctccaagtac acccacgact acgccgaccc ccgctccgtc gagcggtcgc gcgacggcag    840
cagcttcgcc gccgacgact gggacgaccg ccgcggacg atagaggaga tccaggccat    900
gctgcagacg aggaaggacg cggcgctcaa gcgtgagagg gcgctgtcct acgccttctc    960
gcatcaactt tggaggaacc cggcgccggc ggcggatgag atggacgtgg acggcggcgg   1020
gcagcagccg cggtggatga cgtcgcgcgc gtccttcgac acgaaccgga gcagcagcat   1080
```

```
ccgcggcgcg gcggtgcccg ggcgcgcgtc catggaccac cgcgagcccg tgaagacgct    1140
ggggatggac acggcgcggc ccttctcgta ctcgacgccg cggcagcagg cgccgtcgtc    1200
ctcgccgatg caccaccgcg ggcactcgcc ggtgacgccg tcgccgggga aggcgcggcc    1260
cccgatccag gtccggtcgg cgagcccgcg cgtggaccgc ggcgcggggcg gcgggagcta    1320 cacgccgagc ctgctgcact cccagcggca ccaccaccac caggcggggg cggcggtgcc    1380
caactacatg gcggcgacgg agtcggccaa ggcccgggtg cggtcccaga gcgcgccgcg    1440
gcagcggccc gcgacgcccg agcgcgaccg gctctccggc ggcggcggga gcgcgaagaa    1500
gcggctgtcg ttcccggcgg cggcagaggc gtacgcgcag tccctgcgga gcccgagctt    1560
caagagcgcg gcggggcggt tctcgtcgga gcagcggtcg acggtgtcgt cgtcgtgcgc    1620
ggagagcctc ggcggagagc cggcgtcgcc gtcgtccacc accgacctcc gccgctggct    1680
ccgctgaggg ccggccggcc gtccgttctc cgttgtagca gtaacgccgc cttttggctc    1740
ggcagacacg accacgtgcc cctgtagcat catcttctct ctcggtgtaa ttcatggcag    1800 ctttttttcga gc                                                       1812
```

<210> SEQ ID NO 96
<211> LENGTH: 361
<212> TYPE: PRT
<213> ORGANISM: Panicum virgatum
<220> FEATURE:
<221> NAME/KEY: misc_feature
<223> OTHER INFORMATION: Ceres CLONE ID no.1780908
<220> FEATURE:
<221> NAME/KEY: misc_feature
<223> OTHER INFORMATION: Score of 598.0 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86

<400> SEQUENCE: 96

```
Met Thr Leu Arg Cys Met Gln Ala Leu Val Arg Val Gln Ala Arg Val
1               5                   10                  15

Arg Asp Gln Arg Met Arg Leu Ser Gln Asp Ser Met Ser Leu Ser Met
            20                  25                  30

Pro Leu Ser Ala Ala Gly Ala Ala Ala Ala Pro Cys Gly Ser Ser Lys
        35                  40                  45

Ser Ser Tyr Ser Val Asp Thr Ser Thr Phe Trp Asp Ser Lys Tyr Thr
    50                  55                  60

His Asp Tyr Ala Asp Arg Arg Ser Val Glu Arg Ser Arg Asp Gly Ser
65                  70                  75                  80

Ser Phe Ala Ala Asp Asp Trp Asp Asp Arg Pro Arg Thr Ile Glu Glu
                85                  90                  95

Ile Gln Ala Met Leu Gln Thr Arg Lys Asp Ala Ala Leu Lys Arg Glu
            100                 105                 110

Arg Ala Leu Ser Tyr Ala Phe Ser His Gln Leu Trp Arg Asn Pro Ala
        115                 120                 125

Pro Ala Ala Asp Glu Met Asp Val Asp Gly Gly Gln Gln Pro Arg
    130                 135                 140

Trp Met Thr Ser Arg Ala Ser Phe Asp Thr Asn Arg Ser Ser Ile
145                 150                 155                 160

Arg Gly Ala Ala Val Pro Gly Arg Ala Ser Met Asp His Arg Glu Pro
                165                 170                 175

Val Lys Thr Leu Gly Met Asp Thr Ala Arg Pro Phe Ser Tyr Ser Thr
            180                 185                 190
```

```
Pro Arg Gln Gln Ala Pro Ser Ser Pro Met His His Arg Gly His
        195                 200                 205

Ser Pro Val Thr Pro Ser Pro Gly Lys Ala Arg Pro Pro Ile Gln Val
    210                 215                 220

Arg Ser Ala Ser Pro Arg Val Asp Arg Gly Ala Gly Gly Ser Tyr
225                 230                 235                 240

Thr Pro Ser Leu Leu His Ser Gln Arg His His His Gln Ala Gly
                245                 250                 255

Ala Ala Val Pro Asn Tyr Met Ala Ala Thr Glu Ser Ala Lys Ala Arg
            260                 265                 270

Val Arg Ser Gln Ser Ala Pro Arg Gln Arg Pro Ala Thr Pro Glu Arg
        275                 280                 285

Asp Arg Leu Ser Gly Gly Gly Ser Ala Lys Lys Arg Leu Ser Phe
290                 295                 300

Pro Ala Ala Glu Ala Tyr Ala Gln Ser Leu Arg Ser Pro Ser Phe
305                 310                 315                 320

Lys Ser Ala Ala Gly Arg Phe Ser Ser Glu Gln Arg Ser Thr Val Ser
                325                 330                 335

Ser Ser Cys Ala Glu Ser Leu Gly Gly Glu Pro Ala Ser Pro Ser Ser
            340                 345                 350

Thr Thr Asp Leu Arg Arg Trp Leu Arg
        355                 360

<210> SEQ ID NO 97
<211> LENGTH: 1398
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1520883
<220> FEATURE:
<221> NAME/KEY: misc_feature
<223> OTHER INFORMATION: Encodes the peptide sequence at SEQ ID NO 98

<400> SEQUENCE: 97
atggggaaga aaggaaaagg atggtttaca tctgtgaaga gagtgttcaa atcatcatct      60
cctaaggaat taccagtagg gaaaaagaaa gacaacgcag agaaatggca acatgaggct     120
ccagaagttg tgtcattaga gcatttttcct actggaagtt ctcctgatgt tacaaatgat     180
gagagcaatg tatcaactcc agtaactgaa gatagaaatc atgccattgc tgtggcagta     240
gcgactgctg ccgcagcaga agctgcggtt gcagctgctc aagcggcggc taaagttgtt     300
cgcttagctg gttatggacg acaatcaaag gaagaaagag ctgccatcct catacaatca     360
ttctataggg gctaccttgc tcggcgtgcc ttacgcgcat tgaagggatt ggtgaggctc     420
caagcattag tgagaggcca caatgtaaga aagcaagcac aaatgacaat gagaagcatg     480
caagctcttg ttcgtgtgca agcaagagta agacaagaa gacttgaatt agctcacgag     540
aagcttcaaa ggaagacaga ggaagaagat gaacgaagac taccagtgga cgaagacttt     600
atgaatccaa agaatccatt gaagagttat aaatgggata ggaggaatca aagttcagat     660
aatttcaaag aaaatgcttc aaagaagcat gatgctgtca tgaaaagaga gagagccctt     720
gcttatgctt atgccttcca gcagcagcag cagcaacaat tactctcaca aaatagtcct     780
aatggtaaag aaacaggaca tttttgtgaac gaacacgaga agtgcaatg gggatggaat     840 tggcttgaga gatggatgtc agcacaatca tataacgtgc gtcaatcggg tccaaatgaa     900
gggtcttacg tgacagtaaa cacaactaca accacgacca ccacagagga catgtccgag     960
```

```
aagacagtag agatggacat ggtgacccca acaggcacta gcaatcccaa catgggcatg    1020
ctagacacca atccatattc gaatcgaccc caatggcaat caagttcaag caatgtacgt    1080
agctacatgg ctccgaccca gtccgcaaag gcgaaagtgc gttctcaaag tttgatcaag    1140
caacgtgccc cagcgacacc tctgtggaat ccatccacca agaaagattc aagcattgtt    1200
ggtccaggtt gtgattcttc cagttcaggt ggtggaacaa caacttatca cgctccaaga    1260
agtcctagcc ccaaacataa cgggatgcgc ctgcattcga gaagacatgc tggtggatat    1320
agccctgatt tcaatggcgg tgatgattgg aggttgcctc ctcttgatgg tcatggatgg    1380
aggaatgatt ttggttga                                                   1398
```

<210> SEQ ID NO 98
<211> LENGTH: 309
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1520883
<220> FEATURE:
<221> NAME/KEY: misc_feature
<223> OTHER INFORMATION: Score of 495.7 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86

<400> SEQUENCE: 98

```
Met Arg Ser Met Gln Ala Leu Val Arg Val Gln Ala Arg Val Arg Ala
1               5                   10                  15

Arg Arg Leu Glu Leu Ala His Glu Lys Leu Gln Arg Lys Thr Glu Glu
            20                  25                  30

Glu Asp Glu Arg Arg Leu Pro Val Asp Glu Asp Phe Met Asn Pro Lys
        35                  40                  45

Asn Pro Leu Lys Ser Tyr Lys Trp Asp Arg Arg Asn Gln Ser Ser Asp
    50                  55                  60

Asn Phe Lys Glu Asn Ala Ser Lys Lys His Asp Ala Val Met Lys Arg
65                  70                  75                  80

Glu Arg Ala Leu Ala Tyr Ala Tyr Ala Phe Gln Gln Gln Gln Gln Gln
                85                  90                  95

Gln Leu Leu Ser Gln Asn Ser Pro Asn Gly Lys Glu Thr Gly His Phe
            100                 105                 110

Val Asn Glu His Glu Lys Met Gln Trp Gly Trp Asn Trp Leu Glu Arg
        115                 120                 125

Trp Met Ser Ala Gln Ser Tyr Asn Val Arg Gln Ser Gly Pro Asn Glu
    130                 135                 140

Gly Ser Tyr Val Thr Val Asn Thr Thr Thr Thr Thr Thr Thr Thr Glu
145                 150                 155                 160

Asp Met Ser Glu Lys Thr Val Glu Met Asp Met Val Thr Pro Thr Gly
                165                 170                 175

Thr Ser Asn Pro Asn Met Gly Met Leu Asp Thr Asn Pro Tyr Ser Asn
            180                 185                 190

Arg Pro Gln Trp Gln Ser Ser Ser Asn Val Arg Ser Tyr Met Ala
        195                 200                 205

Pro Thr Gln Ser Ala Lys Ala Lys Val Arg Ser Gln Ser Leu Ile Lys
    210                 215                 220

Gln Arg Ala Pro Ala Thr Pro Leu Trp Asn Pro Ser Thr Lys Lys Asp
225                 230                 235                 240
```

```
Ser Ser Ile Val Gly Pro Gly Cys Asp Ser Ser Ser Gly Gly Gly
            245                 250                 255

Thr Thr Thr Tyr His Ala Pro Arg Ser Pro Ser Pro Lys His Asn Gly
            260                 265                 270

Met Arg Leu His Ser Arg Arg His Ala Gly Gly Tyr Ser Pro Asp Phe
            275                 280                 285

Asn Gly Gly Asp Asp Trp Arg Leu Pro Pro Leu Asp Gly His Gly Trp
            290                 295                 300

Arg Asn Asp Phe Gly
305

<210> SEQ ID NO 99
<211> LENGTH: 1445
<212> TYPE: DNA
<213> ORGANISM: Arabidopsis thaliana
<220> FEATURE:
<221> NAME/KEY: misc_feature
<223> OTHER INFORMATION: Ceres CLONE ID no.148018
<220> FEATURE:
<221> NAME/KEY: misc_feature
<223> OTHER INFORMATION: Encodes the peptide sequence at SEQ ID NO 100

<400> SEQUENCE: 99
attgggattt catttagata attttttttt gggtcttgat ctaagttttg ttctttctaa    60
tttggtaagg caagaagagc attaagagca ttaaaagggt tagtgaagct acaagcattg   120 gtgagggggac ataatgtgag aaagcaagct aaaatgacat taaggtgtat gcaagctctg   180
gttcgagtcc agtctcgtgt gcttgaccaa cgcaaacgct tgtctcatga cggtagtcgc   240
aaatccgcgt tcagtgactc tcacgctgtt tttgaatctc gctatcttca agatttgtca   300
gatcgacaat ccatgtcaag agaaggaagc agcgccgcgg aagattggga tgaccgacca   360
cacacgatag acgcagtgaa agtgatgcta caacggagac gggacacagc attgagacat   420
gacaagacta atttgtcaca agctttctct caaaagatgt ggaggacggt tggtaaccaa   480
tccacggaag acaccacga ggtagaactt gaagaggaaa ggccaaaatg cttgaccgg    540 tggatggcta ctagaccgtg ggataaacga gctagtagta gagcttcggt tgaccaaagg   600
gtttcagtta aaaccgttga atcgacact tctcagcctt actcaagaac aggagcagga   660
agcccgagtc gtggccaaag acctagttcc ccatcaagaa ctagccacca ttaccaatcc   720
cgcaataatt tctcagccac tccatctccg gctaagtcta gaccaatact tattcggtca   780
gctagtccac ggtgccagag agacccgagg gaagaccgtg accgagcagc ttatagttat   840
acatcaaaca caccaagctt gagatccaat tatagtttca cagctaggag tggatgtaca   900
ttagtaccac aatggttaat aatgcatcat tgttgcctaa ttacatgcg agtacagagt   960 cagctaaagc gaggatccgg tctcatagtg caccgaggca acggccctca actcccgaga  1020
gggaccgtgc ggstttgct acaagaaacg rytctsgtat ccggtaccac cgccagcgga  1080
gtatgaggac aataatagct taaggagtcc aagctttaag agtgtggctg gttcacattt  1140
tggtggaatg ttagagcagc aatcgaatta ctcttcatgt tgcactgagt ctaacggtgt  1200
tgagatctct ccagcttcta ctagtgactt taggaattgg cttagatgat tggtggtgat  1260
gccaaatcaa ctgtcaagat ctttcatcat cctccaggaa aagaacgttt taaaatttta  1320
tattccagaa gaaacaaac acttttatat tgtgtcgttg aggttgattt gtgtttggaa  1380
gataagttta ttgacctatt gatctgtaac ttcataagat tttgaaacgt tagaagattc  1440
aaaag                                                              1445
```

```
<210> SEQ ID NO 100
<211> LENGTH: 310
<212> TYPE: PRT
<213> ORGANISM: Arabidopsis thaliana
<220> FEATURE:
<221> NAME/KEY: misc_feature
<223> OTHER INFORMATION: Ceres CLONE ID no.148018
<220> FEATURE:
<221> NAME/KEY: misc_feature
<223> OTHER INFORMATION: Score of 458.7 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86
<220> FEATURE:
<221> NAME/KEY: misc_feature
<222> LOCATION: (294)..(294)
<223> OTHER INFORMATION: Xaa is any aa, unknown, or other
<220> FEATURE:
<221> NAME/KEY: misc_feature
<222> LOCATION: (295)..(295)
<223> OTHER INFORMATION: Xaa is any aa, unknown, or other
<220> FEATURE:
<221> NAME/KEY: misc_feature
<222> LOCATION: (300)..(300)
<223> OTHER INFORMATION: Xaa is any aa, unknown, or other
<220> FEATURE:
<221> NAME/KEY: misc_feature
<222> LOCATION: (301)..(301)
<223> OTHER INFORMATION: Xaa is any aa, unknown, or other

<400> SEQUENCE: 100

Met Thr Leu Arg Cys Met Gln Ala Leu Val Arg Val Gln Ser Arg Val
1               5                   10                  15

Leu Asp Gln Arg Lys Arg Leu Ser His Asp Gly Ser Arg Lys Ser Ala
            20                  25                  30

Phe Ser Asp Ser His Ala Val Phe Glu Ser Arg Tyr Leu Gln Asp Leu
        35                  40                  45

Ser Asp Arg Gln Ser Met Ser Arg Glu Gly Ser Ser Ala Ala Glu Asp
    50                  55                  60

Trp Asp Arg Pro His Thr Ile Asp Ala Val Lys Val Met Leu Gln
65                  70                  75                  80

Arg Arg Arg Asp Thr Ala Leu Arg His Asp Lys Thr Asn Leu Ser Gln
                85                  90                  95

Ala Phe Ser Gln Lys Met Trp Arg Thr Val Gly Asn Gln Ser Thr Glu
            100                 105                 110

Gly His His Glu Val Glu Leu Glu Glu Arg Pro Lys Trp Leu Asp
        115                 120                 125

Arg Trp Met Ala Thr Arg Pro Trp Asp Lys Arg Ala Ser Ser Arg Ala
    130                 135                 140

Ser Val Asp Gln Arg Val Ser Val Lys Thr Val Glu Ile Asp Thr Ser
145                 150                 155                 160

Gln Pro Tyr Ser Arg Thr Gly Ala Gly Ser Pro Ser Arg Gly Gln Arg
                165                 170                 175

Pro Ser Ser Pro Ser Arg Thr Ser His His Tyr Gln Ser Arg Asn Asn
            180                 185                 190

Phe Ser Ala Thr Pro Ser Pro Ala Lys Ser Arg Pro Ile Leu Ile Arg
        195                 200                 205

Ser Ala Ser Pro Arg Cys Gln Arg Asp Pro Arg Glu Asp Arg Asp Arg
    210                 215                 220

Ala Ala Tyr Ser Tyr Thr Ser Asn Thr Pro Ser Leu Arg Ser Asn Tyr
225                 230                 235                 240
```

-continued

```
Ser Phe Thr Ala Arg Ser Gly Cys Thr Leu Val Pro Gln Trp Leu Ile
            245                 250                 255

Met His His Cys Cys Leu Ile Thr Trp Arg Val Gln Ser Gln Leu Lys
            260                 265                 270

Arg Gly Ser Gly Leu Ile Val His Arg Gly Asn Gly Pro Gln Leu Pro
            275                 280                 285

Arg Gly Thr Val Arg Xaa Xaa Leu Gln Glu Thr Xaa Xaa Val Ser Gly
            290                 295                 300

Thr Thr Ala Ser Gly Val
305                 310

<210> SEQ ID NO 101
<211> LENGTH: 364
<212> TYPE: PRT
<213> ORGANISM: Arabidopsis thaliana
<220> FEATURE:
<221> NAME/KEY: misc_feature
<223> OTHER INFORMATION: Public GI ID no.18378797
<220> FEATURE:
<221> NAME/KEY: misc_feature
<223> OTHER INFORMATION: Score of 546.8 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86

<400> SEQUENCE: 101

Met Thr Leu Arg Cys Met Gln Ala Leu Val Arg Val Gln Ser Arg Val
1               5                   10                  15

Leu Asp Gln Arg Lys Arg Leu Ser His Asp Gly Ser Arg Lys Ser Ala
            20                  25                  30

Phe Ser Asp Ser His Ala Val Phe Glu Ser Arg Tyr Leu Gln Asp Leu
        35                  40                  45

Ser Asp Arg Gln Ser Met Ser Arg Glu Gly Ser Ser Ala Ala Glu Asp
    50                  55                  60

Trp Asp Asp Arg Pro His Thr Ile Asp Ala Val Lys Val Met Leu Gln
65                  70                  75                  80

Arg Arg Arg Asp Thr Ala Leu Arg His Asp Lys Thr Asn Leu Ser Gln
                85                  90                  95

Ala Phe Ser Gln Lys Met Trp Arg Thr Val Gly Asn Gln Ser Thr Glu
            100                 105                 110

Gly His His Glu Val Glu Leu Glu Glu Glu Arg Pro Lys Trp Leu Asp
        115                 120                 125

Arg Trp Met Ala Thr Arg Pro Trp Asp Lys Arg Ala Ser Ser Arg Ala
    130                 135                 140

Ser Val Asp Gln Arg Val Ser Val Lys Thr Val Glu Ile Asp Thr Ser
145                 150                 155                 160

Gln Pro Tyr Ser Arg Thr Gly Ala Gly Ser Pro Ser Arg Gly Gln Arg
                165                 170                 175

Pro Ser Ser Pro Ser Arg Thr Ser His His Tyr Gln Ser Arg Asn Asn
            180                 185                 190

Phe Ser Ala Thr Pro Ser Pro Ala Lys Ser Arg Pro Ile Leu Ile Arg
        195                 200                 205

Ser Ala Ser Pro Arg Cys Gln Arg Asp Pro Arg Glu Asp Arg Asp Arg
    210                 215                 220

Ala Ala Tyr Ser Tyr Thr Ser Asn Thr Pro Ser Leu Arg Ser Asn Tyr
225                 230                 235                 240
```

```
Ser Phe Thr Ala Arg Ser Gly Cys Ser Ile Ser Thr Met Val Asn
            245                 250                 255

Asn Ala Ser Leu Leu Pro Asn Tyr Met Ala Ser Thr Glu Ser Ala Lys
        260                 265                 270

Ala Arg Ile Arg Ser His Ser Ala Pro Arg Gln Arg Pro Ser Thr Pro
            275                 280                 285

Glu Arg Asp Arg Ala Gly Leu Val Lys Lys Arg Leu Ser Tyr Pro Val
        290                 295                 300

Pro Pro Pro Ala Glu Tyr Glu Asp Asn Asn Ser Leu Arg Ser Pro Ser
305                 310                 315                 320

Phe Lys Ser Val Ala Gly Ser His Phe Gly Gly Met Leu Glu Gln Gln
            325                 330                 335

Ser Asn Tyr Ser Ser Cys Cys Thr Glu Ser Asn Gly Val Glu Ile Ser
            340                 345                 350

Pro Ala Ser Thr Ser Asp Phe Arg Asn Trp Leu Arg
            355                 360
```

<210> SEQ ID NO 102
<211> LENGTH: 364
<212> TYPE: PRT
<213> ORGANISM: Arabidopsis thaliana
<220> FEATURE:
<221> NAME/KEY: misc_feature
<223> OTHER INFORMATION: Public GI ID no.21553500
<220> FEATURE:
<221> NAME/KEY: misc_feature
<223> OTHER INFORMATION: Score of 524.9 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86
<220> FEATURE:
<221> NAME/KEY: misc_feature
<222> LOCATION: (288)..(288)
<223> OTHER INFORMATION: Xaa is any aa, unknown, or other
<220> FEATURE:
<221> NAME/KEY: misc_feature
<222> LOCATION: (294)..(294)
<223> OTHER INFORMATION: Xaa is any aa, unknown, or other
<220> FEATURE:
<221> NAME/KEY: misc_feature
<222> LOCATION: (296)..(296)
<223> OTHER INFORMATION: Xaa is any aa, unknown, or other
<220> FEATURE:
<221> NAME/KEY: misc_feature
<222> LOCATION: (300)..(300)
<223> OTHER INFORMATION: Xaa is any aa, unknown, or other
<220> FEATURE:
<221> NAME/KEY: misc_feature
<222> LOCATION: (301)..(301)
<223> OTHER INFORMATION: Xaa is any aa, unknown, or other

<400> SEQUENCE: 102

```
Met Thr Leu Arg Cys Met Gln Ala Leu Val Arg Val Gln Ser Arg Val
1               5                   10                  15

Leu Asp Gln Arg Lys Arg Leu Ser His Asp Gly Ser Arg Lys Ser Ala
            20                  25                  30

Phe Ser Asp Ser His Ala Val Phe Glu Ser Arg Tyr Leu Gln Asp Leu
        35                  40                  45

Ser Asp Arg Gln Ser Met Ser Arg Glu Gly Ser Ser Ala Ala Glu Asp
    50                  55                  60

Trp Asp Asp Arg Pro His Thr Ile Asp Ala Val Lys Val Met Leu Gln
65                  70                  75                  80

Arg Arg Arg Asp Thr Ala Leu Arg His Asp Lys Thr Asn Leu Ser Gln
            85                  90                  95
```

```
Ala Phe Ser Gln Lys Met Trp Arg Thr Val Gly Asn Gln Ser Thr Glu
                100                 105                 110

Gly His His Glu Val Glu Leu Glu Glu Arg Pro Lys Trp Leu Asp
            115                 120                 125

Arg Trp Met Ala Thr Arg Pro Trp Asp Lys Arg Ala Ser Ser Arg Ala
130                 135                 140

Ser Val Asp Gln Arg Val Ser Val Lys Thr Val Glu Ile Asp Thr Ser
145                 150                 155                 160

Gln Pro Tyr Ser Arg Thr Gly Ala Gly Ser Pro Ser Arg Gly Gln Arg
                165                 170                 175

Pro Ser Ser Pro Ser Arg Thr Ser His His Tyr Gln Ser Arg Asn Asn
                180                 185                 190

Phe Ser Ala Thr Pro Ser Pro Ala Lys Ser Arg Pro Ile Leu Ile Arg
                195                 200                 205

Ser Ala Ser Pro Arg Cys Gln Arg Asp Pro Arg Glu Asp Arg Asp Arg
210                 215                 220

Ala Ala Tyr Ser Tyr Thr Ser Asn Thr Pro Ser Leu Arg Ser Asn Tyr
225                 230                 235                 240

Ser Phe Thr Ala Arg Ser Gly Cys Ser Ile Ser Thr Thr Met Val Asn
                245                 250                 255

Asn Ala Ser Leu Leu Pro Asn Tyr Met Ala Ser Thr Glu Ser Ala Lys
            260                 265                 270

Ala Arg Ile Arg Ser His Ser Ala Pro Arg Gln Arg Pro Ser Thr Xaa
                275                 280                 285

Glu Arg Asp Arg Ala Xaa Leu Xaa Lys Lys Arg Xaa Xaa Tyr Pro Val
            290                 295                 300

Pro Pro Pro Ala Glu Tyr Glu Asp Asn Asn Ser Leu Arg Ser Pro Ser
305                 310                 315                 320

Phe Lys Ser Val Ala Gly Ser His Phe Gly Gly Met Leu Glu Gln Gln
                325                 330                 335

Ser Asn Tyr Ser Ser Cys Cys Thr Glu Ser Asn Gly Val Glu Ile Ser
                340                 345                 350

Pro Ala Ser Thr Ser Asp Phe Arg Asn Trp Leu Arg
                355                 360
```

<210> SEQ ID NO 103
<211> LENGTH: 1713
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1444522
<220> FEATURE:
<221> NAME/KEY: misc_feature
<223> OTHER INFORMATION: Encodes the peptide sequence at SEQ ID NO 104

<400> SEQUENCE: 103

```
atggggaaga agggaggtag ctcatggttg actgctgtga aaagggcgtt tagatctcca      60
actaaagaaa gtgacaagag ggctactggg gttggccatg accaagaaga agatgaagaa     120
aagaagagag ggaagagaag atggttattt aggaaaccta caaatcaaga aacggcgaca     180
caacagaacc tgtcaaaggc aggaaatgtt aaggcatccc caggtggtgg tggaggtgct     240
ccagcagacc atgtgtcggc agctgcagca gctgagcaaa ggcatgcaat tgcagtagca     300
gttgctactg cagctgcagc tgaagctgct gtagccactg cccaggcggc ggcggaggtt     360
gctcggctca ctaggccttc atatcatcct agagaacatt atgctgccat tgtcattcaa     420
```

```
acagctttta gaggatactt ggcaaggcgg gctcttcgtg cacttaaagg gctagtgaag    480
ttgcaagctt tagtaagggg acacaatgtg agaaaacagg ccaagatgac cctgcgatgc    540
atgcaagctc tggctcgagt gcaggctcga gtgcttgatc aacgcgtgag actttcacat    600
gaaggcagca ggaaatctgc atttagtgac accaatagcg tgcttgaatc gcgatatctt    660
caagacattt cagatagaaa atccatgtca agagaaagca gtagcattgc agatgattgg    720
gatgatcggc cacactccat tgaggaagtc aaggccatgt tgcaacgcag gaaagaagct    780
gcgttcaagc gtgaaaagac cttatctcaa gctttctctc agcagctcat ggctaattgg    840
ttcaattttt tcaaacccat gtccaagata tggagaaatg gcagaagccc atcaaatggc    900
aatgaagatg agctccaaga aagaccacaa tggcttgatc aatggatgcc tgcaaagcca    960
tgggacaata gcagcagagc aagagcttca actgatcaaa gagacccat caaaactgta    1020
gaaattgaca cctcccaacc ttattcatat ttagttccta attttagaag aacaaaccaa    1080
aaccaacatc accaacacca gagatccaat tcatcaaaca atggtgtggc acactctgct    1140
ccttctccac tccatagagc tcatcaaact gctccactcc accactctcc tatcacaccc    1200
tccccatcaa aaactaggcc tcttcaggtt cgttcagcta gtccacgatg tgcaagagaa    1260
gatagaagtt gtaattcctc tcaaacacca gtttaaggt ccaattattt ttacaatgga    1320
agtttgaatc aacatggaat caggggtggt gctagtgtta gtagtaatgg taatgctaca    1380
ttgccaaatt acatggctgc aaccgagtct gccaaggcta gattgagatc acagagtgca    1440
ccaaggcaaa gaccatcaac accagaacga gaccggattg ggtctgcaag aaaacggctt    1500
tcgtatccag cccccgaccc ttgtgatgtc ggtatagttt atggcggtgc tggttacggc    1560
catggtttaa ggagtccaag ctttaagagc gtgagcggtt cacgtttggg tggactagaa    1620
caacagtcta actattcttc ttgctgtacg gatagctttg gtggtgagct ttcccctttct    1680
tcaactaacg atcttaggag gtggttgaga tga                                 1713
```

<210> SEQ ID NO 104
<211> LENGTH: 395
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1444522
<220> FEATURE:
<221> NAME/KEY: misc_feature
<223> OTHER INFORMATION: Score of 439.2 for HMM of FIGURE 1.
<220> FEATURE:
<221> NAME/KEY: misc_feature
<223> OTHER INFORMATION: Functional Homolog Of Ceres SEEDLINE ID no.
      ME08768 at SEQ ID NO. 86

<400> SEQUENCE: 104

Met Thr Leu Arg Cys Met Gln Ala Leu Ala Arg Val Gln Ala Arg Val
1               5                   10                  15

Leu Asp Gln Arg Val Arg Leu Ser His Glu Gly Ser Arg Lys Ser Ala
            20                  25                  30

Phe Ser Asp Thr Asn Ser Val Leu Glu Ser Arg Tyr Leu Gln Asp Ile
        35                  40                  45

Ser Asp Arg Lys Ser Met Ser Arg Glu Ser Ser Ile Ala Asp Asp
    50                  55                  60

Trp Asp Asp Arg Pro His Ser Ile Glu Glu Val Lys Ala Met Leu Gln
65                  70                  75                  80

Arg Arg Lys Glu Ala Ala Phe Lys Arg Glu Lys Thr Leu Ser Gln Ala

```
                    85                  90                  95
    Phe Ser Gln Gln Leu Met Ala Asn Trp Phe Asn Phe Lys Pro Met
                   100                 105                 110

Ser Lys Ile Trp Arg Asn Gly Arg Ser Pro Ser Asn Gly Asn Glu Asp
                   115                 120                 125

Glu Leu Gln Glu Arg Pro Gln Trp Leu Asp Gln Trp Met Pro Ala Lys
    130                 135                 140

Pro Trp Asp Asn Ser Ser Arg Ala Arg Ala Ser Thr Asp Gln Arg Asp
    145                 150                 155                 160

Pro Ile Lys Thr Val Glu Ile Asp Thr Ser Gln Pro Tyr Ser Tyr Leu
                    165                 170                 175

Val Pro Asn Phe Arg Arg Thr Asn Gln Asn Gln His His Gln His Gln
                    180                 185                 190

Arg Ser Asn Ser Ser Asn Asn Gly Val Ala His Ser Ala Pro Ser Pro
                    195                 200                 205

Leu His Arg Ala His Gln Thr Ala Pro Leu His His Ser Pro Ile Thr
                    210                 215                 220

Pro Ser Pro Ser Lys Thr Arg Pro Leu Gln Val Arg Ser Ala Ser Pro
    225                 230                 235                 240

Arg Cys Ala Arg Glu Asp Arg Ser Cys Asn Ser Ser Gln Thr Pro Ser
                    245                 250                 255

Leu Arg Ser Asn Tyr Phe Tyr Asn Gly Ser Leu Asn Gln His Gly Ile
                    260                 265                 270

Arg Gly Gly Ala Ser Val Ser Ser Asn Gly Asn Ala Thr Leu Pro Asn
                    275                 280                 285

Tyr Met Ala Ala Thr Glu Ser Ala Lys Ala Arg Leu Arg Ser Gln Ser
                    290                 295                 300

Ala Pro Arg Gln Arg Pro Ser Thr Pro Glu Arg Asp Arg Ile Gly Ser
    305                 310                 315                 320

Ala Arg Lys Arg Leu Ser Tyr Pro Ala Pro Asp Pro Cys Asp Val Gly
                    325                 330                 335

Ile Val Tyr Gly Gly Ala Gly Tyr Gly His Gly Leu Arg Ser Pro Ser
                    340                 345                 350

Phe Lys Ser Val Ser Gly Ser Arg Leu Gly Gly Leu Glu Gln Gln Ser
                    355                 360                 365

Asn Tyr Ser Ser Cys Cys Thr Asp Ser Phe Gly Gly Glu Leu Ser Pro
                    370                 375                 380

Ser Ser Thr Asn Asp Leu Arg Arg Trp Leu Arg
    385                 390                 395

<210> SEQ ID NO 105
<211> LENGTH: 1443
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1467519
<220> FEATURE:
<221> NAME/KEY: misc_feature
<223> OTHER INFORMATION: Encodes the peptide sequence at SEQ ID NO 106

<400> SEQUENCE: 105
atggggaaga aaggaaaagg atggtttaca tctgtgaaga gagtgttcaa atcatcatct      60
cctaaggaat taccagtagg gaaaaagaaa gacaacgcag agaaatggca acatgaggct     120
ccagaagttg tgtcattaga gcattttcct actggaagtt ctcctgatgt tacaaatgat     180
```

-continued

```
gagagcaatg tatcaactcc agtaactgaa gatagaaatc atgccattgc tgtggcagta    240
gcgactgctg ccgcagcaga agctgcggtt gcagctgctc aagcggcggc taaagttgtt    300
cgcttagctg gttatggacg acaatcaaag gaagaaagag ctgccatcct catacaatca    360
ttctataggg gctaccttgt aatcccttc ttcatttcac tttattttga tcaatataat     420
ctggctcggc gtgccttacg cgcattgaag ggattggtga ggctccaagc attagtgaga    480
ggccacaatg taagaaagca agcacaaatg acaatgagaa gcatgcaagc tcttgttcgt    540
gtgcaagcaa gagtaagagc aagaagactt gaattagctc acgagaagct tcaaaggaag    600
acagaggaag aagatgaacg aagactacca gtggacgaag actttatgaa tccaaagaat    660
ccattgaaga gttataaatg ggataggagg aatcaaagtt cagataattt caaagaaaat    720
gcttcaaaga agcatgatgc tgtcatgaaa agagagagag cccttgctta tgcttatgcc    780
ttccagcagc agcagcagca acaattactc tcacaaaata gtcctaatgg taagaaaaca    840
ggacattttg tgaacgaaca cgagaagatg caatggggat ggaattggct tgagagatgg    900
atgtcagcac aatcatataa cgtgcgtcaa tcgggtccaa atgaagggtc ttacgtgaca    960
gtaaacacaa ctacaaccac gaccaccaca gaggacatgt ccgagaagac agtagagatg   1020
gacatggtga cccaacagg cactagcaat cccaacatgg gcatgctaga caccaatcca    1080
tattcgaatc gaccccaatg gcaatcaagt tcaagcaatg tacgtagcta catggctccg    1140
acccagtccg caaaggcgaa agtgcgttct caaagtttga tcaagcaacg tgccccagcg    1200
acacctctgt ggaatccatc caccaagaaa gattcaagca ttgttggtcc aggttgtgat    1260
tcttccagtt caggtggtgg aacaacaact tatcacgctc caagaagtcc tagccccaaa    1320
cataacggga tgcgcctgca ttcgagaaga catgctggtg gatatagccc tgatttcaat    1380
ggcggtgatg attggaggtt gcctcctctt gatggtcatg gatggaggaa tgattttggt    1440
tga                                                                  1443
```

<210> SEQ ID NO 106
<211> LENGTH: 309
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1467519
<220> FEATURE:
<221> NAME/KEY: misc_feature
<223> OTHER INFORMATION: Score of 495.7 for HMM of FIGURE 1.
<220> FEATURE:
<221> NAME/KEY: misc_feature
<223> OTHER INFORMATION: Functional Homolog Of Ceres SEEDLINE ID no.
    ME08768 at SEQ ID NO. 86

<400> SEQUENCE: 106

Met Arg Ser Met Gln Ala Leu Val Arg Val Gln Ala Arg Val Arg Ala
1               5                   10                  15

Arg Arg Leu Glu Leu Ala His Glu Lys Leu Gln Arg Lys Thr Glu Glu
            20                  25                  30

Glu Asp Glu Arg Arg Leu Pro Val Asp Glu Asp Phe Met Asn Pro Lys
        35                  40                  45

Asn Pro Leu Lys Ser Tyr Lys Trp Asp Arg Arg Asn Gln Ser Ser Asp
    50                  55                  60

Asn Phe Lys Glu Asn Ala Ser Lys Lys His Asp Ala Val Met Lys Arg
65                  70                  75                  80

Glu Arg Ala Leu Ala Tyr Ala Tyr Ala Phe Gln Gln Gln Gln Gln Gln
                85                  90                  95

Gln Leu Leu Ser Gln Asn Ser Pro Asn Gly Lys Glu Thr Gly His Phe
            100                 105                 110

Val Asn Glu His Glu Lys Met Gln Trp Gly Trp Asn Trp Leu Glu Arg
            115                 120                 125

Trp Met Ser Ala Gln Ser Tyr Asn Val Arg Gln Ser Gly Pro Asn Glu
130                 135                 140

Gly Ser Tyr Val Thr Val Asn Thr Thr Thr Thr Thr Thr Thr Thr Glu
145                 150                 155                 160

Asp Met Ser Glu Lys Thr Val Glu Met Asp Met Val Thr Pro Thr Gly
            165                 170                 175

Thr Ser Asn Pro Asn Met Gly Met Leu Asp Thr Asn Pro Tyr Ser Asn
            180                 185                 190

Arg Pro Gln Trp Gln Ser Ser Ser Asn Val Arg Ser Tyr Met Ala
            195                 200                 205

Pro Thr Gln Ser Ala Lys Ala Lys Val Arg Ser Gln Ser Leu Ile Lys
210                 215                 220

Gln Arg Ala Pro Ala Thr Pro Leu Trp Asn Pro Ser Thr Lys Lys Asp
225                 230                 235                 240

Ser Ser Ile Val Gly Pro Gly Cys Asp Ser Ser Ser Gly Gly Gly
            245                 250                 255

Thr Thr Thr Tyr His Ala Pro Arg Ser Pro Ser Pro Lys His Asn Gly
            260                 265                 270

Met Arg Leu His Ser Arg Arg His Ala Gly Gly Tyr Ser Pro Asp Phe
            275                 280                 285

Asn Gly Gly Asp Asp Trp Arg Leu Pro Pro Leu Asp Gly His Gly Trp
            290                 295                 300

Arg Asn Asp Phe Gly
305

<210> SEQ ID NO 107
<211> LENGTH: 291
<212> TYPE: PRT
<213> ORGANISM: Oryza sativa subsp. indica
<220> FEATURE:
<221> NAME/KEY: misc_feature
<223> OTHER INFORMATION: Public GI ID no.125559938
<220> FEATURE:
<221> NAME/KEY: misc_feature
<223> OTHER INFORMATION: Score of 403.9 for HMM of FIGURE 1.
<220> FEATURE:
<221> NAME/KEY: misc_feature
<223> OTHER INFORMATION: Functional Homolog Of Ceres SEEDLINE ID no.
    ME08768 at SEQ ID NO. 86

<400> SEQUENCE: 107

Met Gln Arg Leu Gln Glu Arg Ser Arg Asp Gly Ser Ser Phe Ala Ala
1               5                   10                  15

Gly Asp Asp Trp Asp Asp Arg Pro Arg Thr Ile Glu Glu Ile Gln Ala
            20                  25                  30

Met Leu Gln Thr Arg Lys Asp Ala Ala Leu Lys Arg Glu Arg Ala Leu
            35                  40                  45

Ser Tyr Ala Phe Ser His Gln Ile Trp Arg Asn Pro Ala Pro Ser Val
        50                  55                  60

Glu Glu Met Asp Val Asp Gly Gln Pro Arg Trp Ala Glu Arg Trp Met
65                  70                  75                  80

Ala Ser Arg Ala Ser Phe Asp Thr Ser Arg Ser Thr Val Arg Ala Ser
            85                  90                  95

Ala Ala Ala Ala Pro Gly Arg Ala Ser Thr Asp His Arg Asp Gln Val
            100                 105                 110

Lys Thr Leu Glu Ile Asp Thr Ala Arg Pro Phe Ser Tyr Ser Thr Pro
    115                 120                 125

Arg Arg His Gly Asn Ala Ser Tyr His Ala Ser Ser Ser Pro Met His
    130                 135                 140

Arg Ala His His Ser Pro Val Thr Pro Ser Pro Ser Lys Ala Arg
145                 150                 155                 160

Pro Pro Ile Gln Val Arg Ser Ala Ser Pro Arg Val Glu Arg Gly Gly
                165                 170                 175

Gly Gly Gly Gly Ser Tyr Thr Pro Ser Leu His Ser His Arg His His
            180                 185                 190

Ala Ser Ser Gly Gly Ala Ala Ala Val Pro Asn Tyr Met Ala Ala Thr
        195                 200                 205

Glu Ser Ala Lys Ala Arg Asp Val Ile Arg Gly Ala Ala Arg Arg Gly
    210                 215                 220

Ala Lys Lys Arg Leu Ser Phe Pro Val Pro Ile Asp Pro Tyr Gly Ala
225                 230                 235                 240

Tyr Ala Gln Ser Leu Arg Ser Pro Ser Phe Lys Ser Ala Ala Gly Arg
                245                 250                 255

Phe Ser Ser Glu Gln Arg Ser Asn Val Ser Ser Ser Cys Ala Glu Ser
            260                 265                 270

Leu Gly Gly Asp Val Val Ser Pro Ser Ser Thr Thr Asp Leu Arg Arg
        275                 280                 285

Trp Leu Arg
    290

<210> SEQ ID NO 108
<211> LENGTH: 1509
<212> TYPE: DNA
<213> ORGANISM: Arabidopsis thaliana
<220> FEATURE:
<221> NAME/KEY: misc_feature
<223> OTHER INFORMATION: Ceres SEEDLINE ID no.ME19173
<220> FEATURE:
<221> NAME/KEY: misc_feature
<223> OTHER INFORMATION: Encodes the peptide sequence at SEQ ID NO. 109

<400> SEQUENCE: 108
acattctccg atattctctc tctctctatc aatctctcac tctcaaactt tctacatacc      60
tgaagaaaaa aataatctac gaattcgagc caaaagatc gaaactttt aatctatggg      120 tgcttcaggg aaatgggtca agtccattat cggtctcaag aagctagaga aggatgaaat      180
cgaaaagggt aatgggaaaa acaagaaatg gaagctatgg aggactactt cagtagattc      240
atggaagggt tttcgaggaa acatcggtc tgattcagac ggtgttgatt cttctactgt      300
ttactctgct gctgttgcta ctgttcttag agctcctcct aaagatttca agctgttag      360 agaagaatgg gctgctatta gaatccaaac cgcttttcgt ggattcttgg cgagaagagc      420
gttgagggca ttgaaaggga tagtgaggtt acaagcttta gtgagaggaa gacaagttag      480
gaaacaagca gctgttacat tgagatgcat gcaagctttg gtgagagtac aagctcgtgt      540
tagagctcgt cgtgtgagga tgactgttga aggacaagct gttcaaaagc ttttagatga      600
acatagaacc aaatctgatc tcttgaaaga agtcgaggaa gggtggtgtg ataggaaagg      660
tactgtggat gatattaagt caaagttgca gcagagacaa gaaggtgctt ttaagaggga      720
acgtgctttg gcttatgctc ttgctcaaaa gcaatggagg tcaactacta gctcaaacct      780

-continued

```
taagacgaat agttcgattt cgtatcttaa aagtcaagag tttgataaga atagttgggg    840
atggagttgg ttggagcgtt ggatggctgc taggccatgg gagactagac ttatggacac    900
tgttgatacc gctgccacgc ctcctcctct gcctcataaa catttgaaat caccggaaac    960
tgcggatgtt gttcaagtta gaagaaacaa tgtgaccact agagtatctg caaaacctcc    1020
tcctcatatg ctgtcttcaa gtcctggtta tgagtttaac gagagctcag gttcatcctc    1080
gatttgtact tcaactacgc ctgtttctgg aaaaactgga cttgtttcag ataactctag    1140
cagtcaagca aaaaagcaca agccaagtta catgagcttg actgaatcga caaaggctaa    1200
gcgaagaact aaccgcggtc tcaggcaatc tatggatgag tttcagtta tgaagaactc    1260 tggaatgttt acaggggaat tgaagactag tccttcctca gatccttttg ttagtttctc    1320
caaaccactc ggtgttccta ctcgattcga gaagccgaga ggttaaatgt gaccttgtta    1380
gattggagtt tcaacagctt gttgttgtct tgtgtgttgt gagatatctg tgtatgttgt    1440
taattgttct ttttcctttg gaactacatt ggagttttga atttaaatat aaatttcagt    1500
cttgcttttt                                                            1509
```

<210> SEQ ID NO 109
<211> LENGTH: 416
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME19173
<220> FEATURE:
<221> NAME/KEY: misc_feature
<223> OTHER INFORMATION: Score of 954.4 for HMM of FIGURE 3.
<220> FEATURE:
<221> NAME/KEY: misc_feature
<222> LOCATION: (84)..(104)
<223> OTHER INFORMATION: Pfam Name: IQ Pfam Description: IQ calmodulin-
      binding motif

<400> SEQUENCE: 109

Met Gly Ala Ser Gly Lys Trp Val Lys Ser Ile Ile Gly Leu Lys Lys
1               5                   10                  15

Leu Glu Lys Asp Glu Ile Glu Lys Gly Asn Gly Lys Asn Lys Lys Trp
            20                  25                  30

Lys Leu Trp Arg Thr Thr Ser Val Asp Ser Trp Lys Gly Phe Arg Gly
        35                  40                  45

Lys His Arg Ser Asp Ser Asp Gly Val Asp Ser Ser Thr Val Tyr Ser
    50                  55                  60

Ala Ala Val Ala Thr Val Leu Arg Ala Pro Pro Lys Asp Phe Lys Ala
65                  70                  75                  80

Val Arg Glu Glu Trp Ala Ala Ile Arg Ile Gln Thr Ala Phe Arg Gly
                85                  90                  95

Phe Leu Ala Arg Arg Ala Leu Arg Ala Leu Lys Gly Ile Val Arg Leu
            100                 105                 110

Gln Ala Leu Val Arg Gly Arg Gln Val Arg Lys Gln Ala Ala Val Thr
        115                 120                 125

Leu Arg Cys Met Gln Ala Leu Val Arg Val Gln Ala Arg Val Arg Ala
    130                 135                 140

Arg Arg Val Arg Met Thr Val Glu Gly Gln Ala Val Gln Lys Leu Leu
145                 150                 155                 160

Asp Glu His Arg Thr Lys Ser Asp Leu Leu Lys Glu Val Glu Glu Gly
                165                 170                 175

Trp Cys Asp Arg Lys Gly Thr Val Asp Asp Ile Lys Ser Lys Leu Gln

```
                 180                 185                 190
Gln Arg Gln Glu Gly Ala Phe Lys Arg Glu Arg Ala Leu Ala Tyr Ala
                195                 200                 205

Leu Ala Gln Lys Gln Trp Arg Ser Thr Thr Ser Ser Asn Leu Lys Thr
            210                 215                 220

Asn Ser Ser Ile Ser Tyr Leu Lys Ser Gln Glu Phe Asp Lys Asn Ser
225                 230                 235                 240

Trp Gly Trp Ser Trp Leu Glu Arg Trp Met Ala Ala Arg Pro Trp Glu
                245                 250                 255

Thr Arg Leu Met Asp Thr Val Asp Thr Ala Ala Thr Pro Pro Pro Leu
            260                 265                 270

Pro His Lys His Leu Lys Ser Pro Glu Thr Ala Asp Val Val Gln Val
        275                 280                 285

Arg Arg Asn Asn Val Thr Thr Arg Val Ser Ala Lys Pro Pro Pro His
    290                 295                 300

Met Leu Ser Ser Ser Pro Gly Tyr Glu Phe Asn Glu Ser Ser Gly Ser
305                 310                 315                 320

Ser Ser Ile Cys Thr Ser Thr Thr Pro Val Ser Gly Lys Thr Gly Leu
                325                 330                 335

Val Ser Asp Asn Ser Ser Ser Gln Ala Lys Lys His Lys Pro Ser Tyr
            340                 345                 350

Met Ser Leu Thr Glu Ser Thr Lys Ala Lys Arg Arg Thr Asn Arg Gly
        355                 360                 365

Leu Arg Gln Ser Met Asp Glu Phe Gln Phe Met Lys Asn Ser Gly Met
    370                 375                 380

Phe Thr Gly Glu Leu Lys Thr Ser Pro Ser Ser Asp Pro Phe Val Ser
385                 390                 395                 400

Phe Ser Lys Pro Leu Gly Val Pro Thr Arg Phe Glu Lys Pro Arg Gly
                405                 410                 415

<210> SEQ ID NO 110
<211> LENGTH: 442
<212> TYPE: PRT
<213> ORGANISM: Oryza sativa subsp. japonica
<220> FEATURE:
<221> NAME/KEY: misc_feature
<223> OTHER INFORMATION: Public GI ID no.115435054
<220> FEATURE:
<221> NAME/KEY: misc_feature
<223> OTHER INFORMATION: Score of 949.2 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 110

Met Gly Gly Ser Gly Lys Trp Val Lys Ser Leu Ile Gly Leu Lys Lys
1               5                   10                  15

Pro Asp Arg Glu Asp Cys Lys Glu Lys Leu Gln Val Pro Ser Val Asn
            20                  25                  30

Gly Arg Gly Gly Gly Lys Gly Arg Lys Trp Lys Leu Trp Arg Ser Ser
        35                  40                  45

Ser Gly Asp His Gly Ser Leu Trp Arg Gly Ser Arg Gly Gly Gly Gly
    50                  55                  60
```

```
Gly Gly Gly His His Arg Ser Ala Ser Ser Asp Ala Ser Asp Asp Ala
 65                  70                  75                  80

Ser Ser Ala Ala Ala Asp Pro Phe Thr Ala Ala Val Ala Thr Val Ala
                 85                  90                  95

Arg Ala Pro Ala Lys Asp Phe Met Ala Val Arg Gln Glu Trp Ala Ala
            100                 105                 110

Ile Arg Val Gln Thr Ala Phe Arg Gly Phe Leu Ala Arg Arg Ala Leu
        115                 120                 125

Arg Ala Leu Lys Gly Leu Val Arg Leu Gln Ala Ile Val Arg Gly Arg
    130                 135                 140

Gln Val Arg Lys Gln Ala Ala Val Thr Leu Arg Cys Met Gln Ala Leu
145                 150                 155                 160

Val Arg Val Gln Ala Arg Ile Arg Ala Arg Arg Val Arg Met Ser Thr
                165                 170                 175

Glu Gly Gln Ala Val Gln Lys Leu Leu Glu Ala Arg Arg Thr Lys Leu
            180                 185                 190

Asp Ile Leu Arg Glu Ala Glu Glu Gly Trp Cys Asp Ser Gln Gly Thr
        195                 200                 205

Leu Glu Asp Val Arg Val Lys Leu Gln Lys Arg Gln Glu Gly Ala Ile
    210                 215                 220

Lys Arg Glu Arg Ala Ile Ala Tyr Ala Tyr Ser Gln Ile Glu Gly
225                 230                 235                 240

Ala Thr Lys Cys Asn Gln Pro Lys Pro Thr Ser Tyr Gly Arg Leu
                245                 250                 255

Asn Gln Ser Gly Met Leu Leu Lys His Gln His Phe Asp Lys Ser Asn
            260                 265                 270

Gly Asn Trp Ser Trp Leu Glu Arg Trp Met Ala Ala Arg Pro Trp Glu
        275                 280                 285

Asn Arg Leu Met Glu Glu His Asn Gln Thr Asn Ser Ser Pro Asp
    290                 295                 300

Leu Leu Ser Ser Lys Asn Cys Glu Asp Ser Phe Gly Ile Leu Gly Asp
305                 310                 315                 320

Phe Ser Glu Pro Asn Ser Val Lys Val Arg Lys Asn Asn Val Ser Lys
                325                 330                 335

Arg Val Cys Ala Lys Pro Val Val Ser His His Gln Arg Ile Lys
            340                 345                 350

Ala Gln Ser Ile Ser Ser Leu Ser Thr Glu Leu His Asn Asp Glu Ser
        355                 360                 365

Ser Ala Ser Ser Ser Cys Phe Ala Ser Thr Pro Ile Ser Phe Ser
    370                 375                 380

Thr Phe Val Thr Thr Glu Lys Thr Glu Asp Ser Ile Arg Ala Arg Pro
385                 390                 395                 400

Asn Tyr Met Asn Met Thr Glu Ser Ile Lys Ala Lys Arg Lys Ala Cys
                405                 410                 415

Asn Ala Gln Arg Thr Thr Ala Gly Lys Leu Met Glu Asp Arg Lys Ala
            420                 425                 430

Ser Gly Val Glu Leu Lys Val Ala Gln Val
        435                 440

<210> SEQ ID NO 111
<211> LENGTH: 1661
<212> TYPE: DNA
<213> ORGANISM: Gossypium hirsutum
<220> FEATURE:
<221> NAME/KEY: misc_feature
```

<223> OTHER INFORMATION: Ceres CLONE ID no.1847857
<220> FEATURE:
<221> NAME/KEY: misc_feature
<223> OTHER INFORMATION: Encodes the peptide sequence at SEQ ID NO 112

<400> SEQUENCE: 111

```
attttttttc tctttgagtc ttgttgaaga cttgaggttc tctccccccc ccccaccttt      60
ttttggtgca aaaagatttc cttttttgtca ctcatactct gttatcaatt gtttccatcg    120
tagcccattt ccttttttctt ttcttaaata acagttgttt gtatctctga gaaaaatata    180
tactttgaaa ctaccatggg tgcttcagcg aaatgggtga aatctcttat tggtctcaag    240
aaaactgtaa aagatgacca agaaaagatg ggtggcaaga gcaagaaatg gaagctatgg    300
aggagttctt caggggatgg aataggttcc tcatggaagg gttttaaagg aaagtttaaa    360
gcagattacg aaggatctga ttcttcacca aggtctgaag ctttctctgc tgccatggct    420
gctgtggttc gagctcctcc taaagatttc agggttgtaa ggcaagaatg ggctgctatc    480
cgcattcaaa ctgcttttccg aggcttcttg gcaagaaggg ctttaagggc tttaaaggga    540
gtcgttagga tccaagcctt tgttcgcggt cgacaggtga ggaaacaggc tgctgtgaca    600
ctccggtgca tgcaagctct cgttcgtgtc caagctcgtg ttagagctcg tcgtgtccga    660
atgtccatcg agggccaggc agttcaaaag atactcgatg aacaccgcag caaggccgaa    720
ctcttgaaac aagccgagga gggctggtgt gatagtaaag gaacattgga tgatgttaca    780
ataaagctac aactgagaca agaaggtgct ttcaagagag aacgagcact tgcttattct    840
cttgcacaaa agcaatggag attgaacatg gattcaaata ctcgaacaaa tagttcggtt    900
tcagttccat atctcaaaaa ccaagtgttt gataagaata gttggggatg gagttggctt    960
gaacgttgga tggcagcccg gccgtgggaa actcgattga tggagcaatc acaggcagac   1020
ccttccgaac caactccacc atcgaaaact tgttcagagt ctagaaagat tactagaccg   1080
accgaaccat gttcagtgaa ggtacgaaag aacaatgtca aactaggatt tcagcaaag   1140
cctccccata ttggtcaagg tactagatca tcatcgagtc caagttccga attccggttc   1200
gaagagagct ccgcatcatc atcgatatgc acatctacaa cacgggtctc gtggaataca   1260
atgccgactt cagagagaac ggagaagacg gggaatagta ggccaaacta tatgaacttg   1320
acagagtcta ccaaggccaa acaaagagct gcaaatcatg ccttacgaag aatccaaatg   1380
cagtccatgg atgagttcca gttaaagaaa acagctggtt tgtatgatgg ggattcaaag   1440
agtagtgtgg ggtcggatcc tacggtccat atgtctcggc cactgtatcc accaacaaga   1500
ttaggttaaa agtggttgtg tctgtgatta agtagatcgt cagttttatt atgttttcca   1560
acatcttgtt tagttttagt gtgatgtagc aaacaagttg ttgagtgttt ttgtatctaa   1620
ttcgacggca attcattctg caaaaaaaaa aaaaaaaaa a                          1661
```

<210> SEQ ID NO 112
<211> LENGTH: 437
<212> TYPE: PRT
<213> ORGANISM: Gossypium hirsutum
<220> FEATURE:
<221> NAME/KEY: misc_feature
<223> OTHER INFORMATION: Ceres CLONE ID no.1847857
<220> FEATURE:
<221> NAME/KEY: misc_feature
<223> OTHER INFORMATION: Score of 1019.5 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:

<221> NAME/KEY: misc_feature
<222> LOCATION: (91)..(111)
<223> OTHER INFORMATION: Pfam Name: IQ Pfam Description: IQ calmodulin-
      binding motif

<400> SEQUENCE: 112

| Met | Gly | Ala | Ser | Ala | Lys | Trp | Val | Lys | Ser | Leu | Ile | Gly | Leu | Lys | Lys |
|---|---|---|---|---|---|---|---|---|---|---|---|---|---|---|---|
| 1 | | | | 5 | | | | | 10 | | | | | 15 | |

| Thr | Val | Lys | Asp | Asp | Gln | Glu | Lys | Met | Gly | Gly | Lys | Ser | Lys | Lys | Trp |
|---|---|---|---|---|---|---|---|---|---|---|---|---|---|---|---|
| | | | 20 | | | | | 25 | | | | | 30 | | |

| Lys | Leu | Trp | Arg | Ser | Ser | Gly | Asp | Gly | Ile | Gly | Ser | Ser | Trp | Lys |
|---|---|---|---|---|---|---|---|---|---|---|---|---|---|---|
| | | | 35 | | | | 40 | | | | | 45 | | |

| Gly | Phe | Lys | Gly | Lys | Phe | Lys | Ala | Asp | Tyr | Glu | Gly | Ser | Asp | Ser | Ser |
|---|---|---|---|---|---|---|---|---|---|---|---|---|---|---|---|
| | 50 | | | | | 55 | | | | | 60 | | | | |

| Pro | Arg | Ser | Glu | Ala | Phe | Ser | Ala | Ala | Met | Ala | Ala | Val | Val | Arg | Ala |
|---|---|---|---|---|---|---|---|---|---|---|---|---|---|---|---|
| 65 | | | | | 70 | | | | | 75 | | | | | 80 |

| Pro | Pro | Lys | Asp | Phe | Arg | Val | Val | Arg | Gln | Glu | Trp | Ala | Ala | Ile | Arg |
|---|---|---|---|---|---|---|---|---|---|---|---|---|---|---|---|
| | | | | 85 | | | | | 90 | | | | | 95 | |

| Ile | Gln | Thr | Ala | Phe | Arg | Gly | Phe | Leu | Ala | Arg | Arg | Ala | Leu | Arg | Ala |
|---|---|---|---|---|---|---|---|---|---|---|---|---|---|---|---|
| | | | 100 | | | | | 105 | | | | | 110 | | |

| Leu | Lys | Gly | Val | Val | Arg | Ile | Gln | Ala | Phe | Val | Arg | Gly | Arg | Gln | Val |
|---|---|---|---|---|---|---|---|---|---|---|---|---|---|---|---|
| | | 115 | | | | | 120 | | | | | 125 | | | |

| Arg | Lys | Gln | Ala | Ala | Val | Thr | Leu | Arg | Cys | Met | Gln | Ala | Leu | Val | Arg |
|---|---|---|---|---|---|---|---|---|---|---|---|---|---|---|---|
| | 130 | | | | | 135 | | | | | 140 | | | | |

| Val | Gln | Ala | Arg | Val | Arg | Ala | Arg | Arg | Val | Arg | Met | Ser | Ile | Glu | Gly |
|---|---|---|---|---|---|---|---|---|---|---|---|---|---|---|---|
| 145 | | | | | 150 | | | | | 155 | | | | | 160 |

| Gln | Ala | Val | Gln | Lys | Ile | Leu | Asp | Glu | His | Arg | Ser | Lys | Ala | Glu | Leu |
|---|---|---|---|---|---|---|---|---|---|---|---|---|---|---|---|
| | | | | 165 | | | | | 170 | | | | | 175 | |

| Leu | Lys | Gln | Ala | Glu | Glu | Gly | Trp | Cys | Asp | Ser | Lys | Gly | Thr | Leu | Asp |
|---|---|---|---|---|---|---|---|---|---|---|---|---|---|---|---|
| | | | 180 | | | | | 185 | | | | | 190 | | |

| Asp | Val | Thr | Ile | Lys | Leu | Gln | Leu | Arg | Gln | Glu | Gly | Ala | Phe | Lys | Arg |
|---|---|---|---|---|---|---|---|---|---|---|---|---|---|---|---|
| | | 195 | | | | | 200 | | | | | 205 | | | |

| Glu | Arg | Ala | Leu | Ala | Tyr | Ser | Leu | Ala | Gln | Lys | Gln | Trp | Arg | Leu | Asn |
|---|---|---|---|---|---|---|---|---|---|---|---|---|---|---|---|
| 210 | | | | | 215 | | | | | 220 | | | | | |

| Met | Asp | Ser | Asn | Thr | Arg | Thr | Asn | Ser | Ser | Val | Ser | Val | Pro | Tyr | Leu |
|---|---|---|---|---|---|---|---|---|---|---|---|---|---|---|---|
| 225 | | | | | 230 | | | | | 235 | | | | | 240 |

| Lys | Asn | Gln | Val | Phe | Asp | Lys | Asn | Ser | Trp | Gly | Trp | Ser | Trp | Leu | Glu |
|---|---|---|---|---|---|---|---|---|---|---|---|---|---|---|---|
| | | | | 245 | | | | | 250 | | | | | 255 | |

| Arg | Trp | Met | Ala | Ala | Arg | Pro | Trp | Glu | Thr | Arg | Leu | Met | Glu | Gln | Ser |
|---|---|---|---|---|---|---|---|---|---|---|---|---|---|---|---|
| | | | 260 | | | | | 265 | | | | | 270 | | |

| Gln | Ala | Asp | Pro | Ser | Glu | Pro | Thr | Pro | Ser | Lys | Thr | Cys | Ser | Glu |
|---|---|---|---|---|---|---|---|---|---|---|---|---|---|---|
| | | | 275 | | | | | 280 | | | | | 285 | |

| Ser | Arg | Lys | Ile | Thr | Arg | Pro | Thr | Glu | Pro | Cys | Ser | Val | Lys | Val | Arg |
|---|---|---|---|---|---|---|---|---|---|---|---|---|---|---|---|
| | 290 | | | | | 295 | | | | | 300 | | | | |

| Lys | Asn | Asn | Val | Thr | Thr | Arg | Ile | Ser | Ala | Lys | Pro | Pro | His | Ile | Gly |
|---|---|---|---|---|---|---|---|---|---|---|---|---|---|---|---|
| 305 | | | | | 310 | | | | | 315 | | | | | 320 |

| Gln | Gly | Thr | Arg | Ser | Ser | Ser | Pro | Ser | Glu | Phe | Arg | Phe | Glu |
|---|---|---|---|---|---|---|---|---|---|---|---|---|---|
| | | | | 325 | | | | | 330 | | | | 335 |

| Glu | Ser | Ser | Ala | Ser | Ser | Ser | Ile | Cys | Thr | Ser | Thr | Thr | Arg | Val | Ser |
|---|---|---|---|---|---|---|---|---|---|---|---|---|---|---|---|
| | | | 340 | | | | | 345 | | | | | 350 | | |

| Trp | Asn | Thr | Met | Pro | Thr | Ser | Glu | Arg | Thr | Glu | Lys | Thr | Gly | Asn | Ser |
|---|---|---|---|---|---|---|---|---|---|---|---|---|---|---|---|
| | | 355 | | | | | 360 | | | | | 365 | | | |

| Arg | Pro | Asn | Tyr | Met | Asn | Leu | Thr | Glu | Ser | Thr | Lys | Ala | Lys | Gln | Arg |
|---|---|---|---|---|---|---|---|---|---|---|---|---|---|---|---|
| | 370 | | | | | 375 | | | | | 380 | | | | |

Ala Ala Asn His Ala Leu Arg Arg Ile Gln Met Gln Ser Met Asp Glu
385                 390                 395                 400

Phe Gln Leu Lys Lys Thr Ala Gly Leu Tyr Asp Gly Asp Ser Lys Ser
                405                 410                 415

Ser Val Gly Ser Asp Pro Thr Val His Met Ser Arg Pro Leu Tyr Pro
            420                 425                 430

Pro Thr Arg Leu Gly
        435

<210> SEQ ID NO 113
<211> LENGTH: 1353
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1455219
<220> FEATURE:
<221> NAME/KEY: misc_feature
<223> OTHER INFORMATION: Encodes the peptide sequence at SEQ ID NO 114

<400> SEQUENCE: 113
atgggtgcat caggaaaatg ggtgaaatcc attataggtc taaaaaagtc tgataaagat      60
caagaccaat atgagaaggt gagtggaaag agcaagaaat ggaagctatg gaggagttca     120
tcaggagatt tggggtcttc atggaagggt ttcaaaggga accacagagc agcatcagag     180
gcatcgggtt cttcaccact ggctgatcca tttactgctg caatggctac tgtggttaga     240
gctcctccta aggatttcag ggttgtcagg caagaatggg ctgctatcag gattcaaact     300
gcttttcgtg gattcttggc aagaagggct ctgagggcct tgaaaggagt ggtgagactc     360
caagctctag ttcgaggtcg acaagtgagg aagcaggctg cagtgacact taagtgcatg     420
caagctcttg ttcgtgttca agctcatgtt agggctcgtc gtgtgcgaat gtccttagaa     480
gggcaggcag tgcagaatat gctgaatgag cgacgtagca aggctgacct cttgaaacat     540
gctgaggaag ggtggtgtga tagaaagggg acattagaag acgtgaagtc aaaactgcaa     600
atgaggcaag aaggagcctt caagagagaa agagctattg cttactccct tgctcaaaaa     660
caatggagat caaaccccag ctcaaacact cgacccaata actcggtata ttcttttcaag    720 aatgaggagt ttgataagaa tagctgggga tggagttggc ttgaacgttg gatggcagcc     780
aagccatggg agactagatt gatggaacaa acccatactg atccctcagt gactccacca     840
cccaagtcct gtgtagatgc aagcacacat tcgaaatcct tgaacaaag ttcagtgaaa      900 gtgagaaaga caatgtaac cactagaatt tcagcgagac tccaatcgg gcatgttact      960 cgctcatctt caagtccaag ttctgaagtc cgctttgatg agagctcagc ttcttcatca    1020
atttgtactt ctacaacacc aatatcagga aacactggct tggcctcaga taaaacagag   1080
gagagtggta acagcaggcc aaactacatg aacctgaccg agtcaaccaa ggcaaagcaa   1140
aacacatcca gtcatttatt tcataggatt caaaggcagt ccatggatga gtttcagttt   1200
ttcaaaaagt cagcggcgtt ctcaaatgga gattcaaaaa gcagtgctgg ttctgatcct   1260
tcagttaatt tatccaagcc actttgcttg ccgacaagat ttgataagaa ctcgatgaaa   1320
caaataagag gaacggatca tttgtatgcc tag                                1353

<210> SEQ ID NO 114
<211> LENGTH: 450
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1455219
<220> FEATURE:
<221> NAME/KEY: misc_feature
<223> OTHER INFORMATION: Score of 1091.4 for HMM of FIGURE 3.
<220> FEATURE:
<221> NAME/KEY: misc_feature
<223> OTHER INFORMATION: Functional Homolog Of Ceres SEEDLINE ID no.
    ME19173 at SEQ ID NO. 109
<220> FEATURE:
<221> NAME/KEY: misc_feature
<222> LOCATION: (92)..(112)
<223> OTHER INFORMATION: Pfam Name: IQ Pfam Description: IQ calmodulin-
    binding motif

<400> SEQUENCE: 114

```
Met Gly Ala Ser Gly Lys Trp Val Lys Ser Ile Ile Gly Leu Lys Lys
1               5                   10                  15

Ser Asp Lys Asp Gln Asp Gln Tyr Glu Lys Val Ser Gly Lys Ser Lys
            20                  25                  30

Lys Trp Lys Leu Trp Arg Ser Ser Gly Asp Leu Gly Ser Ser Trp
        35                  40                  45

Lys Gly Phe Lys Gly Asn His Arg Ala Ala Ser Glu Ala Ser Gly Ser
    50                  55                  60

Ser Pro Leu Ala Asp Pro Phe Thr Ala Ala Met Ala Thr Val Val Arg
65                  70                  75                  80

Ala Pro Pro Lys Asp Phe Arg Val Val Arg Gln Glu Trp Ala Ala Ile
                85                  90                  95

Arg Ile Gln Thr Ala Phe Arg Gly Phe Leu Ala Arg Arg Ala Leu Arg
            100                 105                 110

Ala Leu Lys Gly Val Val Arg Leu Gln Ala Leu Val Arg Gly Arg Gln
        115                 120                 125

Val Arg Lys Gln Ala Ala Val Thr Leu Lys Cys Met Gln Ala Leu Val
    130                 135                 140

Arg Val Gln Ala His Val Arg Ala Arg Arg Val Arg Met Ser Leu Glu
145                 150                 155                 160

Gly Gln Ala Val Gln Asn Met Leu Asn Glu Arg Arg Ser Lys Ala Asp
                165                 170                 175

Leu Leu Lys His Ala Glu Glu Gly Trp Cys Asp Arg Lys Gly Thr Leu
            180                 185                 190

Glu Asp Val Lys Ser Lys Leu Gln Met Arg Gln Glu Gly Ala Phe Lys
        195                 200                 205

Arg Glu Arg Ala Ile Ala Tyr Ser Leu Ala Gln Lys Gln Trp Arg Ser
    210                 215                 220

Asn Pro Ser Ser Asn Thr Arg Pro Asn Asn Ser Val Tyr Ser Phe Lys
225                 230                 235                 240

Asn Glu Glu Phe Asp Lys Asn Ser Trp Gly Trp Ser Trp Leu Glu Arg
                245                 250                 255

Trp Met Ala Ala Lys Pro Trp Glu Thr Arg Leu Met Glu Gln Thr His
            260                 265                 270

Thr Asp Pro Ser Val Thr Pro Pro Lys Ser Cys Val Asp Ala Ser
        275                 280                 285

Thr His Ser Lys Ser Phe Glu Gln Ser Ser Val Lys Val Arg Lys Asn
    290                 295                 300

Asn Val Thr Thr Arg Ile Ser Ala Arg Pro Pro Ile Gly His Val Thr
305                 310                 315                 320

Arg Ser Ser Ser Ser Pro Ser Ser Glu Val Arg Phe Asp Glu Ser Ser
                325                 330                 335
```

```
Ala Ser Ser Ser Ile Cys Thr Ser Thr Thr Pro Ile Ser Gly Asn Thr
                340                 345                 350

Gly Leu Ala Ser Asp Lys Thr Glu Glu Ser Gly Asn Ser Arg Pro Asn
        355                 360                 365

Tyr Met Asn Leu Thr Glu Ser Thr Lys Ala Lys Gln Asn Thr Ser Ser
370                 375                 380

His Leu Phe His Arg Ile Gln Arg Gln Ser Met Asp Glu Phe Gln Phe
385                 390                 395                 400

Phe Lys Lys Ser Ala Ala Phe Ser Asn Gly Asp Ser Lys Ser Ser Ala
                405                 410                 415

Gly Ser Asp Pro Ser Val Asn Leu Ser Lys Pro Leu Cys Leu Pro Thr
            420                 425                 430

Arg Phe Asp Lys Asn Ser Met Lys Gln Ile Arg Gly Thr Asp His Leu
        435                 440                 445

Tyr Ala
    450

<210> SEQ ID NO 115
<211> LENGTH: 1433
<212> TYPE: DNA
<213> ORGANISM: Zea mays
<220> FEATURE:
<221> NAME/KEY: misc_feature
<223> OTHER INFORMATION: Ceres CLONE ID no.352452
<220> FEATURE:
<221> NAME/KEY: misc_feature
<223> OTHER INFORMATION: Encodes the peptide sequence at SEQ ID NO 116

<400> SEQUENCE: 115
cccacacggc agcaggcagg gcgccatctc ctagcagctc ctcccatggc gtcctctgcc      60
cttcttctcc tccatggccg ccgaagcccc tcccatggcc gacgctctct gctccagccc     120
ctccagcagc tatggcgtcc ccctcctcc ccttcttctt cctcaagcca gcaggcacct      180
ccctctactc cctgcgcgca gcagcagcca tggcgctgcc tctcttctcc atggcgagta     240
gcagctcatt cacctctctc tcccatggcg tgctgctcca gtcggcctcc cttctccccc     300
tcggctcctt cctccaggcc gggccgtgca gaagctgctc gaggcgcgcc gcacccagat     360
ggatatcctc agggaagccg aggaaggatg gtgtgacagc cagggaacac ttgaacaagt     420
gagggtcaag ctgcagaagc ggcaggaggg cgcaatcaag cgtgagcggg ctatcgccta     480
tgcatattcg cagcaggccg acggtgctgc caaatgcaat ccaccgaagc ttacttccaa     540
tggactggtg aaccactccg gcatgctgct caagcaccag aacttagaca agggcaacgg     600
caactggagc tggctggaga ggtggatggc agcgcggcca tgggagaaca ggctgatgga     660
ggagcacaac tccagctccc cggacttccg gtcctccaag aactgcgagg actcctttgg     720
tgtgctcggc gacttctctg aaccgaactc agtgaaggtg cgcaagaaca atgtcagcaa     780
gcgggtctgc gcaaaacctc cagggccaac acacgcccac ggacatcatc agcgcctcaa     840
ggcccagtcg atctcgtctc tgagcactga gctgcacaac gacgagagct ccgcgtcctc     900
ctcgtcttgc tttgcgtcta cccctatatc attcacactt gtggcttcgg agaagaccga     960
ggacagcgtc aggacgagac ccaactacat gagcatgacg gagtcgatca aggctaagca    1020
gaaggcatgc agcgcccaga ggacggtggc gctgaagcaa tgtgatgata ggaaagccat    1080
gagcgccgag ttgaaggtcg ctcaggtgtg actgtttcgt ggaactccat gcagagatgg    1140
agccgacttc gacatcctct ctatgcccta ggatgtgttg cttggtgtct tgccacattc    1200
ttgagtggct cggtgctgca ttcctgagtt gtcctcctgt tgctgggtgt ctgattattc    1260
```

```
aacttcttgt tgtcagattg catctttgtt cagtcattgt ggctgcatct ttgttcagcc   1320
gttgtggctt tgtcagtggt agagtctctg taagatagtt ctttgagtag acagcattgt   1380
ggatttcttt cctgggtgtt gatttcaggt caaaaaagac aggataattt act          1433
```

<210> SEQ ID NO 116
<211> LENGTH: 250
<212> TYPE: PRT
<213> ORGANISM: Zea mays
<220> FEATURE:
<221> NAME/KEY: misc_feature
<223> OTHER INFORMATION: Ceres CLONE ID no.352452
<220> FEATURE:
<221> NAME/KEY: misc_feature
<223> OTHER INFORMATION: Score of 121.9 for HMM of FIGURE 3.
<220> FEATURE:
<221> NAME/KEY: misc_feature
<223> OTHER INFORMATION: Functional Homolog Of Ceres SEEDLINE ID no.
    ME19173 at SEQ ID NO. 109

<400> SEQUENCE: 116

```
Met Asp Ile Leu Arg Glu Ala Glu Glu Gly Trp Cys Asp Ser Gln Gly
1               5                   10                  15

Thr Leu Glu Gln Val Arg Val Lys Leu Gln Lys Arg Gln Glu Gly Ala
            20                  25                  30

Ile Lys Arg Glu Arg Ala Ile Ala Tyr Ala Tyr Ser Gln Gln Ala Asp
        35                  40                  45

Gly Ala Ala Lys Cys Asn Pro Pro Lys Leu Thr Ser Asn Gly Leu Val
    50                  55                  60

Asn His Ser Gly Met Leu Leu Lys His Gln Asn Leu Asp Lys Gly Asn
65                  70                  75                  80

Gly Asn Trp Ser Trp Leu Glu Arg Trp Met Ala Ala Arg Pro Trp Glu
                85                  90                  95

Asn Arg Leu Met Glu Glu His Asn Ser Ser Ser Pro Asp Phe Arg Ser
            100                 105                 110

Ser Lys Asn Cys Glu Asp Ser Phe Gly Val Leu Gly Asp Phe Ser Glu
        115                 120                 125

Pro Asn Ser Val Lys Val Arg Lys Asn Val Ser Lys Arg Val Cys
    130                 135                 140

Ala Lys Pro Pro Gly Pro Thr His Ala His Gly His His Gln Arg Leu
145                 150                 155                 160

Lys Ala Gln Ser Ile Ser Ser Leu Ser Thr Glu Leu His Asn Asp Glu
                165                 170                 175

Ser Ser Ala Ser Ser Ser Ser Cys Phe Ala Ser Thr Pro Ile Ser Phe
            180                 185                 190

Thr Leu Val Ala Ser Glu Lys Thr Glu Asp Ser Val Arg Thr Arg Pro
        195                 200                 205

Asn Tyr Met Ser Met Thr Glu Ser Ile Lys Ala Lys Gln Lys Ala Cys
    210                 215                 220

Ser Ala Gln Arg Thr Val Ala Leu Lys Gln Cys Asp Asp Arg Lys Ala
225                 230                 235                 240

Met Ser Ala Glu Leu Lys Val Ala Gln Val
                245                 250
```

<210> SEQ ID NO 117
<211> LENGTH: 1949
<212> TYPE: DNA
<213> ORGANISM: Triticum aestivum
<220> FEATURE:

<221> NAME/KEY: misc_feature
<223> OTHER INFORMATION: Ceres CLONE ID no.787908
<220> FEATURE:
<221> NAME/KEY: misc_feature
<223> OTHER INFORMATION: Encodes the peptide sequence at SEQ ID NO 118

<400> SEQUENCE: 117

```
acacaggcag gcagccgagc cgagcgagca ataattcgca ccggcacaca ggagcggcag      60
taatggccgc gtggtgccgg tgccagtagc aggcaggcag gcaggggagt agcgccactg     120
cactgggcac tgctgacgct tcgagcccac gctcttccct ccaccccttgc ccctccctcc    180
cgaaactccc tccctcccctt ggcctcctca ggcctcccaa tctcgcagag cggcggccgt    240
cattggccgg cggcggtgcg cggccccggt tgtttcctcc ggcgtcaggt gcccgtgatc    300
tggttgttgc agaggcggcg aggtgaggtg acgcggcggc gcgatgaggt ggctcaagtc    360
gttggttggg ctgaggaagg tggagaggca gcagcagcgc cgcaaggagg atggcgacgc    420
cggcccaaca aaaacagatg ccgtcgatca gttccacttc caggatcagc actcccagga    480
tcacgctagc cttgtcggac cagaagagtt ccctgatgaa aatggtccgt cagaagatga    540
gtgcgataca ccttcatgct caggacctgg tttcagtatg cttagtgtgc cactgcctca    600
aacagaagag gagctcaaag agatctgggc tgccacaatt attcagactg catatagagc    660
cctactggct aggagagccc gccgagcttt aaaaggactg gttaggcttc aagcccttgt    720
aaggggtcat atagtgagaa agcaagctgc tataacactt cggtgtatgc aagctttggt    780
cagggtacaa gcccgtgtta gagcaaggcg ggttcgtgtg gccttggaaa atcagatgga    840
tgagcaacaa ataatgtag aagagcaaac ggacgaggca catgttcgag aagttgagga    900
tgggtggtgc gatagtatag ggtctgtgga agacatccaa gcaaaattgt tgaagaggca    960
ggaagcagca gccaagcgtg agagagccat ggcctatgcc ctttctcacc agtggcaagc   1020
aggttcaagg caacaggcag ccattacagc ttctgaacta gacaggaaca gctggagctg   1080
gaattggctg gagagatgga tggccgtccg cccgtgggag agtcggttcc ttggcatgta   1140
cgcagcagat ggaattgcca ttgataccgg agcgcacaat gctgagggaa atgcaaccaa   1200
ggctccatac aggaaacctg tgaaaaagca ggtttcagct cttcattcaa gtgtgttgat   1260
ccagaaggcc cgcccctcga actcggaggg tggtggctcc ttgtcgaacc cgtctgccgg   1320
ttcggcgtca gctaaaccga acggaagct gccaccaaag gaaggttctg atgaagtctc    1380
gtctcgtctt tcgggacttg gtgcccggag cagtagtaat cctaaggaga ggcctgggca   1440
gttacaacct cgggccaaca agaggttctc cttgcctggc actggcacag aagttggcaa   1500
acggcaagtg aataaacctg cggtgaaccg atcccccaag gctaccgaag actccccagc   1560
gctggaaggg aagcatcgcc gtgccggttc cgttggtctg ctgctcaaga gagttgagct   1620
gcaggcttga caagccatct gaagcccat ctaccgtcgt caaggttcga agtcagcatg    1680
ctgcgctctg atacatgggc ggccttagat tctggaaggt ccattggagc aatgtgcatt   1740
tatttcttag ccatattata ggtatgcagt caaaatgctc atctcaggag atgagatcta   1800
gctagtgctt ggatatgtat gtgctggtca gctggtgcct ctagtcctgg aggttaccat   1860
agcttgtact gttgtatttg tagctaagag caagtatggg ctcacatttt ctggaactat   1920
tttttgtaca atgaaaaaaa aaaaaaaaa                                    1949
```

<210> SEQ ID NO 118
<211> LENGTH: 428
<212> TYPE: PRT
<213> ORGANISM: Triticum aestivum -continued

```
<220> FEATURE:
<221> NAME/KEY: misc_feature
<223> OTHER INFORMATION: Ceres CLONE ID no.787908
<220> FEATURE:
<221> NAME/KEY: misc_feature
<223> OTHER INFORMATION: Score of 891.9 for HMM of FIGURE 3.
<220> FEATURE:
<221> NAME/KEY: misc_feature
<223> OTHER INFORMATION: Functional Homolog Of Ceres SEEDLINE ID no.
    ME19173 at SEQ ID NO. 109
<220> FEATURE:
<221> NAME/KEY: misc_feature
<222> LOCATION: (94)..(112)
<223> OTHER INFORMATION: Pfam Name: IQ Pfam Description: IQ calmodulin-
    binding motif

<400> SEQUENCE: 118

Met Arg Trp Leu Lys Ser Leu Val Gly Leu Arg Lys Val Glu Arg Gln
1               5                   10                  15

Gln Gln Arg Arg Lys Glu Asp Gly Asp Ala Gly Pro Thr Lys Thr Asp
            20                  25                  30

Ala Val Asp Gln Phe His Phe Gln Asp Gln His Ser Gln Asp His Ala
        35                  40                  45

Ser Leu Val Gly Pro Glu Glu Phe Pro Asp Glu Asn Gly Pro Ser Glu
    50                  55                  60

Asp Glu Cys Asp Thr Pro Ser Cys Ser Gly Pro Gly Phe Ser Met Leu
65                  70                  75                  80

Ser Val Pro Leu Pro Gln Thr Glu Glu Leu Lys Glu Ile Trp Ala
                85                  90                  95

Ala Thr Ile Ile Gln Thr Ala Tyr Arg Ala Leu Leu Ala Arg Arg Ala
            100                 105                 110

Arg Arg Ala Leu Lys Gly Leu Val Arg Leu Gln Ala Leu Val Arg Gly
        115                 120                 125

His Ile Val Arg Lys Gln Ala Ala Ile Thr Leu Arg Cys Met Gln Ala
    130                 135                 140

Leu Val Arg Val Gln Ala Arg Val Arg Ala Arg Arg Val Arg Val Ala
145                 150                 155                 160

Leu Glu Asn Gln Met Asp Glu Gln Gln Asn Asn Val Glu Glu Gln Thr
                165                 170                 175

Asp Glu Ala His Val Arg Glu Val Glu Asp Gly Trp Cys Asp Ser Ile
            180                 185                 190

Gly Ser Val Glu Asp Ile Gln Ala Lys Leu Leu Lys Arg Gln Glu Ala
        195                 200                 205

Ala Ala Lys Arg Glu Arg Ala Met Ala Tyr Ala Leu Ser His Gln Trp
    210                 215                 220

Gln Ala Gly Ser Arg Gln Gln Ala Ala Ile Thr Ala Ser Glu Leu Asp
225                 230                 235                 240

Arg Asn Ser Trp Ser Trp Asn Trp Leu Glu Arg Trp Met Ala Val Arg
                245                 250                 255

Pro Trp Glu Ser Arg Phe Leu Gly Met Tyr Ala Ala Asp Gly Ile Ala
            260                 265                 270

Ile Asp Thr Gly Ala His Asn Ala Glu Gly Asn Ala Thr Lys Ala Pro
        275                 280                 285

Tyr Arg Lys Pro Val Lys Lys Gln Val Ser Ala Leu His Ser Ser Val
    290                 295                 300

Leu Ile Gln Lys Ala Arg Pro Ser Asn Ser Glu Gly Gly Gly Ser Leu
305                 310                 315                 320

Ser Asn Pro Ser Ala Gly Ser Ala Ser Ala Lys Pro Lys Arg Lys Leu
```

```
                    325                 330                 335
Pro Pro Lys Glu Gly Ser Asp Glu Val Ser Ser Arg Leu Ser Gly Leu
            340                 345                 350

Gly Ala Arg Ser Ser Ser Asn Pro Lys Glu Arg Pro Gly Gln Leu Gln
                355                 360                 365

Pro Arg Ala Asn Lys Arg Phe Ser Leu Pro Gly Thr Gly Thr Glu Val
            370                 375                 380

Gly Lys Arg Gln Val Asn Lys Pro Ala Val Asn Arg Ser Pro Lys Ala
385                 390                 395                 400

Thr Glu Asp Ser Pro Ala Leu Glu Gly Lys His Arg Arg Ala Gly Ser
                405                 410                 415

Val Gly Leu Leu Leu Lys Arg Val Glu Leu Gln Ala
            420                 425

<210> SEQ ID NO 119
<211> LENGTH: 442
<212> TYPE: PRT
<213> ORGANISM: Unknown
<220> FEATURE:
<223> OTHER INFORMATION: Plant derived amino acid sequence
<220> FEATURE:
<221> NAME/KEY: misc_feature
<223> OTHER INFORMATION: Ceres LOCUS ID no. Os01m00929_AP002743
<220> FEATURE:
<221> NAME/KEY: misc_feature
<223> OTHER INFORMATION: Score of 949.2 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 119

Met Gly Gly Ser Gly Lys Trp Val Lys Ser Leu Ile Gly Leu Lys Lys
1               5                   10                  15

Pro Asp Arg Glu Asp Cys Lys Glu Lys Leu Gln Val Pro Ser Val Asn
                20                  25                  30

Gly Arg Gly Gly Gly Lys Gly Arg Lys Trp Lys Leu Trp Arg Ser Ser
            35                  40                  45

Ser Gly Asp His Gly Ser Leu Trp Arg Gly Ser Arg Gly Gly Gly Gly
        50                  55                  60

Gly Gly Gly His His Arg Ser Ala Ser Ser Asp Ala Ser Asp Asp Ala
65                  70                  75                  80

Ser Ser Ala Ala Ala Asp Pro Phe Thr Ala Val Ala Thr Val Ala
                85                  90                  95

Arg Ala Pro Ala Lys Asp Phe Met Ala Val Arg Gln Glu Trp Ala Ala
                100                 105                 110

Ile Arg Val Gln Thr Ala Phe Arg Gly Phe Leu Ala Arg Arg Ala Leu
            115                 120                 125

Arg Ala Leu Lys Gly Leu Val Arg Leu Gln Ala Ile Val Arg Gly Arg
        130                 135                 140

Gln Val Arg Lys Gln Ala Ala Val Thr Leu Arg Cys Met Gln Ala Leu
145                 150                 155                 160

Val Arg Val Gln Ala Arg Ile Arg Ala Arg Arg Val Arg Met Ser Thr
                165                 170                 175

Glu Gly Gln Ala Val Gln Lys Leu Leu Glu Ala Arg Arg Thr Lys Leu
```

```
                    180                 185                 190
Asp Ile Leu Arg Glu Ala Glu Glu Gly Trp Cys Asp Ser Gln Gly Thr
            195                 200                 205
Leu Glu Asp Val Arg Val Lys Leu Gln Lys Arg Gln Glu Gly Ala Ile
        210                 215                 220
Lys Arg Glu Arg Ala Ile Ala Tyr Ala Tyr Ser Gln Gln Ile Glu Gly
225                 230                 235                 240
Ala Thr Lys Cys Asn Gln Gln Pro Lys Pro Thr Ser Tyr Gly Arg Leu
            245                 250                 255
Asn Gln Ser Gly Met Leu Leu Lys His Gln His Phe Asp Lys Ser Asn
        260                 265                 270
Gly Asn Trp Ser Trp Leu Glu Arg Trp Met Ala Ala Arg Pro Trp Glu
    275                 280                 285
Asn Arg Leu Met Glu Glu His Asn Gln Thr Asn Ser Ser Ser Pro Asp
        290                 295                 300
Leu Leu Ser Ser Lys Asn Cys Glu Asp Ser Phe Gly Ile Leu Gly Asp
305                 310                 315                 320
Phe Ser Glu Pro Asn Ser Val Lys Val Arg Lys Asn Asn Val Ser Lys
            325                 330                 335
Arg Val Cys Ala Lys Pro Val Val Ser His His Gln Arg Ile Lys
        340                 345                 350
Ala Gln Ser Ile Ser Ser Leu Ser Thr Glu Leu His Asn Asp Glu Ser
        355                 360                 365
Ser Ala Ser Ser Ser Ser Cys Phe Ala Ser Thr Pro Ile Ser Phe Ser
    370                 375                 380
Thr Phe Val Thr Thr Glu Lys Thr Glu Asp Ser Ile Arg Ala Arg Pro
385                 390                 395                 400
Asn Tyr Met Asn Met Thr Glu Ser Ile Lys Ala Lys Lys Ala Cys
            405                 410                 415
Asn Ala Gln Arg Thr Thr Ala Gly Lys Leu Met Glu Asp Arg Lys Ala
        420                 425                 430
Ser Gly Val Glu Leu Lys Val Ala Gln Val
        435                 440

<210> SEQ ID NO 120
<211> LENGTH: 1801
<212> TYPE: DNA
<213> ORGANISM: Zea mays
<220> FEATURE:
<221> NAME/KEY: misc_feature
<223> OTHER INFORMATION: Ceres CLONE ID no.246398
<220> FEATURE:
<221> NAME/KEY: misc_feature
<223> OTHER INFORMATION: Encodes the peptide sequence at SEQ ID NO 121

<400> SEQUENCE: 120
gtctcgtctc tacgcccgct ctccactctt cctcccaaag cctgccgccg cgtgggggt       60 tgcttgctgg ctgcccgctc ctctccctgc tcctcctgtg tctgccgccc accgcttccg    120
ggaacaagtc cggttgccgc cgccgccgtc gctgctctgt ccgagaggag gaggaacag    180 agcgggatgg gagggtccgg gaagtgggtc aagtcgctga tagggctcaa gaagcagccc    240
gagaaggaag actgcaagga caagctgcag ctcccatcag tccacggcgg aggattgcga    300
ggcaagggcc gcaggtggaa gctgtggcgg acctcctccg gcgaccaggg ctccatgtgg    360
cgcggctcca gaggcggcag ccagcgctcg gcggcgtcgg aggcctcgga cgacgcgtcc    420
tcggtggccg ccgtccccgc cgacccgttc acggccgccg tcgccaccgt cgcccgcgcc    480
```

```
ccggccaggg acttcatggc cgtccgccag gagtgggccg ccatccgcgt ccagaccgcg    540
ttccgcgggt tcttggctcg gcgggcgctc cgggcgctca aggggctggt gcggctccag    600
gcgatcgtgc gcgggcggca ggtgcggaag caggcggccg tgacgctgcg gtgcatgcag    660
gcgctggtgc gggtgcaggc gcgcatccgg gcgcgccgcg tgcgcatgtc caccgagggc    720
caggccgtgc agaagctgct cgaggcgcgc cgcacccaga tggatatcct cagggaagcc    780
gaggaaggat ggtgtgacag ccagggaaca cttgaacaag tgagggtcaa gctgcagaag    840
cggcaggagg gcgcaatcaa gcgtgagcgg ggctatcgcc tatgcatatt cgcagcaggc    900
cgacggtgct gccaaatgca atccaccgaa gcttacttcc aatggactgg tgaaccactc    960
cggcatgctg ctcaagcacc agaacttaga caagggcaac ggcaactgga gctggctgga    1020
gaggtggatg gcagcgcggc catgggagaa caggctgatg gaggagcaca actccagctc    1080
cccggacttc cggtcctcca agaactgcga ggactccttt ggtgtgctcg gcgacttctc    1140
tgaaccgaac tcagtgaaga tgcgcaagaa caatgtcagc aagcgggtct gcgcaaaacc    1200
tccagggcca acacacgccc acggacatca tcagcgcctc aaggcccagt cgatctcgtc    1260
tctgagcact gagctgcaca cgacgagag ctccgcgtcc tcctcgtctt gctttgcgtc    1320 taccctata tcattcacac ttgtggcttc ggagaagacc gaggacagcg tcaggacgag    1380
acccaactac atgagcatga cggagtcgat caaggctaag cagaaggcat gcagcgccca    1440
gaggacggtg gcgctgargc aatgtgatga taggaaagcc atgagcgccg agttgaaggt    1500
cgctcaggtg tgactgtttc gtggaactcc atgcagagat ggagccgact tcgacatcct    1560
ctctatgccc taggatgtgt tgcttggtgt cttgccacat tcttgagtgg ctcggtgctg    1620
cattcctgag ttgtcctcct gttgctgggt gtctgattat tcaacttctt gttgtcagat    1680
tgcatctttg ttcagtcatt gtggctgcat cttttgttcag ccgttgtggc tttgtcagtg    1740
gtagagtctc tgtaagatag ttctttgagt akryagtwtt gkggatktct ktcctrkgtk    1800
t                                                                      1801
```

<210> SEQ ID NO 121
<211> LENGTH: 318
<212> TYPE: PRT
<213> ORGANISM: Zea mays
<220> FEATURE:
<221> NAME/KEY: misc_feature
<223> OTHER INFORMATION: Ceres CLONE ID no.246398
<220> FEATURE:
<221> NAME/KEY: misc_feature
<223> OTHER INFORMATION: Score of 291.2 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 121

Met Gly Gly Ser Gly Lys Trp Val Lys Ser Leu Ile Gly Leu Lys Lys
1               5                   10                  15

Gln Pro Glu Lys Glu Asp Cys Lys Asp Lys Leu Gln Leu Pro Ser Val
            20                  25                  30

His Gly Gly Gly Leu Arg Gly Lys Gly Arg Arg Trp Lys Leu Trp Arg
        35                  40                  45

```
Thr Ser Ser Gly Asp Gln Gly Ser Met Trp Arg Gly Ser Arg Gly Gly
    50              55                  60

Ser Gln Arg Ser Ala Ala Ser Glu Ala Ser Asp Asp Ala Ser Ser Val
65              70                  75                  80

Ala Ala Val Pro Ala Asp Pro Phe Thr Ala Val Ala Thr Val Ala
                85                  90                  95

Arg Ala Pro Ala Arg Asp Phe Met Ala Val Arg Gln Glu Trp Ala Ala
            100                 105                 110

Ile Arg Val Gln Thr Ala Phe Arg Gly Phe Leu Ala Arg Ala Leu
            115                 120                 125

Arg Ala Leu Lys Gly Leu Val Arg Leu Gln Ala Ile Val Arg Gly Arg
130                 135                 140

Gln Val Arg Lys Gln Ala Ala Val Thr Leu Arg Cys Met Gln Ala Leu
145                 150                 155                 160

Val Arg Val Gln Ala Arg Ile Arg Ala Arg Arg Val Arg Met Ser Thr
                165                 170                 175

Glu Gly Gln Ala Val Gln Lys Leu Leu Glu Ala Arg Arg Thr Gln Met
            180                 185                 190

Asp Ile Leu Arg Glu Ala Glu Glu Gly Trp Cys Asp Ser Gln Gly Thr
            195                 200                 205

Leu Glu Gln Val Arg Val Lys Leu Gln Lys Arg Gln Glu Gly Ala Ile
210                 215                 220

Lys Arg Glu Arg Gly Tyr Arg Leu Cys Ile Phe Ala Ala Gly Arg Arg
225                 230                 235                 240

Cys Cys Gln Met Gln Ser Thr Glu Ala Tyr Phe Gln Trp Thr Gly Glu
                245                 250                 255

Pro Leu Arg His Ala Ala Gln Ala Pro Glu Leu Arg Gln Gly Gln Arg
            260                 265                 270

Gln Leu Glu Leu Ala Gly Glu Val Asp Gly Ser Ala Ala Met Gly Glu
            275                 280                 285

Gln Ala Asp Gly Gly Ala Gln Leu Gln Leu Pro Gly Leu Pro Val Leu
            290                 295                 300

Gln Glu Leu Arg Gly Leu Leu Trp Cys Ala Arg Arg Leu Leu
305                 310                 315
```

<210> SEQ ID NO 122
<211> LENGTH: 440
<212> TYPE: PRT
<213> ORGANISM: Oryza sativa subsp. indica
<220> FEATURE:
<221> NAME/KEY: misc_feature
<223> OTHER INFORMATION: Public GI ID no.125527441
<220> FEATURE:
<221> NAME/KEY: misc_feature
<223> OTHER INFORMATION: Score of 619.5 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (87)..(107)
<223> OTHER INFORMATION: Pfam Name: IQ Pfam Description: IQ calmodulin-
      binding motif

<400> SEQUENCE: 122

```
Met Gly Ala Ser Gly Lys Trp Ile Arg Thr Leu Val Gly Leu Arg Pro
1               5                   10                  15

Ala Ala Glu Arg Glu Lys Glu Arg Gly Gly Gly Gly Lys Gly Arg
            20                  25                  30
```

```
Lys Trp Ser Arg Leu Trp Arg Ser Ser Ser Gln Arg Gly Gly Gly
        35                  40                  45

Asn Ala Ser Ala Ser Glu Val Tyr Ser Glu Thr Ser Ser Ser Ala Asp
    50                  55                  60

Ala Leu Ser Ser Val Val Ala Ala Val Val Arg Ala Pro Pro Arg Asp
65                  70                  75                  80

Phe Arg Leu Ile Arg Gln Glu Trp Ala Ala Val Arg Ile Gln Thr Ala
                85                  90                  95

Phe Arg Ala Phe Leu Ala Arg Arg Ala Leu Arg Ala Leu Arg Gly Ile
            100                 105                 110

Val Arg Leu Gln Ala Leu Val Arg Gly Arg Arg Val Arg Lys Gln Leu
            115                 120                 125

Ala Val Thr Leu Lys Cys Met Gln Ala Leu Val Arg Val Gln Ala Arg
            130                 135                 140

Ala Arg Asp Arg Arg Ala Arg Ile Ser Ala Asp Gly Leu Asp Ser Gln
145                 150                 155                 160

Asp Met Leu Asp Glu Arg Gly Gly Arg Val Asp Pro Val Lys Glu Ala
                165                 170                 175

Glu Ala Gly Trp Cys Asp Ser Gln Gly Thr Ala Asp Asp Val Arg Ser
            180                 185                 190

Lys Ile His Met Arg His Glu Gly Ala Ile Lys Arg Glu Arg Ala Leu
            195                 200                 205

Thr Tyr Ala Gln Ser His Gln Arg Cys Ser Asn His Gly Gly Arg Pro
    210                 215                 220

Ser Ser Pro Ala Val Ser Leu Lys His His Gly Asn Gly Ala Thr Arg
225                 230                 235                 240

Ser Asn His Ser Trp Ser Tyr Leu Glu Gly Trp Met Ala Thr Lys Pro
                245                 250                 255

Trp Glu Ser Arg Leu Met Glu Gln Thr His Thr Glu Asn Ser Thr Asn
            260                 265                 270

Ser Arg Cys Ser Glu Ser Val Glu Glu Val Ser Val Gly Gly Pro Lys
            275                 280                 285

Leu Ser Asp Ala Ser Ser Val Lys Ile Arg Arg Asn Asn Val Thr Lys
    290                 295                 300

Arg Val Ala Ala Lys Pro Pro Ser Met Ile Ser Ala Thr Ser Ser Asp
305                 310                 315                 320

Phe Val Cys Asp Glu Ser Ser Pro Ser Thr Ser Ser Val Thr Pro Leu
                325                 330                 335

Ser Ala Asn Asn Ser Leu Ala Thr Glu Arg Arg Ser Asp Cys Gly Gln
            340                 345                 350

Val Gly Gly Pro Ser Tyr Met Ser Leu Thr Lys Ser Ala Lys Ala Arg
            355                 360                 365

Leu Ser Gly Tyr Gly Ser His Lys Pro Pro Leu Gln Arg Gln Arg Ser
    370                 375                 380

Gly Asp Leu Leu His His Asn Arg Met Ala Phe Ser Ser Ile Asp Val
385                 390                 395                 400

Gln Ser Thr Ala Gly Ser Glu Val Ser Val Thr Ser Lys Arg Leu Asn
                405                 410                 415

Ser Leu Ala Leu Lys Gly Arg Ala Thr Arg Ser Leu Asp Lys Glu Asn
            420                 425                 430

Glu Arg Arg Pro Ser Ser Leu Leu
            435                 440
```

-continued

```
<210> SEQ ID NO 123
<211> LENGTH: 420
<212> TYPE: PRT
<213> ORGANISM: Oryza sativa subsp. japonica
<220> FEATURE:
<221> NAME/KEY: misc_feature
<223> OTHER INFORMATION: Public GI ID no.125595056
<220> FEATURE:
<221> NAME/KEY: misc_feature
<223> OTHER INFORMATION: Score of 536.3 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (79)..(99)
<223> OTHER INFORMATION: Pfam Name: IQ Pfam Description: IQ calmodulin-
      binding motif

<400> SEQUENCE: 123

Met Gly Ala Ser Gly Lys Trp Ile Lys Ser Leu Val Ser Leu Lys Ala
1               5                   10                  15

Ala Pro Glu Gly Thr Thr Lys Gly Arg Arg Trp Thr Arg Leu Trp Arg
            20                  25                  30

Ser Ser Ser Ser Ala Ser Ala Ser Ala Ser Thr Ala Gly Asp Ala Ser
        35                  40                  45

Glu Ser Ala Ser Ser Glu Ala Asp Ala Phe Ser Val Val Ala Ala
    50                  55                  60

Val Val Arg Ala Pro Pro Arg Asp Phe Arg Val Ile Arg Gln Glu Trp
65                  70                  75                  80

Ala Ala Val Arg Val Gln Ala Ala Phe Arg Ala Phe Leu Ala Arg Arg
                85                  90                  95

Ala Leu Lys Ala Leu Arg Gly Ile Val Arg Leu Gln Ala Leu Val Arg
            100                 105                 110

Gly Arg Leu Val Arg Arg Gln Leu Ala Val Thr Leu Lys Cys Met Asn
        115                 120                 125

Ala Leu Leu Arg Val Gln Glu Arg Ala Arg Glu Arg Arg Ala Arg Cys
    130                 135                 140

Ser Ala Asp Gly Arg Asp Ser Gln Asp Ala Val Gly Glu Arg Asp Gly
145                 150                 155                 160

Arg Ala Asp Pro Ile Lys Gln Ala Glu Ala Leu Ile Leu Gln Leu Leu
                165                 170                 175

Pro Pro Phe His Asn Glu Gln Trp Cys Asp Ser Gln Gly Ser Val Ser
            180                 185                 190

Glu Val Arg Ser Lys Ile His Met Arg His Asp Ala Val Ala Lys Arg
        195                 200                 205

Glu Arg Ala Ile Ala Tyr Ala Leu Ser His Gln Pro Arg Ser Ser Lys
    210                 215                 220

Gln Ser Ala Arg Pro Ser Ser Pro Ala Arg Ser Leu Arg Asn His Glu
225                 230                 235                 240

Ser Asn Arg Cys Asn His Asp Trp Ser Tyr Ile Glu Gly Trp Met Ala
                245                 250                 255

Thr Lys Pro Trp Glu Ser Arg Leu Met Glu Gln Ser His Ala Glu Leu
            260                 265                 270

Lys Cys Ser Lys Asn Ser Gly Glu Leu Asn Leu Ala Gly Ala Gln Leu
        275                 280                 285

Ser Asn Ala Ser Ser Val Lys Met Arg Gly Asn Arg Val Ala Ala Lys
    290                 295                 300
```

```
Pro Pro Ser Val Leu Ser Ala Ser Ser Asp Phe Pro Cys Asp Val
305                 310                 315                 320

Ser Ser Ala Ser Thr Ser Ser Ala Thr Pro Ala Arg Ser Asp Gly Gly
                325                 330                 335

His Gly Glu Gly Pro Ser Tyr Met Ser Leu Thr Lys Ser Ala Lys Ala
            340                 345                 350

Arg Gln Ser Cys Asn Ser Pro Phe Gln Ile Gln Arg Gln Arg Ser Gly
        355                 360                 365

Gly Met Ser Ser Tyr Lys Arg Val Ala Leu Ser Pro Leu Asp Val Gln
    370                 375                 380

Ser Asn Ala Cys Ser Glu Phe Ser Val Thr Ser Arg Lys Leu Asn Ser
385                 390                 395                 400

Leu Ser Leu Lys Gly Arg Ser Met Thr Arg Ser Leu Asp Lys Glu Asn
                405                 410                 415

Asp Asn Leu Phe
            420

<210> SEQ ID NO 124
<211> LENGTH: 1682
<212> TYPE: DNA
<213> ORGANISM: Zea mays
<220> FEATURE:
<221> NAME/KEY: misc_feature
<223> OTHER INFORMATION: Ceres CLONE ID no.236071
<220> FEATURE:
<221> NAME/KEY: misc_feature
<223> OTHER INFORMATION: Encodes the peptide sequence at SEQ ID NO 125

<400> SEQUENCE: 124
acatcccagt gccgagtgtc cccacacaac caagcggaag cttcggtcga acagagggag      60
taagcagttg cgtttcgcat tgcgcggcgc cgatgggggc gtcggggaag tggatcaagt     120
cgctggtggc cctgaaggcg cccgagaagg cggcggggca aaggcggt cgcaaatggc       180 gtctctggcg gagctcgtcg gccacgtcca gggccagcgc cggcgagggc agtgcgctgg    240
cgtccgagtc ttcttcggcg tcggccgact cgttcaactc ggtcctcgcc gccgtggtcc    300
gcgcgccgcc cagggatttc ctgctcatca ggcaggaatg ggccgccgtc cgcatccata    360
ccgccttccg cggattcttg gcagacggg cgttgaaggc gctgaggggc atcgtccggc     420
tgcaggcgct ggtgcgcggc cggcgcgtgc gcaagcaact ggccgtcacg ctcaagtgca    480
tgcacgcact gctgcgggtg caggaacgcg cccgggagcg ccgggcgcgc tcctccgctg    540
atggccacgg ctcacagggc caggacgcgc tcaacggctg tgccagttct accaaagacg    600
ctatggaaca atggtgtgac cgccacggat ctgttgctga agtaagatca aatttacaca    660
tgaagcatga aggtgcagca aagagagaaa gggcaattgc ctatgctgtg tctcaccagc    720
ctcggggttc aagacagaag gggagaccaa gctctcctgc taactgcgtt agaagccatg    780
atcctaatgg gtgcgatcag gacttcagtt acttagacgg atggatgca acgaagccat      840 gggagaccag atctacggag cgaaaccata gcgactcgca gctcgcgaag cacgaggagc    900
tgaacttgcc cgcctccaag ctttccgatg ccagctcagt taagatcaga agaaacaatg    960
tcacaactag ggtatctgca gcaaagcgtc ctcctccatc ttcagtgctg tcagctgctt   1020
cttccgactc cgcgtgcggc ggcgagagct ctcggtcgag accatcggtg accctgacgt   1080
ctgctaccac caaacactgtc ttagcgtcag aagcaagatc agacagtggc gacaccggag   1140
gcccgaacta catgagcttg accaagtctg ccaaggcgag gctgagtgga tgcagcggca   1200
```

-continued

```
gcagccatca caggtcgttc cagcgaccac ggtccgggga catgtcgagg gtgacactgt    1260
cttcgatcga cacccagagc aacgcgggct cggagatttc agtcacctcg aagagactga    1320
acagcatgtc cctgaacctg aaaggccgga gcttggacaa ggagaacgag gaggattgat    1380
ccatccacca acggacaaag cagctgtcgt aggtctggtg cagtactacc acgcgttcaa    1440
agcagcatct ctgtatttac ggaatttacg gaggaagacg cggtttatct ctttcataaa    1500
ctccacacat gtcacatgtg agagagctct ggcactaggt caccgcttct atcatcatta    1560
tcatccttag tttagtttag tgcgtaagtt ttgtacacat ccaatcgatg tccagttcct    1620
aatttccttg tctctagttt gtacccataa attagtaata taagtactta tatcagcacg    1680
cg                                                                   1682
```

<210> SEQ ID NO 125
<211> LENGTH: 428
<212> TYPE: PRT
<213> ORGANISM: Zea mays
<220> FEATURE:
<221> NAME/KEY: misc_feature
<223> OTHER INFORMATION: Ceres CLONE ID no.236071
<220> FEATURE:
<221> NAME/KEY: misc_feature
<223> OTHER INFORMATION: Score of 873.4 for HMM of FIGURE 3.
<220> FEATURE:
<221> NAME/KEY: misc_feature
<223> OTHER INFORMATION: Functional Homolog Of Ceres SEEDLINE ID no.
    ME19173 at SEQ ID NO. 109
<220> FEATURE:
<221> NAME/KEY: misc_feature
<222> LOCATION: (82)..(102)
<223> OTHER INFORMATION: Pfam Name: IQ Pfam Description: IQ calmodulin-
    binding motif

<400> SEQUENCE: 125

Met Gly Ala Ser Gly Lys Trp Ile Lys Ser Leu Val Ala Leu Lys Ala
1               5                   10                  15

Pro Glu Lys Ala Ala Gly His Lys Gly Gly Arg Lys Trp Arg Leu Trp
            20                  25                  30

Arg Ser Ser Ser Ala Thr Ser Arg Ala Ser Ala Gly Glu Gly Ser Ala
        35                  40                  45

Leu Ala Ser Glu Ser Ser Ser Ala Ser Ala Asp Ser Phe Asn Ser Val
    50                  55                  60

Leu Ala Ala Val Val Arg Ala Pro Pro Arg Asp Phe Leu Leu Ile Arg
65                  70                  75                  80

Gln Glu Trp Ala Ala Val Arg Ile His Thr Ala Phe Arg Gly Phe Leu
                85                  90                  95

Ala Arg Arg Ala Leu Lys Ala Leu Arg Gly Ile Val Arg Leu Gln Ala
            100                 105                 110

Leu Val Arg Gly Arg Arg Val Arg Lys Gln Leu Ala Val Thr Leu Lys
        115                 120                 125

Cys Met His Ala Leu Leu Arg Val Gln Glu Arg Ala Arg Glu Arg Arg
    130                 135                 140

Ala Arg Ser Ser Ala Asp Gly His Gly Ser Gln Gly Gln Asp Ala Leu
145                 150                 155                 160

Asn Gly Cys Ala Ser Ser Thr Lys Asp Ala Met Glu Gln Trp Cys Asp
                165                 170                 175

Arg His Gly Ser Val Ala Glu Val Arg Ser Asn Leu His Met Lys His
            180                 185                 190

Glu Gly Ala Ala Lys Arg Glu Arg Ala Ile Ala Tyr Ala Val Ser His
        195                 200                 205

```
Gln Pro Arg Gly Ser Arg Gln Lys Gly Arg Pro Ser Pro Ala Asn
        210                 215                 220

Cys Val Arg Ser His Asp Pro Asn Gly Cys Asp Gln Asp Phe Ser Tyr
225                 230                 235                 240

Leu Asp Gly Trp Met Ala Thr Lys Pro Trp Glu Thr Arg Ser Thr Glu
            245                 250                 255

Arg Asn His Ser Asp Ser Gln Leu Ala Lys His Glu Glu Leu Asn Leu
        260                 265                 270

Pro Ala Ser Lys Leu Ser Asp Ala Ser Ser Val Lys Ile Arg Arg Asn
    275                 280                 285

Asn Val Thr Thr Arg Val Ser Ala Ala Lys Arg Pro Pro Pro Ser Ser
290                 295                 300

Val Leu Ser Ala Ala Ser Ser Asp Ser Ala Cys Gly Gly Glu Ser Ser
305                 310                 315                 320

Arg Ser Arg Pro Ser Val Thr Leu Thr Ser Ala Thr Thr Asn Thr Val
            325                 330                 335

Leu Ala Ser Glu Ala Arg Ser Asp Ser Gly Asp Thr Gly Gly Pro Asn
        340                 345                 350

Tyr Met Ser Leu Thr Lys Ser Ala Lys Ala Arg Leu Ser Gly Cys Ser
        355                 360                 365

Gly Ser Ser His His Arg Ser Phe Gln Arg Pro Arg Ser Gly Asp Met
370                 375                 380

Ser Arg Val Thr Leu Ser Ser Ile Asp Thr Gln Ser Asn Ala Gly Ser
385                 390                 395                 400

Glu Ile Ser Val Thr Ser Lys Arg Leu Asn Ser Met Ser Leu Asn Leu
            405                 410                 415

Lys Gly Arg Ser Leu Asp Lys Glu Asn Glu Glu Asp
        420                 425

<210> SEQ ID NO 126
<211> LENGTH: 455
<212> TYPE: PRT
<213> ORGANISM: Oryza sativa subsp. indica
<220> FEATURE:
<221> NAME/KEY: misc_feature
<223> OTHER INFORMATION: Public GI ID no.125524760
<220> FEATURE:
<221> NAME/KEY: misc_feature
<223> OTHER INFORMATION: Score of 926.5 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 126

Met Gly Gly Ser Gly Lys Trp Val Lys Ser Leu Ile Gly Leu Lys Lys
1               5                   10                  15

Pro Asp Arg Glu Asp Cys Lys Glu Lys Leu Gln Val Pro Ser Val Asn
            20                  25                  30

Gly Gly Gly Gly Gly Lys Gly Arg Lys Trp Lys Leu Trp Arg Ser Ser
        35                  40                  45

Ser Gly Asp His Gly Ser Leu Trp Arg Gly Ser Arg Gly Gly Gly Gly
    50                  55                  60

Gly Gly Gly His His Arg Ser Ala Ser Ser Asp Ala Ser Asp Asp Ala
```

```
             65                  70                  75                  80
Ser Ser Ala Ala Gly Asp Pro Phe Thr Ala Ala Val Ala Thr Val Ala
                85                  90                  95

Arg Ala Pro Ala Lys Asp Phe Met Ala Val Arg Gln Glu Trp Ala Ala
                100                 105                 110

Ile Arg Val Gln Thr Ala Phe Arg Gly Phe Leu Ala Arg Arg Ala Leu
                115                 120                 125

Arg Ala Leu Lys Gly Leu Val Arg Leu Gln Ala Ile Val Arg Gly Arg
            130                 135                 140

Gln Val Arg Lys Gln Ala Ala Val Thr Leu Arg Cys Met Gln Ala Leu
145                 150                 155                 160

Val Arg Val Gln Ala Arg Ile Arg Ala Arg Arg Val Arg Met Ser Thr
                165                 170                 175

Glu Gly Gln Ala Val Gln Lys Leu Leu Glu Ala Arg Arg Thr Lys Leu
                180                 185                 190

Asp Ile Leu Arg Glu Ala Glu Glu Gly Trp Cys Asp Ser Gln Gly Thr
            195                 200                 205

Leu Glu Asp Val Arg Val Lys Leu Gln Lys Arg Gln Glu Gly Ala Ile
210                 215                 220

Lys Arg Glu Arg Ala Ile Ala Tyr Ala Tyr Ser Gln Gln Ile Glu Gly
225                 230                 235                 240

Ala Thr Lys Cys Asn Phe Trp Thr Lys Cys Val Ile Phe Leu Val Phe
                245                 250                 255

Ala Gln Gln Gln Pro Lys Pro Thr Ser Tyr Gly Arg Leu Asn Gln Ser
                260                 265                 270

Gly Met Leu Leu Lys His Gln His Phe Asp Lys Ser Asn Gly Asn Trp
            275                 280                 285

Ser Trp Leu Glu Arg Trp Met Ala Ala Arg Pro Trp Glu Asn Arg Leu
            290                 295                 300

Met Glu Glu His Asn Gln Thr Asn Ser Ser Pro Asp Leu Leu Ser
305                 310                 315                 320

Ser Lys Asn Cys Glu Asp Ser Phe Gly Ile Leu Gly Asp Phe Ser Glu
                325                 330                 335

Pro Asn Ser Val Lys Val Arg Lys Asn Asn Val Ser Lys Arg Val Cys
                340                 345                 350

Ala Lys Pro Pro Val Val Ser His His Gln Arg Ile Lys Ala Gln Ser
            355                 360                 365

Ile Ser Ser Leu Ser Thr Glu Leu His Asn Asp Glu Ser Ser Ala Ser
            370                 375                 380

Ser Ser Cys Phe Ala Ser Thr Pro Ile Ser Phe Ser Thr Phe Val
385                 390                 395                 400

Thr Thr Glu Lys Thr Glu Asp Ser Ile Arg Ala Arg Pro Asn Tyr Met
                405                 410                 415

Asn Met Thr Glu Ser Ile Lys Ala Lys Arg Lys Ala Cys Asn Ala Gln
                420                 425                 430

Arg Thr Thr Ala Gly Lys Leu Met Glu Asp Arg Lys Ala Ser Gly Val
            435                 440                 445

Glu Leu Lys Val Ala Gln Val
            450                 455

<210> SEQ ID NO 127
<211> LENGTH: 455
<212> TYPE: PRT
<213> ORGANISM: Oryza sativa subsp. japonica
```

-continued

```
<220> FEATURE:
<221> NAME/KEY: misc_feature
<223> OTHER INFORMATION: Public GI ID no.125569365
<220> FEATURE:
<221> NAME/KEY: misc_feature
<223> OTHER INFORMATION: Score of 926.7 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 127

Met Gly Gly Ser Gly Lys Trp Val Lys Ser Leu Ile Gly Leu Lys Lys
1               5                   10                  15

Pro Asp Arg Glu Asp Cys Lys Glu Lys Leu Gln Val Pro Ser Val Asn
            20                  25                  30

Gly Arg Gly Gly Lys Gly Arg Lys Trp Lys Leu Trp Arg Ser Ser
        35                  40                  45

Ser Gly Asp His Gly Ser Leu Trp Arg Gly Ser Arg Gly Gly Cys
50                  55                  60

Cys Gly Gly His His Arg Ser Ala Ser Ser Asp Ala Ser Asp Ala
65                  70                  75                  80

Ser Ser Ala Ala Ala Asp Pro Phe Thr Ala Ala Val Ala Thr Val Ala
                85                  90                  95

Arg Ala Pro Ala Lys Asp Phe Met Ala Val Arg Gln Glu Trp Ala Ala
            100                 105                 110

Ile Arg Val Gln Thr Ala Phe Arg Gly Phe Leu Ala Arg Arg Ala Leu
        115                 120                 125

Arg Ala Leu Lys Gly Leu Val Arg Leu Gln Ala Ile Val Arg Gly Arg
    130                 135                 140

Gln Val Arg Lys Gln Ala Ala Val Thr Leu Arg Cys Met Gln Ala Leu
145                 150                 155                 160

Val Arg Val Gln Ala Arg Ile Arg Ala Arg Arg Val Arg Met Ser Thr
                165                 170                 175

Glu Gly Gln Ala Val Gln Lys Leu Leu Glu Ala Arg Arg Thr Lys Leu
            180                 185                 190

Asp Ile Leu Arg Glu Ala Glu Gly Trp Cys Asp Ser Gln Gly Thr
        195                 200                 205

Leu Glu Asp Val Arg Val Lys Leu Gln Lys Arg Gln Glu Gly Ala Ile
    210                 215                 220

Lys Arg Glu Arg Ala Ile Ala Tyr Ala Tyr Ser Gln Ile Glu Gly
225                 230                 235                 240

Ala Thr Lys Cys Asn Phe Trp Thr Glu Cys Val Ile Phe Leu Val Phe
                245                 250                 255

Ala Gln Gln Gln Pro Lys Pro Thr Ser Tyr Gly Arg Leu Asn Gln Ser
            260                 265                 270

Gly Met Leu Leu Lys His Gln His Phe Asp Lys Ser Asn Gly Asn Trp
        275                 280                 285

Ser Trp Leu Glu Arg Trp Met Ala Ala Arg Pro Trp Glu Asn Arg Leu
    290                 295                 300

Met Glu Glu His Asn Gln Thr Asn Ser Ser Ser Pro Asp Leu Leu Ser
305                 310                 315                 320

Ser Lys Asn Cys Glu Asp Ser Phe Gly Ile Leu Gly Asp Phe Ser Glu
```

```
                    325                 330                 335
Pro Asn Ser Val Lys Val Arg Lys Asn Asn Val Ser Lys Arg Val Cys
                340                 345                 350

Ala Lys Pro Pro Val Val Ser His His Gln Arg Ile Lys Ala Gln Ser
                355                 360                 365

Ile Ser Ser Leu Ser Thr Glu Leu His Asn Asp Glu Ser Ser Ala Ser
    370                 375                 380

Ser Ser Ser Cys Phe Ala Ser Thr Pro Ile Ser Phe Ser Thr Phe Val
385                 390                 395                 400

Thr Thr Glu Lys Thr Glu Asp Ser Ile Arg Ala Arg Pro Asn Tyr Met
                405                 410                 415

Asn Met Thr Glu Ser Ile Lys Ala Lys Arg Lys Ala Cys Asn Ala Gln
                420                 425                 430

Arg Thr Thr Ala Gly Lys Leu Met Glu Asp Arg Lys Ala Ser Gly Val
                435                 440                 445

Glu Leu Lys Val Ala Gln Val
                450                 455

<210> SEQ ID NO 128
<211> LENGTH: 441
<212> TYPE: PRT
<213> ORGANISM: Oryza sativa subsp. japonica
<220> FEATURE:
<221> NAME/KEY: misc_feature
<223> OTHER INFORMATION: Public GI ID no.115439499
<220> FEATURE:
<221> NAME/KEY: misc_feature
<223> OTHER INFORMATION: Score of 617.2 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (87)..(107)
<223> OTHER INFORMATION: Pfam Name: IQ Pfam Description: IQ calmodulin-
      binding motif

<400> SEQUENCE: 128

Met Gly Ala Ser Gly Lys Trp Ile Arg Thr Leu Val Gly Leu Arg Pro
1               5                   10                  15

Ala Ala Glu Arg Glu Lys Glu Arg Gly Gly Gly Gly Lys Gly Arg
                20                  25                  30

Lys Trp Ser Arg Leu Trp Arg Ser Ser Ser Gln Arg Gly Gly Gly
            35                  40                  45

Asn Ala Ser Ala Ser Glu Val Tyr Ser Glu Thr Ser Ser Ser Ala Asp
    50                  55                  60

Ala Leu Ser Ser Val Val Ala Val Val Arg Ala Pro Pro Arg Asp
65                  70                  75                  80

Phe Arg Leu Ile Arg Gln Glu Trp Ala Ala Val Arg Ile Gln Thr Ala
                85                  90                  95

Phe Arg Ala Phe Leu Ala Arg Arg Ala Leu Arg Ala Leu Arg Gly Ile
                100                 105                 110

Val Arg Leu Gln Ala Leu Val Arg Gly Arg Arg Val Arg Lys Gln Leu
                115                 120                 125

Ala Val Thr Leu Lys Cys Met Gln Ala Leu Val Arg Val Gln Ala Arg
                130                 135                 140

Ala Arg Asp Arg Arg Ala Arg Ile Ser Ala Asp Gly Leu Asp Ser Gln
145                 150                 155                 160
```

Asp Met Leu Asp Glu Arg Gly Gly Arg Val Asp His Val Lys Glu Ala
            165                 170                 175

Glu Ala Gly Trp Cys Asp Ser Gln Gly Thr Ala Asp Asp Val Arg Ser
        180                 185                 190

Lys Ile His Met Arg His Glu Gly Ala Ile Lys Arg Glu Arg Ala Arg
    195                 200                 205

Thr Tyr Ala Gln Ser His Gln Arg Cys Ser Asn His Gly Gly Arg Pro
210                 215                 220

Ser Ser Pro Ala Val Ser Leu Lys His His Gly Asn Gly Ala Thr Arg
225                 230                 235                 240

Ser Asn His Ser Trp Ser Tyr Leu Glu Gly Trp Met Ala Thr Lys Pro
                245                 250                 255

Trp Glu Ser Arg Leu Met Glu Gln Thr His Thr Glu Asn Ser Thr Asn
            260                 265                 270

Ser Arg Cys Ser Glu Ser Val Glu Glu Val Ser Val Gly Gly Pro Lys
        275                 280                 285

Leu Ser Asp Ala Ser Ser Val Lys Ile Arg Arg Asn Asn Val Thr Thr
    290                 295                 300

Arg Val Ala Ala Lys Pro Pro Ser Met Ile Ser Ala Thr Ser Ser Asp
305                 310                 315                 320

Phe Val Cys Asp Glu Ser Ser Pro Ser Thr Ser Ser Val Thr Pro Leu
                325                 330                 335

Ser Ala Asn Asn Ser Leu Ala Thr Glu Arg Arg Ser Asp Cys Gly Gln
            340                 345                 350

Val Gly Gly Pro Ser Tyr Met Ser Leu Thr Lys Ser Ala Lys Ala Arg
        355                 360                 365

Leu Ser Gly Tyr Gly Ser His Lys Pro Pro Leu Gln Arg Gln Arg Ser
    370                 375                 380

Gly Asp Leu Leu His His Asn Asn Arg Met Ala Phe Ser Ser Ile Asp
385                 390                 395                 400

Val Gln Ser Thr Ala Gly Ser Glu Val Ser Val Thr Ser Lys Arg Leu
                405                 410                 415

Asn Ser Leu Ala Leu Lys Gly Arg Ala Thr Arg Ser Leu Asp Lys Glu
            420                 425                 430

Asn Glu Arg Arg Pro Ser Ser Leu Leu
        435                 440

<210> SEQ ID NO 129
<211> LENGTH: 416
<212> TYPE: PRT
<213> ORGANISM: Arabidopsis thaliana
<220> FEATURE:
<221> NAME/KEY: misc_feature
<223> OTHER INFORMATION: Public GI ID no.15225258
<220> FEATURE:
<221> NAME/KEY: misc_feature
<223> OTHER INFORMATION: Score of 954.4 for HMM of FIGURE 3.
<220> FEATURE:
<221> NAME/KEY: misc_feature
<223> OTHER INFORMATION: Functional Homolog Of Ceres SEEDLINE ID no.
    ME19173 at SEQ ID NO. 109
<220> FEATURE:
<221> NAME/KEY: misc_feature
<222> LOCATION: (84)..(104)
<223> OTHER INFORMATION: Pfam Name: IQ Pfam Description: IQ calmodulin-
    binding motif

<400> SEQUENCE: 129

Met Gly Ala Ser Gly Lys Trp Val Lys Ser Ile Ile Gly Leu Lys Lys
1               5                   10                  15

Leu Glu Lys Asp Glu Ile Glu Lys Gly Asn Gly Lys Asn Lys Lys Trp
            20                  25                  30

Lys Leu Trp Arg Thr Thr Ser Val Asp Ser Trp Lys Gly Phe Arg Gly
            35                  40                  45

Lys His Arg Ser Asp Ser Asp Gly Val Asp Ser Thr Val Tyr Ser
 50                  55                  60

Ala Ala Val Ala Thr Val Leu Arg Ala Pro Pro Lys Asp Phe Lys Ala
 65                  70                  75                  80

Val Arg Glu Glu Trp Ala Ala Ile Arg Ile Gln Thr Ala Phe Arg Gly
                85                  90                  95

Phe Leu Ala Arg Arg Ala Leu Arg Ala Leu Lys Gly Ile Val Arg Leu
            100                 105                 110

Gln Ala Leu Val Arg Gly Arg Gln Val Arg Lys Gln Ala Ala Val Thr
            115                 120                 125

Leu Arg Cys Met Gln Ala Leu Val Arg Val Gln Ala Arg Val Arg Ala
130                 135                 140

Arg Arg Val Arg Met Thr Val Glu Gly Gln Ala Val Gln Lys Leu Leu
145                 150                 155                 160

Asp Glu His Arg Thr Lys Ser Asp Leu Leu Lys Glu Val Glu Glu Gly
                165                 170                 175

Trp Cys Asp Arg Lys Gly Thr Val Asp Asp Ile Lys Ser Lys Leu Gln
            180                 185                 190

Gln Arg Gln Glu Gly Ala Phe Lys Arg Glu Arg Ala Leu Ala Tyr Ala
            195                 200                 205

Leu Ala Gln Lys Gln Trp Arg Ser Thr Thr Ser Ser Asn Leu Lys Thr
            210                 215                 220

Asn Ser Ser Ile Ser Tyr Leu Lys Ser Gln Glu Phe Asp Lys Asn Ser
225                 230                 235                 240

Trp Gly Trp Ser Trp Leu Glu Arg Trp Met Ala Ala Arg Pro Trp Glu
                245                 250                 255

Thr Arg Leu Met Asp Thr Val Asp Thr Ala Ala Thr Pro Pro Pro Leu
            260                 265                 270

Pro His Lys His Leu Lys Ser Pro Glu Thr Ala Asp Val Val Gln Val
            275                 280                 285

Arg Arg Asn Asn Val Thr Thr Arg Val Ser Ala Lys Pro Pro Pro His
290                 295                 300

Met Leu Ser Ser Ser Pro Gly Tyr Glu Phe Asn Glu Ser Ser Gly Ser
305                 310                 315                 320

Ser Ser Ile Cys Thr Ser Thr Thr Pro Val Ser Gly Lys Thr Gly Leu
                325                 330                 335

Val Ser Asp Asn Ser Ser Ser Gln Ala Lys Lys His Lys Pro Ser Tyr
            340                 345                 350

Met Ser Leu Thr Glu Ser Thr Lys Ala Lys Arg Arg Thr Asn Arg Gly
            355                 360                 365

Leu Arg Gln Ser Met Asp Glu Phe Gln Phe Met Lys Asn Ser Gly Met
            370                 375                 380

Phe Thr Gly Glu Leu Lys Thr Ser Pro Ser Ser Asp Pro Phe Val Ser
385                 390                 395                 400

Phe Ser Lys Pro Leu Gly Val Pro Thr Arg Phe Glu Lys Pro Arg Gly
                405                 410                 415

<210> SEQ ID NO 130
<211> LENGTH: 408

```
<212> TYPE: PRT
<213> ORGANISM: Oryza sativa subsp. japonica
<220> FEATURE:
<221> NAME/KEY: misc_feature
<223> OTHER INFORMATION: Public GI ID no.115465173
<220> FEATURE:
<221> NAME/KEY: misc_feature
<223> OTHER INFORMATION: Score of 554.2 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (79)..(99)
<223> OTHER INFORMATION: Pfam Name: IQ Pfam Description: IQ calmodulin-
      binding motif

<400> SEQUENCE: 130

Met Gly Ala Ser Gly Lys Trp Ile Lys Ser Leu Val Ser Leu Lys Ala
1               5                   10                  15

Ala Pro Glu Gly Thr Thr Lys Gly Arg Arg Trp Thr Arg Leu Trp Arg
            20                  25                  30

Ser Ser Ser Ser Ala Ser Ala Ser Ala Ser Thr Ala Gly Asp Ala Ser
        35                  40                  45

Glu Ser Ala Ser Ser Glu Ala Asp Ala Phe Ser Ser Val Val Ala Ala
50                  55                  60

Val Val Arg Ala Pro Pro Arg Asp Phe Arg Val Ile Arg Gln Glu Trp
65                  70                  75                  80

Ala Ala Val Arg Val Gln Ala Ala Phe Arg Ala Phe Leu Ala Arg Arg
                85                  90                  95

Ala Leu Lys Ala Leu Arg Gly Ile Val Arg Leu Gln Ala Leu Val Arg
            100                 105                 110

Gly Arg Leu Val Arg Arg Gln Leu Ala Val Thr Leu Lys Cys Met Asn
        115                 120                 125

Ala Leu Leu Arg Val Gln Glu Arg Ala Arg Glu Arg Arg Ala Arg Cys
130                 135                 140

Ser Ala Asp Gly Arg Asp Ser Gln Asp Ala Val Gly Glu Arg Asp Gly
145                 150                 155                 160

Arg Ala Asp Pro Ile Lys Gln Ala Glu Glu Gln Trp Cys Asp Ser Gln
                165                 170                 175

Gly Ser Val Ser Glu Val Arg Ser Lys Ile His Met Arg His Asp Ala
            180                 185                 190

Val Ala Lys Arg Glu Arg Ala Ile Ala Tyr Ala Leu Ser His Gln Pro
        195                 200                 205

Arg Ser Ser Lys Gln Ser Ala Arg Pro Ser Ser Pro Ala Arg Ser Leu
210                 215                 220

Arg Asn His Glu Ser Asn Arg Cys Asn His Asp Trp Ser Tyr Ile Glu
225                 230                 235                 240

Gly Trp Met Ala Thr Lys Pro Trp Glu Ser Arg Leu Met Glu Gln Ser
                245                 250                 255

His Ala Glu Leu Lys Cys Ser Lys Asn Ser Gly Glu Leu Asn Leu Ala
            260                 265                 270

Gly Ala Gln Leu Ser Asn Ala Ser Ser Val Lys Met Arg Gly Asn Arg
        275                 280                 285

Val Ala Ala Lys Pro Pro Ser Val Leu Ser Ala Ser Ser Asp Phe
290                 295                 300

Pro Cys Asp Val Ser Ser Ala Ser Thr Ser Ser Ala Thr Pro Ala Arg
305                 310                 315                 320
```

Ser Asp Gly Gly His Gly Glu Gly Pro Ser Tyr Met Ser Leu Thr Lys
            325                 330                 335

Ser Ala Lys Ala Arg Gln Ser Cys Asn Ser Pro Phe Gln Ile Gln Arg
        340                 345                 350

Gln Arg Ser Gly Gly Met Ser Ser Tyr Lys Arg Val Ala Leu Ser Pro
    355                 360                 365

Leu Asp Val Gln Ser Asn Ala Cys Ser Glu Phe Ser Val Thr Ser Arg
370                 375                 380

Lys Leu Asn Ser Leu Ser Leu Lys Gly Arg Ser Met Thr Arg Ser Leu
385                 390                 395                 400

Asp Lys Glu Asn Asp Asn Leu Phe
            405

<210> SEQ ID NO 131
<211> LENGTH: 1164
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1477059
<220> FEATURE:
<221> NAME/KEY: misc_feature
<223> OTHER INFORMATION: Encodes the peptide sequence at SEQ ID NO 132

<400> SEQUENCE: 131

```
atgggtgcat caggaaaatg ggtgaaatcc cttataggtt ttaaaaagtc tgataaagat      60
caagaccatg taaatggcaa gagcaagaaa tggaagctat ggaggagctc atctggtgac     120
ttggggtctt catggaagga ttttaaaggg aaacatagaa cagcgtcaga ggcatcgggt     180
tcttcaccat taactgatcc atttactacc gcaatggcta ctgtggttag agctcctcct     240
aagggtttta gggttgtcag gcaagagtgg gctgctatca ggattcaaac tgctttccgt     300
ggattcttgg caagaagggc tctgagggct ttgaaagcag tggtgagact ccaagctata     360
gttcgaggtc gacaagtgag aaagcaggct gctgtgatgc tttggtgtat gcaggctctt     420
gttcgagttc aagctcgagt cagggctcat cctgtgcgaa tgtccataga agggcaggca     480
gtgcagaata tgctaaatga cgacatagc aaggctgatc tcttgaaaca tgctgaggaa     540
gggtggtgcg atggcaaggg gacattggaa gatgtgaagt caaaactgca aatgaggcaa     600
gaaggagcct tcaagagaga aagagcaatt gcatactccc ttgctcagaa caatggagaa     660
tcaaacccca gctcaaatac tcgaaccaat agctcagtat actcattcaa gaatcaggag     720
tttgataaga atagctgggg atggactagg cctccaattg gcatattac tcgctcatct     780 tccagtccaa gttctgaatt ccgctttgat gagagttcag cttcttcatc aatttgtaca     840
tctacaacac caatatcagg aaacactggc ttggcctctg ataaaacaga ggagagtggt     900
aacagtaggc caaattacat gaacctgacc gagtcaacca aggcaaagca aaaacatcc     960 ggtcatttat ctcataggat ccaaaggcag tctatggatg agtttcagtt tctcaaaaag    1020
tcaggagcat tctcaaatgg agattcgaaa acagtactg gttctgatcc gtcagttaat    1080
ttatctaagc cactttgctt gccaacaaga tttgataaga actcgacgaa acaactaaga    1140
ggaatggatc atttgtatga ttag                                          1164
```

<210> SEQ ID NO 132
<211> LENGTH: 387
<212> TYPE: PRT
<213> ORGANISM: Populus balsamifera subsp. trichocarpa
<220> FEATURE:

```
<221> NAME/KEY: misc_feature
<223> OTHER INFORMATION: Ceres ANNOT ID no.1477059
<220> FEATURE:
<221> NAME/KEY: misc_feature
<223> OTHER INFORMATION: Score of 765.3 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:
<221> NAME/KEY: misc_feature
<222> LOCATION: (89)..(109)
<223> OTHER INFORMATION: Pfam Name: IQ Pfam Description: IQ calmodulin-
      binding motif

<400> SEQUENCE: 132

Met Gly Ala Ser Gly Lys Trp Val Lys Ser Leu Ile Gly Phe Lys Lys
1               5                   10                  15

Ser Asp Lys Asp Gln Asp His Val Asn Gly Lys Ser Lys Lys Trp Lys
            20                  25                  30

Leu Trp Arg Ser Ser Ser Gly Asp Leu Gly Ser Ser Trp Lys Asp Phe
        35                  40                  45

Lys Gly Lys His Arg Thr Ala Ser Glu Ala Ser Gly Ser Ser Pro Leu
    50                  55                  60

Thr Asp Pro Phe Thr Thr Ala Met Ala Thr Val Val Arg Ala Pro Pro
65                  70                  75                  80

Lys Gly Phe Arg Val Val Arg Gln Glu Trp Ala Ala Ile Arg Ile Gln
                85                  90                  95

Thr Ala Phe Arg Gly Phe Leu Ala Arg Arg Ala Leu Arg Ala Leu Lys
            100                 105                 110

Ala Val Val Arg Leu Gln Ala Ile Val Arg Gly Arg Gln Val Arg Lys
        115                 120                 125

Gln Ala Ala Val Met Leu Trp Cys Met Gln Ala Leu Val Arg Val Gln
    130                 135                 140

Ala Arg Val Arg Ala His Pro Val Arg Met Ser Ile Glu Gly Gln Ala
145                 150                 155                 160

Val Gln Asn Met Leu Asn Glu Arg His Ser Lys Ala Asp Leu Leu Lys
                165                 170                 175

His Ala Glu Glu Gly Trp Cys Asp Gly Lys Gly Thr Leu Glu Asp Val
            180                 185                 190

Lys Ser Lys Leu Gln Met Arg Gln Glu Gly Ala Phe Lys Arg Glu Arg
        195                 200                 205

Ala Ile Ala Tyr Ser Leu Ala Gln Lys Gln Trp Arg Ser Asn Pro Ser
    210                 215                 220

Ser Asn Thr Arg Thr Asn Ser Ser Val Tyr Ser Phe Lys Asn Gln Glu
225                 230                 235                 240

Phe Asp Lys Asn Ser Trp Gly Trp Thr Arg Pro Pro Ile Gly His Ile
                245                 250                 255

Thr Arg Ser Ser Ser Ser Pro Ser Ser Glu Phe Arg Phe Asp Glu Ser
            260                 265                 270

Ser Ala Ser Ser Ser Ile Cys Thr Ser Thr Thr Pro Ile Ser Gly Asn
        275                 280                 285

Thr Gly Leu Ala Ser Asp Lys Thr Glu Glu Ser Gly Asn Ser Arg Pro
    290                 295                 300

Asn Tyr Met Asn Leu Thr Glu Ser Thr Lys Ala Lys Gln Lys Thr Ser
305                 310                 315                 320

Gly His Leu Ser His Arg Ile Gln Arg Gln Ser Met Asp Glu Phe Gln
                325                 330                 335
```

Phe Lys Lys Ser Gly Ala Phe Ser Asn Gly Asp Ser Lys Asn Ser
          340                 345                 350

Thr Gly Ser Asp Pro Ser Val Asn Leu Ser Lys Pro Leu Cys Leu Pro
              355                 360                 365

Thr Arg Phe Asp Lys Asn Ser Thr Lys Gln Leu Arg Gly Met Asp His
    370                 375                 380

Leu Tyr Asp
385

<210> SEQ ID NO 133
<211> LENGTH: 1059
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1530547
<220> FEATURE:
<221> NAME/KEY: misc_feature
<223> OTHER INFORMATION: Encodes the peptide sequence at SEQ ID NO 134

<400> SEQUENCE: 133
atgggtgcat caggaaaatg ggtgaaatcc cttataggtt ttaaaaagtc tgataaagat      60
caagaccatg taaatggcaa gagcaagaaa tggaagctat ggaggagctc atctggtgac    120
ttggggtctt catggaagga ttttaaaggg aaacatagaa cagcgtcaga ggcatcgggt    180
tcttcaccat taactgatcc atttactacc gcaatggcta ctgtggttag agctcctcct    240
aagggtttta gggttgtcag gcaagagtgg gctgctatca ggattcaaac tgctttccgt    300
ggattcttgg ctcttgttcg agttcaagct cgagtcaggg ctcatcctgt gcgaatgtcc    360
atagaagggc aggcagtgca gaatatgcta aatgagcgac atagcaaggc tgatctcttg    420
aaacatgctg aggaagggtg gtgcgatggc aaggggacat tggaagatgt gaagtcaaaa    480
ctgcaaatga ggcaagaagg agccttcaag agagaaagag caattgcata ctcccttgct    540
cagaaacaat ggagatcaaa ccccagctca atactcgaa ccaatagctc agtatactca    600
ttcaagaatc aggagtttga taagaatagc tggggatgga ctaggcctcc aattgggcat    660
attactcgct catcttccag tccaagttct gaattccgct tgatgagag ttcagcttct    720 tcatcaattt gtacatctac aacaccaata tcaggaaaca ctggcttggc ctctgataaa    780
acagaggaga gtggtaacag taggccaaat tacatgaacc tgaccgagtc aaccaaggca    840
aagcaaaaaa catccggtca tttatctcat aggatccaaa ggcagtctat ggatgagttt    900
cagtttctca aaaagtcagg agcattctca aatggagatt cgaaaaacag tactggttct    960
gatccgtcag ttaatttatc taagccactt tgcttgccaa caagatttga taagaactcg   1020
acgaaacaac taagaggaat ggatcatttg tatgattag                           1059

<210> SEQ ID NO 134
<211> LENGTH: 352
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1530547
<220> FEATURE:
<221> NAME/KEY: misc_feature
<223> OTHER INFORMATION: Score of 607.6 for HMM of FIGURE 3.
<220> FEATURE:
<221> NAME/KEY: misc_feature
<223> OTHER INFORMATION: Functional Homolog Of Ceres SEEDLINE ID no.
      ME19173 at SEQ ID NO. 109
<220> FEATURE:

```
<221> NAME/KEY: misc_feature
<222> LOCATION: (89)..(109)
<223> OTHER INFORMATION: Pfam Name: IQ Pfam Description: IQ calmodulin-
      binding motif

<400> SEQUENCE: 134
```

| | | | | | | | | | | | | | | | |
|---|---|---|---|---|---|---|---|---|---|---|---|---|---|---|---|
| Met | Gly | Ala | Ser | Gly | Lys | Trp | Val | Lys | Ser | Leu | Ile | Gly | Phe | Lys | Lys |
| 1 | | | | 5 | | | | | 10 | | | | | 15 | |
| Ser | Asp | Lys | Asp | Gln | Asp | His | Val | Asn | Gly | Lys | Ser | Lys | Lys | Trp | Lys |
| | | 20 | | | | | 25 | | | | | 30 | | | |
| Leu | Trp | Arg | Ser | Ser | Gly | Asp | Leu | Gly | Ser | Ser | Trp | Lys | Asp | Phe | |
| | | 35 | | | | 40 | | | | 45 | | | | | |
| Lys | Gly | Lys | His | Arg | Thr | Ala | Ser | Glu | Ala | Ser | Gly | Ser | Ser | Pro | Leu |
| 50 | | | | | 55 | | | | | 60 | | | | | |
| Thr | Asp | Pro | Phe | Thr | Thr | Ala | Met | Ala | Thr | Val | Val | Arg | Ala | Pro | Pro |
| 65 | | | | 70 | | | | | 75 | | | | | 80 | |
| Lys | Gly | Phe | Arg | Val | Val | Arg | Gln | Glu | Trp | Ala | Ala | Ile | Arg | Ile | Gln |
| | | | | 85 | | | | | 90 | | | | | 95 | |
| Thr | Ala | Phe | Arg | Gly | Phe | Leu | Ala | Leu | Val | Arg | Val | Gln | Ala | Arg | Val |
| | | | 100 | | | | | 105 | | | | | 110 | | |
| Arg | Ala | His | Pro | Val | Arg | Met | Ser | Ile | Glu | Gly | Gln | Ala | Val | Gln | Asn |
| | | 115 | | | | | 120 | | | | | 125 | | | |
| Met | Leu | Asn | Glu | Arg | His | Ser | Lys | Ala | Asp | Leu | Leu | Lys | His | Ala | Glu |
| 130 | | | | | 135 | | | | | 140 | | | | | |
| Glu | Gly | Trp | Cys | Asp | Gly | Lys | Gly | Thr | Leu | Glu | Asp | Val | Lys | Ser | Lys |
| 145 | | | | 150 | | | | | 155 | | | | | 160 | |
| Leu | Gln | Met | Arg | Gln | Glu | Gly | Ala | Phe | Lys | Arg | Glu | Arg | Ala | Ile | Ala |
| | | | | 165 | | | | | 170 | | | | | 175 | |
| Tyr | Ser | Leu | Ala | Gln | Lys | Gln | Trp | Arg | Ser | Asn | Pro | Ser | Ser | Asn | Thr |
| | | | 180 | | | | | 185 | | | | | 190 | | |
| Arg | Thr | Asn | Ser | Ser | Val | Tyr | Ser | Phe | Lys | Asn | Gln | Glu | Phe | Asp | Lys |
| | | 195 | | | | | 200 | | | | | 205 | | | |
| Asn | Ser | Trp | Gly | Trp | Thr | Arg | Pro | Pro | Ile | Gly | His | Ile | Thr | Arg | Ser |
| 210 | | | | | 215 | | | | | 220 | | | | | |
| Ser | Ser | Ser | Pro | Ser | Ser | Glu | Phe | Arg | Phe | Asp | Glu | Ser | Ser | Ala | Ser |
| 225 | | | | 230 | | | | | 235 | | | | | 240 | |
| Ser | Ser | Ile | Cys | Thr | Ser | Thr | Thr | Pro | Ile | Ser | Gly | Asn | Thr | Gly | Leu |
| | | | | 245 | | | | | 250 | | | | | 255 | |
| Ala | Ser | Asp | Lys | Thr | Glu | Glu | Ser | Gly | Asn | Ser | Arg | Pro | Asn | Tyr | Met |
| | | | 260 | | | | | 265 | | | | | 270 | | |
| Asn | Leu | Thr | Glu | Ser | Thr | Lys | Ala | Lys | Gln | Lys | Thr | Ser | Gly | His | Leu |
| | | 275 | | | | | 280 | | | | | 285 | | | |
| Ser | His | Arg | Ile | Gln | Arg | Gln | Ser | Met | Asp | Glu | Phe | Gln | Phe | Leu | Lys |
| 290 | | | | | 295 | | | | | 300 | | | | | |
| Lys | Ser | Gly | Ala | Phe | Ser | Asn | Gly | Asp | Ser | Lys | Asn | Ser | Thr | Gly | Ser |
| 305 | | | | 310 | | | | | 315 | | | | | 320 | |
| Asp | Pro | Ser | Val | Asn | Leu | Ser | Lys | Pro | Leu | Cys | Leu | Pro | Thr | Arg | Phe |
| | | | | 325 | | | | | 330 | | | | | 335 | |
| Asp | Lys | Asn | Ser | Thr | Lys | Gln | Leu | Arg | Gly | Met | Asp | His | Leu | Tyr | Asp |
| | | | 340 | | | | | 345 | | | | | 350 | | |

```
<210> SEQ ID NO 135
<211> LENGTH: 1923
<212> TYPE: DNA
<213> ORGANISM: Arabidopsis thaliana
<220> FEATURE:
```

<221> NAME/KEY: misc_feature
<223> OTHER INFORMATION: Ceres SEEDLINE ID no.ME24091
<220> FEATURE:
<221> NAME/KEY: misc_feature
<223> OTHER INFORMATION: Encodes the peptide sequence at SEQ ID NO. 136

<400> SEQUENCE: 135

| | | | | | |
|---|---|---|---|---|---|
| acaaatactc | ttcttcacac | agctttgaat | ccatctgtct | tctcctctct | ctctcttctc | 60 |
| catttgcaat | tacgataatg | tgaaagcaat | aagaagagga | aaagttatct | tcgcacctca | 120 |
| gcaaagatcc | aatcgattcg | attcttaagc | tttttcgtct | tctccgataa | ggtcactact | 180 |
| tagaagccgc | gttgtggttt | agttgactcc | tccaggtttt | atcttcaagc | tttttcgtct | 240 |
| atcagatctg | gtgtcactgt | cttctcatag | gattacatag | agatggggaa | aaaagctaaa | 300 |
| tggttttcaa | gtgttaagaa | agcattcagc | ccagattcaa | agaagtcgaa | gcaaaaattg | 360 |
| gctgagggac | aaaatggtgt | tatctctaat | cctcctgttg | tggataatgt | tagacaatct | 420 |
| tcttcttctc | ctcctcctgc | tcttgctcct | cgtgaagtga | gagtagctga | agtgattgtt | 480 |
| gaacggaaca | gggatctttc | acctccttct | acagcagatg | ctgtgaatgt | tacagctact | 540 |
| gatgtycctg | tagttccatc | ttcatctgct | cctggtgttg | ttcgtcgcgc | tacacctact | 600 |
| cgatttgctg | gaaagtcaaa | cgaagaagcc | gctgctatct | tgatccagac | tatatttaga | 660 |
| ggttatttgg | caaggagagc | gttgcgggca | atgaggggtt | tggtcagact | taagttattg | 720 |
| atggaaggat | ctgttgttaa | gcggcaagct | gcaaatactc | taaatgtgtat | gcagactctc | 780 |
| tctcgtgtac | agtcgcagat | ccgagctagg | agaatcaggr | tgtcagaaga | gaatcaggct | 840 |
| cgccagaaac | aactccttca | gaaacatgct | aaagagctag | ctggcttgaa | gaacggggat | 900 |
| aactggaatg | atagcattca | atcaaaggag | aaagttgaag | cgaatttgct | aagcaagtac | 960 |
| gaggcaacaa | tgagaaggga | aagggcattg | gcttattcat | actctcatca | scaaaactgg | 1020 |
| aagaacaact | ctaaatctgg | aaacccgatg | ttcatggatc | caagcaaccc | gacatggggt | 1080 |
| tggagctggt | tggagagatg | gatggctggt | aggccactag | agagttccga | gaaagaacaa | 1140 |
| agcaacagca | acaatgacaa | tgctgcctcg | gtcaagggct | ctattaaccg | caacgaagct | 1200 |
| gcaaaatctc | taacccgcaa | tggctcaact | caaccaaaca | caccatcatc | cgcaagaggg | 1260 |
| accccaagaa | acaaaaacag | tttcttctca | cctccaactc | cctcaaggct | aaaccaatcc | 1320 |
| tcgaggaaat | ccaatgacga | cgactccaaa | agcacaatct | cggtcctgtc | cgagaggaac | 1380 |
| cgcagacaca | scattgctgg | ttcatcagtc | asagacgatg | agagcctcgc | tggctcacca | 1440 |
| gctctcccga | gctacatggt | tccaactaaa | tcagctcgag | ccaggctcaa | gccccaaagc | 1500 |
| ccattaggtg | gtaccacaca | ggaaaacgaa | gggttcacag | acaaggcatc | agctaagaaa | 1560 |
| cggctctcgt | atccaacttc | gcctgcattg | cctaaaccac | ggcggttctc | agctcccct | 1620 |
| aaggtggaga | gtggcggcgt | taccgtgacc | aacggagcag | gcagctgagg | tatttatttt | 1680 |
| aatataatta | ttttcccact | tatgaatgtg | tccgagattg | ttgtctctta | tgtgttccct | 1740 |
| tcatttcgta | attcatttgt | gcagtgtaag | cgccagtcat | ttattttttt | actataataa | 1800 |
| attttataac | cttttaaaat | tcatgttctt | ttgtttcttt | gaatatttaa | gttatttta | 1860 |
| ttaatgttgg | atgaattgga | atatgatgat | gttatttgta | ttgtaatgca | gatcctttaa | 1920 |
| agc | | | | | | 1923 |

<210> SEQ ID NO 136
<211> LENGTH: 461
<212> TYPE: PRT
<213> ORGANISM: Arabidopsis thaliana -continued

```
<220> FEATURE:
<221> NAME/KEY: misc_feature
<223> OTHER INFORMATION: Ceres SEEDLINE ID no.ME24091
<220> FEATURE:
<221> NAME/KEY: misc_feature
<223> OTHER INFORMATION: Score of 1104.8 for HMM of FIGURE 4.
<220> FEATURE:
<221> NAME/KEY: misc_feature
<222> LOCATION: (88)..(88)
<223> OTHER INFORMATION: Xaa is any aa, unknown, or other
<220> FEATURE:
<221> NAME/KEY: misc_feature
<222> LOCATION: (115)..(135)
<223> OTHER INFORMATION: Pfam Name: IQ Pfam Description: IQ calmodulin-
      binding motif
<220> FEATURE:
<221> NAME/KEY: misc_feature
<222> LOCATION: (180)..(180)
<223> OTHER INFORMATION: Xaa is any aa, unknown, or other
<220> FEATURE:
<221> NAME/KEY: misc_feature
<222> LOCATION: (243)..(243)
<223> OTHER INFORMATION: Xaa is any aa, unknown, or other
<220> FEATURE:
<221> NAME/KEY: misc_feature
<222> LOCATION: (370)..(370)
<223> OTHER INFORMATION: Xaa is any aa, unknown, or other
<220> FEATURE:
<221> NAME/KEY: misc_feature
<222> LOCATION: (377)..(377)
<223> OTHER INFORMATION: Xaa is any aa, unknown, or other

<400> SEQUENCE: 136

Met Gly Lys Lys Ala Lys Trp Phe Ser Ser Val Lys Lys Ala Phe Ser
1               5                   10                  15

Pro Asp Ser Lys Lys Ser Lys Gln Lys Leu Ala Glu Gly Gln Asn Gly
            20                  25                  30

Val Ile Ser Asn Pro Pro Val Val Asp Asn Val Arg Gln Ser Ser Ser
        35                  40                  45

Ser Pro Pro Pro Ala Leu Ala Pro Arg Glu Val Arg Val Ala Glu Val
    50                  55                  60

Ile Val Glu Arg Asn Arg Asp Leu Ser Pro Pro Ser Thr Ala Asp Ala
65                  70                  75                  80

Val Asn Val Thr Ala Thr Asp Xaa Pro Val Val Pro Ser Ser Ser Ala
                85                  90                  95

Pro Gly Val Val Arg Arg Ala Thr Pro Thr Arg Phe Ala Gly Lys Ser
            100                 105                 110

Asn Glu Glu Ala Ala Ala Ile Leu Ile Gln Thr Ile Phe Arg Gly Tyr
        115                 120                 125

Leu Ala Arg Arg Ala Leu Arg Ala Met Arg Gly Leu Val Arg Leu Lys
    130                 135                 140

Leu Leu Met Glu Gly Ser Val Val Lys Arg Gln Ala Ala Asn Thr Leu
145                 150                 155                 160

Lys Cys Met Gln Thr Leu Ser Arg Val Gln Ser Gln Ile Arg Ala Arg
                165                 170                 175

Arg Ile Arg Xaa Ser Glu Glu Asn Gln Ala Arg Gln Lys Gln Leu Leu
            180                 185                 190

Gln Lys His Ala Lys Glu Leu Ala Gly Leu Lys Asn Gly Asp Asn Trp
        195                 200                 205

Asn Asp Ser Ile Gln Ser Lys Glu Lys Val Glu Ala Asn Leu Leu Ser
    210                 215                 220

Lys Tyr Glu Ala Thr Met Arg Arg Glu Arg Ala Leu Ala Tyr Ser Tyr
225                 230                 235                 240
```

```
Ser His Xaa Gln Asn Trp Lys Asn Asn Ser Lys Ser Gly Asn Pro Met
         245                 250                 255

Phe Met Asp Pro Ser Asn Pro Thr Trp Gly Trp Ser Trp Leu Glu Arg
260                 265                 270

Trp Met Ala Gly Arg Pro Leu Glu Ser Ser Glu Lys Glu Gln Ser Asn
        275                 280                 285

Ser Asn Asn Asp Asn Ala Ala Ser Val Lys Gly Ser Ile Asn Arg Asn
290                 295                 300

Glu Ala Ala Lys Ser Leu Thr Arg Asn Gly Ser Thr Gln Pro Asn Thr
305                 310                 315                 320

Pro Ser Ser Ala Arg Gly Thr Pro Arg Asn Lys Asn Ser Phe Phe Ser
                325                 330                 335

Pro Pro Thr Pro Ser Arg Leu Asn Gln Ser Ser Arg Lys Ser Asn Asp
            340                 345                 350

Asp Asp Ser Lys Ser Thr Ile Ser Val Leu Ser Glu Arg Asn Arg Arg
        355                 360                 365

His Xaa Ile Ala Gly Ser Ser Val Xaa Asp Asp Glu Ser Leu Ala Gly
    370                 375                 380

Ser Pro Ala Leu Pro Ser Tyr Met Val Pro Thr Lys Ser Ala Arg Ala
385                 390                 395                 400

Arg Leu Lys Pro Gln Ser Pro Leu Gly Gly Thr Thr Gln Glu Asn Glu
                405                 410                 415

Gly Phe Thr Asp Lys Ala Ser Ala Lys Lys Arg Leu Ser Tyr Pro Thr
            420                 425                 430

Ser Pro Ala Leu Pro Lys Pro Arg Arg Phe Ser Ala Pro Pro Lys Val
        435                 440                 445

Glu Ser Gly Gly Val Thr Val Thr Asn Gly Ala Gly Ser
450                 455                 460

<210> SEQ ID NO 137
<211> LENGTH: 1930
<212> TYPE: DNA
<213> ORGANISM: Zea mays
<220> FEATURE:
<221> NAME/KEY: misc_feature
<223> OTHER INFORMATION: Ceres CLONE ID no.375578
<220> FEATURE:
<221> NAME/KEY: exon
<222> LOCATION: (223)..(1716)
<223> OTHER INFORMATION: Encodes the peptide sequence at SEQ ID NO 138

<400> SEQUENCE: 137
aattcgagtg agcttattgg agactgacat cctaatcgaa aacccggttt atttttcctt      60
cgtcctggat gcgtcggtcg cgtgtttgat ctgactaagc cgcggaggag ggtgctagat     120
gtccgtgcgg tgggcggtgg ctcccgaggg cgaccggagt taggtccttg ccgccttcag     180
tgcggtgggg aagcgagaca ttgaaggcgc agaacccaaa ga atg ggt aag aga       234
                                                Met Gly Lys Arg
                                                  1 gga aag tgg ttt agt gcg gtg aag aaa gtc ttc agc tcc tcc gat cca       282
Gly Lys Trp Phe Ser Ala Val Lys Lys Val Phe Ser Ser Ser Asp Pro
  5              10                  15                  20 gat gga aag gaa gcc aag gcc cag aag gca gac aaa tcg aaa tcc aag       330
Asp Gly Lys Glu Ala Lys Ala Gln Lys Ala Asp Lys Ser Lys Ser Lys
                 25                  30                  35 agg aga tgg cca ttt gga aag tcc aag cac tcg gag cct tcc ata tcg       378
Arg Arg Trp Pro Phe Gly Lys Ser Lys His Ser Glu Pro Ser Ile Ser
         40                  45                  50
```

| | | | | | | | | | | | | | | | |
|---|---|---|---|---|---|---|---|---|---|---|---|---|---|---|---|
| acg | gtg | cca | ggc | act | gct | cca | gca | gta | gct | ccg | ttg | cca | tca | cca | cca | 426 |
| Thr | Val | Pro | Gly | Thr | Ala | Pro | Ala | Val | Ala | Pro | Leu | Pro | Ser | Pro | Pro | |
| | | 55 | | | | 60 | | | | | 65 | | | | | |

```
acg gtg cca ggc act gct cca gca gta gct ccg ttg cca tca cca cca    426
Thr Val Pro Gly Thr Ala Pro Ala Val Ala Pro Leu Pro Ser Pro Pro
        55              60                  65 gca act cag ccc cac tct ctg gag atc aaa gat gtc aat cca gtt gaa    474
Ala Thr Gln Pro His Ser Leu Glu Ile Lys Asp Val Asn Pro Val Glu
 70              75                  80 aca gac agt gag cag aac aag cat gcc tac tcc gtt gcg ctt gcg tct    522
Thr Asp Ser Glu Gln Asn Lys His Ala Tyr Ser Val Ala Leu Ala Ser
 85              90                  95                     100 gct gtc gct gct gaa gct gca gtt gct gcc cag gct gcg gaa            570
Ala Val Ala Ala Glu Ala Ala Val Ala Ala Gln Ala Ala Glu
                105                 110                 115 gtt gtc cgc ctc aca gca gtt acc acg gct gca cca aag atg cct gtt    618
Val Val Arg Leu Thr Ala Val Thr Thr Ala Ala Pro Lys Met Pro Val
            120                 125                 130 agt tcg agg gaa gaa ctt gcc gcc acc aag att cag act gcc ttc agg    666
Ser Ser Arg Glu Glu Leu Ala Ala Thr Lys Ile Gln Thr Ala Phe Arg
            135                 140                 145 ggt tat ctg gca agg aga gca ttg cgt gca cta aga ggg cta gtt aga    714
Gly Tyr Leu Ala Arg Arg Ala Leu Arg Ala Leu Arg Gly Leu Val Arg
        150                 155                 160 ttg aag tcg ctt gtt gat gga aat gct gtc aaa cgc caa acc gct cac    762
Leu Lys Ser Leu Val Asp Gly Asn Ala Val Lys Arg Gln Thr Ala His
165             170                 175                 180 acc ttg caa tgc aca caa gca atg aca aga gtt caa act caa atc tac    810
Thr Leu Gln Cys Thr Gln Ala Met Thr Arg Val Gln Thr Gln Ile Tyr
                185                 190                 195 tct aga agg gtg aag ttg gag gag gag aaa cag gct ctt caa aga caa    858
Ser Arg Arg Val Lys Leu Glu Glu Glu Lys Gln Ala Leu Gln Arg Gln
            200                 205                 210 ctc caa ttg aaa cat caa agg gaa ctt gag aaa atg aag att gat gaa    906
Leu Gln Leu Lys His Gln Arg Glu Leu Glu Lys Met Lys Ile Asp Glu
            215                 220                 225 gat tgg gat cac agc cat caa tcc aaa gag caa att gag gcc aac cta    954
Asp Trp Asp His Ser His Gln Ser Lys Glu Gln Ile Glu Ala Asn Leu
        230                 235                 240 atg atg aaa cag gaa gct gca ctg agg cga gag aga gca ctt gca tat   1002
Met Met Lys Gln Glu Ala Ala Leu Arg Arg Glu Arg Ala Leu Ala Tyr
245             250                 255                 260 gca ttt tct cac cag tgg agg aat tct ggt cga act ata acc cct act   1050
Ala Phe Ser His Gln Trp Arg Asn Ser Gly Arg Thr Ile Thr Pro Thr
                265                 270                 275 ttt acg gaa cct ggg aac ccc aac tgg ggc tgg agc tgg atg gag cgc   1098
Phe Thr Glu Pro Gly Asn Pro Asn Trp Gly Trp Ser Trp Met Glu Arg
            280                 285                 290 tgg atg aca gca aga cca tgg gag agt cgg ttg gcg gcg gca tcg gac   1146
Trp Met Thr Ala Arg Pro Trp Glu Ser Arg Leu Ala Ala Ala Ser Asp
        295                 300                 305 aag gac cct aaa gaa cgt gct gtg aca aag aat gcg agc acc agt gct   1194
Lys Asp Pro Lys Glu Arg Ala Val Thr Lys Asn Ala Ser Thr Ser Ala
    310                 315                 320 gtt cga gta cct gta tcc cgt gcc atc tcg att cag aga cca gca aca   1242
Val Arg Val Pro Val Ser Arg Ala Ile Ser Ile Gln Arg Pro Ala Thr
325             330                 335                 340 cca aac aag tcg agc cgc cca cca agc cgg cag tca ctt tca acc ccg   1290
Pro Asn Lys Ser Ser Arg Pro Pro Ser Arg Gln Ser Leu Ser Thr Pro
                345                 350                 355 cca tcg aag acc ccg tca gcc tca gga aag gcc agg ccg gca agt cca   1338
Pro Ser Lys Thr Pro Ser Ala Ser Gly Lys Ala Arg Pro Ala Ser Pro
            360                 365                 370
```

```
agg aac agt tgg ctg tac aag gag gat gac ctg agg agc atc acg agc   1386
Arg Asn Ser Trp Leu Tyr Lys Glu Asp Asp Leu Arg Ser Ile Thr Ser
            375                 380                 385 atc cgc tcc gag cgc cca agg agg cag agc acg ggt gga ggc tcg gtc   1434
Ile Arg Ser Glu Arg Pro Arg Arg Gln Ser Thr Gly Gly Gly Ser Val
        390                 395                 400 cgg gac gat acc agc ctg acc agc aca cca cct ctc ccc agc tac atg   1482
Arg Asp Asp Thr Ser Leu Thr Ser Thr Pro Pro Leu Pro Ser Tyr Met
405                 410                 415                 420 cag tcg acc gag tct gca cgg gcc aag tct cgg tac cgc agt cta cta   1530
Gln Ser Thr Glu Ser Ala Arg Ala Lys Ser Arg Tyr Arg Ser Leu Leu
            425                 430                 435 ctg act gag aag ctt gag gtt cct gag aga gcg cct ctg gcc cac tcc   1578
Leu Thr Glu Lys Leu Glu Val Pro Glu Arg Ala Pro Leu Ala His Ser
        440                 445                 450 gtt gtc aag aag cgc ctg tcg ttc ccc gtc gtc gag aag cca agc gtt   1626
Val Val Lys Lys Arg Leu Ser Phe Pro Val Val Glu Lys Pro Ser Val
    455                 460                 465 gtg ccg aca gag aag ccc agg gaa aga gtg agg cgc cat tcc gac cct   1674
Val Pro Thr Glu Lys Pro Arg Glu Arg Val Arg Arg His Ser Asp Pro
470                 475                 480 ccg aag gtc gat cct gcg acg ctc aag gat gcc cct gct gcc            1716
Pro Lys Val Asp Pro Ala Thr Leu Lys Asp Ala Pro Ala Ala
            485                 490                 495 tgaccagtga ccaggcctta tgtgattgtt aggtttcgtg ctcttttaac accgtgatgt   1776
attatctgag ttaggttgct tgttcgtgt catcgtatga tctgtccggg ttgattttga   1836
gacagttcta actgtgttta cagacaatgc gtgatgctaa atgtatgtgt ggttggttgg   1896
ctttaaatgt actgatatga tagtatttga tttc                             1930

<210> SEQ ID NO 138
<211> LENGTH: 498
<212> TYPE: PRT
<213> ORGANISM: Zea mays
<220> FEATURE:
<221> NAME/KEY: misc_feature
<223> OTHER INFORMATION: Ceres CLONE ID no.375578
<220> FEATURE:
<221> NAME/KEY: misc_feature
<223> OTHER INFORMATION: Score of 1275.4 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (137)..(157)
<223> OTHER INFORMATION: Pfam Name: IQ Pfam Description: IQ calmodulin-
      binding motif

<400> SEQUENCE: 138

Met Gly Lys Arg Gly Lys Trp Phe Ser Ala Val Lys Val Phe Ser
1               5                   10                  15

Ser Ser Asp Pro Asp Gly Lys Glu Ala Lys Ala Gln Lys Ala Asp Lys
            20                  25                  30

Ser Lys Ser Lys Arg Arg Trp Pro Phe Gly Lys Ser Lys His Ser Glu
        35                  40                  45

Pro Ser Ile Ser Thr Val Pro Gly Thr Ala Pro Ala Val Ala Pro Leu
    50                  55                  60

Pro Ser Pro Pro Ala Thr Gln Pro His Ser Leu Glu Ile Lys Asp Val
65                  70                  75                  80
```

```
Asn Pro Val Glu Thr Asp Ser Glu Gln Asn Lys His Ala Tyr Ser Val
                85                  90                  95
Ala Leu Ala Ser Ala Val Ala Ala Glu Ala Ala Val Ala Ala Gln
            100                 105                 110
Ala Ala Ala Glu Val Val Arg Leu Thr Ala Val Thr Thr Ala Ala Pro
            115                 120                 125
Lys Met Pro Val Ser Ser Arg Glu Glu Leu Ala Ala Thr Lys Ile Gln
            130                 135                 140
Thr Ala Phe Arg Gly Tyr Leu Ala Arg Arg Ala Leu Arg Ala Leu Arg
145                 150                 155                 160
Gly Leu Val Arg Leu Lys Ser Leu Val Asp Gly Asn Ala Val Lys Arg
                165                 170                 175
Gln Thr Ala His Thr Leu Gln Cys Thr Gln Ala Met Thr Arg Val Gln
                180                 185                 190
Thr Gln Ile Tyr Ser Arg Arg Val Lys Leu Glu Glu Glu Lys Gln Ala
            195                 200                 205
Leu Gln Arg Gln Leu Gln Leu Lys His Gln Arg Glu Leu Glu Lys Met
            210                 215                 220
Lys Ile Asp Glu Asp Trp Asp His Ser His Gln Ser Lys Glu Gln Ile
225                 230                 235                 240
Glu Ala Asn Leu Met Met Lys Gln Glu Ala Ala Leu Arg Arg Glu Arg
                245                 250                 255
Ala Leu Ala Tyr Ala Phe Ser His Gln Trp Arg Asn Ser Gly Arg Thr
            260                 265                 270
Ile Thr Pro Thr Phe Thr Glu Pro Gly Asn Pro Asn Trp Gly Trp Ser
            275                 280                 285
Trp Met Glu Arg Trp Met Thr Ala Arg Pro Trp Glu Ser Arg Leu Ala
290                 295                 300
Ala Ala Ser Asp Lys Asp Pro Lys Glu Arg Ala Val Thr Lys Asn Ala
305                 310                 315                 320
Ser Thr Ser Ala Val Arg Val Pro Val Ser Arg Ala Ile Ser Ile Gln
            325                 330                 335
Arg Pro Ala Thr Pro Asn Lys Ser Ser Arg Pro Pro Ser Arg Gln Ser
            340                 345                 350
Leu Ser Thr Pro Pro Ser Lys Thr Pro Ser Ala Ser Gly Lys Ala Arg
            355                 360                 365
Pro Ala Ser Pro Arg Asn Ser Trp Leu Tyr Lys Glu Asp Asp Leu Arg
            370                 375                 380
Ser Ile Thr Ser Ile Arg Ser Glu Arg Pro Arg Arg Gln Ser Thr Gly
385                 390                 395                 400
Gly Gly Ser Val Arg Asp Asp Thr Ser Leu Thr Ser Thr Pro Pro Leu
                405                 410                 415
Pro Ser Tyr Met Gln Ser Thr Glu Ser Ala Arg Ala Lys Ser Arg Tyr
            420                 425                 430
Arg Ser Leu Leu Leu Thr Glu Lys Leu Glu Val Pro Glu Arg Ala Pro
            435                 440                 445
Leu Ala His Ser Val Val Lys Lys Arg Leu Ser Phe Pro Val Val Glu
            450                 455                 460
Lys Pro Ser Val Val Pro Thr Glu Lys Pro Arg Glu Arg Val Arg Arg
465                 470                 475                 480
His Ser Asp Pro Pro Lys Val Asp Pro Ala Thr Leu Lys Asp Ala Pro
                485                 490                 495
Ala Ala
```

<210> SEQ ID NO 139
<211> LENGTH: 1930
<212> TYPE: DNA
<213> ORGANISM: Zea mays
<220> FEATURE:
<221> NAME/KEY: misc_feature
<223> OTHER INFORMATION: Ceres CLONE ID no.375578

<400> SEQUENCE: 139

```
aattcgagtg agcttattgg agactgacat cctaatcgaa aacccggttt attttttctt      60
cgtcctggat gcgtcggtcg cgtgtttgat ctgactaagc cgcggaggag ggtgctagat     120
gtccgtgcgg tgggcggtgg ctcccgaggg cgaccggagt taggtccttg ccgccttcag     180
tgcggtgggg aagcgagaca ttgaaggcgc agaacccaaa gaatgggtaa gagaggaaag     240
tggtttagtg cggtgaagaa agtcttcagc tcctccgatc cagatggaaa ggaagccaag     300
gcccagaagg cagacaaatc gaaatccaag aggagatggc catttggaaa gtccaagcac     360
tcggagcctt ccatatcgac ggtgccaggc actgctccag cagtagctcc gttgccatca     420
ccaccagcaa ctcagcccca ctctctggag atcaaagatg tcaatccagt tgaaacagac     480
agtgagcaga acaagcatgc ctactccgtt gcgcttgcgt ctgctgtcgc tgctgaagct     540
gcagcagttg ctgcccaggc tgctgcggaa gttgtccgcc tcacagcagt taccacggct     600
gcaccaaaga tgcctgttag ttcgagggaa taacttgccg ccaccaagat tcagactgcc     660
ttcaggggtt atctggcaag gagagcattg cgtgcactaa gagggctagt tagattgaag     720
tcgcttgttg atggaaatgc tgtcaaacgc caaaccgctc acaccttgca atgcacacaa     780
gcaatgacaa gagttcaaac tcaaatctac tctagaaggg tgaagttgga ggaggagaaa     840
caggctcttc aaagacaact ccaattgaaa catcaaaggg aacttgagaa aatgaagatt     900
gatgaagatt gggatcacag ccatcaatcc aaagagcaaa ttgaggccaa cctaatgatg     960
aaacaggaag ctgcactgag gcgagagaga gcacttgcat atgcattttc tcaccagtgg    1020
aggaattctg gtcgaactat aacccctact tttacggaac ctgggaaccc caactggggc    1080
tggagctgga tggagcgctg gatgacagca agaccatggg agagtcggtt ggcggcggca    1140
tcggacaagg accctaaaga acgtgctgtg acaaagaatg cgagcaccag tgctgttcga    1200
gtacctgtat cccgtgccat ctcgattcag agaccagcaa caccaaacaa gtcgagccgc    1260
ccaccaagcc ggcagtcact ttcaaccccg ccatcgaaga ccccgtcagc ctcaggaaag    1320
gccaggccgg caagtccaag gaacagttgg ctgtacaagg aggatgacct gaggagcatc    1380
acgagcatcc gctccgagcg cccaaggagg cagagcacgg gtggaggctc ggtccgggac    1440
gataccagcc tgaccagcac accacctctc cccagctaca tgcagtcgac cgagtctgca    1500
cgggccaagt ctcggtaccg cagtctacta ctgactgaga agcttgaggt tcctgagaga    1560
gcgcctctgg cccactccgt tgtcaagaag cgcctgtcgt tccccgtcgt cgagaagcca    1620
agcgttgtgc cgacagagaa gcccagggaa agagtgaggc gccattccga ccctccgaag    1680
gtcgatcctg cgacgctcaa ggatgcccct gctgcctgac cagtgaccag gccttatgtg    1740
attgttaggt ttcgtgctct tttaacaccg tgatgtatta tctgagttag gttgctttgt    1800
tcgtgtcatc gtatgatctg tccgggttga ttttgagaca gttctaactg tgtttacaga    1860
caatgcgtga tgctaaatgt atgtgtggtt ggttggcttt aaatgtactg atatgatagt    1920
atttgatttc                                                           1930
```

```
<210> SEQ ID NO 140
<211> LENGTH: 311
<212> TYPE: PRT
<213> ORGANISM: Zea mays
<220> FEATURE:
<221> NAME/KEY: misc_feature
<223> OTHER INFORMATION: Ceres CLONE ID no.375578
<220> FEATURE:
<221> NAME/KEY: misc_feature
<223> OTHER INFORMATION: Score of 653.4 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 140

Met Thr Arg Val Gln Thr Gln Ile Tyr Ser Arg Arg Val Lys Leu Glu
1               5                   10                  15

Glu Glu Lys Gln Ala Leu Gln Arg Gln Leu Gln Leu Lys His Gln Arg
            20                  25                  30

Glu Leu Glu Lys Met Lys Ile Asp Glu Asp Trp Asp His Ser His Gln
        35                  40                  45

Ser Lys Glu Gln Ile Glu Ala Asn Leu Met Met Lys Gln Glu Ala Ala
    50                  55                  60

Leu Arg Arg Glu Arg Ala Leu Ala Tyr Ala Phe Ser His Gln Trp Arg
65                  70                  75                  80

Asn Ser Gly Arg Thr Ile Thr Pro Thr Phe Thr Glu Pro Gly Asn Pro
                85                  90                  95

Asn Trp Gly Trp Ser Trp Met Glu Arg Trp Met Thr Ala Arg Pro Trp
            100                 105                 110

Glu Ser Arg Leu Ala Ala Ala Ser Asp Lys Asp Pro Lys Glu Arg Ala
        115                 120                 125

Val Thr Lys Asn Ala Ser Thr Ser Ala Val Arg Val Pro Val Ser Arg
    130                 135                 140

Ala Ile Ser Ile Gln Arg Pro Ala Thr Pro Asn Lys Ser Ser Arg Pro
145                 150                 155                 160

Pro Ser Arg Gln Ser Leu Ser Thr Pro Pro Ser Lys Thr Pro Ser Ala
                165                 170                 175

Ser Gly Lys Ala Arg Pro Ala Ser Pro Arg Asn Ser Trp Leu Tyr Lys
            180                 185                 190

Glu Asp Asp Leu Arg Ser Ile Thr Ser Ile Arg Ser Glu Arg Pro Arg
        195                 200                 205

Arg Gln Ser Thr Gly Gly Ser Val Arg Asp Asp Thr Ser Leu Thr
    210                 215                 220

Ser Thr Pro Pro Leu Pro Ser Tyr Met Gln Ser Thr Glu Ser Ala Arg
225                 230                 235                 240

Ala Lys Ser Arg Tyr Arg Ser Leu Leu Leu Thr Glu Lys Leu Glu Val
                245                 250                 255

Pro Glu Arg Ala Pro Leu Ala His Ser Val Val Lys Lys Arg Leu Ser
            260                 265                 270

Phe Pro Val Val Glu Lys Pro Ser Val Val Pro Thr Glu Lys Pro Arg
        275                 280                 285

Glu Arg Val Arg Arg His Ser Asp Pro Pro Lys Val Asp Pro Ala Thr
    290                 295                 300

Leu Lys Asp Ala Pro Ala Ala
305                 310

<210> SEQ ID NO 141
```

```
<211> LENGTH: 217
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME10681
<220> FEATURE:
<221> NAME/KEY: misc_feature
<223> OTHER INFORMATION: Score of 322.9 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 141

Met Gly Lys Lys Gly Lys Trp Phe Gly Ala Val Lys Lys Val Phe Ser
1               5                   10                  15

Pro Glu Ser Lys Glu Lys Lys Glu Ser Asn Ile Asp Arg Gly Ser
            20                  25                  30

Val Lys Ser Met Ser Leu Asn Leu Gly Glu Gly Glu Ile Thr Lys Ala
        35                  40                  45

Phe Asn Arg Arg Asp Ser Lys Leu Glu Lys Pro Ser Pro Thr Pro
    50                  55                  60

Arg Pro Ala Arg Pro Thr Ser Arg His Ser Pro Leu Thr Pro Ser Ala
65                  70                  75                  80

Arg Val Ala Pro Ile Pro Ala Arg Arg Lys Ser Val Thr Pro Lys Asn
                85                  90                  95

Gly Leu Ser Gln Val Asp Asp Ala Arg Ser Val Leu Ser Val Gln
            100                 105                 110

Ser Glu Arg Pro Arg Arg His Ser Ile Ala Thr Ser Thr Val Arg Asp
        115                 120                 125

Asp Glu Ser Leu Thr Ser Ser Pro Ser Leu Pro Ser Tyr Met Val Pro
130                 135                 140

Thr Glu Ser Ala Arg Ala Lys Ser Arg Leu Gln Gly Ser Ala Met Ala
145                 150                 155                 160

Asn Gly Ala Glu Thr Pro Glu Lys Gly Gly Ser Thr Gly Pro Ala Lys
                165                 170                 175

Lys Arg Leu Ser Phe Gln Gly Gly Thr Ala Ala Ala Ser Pro Met Arg
            180                 185                 190

Arg His Ser Gly Pro Pro Lys Val Glu Ile Ala Pro Pro Gln Pro Glu
        195                 200                 205

Ala Leu Val Val Asn Gly Gly Ser Lys
    210                 215

<210> SEQ ID NO 142
<211> LENGTH: 311
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME03140
<220> FEATURE:
<221> NAME/KEY: misc_feature
<223> OTHER INFORMATION: Score of 653.4 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 142

Met Thr Arg Val Gln Thr Gln Ile Tyr Ser Arg Arg Val Lys Leu Glu
1               5                   10                  15
```

```
Glu Glu Lys Gln Ala Leu Gln Arg Gln Leu Gln Leu Lys His Gln Arg
             20                  25                  30

Glu Leu Glu Lys Met Lys Ile Asp Glu Asp Trp Asp His Ser His Gln
         35                  40                  45

Ser Lys Glu Gln Ile Glu Ala Asn Leu Met Met Lys Gln Glu Ala Ala
 50                  55                  60

Leu Arg Arg Glu Arg Ala Leu Ala Tyr Ala Phe Ser His Gln Trp Arg
 65                  70                  75                  80

Asn Ser Gly Arg Thr Ile Thr Pro Thr Phe Thr Glu Pro Gly Asn Pro
                 85                  90                  95

Asn Trp Gly Trp Ser Trp Met Glu Arg Trp Met Thr Ala Arg Pro Trp
            100                 105                 110

Glu Ser Arg Leu Ala Ala Ala Ser Asp Lys Asp Pro Lys Glu Arg Ala
        115                 120                 125

Val Thr Lys Asn Ala Ser Thr Ser Ala Val Arg Val Pro Val Ser Arg
130                 135                 140

Ala Ile Ser Ile Gln Arg Pro Ala Thr Pro Asn Lys Ser Ser Arg Pro
145                 150                 155                 160

Pro Ser Arg Gln Ser Leu Ser Thr Pro Pro Ser Lys Thr Pro Ser Ala
                165                 170                 175

Ser Gly Lys Ala Arg Pro Ala Ser Pro Arg Asn Ser Trp Leu Tyr Lys
            180                 185                 190

Glu Asp Asp Leu Arg Ser Ile Thr Ser Ile Arg Ser Glu Arg Pro Arg
        195                 200                 205

Arg Gln Ser Thr Gly Gly Gly Ser Val Arg Asp Asp Thr Ser Leu Thr
    210                 215                 220

Ser Thr Pro Pro Leu Pro Ser Tyr Met Gln Ser Thr Glu Ser Ala Arg
225                 230                 235                 240

Ala Lys Ser Arg Tyr Arg Ser Leu Leu Leu Thr Glu Lys Leu Glu Val
                245                 250                 255

Pro Glu Arg Ala Pro Leu Ala His Ser Val Val Lys Lys Arg Leu Ser
            260                 265                 270

Phe Pro Val Val Glu Lys Pro Ser Val Val Pro Thr Glu Lys Pro Arg
        275                 280                 285

Glu Arg Val Arg Arg His Ser Asp Pro Pro Lys Val Asp Pro Ala Thr
290                 295                 300

Leu Lys Asp Ala Pro Ala Ala
305                 310
```

<210> SEQ ID NO 143
<211> LENGTH: 421
<212> TYPE: PRT
<213> ORGANISM: Arabidopsis thaliana
<220> FEATURE:
<221> NAME/KEY: misc_feature
<223> OTHER INFORMATION: Ceres SEEDLINE ID no.ME24076
<220> FEATURE:
<221> NAME/KEY: misc_feature
<223> OTHER INFORMATION: Score of 908.3 for HMM of FIGURE 4.
<220> FEATURE:
<221> NAME/KEY: misc_feature
<223> OTHER INFORMATION: Functional Homolog Of Ceres SEEDLINE ID no.
     ME24091 at SEQ ID NO. 136
<220> FEATURE:
<221> NAME/KEY: misc_feature
<222> LOCATION: (60)..(80)
<223> OTHER INFORMATION: Pfam Name: IQ Pfam Description: IQ calmodulin-
     binding motif

<400> SEQUENCE: 143

-continued

```
Leu Glu Val Asn Leu Ser Val Pro Pro Pro Ala Pro Pro Val
1               5                   10                  15

Leu His Gln Ala Glu Glu Val Gly Val Pro Glu Ala Glu Gln Gln
                20                  25                  30

Ser Lys His Val Ala Val Glu Glu Ala Pro Ala Ala Pro Ala Gln
            35                  40                  45

Ala Ser Val Leu Pro Pro Ala Val Pro Thr Gln Glu Leu Ala Ala Val
    50                  55                  60

Lys Ile Gln Thr Ala Phe Arg Gly Tyr Leu Ala Arg Arg Ala Leu Arg
65                      70                  75                  80

Ala Leu Arg Gly Leu Val Arg Leu Lys Ser Leu Val Glu Gly Asn Ser
                85                  90                      95

Val Lys Arg Gln Ser Ala Ser Thr Leu Arg Cys Met Gln Thr Leu Ser
                100                 105                 110

Arg Val Gln Ser Gln Ile Ser Ser Arg Arg Ala Lys Met Ser Glu Glu
            115                 120                 125

Asn Gln Ala Leu Gln Arg Gln Leu Leu Leu Lys Gln Glu Leu Glu Asn
            130                 135                 140

Phe Arg Met Gly Glu Asn Trp Asp Asp Ser Thr Gln Ser Lys Glu Gln
145                 150                 155                 160

Ile Glu Ala Ser Leu Ile Ser Arg Gln Glu Ala Ala Ile Arg Arg Glu
                165                 170                 175

Arg Ala Leu Ala Tyr Ala Phe Ser His Gln Trp Lys Ser Thr Ser Arg
                180                 185                 190

Ser Val Asn Pro Met Phe Val Asp Pro Asn Asn Leu Gln Trp Gly Trp
            195                 200                 205

Ser Trp Leu Glu Arg Trp Met Ala Ala Lys Pro Trp Glu Gly Arg Asn
210                 215                 220

Gly Ala Asp Lys Glu Ser Asn Ile Asp Arg Gly Ser Val Lys Ser Met
225                 230                 235                 240

Ser Leu Asn Leu Gly Glu Gly Glu Ile Thr Lys Ala Phe Asn Arg Arg
                245                 250                 255

Asp Ser Lys Leu Glu Lys Pro Ser Pro Thr Pro Arg Pro Ala Arg
                260                 265                 270

Pro Thr Ser Arg His Ser Pro Leu Thr Pro Ser Ala Arg Val Ala Pro
            275                 280                 285

Ile Pro Ala Arg Arg Lys Ser Val Thr Pro Lys Asn Gly Leu Ser Gln
            290                 295                 300

Val Asp Asp Asp Ala Arg Ser Val Leu Ser Val Gln Ser Glu Arg Pro
305                 310                 315                 320

Arg Arg His Ser Ile Ala Thr Ser Thr Val Arg Asp Asp Glu Ser Leu
                325                 330                 335

Thr Ser Ser Pro Ser Leu Pro Ser Tyr Met Val Pro Thr Glu Ser Ala
                340                 345                 350

Arg Ala Lys Ser Arg Leu Gln Gly Ser Ala Met Ala Asn Gly Ala Glu
            355                 360                 365

Thr Pro Glu Lys Gly Gly Ser Thr Gly Pro Ala Lys Lys Arg Leu Ser
    370                 375                 380

Phe Gln Gly Gly Thr Ala Ala Ala Ser Pro Met Arg Arg His Ser Gly
385                 390                 395                 400

Pro Pro Lys Val Glu Ile Ala Pro Pro Gln Pro Glu Ala Leu Val Val
                405                 410                 415
```

```
Asn Gly Gly Ser Lys
            420

<210> SEQ ID NO 144
<211> LENGTH: 311
<212> TYPE: PRT
<213> ORGANISM: Oryza sativa subsp. japonica
<220> FEATURE:
<221> NAME/KEY: misc_feature
<223> OTHER INFORMATION: Ceres SEEDLINE ID no.ME24217
<220> FEATURE:
<221> NAME/KEY: misc_feature
<223> OTHER INFORMATION: Score of 653.4 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 144

Met Thr Arg Val Gln Thr Gln Ile Tyr Ser Arg Arg Val Lys Leu Glu
1               5                   10                  15

Glu Glu Lys Gln Ala Leu Gln Arg Gln Leu Gln Leu Lys His Gln Arg
            20                  25                  30

Glu Leu Glu Lys Met Lys Ile Asp Glu Asp Trp Asp His Ser His Gln
        35                  40                  45

Ser Lys Glu Gln Ile Glu Ala Asn Leu Met Met Lys Gln Glu Ala Ala
    50                  55                  60

Leu Arg Arg Glu Arg Ala Leu Ala Tyr Ala Phe Ser His Gln Trp Arg
65                  70                  75                  80

Asn Ser Gly Arg Thr Ile Thr Pro Thr Phe Thr Glu Pro Gly Asn Pro
                85                  90                  95

Asn Trp Gly Trp Ser Trp Met Glu Arg Trp Met Thr Ala Arg Pro Trp
            100                 105                 110

Glu Ser Arg Leu Ala Ala Ala Ser Asp Lys Asp Pro Lys Glu Arg Ala
        115                 120                 125

Val Thr Lys Asn Ala Ser Thr Ser Ala Val Arg Val Pro Val Ser Arg
    130                 135                 140

Ala Ile Ser Ile Gln Arg Pro Ala Thr Pro Asn Lys Ser Ser Arg Pro
145                 150                 155                 160

Pro Ser Arg Gln Ser Leu Ser Thr Pro Pro Ser Lys Thr Pro Ser Ala
                165                 170                 175

Ser Gly Lys Ala Arg Pro Ala Ser Pro Arg Asn Ser Trp Leu Tyr Lys
            180                 185                 190

Glu Asp Asp Leu Arg Ser Ile Thr Ser Ile Arg Ser Glu Arg Pro Arg
        195                 200                 205

Arg Gln Ser Thr Gly Gly Ser Val Arg Asp Asp Thr Ser Leu Thr
    210                 215                 220

Ser Thr Pro Pro Leu Pro Ser Tyr Met Gln Ser Thr Glu Ser Ala Arg
225                 230                 235                 240

Ala Lys Ser Arg Tyr Arg Ser Leu Leu Leu Thr Glu Lys Leu Glu Val
                245                 250                 255

Pro Glu Arg Ala Pro Leu Ala His Ser Val Val Lys Arg Leu Ser
            260                 265                 270

Phe Pro Val Glu Lys Pro Ser Val Val Pro Thr Glu Lys Pro Arg
        275                 280                 285

Glu Arg Val Arg Arg His Ser Asp Pro Pro Lys Val Asp Pro Ala Thr
    290                 295                 300

Leu Lys Asp Ala Pro Ala Ala
```

```
305                310
```

<210> SEQ ID NO 145
<211> LENGTH: 500
<212> TYPE: PRT
<213> ORGANISM: Oryza sativa subsp. japonica
<220> FEATURE:
<221> NAME/KEY: misc_feature
<223> OTHER INFORMATION: Public GI ID no.115440873
<220> FEATURE:
<221> NAME/KEY: misc_feature
<223> OTHER INFORMATION: Score of 1281.0 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (142)..(162)
<223> OTHER INFORMATION: Pfam Name: IQ Pfam Description: IQ calmodulin-
      binding motif

<400> SEQUENCE: 145

Met Gly Lys Lys Gly Asn Trp Phe Ser Ala Val Lys Lys Val Phe Ser
1               5                   10                  15

Ser Ser Asp Pro Asp Gly Arg Glu Ala Lys Ile Glu Lys Ala Asp Lys
            20                  25                  30

Ser Arg Ser Arg Arg Lys Trp Pro Phe Gly Lys Ser Lys Lys Ser Asp
        35                  40                  45

Pro Trp Thr Ser Thr Val Ala Val Pro Thr Ser Thr Ala Pro Pro Pro
    50                  55                  60

Gln Pro Pro Pro Pro Pro Thr His Pro Ile Gln Pro Gln Pro Glu
65                  70                  75                  80

Glu Ile Lys Asp Val Lys Ala Val Glu Thr Asp Ser Glu Gln Asn Lys
                85                  90                  95

His Ala Tyr Ser Val Ala Leu Ala Ser Ala Val Ala Ala Glu Ala Ala
            100                 105                 110

Ala Val Ala Ala Gln Ala Ala Ala Glu Val Val Arg Leu Thr Thr Ala
        115                 120                 125

Thr Thr Ala Val Pro Lys Ser Pro Val Ser Ser Lys Asp Glu Leu Ala
    130                 135                 140

Ala Ile Lys Ile Gln Thr Ala Phe Arg Gly Tyr Leu Ala Arg Arg Ala
145                 150                 155                 160

Leu Arg Ala Leu Arg Gly Leu Val Arg Leu Lys Ser Leu Val Asp Gly
                165                 170                 175

Asn Ala Val Lys Arg Gln Thr Ala His Thr Leu His Cys Thr Gln Thr
            180                 185                 190

Met Thr Arg Val Gln Thr Gln Ile Tyr Ser Arg Arg Val Lys Met Glu
        195                 200                 205

Glu Glu Lys Gln Ala Leu Gln Arg Gln Leu Gln Leu Lys His Gln Arg
    210                 215                 220

Glu Leu Glu Lys Met Lys Ile Asp Glu Asp Trp Asp His Ser His Gln
225                 230                 235                 240

Ser Lys Glu Gln Val Glu Thr Ser Leu Met Met Lys Gln Glu Ala Ala
                245                 250                 255

Leu Arg Arg Glu Arg Ala Leu Ala Tyr Ala Phe Ser His Gln Trp Lys
            260                 265                 270

Asn Ser Gly Arg Thr Ile Thr Pro Thr Phe Thr Asp Gln Gly Asn Pro
        275                 280                 285

```
Asn Trp Gly Trp Ser Trp Met Glu Arg Trp Met Thr Ser Arg Pro Trp
            290                 295                 300

Glu Ser Arg Val Ile Ser Asp Lys Asp Pro Lys Asp His Tyr Ser Thr
305                 310                 315                 320

Lys Asn Pro Ser Thr Ser Ala Ser Arg Thr Tyr Val Pro Arg Ala Ile
                325                 330                 335

Ser Ile Gln Arg Pro Ala Thr Pro Asn Lys Ser Ser Arg Pro Pro Ser
                340                 345                 350

Arg Gln Ser Pro Ser Thr Pro Pro Ser Arg Val Pro Ser Val Thr Gly
                355                 360                 365

Lys Ile Arg Pro Ala Ser Pro Arg Asp Ser Trp Leu Tyr Lys Glu Asp
    370                 375                 380

Asp Leu Arg Ser Ile Thr Ser Ile Arg Ser Glu Arg Pro Arg Arg Gln
385                 390                 395                 400

Ser Thr Gly Gly Ala Ser Val Arg Asp Asp Ala Ser Leu Thr Ser Thr
                405                 410                 415

Pro Ala Leu Pro Ser Tyr Met Gln Ser Thr Glu Ser Ala Arg Ala Lys
                420                 425                 430

Ser Arg Tyr Arg Ser Leu Leu Thr Asp Arg Phe Glu Val Pro Glu Arg
                435                 440                 445

Val Pro Leu Val His Ser Ser Ile Lys Lys Arg Leu Ser Phe Pro Val
450                 455                 460

Ala Asp Lys Pro Asn Gly Glu His Ala Asp Lys Leu Met Glu Arg Gly
465                 470                 475                 480

Arg Arg His Ser Asp Pro Pro Lys Val Asp Pro Ala Ser Leu Lys Asp
                485                 490                 495

Val Pro Val Ser
            500

<210> SEQ ID NO 146
<211> LENGTH: 1695
<212> TYPE: DNA
<213> ORGANISM: Triticum aestivum
<220> FEATURE:
<221> NAME/KEY: misc_feature
<223> OTHER INFORMATION: Ceres CLONE ID no.826796
<220> FEATURE:
<221> NAME/KEY: misc_feature
<223> OTHER INFORMATION: Encodes the peptide sequence at SEQ ID NO 147

<400> SEQUENCE: 146
ataggacttc acagacagac tgactcaatc ctaacccaat ccctcccatg cttccatcta      60
ctctagcaga aattgcagag gaggttggcc gccgccggct ccagcgcagg cgcagcctac     120
ccgcgggatc tgacgccctc cgcctcctac ctcgaggcac gcgcctcagg ctcagctccc     180
ccgcccgccc tccccgcta ccccgacgac ttccaagagg aggagcatga aattgagcat      240
gtcgccgccg cgccagcgcc agcgccagcc acggatgcgc cgctacctgc ccctcctgcc     300
gccgcaccac cacaggttca ggctgccatt gcgccggctt cttcctcttg tgtcatgtcc     360
agggagctcg ccgccaccaa gatccagacc gccttccgag gtcacctggc aagaagggcg     420
ctgcgggcat tgaaaggcct ggtcagactc aagtcgctgg tccaaggcca ctccgtcaag     480
cgccaggcca ccagcacgct tcgctgcatg cagactctgt cccgggtcca gtccaagata     540
cggacgagga ggatcaagat ggccgaggag aaccaggccc ttcagcgcca gctcttgttg     600
aaccaggaac tagagactct caggatggga gatcagtgga ataccagcct gcagtccaag     660
gagcaaatcg aggcgagcct cgtgagcagg caagaggccg cggctagaag agaacgggct     720
```

-continued

```
ctcgcatacg cattctccca ccagtggaag agcacctcaa ggtctgccaa cccgatgttc      780
gtggacccga gtaacccgca ctggggctgg agctggctgg agcggtggat ggcgtcgagg      840
ccgttcgacg ccgcaacgg ggcgtccgag aaggagggca gcagcgtcga ccgcacgtcg       900
gtgcacagca ccagcctgag catgaacctc ggagaaggtg agacggtcac aaaggcggac     960
aaccaggtgg tggactcttt gaagccgaat gatgataagc cgccgccgct ttcgactccg    1020
aagccgtccg ccctgcccc caggcagtcc ccgtcgacgc cctcgccggc gctggcgagg     1080
aagaagagcg cgacgcccaa gagtggagac tgcgacggcg acgacgcgag gagcgtggtc    1140
agcactgtcc ggtccgagcg gccccggagg cacagcatcg gcgcgtccag cgtgcgtgac    1200
gacgcgggct cttccccgtc ggtgccgagc tacatggcgg ccaccaagtc ggcgtcggcc    1260
agggccaagt cgcgtgtgca gagcccgacg ctgaccgagg tgctgctca agctgagacg     1320 ctggagaaag gatggtcttc tgtgggttca gcgaagaagc ggctgtcctt tccggctggg    1380
acgccaccgc cggtgccggc ggcggcggcg aggcggcact ccgggcctcc caaggtgcgg    1440
caggcgggcg tggaaggtgg tacggaggaa cgggactcgt cccttgcgtg acatcatggg    1500
aagcagatta tggtgtggag cagagcagag cggaatttgt tgcatttgtt gagtgaaagg    1560
aacgcagaat gtgtgttgtg tggatccatt ggatttgatt tgatttgtat gatggcagta    1620
ttcctatttg attattcatt gaataatata agtatctgta atgaagataa aaggagggga    1680
cacgaacatt atttc                                                     1695
```

<210> SEQ ID NO 147
<211> LENGTH: 378
<212> TYPE: PRT
<213> ORGANISM: Triticum aestivum
<220> FEATURE:
<221> NAME/KEY: misc_feature
<223> OTHER INFORMATION: Ceres CLONE ID no.826796
<220> FEATURE:
<221> NAME/KEY: misc_feature
<223> OTHER INFORMATION: Score of 903.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (4)..(24)
<223> OTHER INFORMATION: Pfam Name: IQ Pfam Description: IQ calmodulin-
      binding motif

<400> SEQUENCE: 147

```
Met Ser Arg Glu Leu Ala Ala Thr Lys Ile Gln Thr Ala Phe Arg Gly
1               5                   10                  15

His Leu Ala Arg Arg Ala Leu Arg Ala Leu Lys Gly Leu Val Arg Leu
            20                  25                  30

Lys Ser Leu Val Gln Gly His Ser Val Lys Arg Gln Ala Thr Ser Thr
        35                  40                  45

Leu Arg Cys Met Gln Thr Leu Ser Arg Val Gln Ser Lys Ile Arg Thr
    50                  55                  60

Arg Arg Ile Lys Met Ala Glu Glu Asn Gln Ala Leu Gln Arg Gln Leu
65                  70                  75                  80

Leu Leu Asn Gln Glu Leu Glu Thr Leu Arg Met Gly Asp Gln Trp Asn
                85                  90                  95

Thr Ser Leu Gln Ser Lys Glu Gln Ile Glu Ala Ser Leu Val Ser Arg
            100                 105                 110
```

```
Gln Glu Ala Ala Ala Arg Arg Glu Arg Ala Leu Ala Tyr Ala Phe Ser
            115                 120                 125

His Gln Trp Lys Ser Thr Ser Arg Ser Ala Asn Pro Met Phe Val Asp
        130                 135                 140

Pro Ser Asn Pro His Trp Gly Trp Ser Trp Leu Glu Arg Trp Met Ala
145                 150                 155                 160

Ser Arg Pro Phe Asp Gly Arg Asn Gly Ala Ser Glu Lys Glu Gly Ser
                165                 170                 175

Ser Val Asp Arg Thr Ser Val His Ser Thr Ser Leu Ser Met Asn Leu
            180                 185                 190

Gly Glu Gly Glu Thr Val Thr Lys Ala Asp Asn Gln Val Val Asp Ser
        195                 200                 205

Leu Lys Pro Asn Asp Asp Lys Pro Pro Leu Ser Thr Pro Lys Pro
    210                 215                 220

Ser Gly Pro Ala Pro Arg Gln Ser Pro Ser Thr Pro Ser Pro Ala Leu
225                 230                 235                 240

Ala Arg Lys Lys Ser Ala Thr Pro Lys Ser Gly Asp Cys Asp Gly Asp
                245                 250                 255

Asp Ala Arg Ser Val Val Ser Thr Val Arg Ser Glu Arg Pro Arg Arg
            260                 265                 270

His Ser Ile Gly Ala Ser Val Arg Asp Asp Ala Gly Ser Ser Pro
        275                 280                 285

Ser Val Pro Ser Tyr Met Ala Ala Thr Lys Ser Ala Ser Ala Arg Ala
290                 295                 300

Lys Ser Arg Val Gln Ser Pro Thr Leu Thr Glu Gly Ala Ala Gln Ala
305                 310                 315                 320

Glu Thr Leu Glu Lys Gly Trp Ser Ser Val Gly Ser Ala Lys Lys Arg
                325                 330                 335

Leu Ser Phe Pro Ala Gly Thr Pro Pro Val Pro Ala Ala Ala
            340                 345                 350

Arg Arg His Ser Gly Pro Pro Lys Val Arg Gln Ala Gly Val Glu Gly
        355                 360                 365

Gly Thr Glu Glu Arg Asp Ser Ser Leu Ala
370                 375

<210> SEQ ID NO 148
<211> LENGTH: 1470
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1465047
<220> FEATURE:
<221> NAME/KEY: misc_feature
<223> OTHER INFORMATION: Encodes the peptide sequence at SEQ ID NO 149

<400> SEQUENCE: 148
atggggaaaa gagggagttg gttctctgct ttgaagaaag ccctcggttc ctctaagaaa      60
tccaaatcaa agaagaaatg gtcagaaaaa gagaagaacc gggatctagg tgtttcttca     120
catgaagaaa ccgttgcacc ctctctttct cctcctcgta caccacctcc tcctacagca     180
gaagatgtga aattaactga agctgagaac gagcagagca agcatgctta ttccgtggcg     240
cttgccactg ctgtggcagc tgaggcagct gttgcagccg cccaggctgc cgctgaggtt     300
gttcggctta ctacagtggc acattactct ggaaaatcga aggaggaaat agctgcaatc     360
aggattcaaa cagcatttag aggatacctg gcgaggaggg cattacgtgc tttgagaggg     420
```

```
ctggtgagat tgaagtcatt gatacaaggg caatctgtca acggcaagc aactgccaca      480 ttacgagcca tgcagactct tgctcgtgtg cagtctcaga ttcgtgcaag aaggatcaga      540
atgtccgagg aaaatgaggc cctccaacgg cagctccagc agaaacatga caaagaactt      600
gagaagttga aacttctat tggagaacaa tgggatgata gcccacaatc aaaggaagaa       660
gttgaagcca gcctactaca aaagcaagaa gctgccatga aagagaaag ggcactggct      720 tatgcatact cgcatcagca aatgtggaag caatcttcaa aatcagcaaa tgctacattc      780
atggatccaa acaatcctcg ttggggatgg agttggttag agaggtggat ggcagcccga      840
ccttgggaga gccgaagcac aatagataac aatgatcggg cctctgttaa gagtacaaca      900
agccgtacca tgtctcttgg agaaatcagc agagcttatt ctcgtcgtga tcttaaccat      960
gacaataaag cttctcctgg tgcgcaaaaa tcaagtcggc ctcccagtcg gcaatcacct     1020
tctactcccc cctctaaggc accatctaca tcttcagtaa cagggaaagc aaagccacca     1080
agccctagag ggagtgcttg gggaggagac gaggactcca ggagcacatt cagtgtccag     1140
tctgagcgct atcggagaca tagcatagca gggtcatcaa taagagatga tgagagtctt     1200
gcaagttcgc cttcagttcc aagttacatg gcacccacac ggtcacagtc agcaaaggca     1260
aaatcccgct tgtcaagccc gttaggcata gataataatg ggacaccaga taaggcatca     1320
gtgggttatg taaagaagcg gctttccttc tctgcttcac cagctggagc aaggagacac     1380
tctggtcctc ctagggtgga tgccagtgct gttaaagaca ttcaaatgca cagagaagag     1440
aaaatgagca atggagcaag cagcaagtag                                      1470
```

<210> SEQ ID NO 149
<211> LENGTH: 326
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no.1465047
<220> FEATURE:
<221> NAME/KEY: misc_feature
<223> OTHER INFORMATION: Score of 746.5 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 149

Met Gln Thr Leu Ala Arg Val Gln Ser Gln Ile Arg Ala Arg Arg Ile
1               5                   10                  15

Arg Met Ser Glu Glu Asn Glu Ala Leu Gln Arg Gln Leu Gln Gln Lys
            20                  25                  30

His Asp Lys Glu Leu Glu Lys Leu Arg Thr Ser Ile Gly Glu Gln Trp
        35                  40                  45

Asp Asp Ser Pro Gln Ser Lys Glu Glu Val Glu Ala Ser Leu Leu Gln
    50                  55                  60

Lys Gln Glu Ala Ala Met Arg Arg Glu Arg Ala Leu Ala Tyr Ala Tyr
65                  70                  75                  80

Ser His Gln Gln Met Trp Lys Gln Ser Ser Lys Ser Ala Asn Ala Thr
                85                  90                  95

Phe Met Asp Pro Asn Asn Pro Arg Trp Gly Trp Ser Trp Leu Glu Arg
            100                 105                 110

Trp Met Ala Ala Arg Pro Trp Glu Ser Arg Ser Thr Ile Asp Asn Asn
        115                 120                 125

Asp Arg Ala Ser Val Lys Ser Thr Thr Ser Arg Thr Met Ser Leu Gly

```
                    130                 135                 140
Glu Ile Ser Arg Ala Tyr Ser Arg Arg Asp Leu Asn His Asp Asn Lys
145                 150                 155                 160

Ala Ser Pro Gly Ala Gln Lys Ser Ser Arg Pro Ser Arg Gln Ser
                165                 170                 175

Pro Ser Thr Pro Pro Ser Lys Ala Pro Ser Thr Ser Val Thr Gly
            180                 185                 190

Lys Ala Lys Pro Pro Ser Pro Arg Gly Ser Ala Trp Gly Gly Asp Glu
            195                 200                 205

Asp Ser Arg Ser Thr Phe Ser Val Gln Ser Glu Arg Tyr Arg Arg His
            210                 215                 220

Ser Ile Ala Gly Ser Ser Ile Arg Asp Asp Glu Ser Leu Ala Ser Ser
225                 230                 235                 240

Pro Ser Val Pro Ser Tyr Met Ala Pro Thr Arg Ser Gln Ser Ala Lys
                245                 250                 255

Ala Lys Ser Arg Leu Ser Ser Pro Leu Gly Ile Asp Asn Asn Gly Thr
            260                 265                 270

Pro Asp Lys Ala Ser Val Gly Tyr Val Lys Lys Arg Leu Ser Phe Ser
            275                 280                 285

Ala Ser Pro Ala Gly Ala Arg Arg His Ser Gly Pro Pro Arg Val Asp
            290                 295                 300

Ala Ser Ala Val Lys Asp Ile Gln Met His Arg Glu Glu Lys Met Ser
305                 310                 315                 320

Asn Gly Ala Ser Ser Lys
                325
```

<210> SEQ ID NO 150
<211> LENGTH: 1901
<212> TYPE: DNA
<213> ORGANISM: Gossypium hirsutum
<220> FEATURE:
<221> NAME/KEY: misc_feature
<223> OTHER INFORMATION: Ceres CLONE ID no.1919901
<220> FEATURE:
<221> NAME/KEY: misc_feature
<223> OTHER INFORMATION: Encodes the peptide sequence at SEQ ID NO 151

<400> SEQUENCE: 150

```
aactttctct agttatcctc tgcaaatgcc aacctgttct tttattatta ttttccgcca      60
tttttgctct ctttcaagca ttttttttt gcctagatcc acttctctct ctttgatttt     120
taattactgc attttgttt  taatacacaa taagaacaac taagagatag aatgtgactt     180
atcaatcttt taactgagat ctgtgagaat ttttctatgt accaaggaat tatttacaga     240
tgggaaaaaa aggtggctgg ctttctattg tgaagaaagc tttgagccct gaatccaaga     300
aatctcagca ccaaactcca aagccaaaga aaaaatggtt cggaaaaagc aaaaatttga     360
gccctgtgtc tgtgcctgaa gaaactgaag tgataactga agatgcaaag ctaaagaag      420
ctgaaaacga acaaagcaaa catgccactc tgtggctct  tgccaccgct gtggcggccg     480
aggcagcggt ggcagctgct caggcggctg ctgaagttgt ccgtctcact tctcagccgc     540
gccatctggg gaagtcaaag gaggaaatag ctgctatcag gattcaaaca gcatttcgtg     600
gatatttggc taggagggca ctgcgagctt tgagagggtt ggtaaggttg aaatcgttga     660
tcagagggca atccgtcaaa cgccaagcaa ctacaacgtt aagatgcatg cagactctag     720
ctcgtctgca gtctgagatt tctgcaagga ggattagaat gtcagaagag aaccaggctc     780
ttcagcgcca gcttcaacag aaatgccaga aagagctcga aagttgaga  gctcccatga     840
```

-continued

```
gagaagactg gaacgatagt acacagtcga aggagcagat cgaagcaaga caacaaaata      900
agcaaggagc tactatgaaa agggaaagag cattggctta tgcatactgt caccagcgat      960
cgtggaagaa ctgttctaga tcagtgaatc aaacatttat ggatccgagt aattcacact     1020
ggggttggag ttggttagag cgatggatgg cagcccgacc atgggaagtc aaagcacaa      1080 ctgataacaa tgaccgtggc tcagtcaaga gtatgggtgc ttgttcgata tctataagtg     1140
aaatcagcag agcttattct cgaagagatc ttaacaatga taacaaacca tctccaacac     1200
ctcagaagtc aagtcgagtt cctagccgcc agtctccatc gactccacct tcaaaggcac     1260
cttcgatttc atcggtttct ggtaaaacaa gactgccaag tccgagagga agtcaatggg     1320
gagggtatga agactcaagg agcatactca gtacccggtc tgatcgttat aggagacata     1380
gcattgcagg gtcctcaatg agagacgatg agagccttac aagctcacct gcagttccaa     1440
gttatatggc accaacacag tccacaaagg ccaggtccca cataccaagc cccttaggaa     1500
gtggcacacc agataggaga gtggcagggt ctgcaaagaa acggcttttg ttcccagcat     1560
ccccagccag tagtaggaga cattcagagc ctcctaaagt ggacataagt gaggctagaa     1620
agaatcagca tgcaccaagc aatggaaggc aagtggcttg gtgaagagtg caacaaaagt     1680
tagattgaat aaacatggaa gggttatttc aacttgaagt tcttgtagtg tggttgtgat     1740 tatcttttc ttcctaggtt ttatgattat taattataaa agggttactt ttttctgggt      1800
gagatttagt ttattgtttg tggttgacaa acattcttaa aaatcttcaa gtttagtttc     1860
aattcatgaa atttgtaatt aaaaaaaaaa aaaaaaaaa a                          1901
```

<210> SEQ ID NO 151
<211> LENGTH: 474
<212> TYPE: PRT
<213> ORGANISM: Gossypium hirsutum
<220> FEATURE:
<221> NAME/KEY: misc_feature
<223> OTHER INFORMATION: Ceres CLONE ID no.1919901
<220> FEATURE:
<221> NAME/KEY: misc_feature
<223> OTHER INFORMATION: Score of 1214.2 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (109)..(129)
<223> OTHER INFORMATION: Pfam Name: IQ Pfam Description: IQ calmodulin-
      binding motif

<400> SEQUENCE: 151

Met Gly Lys Lys Gly Gly Trp Leu Ser Ile Val Lys Lys Ala Leu Ser
1               5                   10                  15

Pro Glu Ser Lys Lys Ser Gln His Gln Thr Pro Lys Pro Lys Lys Lys
                20                  25                  30

Trp Phe Gly Lys Ser Lys Asn Leu Ser Pro Val Ser Val Pro Glu Glu
            35                  40                  45

Thr Glu Val Ile Thr Glu Asp Ala Lys Leu Lys Glu Ala Glu Asn Glu
        50                  55                  60

Gln Ser Lys His Ala Tyr Ser Val Ala Leu Ala Thr Ala Val Ala Ala
65                  70                  75                  80

Glu Ala Ala Val Ala Ala Ala Gln Ala Ala Glu Val Val Arg Leu
                85                  90                  95

Thr Ser Gln Pro Arg His Leu Gly Lys Ser Lys Glu Glu Ile Ala Ala

```
            100                 105                 110
Ile Arg Ile Gln Thr Ala Phe Arg Gly Tyr Leu Ala Arg Arg Ala Leu
            115                 120                 125

Arg Ala Leu Arg Gly Leu Val Arg Leu Lys Ser Leu Ile Arg Gly Gln
        130                 135                 140

Ser Val Lys Arg Gln Ala Thr Thr Thr Leu Arg Cys Met Gln Thr Leu
145                 150                 155                 160

Ala Arg Leu Gln Ser Glu Ile Ser Ala Arg Arg Ile Arg Met Ser Glu
                165                 170                 175

Glu Asn Gln Ala Leu Gln Arg Gln Leu Gln Gln Lys Cys Gln Lys Glu
            180                 185                 190

Leu Glu Lys Leu Arg Ala Pro Met Arg Glu Asp Trp Asn Asp Ser Thr
        195                 200                 205

Gln Ser Lys Glu Gln Ile Glu Ala Arg Gln Gln Asn Lys Gln Gly Ala
    210                 215                 220

Thr Met Lys Arg Glu Arg Ala Leu Ala Tyr Ala Tyr Cys His Gln Arg
225                 230                 235                 240

Ser Trp Lys Asn Cys Ser Arg Ser Val Asn Gln Thr Phe Met Asp Pro
                245                 250                 255

Ser Asn Ser His Trp Gly Trp Ser Trp Leu Glu Arg Trp Met Ala Ala
            260                 265                 270

Arg Pro Trp Glu Val Gln Ser Thr Thr Asp Asn Asn Asp Arg Gly Ser
        275                 280                 285

Val Lys Ser Met Gly Ala Cys Ser Ile Ser Ile Ser Glu Ile Ser Arg
    290                 295                 300

Ala Tyr Ser Arg Arg Asp Leu Asn Asn Asp Asn Lys Pro Ser Pro Thr
305                 310                 315                 320

Pro Gln Lys Ser Ser Arg Val Pro Ser Arg Gln Ser Pro Ser Thr Pro
                325                 330                 335

Pro Ser Lys Ala Pro Ser Ile Ser Ser Val Ser Gly Lys Thr Arg Leu
            340                 345                 350

Pro Ser Pro Arg Gly Ser Gln Trp Gly Gly Tyr Glu Asp Ser Arg Ser
        355                 360                 365

Ile Leu Ser Thr Arg Ser Asp Arg Tyr Arg Arg His Ser Ile Ala Gly
    370                 375                 380

Ser Ser Met Arg Asp Asp Glu Ser Leu Thr Ser Ser Pro Ala Val Pro
385                 390                 395                 400

Ser Tyr Met Ala Pro Thr Gln Ser Thr Lys Ala Arg Ser His Ile Pro
                405                 410                 415

Ser Pro Leu Gly Ser Gly Thr Pro Asp Arg Arg Val Ala Gly Ser Ala
            420                 425                 430

Lys Lys Arg Leu Leu Phe Pro Ala Ser Pro Ala Ser Ser Arg Arg His
        435                 440                 445

Ser Glu Pro Pro Lys Val Asp Ile Ser Glu Ala Arg Lys Asn Gln His
    450                 455                 460

Ala Pro Ser Asn Gly Arg Gln Val Ala Trp
465                 470
```

<210> SEQ ID NO 152
<211> LENGTH: 1362
<212> TYPE: DNA
<213> ORGANISM: Glycine max
<220> FEATURE:
<221> NAME/KEY: misc_feature
<223> OTHER INFORMATION: Ceres CLONE ID no.520008

```
<220> FEATURE:
<221> NAME/KEY: misc_feature
<223> OTHER INFORMATION: Encodes the peptide sequence at SEQ ID NO 153

<400> SEQUENCE: 152
atgcattcac tcatcaggtt tttttaaaaa aaaaaaattc tcatcaattt acacatgcga      60
gaaaatgggt gaaaaattta atacgaactg aaaaatcttt caaaaatatc gcatattata     120
aacactaaaa tgagaaatca agcatcctta ttatactata tggatatact cttcactgtt     180
tctttatctc ttgaatctgt tatactttcc aactgagact taggcctgat tcctgataag     240
tgcacgagtc ctttcctatc ttgtcactat cttcagagcc atatcctctg cactctcctt     300
tctcactgcc acgatgatct tttgcataat ccaatgatat gctaatgctt tgttaagtaa     360
gttgcagcgt aaattcttcc tcaattttgt caatggaagt atttttgttac tgaaataaag    420
tggcatgcta tattatgtaa catattttga atgaatagca ttctgcctat gatatgattt     480
tcaatcataa gtgtaagttc cttgatgctg tcaacaaatt cagtgtttga tatttggggg     540
caaaaaatat ttggcagcaa aactggaaga actcgtctag atctgtaaat ccaatgttta     600
tggatccaac taatccgagc tggggttgga gctggttgga acgatggatg gcagcccgac     660
cttgggagag ccgtagccat atggataaag agttgaatga ccactcctcc ataagaagct     720
caagccgcag cattaccggt ggagaaatca gcaagtcatt tgctcgtttc cagctcaatt     780
cggaaaagca ctctccaaca gccagccaga tcctggctc ccctagcttt cagtccactc     840
cttccaagcc agcttcatca tctgctaaga accaaagaa ggtaagtcca agcccaaggg     900
gcagctgggt tatggacgag gactccaaaa gcttggtcag tgtacactct gaccggttcc     960
ggaggcactc cattgccggt tcatcggtga gagatgacga gagccttgct agctctccag    1020
cagttccaag ctcatggtg ccaactcaat ctgcaaaagc caagtccagg acacaaagtc    1080
cattagcctc agaaaatgca aaagcagaga aaggttcctt tgggagtgca agaagcggc    1140
tttctttccc agcttcacct gccaggccaa ggcgccattc aggtccacca aaggttgaaa    1200
gcagcagctt aaatgcagag ttagctgtgg acaagggtgt ggacagttga tcatacaagt    1260
aaaaggatgg aaaagcatta agtaggatt gaaaatatat cactgaagaa ataaaacaaa    1320
aagagtttat ttaaaaaaaa aaaaaaaaaa aaaaaaaaa aa                        1362

<210> SEQ ID NO 153
<211> LENGTH: 218
<212> TYPE: PRT
<213> ORGANISM: Glycine max
<220> FEATURE:
<221> NAME/KEY: misc_feature
<223> OTHER INFORMATION: Ceres CLONE ID no.520008
<220> FEATURE:
<221> NAME/KEY: misc_feature
<223> OTHER INFORMATION: Score of 156.2 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136

<400> SEQUENCE: 153

Met Phe Met Asp Pro Thr Asn Pro Ser Trp Gly Trp Ser Trp Leu Glu
1               5                   10                  15

Arg Trp Met Ala Ala Arg Pro Trp Glu Ser Arg Ser His Met Asp Lys
            20                  25                  30

Glu Leu Asn Asp His Ser Ser Ile Arg Ser Ser Ser Arg Ser Ile Thr
        35                  40                  45
```

```
Gly Gly Glu Ile Ser Lys Ser Phe Ala Arg Phe Gln Leu Asn Ser Glu
 50                  55                  60

Lys His Ser Pro Thr Ala Ser Gln Asn Pro Gly Ser Pro Ser Phe Gln
 65                  70                  75                  80

Ser Thr Pro Ser Lys Pro Ala Ser Ser Ala Lys Lys Pro Lys Lys
                 85                  90                  95

Val Ser Pro Ser Pro Arg Gly Ser Trp Val Met Asp Glu Asp Ser Lys
                100                 105                 110

Ser Leu Val Ser Val His Ser Asp Arg Phe Arg Arg His Ser Ile Ala
                115                 120                 125

Gly Ser Ser Val Arg Asp Asp Glu Ser Leu Ala Ser Ser Pro Ala Val
                130                 135                 140

Pro Ser Tyr Met Val Pro Thr Gln Ser Ala Lys Ala Lys Ser Arg Thr
145                 150                 155                 160

Gln Ser Pro Leu Ala Ser Glu Asn Ala Lys Ala Glu Lys Gly Ser Phe
                165                 170                 175

Gly Ser Ala Lys Lys Arg Leu Ser Phe Pro Ala Ser Pro Ala Arg Pro
                180                 185                 190

Arg Arg His Ser Gly Pro Pro Lys Val Glu Ser Ser Leu Asn Ala
                195                 200                 205

Glu Leu Ala Val Asp Lys Gly Val Asp Ser
210                 215
```

<210> SEQ ID NO 154
<211> LENGTH: 445
<212> TYPE: PRT
<213> ORGANISM: Arabidopsis thaliana
<220> FEATURE:
<221> NAME/KEY: misc_feature
<223> OTHER INFORMATION: Public GI ID no.7413581
<220> FEATURE:
<221> NAME/KEY: misc_feature
<223> OTHER INFORMATION: Score of 1020.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (114)..(134)
<223> OTHER INFORMATION: Pfam Name: IQ Pfam Description: IQ calmodulin-
      binding motif

<400> SEQUENCE: 154

```
Met Gly Lys Lys Ala Lys Trp Phe Ser Ser Val Lys Lys Ala Phe Ser
1                   5                  10                  15

Pro Asp Ser Lys Ser Lys Gln Lys Leu Ala Glu Gly Gln Asn Gly Val
                 20                  25                  30

Ile Ser Asn Pro Pro Val Val Asp Asn Val Arg Gln Ser Ser Ser Ser
                 35                  40                  45

Pro Pro Pro Ala Leu Ala Pro Arg Glu Val Arg Val Ala Glu Val Ile
                 50                  55                  60

Val Glu Arg Asn Arg Asp Leu Ser Pro Pro Ser Thr Ala Asp Ala Val
 65                  70                  75                  80

Asn Val Thr Ala Thr Asp Val Pro Val Val Pro Ser Ser Ser Ala Pro
                 85                  90                  95

Gly Val Val Arg Arg Ala Thr Pro Thr Arg Phe Ala Gly Lys Ser Asn
                100                 105                 110

Glu Glu Ala Ala Ala Ile Leu Ile Gln Thr Ile Phe Arg Gly Tyr Leu
                115                 120                 125
```

```
Ala Arg Arg Ala Leu Arg Ala Met Arg Gly Leu Val Arg Leu Lys Leu
        130                 135                 140

Leu Met Glu Gly Ser Val Val Lys Arg Gln Ala Ala Asn Thr Leu Lys
145                 150                 155                 160

Cys Met Gln Thr Leu Ser Arg Val Gln Ser Gln Ile Arg Ala Arg Arg
                165                 170                 175

Ile Arg Met Ser Glu Glu Asn Gln Ala Arg Gln Lys Gln Leu Leu Gln
            180                 185                 190

Lys His Ala Lys Glu Leu Ala Gly Leu Lys Asn Gly Asp Asn Trp Asn
        195                 200                 205

Asp Ser Ile Gln Ser Lys Glu Lys Val Glu Ala Asn Leu Leu Ser Lys
    210                 215                 220

Tyr Glu Ala Thr Met Arg Arg Glu Arg Ala Leu Ala Tyr Ser Tyr Ser
225                 230                 235                 240

His Gln Gln Asn Trp Lys Asn Asn Ser Lys Ser Gly Asn Pro Met Phe
                245                 250                 255

Met Asp Pro Ser Asn Pro Thr Trp Val Pro Arg Lys Asn Lys Ser Asn
            260                 265                 270

Ser Asn Asn Asp Asn Ala Ala Ser Val Lys Gly Ser Ile Asn Arg Asn
        275                 280                 285

Glu Ala Ala Lys Ser Leu Thr Arg Asn Gly Ser Thr Gln Pro Asn Thr
    290                 295                 300

Pro Ser Ser Ala Arg Gly Thr Pro Arg Asn Lys Asn Ser Phe Phe Ser
305                 310                 315                 320

Pro Pro Thr Pro Ser Arg Leu Asn Gln Ser Ser Arg Lys Ser Asn Asp
                325                 330                 335

Asp Asp Ser Lys Ser Thr Ile Ser Val Leu Ser Glu Arg Asn Arg Arg
            340                 345                 350

His Ser Ile Ala Gly Ser Ser Val Arg Asp Asp Glu Ser Leu Ala Gly
        355                 360                 365

Ser Pro Ala Leu Pro Ser Tyr Met Val Pro Thr Lys Ser Ala Arg Ala
    370                 375                 380

Arg Leu Lys Pro Gln Ser Pro Leu Gly Gly Thr Thr Gln Glu Asn Glu
385                 390                 395                 400

Gly Phe Thr Asp Lys Ala Ser Ala Lys Lys Arg Leu Ser Tyr Pro Thr
                405                 410                 415

Ser Pro Ala Leu Pro Lys Pro Arg Arg Phe Ser Ala Pro Pro Lys Val
            420                 425                 430

Glu Ser Gly Gly Val Thr Val Thr Asn Gly Ala Gly Ser
        435                 440                 445

<210> SEQ ID NO 155
<211> LENGTH: 1806
<212> TYPE: DNA
<213> ORGANISM: Zea mays
<220> FEATURE:
<221> NAME/KEY: misc_feature
<223> OTHER INFORMATION: Ceres CLONE ID no.228069
<220> FEATURE:
<221> NAME/KEY: misc_feature
<223> OTHER INFORMATION: Encodes the peptide sequence at SEQ ID NO 156

<400> SEQUENCE: 155
gagccgcgga ggagcagcgg cgcatcgcaa cactaaccaa agtcctcctc tccaggtgcc      60
gagccagggt gactgttccg aggagcgtgg cgtggaccca tggggaagaa gggcaagtgg     120
```

```
ttcggtgccg tcaagaaggt cttcagcccc gaatccaagg agaagaaaga ggagaggcta    180
aggaggaaat cagcagctag caacccagca ccggtagatc tgaccccatc tacctccctg    240
gaagtcaatg tttcggtgcc accccctccg gctcctcctc cagttcctcg ccagaccgac    300
gaggtcaggg tccccgaagc cgagcaggag cagagcaagc atgtcaccct ggaggaggcc    360
cctgctgctg ctgctgcccc agcacaggcg tcggtgctgc acctggtgc gccaaccgaa    420
gagctcgccg caatcaagat ccagaccgcc ttccgaggtt acctggcaag agggcacta    480
agagcactac gaggccttgt acgattgaag tcattggttg agggtaattc agttaagcgt    540
caatctgcaa gcactctgcg ctgtatgcaa actctatcgc gggtgcagtc acaaatacga    600
tctaggagag caaagatgtc cgaggagaac caggccctcc aacgccagct cctacttaaa    660
caggaactgg agaatttcag aatgggtgag aactgggacg acagcactca atccaaggag    720
caaatcgagg caagcctaat aagcaggcaa gaggcagcga taagaagaga aagagctctt    780
gcatatgcat tttcacatca gtggaagagc acatcaagat ctgcgaaccc aatgtttgta    840
gacccaaata acttgcagtg gggctggagc tggttggagc gctggatggc agcaaaacct    900
tgggagggac gcaatgggac cgacaaggag agcaacattg atcgcggctc cgtcaagaat    960
atgagcttga accttggagt tggagagggt gagatcacaa aagctttcaa ccgccgggac   1020
tcaaagccag agaagccatc accaccgact ccaaaaccgg cccgtccagc ttccaggcaa   1080
tccccttcga cgccctctgc tagagtggcc ccaatacctg cgaggaggaa atccagcacg   1140
ccaaagaatg ggctttcaca ggtggacgat gacgtgagga gcgtgctcag tgtgcagtct   1200
gagcgaccaa ggaggcacag catagccacg acgtcgacca tgcgggacga tgagagcctc   1260
gcgagctccc cgtcgctccc gagctacatg gttcccacag aatctgcgag ggccaaatct   1320
cgcacagcaa cggccaatgg cgcagagacg cctgagaaag gaggctctgc tggaccagtc   1380
aagaagaggt tgtctttcca aggtggagct gcggctgcct caccgatgcg acggcattct   1440
ggccctccca aggtggagag cgctgtgaag gacattgctg cgccaccaca gcctgaggcc   1500
ttggtagcca atggtggtgg aagcaagtga cttgtattga caagttccag gatggggag    1560
cgggttatgg tcttatggag ggacatgttt catccgtgaa cagaagttaa gagtggtgcc   1620
ggatctacga atggtttgaa ttgttttccc gttacaacca cattgtttgc tgtataagat   1680
tcactgtacc tgccagttgg ttccatttgt tgttttctgt aaaacaaaca tcaatttgtc   1740
actagaatct gtgatgcttg tatgtaaaca ggtcctctat ttatgtgagc catatatttc   1800
attttc                                                              1806
```

<210> SEQ ID NO 156
<211> LENGTH: 476
<212> TYPE: PRT
<213> ORGANISM: Zea mays
<220> FEATURE:
<221> NAME/KEY: misc_feature
<223> OTHER INFORMATION: Ceres CLONE ID no.228069
<220> FEATURE:
<221> NAME/KEY: misc_feature
<223> OTHER INFORMATION: Score of 953.8 for HMM of FIGURE 4.
<220> FEATURE:
<221> NAME/KEY: misc_feature
<223> OTHER INFORMATION: Functional Homolog Of Ceres SEEDLINE ID no.
    ME24091 at SEQ ID NO. 136
<220> FEATURE:
<221> NAME/KEY: misc_feature
<222> LOCATION: (108)..(128)
<223> OTHER INFORMATION: Pfam Name: IQ Pfam Description: IQ calmodulin-
    binding motif

```
<400> SEQUENCE: 156

Met Gly Lys Lys Gly Lys Trp Phe Gly Ala Val Lys Val Phe Ser
1               5                   10                  15

Pro Glu Ser Lys Glu Lys Lys Glu Glu Arg Leu Arg Arg Lys Ser Ala
            20                  25                  30

Ala Ser Asn Pro Ala Pro Val Asp Leu Thr Pro Ser Thr Ser Leu Glu
        35                  40                  45

Val Asn Val Ser Val Pro Pro Pro Ala Pro Pro Val Pro Arg
    50                  55                  60

Gln Thr Asp Glu Val Arg Val Pro Glu Ala Glu Gln Glu Gln Ser Lys
65                  70                  75                  80

His Val Thr Leu Glu Glu Ala Pro Ala Ala Ala Ala Pro Ala Gln
                85                  90                  95

Ala Ser Val Leu Pro Pro Gly Ala Pro Thr Glu Glu Leu Ala Ala Ile
            100                 105                 110

Lys Ile Gln Thr Ala Phe Arg Gly Tyr Leu Ala Arg Arg Ala Leu Arg
            115                 120                 125

Ala Leu Arg Gly Leu Val Arg Leu Lys Ser Leu Val Glu Gly Asn Ser
130                 135                 140

Val Lys Arg Gln Ser Ala Ser Thr Leu Arg Cys Met Gln Thr Leu Ser
145                 150                 155                 160

Arg Val Gln Ser Gln Ile Arg Ser Arg Arg Ala Lys Met Ser Glu Glu
                165                 170                 175

Asn Gln Ala Leu Gln Arg Gln Leu Leu Leu Lys Gln Glu Leu Glu Asn
            180                 185                 190

Phe Arg Met Gly Glu Asn Trp Asp Asp Ser Thr Gln Ser Lys Glu Gln
            195                 200                 205

Ile Glu Ala Ser Leu Ile Ser Arg Gln Glu Ala Ile Arg Arg Glu
210                 215                 220

Arg Ala Leu Ala Tyr Ala Phe Ser His Gln Trp Lys Ser Thr Ser Arg
225                 230                 235                 240

Ser Ala Asn Pro Met Phe Val Asp Pro Asn Asn Leu Gln Trp Gly Trp
                245                 250                 255

Ser Trp Leu Glu Arg Trp Met Ala Ala Lys Pro Trp Glu Gly Arg Asn
            260                 265                 270

Gly Thr Asp Lys Glu Ser Asn Ile Asp Arg Gly Ser Val Lys Asn Met
            275                 280                 285

Ser Leu Asn Leu Gly Val Gly Glu Gly Glu Ile Thr Lys Ala Phe Asn
290                 295                 300

Arg Arg Asp Ser Lys Pro Glu Lys Pro Ser Pro Thr Pro Lys Pro
305                 310                 315                 320

Ala Arg Pro Ala Ser Arg Gln Ser Pro Thr Pro Ser Ala Arg Val
            325                 330                 335

Ala Pro Ile Pro Ala Arg Arg Lys Ser Ser Thr Pro Lys Asn Gly Leu
            340                 345                 350

Ser Gln Val Asp Asp Asp Val Arg Ser Val Leu Ser Val Gln Ser Glu
            355                 360                 365

Arg Pro Arg Arg His Ser Ile Ala Thr Thr Ser Thr Met Arg Asp Asp
370                 375                 380

Glu Ser Leu Ala Ser Ser Pro Ser Leu Pro Ser Tyr Met Val Pro Thr
385                 390                 395                 400

Glu Ser Ala Arg Ala Lys Ser Arg Thr Ala Thr Ala Asn Gly Ala Glu
                405                 410                 415
```

Thr Pro Glu Lys Gly Gly Ser Ala Gly Pro Val Lys Lys Arg Leu Ser
            420                 425                 430

Phe Gln Gly Gly Ala Ala Ala Ala Ser Pro Met Arg Arg His Ser Gly
        435                 440                 445

Pro Pro Lys Val Glu Ser Ala Val Lys Asp Ile Ala Ala Pro Pro Gln
    450                 455                 460

Pro Glu Ala Leu Val Ala Asn Gly Gly Ser Lys
465                 470                 475

<210> SEQ ID NO 157
<211> LENGTH: 1703
<212> TYPE: DNA
<213> ORGANISM: Glycine max
<220> FEATURE:
<221> NAME/KEY: misc_feature
<223> OTHER INFORMATION: Ceres CLONE ID no.467508
<220> FEATURE:
<221> NAME/KEY: misc_feature
<223> OTHER INFORMATION: Encodes the peptide sequence at SEQ ID NO 158

<400> SEQUENCE: 157

| | | | | | |
|---|---|---|---|---|---|
| aaaccatcct | ctcttagcat | ttggcaagat | ctgatttccc | tcttcacaag | gagagaaata | 60 |
| gaaaggcata | tgatcttctt | caagttgcaa | tcttttttaga | gagagagggt | tagaagaaca | 120 |
| acatacttga | gatctgtcac | tttgtttgag | ttcagatctt | caaagtttcc | ttccttgttc | 180 |
| ttttggtgca | aaggatcaaa | ttaaggaatg | ccaaatgggg | aggaagggga | attggttttc | 240 |
| cagtgtgatg | aaagctctca | gtcctgactc | aaaggagaag | aaagaacaga | atcaagtaa | 300 |
| atctaagaag | aaatggtttg | ggaagcaaaa | attggagact | tcagtctcat | actcagaagc | 360 |
| tcataaagca | ccaccaccac | cgcgacctat | tcctccacca | gaagcgatta | aattaactga | 420 |
| tattgaaaat | gaaatcagtc | atgatcacga | ctatgttgtt | gaagttgcaa | ctgccatgga | 480 |
| tgccgaggaa | cctgttcctt | ctgttcagat | agaacctgtt | agggttgaag | ctgccccaat | 540 |
| tgctcattat | gctggtaaac | caaggatga | agtggcagct | atcaaaattc | aaacagcttt | 600 |
| tcgtggatac | ttggcaagaa | gagcattgcg | ggctttaagg | gggctggtca | ggttgaaatt | 660 |
| attgatggaa | gggccagttg | ttaaacgcca | agccacaagt | accctccact | ctatgcagac | 720 |
| attatctcgc | ttgcagtctc | agattcgttc | aaggaggatc | agaatgttag | aggagaatca | 780 |
| ggctctgcag | agacagctct | tacagaagca | tgcaagagag | cttgagagct | gcggatggg | 840 |
| agaggaatgg | gatgacagcc | tacaatcaaa | agaacaaatc | gaagccaagt | tacttagcaa | 900 |
| gtatgaagct | actacgagaa | gagaaagagc | gctggcttat | gcattcactc | atcagcaaaa | 960 |
| ttggaagaac | tcatctagat | ctgtaaatcc | aatgttcatg | gatccaacca | atccaagctg | 1020 |
| gggttggagc | tggttggaac | gatggatggc | agcccgacct | tgggagagcc | gtagccatat | 1080 |
| ggataaagag | ttgaatgacc | actcatccgt | aagaagctca | agccgcagta | ttaccggtgg | 1140 |
| agaaatcagc | aagtcatttg | ctcgtttcca | gctcaatttg | gaaaagcact | tccaacagc | 1200 |
| ctgccagaat | cctggctcac | ctagctttca | gtccactcct | tccaagccag | cttcaatatc | 1260 |
| tgctaagaaa | ccaaagaagg | taagtccaag | cccaagggc | agctgggtta | cagacgagga | 1320 |
| ctccaaaagc | ttggtcagtg | tacagtcaga | ccggttccgg | aggcactcca | ttgccggttc | 1380 |
| attggtgaga | gatgatgaga | gccttgctag | ctctccagca | gttccaagct | acatggtgcc | 1440 |
| aactcaatct | gcaaaagcca | agtccaggac | acaaagtcca | ttagcccccag | aaaatggaaa | 1500 |
| agcagagaaa | ggttcctttg | ggagtgcgaa | gaagcggctt | tctttcccag | cttcacctgc | 1560 |

-continued

```
caggccaagg cgccattcag gtccaccaaa ggtagaaagc agcagcttaa atgcagagtt    1620
agctgtggac aagggtgtgg acagttgatc atacaagtaa aaggatggaa aaacattaaa    1680
gtaggattga aaatatatca ctg                                            1703
```

<210> SEQ ID NO 158
<211> LENGTH: 477
<212> TYPE: PRT
<213> ORGANISM: Glycine max
<220> FEATURE:
<221> NAME/KEY: misc_feature
<223> OTHER INFORMATION: Ceres CLONE ID no.467508
<220> FEATURE:
<221> NAME/KEY: misc_feature
<223> OTHER INFORMATION: Score of 852.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (119)..(139)
<223> OTHER INFORMATION: Pfam Name: IQ Pfam Description: IQ calmodulin-
      binding motif

<400> SEQUENCE: 158

```
Met Gly Arg Lys Gly Asn Trp Phe Ser Ser Val Met Lys Ala Leu Ser
 1               5                  10                  15

Pro Asp Ser Lys Glu Lys Lys Glu Gln Lys Ser Ser Lys Ser Lys Lys
            20                  25                  30

Lys Trp Phe Gly Lys Gln Lys Leu Glu Thr Ser Val Ser Tyr Ser Glu
        35                  40                  45

Ala His Lys Ala Pro Pro Pro Arg Pro Ile Pro Pro Glu Ala
    50                  55                  60

Ile Lys Leu Thr Asp Ile Glu Asn Glu Ile Ser His Asp His Asp Tyr
65                  70                  75                  80

Val Val Glu Val Ala Thr Ala Met Asp Ala Glu Glu Pro Val Pro Ser
                85                  90                  95

Val Gln Ile Glu Pro Val Arg Val Glu Ala Ala Pro Ile Ala His Tyr
            100                 105                 110

Ala Gly Lys Pro Lys Asp Glu Val Ala Ala Ile Lys Ile Gln Thr Ala
        115                 120                 125

Phe Arg Gly Tyr Leu Ala Arg Arg Ala Leu Arg Ala Leu Arg Gly Leu
    130                 135                 140

Val Arg Leu Lys Leu Leu Met Glu Gly Pro Val Val Lys Arg Gln Ala
145                 150                 155                 160

Thr Ser Thr Leu His Ser Met Gln Thr Leu Ser Arg Leu Gln Ser Gln
                165                 170                 175

Ile Arg Ser Arg Arg Ile Arg Met Leu Glu Glu Asn Gln Ala Leu Gln
            180                 185                 190

Arg Gln Leu Leu Gln Lys His Ala Arg Glu Leu Glu Ser Leu Arg Met
        195                 200                 205

Gly Glu Glu Trp Asp Asp Ser Leu Gln Ser Lys Glu Gln Ile Glu Ala
    210                 215                 220

Lys Leu Leu Ser Lys Tyr Glu Ala Thr Thr Arg Arg Glu Arg Ala Leu
225                 230                 235                 240

Ala Tyr Ala Phe Thr His Gln Gln Asn Trp Lys Asn Ser Ser Arg Ser
                245                 250                 255

Val Asn Pro Met Phe Met Asp Pro Thr Asn Pro Ser Trp Gly Trp Ser
            260                 265                 270
```

```
Trp Leu Glu Arg Trp Met Ala Ala Arg Pro Trp Glu Ser Arg Ser His
            275                 280                 285

Met Asp Lys Glu Leu Asn Asp His Ser Ser Val Arg Ser Ser Ser Arg
    290                 295                 300

Ser Ile Thr Gly Gly Glu Ile Ser Lys Ser Phe Ala Arg Phe Gln Leu
305                 310                 315                 320

Asn Leu Glu Lys His Ser Pro Thr Ala Cys Gln Asn Pro Gly Ser Pro
                325                 330                 335

Ser Phe Gln Ser Thr Pro Ser Lys Pro Ala Ser Ile Ser Ala Lys Lys
                340                 345                 350

Pro Lys Lys Val Ser Pro Ser Pro Arg Gly Ser Trp Val Thr Asp Glu
                355                 360                 365

Asp Ser Lys Ser Leu Val Ser Val Gln Ser Asp Arg Phe Arg Arg His
    370                 375                 380

Ser Ile Ala Gly Ser Leu Val Arg Asp Asp Glu Ser Leu Ala Ser Ser
385                 390                 395                 400

Pro Ala Val Pro Ser Tyr Met Val Pro Thr Gln Ser Ala Lys Ala Lys
                405                 410                 415

Ser Arg Thr Gln Ser Pro Leu Ala Pro Glu Asn Gly Lys Ala Glu Lys
                420                 425                 430

Gly Ser Phe Gly Ser Ala Lys Lys Arg Leu Ser Phe Pro Ala Ser Pro
                435                 440                 445

Ala Arg Pro Arg Arg His Ser Gly Pro Pro Lys Val Glu Ser Ser Ser
    450                 455                 460

Leu Asn Ala Glu Leu Ala Val Asp Lys Gly Val Asp Ser
465                 470                 475

<210> SEQ ID NO 159
<211> LENGTH: 1495
<212> TYPE: DNA
<213> ORGANISM: Gossypium hirsutum
<220> FEATURE:
<221> NAME/KEY: misc_feature
<223> OTHER INFORMATION: Ceres CLONE ID no.1829581
<220> FEATURE:
<221> NAME/KEY: misc_feature
<223> OTHER INFORMATION: Encodes the peptide sequence at SEQ ID NO 160

<400> SEQUENCE: 159
attattttca atgcaattta agagttttat ttattttatg ttataaattt tttaacctct      60
aaatatgatt tgaaatgtta attccattgg ttgttttggg ttttgaagga gaatttattg     120
aggaatgggc aaaaaaggaa gctggtttac tgctgtgaag aaagttctaa gccttgaacc     180
caacaaagaa gagaagattc aaaaatccaa gaaaaatggg gttaaattac ctgagaagat     240
caaaggaagc aaacgtgaca actggttcgc tccggccacc accatggtga ccggcgcgtt     300
ggttcgcctt actttgtcgc cacactactt gggaaaatca atggaggaaa tagctactgt     360
taagattcaa actgtgtttc gaggatacct ggcgaggaag gcattgcgag atttgagagg     420
gttagagagg ttgaaatcat tgatacaagg gcaatccatg aaacgacaag ccactattac     480
gttacgatgc atgcggacac ttgctcgagt gcagtcccaa actcgaacaa ggcaactcag     540
agtgtctgaa caaaaccgag cacttcaaaa gcatcttcaa actaaatacg aaaaacagtt     600
gcaaaattcc aaatcttaca tgggagaaga ttggaatgta agtactaagt ctaaagagca     660
aatgcaagca aaacaacaat atagacaagt agcagccatg cgaagggaga gagctttagc     720
ttactcattt actcatcagc gatcctggaa ggtcacttgt agatcgatga atcacacatc     780
```

-continued

```
tatggatcca tttaatccta aatggagctg gagttggtta gagcgatgga tgtcaactcg      840
accatgggag attcaaaatg caccggataa caatgatcat ggcccaagta agagtgttgg      900
tgctgagata accaaagcta agtctcaaag tgatgttaac aatgatcaca ataaacaatc      960
ttcaacaccg gcaaaaccga ttcgacctcc gaaccgtagg tcctcttcga ctccaccgtc     1020
taaaacgcat tctatttcta gcaagaaggg attggaaagc cccagtccga cacgaattca     1080
gttgcctgat tgttacaaga ggcatagcat cggaggctta tcattggaga gacgatga       1140
ggtctttgca aactcaccac ctaataataa ataccggca cgttcgtcat caaaggaccg      1200
gtctcgacca ccgagcatta tagaaatcc agttaatact aggagacatt ctggtcctcc      1260
gaaagttgat attttttcca actaaggaag aaatgccaaa caatgacaaa ggcaggtagt     1320
ttatgaagca tagacacttt agtcgcgagt gccggccaca tgtttaatat tgaaatggct     1380
ccgacacaat caaatgtgtg ttggttatat gacgatatat ttttcaaaa aatcaaatac      1440
tatcagaaaa aaatataaag aaagattaat tggataaaaa aaaaaaaaaa aaaaa          1495

<210> SEQ ID NO 160
<211> LENGTH: 386
<212> TYPE: PRT
<213> ORGANISM: Gossypium hirsutum
<220> FEATURE:
<221> NAME/KEY: misc_feature
<223> OTHER INFORMATION: Ceres CLONE ID no.1829581
<220> FEATURE:
<221> NAME/KEY: misc_feature
<223> OTHER INFORMATION: Score of 365.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (75)..(95)
<223> OTHER INFORMATION: Pfam Name: IQ Pfam Description: IQ calmodulin-
      binding motif

<400> SEQUENCE: 160

Met Gly Lys Lys Gly Ser Trp Phe Thr Ala Val Lys Val Leu Ser
1               5                   10                  15

Leu Glu Pro Asn Lys Glu Lys Ile Gln Lys Ser Lys Lys Asn Gly
                20                  25                  30

Val Lys Leu Pro Glu Lys Ile Lys Gly Ser Lys Arg Asp Asn Trp Phe
                35                  40                  45

Ala Pro Ala Thr Thr Met Val Thr Gly Ala Leu Val Arg Leu Thr Leu
50                  55                  60

Ser Pro His Tyr Leu Gly Lys Ser Met Glu Glu Ile Ala Thr Val Lys
65                  70                  75                  80

Ile Gln Thr Val Phe Arg Gly Tyr Leu Ala Arg Lys Ala Leu Arg Asp
                85                  90                  95

Leu Arg Gly Leu Glu Arg Leu Lys Ser Leu Ile Gln Gly Gln Ser Met
                100                 105                 110

Lys Arg Gln Ala Thr Ile Thr Leu Arg Cys Met Arg Thr Leu Ala Arg
            115                 120                 125

Val Gln Ser Gln Thr Arg Thr Arg Gln Leu Arg Val Ser Glu Gln Asn
        130                 135                 140

Arg Ala Leu Gln Lys His Leu Gln Thr Lys Tyr Glu Lys Gln Leu Gln
145                 150                 155                 160

Asn Ser Lys Ser Tyr Met Gly Glu Asp Trp Asn Val Ser Thr Lys Ser
```

```
                165                 170                 175
Lys Glu Gln Met Gln Ala Lys Gln Gln Tyr Arg Gln Val Ala Ala Met
            180                 185                 190

Arg Arg Glu Arg Ala Leu Ala Tyr Ser Phe Thr His Gln Arg Ser Trp
        195                 200                 205

Lys Val Thr Cys Arg Ser Met Asn His Thr Ser Met Asp Pro Phe Asn
    210                 215                 220

Pro Lys Trp Ser Trp Ser Trp Leu Glu Arg Trp Met Ser Thr Arg Pro
225                 230                 235                 240

Trp Glu Ile Gln Asn Ala Pro Asp Asn Asn Asp His Gly Pro Ser Lys
                245                 250                 255

Ser Val Gly Ala Glu Ile Thr Lys Ala Lys Ser Gln Ser Asp Val Asn
            260                 265                 270

Asn Asp His Asn Lys Gln Ser Ser Thr Pro Ala Lys Pro Ile Arg Pro
        275                 280                 285

Pro Asn Arg Arg Ser Ser Ser Thr Pro Pro Ser Lys Thr His Ser Ile
    290                 295                 300

Ser Ser Lys Lys Gly Leu Glu Ser Pro Ser Pro Thr Arg Ile Gln Leu
305                 310                 315                 320

Pro Asp Cys Tyr Lys Arg His Ser Ile Gly Gly Leu Ser Leu Glu Arg
                325                 330                 335

Asp Asp Glu Val Phe Ala Asn Ser Pro Pro Asn Asn Lys Ile Pro Ala
            340                 345                 350

Arg Ser Ser Ser Lys Asp Arg Ser Arg Pro Pro Ser Ile Asn Arg Asn
        355                 360                 365

Pro Val Asn Thr Arg Arg His Ser Gly Pro Pro Lys Val Asp Ile Phe
    370                 375                 380

Ser Asn
385

<210> SEQ ID NO 161
<211> LENGTH: 1543
<212> TYPE: DNA
<213> ORGANISM: Zea mays
<220> FEATURE:
<221> NAME/KEY: misc_feature
<223> OTHER INFORMATION: Ceres CLONE ID no.229668
<220> FEATURE:
<221> NAME/KEY: misc_feature
<223> OTHER INFORMATION: Encodes the peptide sequence at SEQ ID NO 162

<400> SEQUENCE: 161
cttggaagtc aatctttcgg tgccaccgcc tccagctcct cccccagttc ttcaccaggc      60
cgaggaggtt ggggtccctg aagccgagca ggagcagagc aagcatgtcg ccgtggagga    120
ggcccctgct gccgccccag cgcaggcgtc ggtgctgcca cctgctgtgc aacccaaga    180 gctcgccgca gtcaagatcc agaccgcctt ccgaggttac ctggcaagga gggcactacg    240
agcactgcga ggccttgttc gattgaagtc attggttgag ggtaattcag taaagcgtca    300
atctgcaagc actctgcgct gcatgcaaac tctatcacgg gtgcagtcac agatatcttc    360
caggagagca aagatgtccg aggagaacca ggctctccaa cgccagctcc tacttaaaca    420
ggaactggag aatttcagaa tgggtgagaa ctgggatgac agcacccaat ccaaggagca    480
aatcgaggca agcctgataa gcaggcaaga ggcggcgata agaagagaaa gagcgcttgc    540
atatgcattt tcacaccagt ggaagagtac atcgagatct gtcaacccaa tgtttgtaga    600
cccaaacaac ctgcagtggg gctggagctg gctggagcgc tggatggcag caaaaccatg    660
```

-continued

```
ggaaggccgc aatggggctg acaaggagag caacattgac cggggatccg ttaagagcat    720
gagcttgaac cttggagagg gtgagatcac aaaagctttc aaccgccggg actcaaagct    780
agaaaagcca tcgccgccaa ctccaagacc ggcccgtcca acttccaggc attcccettt    840 gacgccctct gctagagtgg caccgatacc tgcgaggaga aaatctgtca cgcccaagaa    900
cgggctttca caggtggacg atgacgcgag gagcgtgctc agtgtgcagt ctgagcggcc    960
aaggaggcac agtatagcca cctcgactgt gcgggacgac gagagcctca cgagctcccc    1020
gtcgctccca agctacatgg ttcccacaga atctgcaagg ccaaatctc gcctccaggg    1080 ttcagcaatg ccaatggcg cagagacacc tgagaaagga ggctcaactg gaccagccaa    1140
gaagaggtta tccttccagg gtggaactgc ggctgcctcg ccaatgcgac gacattctgg    1200
tcctcccaag gtggagatcg cgccaccaca accagaggcc ttggtagtca atggtggaag    1260
caagtgacac atatgtgatg agtaccagga tgagaaacgg attatgaaga tattagtttc    1320
attttcatcc atgaatagaa gttaaaagtg gtatcatatc tatgaatggt ttcaattgtt    1380
tttctgttac aaccacatta tttgctatat acgattcaca gtacctgcca gttgattcca    1440
ttggttgttt ctgtaaaaca aatatcaatt tgtcactaga atctgtgatg tttgtatgta    1500
aacagatcct ctatttatgt gagacatata tttcttttct ttc                      1543
```

<210> SEQ ID NO 162
<211> LENGTH: 421
<212> TYPE: PRT
<213> ORGANISM: Zea mays
<220> FEATURE:
<221> NAME/KEY: misc_feature
<223> OTHER INFORMATION: Ceres CLONE ID no.229668
<220> FEATURE:
<221> NAME/KEY: misc_feature
<223> OTHER INFORMATION: Score of 908.3 for HMM of FIGURE 4.
<220> FEATURE:
<221> NAME/KEY: misc_feature
<223> OTHER INFORMATION: Functional Homolog Of Ceres SEEDLINE ID no.
    ME24091 at SEQ ID NO. 136
<220> FEATURE:
<221> NAME/KEY: misc_feature
<222> LOCATION: (60)..(80)
<223> OTHER INFORMATION: Pfam Name: IQ Pfam Description: IQ calmodulin-
    binding motif

<400> SEQUENCE: 162

Leu Glu Val Asn Leu Ser Val Pro Pro Pro Ala Pro Pro Pro Val
1               5                   10                  15

Leu His Gln Ala Glu Glu Val Gly Val Pro Glu Ala Glu Gln Glu Gln
            20                  25                  30

Ser Lys His Val Ala Val Glu Glu Ala Pro Ala Ala Pro Ala Gln
        35                  40                  45

Ala Ser Val Leu Pro Pro Ala Val Pro Thr Gln Glu Leu Ala Ala Val
    50                  55                  60

Lys Ile Gln Thr Ala Phe Arg Gly Tyr Leu Ala Arg Arg Ala Leu Arg
65                  70                  75                  80

Ala Leu Arg Gly Leu Val Arg Leu Lys Ser Leu Val Glu Gly Asn Ser
                85                  90                  95

Val Lys Arg Gln Ser Ala Ser Thr Leu Arg Cys Met Gln Thr Leu Ser
            100                 105                 110

Arg Val Gln Ser Gln Ile Ser Ser Arg Arg Ala Lys Met Ser Glu Glu
        115                 120                 125

Asn Gln Ala Leu Gln Arg Gln Leu Leu Leu Lys Gln Glu Leu Glu Asn

```
                130             135             140
Phe Arg Met Gly Glu Asn Trp Asp Asp Ser Thr Gln Ser Lys Glu Gln
145                 150                 155                 160

Ile Glu Ala Ser Leu Ile Ser Arg Gln Glu Ala Ala Ile Arg Arg Glu
                165                 170                 175

Arg Ala Leu Ala Tyr Ala Phe Ser His Gln Trp Lys Ser Thr Ser Arg
            180                 185                 190

Ser Val Asn Pro Met Phe Val Asp Pro Asn Asn Leu Gln Trp Gly Trp
        195                 200                 205

Ser Trp Leu Glu Arg Trp Met Ala Ala Lys Pro Trp Glu Gly Arg Asn
    210                 215                 220

Gly Ala Asp Lys Glu Ser Asn Ile Asp Arg Gly Ser Val Lys Ser Met
225                 230                 235                 240

Ser Leu Asn Leu Gly Glu Gly Glu Ile Thr Lys Ala Phe Asn Arg Arg
                245                 250                 255

Asp Ser Lys Leu Glu Lys Pro Ser Pro Thr Pro Arg Pro Ala Arg
            260                 265                 270

Pro Thr Ser Arg His Ser Pro Leu Thr Pro Ser Ala Arg Val Ala Pro
        275                 280                 285

Ile Pro Ala Arg Arg Lys Ser Val Thr Pro Lys Asn Gly Leu Ser Gln
    290                 295                 300

Val Asp Asp Ala Arg Ser Val Leu Ser Val Gln Ser Glu Arg Pro
305                 310                 315                 320

Arg Arg His Ser Ile Ala Thr Ser Thr Val Arg Asp Asp Glu Ser Leu
                325                 330                 335

Thr Ser Ser Pro Ser Leu Pro Ser Tyr Met Val Pro Thr Glu Ser Ala
            340                 345                 350

Arg Ala Lys Ser Arg Leu Gln Gly Ser Ala Met Ala Asn Gly Ala Glu
        355                 360                 365

Thr Pro Glu Lys Gly Gly Ser Thr Gly Pro Ala Lys Lys Arg Leu Ser
    370                 375                 380

Phe Gln Gly Gly Thr Ala Ala Ala Ser Pro Met Arg Arg His Ser Gly
385                 390                 395                 400

Pro Pro Lys Val Glu Ile Ala Pro Pro Gln Pro Glu Ala Leu Val Val
                405                 410                 415

Asn Gly Gly Ser Lys
            420

<210> SEQ ID NO 163
<211> LENGTH: 500
<212> TYPE: PRT
<213> ORGANISM: Oryza sativa subsp. indica
<220> FEATURE:
<221> NAME/KEY: misc_feature
<223> OTHER INFORMATION: Public GI ID no.125550655
<220> FEATURE:
<221> NAME/KEY: misc_feature
<223> OTHER INFORMATION: Score of 911.0 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (107)..(121)
<223> OTHER INFORMATION: Pfam Name: IQ Pfam Description: IQ calmodulin-
      binding motif

<400> SEQUENCE: 163
```

-continued

```
Met Gly Lys Lys Gly Lys Trp Phe Gly Ala Val Lys Lys Val Phe Ser
1               5                   10                  15

Pro Glu Ser Lys Glu Lys Lys Glu Glu Arg Leu Arg Arg Lys Leu Ala
            20                  25                  30

Ala Ser Asn Pro Asn Pro Pro Asp Leu Thr Pro Ser Ala Ser Leu Glu
        35                  40                  45

Val Asn Val Ser Val Pro Pro Pro Pro Pro Pro Val Gln Gln
    50                  55                  60

Ile Glu Glu Val Lys Val Pro Glu Val Glu Gln Gln Ser Lys His
65                  70                  75                  80

Val Thr Val Glu Ala Val Pro Glu Ala Val Pro Val Pro Ala Gln Thr
                85                  90                  95

Ser Ser Leu Pro Pro Gly Val Ser Arg Glu Glu Gln Ala Ala Ile Lys
            100                 105                 110

Ile Gln Thr Ala Phe Arg Gly Tyr Leu Leu Ser Glu Asn Ser Ser Trp
        115                 120                 125

Leu Phe Ile Ser Ser Ala Ala Phe Ile Tyr His Cys Val Gly Ala Asn
    130                 135                 140

Ile Thr Lys Ala Arg Arg Ala Leu Arg Ala Leu Arg Gly Leu Val Arg
145                 150                 155                 160

Leu Lys Ser Leu Val Glu Gly Asn Ser Val Lys Arg Gln Ala Ala Ser
            165                 170                 175

Thr Leu Arg Cys Met Gln Thr Leu Ala Arg Val Gln Ser Gln Ile Arg
                180                 185                 190

Ser Arg Arg Leu Lys Met Ser Glu Glu Asn Gln Ala Leu Gln Arg Gln
            195                 200                 205

Leu Leu Leu Lys Gln Glu Leu Glu Ser Leu Arg Met Gly Glu Gln Trp
    210                 215                 220

Asp Asp Ser Thr Gln Ser Lys Glu Gln Ile Glu Ala Ser Leu Ile Ser
225                 230                 235                 240

Arg Gln Glu Ala Ala Val Arg Arg Glu Arg Ala Leu Ala Tyr Ala Phe
                245                 250                 255

Ser His Gln Trp Lys Ser Thr Ser Arg Ser Val Asn Pro Met Phe Val
            260                 265                 270

Asp Pro Asn Asn Pro Gln Trp Gly Trp Ser Trp Leu Glu Arg Trp Met
        275                 280                 285

Ala Ala Lys Pro Trp Glu Gly Arg Ala Gly Thr Asp Lys Glu Ser Asn
    290                 295                 300

Leu Asp Arg Ala Ser Ala Lys Ser Ala Ser Leu Asn Leu Gly Glu Gly
305                 310                 315                 320

Glu Ile Thr Lys Ala Phe Asn Arg Arg Gly Ser Lys Pro Asp Lys Ser
                325                 330                 335

Ser Pro Thr Thr Pro Lys Leu Thr Arg Pro Ala Ser Arg Gln Ser Pro
            340                 345                 350

Ser Thr Pro Ser Ala Lys Val Ser Pro Ile Phe Ala Lys Lys Ser
        355                 360                 365

Ala Thr Pro Lys Asn Gly Leu Ser Gln Val Asp Asp Ala Lys Ser
    370                 375                 380

Val Phe Ser Val Gln Ser Glu Arg Pro Arg His Ser Ile Ala Thr
385                 390                 395                 400

Ser Thr Val Arg Asp Asp Glu Ser Leu Ala Ser Ser Pro Ser Val Pro
                405                 410                 415

Ser Tyr Met Ala Pro Thr Lys Ser Ala Arg Ala Lys Leu Arg Leu Gln
```

```
                       420                425                430
Gly Ser Ala Val Thr Asp Gly Ala Glu Thr Pro Pro Glu Lys Val Ala
            435                440                445

Ser Val Gly Ser Val Lys Lys Lys Leu Ser Phe Gln Ala Gly Met Val
        450                455                460

Pro Pro Ser Pro Met Arg Arg His Ser Gly Pro Pro Lys Val Glu Val
465                470                475                480

Val Lys Asp Ile Ala Glu Pro Pro Gln Pro Glu Ala Leu Val Ile Asn
                485                490                495

Gly Gly Ser Lys
            500

<210> SEQ ID NO 164
<211> LENGTH: 1923
<212> TYPE: DNA
<213> ORGANISM: Arabidopsis thaliana
<220> FEATURE:
<221> NAME/KEY: misc_feature
<223> OTHER INFORMATION: Ceres CLONE ID no.106263
<220> FEATURE:
<221> NAME/KEY: misc_feature
<223> OTHER INFORMATION: Encodes the peptide sequence at SEQ ID NO 165

<400> SEQUENCE: 164
acaaatactc ttcttcacac agctttgaat ccatctgtct tctcctctct ctctcttctc      60
catttgcaat tacgataatg tgaaagcaat aagaagagga aaagttatct tcgcacctca    120
gcaaagatcc aatcgattcg attcttaagc ttttttcgtct tctccgataa ggtcactact    180
tagaagccgc gttgtggttt agttgactcc tccaggtttt atcttcaagc ttttttcgtct    240 atcagatctg gtgtcactgt cttctcatag gattacatag agatggggaa aaaagctaaa    300
tggttttcaa gtgttaagaa agcattcagc ccagattcaa agaagtcgaa gcaaaaattg    360
gctgagggac aaaatggtgt tatctctaat cctcctgttg tggataatgt tagacaatct    420
tcttcttctc ctcctcctgc tcttgctcct cgtgaagtga gagtagctga agtgattgtt    480
gaacggaaca gggatctttc acctccttct acagcagatg ctgtgaatgt tacagctact    540
gatgtycctg tagttccatc ttcatctgct cctggtgttg ttcgtcgcgc tacacctact    600
cgatttgctg gaaagtcaaa cgaagaagcc gctgctatct tgatccagac tatatttaga    660
ggttatttgg caaggagagc gttgcgggca atgaggggtt tggtcagact taagttattg    720
atggaaggat ctgttgttaa gcggcaagct gcaaatactc taaaatgtat gcagactctc    780
tctcgtgtac agtcgcagat ccgagctagg agaatcaggr tgtcagaaga gaatcaggct    840
cgccagaaac aactccttca gaaacatgct aaagagctag ctggcttgaa gaacggggat    900
aactggaatg atagcattca atcaaaggag aaagttgaag cgaatttgct aagcaagtac    960
gaggcaacaa tgagaaggga aagggcattg gcttattcat actctcatca scaaaactgg   1020
aagaacaact ctaaatctgg aaacccgatg ttcatggatc caagcaaccc gacatggggt   1080
tggagctggt tggagagatg gatggctggt aggccactag agagttccga gaaagaacaa   1140
agcaacagca acaatgacaa tgctgcctcg gtcaagggct ctattaaccg caacgaagct   1200
gcaaaatctc taacccgcaa tggctcaact caaccaaaca caccatcatc cgcaagaggg   1260
accccaagaa acaaaaacag tttcttctca cctccaactc cctcaaggct aaaccaatcc   1320
tcgaggaaat ccaatgacga cgactccaaa agcacaatct cggtcctgtc cgagaggaac   1380
cgcagacaca scattgctgg ttcatcagtc asagacgatg agagcctcgc tggctcacca   1440
```

-continued

```
gctctcccga gctacatggt tccaactaaa tcagctcgag ccaggctcaa gccccaaagc    1500
ccattaggtg gtaccacaca ggaaaacgaa gggttcacag acaaggcatc agctaagaaa    1560
cggctctcgt atccaacttc gcctgcattg cctaaaccac ggcggttctc agctccccct    1620
aaggtggaga gtggcggcgt taccgtgacc aacggagcag gcagctgagg tattttattt    1680
aatataatta ttttcccact tatgaatgtg tccgagattg ttgtctctta tgtgttccct    1740
tcatttcgta attcatttgt gcagtgtaag cgccagtcat ttattttttt actataataa    1800
attttataac cttttaaaat tcatgttctt tgtttctttt gaatatttaa gttattttta    1860
ttaatgttgg atgaattgga atatgatgat gttatttgta ttgtaatgca gatcctttaa    1920
agc                                                                  1923

<210> SEQ ID NO 165
<211> LENGTH: 461
<212> TYPE: PRT
<213> ORGANISM: Arabidopsis thaliana
<220> FEATURE:
<221> NAME/KEY: misc_feature
<223> OTHER INFORMATION: Ceres CLONE ID no.106263
<220> FEATURE:
<221> NAME/KEY: misc_feature
<223> OTHER INFORMATION: Score of 1104.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (88)..(88)
<223> OTHER INFORMATION: Xaa is any aa, unknown, or other
<220> FEATURE:
<221> NAME/KEY: misc_feature
<222> LOCATION: (115)..(135)
<223> OTHER INFORMATION: Pfam Name: IQ Pfam Description: IQ calmodulin-
      binding motif
<220> FEATURE:
<221> NAME/KEY: misc_feature
<222> LOCATION: (180)..(180)
<223> OTHER INFORMATION: Xaa is any aa, unknown, or other
<220> FEATURE:
<221> NAME/KEY: misc_feature
<222> LOCATION: (243)..(243)
<223> OTHER INFORMATION: Xaa is any aa, unknown, or other
<220> FEATURE:
<221> NAME/KEY: misc_feature
<222> LOCATION: (370)..(370)
<223> OTHER INFORMATION: Xaa is any aa, unknown, or other
<220> FEATURE:
<221> NAME/KEY: misc_feature
<222> LOCATION: (377)..(377)
<223> OTHER INFORMATION: Xaa is any aa, unknown, or other

<400> SEQUENCE: 165

Met Gly Lys Lys Ala Lys Trp Phe Ser Ser Val Lys Lys Ala Phe Ser
1               5                   10                  15

Pro Asp Ser Lys Lys Ser Lys Gln Lys Leu Ala Glu Gly Gln Asn Gly
            20                  25                  30

Val Ile Ser Asn Pro Pro Val Val Asp Asn Val Arg Gln Ser Ser Ser
        35                  40                  45

Ser Pro Pro Pro Ala Leu Ala Pro Arg Glu Val Arg Val Ala Glu Val
    50                  55                  60

Ile Val Glu Arg Asn Arg Asp Leu Ser Pro Pro Ser Thr Ala Asp Ala
65                  70                  75                  80

Val Asn Val Thr Ala Thr Asp Xaa Pro Val Pro Ser Ser Ser Ala
                85                  90                  95
```

```
Pro Gly Val Val Arg Arg Ala Thr Pro Thr Arg Phe Ala Gly Lys Ser
            100                 105                 110

Asn Glu Glu Ala Ala Ala Ile Leu Ile Gln Thr Ile Phe Arg Gly Tyr
        115                 120                 125

Leu Ala Arg Arg Ala Leu Arg Ala Met Arg Gly Leu Val Arg Leu Lys
    130                 135                 140

Leu Leu Met Glu Gly Ser Val Val Lys Arg Gln Ala Ala Asn Thr Leu
145                 150                 155                 160

Lys Cys Met Gln Thr Leu Ser Arg Val Gln Ser Ile Arg Ala Arg
                165                 170                 175

Arg Ile Arg Xaa Ser Glu Glu Asn Gln Ala Arg Gln Lys Gln Leu Leu
            180                 185                 190

Gln Lys His Ala Lys Glu Leu Ala Gly Leu Lys Asn Gly Asp Asn Trp
        195                 200                 205

Asn Asp Ser Ile Gln Ser Lys Glu Lys Val Glu Ala Asn Leu Leu Ser
    210                 215                 220

Lys Tyr Glu Ala Thr Met Arg Arg Glu Arg Ala Leu Ala Tyr Ser Tyr
225                 230                 235                 240

Ser His Xaa Gln Asn Trp Lys Asn Asn Ser Lys Ser Gly Asn Pro Met
                245                 250                 255

Phe Met Asp Pro Ser Asn Pro Thr Trp Gly Trp Ser Trp Leu Glu Arg
            260                 265                 270

Trp Met Ala Gly Arg Pro Leu Glu Ser Ser Glu Lys Glu Gln Ser Asn
        275                 280                 285

Ser Asn Asn Asp Asn Ala Ala Ser Val Lys Gly Ser Ile Asn Arg Asn
    290                 295                 300

Glu Ala Ala Lys Ser Leu Thr Arg Asn Gly Ser Thr Gln Pro Asn Thr
305                 310                 315                 320

Pro Ser Ser Ala Arg Gly Thr Pro Arg Asn Lys Asn Ser Phe Phe Ser
                325                 330                 335

Pro Pro Thr Pro Ser Arg Leu Asn Gln Ser Ser Arg Lys Ser Asn Asp
            340                 345                 350

Asp Asp Ser Lys Ser Thr Ile Ser Val Leu Ser Glu Arg Asn Arg Arg
        355                 360                 365

His Xaa Ile Ala Gly Ser Ser Val Xaa Asp Asp Glu Ser Leu Ala Gly
    370                 375                 380

Ser Pro Ala Leu Pro Ser Tyr Met Val Pro Thr Lys Ser Ala Arg Ala
385                 390                 395                 400

Arg Leu Lys Pro Gln Ser Pro Leu Gly Gly Thr Thr Gln Glu Asn Glu
                405                 410                 415

Gly Phe Thr Asp Lys Ala Ser Ala Lys Lys Arg Leu Ser Tyr Pro Thr
            420                 425                 430

Ser Pro Ala Leu Pro Lys Pro Arg Arg Phe Ser Ala Pro Pro Lys Val
        435                 440                 445

Glu Ser Gly Gly Val Thr Val Thr Asn Gly Ala Gly Ser
    450                 455                 460

<210> SEQ ID NO 166
<211> LENGTH: 430
<212> TYPE: PRT
<213> ORGANISM: Arabidopsis thaliana
<220> FEATURE:
<221> NAME/KEY: misc_feature
<223> OTHER INFORMATION: Public GI ID no.15231175
<220> FEATURE:
<221> NAME/KEY: misc_feature
```

<223> OTHER INFORMATION: Score of 592.8 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (108)..(128)
<223> OTHER INFORMATION: Pfam Name: IQ Pfam Description: IQ calmodulin-
      binding motif

<400> SEQUENCE: 166

Met Gly Lys Ser Trp Phe Ser Ala Val Lys Ala Leu Ser Pro Glu
1               5                   10                  15

Pro Lys Gln Lys Glu Gln Lys Pro His Lys Ser Lys Trp Phe
            20                  25                  30

Gly Lys Ser Lys Lys Leu Asp Val Thr Asn Ser Gly Ala Ala Tyr Ser
            35                  40                  45

Pro Arg Thr Val Lys Asp Ala Lys Leu Lys Glu Ile Glu Glu Gln Gln
        50                  55                  60

Ser Arg His Ala Tyr Ser Val Ala Ile Ala Thr Ala Ala Ala Glu
65                  70                  75                  80

Ala Ala Val Ala Ala Ala Gln Ala Ala Glu Val Val Arg Leu Ser
                85                  90                  95

Ala Leu Ser Arg Phe Pro Gly Lys Ser Met Glu Glu Ile Ala Ala Ile
            100                 105                 110

Lys Ile Gln Thr Ala Phe Arg Gly Tyr Met Ala Arg Arg Ala Leu Arg
            115                 120                 125

Ala Leu Arg Gly Leu Val Arg Leu Lys Ser Leu Val Gln Gly Lys Cys
        130                 135                 140

Val Arg Arg Gln Ala Thr Ser Thr Leu Gln Ser Met Gln Thr Leu Ala
145                 150                 155                 160

Arg Val Gln Tyr Gln Ile Arg Glu Arg Leu Arg Leu Ser Glu Asp
                165                 170                 175

Lys Gln Ala Leu Thr Arg Gln Leu Gln Gln Lys His Asn Lys Asp Phe
            180                 185                 190

Asp Lys Thr Gly Glu Asn Trp Asn Asp Ser Thr Leu Ser Arg Glu Lys
        195                 200                 205

Val Glu Ala Asn Met Leu Asn Lys Gln Val Ala Thr Met Arg Arg Glu
210                 215                 220

Lys Ala Leu Ala Tyr Ala Phe Ser His Gln Asn Thr Trp Lys Asn Ser
225                 230                 235                 240

Thr Lys Met Gly Ser Gln Thr Phe Met Asp Pro Asn Asn Pro His Trp
                245                 250                 255

Gly Trp Ser Trp Leu Glu Arg Trp Met Ala Ala Arg Pro Asn Glu Asn
            260                 265                 270

His Ser Leu Thr Pro Asp Asn Ala Glu Lys Asp Ser Ser Ala Arg Ser
        275                 280                 285

Val Ala Ser Arg Ala Met Ser Glu Met Ile Pro Arg Gly Lys Asn Leu
    290                 295                 300

Ser Pro Arg Gly Lys Thr Pro Asn Ser Arg Arg Gly Ser Ser Pro Arg
305                 310                 315                 320

Val Arg Gln Val Pro Ser Glu Asp Ser Asn Ser Ile Val Ser Phe Gln
                325                 330                 335

Ser Glu Gln Pro Cys Asn Arg Arg His Ser Thr Cys Gly Ser Ile Pro
            340                 345                 350

```
Ser Thr Arg Asp Asp Glu Ser Phe Thr Ser Ser Phe Ser Gln Ser Val
        355                 360                 365

Pro Gly Tyr Met Ala Pro Thr Gln Ala Ala Lys Ala Arg Ala Arg Phe
370                 375                 380

Ser Asn Leu Ser Pro Leu Ser Ser Glu Lys Thr Ala Lys Lys Arg Leu
385                 390                 395                 400

Ser Phe Ser Gly Ser Pro Lys Thr Val Arg Arg Phe Ser Gly Pro Pro
            405                 410                 415

Lys Leu Glu Ser Asn Val Thr Lys Lys Asp Thr Asn Leu Ala
                420                 425                 430

<210> SEQ ID NO 167
<211> LENGTH: 461
<212> TYPE: PRT
<213> ORGANISM: Arabidopsis thaliana
<220> FEATURE:
<221> NAME/KEY: misc_feature
<223> OTHER INFORMATION: Public GI ID no.145357576
<220> FEATURE:
<221> NAME/KEY: misc_feature
<223> OTHER INFORMATION: Score of 1118.9 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (115)..(135)
<223> OTHER INFORMATION: Pfam Name: IQ Pfam Description: IQ calmodulin-
      binding motif

<400> SEQUENCE: 167

Met Gly Lys Lys Ala Lys Trp Phe Ser Ser Val Lys Lys Ala Phe Ser
1               5                   10                  15

Pro Asp Ser Lys Lys Ser Lys Gln Lys Leu Ala Glu Gly Gln Asn Gly
            20                  25                  30

Val Ile Ser Asn Pro Pro Val Val Asp Asn Val Arg Gln Ser Ser Ser
        35                  40                  45

Ser Pro Pro Pro Ala Leu Ala Pro Arg Glu Val Arg Val Ala Glu Val
50                  55                  60

Ile Val Glu Arg Asn Arg Asp Leu Ser Pro Pro Ser Thr Ala Asp Ala
65                  70                  75                  80

Val Asn Val Thr Ala Thr Asp Val Pro Val Pro Ser Ser Ser Ala
                85                  90                  95

Pro Gly Val Val Arg Arg Ala Thr Pro Thr Arg Phe Ala Gly Lys Ser
            100                 105                 110

Asn Glu Glu Ala Ala Ala Ile Leu Ile Gln Thr Ile Phe Arg Gly Tyr
        115                 120                 125

Leu Ala Arg Arg Ala Leu Arg Ala Met Arg Gly Leu Val Arg Leu Lys
    130                 135                 140

Leu Leu Met Glu Gly Ser Val Val Lys Arg Gln Ala Ala Asn Thr Leu
145                 150                 155                 160

Lys Cys Met Gln Thr Leu Ser Arg Val Gln Ser Gln Ile Arg Ala Arg
                165                 170                 175

Arg Ile Arg Met Ser Glu Glu Asn Gln Ala Arg Gln Lys Gln Leu Leu
            180                 185                 190

Gln Lys His Ala Lys Glu Leu Ala Gly Leu Lys Asn Gly Asp Asn Trp
        195                 200                 205

Asn Asp Ser Ile Gln Ser Lys Glu Lys Val Glu Ala Asn Leu Leu Ser
    210                 215                 220
```

```
Lys Tyr Glu Ala Thr Met Arg Arg Glu Arg Ala Leu Ala Tyr Ser Tyr
225                 230                 235                 240

Ser His Gln Gln Asn Trp Lys Asn Asn Ser Lys Ser Gly Asn Pro Met
            245                 250                 255

Phe Met Asp Pro Ser Asn Pro Thr Trp Gly Trp Ser Trp Leu Glu Arg
        260                 265                 270

Trp Met Ala Gly Arg Pro Leu Glu Ser Ser Glu Lys Glu Gln Ser Asn
    275                 280                 285

Ser Asn Asn Asp Asn Ala Ala Ser Val Lys Gly Ser Ile Asn Arg Asn
290                 295                 300

Glu Ala Ala Lys Ser Leu Thr Arg Asn Gly Ser Thr Gln Pro Asn Thr
305                 310                 315                 320

Pro Ser Ser Ala Arg Gly Thr Pro Arg Asn Lys Asn Ser Phe Phe Ser
                325                 330                 335

Pro Pro Thr Pro Ser Arg Leu Asn Gln Ser Ser Arg Lys Ser Asn Asp
            340                 345                 350

Asp Asp Ser Lys Ser Thr Ile Ser Val Leu Ser Glu Arg Asn Arg Arg
        355                 360                 365

His Ser Ile Ala Gly Ser Ser Val Arg Asp Asp Glu Ser Leu Ala Gly
    370                 375                 380

Ser Pro Ala Leu Pro Ser Tyr Met Val Pro Thr Lys Ser Ala Arg Ala
385                 390                 395                 400

Arg Leu Lys Pro Gln Ser Pro Leu Gly Gly Thr Thr Gln Glu Asn Glu
                405                 410                 415

Gly Phe Thr Asp Lys Ala Ser Ala Lys Lys Arg Leu Ser Tyr Pro Thr
            420                 425                 430

Ser Pro Ala Leu Pro Lys Pro Arg Arg Phe Ser Ala Pro Pro Lys Val
        435                 440                 445

Glu Ser Gly Gly Val Thr Val Thr Asn Gly Ala Gly Ser
    450                 455                 460

<210> SEQ ID NO 168
<211> LENGTH: 474
<212> TYPE: PRT
<213> ORGANISM: Oryza sativa subsp. indica
<220> FEATURE:
<221> NAME/KEY: misc_feature
<223> OTHER INFORMATION: Public GI ID no.125528277
<220> FEATURE:
<221> NAME/KEY: misc_feature
<223> OTHER INFORMATION: Score of 1169.9 for HMM of FIGURE 4.
<220> FEATURE:
<221> NAME/KEY: misc_feature
<223> OTHER INFORMATION: Functional Homolog Of Ceres SEEDLINE ID no.
      ME24091 at SEQ ID NO. 136
<220> FEATURE:
<221> NAME/KEY: misc_feature
<222> LOCATION: (142)..(162)
<223> OTHER INFORMATION: Pfam Name: IQ Pfam Description: IQ calmodulin-
      binding motif

<400> SEQUENCE: 168

Met Gly Lys Lys Gly Asn Trp Phe Ser Ala Val Lys Val Phe Ser
1               5                   10                  15

Ser Ser Asp Pro Asp Gly Arg Glu Ala Lys Ile Glu Lys Ala Asp Lys
            20                  25                  30

Ser Arg Ser Arg Arg Lys Trp Pro Phe Gly Lys Ser Lys Lys Ser Asp
        35                  40                  45

Pro Trp Thr Ser Thr Val Ala Val Pro Thr Ser Thr Ala Pro Pro Pro
```

-continued

```
            50                  55                  60
Gln Pro Pro Pro Pro Pro Thr His Pro Ile Gln Pro Gln Pro Glu
 65                  70                  75                  80
Glu Ile Lys Asp Val Lys Ala Val Glu Thr Asp Ser Glu Gln Asn Lys
                 85                  90                  95
His Ala Tyr Ser Val Ala Leu Ala Ser Ala Val Ala Ala Glu Ala Ala
                100                 105                 110
Ala Val Ala Ala Gln Ala Ala Glu Val Val Arg Leu Thr Thr Ala
                115                 120                 125
Thr Thr Ala Val Pro Lys Ser Pro Val Ser Ser Lys Asp Glu Leu Ala
130                 135                 140
Ala Ile Lys Ile Gln Thr Ala Phe Arg Gly Tyr Leu Ala Arg Arg Ala
145                 150                 155                 160
Leu Arg Ala Leu Arg Gly Leu Val Arg Leu Lys Ser Leu Val Asp Gly
                165                 170                 175
Asn Ala Val Lys Arg Gln Thr Ala His Thr Leu His Cys Thr Gln Thr
                180                 185                 190
Met Thr Arg Val Gln Thr Gln Ile Tyr Ser Arg Arg Val Lys Met Glu
                195                 200                 205
Glu Glu Lys Gln Ala Leu Gln Arg Gln Leu Gln Leu Lys His Gln Arg
210                 215                 220
Glu Leu Glu Lys Met Lys Ile Asp Glu Asp Trp Asp His Ser His Gln
225                 230                 235                 240
Ser Lys Glu Gln Trp Lys Asn Ser Gly Arg Thr Ile Thr Pro Thr Phe
                245                 250                 255
Thr Asp Gln Gly Asn Pro Asn Trp Gly Trp Ser Trp Met Glu Arg Trp
                260                 265                 270
Met Thr Ser Arg Pro Trp Glu Ser Arg Val Ile Ser Asp Lys Asp Pro
                275                 280                 285
Lys Asp His Tyr Ser Thr Lys Asn Pro Ser Thr Ser Ala Ser Arg Thr
290                 295                 300
Tyr Val Pro Arg Ala Ile Ser Ile Gln Arg Pro Ala Thr Pro Asn Lys
305                 310                 315                 320
Ser Ser Arg Pro Pro Ser Arg Gln Ser Pro Ser Thr Pro Pro Ser Arg
                325                 330                 335
Val Pro Ser Val Thr Gly Lys Ile Arg Pro Ala Ser Pro Arg Asp Ser
                340                 345                 350
Trp Leu Tyr Lys Glu Asp Asp Leu Arg Ser Ile Thr Ser Ile Arg Ser
                355                 360                 365
Glu Arg Pro Arg Arg Gln Ser Thr Gly Gly Ala Ser Val Arg Asp Asp
                370                 375                 380
Ala Ser Leu Thr Ser Thr Pro Ala Leu Pro Ser Tyr Met Gln Ser Thr
385                 390                 395                 400
Glu Ser Ala Arg Ala Lys Ser Arg Tyr Arg Ser Leu Leu Thr Asp Arg
                405                 410                 415
Phe Glu Val Pro Glu Arg Val Pro Leu Val His Ser Ser Ile Lys Lys
                420                 425                 430
Arg Leu Ser Phe Pro Val Ala Asp Lys Pro Asn Gly Glu His Ala Asp
                435                 440                 445
Lys Leu Met Glu Arg Gly Arg Arg His Ser Asp Pro Pro Lys Val Asp
                450                 455                 460
```

```
Pro Ala Ser Leu Lys Asp Val Pro Val Ser
465                 470
```

NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

CROSS-REFERENCE TO RELATED APPLICATIONS

This application is a Divisional of application Ser. No. 16/750,667, filed on Jan. 23, 2020 (now U.S. Pat. No. 11,028,405), which is a Divisional of application Ser. No. 16/265,525, filed on Feb. 1, 2019 (now U.S. Pat. No. 10,619,166), which is a Divisional of application Ser. No. 15/962,986, filed on Apr. 25, 2018 (now U.S. Pat. No. 10,233,461), which is a Divisional of application Ser. No. 15/679,052, filed on Aug. 16, 2017 (now U.S. Pat. No. 10,006,043), which is a Divisional of application Ser. No. 13/465,841, filed on May 7, 2012 (now U.S. Pat. No. 9,765,355), which is a Divisional of application Ser. No. 11/858,117, filed on Sep. 19, 2007 (abandoned), which is a Continuation in Part of Application No. PCT/US2007/006544, filed on Mar. 14, 2007, and claims priority under 35 U.S.C § 120 of Application No. PCT/US2007/06544, which claims priority under 35 U.S.C. § 119 of U.S. Provisional Application No. 60/782,735, filed on Mar. 14, 2006, the contents of each of which are hereby incorporated by reference in their entirety.

TECHNICAL FIELD

The present invention relates to isolated nucleic acid molecules and their corresponding encoded polypeptides able to enhance plant growth under saline and/or oxidative stress conditions. The present invention further relates to using the nucleic acid molecules and polypeptides to make transgenic plants, plant cells, plant materials or seeds of a plant having improved growth rate, vegetative growth, seedling vigor and/or biomass under saline and/or oxidative stress conditions as compared to wild-type plants grown under similar conditions.

BACKGROUND

Plants specifically improved for agriculture, horticulture, biomass conversion, and other industries (e.g. paper industry, plants as production factories for proteins or other compounds) can be obtained using molecular technologies. As an example, great agronomic value can result from enhancing plant growth in saline and/or oxidative stress conditions.

Salinity

A wide variety agriculturally important plant species demonstrate significant sensitivity to saline and/or oxidative stress conditions. Upon salt concentration exceeding a relatively low threshold, many plants suffer from stunted growth, necrosis, and death that results in an overall stunted appearance and reduced yields of plant material, seeds, fruit and other valuable products. Physiologically, plants challenged with salinity experience disruption in ion and water homeostasis, inhibition of metabolism, and damage to cellular membranes that result in developmental arrest and cell death (Huh et al. (2002) *Plant J*, 29(5): 649-59).

In many of the world's most productive agricultural regions, agricultural activities themselves lead to increased water and soil salinity, which threatens their sustained productivity. One example is crop irrigation in arid regions that have abundant sunlight. After irrigation water is applied to cropland, it is removed by the processes of evaporation and transpiration. While these processes remove water from the soil, they leave behind dissolved salts carried in irrigation water. Consequently, soil and groundwater salt concentrations build over time, rendering the land and shallow groundwater saline and thus damaging to crops.

In addition to human activities, natural geological processes have created vast tracts of saline land that would be highly productive if not saline. In total, approximately 20% of the irrigated lands are negatively affected by salinity. (Yamaguchi and Blumwald, 2005, *Trends in Plant Science*, 10: 615-620). For these and other reasons, it is of great interest and importance to identify genes that confer improved salt tolerance characteristics to thereby enable one to create transgenic plants (such as crop plants) with enhanced growth and/or productivity characteristics in saline conditions.

Despite this progress, today there continues to be a great need for generally applicable processes that improve forest or agricultural plant growth to suit particular needs depending on specific environmental conditions. To this end, the present invention is directed to advantageously manipulating plant tolerance to salinity in order to maximize the benefits of various crops depending on the benefit sought, and is characterized by expression of recombinant DNA molecules in plants. These molecules may be from the plant itself, and simply expressed at a higher or lower level, or the molecules may be from different plant species.

Oxidative Stress

Plants lead a sessile lifestyle and so are generally destined to reside where their seed germinates. Consequently, they can be exposed to unfavorable environmental conditions arising from weather, pollution and location. Stress conditions, such as extremes in temperature, drought and desiccation, salinity, soil nutrient content, heavy metals, UV radiation, pollutants such as ozone and $SO_2$, mechanical stress, high light and pathogen attack, have a large impact on plant growth and development. These types of stress exposure induce formation of toxic oxygen species, which are generated in all aerobic cells and are associated with oxidative damage at the cellular level. Several recently published reports have characterized toxic oxygen species generation and the subsequent oxidative damage caused by abiotic stresses (see Larkindale and Knight (2002); Borsani et al. (2001); Lee et al (2004); Aroca et al (2005); Luna et al (2005); and Noctor et al (2002)).

The toxic oxygen species are referred to as reactive oxygen species (ROS), reactive oxygen intermediates (ROI) or activated oxygen species (AOS) and are partially reduced or activated derivatives of oxygen. ROS/ROI/AOS include the oxygen-centered superoxide ($O_2$) and hydroxyl (.OH) free radicals as well as hydrogen peroxide ($H_2O_2$), nitric oxide (NO) and $O_2^1$. These oxygen species are generated as byproducts from reactions that occur during photosynthesis, respiration and photorespiration, and are predominantly formed in the chloroplasts, mitochondria, endoplasmic reticulum, microbodies (e.g. peroxisomes and glyoxysomes), plasma membranes and cell walls. While the toxicity of $O_2^-$ and $H_2O_2$ themselves is relatively low, their metal-dependent conversion to highly toxic .OH is thought to be responsible for the majority of the biological damage associated with these molecules.

Oxidative stress damages cell structure and affects cell metabolism and catabolism. Membrane lipids are subject to oxidation by ROS/ROI/AOS, resulting in accumulation of high molecular weight, cross-linked fatty acids and phospholipids. Oxidative attack on proteins results in site-specific amino acid modifications, fragmentation of the peptide chain, aggregation of cross-linked reaction products, altered electrical charge and increased susceptibility to proteolysis, all of which frequently leads to elimination of enzyme activity. ROS/ROI/AOS that generate oxygen free radicals, such as ionizing radiation, also induce numerous lesions in DNA at both the sugar and base moieties which cause deletions, mutation and other lethal genetic effects such as base degradation, single strand breakage and cross-linking to proteins. Morphologically, the adverse effects of high levels of ROS accumulation are manifested as stunted growth and necrotic lesions.

Although capable of producing damage, ROS/ROI/AOS are also key regulators of metabolic and defense pathways, playing roles as signaling or secondary messenger molecules. For example, pathogen-induced ROS/ROI/AOS production is critical in disease resistance where these molecules are involved at three different levels: penetration resistance, hypersensitive response (HR) and systemic acquired resistance (Levine et al. (1994); Lamb and Dixon (1997); Zhou et al. (2000); Aviv et al. (2002)). In penetration resistance, ROS/ROI/AOS function by reinforcing cell walls through polyphenolic cross-linking. With respect to hypersensitive response, $H_2O_2$ is an active signaling molecule whose effect is dose dependent. At high dosages, $H_2O_2$ triggers hypersensitive cell death and thus restricts the pathogen to local infection sites (Lamb and Dixon (1997)) while low dosages block cell cycle progression (Reichheld et al. (1999)) and signal secondary wall differentiation (Potikha et al. (1999)). Lastly, ROS/ROI/AOS molecules play a role in broad-spectrum systemic acquired disease resistance by triggering micro-HR systematically after the first pathogen inoculation.

In the signal cascades leading to oxidative stress, salicylic acid (SA) has been identified as an important signaling molecule to mediate ROS/ROI/AOS accumulation in various stress conditions, such as salt and osmotic stress (Borsani et al. (2001)), drought (Senaratna et al. (2000)), heat (Dat et al. (1998)), cold (Scott et al. (2004)), UV-light (Surplus et al. (1998)), paraquat (Kim et al. (2003)) and disease resistance against different pathogens (Zhou et al. (2004)). High levels of SA induce $H_2O_2$ production as well as cell death.

Several signaling components required for SA-mediated ROS/ROI/AOS accumulation and gene expression have been characterized. For example, NPR1 is required for SA-induced PR gene expression and disease resistance (Cao et al. (1994)). The mutations in eds1 and eds5 block SA-mediated signaling and enhance disease susceptibility (Rusterucci et al. (2001)). Over-expression of NahG in various plant species also suppresses SA-induced responses to both abiotic and biotic stresses (Delaney et al. (1994)). Recently, Scott and colleagues (2004) reported that chilling treatment induced accumulation of SA in *Arabidopsis* and the degradation of SA by overexpression of NahG enhanced cold tolerance in a transgenic plant.

SA, as a phytohormone, also promotes early flowering (Martinez et al. (2004)). SA at various levels may play different roles in plant growth and stress responses. However, most of the time, the increased tolerance to high levels of SA appears to be beneficial, since it reduces the side effects of SA accumulation while stimulating SA-mediated stress responses.

Similarly, NO is capable of generating ROS/ROI/AOS and is a plant signaling molecule involved in the regulation of seed germination, stomatal closure (Mata and Lamattina (2001); Desikan et al (2002)), flowering time (He et al. (2004)), antioxidant reactions to suppress cell death (Beligni et al. (2002)) and tolerance to biotic and abiotic stress conditions (Mata and Lamattina (2001)). While the effects of NO can be mimicked through the application of sodium nitroprusside (SNP), endogenous NO production in plants results from the activity of a nitric oxide synthase that uses L-arginine (Guo et al. (2003)) as well as nitrate reductase-mediated reactions (Desikan et al (2002)). NO can react with redox centers in proteins and membranes, thereby causing cell damage and inducing cell death.

In order to control the two-fold nature of ROS/ROI/AOS molecules, plants have developed a sophisticated regulatory system which involves both production and scavenging of ROS/ROI/AOS in cells. During normal growth and development, this pathway monitors the level of ROS/ROI/AOS produced by metabolism and controls the expression and activity of ROS/ROI/AOS scavenging pathways. The major ROS/ROI/AOS scavenging mechanisms include the action of the superoxide dismutase (SOD), ascrobate perioxidase (APX) and catalase (CAT) enzymes as well as nonenzymatic components such as ascorbic acid, α-tocopherol and glutathione.

The antioxidant enzymes are believed to be critical components in preventing oxidative stress, in part because pretreatment of plants with one form of stress, and which induces expression of these enzymes, can increase tolerance for a different stress (cross-tolerance) Allen (1995)). In addition, plant lines selected for resistance to herbicides that function by inducing ROS/ROI/AOS generally have increased levels of one or more of these antioxidant enzymes and also exhibit cross-tolerance (Gressel and Galun (1994)).

Plant development and yield depend on the ability of the plant to manage oxidative stress, whether it is via the signaling or the scavenging pathways. Consequently, improvements in a plant's ability to withstand oxidative stress, or to obtain a higher degree of cross-tolerance once oxidative stress has been experienced, has significant value in agriculture. The sequences and methods of the invention provide the means by which tolerance to oxidative stress can be improved, either via the signaling or the scavenging pathways.

The availability and sustainability of a stream of food and feed for people and domesticated animals has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy.

Manipulation of crop performance has been accomplished conventionally for centuries through selection and plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through the introduction and expression of recombinant nucleic acid molecules in plants, researchers are now poised to provide the community with plant species tailored to grow more efficiently and yield more product despite suboptimal geographic and/or climatic environments. These new approaches have the additional advantage of not being limited to one plant species, but instead being applicable to multiple different plant species (Zhang et al. (2004) *Plant Physiol.* 135:615; Zhang et al. (2001) *Proc. Natl. Acad. Sci. USA* 98:12832).

SUMMARY

This document provides methods and materials related to plants having modulated levels of tolerance to salinity and/or oxidative stress. For example, this document provides transgenic plants and plant cells having increased levels of tolerance to salinity and/or oxidative stress, nucleic acids used to generate transgenic plants and plant cells having increased levels of tolerance to salinity and/or oxidative stress, and methods for making plants and plant cells having increased levels of tolerance to salinity and/or oxidative stress. Such plants and plant cells provide the opportunity to produce crops or plants under saline and/or oxidative stress conditions without stunted growth and diminished yields. Increased levels of tolerance to salinity and/or oxidative stress may be useful to produce biomass which may be converted to a liquid fuel or other chemicals and/or to produce food and feed on land that is currently marginally productive, resulting in an overall expansion of arable land.

Methods of producing a plant and/or plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 30 using an HMM generated from the amino acid sequences depicted in one of FIGS. 1-6. The plant and/or plant tissue has a difference in the level of tolerance to salinity and/or oxidative stress as compared to the corresponding level in tolerance to salinity and/or oxidative stress of a control plant that does not comprise the exogenous nucleic acid. In some embodiments the amino acid sequence of the polypeptide has an HMM bit score greater than about 400 using an HMM generated from the amino acid sequences depicted in FIG. 1. In some embodiments the amino acid sequence of the polypeptide has an HMM bit score greater than about 30 using an HMM generated from the amino acid sequences depicted in FIG. 2. In some embodiments the amino acid sequence of the polypeptide has an HMM bit score greater than about 120 using an HMM generated from the amino acid sequences depicted in FIG. 3. In some embodiments the amino acid sequence of the polypeptide has an HMM bit score greater than about 150 using an HMM generated from the amino acid sequences depicted in FIG. 4. In some embodiments the amino acid sequence of the polypeptide has an HMM bit score greater than about 425 using an HMM generated from the amino acid sequences depicted in FIG. 5. In some embodiments the amino acid sequence of the polypeptide has an HMM bit score greater than about 550 using an HMM generated from the amino acid sequences depicted in FIG. 6.

In another aspect, a method comprises growing a plant cell comprising an exogenous nucleic acid. The exogenous nucleic acid comprises a regulatory region operably linked to a nucleotide sequence encoding a polypeptide having 85 percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. A plant produced from the plant cell has a difference in the level of tolerance to salinity and/or oxidative stress as compared to the corresponding level in a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 85 percent or greater sequence identity to at least a fragment of a nucleotide sequence set forth in SEQ ID NOs. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of salinity and/or oxidative stress tolerance as compared to the corresponding level in a control plant that does not comprise the exogenous nucleic acid.

Methods of modulating the level of salt tolerance and/or oxidative stress tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than 30, using an HMM generated from the amino acid sequences depicted in one of FIGS. 1-6. A plant and/or plant tissue produced from the plant cell has a difference in the level of tolerance to salinity and/or oxidative stress as compared to the corresponding level in a control plant that does not comprise the exogenous nucleic acid.

In another aspect, a method comprises introducing into a plant cell an exogenous nucleic acid that comprises a regulatory region operably linked to a nucleotide sequence encoding a polypeptide having 85% percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. A plant and/or plant tissue produced from the plant cell has a difference in the level of tolerance to salinity or oxidative stress as compared to the corresponding level in a control plant that does not comprise the exogenous nucleic acid.

In some embodiments, the methods comprise introducing into the plant cell an exogenous nucleic acid encoding polypeptides selected from the group consisting of SEQ ID NOs: 43, 44, 45, 86, 140, 141, 142, 143, 144, and amino acid coordinates 1 to 135 of SEQ ID NO: 140. A plant and/or plant tissue produced from the plant cell has a difference in the level of tolerance to salinity as compared to the corresponding level in a control plant that does not comprise the exogenous nucleic acid. In some embodiments, the methods comprise introducing into the plant cell an exogenous nucleic acid encoding polypeptides selected from the group consisting of SEQ ID NO: 136, and 141, and a plant and/or plant tissue produced from the plant cell has a difference in the level of tolerance to oxidative stress as compared to the corresponding level in a control plant that does not comprise the exogenous nucleic acid.

In another aspect, a method comprises introducing into a plant cell an exogenous nucleic acid, that comprises a regulatory region operably linked to a nucleotide sequence having 85 percent or greater sequence identity to a nucleotide sequence set forth in SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than 30, using an HMM based on the amino acid sequences depicted in one of FIGS. 1-6. The plant and/or plant tissue has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence encoding a polypeptide having 85 percent or greater sequence identity to an amino acid sequence selected from the group consisting of SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 A plant and/or plant tissue produced from the plant cell has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence having 85 percent or greater sequence identity to at least a fragment of a nucleotide sequence selected from the group consisting of SEQ ID Nos. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid. A transgenic plant comprising such a plant cell is also provided. In some embodiments, the transgenic plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet). Some embodiments are related to products comprising seed or vegetative tissue from transgenic plants as described above. Some embodiments relate to food or feed products from transgenic plants as described above.

In another aspect, an isolated nucleic acid comprises a nucleotide sequence encoding a polypeptide having 80% or greater sequence identity to the amino acid sequence set forth in SEQ ID Nos. 2, 4, 6, 22, 27, 29, 49, 52, 54, 56, 60, 62, 68, 76, 83, 88, 90, 96, 98, 104, 106, 112, 114, 132, 134, 149, 151, or 160.

In another aspect, methods of identifying a genetic polymorphism associated with variation in the level of salinity and/or oxidative stress tolerance are provided. The methods include providing a population of plants, and determining whether one or more genetic polymorphisms in the population are genetically linked to the locus for a polypeptide selected from the group consisting of the polypeptides depicted in FIGS. 1-6 and functional homologs thereof. The correlation between variation in the level of salinity tolerance and/or oxidative stress tolerance in plants and/or plant tissues of the population and the presence of the one or more polymorphisms in plants of the population is measured, thereby permitting identification of whether or not the one or more polymorphisms are associated with such variation.

In another aspect, methods of making a plant line is provided. The methods include determining whether one or more genetic polymorphisms in a population of plants is associated with the locus for a polypeptide selected from the group consisting of the polypeptides depicted in FIGS. 1-6 and functional homologs thereof, identifying one or more plants in the population in which the presence of at least one allele at the one or more polymorphisms is associated with variation in salt tolerance or oxidative stress tolerance, crossing each of the one or more identified plants with itself or a different plant to produce seed, crossing at least one progeny plant grown from said seed with itself or a different plant, and repeating the crossing steps for an additional 0-5 generations to make the plant line. The at least one allele will be present in the plant line. The method of making a plant line may be applied, for example, to a population of switchgrass plants.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

Figure 1:
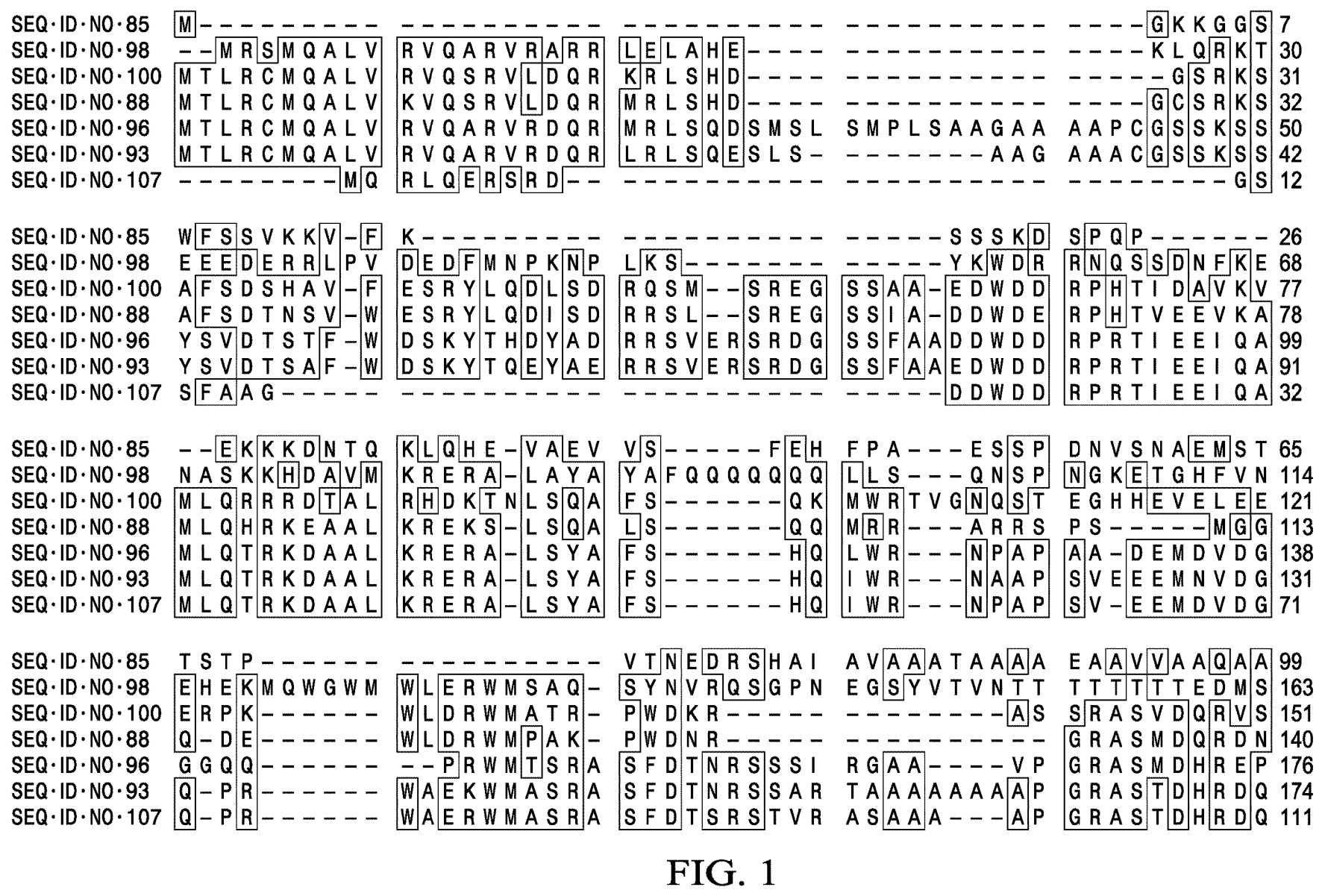
Figure 1:
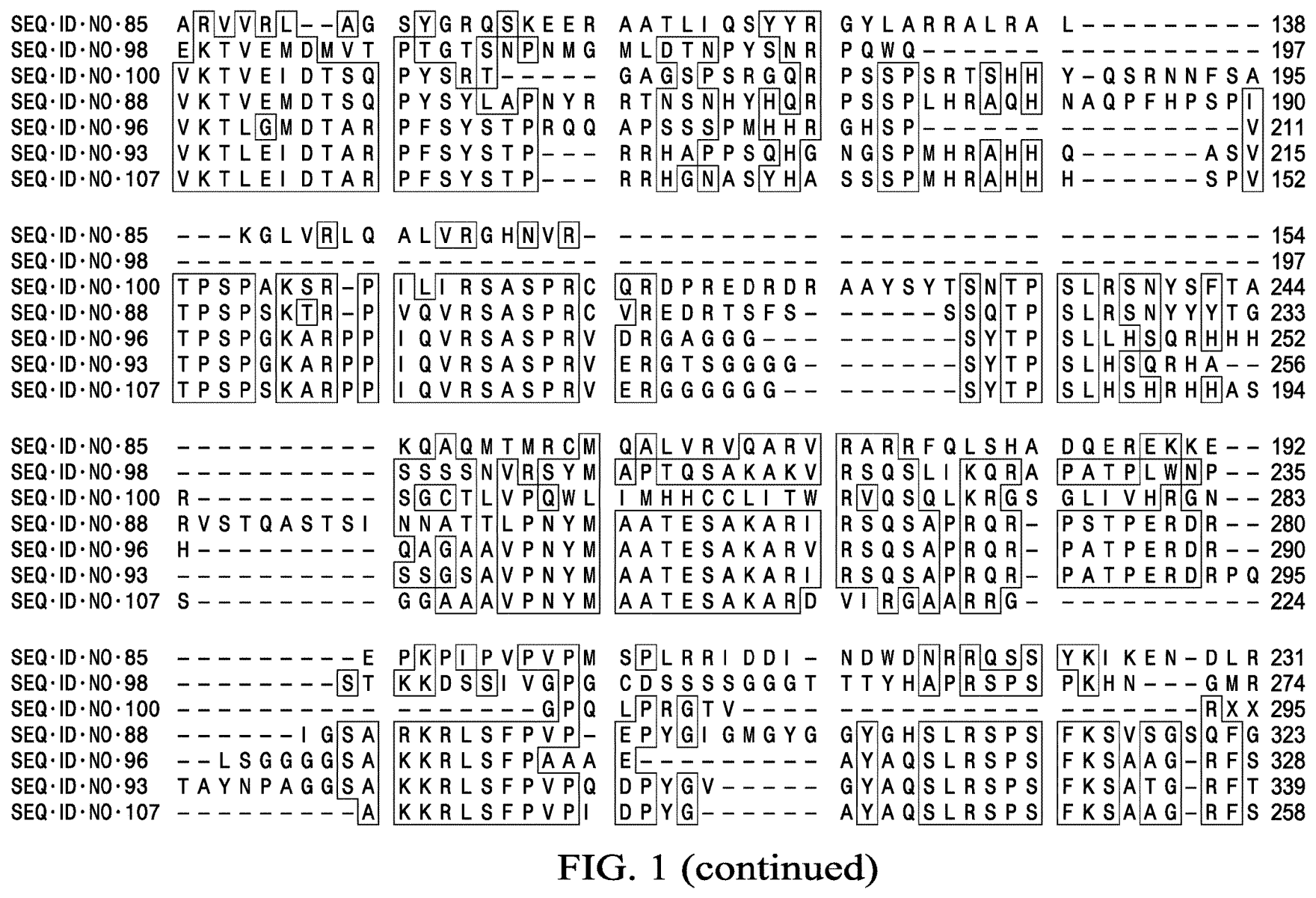

FIG. 1 is an alignment of amino acid sequences of homologues of (ME08768; SEQ ID NO: 86). In all the alignment Figures shown herein, a dash in an aligned sequence represents a gap, i.e., a lack of an amino acid at that position. Identical amino acids or conserved amino acid substitutions among aligned sequences are identified by boxes. FIG. 1 and the other alignment Figures provided herein were generated using the program MUSCLE version 3.52

FIG. 2 is an alignment of amino acid sequences of homologues of ME06748 (SEQ ID NO: 41).

FIG. 3 is an alignment of amino acid sequences of homologues of ME19173 (SEQ ID NO: 109).

FIG. 4 is an alignment of amino acid sequences of homologues of ME02064C (SEQ ID NO: 140).

FIG. 5 is an alignment of amino acid sequences of homologues of Ceres Clone ID No. 1792354 (SEQ ID NO:2).

FIG. 6 is an alignment of amino acid sequences of homologues of Ceres Clone ID No. 56784328 (SEQ ID NO: 35).

DETAILED DESCRIPTION

The invention features methods and materials related to modulating salinity tolerance and/or oxidative stress tolerance levels in plants and/or plant tissues. In some embodiments, the plants may also have increased biomass and/or yield. The methods can include transforming a plant cell with a nucleic acid encoding a salinity and/or oxidative stress tolerance-modulating polypeptide, wherein expression of the polypeptide results in a modulated level of salinity tolerance and/or oxidative stress tolerance. Plant cells produced using such methods can be grown to produce plants having an increased salinity tolerance, oxidative stress tolerance, and/or biomass, in comparison to wild type plants grown under the same conditions. Such plants, and the seeds of such plants, may be used to produce, for example, yield and/or biomass utilized for biofuel production, such as, but not limited to, ethanol and butanol.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

Oxidative stress: Plant species vary in their capacity to tolerate ROS/ROI/AOS. "Oxidative stress" can be defined as the set of environmental conditions under which a plant will begin to suffer the effects of elevated ROS/ROI/AOS concentration, such as decreases in enzymatic activity, DNA breakage, DNA-protein crosslinking, necrosis and stunted growth. For these reasons, plants experiencing oxidative stress typically exhibit a significant reduction in biomass and/or yield.

Elevated oxidative stress may be caused by natural, geological processes and by human activities, such as pollution. Since plant species vary in their capacity to tolerate oxidative stress, the precise environmental conditions that cause stress cannot be generalized. However, under oxidative stress conditions, oxidative stress tolerant plants produce higher biomass, yield and survivorship than plants that are not oxidative stress tolerant. Differences in physical appearance, recovery and yield can be quantified Photosynthetic efficiency: photosynthetic efficiency, or electron transport via photosystem II, is estimated by the relationship between Fm, the maximum fluorescence signal and the variable fluorescence, Fv. A reduction in the optimum quantum yield (Fv/Fm) indicates stress and can be used to monitor the performance of transgenic plants compared to non-transgenic plants under salt or oxidative stress conditions.

Salicylic Acid Growth Index (SAGI): Photosynthetic efficiency x seedling area.

Salt growth index (SGI): Photosynthetic efficiency x seedling area (under salinity stress condition).

Salinity: Plant species vary in their capacity to tolerate salinity. "Salinity" can be defined as the set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Elevated salinity may be caused by natural, geological processes and by human activities, such as pollution. Since plant species vary in their capacity to tolerate salinity, the precise environmental conditions that cause stress cannot be generalized. However, under saline conditions, salinity tolerant plants produce higher biomass, yield and survivorship than plants that are not saline tolerant. Differences in physical appearance, recovery and yield can be quantified.

Elevated salinity may be caused by natural, geological processes and by human activities, such as irrigation. Since plant species vary in their capacity to tolerate water deficit, the precise environmental salt conditions that cause stress cannot be generalized. However, under saline conditions, salt tolerant plants produce higher biomass, yield and survivorship than plants that are not salt tolerant. Differences in physical appearance, recovery and yield can be quantified and statistically analyzed using well known measurement and analysis methods.

II. POLYPEPTIDES

Polypeptides described herein include salinity tolerance and/or oxidative stress tolerance-modulating polypeptides. Salinity tolerance and/or oxidative stress tolerance-modulating polypeptides can be effective to modulate salinity tolerance and/or oxidative stress tolerance levels when expressed in a plant or plant cell. Such polypeptides typically contain at least one domain indicative of salinity tolerance and/or oxidative stress tolerance-modulating polypeptides, as described in more detail herein. Salinity tolerance and/or oxidative stress tolerance-modulating polypeptides typically have an HMM bit score that is greater than 30, as described in more detail herein. In some embodiments, salinity tolerance and/or oxidative stress tolerance-modulating polypeptides have greater than 85% identity to SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 as described in more detail herein.

A. Domains Indicative of Salinity Tolerance and/or Oxidative Stress Tolerance-Modulating Polypeptides A salinity tolerance and/or oxidative stress tolerance-modulating polypeptide can contain an IQ calmodulin-binding motif domain, which is predicted to be characteristic of an salinity tolerance and/or oxidative stress tolerance-modulating polypeptide. Calmodulin (CaM) is recognized as a major calcium sensor and orchestrator of regulatory events through its interaction with a diverse group of cellular proteins. Three classes of recognition motifs exist for many of the known CaM binding proteins; the IQ motif as a consensus for $Ca^{2+}$-independent binding and two related motifs for $Ca2^+$-dependent binding, termed 18-14 and 1-5-10 based on the position of conserved hydrophobic residues PUBMED:9141499.

For example, the regulatory domain of scallop myosin is a three-chain protein complex that switches on this motor in response to $Ca2^+$ binding. Side-chain interactions link the two light chains in tandem to adjacent segments of the heavy chain bearing the IQ-sequence motif. The $Ca^{2+}$-binding site is a novel EF-hand motif on the essential light chain and is stabilized by linkages involving the heavy chain and both light chains, accounting for the requirement of all three chains for $Ca2^+$ binding and regulation in the intact myosin molecule PUB MED: 8127365.

For example, SEQ ID NO:86 sets forth the amino acid sequence of an *Arabidopsis* clone, identified herein as Ceres SEEDLINE ID no. ME08768, that is predicted to encode a polypeptide containing a IQ calmodulin-binding motif domain from residues 116-136.

In some embodiments, a salinity tolerance and/or oxidative stress tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the salinity tolerance and/or oxidative stress tolerance-modulating activity of a truncated polypeptide. In some embodiments, a truncated polypeptide is a dominant negative polypeptide. SEQ ID NO: 138 sets forth the amino sequence of a salinity tolerance and/or oxidative stress tolerance-modulating polypeptide that is truncated at the 5' end relative to the naturally occurring polypeptide. Expression in a plant of such a truncated polypeptide confers a difference in the level of salinity tolerance and/or oxidative stress tolerance in a plant and/or plant tissue as compared to the corresponding level a control plant and/or tissue thereof that does not comprise the truncation.

B. Functional Homologs Identified by Reciprocal BLAST

In some embodiments, one or more functional homologs of a reference salinity tolerance and/or oxidative stress tolerance-modulating polypeptide defined by one or more of the pfam descriptions indicated above are suitable for use as salinity tolerance and/or oxidative stress tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a salinity tolerance and/or oxidative stress tolerance-modulating polypeptide, or by combining domains from the coding sequences for different naturally-occurring salinity tolerance and/or oxidative stress tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of salinity tolerance and/or oxidative stress tolerance-modulating polypeptides. Sequence analysis can involve BLAST, Reciprocal BLAST, or PSI-BLAST analysis of nonredundant databases using a salinity tolerance and/or oxidative stress tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a salinity tolerance and/or oxidative stress tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in salinity tolerance and/or oxidative stress tolerance-modulating polypeptides, e.g., conserved functional domains.

Conserved regions can be identified by locating a region within the primary amino acid sequence of a salinity tolerance and/or oxidative stress tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NO: 86 are provided in FIG. 1 and in the Sequence Listing. Such functional homologs include (SEQ ID NO: 88, 90, 91, 93, 94, 96, 98, 100, 101, 102, 104, 106, and 107). In some cases, a functional homolog of SEQ ID NO: 86 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 86.

Figure 2:
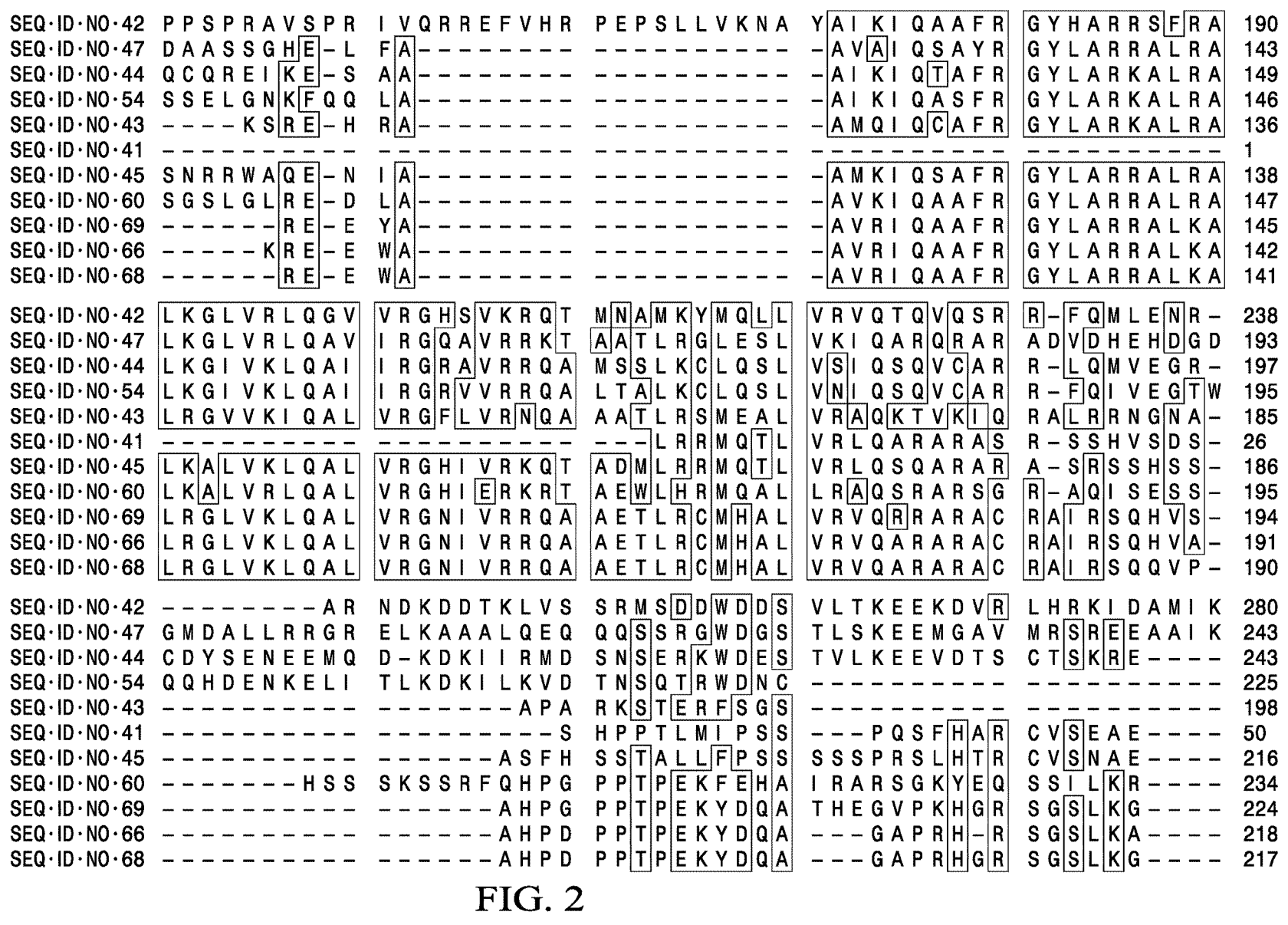
Figure 2:
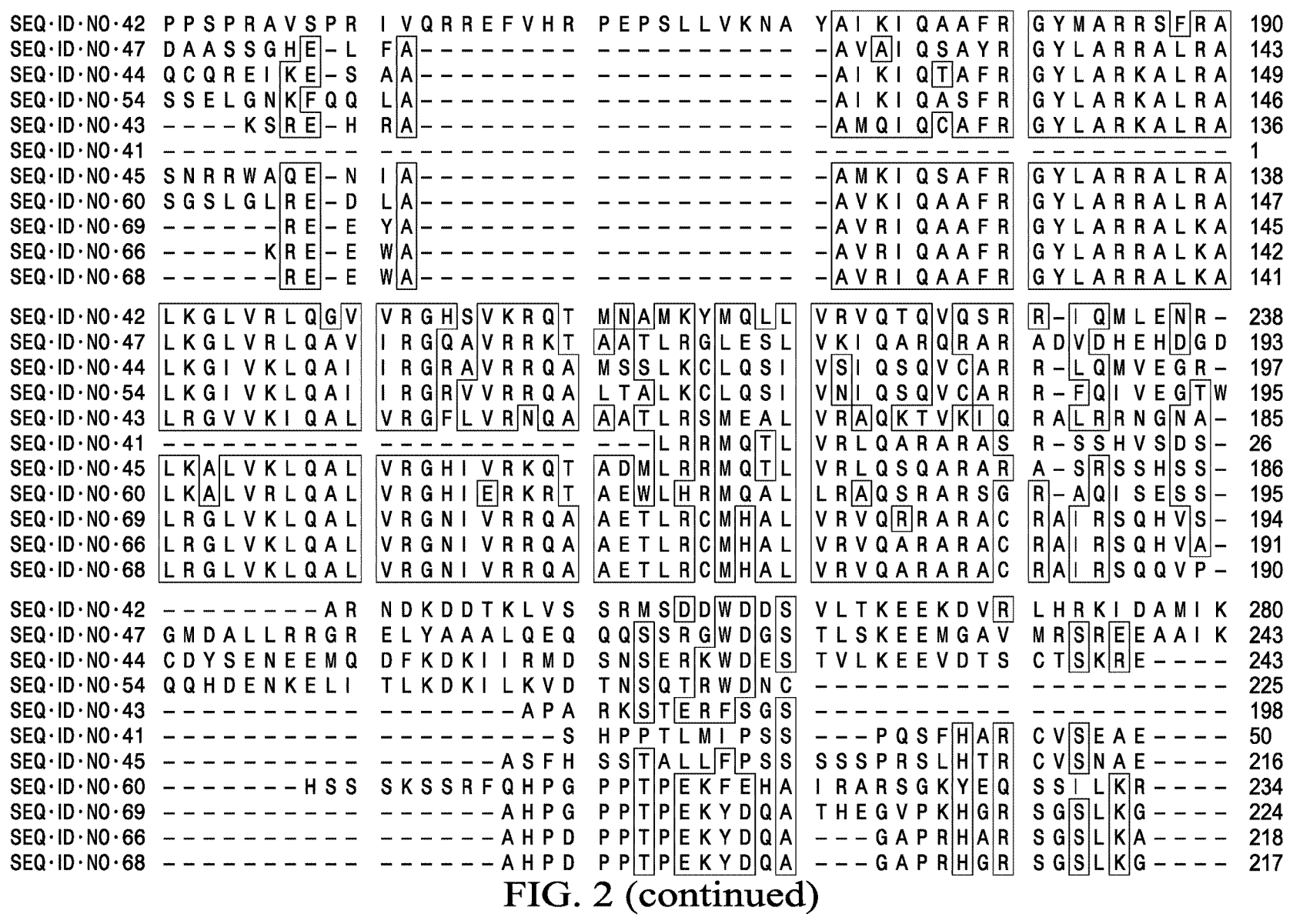
Figure 2:
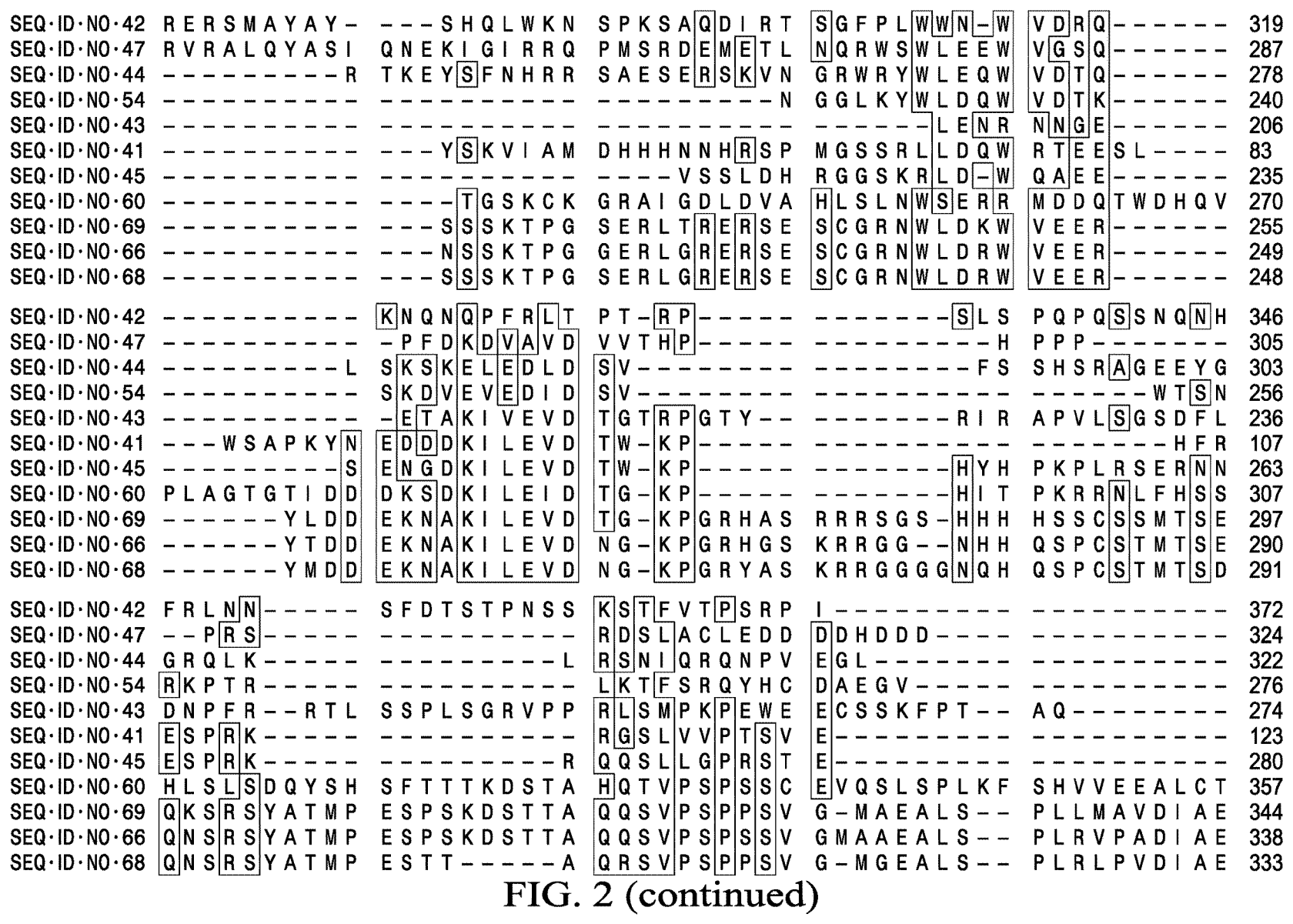
Figure 2:
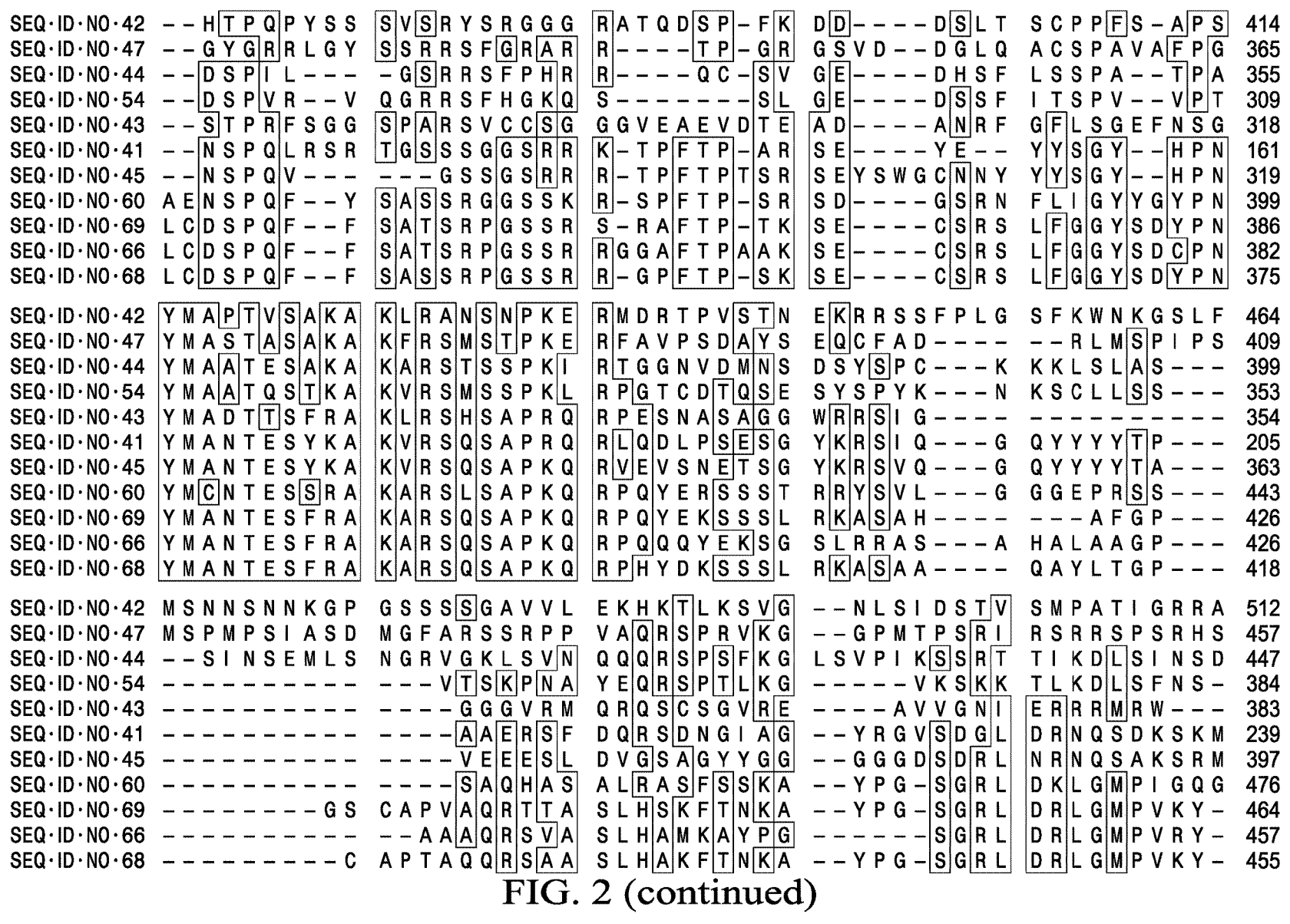

Amino acid sequences of functional homologs of the polypeptide set forth in SEQ ID NO: 41 are provided in FIG. 2. Such functional homologs include (SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84). In some cases, a functional homolog of SEQ ID NO: 41 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41.

Figure 3:
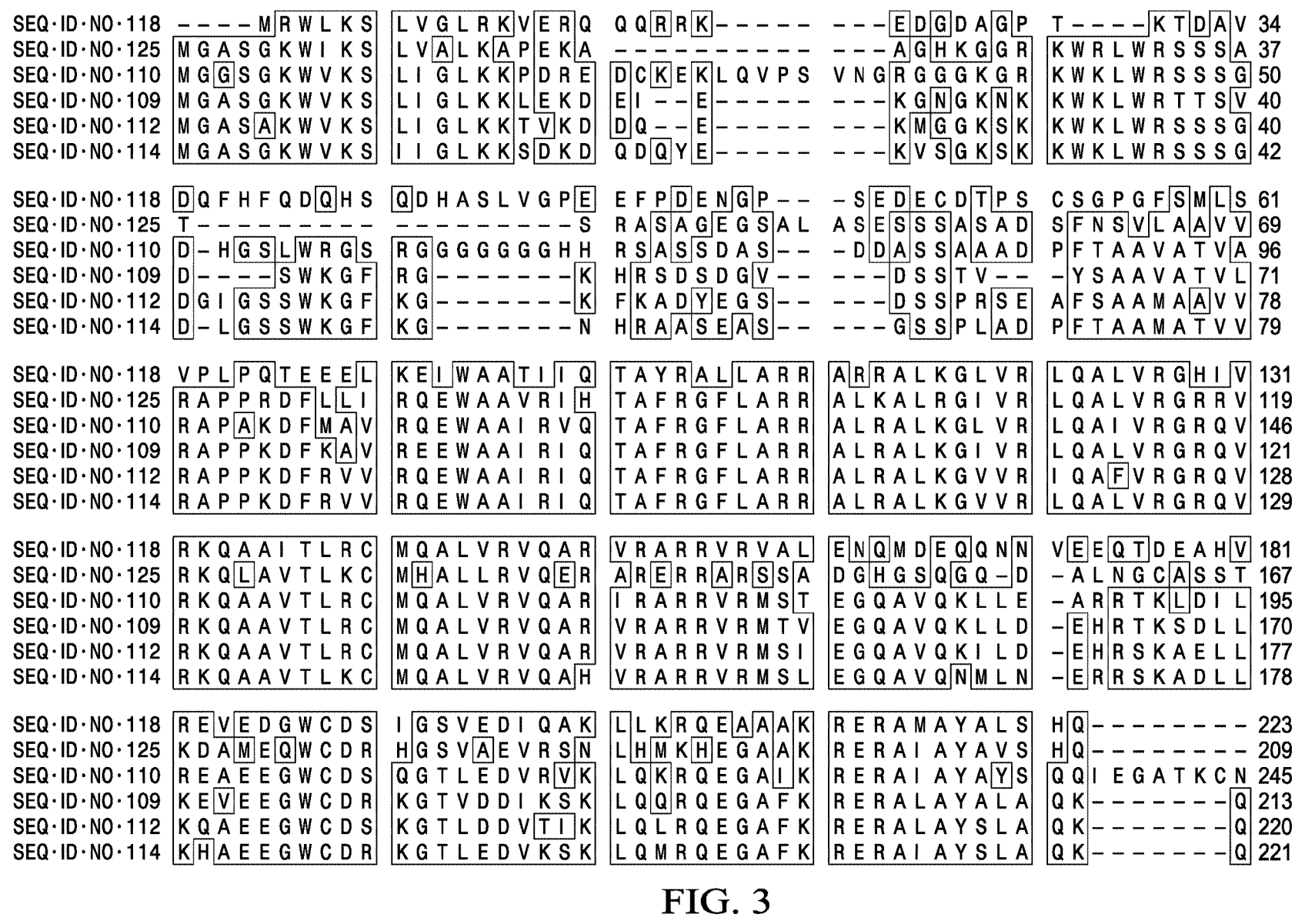
Figure 3:
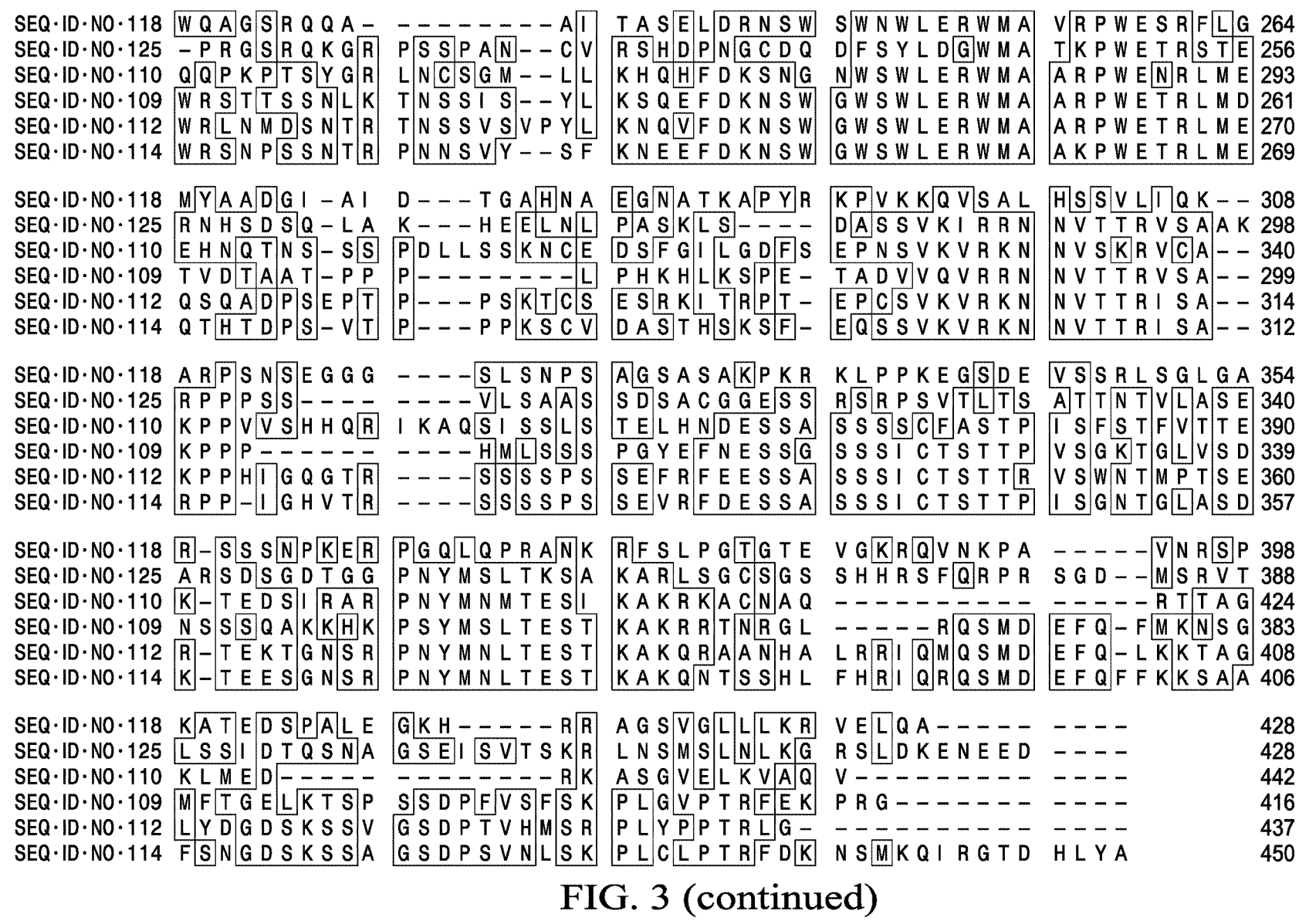

Amino acid sequences of functional homologs of the polypeptide set forth in SEQ ID NO: 109 are provided in FIG. 3. Such functional homologs include (SEQ ID NO: 110, 112, 114, 116, 118, 119, 121, 122, 123, 125, 126, 127, 128, 129, 130, 132, and 134). In some cases, a functional homolog of SEQ ID NO: 109 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109.

Figure 4:
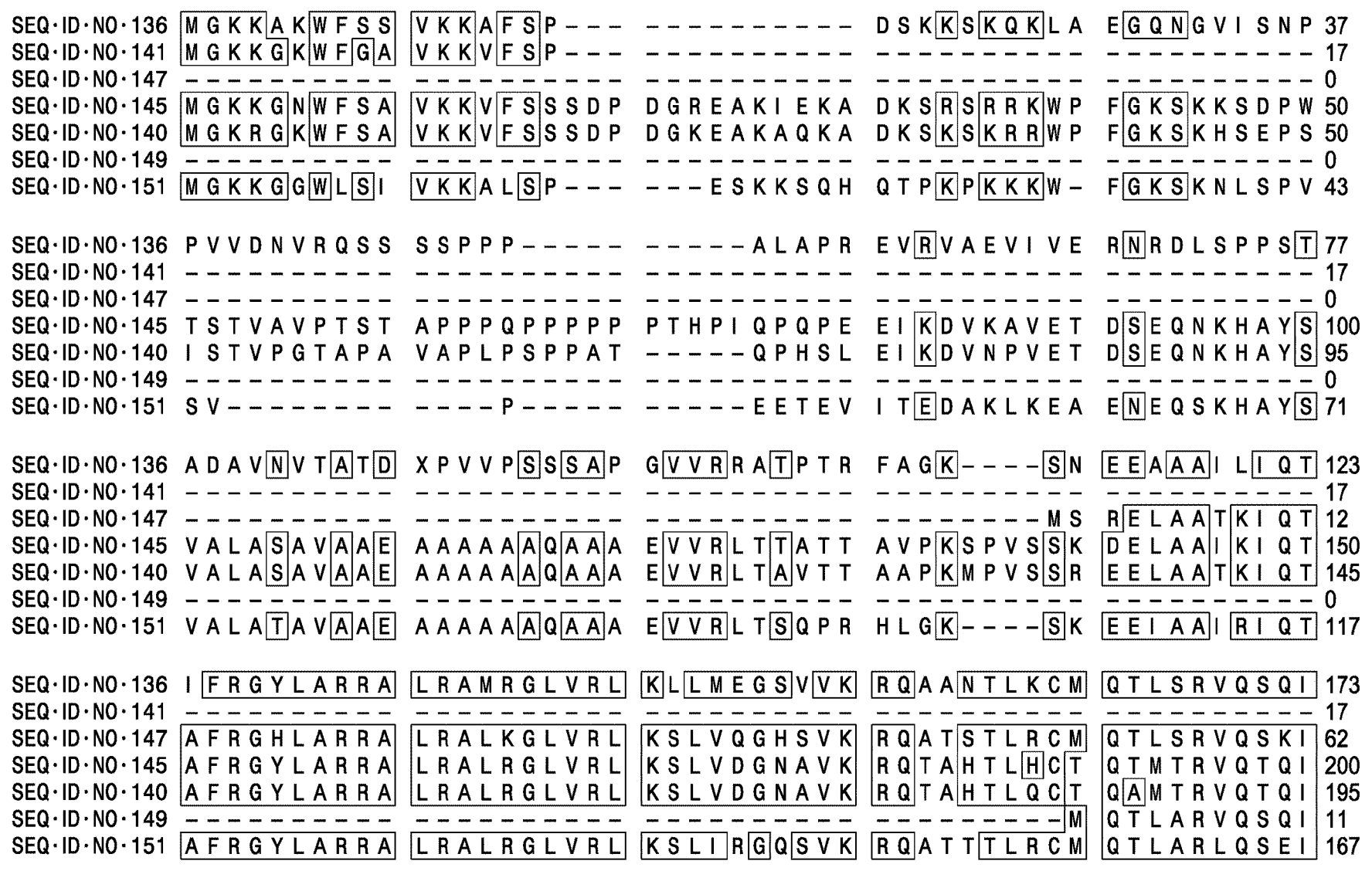
Figure 4:
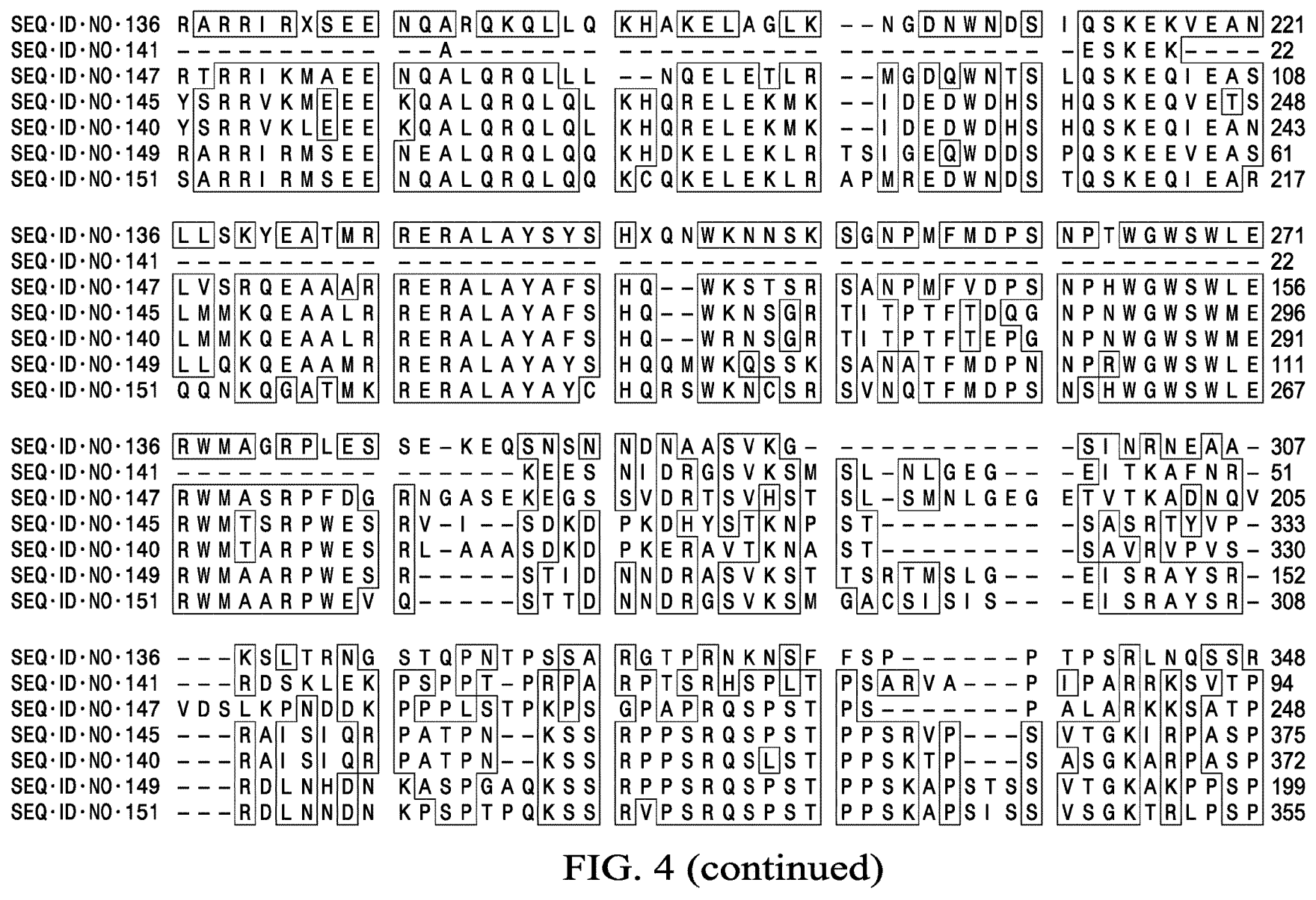
Figure 4:
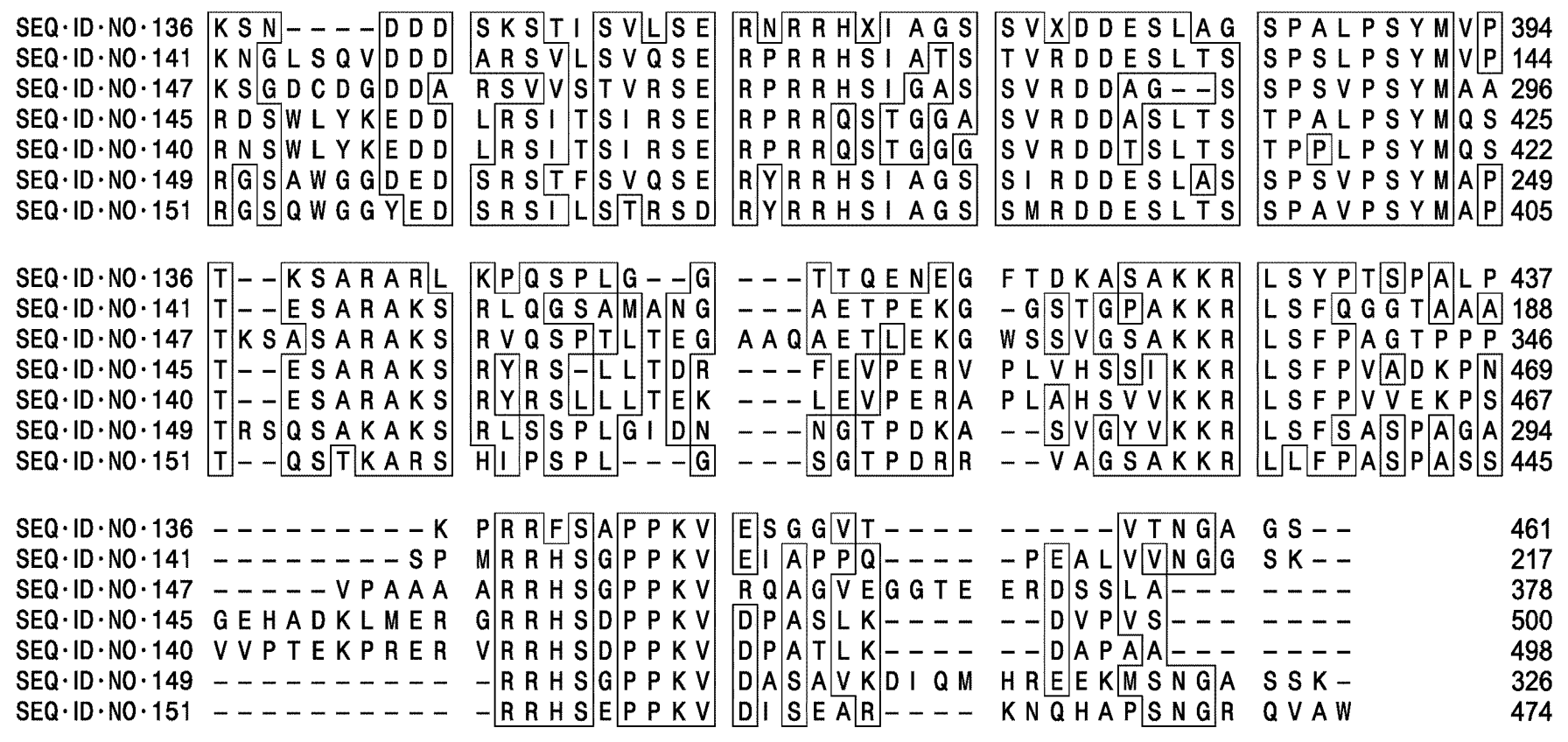

Amino acid sequences of functional homologs of the polypeptide set forth in SEQ ID NO:140 are provided in FIG. 4. Such functional homologs include (SEQ ID NO: 136, 138, 140, 141, 142, 143, 144, 145, 147, 149, 151, 153, 154, 156, 158, 160, 162, 163, 165, 166, 167, and 168). In some cases, a functional homolog of SEQ ID NO: 140 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140.

Figure 5:
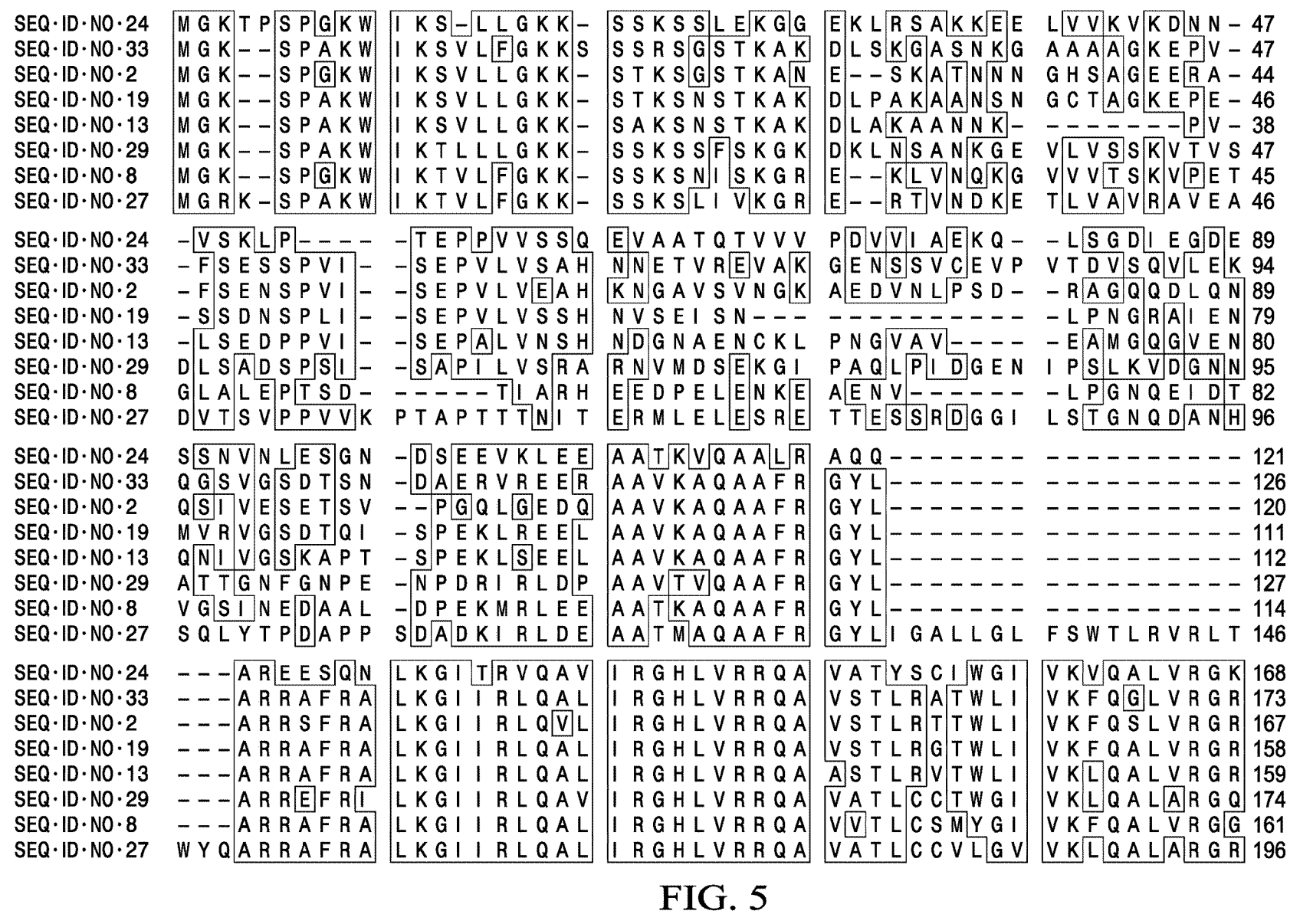
Figure 5:
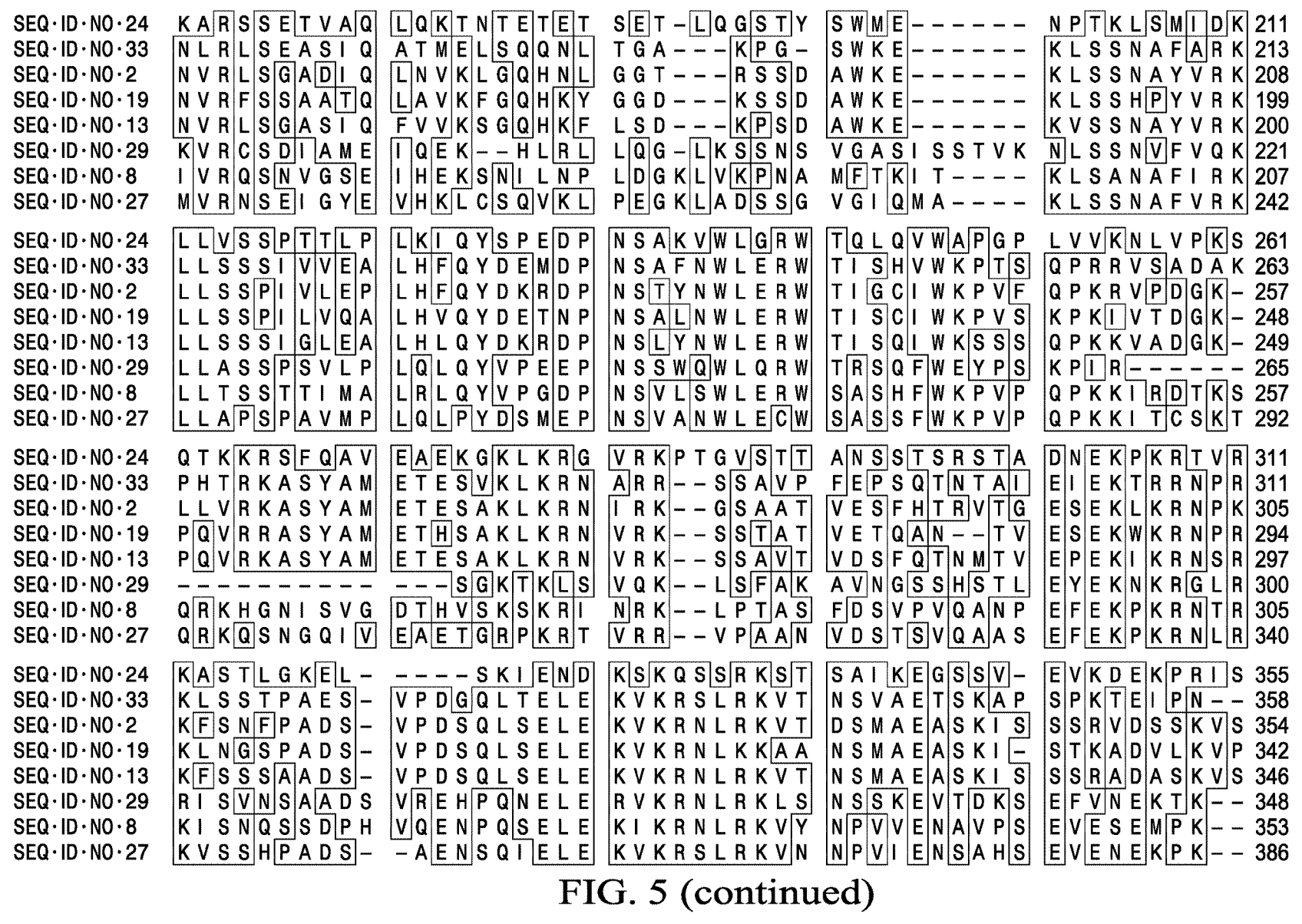
Figure 5:
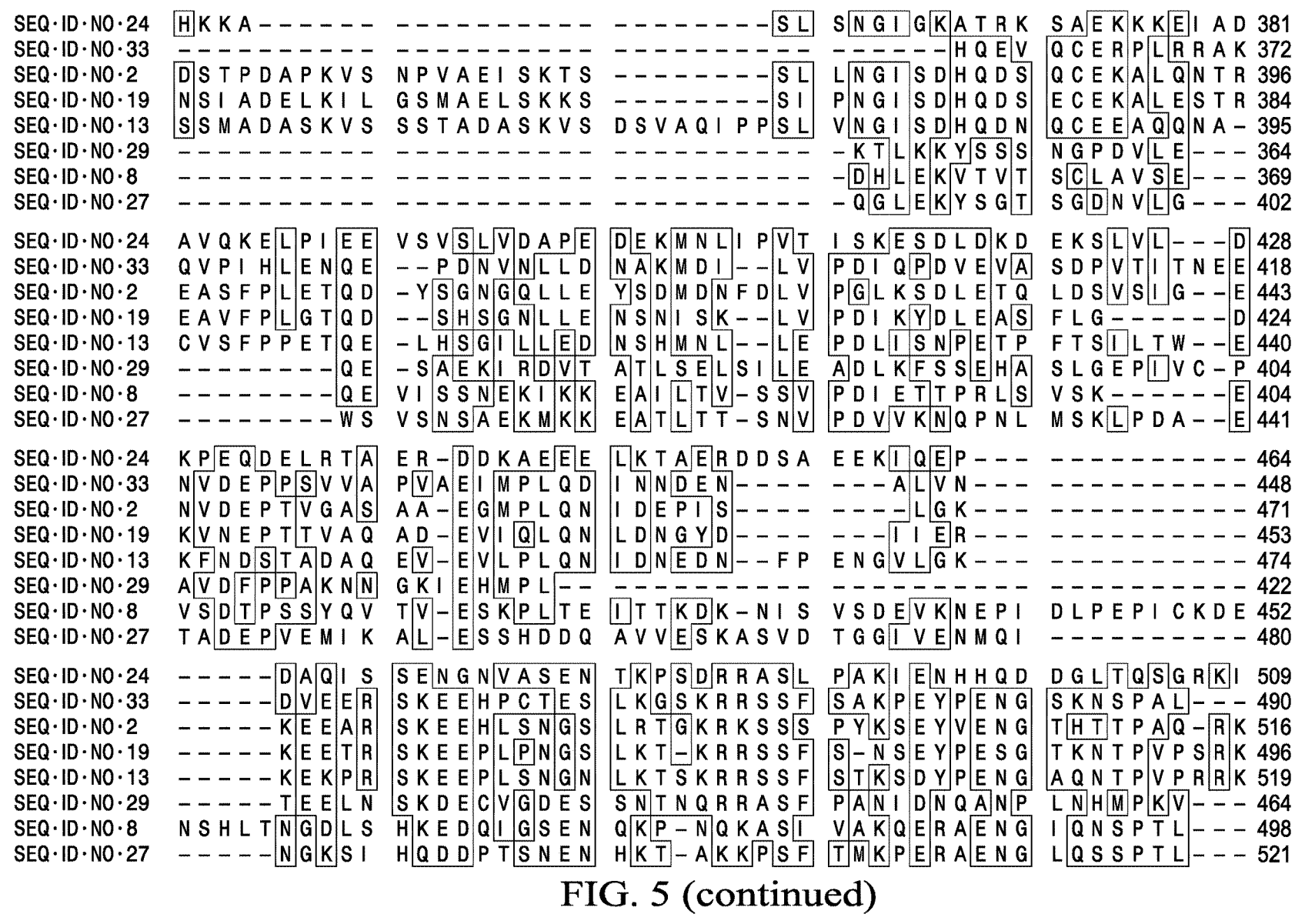

Amino acid sequences of functional homologs of the polypeptide set forth in SEQ ID NO: 2 are provided in FIG. 5. Such functional homologs include (SEQ ID NO: 2, 4, 6, 8, 9, 11, 13, 14, 15, 17, 19, 20, 22, 23, 24, 25, 27, 29, 30, 31, and 33). In some cases, a functional homolog of SEQ ID NO: 2 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2.

Amino acid sequences of functional homologs of the polypeptide set forth in SEQ ID NO: 35 are provided in FIG. 6. Such functional homologs include (SEQ ID NO: 35, 36, 37, 38, and 39). In some cases, a functional homolog of SEQ ID NO: 35 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35.

The identification of conserved regions in a salinity tolerance and/or oxidative stress tolerance-modulating polypeptide facilitates production of variants of salinity tolerance and/or oxidative stress tolerance-modulating polypeptides. Variants of salinity tolerance and/or oxidative stress tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1 thru 6. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologues Identified by HMM

In some embodiments, useful salinity and/or oxidative stress tolerance-modulating polypeptides include those that fit a Hidden Markov Model based on the polypeptides set forth in any one of FIGS. 1-6. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web. Hmmbuild outputs the model as a text file.

The HMM for a group of functional homologs can be used to determine the likelihood that a candidate salinity tolerance and/or oxidative stress tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

As those of skill in the art would appreciate, the HMM scores provided in the sequence listing are merely exemplary. Since multiple sequence alignment algorithms, such as ProbCons, can only generate near-optimal results, slight variations of the model can arise due to factors such as the order in which sequences are processed for alignment. Nevertheless, HMM score variability is minor, and so the HMM scores in the sequence listing are representative of models made with the respective sequences.

The salinity and/or oxidative stress-modulating polypeptides discussed below fit the indicated HMM with an HMM bit score greater than 20 (e.g., greater than 20, 30, 40, 50, 60, 70, 80, 90, 100, 200, 300, 400, or 500). In some embodiments, the HMM bit score of a salinity and/or oxidative stress-modulating polypeptide discussed below is about 50%, 60%, 70%, 80%, 90%, or 95% of the HMM bit score of a functional homolog provided in the Sequence Listing. In some embodiments, a salinity and/or oxidative stress-modulating polypeptide discussed below fits the indicated HMM with an HMM bit score greater than 20, and has a domain indicative of an salinity and/or oxidative stress-modulating polypeptide. In some embodiments, a salinity and/or oxidative stress-modulating polypeptide discussed below fits the indicated HMM with an HMM bit score greater than 20, and has 85% or greater sequence identity (e.g., 75%, 80%, 85%, 90%, 95%, or 100% sequence identity) to an amino acid sequence shown in any one of FIGS. 1 thru 6 or to an amino acid sequence correlated in the Sequence Listing to a any one of FIGS. 1 thru 6._.

In the Sequence Listing polypeptides are provided that have HMM bit scores greater than 400, 450, 500, 550, 600, 650, 700, 750, 800, 850, 900, 950, 1000, 1050, or 1100, when fitted to an HMM generated from the amino acid sequences set forth in FIG. 1. Such polypeptides include Ceres SEEDLINE ID no. ME08768, Ceres CLONE ID no. 1943807, Ceres ANNOT ID no. 1471392, Public GI ID no. 6715635, Ceres CLONE ID no. 910109, Public GI ID no. 115474509, Ceres CLONE ID no. 1780908, Ceres ANNOT ID no. 1520883, Ceres CLONE ID no. 148018, Public GI ID no. 18378797, Public GI ID no. 21553500, Ceres ANNOT ID no. 1444522, Ceres ANNOT ID no. 146751, and Public GI ID no. 125559938 (SEQ ID NO: 86, 88, 90, 91, 93, 94, 96, 98, 100, 101, 102, 104, 106, and 107)

In the Sequence Listing polypeptides are provided that have HMM bit scores greater than 30, 50, 100, 150, 200, 250, 300, 350, 400, 450, 500, 550, 600, 650, 700, 750, 800, 850, 900, 950, or 1000 when fitted to an HMM generated from the amino acid sequences set forth in FIG. 2. Such polypeptides include Ceres SEEDLINE ID no. ME06748, Ceres SEEDLINE ID no. ME20711, Ceres SEEDLINE ID no. ME18973, Ceres SEEDLINE ID no. ME08732, Ceres SEEDLINE ID no. ME19657, Ceres CLONE ID no. 835818, Ceres CLONE ID no. 1796745, Public GI ID no. 125543896, Ceres ANNOT ID no. 1483984, Ceres CLONE ID no. 1924654, Ceres ANNOT ID no. 1468861, Ceres CLONE ID no. 1641776, Ceres ANNOT ID no. 1438750, Ceres ANNOT ID no. 1447395, Public GI ID no. 79482785, Public GI ID no. 3292832, Ceres CLONE ID no. 1559074, Ceres CLONE ID no. 1726548, Public GI ID no. 115459996, Ceres CLONE ID no. 697034, Ceres CLONE ID no. 353438, Public GI ID no. 125593074, Ceres CLONE ID no. 1920115, Ceres CLONE ID no. 21821, Ceres CLONE ID no. 560066, Public GI ID no. 115453071, Ceres CLONE ID no. 1968211, and Public GI ID no. 116310011 (SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84).

In the Sequence Listing polypeptides are provided that have HMM bit scores greater than 120, 150, 200, 250, 300, 350, 400, 450, 500, 550, 600, 650, 700, 750, 800, 850, 900, 950, 1000, 1050, 1100, 1150, or 1200 when fitted to an HMM generated from the amino acid sequences set forth in FIG. 3. Such polypeptides include Ceres SEEDLINE ID no. ME19173, Public GI ID no. 115435054, Ceres CLONE ID no. 1847857, Ceres ANNOT ID no. 1455219, Ceres CLONE ID no. 352452, Ceres CLONE ID no. 787908, Ceres LOCUS ID no. Os01m00929_AP002743, Ceres CLONE ID no. 246398, Public GI ID no. 125527441, Public GI ID no. 125595056, Ceres CLONE ID no. 236071, Public GI ID no. 125524760, Public GI ID no. 125569365, Public GI ID no. 115439499, Public GI ID no. 15225258, Public GI ID no. 115465173, Ceres ANNOT ID no. 1477059, and Ceres ANNOT ID no. 1530547 (SEQ ID NO: 110, 112, 114, 116, 118, 119, 121, 122, 123, 125, 126, 127, 128, 129, 130, 132, and 134).

In the Sequence Listing polypeptides are provided that have HMM bit scores greater than 150, 200, 250, 300, 350, 400, 450, 500, 550, 600, 650, 700, 750, 800, 850, 900, 950, 1000, 1050, 1100, 1150, 1200, 1250, 1300, or 1350 when fitted to an HMM generated from the amino acid sequences set forth in FIG. 4. Such polypeptides include Ceres SEEDLINE ID no. ME24091, Ceres CLONE ID no. 375578, Ceres CLONE ID no. 375578, Ceres SEEDLINE ID no. ME10681, Ceres SEEDLINE ID no. ME03140, Ceres SEEDLINE ID no. ME24076, Ceres SEEDLINE ID no. ME24217, Public GI ID no. 115440873, Ceres CLONE ID no. 826796, Ceres ANNOT ID no. 1465047, Ceres CLONE ID no. 1919901, Ceres CLONE ID no. 520008, Public GI ID no. 7413581, Ceres CLONE ID no. 228069, Ceres CLONE ID no. 467508, Ceres CLONE ID no. 1829581, Ceres CLONE ID no. 229668, Public GI ID no. 125550655, Ceres CLONE ID no. 106263, Public GI ID no. 15231175, Public GI ID no. 145357576, and Public GI ID no. 125528277 (SEQ ID NO: 136, 138, 140, 141, 142, 143, 144, 145, 147, 149, 151, 153, 154, 156, 158, 160, 162, 163, 165, 166, 167, and 168).

In the Sequence Listing polypeptides are provided that have HMM bit scores greater than 425, 450, 500, 550, 600, 650, 700, 750, 800, 850, 900, 950, 1000, 1050, 1100, 1150, 1200, 1250, 1300, 1350, 1400, 1450, 1500, or 1550, when fitted to an HMM generated from the amino acid sequences set forth in FIG. 5. Such polypeptides include Ceres CLONE ID no. 1792354, Ceres CLONE ID no. 1925477, Ceres ANNOT ID no. 1521592, Ceres CLONE ID no. 463594, Public GI ID no. 22330633, Ceres CLONE ID no. 345954, Ceres LOCUS ID no. Os01m05025_AP003288, GI ID no. 56784330, Public GI ID no. 125527495, Public GI ID no. 125553119, Ceres CLONE ID no. 236431, Ceres CLONE ID no. 908518, Public GI ID no. 115465121, Ceres CLONE ID no. 1791910, Public GI ID no. 125595019, Public GI ID no. 42568886, Public GI ID no. 2947062, Ceres ANNOT ID no. 1468228, Ceres CLONE ID no. 1942388, Public GI ID no. 12324824, Public GI ID no. 5882749, and Ceres CLONE ID no. 325403 (SEQ ID NO: 2, 4, 6, 8, 9, 11, 13, 14, 15, 17, 19, 20, 22, 23, 24, 25, 27, 29, 30, 31, and 33).

In the Sequence Listing polypeptides are provided that have HMM bit scores greater than 550, 600, 650, or 700 when fitted to an HMM generated from the amino acid sequences set forth in FIG. 6. Such polypeptides include Ceres GI ID no. 56784328, Public GI ID no. 56784330, Public GI ID no. 125528718, Public GI ID no. 125572975, and Public GI ID no. 125528716 (SEQ ID NO: 35, 36, 37, 38, and 39).

D. Percent Identity

In some embodiments, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. Polypeptides having such a percent sequence identity often have a domain indicative of a salinity and/or oxidative stress-modulating polypeptide and/or have an HMM bit score that is greater than 20, as discussed above. Examples of amino acid sequences of salinity and/or oxidative stress tolerance-modulating polypeptides having at least 85% sequence identity to one of the amino acid sequences set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 are provided in FIGS. 1-6.

"Percent sequence identity" refers to the degree of sequence identity between any given reference sequence, e.g., SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140, and a candidate salinity and/or oxidative stress-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one or more of the amino acid sequence set forth in SEQ ID NO: 86 Amino acid sequences of polypeptides having high sequence identity to the polypeptide set forth in SEQ ID NO: 86 are provided in the Sequence Listing. Such polypeptides include SEQ ID NO: 88, 90, 91, 93, 94, 96, 98, 100, 101, 102, 104, 106, and 107.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41. Amino acid sequences of polypeptides having high sequence identity to the polypeptide set forth in SEQ ID NO: 41 are provided in the Sequence Listing. Such polypeptides include SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109. Amino acid sequences of polypeptides having high sequence identity to the polypeptide set forth in SEQ ID NO: 109 are provided in the Sequence Listing. Such polypeptides include SEQ ID NO: 110, 112, 114, 116, 118, 119, 121, 122, 123, 125, 126, 127, 128, 129, 130, 132, and 134.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140. Amino acid sequences of polypeptides having high sequence identity to the polypeptide set forth in SEQ ID NO: 140 are provided in the Sequence Listing. Such polypeptides include SEQ ID NO: 136, 138, 141, 142, 143, 144, 145, 147, 149, 151, 153, 154, 156, 158, 160, 162, 163, 165, 166, 167, and 168.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having high sequence identity to the polypeptide set forth in SEQ ID NO: 2 are provided in the Sequence Listing. Such polypeptides include SEQ ID NO: 4, 6, 8, 9, 11, 13, 14, 15, 17, 19, 20, 22, 23, 24, 25, 27, 29, 30, 31, and 33.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35. Amino acid sequences of polypeptides having high sequence identity to the polypeptide set forth in SEQ ID NO: 35 are provided in the Sequence Listing. Such polypeptides include SEQ ID NO: 36, 37, 38, and 39.

E. Other Sequences

It should be appreciated that a salinity and/or oxidative stress tolerance-modulating polypeptide can include additional amino acids that are not involved in salinity and/or oxidative stress tolerance modulation, and thus such a polypeptide can be longer than would otherwise be the case. For example, a salinity and/or oxidative stress-tolerance modulating polypeptide can include a purification tag, a chloroplast transit peptide, an amyloplast transit peptide, a mitochondrial transit peptide, or a leader sequence added to the amino or carboxy terminus. In some embodiments, a salinity and/or oxidative stress-tolerance modulating polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate salinity and/or oxidative stress tolerance levels when transcribed in a plant or plant cell. Such nucleic acids include, without limitation, those that encode a salinity and/or oxidative stress tolerance-modulating polypeptide and those that can be used to inhibit expression of a salinity tolerance and/or oxidative stress tolerance-modulating polypeptide via a nucleic acid based method.

A. Nucleic Acids Encoding Salinity Tolerance and/or Oxidative Stress Tolerance-Modulating Polypeptides Nucleic acids encoding salinity tolerance and/or oxidative stress tolerance-modulating polypeptides are described herein. Such nucleic acids include SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, as described in more detail below.

A salinity tolerance and/or oxidative stress tolerance-modulating nucleic acid can comprise the nucleotide sequence set forth in SEQ ID NO: 85. Alternatively, a salinity tolerance and/or oxidative stress tolerance-modulating nucleic acid can be a variant of the nucleic acid having the nucleotide sequence set forth in SEQ ID NO: 85. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 85, 87, 89, 92, 95, 97, 99, 103, and 105.

A salinity tolerance and/or oxidative stress tolerance-modulating nucleic acid can comprise the nucleotide sequence set forth in SEQ ID NO: 40. Alternatively, a salinity tolerance and/or oxidative stress tolerance-modulating nucleic acid can be a variant of the nucleic acid having the nucleotide sequence set forth in SEQ ID NO: 40. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 40, 46, 48, 51, 53, 55, 57, 59, 61, 65, 67, 70, 72, 75, 77, 79, and 82.

A salinity tolerance and/or oxidative stress tolerance-modulating nucleic acid can comprise the nucleotide sequence set forth in SEQ ID NO: 108. Alternatively, a salinity tolerance and/or oxidative stress tolerance-modulating nucleic acid can be a variant of the nucleic acid having the nucleotide sequence set forth in SEQ ID NO: 108. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 108, 111, 113, 115, 117, 120, 124, 131, and 133.

A salinity tolerance and/or oxidative stress tolerance-modulating nucleic acid can comprise the nucleotide sequence set forth in SEQ ID NO: 139. Alternatively, a salinity tolerance and/or oxidative stress tolerance-modulating nucleic acid can be a variant of the nucleic acid having the nucleotide sequence set forth in SEQ ID NO: 139. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 135, 137, 139, 146, 148, 150, 152, 155, 157, 159, 161, and 164.

A salinity tolerance and/or oxidative stress tolerance-modulating nucleic acid can comprise the nucleotide sequence set forth in SEQ ID NO: 1. Alternatively, a salinity tolerance and/or oxidative stress tolerance-modulating nucleic acid can be a variant of the nucleic acid having the nucleotide sequence set forth in SEQ ID NO: 1. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1, 3, 5, 7, 10, 12, 16, 18, 21, 26, 28, and 32.

A salinity tolerance and/or oxidative stress tolerance-modulating nucleic acid can comprise the nucleotide sequence set forth in SEQ ID NO: 34. Alternatively, a salinity tolerance and/or oxidative stress tolerance-modulating nucleic acid can be a variant of the nucleic acid having the nucleotide sequence set forth in SEQ ID NO: 34. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:34.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Salinity Tolerance and/or Oxidative Stress Tolerance-Modulating Polypeptide A nucleic acid encoding one of the salinity tolerance and/or oxidative stress tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular salinity tolerance and/or oxidative stress tolerance-modulating polypeptide; i.e., for many amino acids, there is more than one nucleotide triplet that serves as the codon for the amino acid. Thus, codons in the coding sequence for a given salinity tolerance and/or oxidative stress tolerance-modulating polypeptide can be modified such that optimal expression in a particular plant species is obtained, using appropriate codon bias tables for that species.

In some cases, expression of a salinity tolerance and/or oxidative stress tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a salinity tolerance and/or oxidative stress tolerance-Modulating Polypeptide Polynucleotides and recombinant constructs described herein can be used to inhibit expression of a salinity tolerance and/or oxidative stress tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, Oct. 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a salinity tolerance and/or oxidative stress tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the salinity tolerance and/or oxidative stress tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a salinity tolerance and/or oxidative stress tolerance-modulating polypeptide, and the other strand of the stem portion of the double stranded RNA comprises a sequence that is similar or identical to the sequence that is complementary to the 3' or 5' untranslated region, respectively, of the mRNA encoding the salinity tolerance and/or oxidative stress tolerance-modulating polypeptide. In other embodiments, one strand of the stem portion of a double stranded RNA comprises a sequence that is similar or identical to the sequence of an intron in the pre-mRNA encoding a salinity tolerance and/or oxidative stress tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a salinity tolerance and/or oxidative stress tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a salinity tolerance and/or oxidative stress tolerance-modulating polypeptide. In some embodiments, the sense or antisense sequence is identical or complementary to a sequence of the regulatory region that drives transcription of the gene encoding a salinity tolerance and/or oxidative stress tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a salinity tolerance and/or oxidative stress tolerance-modulating polypeptide described herein. The sense sequence complementary to the antisense sequence can be a sequence present within the mRNA of the salinity tolerance and/or oxidative stress tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate salinity tolerance and/or oxidative stress tolerance levels. A recombinant nucleic acid construct can comprise a nucleic acid encoding a salinity tolerance and/or oxidative stress tolerance-modulating polypeptide as described herein, operably linked to a regulatory region suitable for expressing the salinity tolerance and/or oxidative stress tolerance-modulating polypeptide in the plant or cell. Thus, a nucleic acid can comprise a coding sequence that encodes any of the salinity tolerance and/or oxidative stress tolerance-modulating polypeptides as set forth in SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164. Examples of nucleic acids encoding salinity tolerance and/or oxidative stress tolerance-modulating polypeptides are set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. The salinity tolerance and/or oxidative stress tolerance-modulating polypeptide encoded by a recombinant nucleic acid can be a native salinity tolerance and/or oxidative stress tolerance-modulating polypeptide, or can be heterologous to the cell. In some cases, the recombinant construct contains a nucleic acid that inhibits expression of a salinity tolerance and/or oxidative stress tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable promoters initiate transcription only, or predominantly, in certain cell types. The choice of regulatory regions to be included in a recombinant construct depends on several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110:1069-1079 (1996).

Examples of various classes of regulatory regions are described below. Some of the regulatory regions indicated below as well as additional regulatory regions are described in more detail in U.S. Patent Application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a salt and/or oxidative stress tolerance modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant having the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous salinity tolerance and/or oxidative stress tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a salinity tolerance and/or oxidative stress tolerance-modulating polypeptide or nucleic acid. Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of salinity tolerance and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a salinity tolerance and/or oxidative stress tolerance level relative to a control plant that lacks the transgene. Selected or screened transgenic plants have an altered phenotype as compared to a corresponding control plant, as described in the "Transgenic Plant Phenotypes" section herein.

A population of transgenic plants can be screened and/or selected for those members of the population that have a trait or phenotype conferred by expression of the transgene. For example, a population of progeny of a single transformation event can be screened for those plants having a desired level of expression of a saline and/or oxidative stress tolerance-modulating polypeptide and/or nucleic acid. Physical and biochemical methods can be used to identify expression levels. These include Southern analysis or PCR amplification for detection of a polynucleotide; Northern blots, RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of saline and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a saline and/or oxidative stress tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica., Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a species (e.g., Saccharum sp. X Miscanthus sp.)

D. Transgenic Plant Phenotypes

In some embodiments, a plant in which expression of a salinity and/or oxidative stress modulating polypeptide is modulated can have increased levels of tolerance to salinity and/or oxidative stress. For example, a salinity and/or oxidative stress-modulating polypeptide described herein can be expressed in a transgenic plant, resulting in increased levels of tolerance to salinity and/or oxidative stress. The salinity and/or oxidative stress tolerance levels can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to those levels in a corresponding control plant that does not express the transgene.

The nucleic acid molecules and polypeptides of the present invention are of interest because when the nucleic acid molecules are mis-expressed (i.e., when expressed at a non-natural location or in an increased or decreased amount relative to wild-type) they produce plants that exhibit improved salt tolerance and/or oxidation tolerance as compared to wild-type plants, as evidenced in part by the results of various experiments disclosed below. In particular, plants transformed with the nucleic acid molecules and polypeptides of the present invention can have any of a number of modified characteristics as compared to wild-type plants. Examples of modified characteristics include photosynthetic efficiency, seedling area, and biomass as it may be measured by plant height, leaf or rosette area, or dry mass. The modified characteristics may be observed and measured at different plant developmental stages, e.g. seed, seedling, bolting, senescense, etc. Often, salt or oxidative tolerance can be expressed as ratios or combinations of measurements, such as salt growth index values, or salicylic acid growth index values. For example, plants transformed with the sequences of the present invention can exhibit increases in SGI, seedling area and/or SAGI values of at least 5%, at least 10%, at least 25%, at least 50%, at least 75%, at least 100%, at least 200%, at least 300%, at least 400%, or even at least 500%. These traits can be used to exploit or maximize plant products. For example, the nucleic acid molecules and polypeptides of the present invention are used to increase the expression of genes that cause the plant to have improved biomass, growth rate and/or seedling vigor in saline and/or oxidative conditions, in comparison to wild type plants under the same conditions.

Because the disclosed sequences and methods increase vegetative growth and growth rate in saline and/or oxidative conditions, the disclosed methods can be used to enhance plant growth in plants grown in saline and/or oxidative conditions. For example, plants of the present invention show, under saline and/or oxidative conditions, increased photosynthetic efficiency and increased seedling area as compared to a plant of the same species that is not genetically modified for substantial vegetative growth. Examples of increases in biomass production include increases of at least 5%, at least 20%, or even at least 50%, when compared to an amount of biomass production by a wild-type plant of the same species under identical conditions.

Typically, a difference in the amount of tolerance to salinity and/or oxidative stress in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of tolerance to salinity and/or oxidative stress is statistically significant at $p<0.01$, $p<0.005$, or $p<0.001$.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, 51 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate salinity tolerance and/or oxidative stress tolerance content is useful in plant breeding, because genetic polymorphisms exhibiting a degree of linkage with loci for such polypeptides are more likely to be correlated with variation in a salinity tolerance and/or oxidative stress tolerance trait. For example, genetic polymorphisms linked to the loci for such polypeptides are more likely to be useful in marker-assisted breeding programs to create lines having a desired modulation in the salinity tolerance and/or oxidative stress tolerance traits.

Thus, one aspect of the invention includes methods of identifying whether one or more genetic polymorphisms are associated with variation in a salinity tolerance and/or oxidative stress tolerance trait. Such methods involve determining whether genetic polymorphisms in a given population exhibit linkage with the locus for one of the polypeptides depicted in FIGS. 1 thru 6 and/or a functional homolog thereof, such as, but not limited to, those in the Sequence Listing. The correlation is measured between variation in the salinity tolerance and/or oxidative stress tolerance traits in plants of the population and the presence of the genetic polymorphism(s) in plants of the population, thereby identifying whether or not the genetic polymorphism(s) are associated with variation for the traits. If the presence of a particular allele is statistically significantly correlated with a desired modulation in the salinity tolerance and/or oxidative stress tolerance traits, the allele is associated with variation for one or both of the traits and is useful as a marker for one or more of the traits. If, on the other hand, the presence of a particular allele is not significantly correlated with the desired modulation, the allele is not associated with variation for one or more of the traits and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "Arabidopsis Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the salinity tolerance and/or oxidative stress tolerance trait(s). Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, other biofuel molecules, and/or sugar-derived co-products per kilogram of plant material, relative to control plants. By providing higher yields at an equivalent or even decreased cost of production relative to controls, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

Enhanced salt and/or oxidative stress tolerance gives the opportunity to grow crops in saline or oxidative stress conditions without stunted growth and diminished yields due to salt-induced ion imbalance, disruption of water homeostasis, inhibition of metabolism, damage to membranes, and/or cell death. The ability to grow plants in saline or oxidative stress conditions would result in an overall expansion of arable land and increased output of land currently marginally productive due to elevated salinity or oxidative stress conditions.

Seed or seedling vigor is an important characteristic that can greatly influence successful growth of a plant, such as crop plants. Adverse environmental conditions, such as saline and/or oxidative conditions, can affect a plant growth cycle, germination of seeds and seedling vigor (i.e. vitality and strength under such conditions can differentiate between successful and failed plant growth). Seedling vigor has often been defined to comprise the seed properties that determine "the potential for rapid, uniform emergence and development of normal seedlings under a wide range of field conditions". Hence, it would be advantageous to develop plant seeds with increased vigor, particularly in elevated salinity and/or in oxidative stress conditions.

For example, increased seedling vigor would be advantageous for cereal plants such as rice, maize, wheat, etc. production. For these crops, germination and growth can often be slowed or stopped by salination and/or oxidation. Genes associated with increased seed vigor under saline and/or oxidative stress conditions have therefore been sought for producing improved plant varieties. (Walia et al. (2005) *Plant Physiology* 139:822-835).

The invention will be further described in the following examples, which do not limit the scope of the invention described in the claims.

VII. EXAMPLES

Example 1: *Agrobacterium*-Mediated Transformation of *Arabidopsis*

Host Plants and Transgenes: Wild-type *Arabidopsis thaliana* Wassilewskija (WS) plants were independently transformed with Ti plasmids containing clones encoding polypeptides at SEQ ID NOs: 43, 44, 45, 86, 136, 138, 140, 141, 142, 143, 144, and amino acid coordinates 1 to 135 of SEQ ID NO: 140. Examples include Ceres CLONE ID no. 1792354, Ceres SEEDLINE ID no. ME06748, Ceres SEEDLINE ID no. ME08768, Ceres SEEDLINE ID no. ME19173, and Ceres CLONE ID no. 375578. Unless otherwise indicated, each Ceres Clone and/or Seedline derived from a Clone is in the sense orientation relative to either the 35S promoter in a Ti plasmid. A Ti plasmid vector useful for these constructs, CRS 338, contains the Ceres-constructed, plant selectable marker gene phosphinothricin acetyltransferase (PAT), which confers herbicide resistance to transformed plants.

Preparation of Soil Mixture: 24L Sunshine Mix #5 soil (Sun Gro Horticulture, Ltd., Bellevue, Wash.) is mixed with 16L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, MO), 3 Tbsp OSMOCOTE® 14-14-14 (Hummert, Earth City, MO) and 1 Tbsp Peters fertilizer 20-20-20 (J. R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µL 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

Example 2: Saline Condition Screening

Saline condition screening: Screening is routinely performed by high-salt agar plate assay and also by high-salt soil assay. Traits assessed in high-salt conditions include: seedling area, photosynthesis efficiency, salt growth index and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under salt stress conditions.

Salt growth index=seedling area×photosynthesis efficiency (Fv/Fm).

Regeneration ability: the ability of a plant to regenerate shoots in saline soil after stems are cut off and the soil is irrigated with 200 mM NaCl solution.

Transformant identification: PCR was used to amplify the cDNA insert in one randomly chosen $T_2$ plant. This PCR product was then sequenced to confirm the sequence in the plants.

Identification of Tolerant Plant to Salt Stress: A superpool of seeds was screened for transgenic plants that show enhanced tolerance to SA, as detailed below, and high salt. Three independent candidate plants were sequenced and the transgene sequence matched ME02064.

Assessing Tolerance to Salt Stress: Generally, between four and ten independently transformed plant lines are selected and qualitatively evaluated for their tolerance to salt stress in the $T_1$ generation. Two or three of the transformed lines that qualitatively show the strongest tolerance to salt stress in the $T_1$ generation are selected for further evaluation in the $T_2$ and $T_3$ generations. This evaluation involves sowing seeds from the selected transformed plant lines on MS agar plates containing either 100 mM or 150 mM NaCl and incubating the seeds for 5 to 14 days to allow for germination and growth. For example, for ME02064 five T2 events were compared to wild-type Ws for salt stress tolerance on salt plates. Three events, ME02064-01, -03 and -04 were selected based on the measurement of seedling area on 36 plants of each event as compared to the control, Ws. Further evaluation of salt tolerance in ME02064-01, -03 and -04 was performed with $T_2$ and $T_3$ generations.

Calculating SGI: After germination and growth, seedling area and photosynthesis efficiency of transformed lines and a wild-type control are determined. From these measurements, the Salt Growth Index (SGI) is calculated and compared between wild-type and transformed seedlings. The SGI calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

Example 3: Oxidative Stress Conditions Screening

Under normal growth conditions, *Arabidopsis* rosette contains about 0.5 µg/g fresh weight of free SA. In response to stress conditions or pathogen attacks, the free SA levels can reach as high as 10 µg/g fresh weight, which is approximately equivalent to 60 µM. The exogenous application of 100-500 µM SA to *Arabidopsis* leaves by spraying is able to induce strong defense responses without triggering obvious necrotic lesion formation. Once the SA concentration increases to 5 mM or above, the cell death in form of necrotic lesions will appear on the sprayed leaves. If SA is applied through growth media, *Arabidopsis* is more sensitive to SA-induced oxidative stress, probably because of continuous absorption. The addition of 100-150 µM SA to growth media significant reduces plant growth but does not kills the plants in wild type *Arabidopsis* Ws. Therefore we use this range of SA to screen for enhanced oxidative stress tolerance.

Salicylic Acid Screening: Screening is routinely performed by agar plate assay using 100 µM or 150 µM exogenous sodium salicylate. Media contains ½×MS (Sigma), 150 µM sodium salicylate (Sigma), 0.5 g MES hydrate (Sigma) and 0.7% phytagar (EM Science), adjusted to pH 5.7 using 10N KOH.

To screen superpools, seeds are surface sterilized in 30% bleach solution for 5 minutes and then rinsed repeatedly with sterile water. Approximately 2500 seeds are sown on media plates in a monolayer at a density of 850 seeds per plate. Wild-type and positive controls are grown on comparable plates. Plates are wrapped with vent tape and placed at 4° C. in the dark for three days to stratify. At the end of this time, plates are transferred to a Conviron growth chamber set at 22° C., 16:8 hour light:dark cycle, 70% humidity with a combination of incandescent and fluorescent lamps emitting a light intensity of ~100 µEinsteins.

Seedlings are screened daily starting at 6 days. Seedlings that grow larger and stay greener compared to WS control plants are selected as positive candidates and transferred to soil for recovery and seed set.

Candidate plants are re-screened by placing 36 seeds from each candidate together with a WS control on the same sodium salicylate plate. Plates are treated as described above and seedling screening begun after at 4 days after germination. Leaf tissue is harvested from confirmed tolerant candidates for DNA extraction and amplification of the transgene by PCR.

Alternatively, superpool seeds are sown directly on soil and sprayed with 10 mM SA. Leaf tissue is harvested from tolerant candidate plants to isolate DNA for PCR amplification of the transgene and subsequent sequencing of the PCR product.

Traits assessed under sodium salicylate conditions include: seedling area, photosynthesis efficiency, salicylic acid growth index (SAG) and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under oxidative stress conditions.

Salicylic Acid Growth (SAG) Index=seedling area $(cm^2)$× photosynthesis efficiency (Fv/Fm).

PCR was used to amplify the cDNA insert in one randomly chosen $T_2$ plant. This PCR product was then sequenced to confirm the sequence in the plants.

Assessing Tolerance to Oxidative Stress: Initially, All available independently transformed T2 plant lines are qualitatively evaluated for their tolerance to oxidative stress as compared to wild-type controls. The positive transgenic lines that qualitatively show the strongest tolerance to oxidative stress are selected for further evaluation in the $T_2$ and $T_3$ generations using internal non-transgenic segregants as controls. This evaluation involves sowing seeds from the selected transformed plant lines on MS agar plates containing 100 µM or 150 µM sodium salicylate and incubating the seeds for at least 4 days to allow for germination and growth and transgene status analysis.

Calculating SAG: After germination and growth, seedling area and photosynthesis efficiency of transformed lines and a wild-type control are determined. From these measurements, the Salicylic Acid Growth Index (SAG) is calculated and compared between wild-type and transformed seedlings. The SAG calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

In some cases, validation is performed using media that is further supplemented with 100 uM SNP.

Example 4: ME02064 (Ceres Clone 375578; SEQ ID No.138)

Wild-type *Arabidopsis thaliana* Wassilewskija was transformed with a Ti plasmid carrying the 35S promoter and Ceres Clone 375578. Three transformed lines, ME02064-01 and ME02064-03, ME02064-04, showed the strongest qualitative tolerance to salt stress in a prevalidation assay (Table 4-1). Their tolerance to 150 mM NaCl was further evaluated in a validation assay for two generations. Segregation ratios (BASTA™ resistant: BASTA™ sensitive) indicated ME02064-01 and ME02064-03, ME02064-04 transformed lines each carry one copy of the transgene.

TABLE 4-1

Prevalidation assay of ME02064 salt tolerance as compared to wild-type Ws

|  | Ws Wild-type | ME02064-01 | ME02064-02 | ME02064-03 | ME02064-04 | ME02064-05 |
|---|---|---|---|---|---|---|
| Mean* | 0.0359 | 0.0435 | 0.0346 | 0.0441 | 0.0438 | 0.0305 |
| Standard Error | 0.0016 | 0.0048 | 0.004 | 0.0041 | 0.0035 | 0.0019 |

*Average seedling area of 36 plants grown on MS agar plates containing 150 mM NaCl for 14 days When grown on MS agar plates containing 150 mM NaCl, ME02064-01 and ME02064-03, ME02064-04 transgenic plants showed significantly greater seedling area and SGI relative to non-transgenic plants. As shown in Table 4-2, the T2-generation SGI value for ME02064-01 seedlings increased by 110% while ME02064-03 seedlings increased by 131% and ME02064-04 seedlings increased by 72% compared to non-transgenic control seedlings. In the $T_3$ generation, the SGI increase was 43% for ME02064-01, 47% for ME02064-03, and 64% for ME02064-04. The differences between transgenic and non-transgenic seedlings are statistically significant, and clearly demonstrate that the enhanced tolerance to salt stress was a result of the ectopic expression of Ceres Clone 375578 in the ME02064 transformant lines.

TABLE 4-2

Validation assay of ME02064 on salt tolerance in two generations

| ME Events | SGI* of transgenics | | | SGI of pooled non-transgenics | | | t-Test | | % of SGI increase |
|---|---|---|---|---|---|---|---|---|---|
|  | Avg | SE | N | Avg | SE | N | t-value | $t_{0.05}$ |  |
| ME02064-01-$T_2$ | 2.057 | 0.249 | 12 | 0.977 | 0.205 | 17 | 3.35 | 1.70 | 110.5 |
| ME02064-03-$T_2$ | 2.237 | 0.371 | 5 | 0.968 | 0.140 | 24 | 3.20 | 1.70 | 131.1 |
| ME02064-04-$T_2$ | 1.810 | 0.146 | 14 | 1.055 | 0.135 | 13 | 3.81 | 1.70 | 71.6 |
| ME02064-01-$T_3$ | 2.438 | 0.170 | 21 | 1.708 | 0.289 | 9 | 2.18 | 1.70 | 42.7 |
| ME02064-03-$T_3$ | 2.837 | 0.257 | 20 | 1.927 | 0.271 | 14 | 2.43 | 1.70 | 47.2 |
| ME02064-04-$T_3$ | 2.770 | 0.318 | 16 | 1.688 | 0.188 | 19 | 2.93 | 1.70 | 64.1 |

*SGI (Salt Growth Index) = seedling area x Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Example 5: ME03140; Clone 375578; SEQ ID No.142

Wild-type *Arabidopsis thaliana* Wassilewskija was transformed with a Ti plasmid carrying the 35S promoter operatively linked to Ceres Clone 375578 (SEQ ID NO: 142), and five transgenic lines, ME03140-01, ME03140-02, ME03140-03, ME03140-04 and ME03140-05 were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME03140-01, ME03140-02, ME03140-03, ME03140-04 and ME03140-05 transgenic plants showed significantly greater seedling area and SGI relative to non-transgenic plants. As shown in Table 5, the T2-generation SGI value for ME03140-01 seedlings increased 102.18%, ME03140-02 seedlings increased 60.78%, ME03140-03 seedlings increased 120.32%, ME03140-04 seedlings increased 45.07% and ME03140-05 seedlings increased 90.53% as compared to non-transgenic control seedlings. The differences in SGI values between transgenic and non-transgenic seedlings have statistically significant P values for all transgenic lines, and these quantitative experiments clearly demonstrate that ectopic expression of Ceres Clone 375578 confers enhanced tolerance to salt stress in transgenic seedlings.

TABLE 5

Validation assay of ME03140 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME03140-01-$T_2$ | 4.34 | 0.590403017 | 17 | 2.15 | 0.478695 | 26 | 3.10E−03 | 102.18% |
| ME03140-02-$T_2$ | 4.09 | 0.395692005 | 18 | 2.54 | 0.367281 | 28 | 3.22E−03 | 60.78% |
| ME03140-03-$T_2$ | 4.03 | 0.646365854 | 12 | 1.83 | 0.397508 | 36 | 2.86E−03 | 120.32% |
| ME03140-04-$T_2$ | 4.86 | 0.534320049 | 17 | 3.35 | 0.446161 | 36 | 1.74E−02 | 45.07% |
| ME03140-05-$T_2$ | 4.31 | 0.5237326 | 25 | 2.26 | 0.665646 | 20 | 9.91E−03 | 90.53% |

*SGI (Salt Growth Index) = seedling area × Fv/Fm (photosynthesis efficiency)

Summary of Results:

Ectopic expression of Ceres Clone 375578 under the control of the 35S promoter enhances tolerance to salt stress that causes necrotic lesions and stunted growth in wild-type Ws seedlings.

Example 6: ME08732; Clone 560066; SEQ ID No. 44

Wild-type *Arabidopsis thaliana* Wassilewskija was transformed with a Ti plasmid carrying the 35S promoter operatively linked to Ceres Clone 560066 (SEQ ID NO: 44), and three transgenic lines, ME08732-01, ME08732-02 and ME08732-03, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08732-01, ME08732-02 and ME08732-03 transgenic plants showed significantly greater seedling area and SGI relative to non-transgenic plants. As shown in Table 6, the T2-generation SGI value for ME08732-01 seedlings increased 88.35%, ME08732-02 seedlings increased 41.72% and ME08732-03 seedlings increased 26.23%, as compared to non-transgenic control seedlings. The differences in SGI values between transgenic and non-transgenic seedlings have statistically significant P values for ME08732-01 and ME08732-02 transgenic lines, and these quantitative experiments clearly demonstrate that ectopic expression of Ceres Clone 560066 confers enhanced tolerance to salt stress in transgenic seedlings.

Summary of Results:

Ectopic expression of Ceres Clone 560066 under the control of the 35S promoter enhances tolerance to salt stress that causes necrotic lesions and stunted growth in wild-type Ws seedlings.

Example 7: ME08768; Clone 539458; SEQ ID No.86

Wild-type *Arabidopsis thaliana* Wassilewskija was transformed with a Ti plasmid carrying the 35S promoter operatively linked to Ceres Clone 539458 (SEQ ID NO: 86), and five transgenic lines, ME08768-01, ME08768-02, ME08768-03, ME08768-04 and ME08768-05, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08768-01, ME08768-02, ME08768-03, ME08768-04 and ME08768-05 transgenic plants showed significantly greater seedling area and SGI relative to non-transgenic plants. As shown in Table 7, the T2-generation SGI value for ME08768-01 seedlings increased 80.04%, ME008768-02 seedlings increased 111.63%, ME008768-03 seedlings increased 22.62%, ME008768-04 seedlings increased 115.40% and ME008768-05 seedlings increased 74.41% as compared to non-transgenic control seedlings. The differences in SGI values between transgenic and non-transgenic seedlings have statistically significant P values for ME08768-01, ME08768-02, ME08768-04 and ME08768-05 transgenic lines, and these quantitative experiments clearly demonstrate that ectopic expression of Ceres Clone 539458 confers enhanced tolerance to salt stress in transgenic seedlings.

TABLE 6

Validation assay of ME08732 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08732-01-$T_2$ | 4.07 | 0.164301729 | 24 | 2.16 | 0.472565 | 14 | 2.57E−04 | 88.35% |
| ME08732-02-$T_2$ | 3.42 | 0.391450599 | 21 | 2.41 | 0.336042 | 26 | 2.86E−02 | 41.72% |
| ME08732-03-$T_2$ | 4.71 | 0.566761111 | 10 | 3.73 | 0.285925 | 52 | 6.44E−02 | 26.23% |

*SGI (Salt Growth Index) = seedling area × Fv/Fm (photosynthesis efficiency)

TABLE 7

Validation assay of ME08768 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08768-01-$T_2$ | 14.48 | 1.254125111 | 20 | 8.04 | 1.321838 | 26 | 4.91E−04 | 80.04% |
| ME08768-02-$T_2$ | 11.09 | 0.822117225 | 20 | 5.24 | 0.751908 | 32 | 1.55E−06 | 111.63% |
| ME08768-03-$T_2$ | 13.72 | 1.676864172 | 21 | 11.19 | 1.57188 | 30 | 0.1380406 | 22.62% |
| ME08768-04-$T_2$ | 14.82 | 1.3958585 | 16 | 6.88 | 0.777162 | 40 | 3.58E−06 | 115.40% |
| ME08768-05-$T_2$ | 10.02 | 1.365308 | 13 | 5.75 | 0.751134 | 38 | 4.23E−03 | 74.41% |

*SGI (Salt Growth Index) = seedling area × Fv/Fm (photosynthesis efficiency)

Summary of Results:
Ectopic expression of Ceres Clone 539458 under the control of the 35S promoter enhances tolerance to salt stress that causes necrotic lesions and stunted growth in wild-type Ws seedlings.

Example 8: ME10681; Clone 335348 SEQ ID No.141

Wild-type *Arabidopsis thaliana* Wassilewskija was transformed with a Ti plasmid carrying the 35S promoter operatively linked to Ceres Clone 335348 (SEQ ID NO: 141), and six transgenic lines, ME10681-01-$T_2$, ME10681-01-T3, ME10681-02-$T_2$, ME10681-02-T3, ME10681-04-$T_2$ and ME10681-05-$T_2$, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME10681-01-$T_2$, ME10681-01-$T_3$, ME10681-02-$T_2$, ME10681-02-$T_3$, ME10681-04-$T_2$ and ME10681-05-$T_2$ transgenic plants showed significantly greater seedling area and SGI relative to non-transgenic plants. As shown in Table 8, the T2-generation SGI value for ME010681-01-$T_2$ seedlings increased 39.17%, ME010681-01-$T_3$ seedlings increased 19.77%%, ME10681-02-$T_2$ seedlings increased 119.17%, ME10681-02-$T_3$ seedlings increased 6.21%, ME010681-04-$T_2$ seedlings increased 113.51% and ME010681-05-$T_2$ seedlings increased 103.98%, as compared to non-transgenic control seedlings. The differences in SGI values between transgenic and non-transgenic seedlings have statistically significant P values for ME10681-01-$T_3$, ME10681-02-$T_2$, ME10681-04-$T_2$ and ME10681-05-$T_2$ transgenic lines, and these quantitative experiments clearly demonstrate that ectopic expression of Ceres Clone 335348 confers enhanced tolerance to salt stress in transgenic seedlings.

TABLE 8

Validation assay of ME10681 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME10681-01-$T_2$ | 3.87 | 0.683711333 | 9 | 2.78 | 0.302501 | 48 | 7.54E−02 | 39.17% |
| ME10681-01-$T_3$ | 4.7 | 0.31544415 | 23 | 3.93 | 0.3015141 | 43 | 3.99E−02 | 19.77% |
| ME10681-02-$T_2$ | 4.13 | 0.3353564 | 25 | 1.89 | 0.3969 | 22 | 4.16E−05 | 119.17% |
| ME10681-02-$T_3$ | 3.65 | 0.258400663 | 31 | 3.44 | 0.3060094 | 34 | 0.2980488 | 6.21% |
| ME10681-04-$T_2$ | 6.22 | 0.478672159 | 12 | 2.91 | 0.39405 | 30 | 2.04E−06 | 113.51% |
| ME10681-05-$T_2$ | 5.25 | 0.391550037 | 20 | 2.57 | 0.4265902 | 30 | 1.44E−05 | 103.98% |

*SGI (Salt Growth Index) = seedling area × Fv/Fm (photosynthesis efficiency)

Summary of Results:
Ectopic expression of Ceres Clone 335348 under the control of the 35S promoter enhances tolerance to salt stress that causes necrotic lesions and stunted growth in wild-type Ws seedlings.

Example 9: ME18973; Ceres cDNA ID 23457556; SEQ ID No.43

Wild-type *Arabidopsis thaliana* Wassilewskija was transformed with a Ti plasmid carrying the 35S promoter operatively linked to Ceres cDNA ID 23457556 (SEQ ID NO: 43), and six transgenic lines, ME18973-01-$T_2$, ME18973-02-$T_2$, ME18973-02-01-$T_3$, ME18973-03-$T_2$, ME18973-05-$T_2$ and ME18973-05-03-$T_3$ were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME18973-01, ME18973-02-$T_2$, ME18973-02-01-$T_3$, ME18973-03-$T_2$, ME18973-05-$T_2$ and ME18973-05-03-$T_3$ transgenic plants showed significantly greater seedling area and SGI relative to non-transgenic plants. As shown in Table 9, the T2 & T3-generation SGI value for ME018973-01-$T_2$ seedlings increased 230.01%, ME18973-02-$T_2$ seedlings increased 22.44%, ME18973-02-01-$T_3$ seedlings increased 14.96%, ME18973-05-$T_2$ seedlings increased 16.12% and ME18973-05-03-$T_3$ seedlings increased 13.97%, as compared to non-transgenic control seedlings. The differences in SGI values between transgenic and non-transgenic seedlings have statistically significant P values for the ME18973 transgenic lines, and these quantitative experiments clearly demonstrate that ectopic expression of Ceres cDNA ID 23457556 results in enhanced tolerance to salt stress in transgenic seedlings.

tively linked to Ceres cDNA ID 23621377 (SEQ ID NO: 45), and two transgenic lines, ME19657-01-$T_2$, ME19657-01-05-$T_3$, ME19657-01-08-$T_3$, ME19657-02-$T_2$, ME19657-03-$T_2$, ME19657-04-$T_2$ and ME19657-04-01-$T_3$, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME19657-01-$T_2$, ME19657-01-05-$T_3$, ME19657-01-08-$T_3$, ME19657-02-$T_2$, ME19657-03-$T_2$, ME19657-04-$T_2$ and ME19657-04-01-$T_3$ transgenic plants showed significantly greater seedling area and SGI relative to non-transgenic plants. As shown in Table 10, the T2 & T3-generation SGI value for ME19657-01-$T_2$ seedlings increased 82.29%, ME19657-01-05-$T_3$ seedlings increased 82.29%, ME19657-01-08-$T_3$ seedlings increased 21.90%, ME19657-02-$T_2$ seedlings increased 39.50%, ME19657-03-$T_2$ seedlings increased 98.28%, and ME19657-04-$T_2$ seedlings increased

TABLE 9

Validation assay of ME18973 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME18973-01-$T_2$ | 4.41 | 0.253654648 | 26 | 1.34 | 0.367022 | 18 | 1.03E−08 | 230.01% |
| ME18973-02-$T_2$ | 4.47 | 0.373604899 | 27 | 3.65 | 0.526316 | 18 | 0.1058348 | 22.44% |
| ME18973-02-01-$T_3$ | 4.82 | 0.205971746 | 44 | 4.19 | 0.3832982 | 25 | 7.71E−02 | 14.96% |
| ME18973-05-$T_2$ | 4.74 | 0 | 1 | 4.09 | 0.503725 | 26 | 0.160517 | 16.12% |
| ME18973-05-03-$T_3$ | 4.38 | 0.233610226 | 32 | 3.84 | 0.503725 | 37 | 6.89E−02 | 13.97% |

*SGI (Salt Growth Index) = seedling area × Fv/Fm (photosynthesis efficiency)

Summary of Results:
Ectopic expression of Ceres cDNA ID 23457556 under the control of the 35S promoter enhances tolerance to salt stress that causes necrotic lesions and stunted growth in wild-type Ws seedlings.

Example 10: ME19657; cDNA ID 23621377; SEQ ID No.45

Wild-type *Arabidopsis thaliana* Wassilewskija was transformed with a Ti plasmid carrying the 35S promoter opera- 4.38% and ME19657-04-01-$T_2$ seedlings increased 7.44%, as compared to non-transgenic control seedlings. The differences in SGI values between transgenic and non-transgenic seedlings have statistically significant P values for ME19657-01-$T_2$, ME19657-01-05-$T_3$, ME19657-01-08-$T_3$, ME19657-02-$T_2$ and ME19657-03-$T_2$ transgenic lines, and these quantitative experiments clearly demonstrate that ectopic expression of Ceres cDNA ID 23621377 results in enhanced tolerance to salt stress in transgenic seedlings.

TABLE 10

Validation assay of ME19657 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME19657-01-$T_2$ | 4.54 | 0.311964078 | 21 | 2.49 | 0.539972 | 15 | 5.62E−05 | 82.29% |
| ME19657-01-05-$T_3$ | 0.7 | 0.311964078 | 21 | 0.7 | 0.5399721 | 15 | 1.18E−03 | 82.29% |
| ME19657-01-08-$T_3$ | 5.4 | 0.278520121 | 27 | 4.43 | 0.3061552 | 36 | 1.18E−03 | 21.90% |
| ME19657-02-$T_2$ | 3.97 | 0.32089576 | 23 | 2.84 | 0.527849 | 18 | 0.0111868 | 39.50% |

TABLE 10-continued

Validation assay of ME19657 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME19657-03-T$_2$ | 4.79 | 0.313786256 | 22 | 2.41 | 0.299954 | 22 | 3.83E−02 | 98.28% |
| ME19657-04-T$_2$ | 3.67 | 0.341681304 | 15 | 3.52 | 0.324049 | 40 | 1.15E−06 | 4.38% |
| ME19657-04-01-T$_3$ | 4.56 | 0.495154 | 9 | 4.25 | 0.3487774 | 37 | 0.3723989 | 7.44% |

*SGI (Salt Growth Index) = seedling area × Fv/Fm (photosynthesis efficiency)

Summary of Results:

Ectopic expression of Ceres cDNA ID 23621377 under the control of the 35S promoter enhances tolerance to salt stress that causes necrotic lesions and stunted growth in wild-type Ws seedlings.

Example 11: ME24076; Clone 229668; SEQ ID No. 143

Wild-type *Arabidopsis thaliana* Wassilewskija was transformed with a Ti plasmid carrying the 35S promoter operatively linked to Ceres Clone: 229668 (SEQ ID NO: 143), and two transgenic lines, ME24076-01 and ME24076-02, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, only ME024076-01-T$_2$ and transgenic plants showed significantly greater seedling area and SGI relative to non-transgenic plants. As shown in Table 11, the T2-generation SGI value for ME24076-01-T$_2$ seedlings increased 65.57% and ME24076-02-T$_2$ seedlings decreased by 1.12%, as compared to non-transgenic control seedlings. The differences in SGI values between transgenic and non-transgenic seedlings have statistically significant P values for transgenic line ME24076-01, and these quantitative experiments clearly demonstrate that ectopic expression of Ceres Clone 229668 results in enhanced tolerance to salt stress in transgenic seedlings.

Summary of Results:

Ectopic expression of Ceres Clone 229668 under the control of the 35S promoter enhances tolerance to salt stress that causes necrotic lesions and stunted growth in wild-type Ws seedlings.

Example 12: ME24217; Clone 375578; SEQ ID No. 144

Wild-type *Arabidopsis thaliana* Wassilewskija was transformed with a Ti plasmid carrying the 35S promoter operatively linked to Ceres Clone 375578 (SEQ ID NO: 144), and two transgenic lines, ME24217-07-T$_2$ and ME24217-09-T$_2$, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME24217-07-T$_2$ and ME24217-09-T$_2$ transgenic plants showed significantly greater seedling area and SGI relative to non-transgenic plants. As shown in Table 12, the T2-generation SGI value for ME24217-07 seedlings increased 30.41% and ME24217-09 seedlings increased 134.46%, as compared to non-transgenic control seedlings. The differences in SGI values between transgenic and non-transgenic seedlings have statistically significant P values for ME24217-07-T$_2$ and ME24217-09-T$_2$ transgenic lines, and these quantitative experiments clearly demonstrate that ectopic expression of Ceres Clone 375578 results in enhanced tolerance to salt stress in transgenic seedlings.

TABLE 11

Validation assay of ME24076 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME24076-01-T$_2$ | 11.18 | 0.924279499 | 17 | 6.75 | 0.9761984 | 32 | 9.45E−04 | 65.57% |
| ME24076-02-T$_2$ | 0.7 | 0.082529059 | 10 | 0.7 | 0.0506174 | 48 | 0.4675565 | −1.12% |

*SGI (Salt Growth Index) = seedling area × Fv/Fm (photosynthesis efficiency)

TABLE 12

Validation assay of ME24217 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME24217-07-T$_2$ | 4.69 | 0.413823734 | 20 | 3.6 | 0.4284669 | 30 | 3.62E−02 | 30.41% |
| ME24217-09-T$_2$ | 4.92 | 0.446345081 | 22 | 2.1 | 0.506974 | 22 | 7.20E−05 | 134.46% |

*SGI (Salt Growth Index) = seedling area × Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Example 13: ME02064C; Clone 375578C; SEQ ID No. 140

Wild-type *Arabidopsis thaliana* Wassilewskija was transformed with a Ti plasmid carrying the 35S promoter operatively linked to Ceres Clone 375578 (SEQ ID NO: 140), and six transgenic lines, ME02064C-01-T$_2$, ME02064C-02-T$_2$, ME02064C-03-T$_2$, ME02064C-04-T$_2$, ME02064C-05-T$_2$ and ME02064C-06-T$_2$ were investigated for tolerance to salt stress. When grown on MS agar plates containing 150 mM NaCl, most of these transgenic lines did not show tolerance to salt stress in quantitative assays as compared to non-transgenic control seedlings.

Table 13 shows that, when grown on MS agar plates containing 100 mM NaCl, the T2-generation SGI value for: ME02064C-01-T$_2$ seedlings as compared to non-transgenic control seedlings was 0.55%; ME02064C-02-T$_2$ seedlings as compared to non-transgenic control seedlings was 1.31%; ME02064C-03-T$_2$ seedlings as compared to non-transgenic control seedlings was 9.67%; ME02064C-04-T$_2$ seedlings as compared to non-transgenic control seedlings was −7.78%; ME02064C-05-T$_2$ seedlings as compared to non-transgenic control seedlings was −15.77%; and ME02064C-06-T$_2$ seedlings as compared to non-transgenic control seedlings 17.78%.

Example 14: ME02064P1; Clone 375578P1—Amino Acids 1 to 135 of SEQ ID No. 140

Wild-type *Arabidopsis thaliana* Wassilewskija was transformed with a Ti plasmid carrying the 35S promoter operatively linked to a nucleic acid encoding Ceres Clone 375578P1 (amino acids 1 to 135 of SEQ ID NO: 140), a 3' truncation variant of Ceres Clone 375578 described above in Example 1. Five transgenic lines, ME02064P1-03-T$_2$, ME02064P1-07-T$_2$, ME02064P1-09-T$_2$, ME02064P1-10-T$_2$ and ME02064P1-15-T$_2$ were investigated for tolerance to salt stress. All five of these transgenic lines showed tolerance to salt stress in quantitative assays as compared to non-transgenic control seedlings. As shown in Table 10, the T2-generation SGI value for ME02064P1 seedlings increased by 32.57%, 89.52%, 66.84%, 25.43%, 36.95%. compared to non-transgenic control seedlings.

When grown on MS agar plates containing 150 mM NaCl, ME02064P1-03, ME02064P1-07, ME02064P1-09, ME02064P1-10 and ME02064P1-15 transgenic plants showed significantly greater seedling area and SGI relative to non-transgenic plants. As shown in Table 14, the T2-generation SGI value for ME02064P1-03 seedlings increased 32.57%, ME02064P1-07 seedlings increased 89.52%, ME02064P1-09 seedlings increased 66.84%, ME02064P1-10 seedlings increased 25.43% and ME02064P1-15 seedlings increased 36.95% as compared to non-transgenic con-

TABLE 13

Validation assay of ME02064C salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064C-01-T$_2$ | 10.89 | 0.735174679 | 33 | 10.83 | 0.707901 | 34 | 0.4769106 | 0.55% |
| ME02064C-02-T$_2$ | 10.7 | 0.595225094 | 50 | 10.56 | 0.971548 | 21 | 0.4517289 | 1.31% |
| ME02064C-03-T$_2$ | 9.39 | 0.582009053 | 48 | 8.56 | 0.958475 | 23 | 0.2314441 | 9.67% |
| ME02064C-04-T$_2$ | 10.66 | 0.555387069 | 51 | 11.56 | 1.046386 | 21 | 0.2252269 | −7.78% |
| ME02064C-05-T$_2$ | 10.84 | 0.60377588 | 48 | 12.87 | 0.839921 | 24 | 2.68E−02 | −15.77% |
| ME02064C-06-T$_2$ | 12.55 | 0.608556025 | 44 | 10.65 | 0.764179 | 28 | 2.83E−02 | 17.78% |

*SGI (Salt Growth Index) = seedling area × Fv/Fm (photosynthesis efficiency)

Summary of results:
Ectopic expression of Ceres Clone 375578 under the control of the 35S might not promote enhances tolertrol seedlings. The differences in SGI values between transgenic and non-transgenic seedlings have statistically significant under P values for transgenic lines ME02064P1-

03-$T_2$, ME02064P1-07-$T_2$, ME02064P1-09-$T_2$, ME02064P1-10-$T_2$ and ME02064P1-15-$T_2$, and these quantitative experiments clearly demonstrate that ectopic expression of Ceres Clone 375587P1 results in enhanced tolerance to salt stress in transgenic seedlings.

TABLE 14

Validation assay of ME02064P1 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P1-03-$T_2$ | 10.76 | 0.507929031 | 47 | 8.12 | 0.925474 | 25 | 7.29E−03 | 32.57% |
| ME02064P1-07-$T_2$ | 13.26 | 0.561088966 | 54 | 7 | 1.165372 | 16 | 3.87E−06 | 89.52% |
| ME02064P1-09-$T_2$ | 12.23 | 0.654850534 | 54 | 7.33 | 1.141553 | 17 | 1.99E−04 | 66.84% |
| ME02064P1-10-$T_2$ | 15.63 | 0.570291003 | 40 | 12.46 | 0.845552 | 32 | 1.36E−03 | 25.43% |
| ME02064P1-15-$T_2$ | 11.84 | 0.607966 | 42 | 8.64 | 0.959856 | 30 | 3.20E−03 | 36.95% |

*SGI (Salt Growth Index) = seedling area × Fv/Fm (photosynthesis efficiency)

Summary of Results:
Ectopic expression of Clone 375587P1 under the control of the 35S promoter enhances tolerance to salt stress.

Example 15: ME02064P2; Clone 375578P2—Amino Acids 188 to 498 of SEQ ID No.140

Wild-type *Arabidopsis thaliana* Wassilewskija was transformed with a Ti plasmid carrying the 35S promoter and a nucleic acid encoding Ceres Clone 375578P2 (amino acids 188 to 498 of SEQ ID NO: 140), a 5' truncation variant of Ceres Clone 375578 described above in Example 1. Eight ME02064P2 transgenic lines were investigated for tolerance to salt. Four transgenic lines, ME02064P2-01-$T_2$, ME02064CP2-04-$T_2$, ME02064P2-05-$T_2$, ME02064P2-06-$T_2$ ME02064P2-07-$T_2$, ME02064P2-$T_2$-08 and ME02064P2-09-$T_2$ did show statistically significant salt tolerance in quantitative assays as compared to non-transgenic control seedlings; and one transgenic lines, ME02064P2-10-$T_2$, showed statistically significant reduction in salt tolerance as compared to non-transgenic control seedlings.

Table 15 shows that, when grown on MS agar plates containing 100 mM NaCl, the T2-generation SGI value for: ME02064P2-01-$T_2$ seedlings as compared to non-transgenic control seedlings was 1.62%, ME02064P2-04-$T_2$ seedlings as compared to non-transgenic control seedlings was 20.31%, ME02064P2-05-$T_2$ seedlings as compared to non-transgenic control seedlings was 31.24%, ME02064P2-06-$T_2$ seedlings as compared to non-transgenic control seedlings was 41.14%, ME02064P2-07-$T_2$ seedlings as compared to non-transgenic control seedlings was 15.91%, ME02064P2-08-$T_2$ seedlings as compared to non-transgenic control seedlings was 40.82%, ME02064P2-09-$T_2$ seedlings as compared to non-transgenic control seedlings was 135.79%, and ME02064P2-10-$T_2$ was −12.36% as compared to non-transgenic control seedlings.

When grown on MS agar plates containing 100 mM NaCl, ME02064P2-01-$T_2$, ME02064P2-04-$T_2$, ME02064P2-05-$T_2$, ME02064P2-06-$T_2$, ME02064P2-07-$T_2$, ME02064P2-08-$T_2$ and ME02064P2-09-$T_2$ transgenic plants showed significantly greater seedling area and SGI relative to non-transgenic plants. However as shown in Table 3, the T2-generation SGI value for ME02064P2-10-$T_2$ seedlings showed a decrease in SGI compared to non-transgenic control seedlings.

TABLE 15

Validation assay of ME02064P2 on salt tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P2-01-$T_2$ | 9.84 | 0.687493743 | 53 | 9.68 | 1.261045 | 19 | 0.4567634 | 1.62% |
| ME02064P2-04-$T_2$ | 5.2 | 0.558723451 | 47 | 4.32 | 0.560634 | 25 | 0.1357713 | 20.31% |
| ME02064P2-05-$T_2$ | 8.42 | 0.714218299 | 45 | 6.41 | 0.623421 | 27 | 0.0190578 | 31.24% |
| ME02064P2-06-$T_2$ | 8.56 | 0.515029349 | 48 | 6.07 | 0.654098 | 24 | 1.88E−03 | 41.14% |
| ME02064P2-07-$T_2$ | 12.3 | 0.647077232 | 47 | 10.61 | 0.8768 | 25 | 6.29E−02 | 15.91% |
| ME02064P2-08-$T_2$ | 9.16 | 0.724681422 | 37 | 6.51 | 0.73405 | 35 | 6.08E−03 | 40.82% |

TABLE 15-continued

Validation assay of ME02064P2 on salt tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P2-09-T$_2$ | 5.72 | 0.489863069 | 47 | 2.43 | 0.182583 | 24 | 1.19E−08 | 135.79% |
| ME02064P2-10-T$_2$ | 9.32 | 0.908174851 | 21 | 10.63 | 0.70877 | 51 | 0.1289273 | 12.36% |

*SGI (Salt Growth Index) = seedling area × Fv/Fm (photosynthesis efficiency)

Summary of Results:

Ectopic expression of Clone 375587P2 under the control of the 35S promoter enhances tolerance to salt stress. Ceres Clone 375578P2 retains the α-β domains of Ceres Clone 375578 located within amino acid residues 137-157 of SEQ ID NO: 140) but does not retain the 6-r domains of Ceres Clone 375578 of SEQ ID NO: 140.

Example 16: ME10681; Clone 335348 SEQ ID No. 141

Wild-type *Arabidopsis thaliana* Wassilewskija was transformed with a Ti plasmid carrying the 35S promoter operatively linked to Ceres cDNA 335348 (SEQ ID NO: 141). Wildtype Ws seedlings showed necrotic lesions and stunted growth on plates containing 100 or 150 μM SA, whereas the transgenic plants showed significantly better growth.

Three transformed lines, ME10681-01, ME10681-02 and ME10681-05, were quantitatively studied by growth on MS agar plates containing 100 μM SA. After 14 days, plates were scanned using an EPSON color scanner or fluorescence scanner and SAGI calculated for each plant. The data is summarized in Table 16.

When grown on MS agar plates containing 100 μM SA, ME10681-02-T$_2$ and ME10681-05-T$_2$ transgenic plants showed significantly increased seedling area and SAGI relative to non-transgenic plants. However ME10681-01-T$_2$ showed a slight decrease in SAGI relative to non-transgenic plants. As shown in Table 12, the T$_2$ generation SAGI value for ME10681-01-T$_2$, ME10681-02-T$_2$ and ME10681-05-T$_2$ seedlings was −3.29%, 17.65% and 51.84%, respectively. The differences between transgenic and non-transgenic seedlings have statistically significant P values for lines ME10681-02-T$_2$ and ME10681-05-T$_2$, and clearly demonstrate enhanced tolerance to oxidative stress is a result of the ectopic expression of Ceres cDNA 36505846 in the ME10681 transformant lines.

Summary of Results:

In sum, ectopic expression of Ceres Clone 335348 under the control of the 35S promoter enhances oxidative stress tolerance that causes necrotic lesions and stunted growth in wild-type WS seedlings.

Example 17: ME24091; Clone 106263; SEQ ID No. 136

Wild-type *Arabidopsis thaliana* Wassilewskija was transformed with a Ti plasmid carrying the 35S promoter operatively linked to Ceres cDNA 016263 (SEQ ID NO: 135). Wildtype Ws seedlings showed necrotic lesions and stunted growth on plates containing 100 or 150 μM SA, whereas the transgenic plants showed significantly better growth.

Ten transformed lines, ME24091-01-T$_2$, ME24091-02-T$_2$, ME24091-03-T$_2$, ME24091-04-T$_2$ ME24091-05-T$_2$, ME24091-06-T$_2$ ME24091-07-T$_2$, ME24091-08-T$_2$, ME24091-09-T$_2$ and ME24091-10-T$_2$, were quantitatively studied by growth on MS agar plates containing 100 μM SA. After 14 days, plates were scanned using an EPSON color scanner or fluorescence scanner and SAGI calculated for each plant.

When grown on MS agar plates containing 100 μM SA, ME24091-01-T$_2$, ME24091-02-T$_2$, ME24091-03-T$_2$, ME24091-04-01-T$_3$, ME24091-04-T$_2$, ME24091-05-01-T$_3$, ME24091-05-T$_2$, ME24091-06-01, ME24091-06, ME24091-07-01, ME24091-07, ME24091-08-01, ME24091-08, ME24091-09-01, ME24091-09, ME24091-10-01 and ME24091-10 transgenic plants showed significantly increased seedling area and SAGI relative to non-transgenic plants. As shown in Table 17, the T$_2$ generation SAGI value for ME24091-01, ME24091-02, ME24091-03, ME24091-04 ME24091-05, ME24091-06 ME24091-07, ME24091-08, ME24091-09 and ME24091-10 seedlings increased by 119.47%, 198.00% and 133.67%, 241.50%, 143.70% and 248.12%, 186.59%, 188.86%, 285.42% and 180.46% respectively. The differences between transgenic and non-transgenic seedlings have statistically significant P

TABLE 16

Salicylic acid validation assay of ME10681 in one generation

| ME Events | Seedling area of transgenics | | | Seedling area of pooled non-transgenics | | | P value | % Seedling area increase |
|---|---|---|---|---|---|---|---|---|
| | Avg | SE | N | Avg | SE | N | | |
| ME10681-01-T$_2$ | 0.56 | 0.096445 | 18 | 0.58 | 0.061856 | 53 | 0.434159 | −3.29% |
| ME10681-02-T$_2$ | 0.67 | 0.06042 | 38 | 0.38 | 0.079644 | 32 | 0.002198 | 17.65% |
| ME10681-05-T$_2$ | 0.68 | 0.072271 | 43 | 0.45 | 0.108539 | 25 | 0.039761 | 51.84% | values for transgenic lines ME24091-01, ME24091-02, ME24091-03, ME24091-04-01, ME24091-04 ME24091-05-01, ME24091-05, ME24091-06-01, ME24091-06, ME24091-07-01, ME24091-07, ME24091-08, ME24091-09-01, ME24091-09, and ME24091-10, and clearly demonstrate that the enhanced tolerance to oxidative stress is a result of the ectopic expression of Ceres Clone 106263 in the ME24091 transformant lines.

TABLE 17

Salicylic acid validation assay of ME24091 in two generations

| ME Events | Seedling area of transgenics | | | Seedling area of pooled non-transgenics | | | P value | % Seedling area increase |
|---|---|---|---|---|---|---|---|---|
| | Avg | SE | N | Avg | SE | N | | |
| ME24091-01-$T_2$ | 0.69 | 0.055882059 | 29 | 0.58 | 0.070002209 | 38 | 0.105475324 | 19.47% |
| ME24091-02-$T_2$ | 0.44 | 0.050576014 | 41 | 0.22 | 0.054717602 | 27 | 0.002577564 | 98.00% |
| ME24091-03-$T_2$ | 0.58 | 0.054269056 | 43 | 0.44 | 0.085715224 | 26 | 0.076183067 | 33.67% |
| ME24091-04-T2 | 0.54 | 0.050859903 | 45 | 0.22 | 0.077668008 | 19 | 0.000634704 | 141.50% |
| ME24091-04-01-$T_3$ | 0.39 | 0.07715765 | 20 | 0.24 | 0.07271465 | 20 | 0.081950663 | 61.93% |
| ME24091-05-$T_2$ | 0.55 | 0.048581793 | 42 | 0.38 | 0.072915009 | 27 | 0.029849118 | 43.70% |
| ME24091-05-01-$T_3$ | 0.38 | 0.068463201 | 21 | 0.15 | 0.05109963 | 30 | 0.005958129 | 144.90% |
| ME24091-06-$T_2$ | 0.71 | 0.049360913 | 39 | 0.29 | 0.063969074 | 23 | 1.13831E−06 | 148.12% |
| ME24091-06-01-$T_2$ | 0.49 | 0.073404661 | 19 | 0.22 | 0.063271768 | 22 | 0.004691952 | 118.19% |
| ME24091-07-$T_2$ | 0.69 | 0.054095931 | 37 | 0.37 | 0.07390372 | 25 | 0.000414138 | 86.59% |
| ME24091-07-01-$T_3$ | 0.49 | 0.052850446 | 33 | 0.19 | 0.049649799 | 22 | 5.3153E−05 | 162.61% |
| ME24091-08-$T_2$ | 0.64 | 0.059981819 | 24 | 0.34 | 0.071776729 | 23 | 0.00111815 | 88.86% |
| ME24091-08-01-$T_3$ | 0.44 | 0.050181996 | 27 | 0.40 | 0.074557785 | 26 | 0.306877156 | 11.48% |
| ME24091-09-$T_2$ | 0.81 | 0.056031311 | 38 | 0.29 | 0.067403065 | 22 | 5.88685E−08 | 185.42% |
| ME24091-09-01-$T_3$ | 0.45 | 0.055439617 | 36 | 0.28 | 0.05131548 | 31 | 0.0116714 | 62.95% |
| ME24091-10-$T_2$ | 0.56 | 0.048643058 | 39 | 0.31 | 0.062146975 | 29 | 0.001240527 | 80.46% |
| ME24091-10-01-$T_3$ | 0.36 | 0.051198395 | 31 | 0.26 | 0.066281225 | 22 | 0.114418402 | 39.44% |

Summary of Results:
In sum, ectopic expression of Ceres cDNA Clone 106263 under the control of the 35S promoter enhances oxidative stress tolerance that causes necrotic lesions and stunted growth in wild-type Ws seedlings.

Example 18: Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID Nos. 2, 35, 41, 43, 44, 45, 86, 109, 135, 136, 138, 140, 141, 142, 143 and to amino acids X-Y of SEQ ID NO: 140 and to amino acids X-Y of SEQ ID NO: 140 are shown in FIGS. 1-6 and the Sequence Listing.

Example 19: Determination of Functional Homologs by Hidden Markov Models

Hidden Markov Models (HMMs) were generated by the program HMMER 2.3.2. To generate each HMM, the default HMMER 2.3.2 program parameters, conFigured for glocal alignments, were used.

An HMM was generated using the sequences shown in FIG. 1 as input. These sequences were input into the model and the HMM bit score for each sequence is shown in the Sequence Listing. Additional sequences were input into the model, and the HMM bit scores for the additional sequences are shown in the Sequence Listing. The results indicate that these additional sequences are functional homologs of SEQ ID NO: 86.

HMMs were also generated using the sequences shown in FIGS. 2-6 as input. These sequences were input into the respective models and the corresponding HMM bit score for each sequence is shown in the Sequence Listing. Additional sequences were input into the models, and the HMM bit scores for the additional sequences are shown in the Sequence Listing. The results indicate that these additional sequences are functional homologs of the groups in FIGS. 2-6.

In an alternative embodiment, the HMM is generated with the proviso that none of the amino acids specifically described in PCT/US2007/06544 are used. In particular the following amino acids appearing in the Sequence Listing of PCT/US2007/06544 are excluded: SEQ ID NO:99, SEQ ID NO:100, SEQ ID NO:102, SEQ ID NO:103, SEQ ID NO:104, SEQ ID NO:180, SEQ ID NO:252, SEQ ID NO:298, SEQ ID NO:300, SEQ ID NO:301, SEQ ID NO:306 and SEQ ID NO:312.

REFERENCES

The following references are cited in the Specification. Each of the references from the patent and periodical literature cited herein is hereby expressly incorporated in its entirety by such citation.

Zhang et al. (2004) *Plant Physiol.* 135:615.
Salomon et al. (1984) *EMBO J.* 3:141.
Herrera-Estrella et al. (1983) *EMBO J.* 2:987.
Escudero et al. (1996) *Plant J.* 10:355.
Ishida et al. (1996) *Nature Biotechnology* 14:745.
May et al. (1995) *Bio/Technology* 13:486)
Armaleo et al. (1990) *Current Genetics* 17:97.
Smith. T. F. and Waterman, M. S. (1981) *Adv. App. Math.* 2:482.
Needleman and Wunsch (1970) *J. Mol. Biol.* 48:443.
Pearson and Lipman (1988) *Proc. Natl. Acad. Sci.* (USA) 85: 2444.
Yamauchi et al. (1996) *Plant Mol Biol.* 30:321-9.
Xu et al. (1995) *Plant Mol. Biol.* 27:237.
Yamamoto et al. (1991) *Plant Cell* 3:371.
P. Tijessen, "Hybridization with Nucleic Acid Probes" In Laboratory Techniques in Biochemistry and Molecular Biology, P. C. vand der Vliet, ed., c. 1993 by Elsevier, Amsterdam.
Bonner et al., (1973) *J. Mol. Biol.* 81:123.
Sambrook et al., *Molecular Cloning: A Laboratory Manual*, Second Edition, Cold Spring Harbor Laboratory Press, 1989, New York.
Shizuya et al. (1992) *Proc. Natl. Acad. Sci. USA*, 89: 8794-8797.
Hamilton et al. (1996) *Proc. Natl. Acad. Sci. USA*, 93: 9975-9979.
Burke et al. (1987) *Science*, 236:806-812.
Sternberg N. et al. (1990) *Proc Nall Acad Sci* USA., 87:103-7.
Bradshaw et al. (1995) *Nucl Acids Res*, 23: 4850-4856.
Frischauf et al. (1983) *J. Mol Biol*, 170: 827-842.
Huynh et al., Glover N M (*ed*) DNA Cloning: A practical Approach, Vol. 1 Oxford: IRL Press (1985).
Walden et al. (1990) *Mol Cell Biol* 1: 175-194.
Vissenberg et al. (2005) *Plant Cell Physiol* 46:192.
Husebye et al. (2002) *Plant Physiol* 128:1180.
Plesch et al. (2001) *Plant J* 28:455.
Weising et al. (1988) *Ann. Rev. Genet.*, 22:421.
Christou (1995) *Euphytica*, v. 85, n. 1-3:13-27.
Newell (2000)
Griesbach (1987) *Plant Sci.* 50:69-77.
Fromm et al. (1985) *Proc. Natl. Acad. Sci. USA* 82:5824.
Paszkowski et al. (1984) *EMBO J.* 3:2717.
Klein et al. (1987) *Nature* 327:773.
Willmitzer, L. (1993) Transgenic Plants. In: iotechnology, A Multi-Volume Comprehensive treatise (H. J. Rehm, G. Reed, A. Püler, P. Stadler, eds., Vol. 2, 627-659, VCH Weinheim-New York-Basel-Cambridge).
*Crit. Rev. Plant. Sci.* 4:1-46.
Fromm et al. (1990) *Biotechnology* 8:833-844.
Cho et al. (2000) *Planta* 210:195-204.
Brootghaerts et al. (2005) *Nature* 433:629-633.
Lincoln et al. (1998) *Plant Mol. Biol.* Rep. 16:1-4.
Lacomme et al. (2001), "Genetically Engineered Viruses" (C. J. A. Ring and E. D. Blair, *Eds*). Pp. 59-99, BIOS Scientific Publishers, Ltd. Oxford, UK.
Huh G H, Damsz B, Matsumoto T K, Reddy M P, Rus A M, Ibeas J I, Narasimhan M L, Bressan R A, Hasegawa P M, 2002, Salt causes ion disequilibrium-induced programmed cell death in yeast and plants. *Plant J* 29(5): 649-59.
Kang D K, Li X M, Ochi K, Horinouchi S, 1999, Possible involvement of cAMP in aerial mycelium formation and secondary metabolism in *Streptomyces griseus*. *Microbiology*, 145 (Pt 5):1161-72.
Kerk D, Bulgrien J, Smith D W, Gribskov M, 2003, *Arabidopsis* proteins containing similarity to the universal stress protein domain of bacteria. *Plant Physiol.* 131(3): 1209-19.
Zhu J K, 2001, Cell signaling under salt, water and cold stresses. *Curr Opin Plant Biol.* 4(5):401-6.
Susstrunk U, Pidoux J, Taubert S, Ullmann A, Thompson C J, 1998, Pleiotropic effects of cAMP on germination, antibiotic biosynthesis and morphological development in *Streptomyces coelicolor. Mol Microbiol* 30(1): 33-46.
Davletova S, Schlauch K, Coutu J, Mittler R., 2005, The zinc-finger protein Zat12 plays a central role in reactive oxygen and abiotic stress signaling in *Arabidopsis*. *Plant Physiol* 139(2): 847-56.
Fowler S G, Cook D, Thomashow M F., 2005, Low temperature induction of *Arabidopsis* CBF1, 2, and 3 is gated by the circadian clock. *Plant Physiol* 137(3):961-8.
Nachin L, Nannmark U, Nystom T (2005) Differential roles of the universal stress proteins of *Escherichia coli* in oxidative stress resistance, adhesion and motility *J Bacteriol* 187(18):6265-72.
Rizhsky L, Davletova S, Liang H, Mittler R, 2004, The zinc finger protein Zat12 is required for cytosolic ascorbate peroxidase 1 expression during oxidative stress in *Arabidopsis*. *J Biol Chem*. 19; 279(12): 11736-43.
Vogel J T, Zarka D G, Van Buskirk H A, Fowler S G, Thomashow M F, 2005, Roles of the CBF2 and ZAT12 transcription factors in configuring the low temperature transcriptome of *Arabidopsis*. *Plant J*. 41(2): 195-211.
Sanchez-Barrena M J, Martinez-Ripoll M, Zhu J K, Albert A., 2005, The structure of the *Arabidopsis thaliana* SOS3: molecular mechanism of sensing calcium for salt stress response *J Mol Biol.* 345(5):1253-64.

Griffen, H. G, and Gasson, M. J. (1995) The Gene (aroK) Encoding Shikimate Kinase I from *E. coli. DNA Seq.*, 5(3):195-197.

Susstrunk et al. (1998) *Mol Microbiol*, 30(1):33-46

Kang et al. (1999) *Microbiology*, 145:1161-72.

Sauter M, Rzewuski G, Marwedel T, Lorbiecke R (2002) The novel ethylene-regulated gene OsUsp1 from rice encodes a member of a plant protein family related to prokaryotic universal stress proteins. *J Exp Bot* 53 (379): 2325-31.

Kasuga et al. (1999) *Nature Biotech* 17: 287-291.

Rus et al. (2001) *PNAS* 98:14150-14155.

Shi et al. (2000) *PNAS* 97:6896-6901.

Apse et al. (1999) *Science* 285:1256-1258.

Zhang et al. (2001) *PNAS* 98:12832-12836.

Berthomieu et al. (2003) *EMBO J* 22:2004-2014.

Ren et al. (2005) *Nat Genet.* 37:1029-30

Davletova et al (2005) *Plant Physiol.* 139:847-56

The invention claimed is:

1. A plant cell transformed with an exogenous nucleic acid, said exogenous nucleic acid comprising a heterologous promoter operably linked to a nucleotide sequence comprising a polynucleotide sequence encoding a polypeptide, wherein said polypeptide comprises an amino acid sequence having 95 percent or greater sequence identity to the amino acid sequence of SEQ ID NO:86, and wherein overexpression of said polypeptide in a transformed plant grown from said transformed plant cell has an increased level of tolerance to salinity or oxidative stress as compared to the corresponding level of tolerance to salinity or oxidative stress of a control plant of the same species cultivated under the same conditions that does not comprise said exogenous nucleic acid.

2. The transformed plant cell of claim 1, wherein the polynucleotide sequence encodes a polypeptide comprising an amino acid sequence having 97 percent or greater sequence identity to the amino acid sequence of SEQ ID NO:86.

3. A transgenic plant comprising the plant cell of claim 1.

4. The transgenic plant of claim 3, wherein said plant is a member of a species selected from the group consisting of *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

5. A seed or vegetative tissue comprising the plant cell of claim 1, wherein said seed or vegetative tissue comprises the exogenous nucleic acid.

6. A food or feed product comprising the seed or vegetative tissue of claim 5, wherein the food or feed product comprises the exogenous nucleic acid.

7. The transformed plant cell of claim 1, wherein the polynucleotide sequence encodes a polypeptide comprising the amino acid sequence of SEQ ID NO:86.

8. The transgenic plant of claim 3, wherein the polynucleotide sequence encodes a polypeptide comprising the amino acid sequence of SEQ ID NO:86.

\* \* \* \* \*